US010906948B2

(12) United States Patent
Serini et al.

(10) Patent No.: US 10,906,948 B2
(45) Date of Patent: Feb. 2, 2021

(54) NON-NATURAL SEMAPHORINS 3 AND THEIR MEDICAL USE

(71) Applicant: Seagull Therapeutics SAS, Illkirch-Graffenstaden (FR)

(72) Inventors: Guido Serini, Moncalieri (IT); Enrico Giraudo, Ciriè (IT); Luca Tamagnone, Turin (IT)

(73) Assignee: Seagull Therapeutics SAS, Illkirch-Graffenstaden (FR)

( * ) Notice: Subject to any disclaimer, the term of this patent is extended or adjusted under 35 U.S.C. 154(b) by 302 days.

(21) Appl. No.: 15/552,511

(22) PCT Filed: Feb. 23, 2016

(86) PCT No.: PCT/EP2016/053750
§ 371 (c)(1),
(2) Date: Aug. 22, 2017

(87) PCT Pub. No.: WO2016/135130
PCT Pub. Date: Sep. 1, 2016

(65) Prior Publication Data

US 2018/0030100 A1 Feb. 1, 2018

(30) Foreign Application Priority Data

Feb. 23, 2015 (EP) .................................... 15156195

(51) Int. Cl.

| | |
|---|---|
| ***C07K 14/435*** | (2006.01) |
| ***C07K 14/47*** | (2006.01) |
| ***A61K 45/06*** | (2006.01) |
| ***C07K 16/26*** | (2006.01) |
| *A61K 38/00* | (2006.01) |
| *A61K 9/00* | (2006.01) |

(52) U.S. Cl.
CPC .......... *C07K 14/4703* (2013.01); *A61K 45/06* (2013.01); *C07K 16/26* (2013.01); *A61K 9/0019* (2013.01); *A61K 38/00* (2013.01); *C07K 2319/00* (2013.01); *C07K 2319/30* (2013.01); *C07K 2319/70* (2013.01); *C07K 2319/73* (2013.01)

(58) Field of Classification Search
None
See application file for complete search history.

(56) References Cited

U.S. PATENT DOCUMENTS

| | | | |
|---|---|---|---|
| 6,344,544 B1 | 2/2002 | Goodman et al. | |
| 2003/0166557 A1 | 9/2003 | Minna et al. | |
| 2010/0247516 A1 | 9/2010 | Neufeld et al. | |
| 2015/0158939 A1* | 6/2015 | Ting ...................... | C07K 16/28 424/134.1 |

FOREIGN PATENT DOCUMENTS

| | | |
|---|---|---|
| WO | 1995007706 A1 | 3/1995 |
| WO | 2011066284 A1 | 6/2011 |
| WO | 2014058915 A2 | 4/2014 |

OTHER PUBLICATIONS

Database BioProject [Online] Jul. 14, 2014 (Jul. 14, 2014), "Predicted: Semaphorin-3B Isoform X2 [Equus Przewalskii]", XP002744032, retrieved from NCBI Accession No. XP_008528038.
Database BioProject [Online] Dec. 6, 2014 (Dec. 6, 2014), "Predicted: Semaphorin-3F[Haliaeetus Leucocephalus]", XP002744034, retrieved from NCBI Accession No. XP_010571212.
Database BioProject [Online] Mar. 7, 2014 (Mar. 7, 2014), Predicted: Semaphorin-3B Isoform X6 [Panthera Tigris Altaica], XP002744033, retrieved from NCBI Accession No. XP_007088627.
Extended European Search Report dated Sep. 9, 2015 issued in EP15156195.8-1410.
International Search Report and Written Opinion dated Jun. 20, 2016 received in PCT/EP2016/053750.
International Preliminary Report on Patentability and Written Opinion dated Sep. 8, 2017 received in PCT/EP2016/053750.
Janssen et al., "Structural Basis of Semaphorin-Plexin Signalling", Nature, vol. 467, pp. 1118-1122 (2010).
Japanese Office Action and English Translation dated Dec. 24, 2019 received in corresponding JP Application JP-A-H09-505725.
JP-A-H09-505725 which is the Japanese Application corresponding to WO 95/07706.
Frankel, et al., "Characterization of Diphtheria Fusion Proteins Targeted to the Human Interleukin-3 Receptor" Protein Engineering, vol. 13, No. 8, 2000, pp. 575-581.
Pakula et al., "Genetic Analysis of Protein Stability and Function" Annu. Rev. 23: 289-310 (1989).

(Continued)

*Primary Examiner* — Michael D Pak
(74) *Attorney, Agent, or Firm* — Michele M. Wales; Inhouse Patent Counsel, LLC

(57) ABSTRACT

The present invention relates to non-naturally occurring, mutated Semaphorin 3 molecules. Particularly, the invention relates to the mutated Semaphorin 3 or the functional fragment thereof that exhibit improved properties and pharmacologic effects, e.g., in the treatment of angiogenic disease and cancer. In addition, the present invention relates to nucleic acid molecules encoding such polypeptides, and vectors and hosts comprising such nucleic acids. The invention further relates to methods for producing the polypeptides of the invention, and to methods of using them in the treatment of disease, in particular in the medical intervention of angiogenic diseases, tumors and/or cancer.

22 Claims, 30 Drawing Sheets

Figure 1:
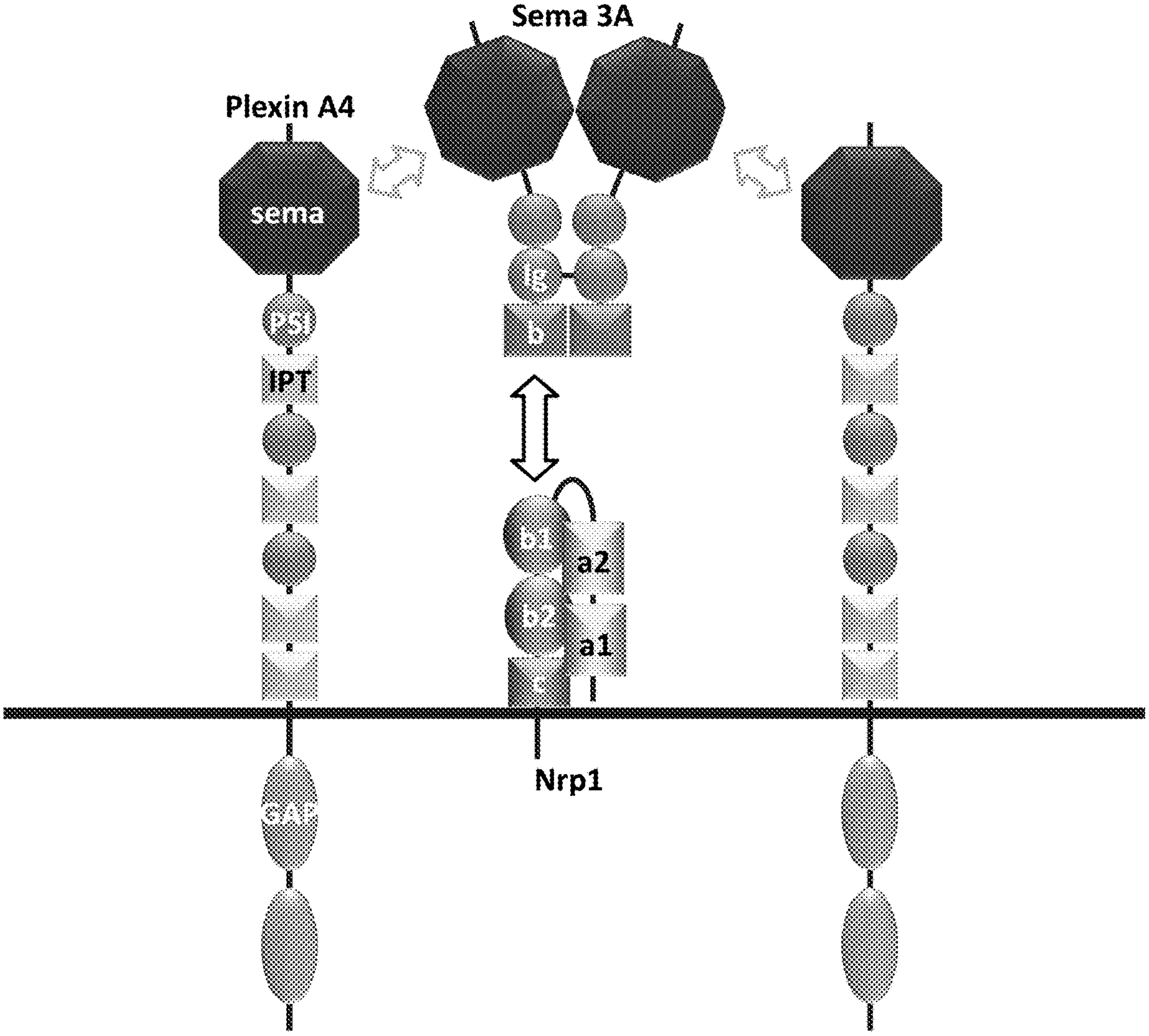

Specification includes a Sequence Listing.

(56) References Cited

OTHER PUBLICATIONS

Roitt et al., “Immunology”, Moskva “Mir”, Chapter 6, 110-111 (2000).

Russian International Search Report and Written Opinion dated Oct. 30, 2019 and received in RU Application 2017128465.

Russian Office Action and English translation dated Oct. 30, 2019 received in corresponding RU Application 2017128465.

Singer et al., “Genes and Genomes”, Moskva “Mir”, vol. 1, pp. 63-64 (1998).

* cited by examiner

Figure 2 (cont. 1).

D

SEMA3A WT

*R&D Systems*

Figure 3.

A

```
Sema3A ---------------MGWFTGIACLFWGVLLTARANYANGKNNVPRLKLSYKEMLESNNV 45
SEMA3A ---------------MGWLTRIVCLFWGVLLTARANYQNGKNNVPRLKLSYKEMLESNNV 45
Sema3D MNVTKDENPRSRSQDLHLFHAWMMLIMTVLFLPVTETS--KQNIPRLKLTYKDLLLSNTC 58
SEMA3D MNANKDERLKARSQDFHLFPALMMLSMTMLFLPVTGTL--KQNIPRLKLTYKDLLLSNSC 58
Sema3B ---------------MGRAEAAAMIPG-LALLWVAGLGDTAPNLPRLRLSFQELQARHGV 44
SEMA3B ---------------MGRAGAAAVIPG-LALLWAVGLGSAAPSPPRLRLSFQELQAWHGL 44
Sema3E --------------MAPAGHILTLLLWGHLLELWTPGHSANPSYPRLRLSHKELLELNRT 46
SEMA3E --------------MASAGHIITLLLWGYLLELWTGGHTADTTHPRLRLSHKELLNLNRT 46
Sema3G --------------MDPSAWAICCLLGSLLFHVGIPSPGPSPSVPRLRLSYRDLLSTNRS 46
SEMA3G --------------MAPSAWAICWLLGGLLLHGGSSGPSPGPSVPRLRLSYRDLLSANRS 46
Sema3C ----------------MAFRAICVLVGVFICSICVRGS--SQPQARVYLTFDELRETKTS 42
SEMA3C ----------------MAFRTICVLVGVFICSICVKGS--SQPQARVYLTFDELRETKTS 42
Sema3F -------------MLVTAFILWASLLTGAWPATPIQDQ--LPATPRVRLSFKELKATGTA 45
SEMA3F -------------MLVAGLLLWASLLTGAWPSFPTQDH--LPATPRVRLSFKELKATGTA 45
                               :                   .*: *:. ::

Sema3A ITFNGLANSSSYHTFLLDEERSRLYVGAKDHIFSFNLVNI-KDFQKIVWPVSYTRRDECK 104
SEMA3A ITFNGLANSSSYHTFLLDEERSRLYVGAKDHIFSFDLVNI-KDFQKIVWPVSYTRRDECK 104
Sema3D IPFLGSSEGLDFQTLLLDEERGILLLGAKDHVFLLSLVDLNKNFKKIYWPAAKERVELCK 118
SEMA3D IPFLGSSEGLDFQTLLLDEERGRLLLGAKDHIFLLSLVDLNKNFKKIYWPAAKERVELCK 118
Sema3B RTFR-LERTCCYEALLVDEERGRLFVGAENHVASLSLDNISKRAKKLAWPAPVEWREECN 103
SEMA3B QTFS-LERTCCYQALLVDEERGRLFVGAENHVASLNLDNISKRAKKLAWPAPVEWREECN 103
Sema3E SIFQSPLGFLDLHTMLLDEYQERLFVGGRDLVYSLNLERVSDGYREIYWPSTAVKVEECI 106
SEMA3E SIFHSPFGFLDLHTMLLDEYQERLFVGGRDLVYSLSLERISDGYKEIHWPSTALKMEECI 106
Sema3G AIFLGPRGSLDLQVMYLDEYRDRLFLGSRDALYSLRLDQAWPDPREVLWLPQPGQKVECV 106
SEMA3G AIFLGPQGSLNLQAMYLDEYRDRLFLGGLDALYSLRLDQAWPDPREVLWPPQPGQREECV 106
Sema3C EYFSLSHQQLDYRILLMDEDQDRIYVGSKDHILSLNINNISQEPLSVFWPASTIKVEECK 102
SEMA3C EYFSLSHHPLDYRILLMDEDQDRIYVGSKDHILSLNINNISQEALSVFWPASTIKVEECK 102
Sema3F HFFNFLLNTTDYRILLKDEDHDRMYVGSKDYVLSLDLHDINREPLIIHWAASPQRIEECI 105
SEMA3F HFFNFLLNTTDYRILLKDEDHDRMYVGSKDYVLSLDLHDINREPLIIHWAASPQRIEECV 105
         *         . :  ** :  : :*. : :  : :         : *         *

Sema3A WAGKDILKECANFIKVLEAYNQTHLYACGTGAFHPICTYIEVGHHPEDNIFKLQDSHFEN 164
SEMA3A WAGKDILKECANFIKVLKAYNQTHLYACGTGAFHPICTYIEIGHHPEDNIFKLENSHFEN 164
Sema3D LAGKDANAECANFIRVLQPYNKTHVYVCGTGAFHPLCGYIDLGANKEELIFKLDTHNLES 178
SEMA3D LAGKDANTECANFIRVLQPYNKTHIYVCGTGAFHPICGYIDLGVYKEDIIFKLDTHNLES 178
Sema3B WAGKDIGTECMNFVKLLHTYNHTHLLACGTGAFHPTCAFVEVGHRLEEPMLQLDRRKLED 163
SEMA3B WAGKDIGTECMNFVKLLHAYNRTHLLACGTGAFHPTCAFVEVGHRAEEPVLRLDPGRIED 163
Sema3E MKGKD-ANECANYIRVLHHYNRTHLLTCATGAFDPHCAFIRVGHHSEEPLFHLESHRSER 165
SEMA3E MKGKD-AGECANYVRVLHHYNRTHLLTCGTGAFDPVCAFIRVGYHLEDPLFHLESPRSER 165
Sema3G RKGKDPLTECANFVRVLQPHNRTHLLACGTGAFQPICTFITVGHRG-EHVLRLDASSVEN 165
SEMA3G RKGRDPLTECANFVRVLQPHNRTHLLACGTGAFQPTCALITVGHRG-EHVLHLEPGSVES 165
Sema3C MAGKDPTHGCGNFVRVIQTFNRTHLYVCGSGAFSPVCTYLNRGRRSEDQVFMIDS-KCES 161
SEMA3C MAGKDPTHGCGNFVRVIQTFNRTHLYVCGSGAFSPVCTYLNRGRRSEDQVFMIDS-KCES 161
Sema3F LSGKDGNGECGNFVRLIQPWNRTHLYVCGTGAYNPMCTYVNRGRRAQDYIFYLEPEKLES 165
SEMA3F LSGKDVNGECGNFVRLIQPWNRTHLYVCGTGAYNPMCTYVNRGRRAQATPWTQTQAVRGR 165
         *:*    * *:::::.  *:**: .*.:**: * *  :  *
```

Figure 3 (cont. 1).

```
Sema3A GRGKSPYDPKLLTASLLIDGELYSGTAADFMGRDFAIFRTLG---HHHPIRTEQHDSRWL 221
SEMA3A GRGKSPYDPKLLTASLLIDGELYSGTAADFMGRDFAIFRTLG---HHHPIRTEQHDSRWL 221
Sema3D GRLKCPFDPQQPFASVMTDEHLYSGTASDFLGKDTAFTRSLGLMQDHHSIRTDISEHHWL 238
SEMA3D GRLKCPFDPQQPFASVMTDEYLYSGTASDFLGKDTAFTRSLGPTHDHHYIRTDISEHYWL 238
Sema3B GKGKTPYDPRHRAASVLVGEELYSGVTADLMGRDFTIFRSLG---QNPSLRTEPHDSRWL 220
SEMA3B GKGKSPYDPRHRAASVLVGEELYSGVAADLMGRDFTIFRSLG---QRPSLRTEPHDSRWL 220
Sema3E GRGRCPFDPNSSFVSTLVGNELFAGLYSDYWGRDSAIFRSMG---KLGHIRTEHDDERLL 222
SEMA3E GRGRCPFDPSSSFISTLIGSELFAGLYSDYWSRDAAIFRSMG---RLAHIRTEHDDERLL 222
Sema3G GRGRCPHEPSRPFASTFVGGELYTGLTADFLGREAMIFRSGG---PRPALRSDSD-QSLL 221
SEMA3G GRGRCPHEPSRPFASTFIDGELYTGLTADFLGREAMIFRSGG---PRPALRSDSD-QSLL 221
Sema3C GKGRCSFNPNVNTVSVMINEELFSGMYIDFMGTDAAIFRSLT---KRNAVRTDQHNSKWL 218
SEMA3C GKGRCSFNPNVNTVSVMINEELFSGMYIDFMGTDAAIFRSLT---KRNAVRTDQHNSKWL 218
Sema3F GKGKCPYDPKLDTASALINEELYAGVYIDFMGTDAAIFRTLG---KQTAMRTDQYNSRWL 222
SEMA3F GSRATDGALRPMPTAPRQDYIFYLEPERLESGKGKCPYDPKL---DTASALINEELYAGV 222
       *             :   .  ::        .       .            :      :

Sema3A NDPRFISAHLIPESDNPEDDKVYFFFRENAIDGE-HSGKATHARIGQICKNDFGGHRSLV 280
SEMA3A NDPKFISAHLISESDNPEDDKVYFFFRENAIDGE-HSGKATHARIGQICKNDFGGHRSLV 280
Sema3D NGAKFIGTFPIPDTYNPDDDKIYFFFRESSQEGS-TSDRSILSRVGRVCKNDVGGQRSLI 297
SEMA3D NGAKFIGTFFIPDTYNPDDDKIYFFFRESSQEGS-TSDKTILSRVGRVCKNDVGGQRSLI 297
Sema3B NEPKFVKVFWIPESENPDDDKIYFFFRESAVEAAPAMGRMSVSRVGQICRNDLGGQRSLV 280
SEMA3B NEPKFVKVFWIPESENPDDDKIYFFFRETAVEAAPALGRLSVSRVGQICRNDVGGQRSLV 280
Sema3E KEPKFVGSYMIPDNEDRDDNKMYFFFTEKALEAENN-AHTIYTRVGRLCVNDMGGQRILV 281
SEMA3E KEPKFVGSYMIPDNEDRDDNKVYFFFTEKALEAENN-AHAIYTRVGRLCVNDVGGQRILV 281
Sema3G HEPRFVMAARIPDNSDRDDDKVYFFFSETVPSPDGGPGHVTISRVGRVCVNDAGGQRVLV 281
SEMA3G HDPRFVMAARIPENSDQDNDKVYFFFSETVPSPDGGSNHVTVSRVGRVCVNDAGGQRVLV 281
Sema3C SEPMFVDAHVIPDGTDPNDAKVYFFFKERLTDNN-RSTKQIHSMIARICPNDTGGQRSLV 277
SEMA3C SEPMFVDAHVIPDGTDPNDAKVYFFFKEKLTDNN-RSTKQIHSMIARICPNDTGGLRSLV 277
Sema3F NDPSFIHAELIPDSAERNDDKLYFFFRERSAEA--PQNPAVYARIGRICLNDDGGHCCLV 280
SEMA3F YIDFMGTDAAIFRTLGKQTAMRTDQYNSRWLND--PSFIHAELIPDSAERNDDKLYFFFR 280
           :     *      :       : .   .                  **      :

Sema3A NKWTTFLKARLICSVPGPNGIDTHFDELQDVFLMNSKDPKNPIVYGVFTTSSNIFKGSAV 340
SEMA3A NKWTTFLKARLICSVPGPNGIDTHFDELQDVFLMNFKDPKNPVVYGVFTTSSNIFKGSAV 340
Sema3D NKWTTFLKARLICSIPGSDGADTHFDELQDIYLLPTRDERNPVVYGVFTTTSSIFKGSAV 357
SEMA3D NKWTTFLKARLICSIPGSDGADTYFDELQDIYLLPTRDERNPVVYGVFTTTSSIFKGSAV 357
Sema3B NKWTTFLKARLVCSVPGVEG-DTHFDQLQDVFLLSSRDRQTPLLYAVFSTSSGVFQGSAV 339
SEMA3B NKWTTFLKARLVCSVPGVEG-DTHFDQLQDVFLLSSRDHRTPLLYAVFSTSSSIFQGSAV 339
Sema3E NKWSTFLKARLVCSVPGMNGIDTYFDELEDVFLLPTRDPKNPVIFGLFNTTSNIFRGHAV 341
SEMA3E NKWSTFLKARLVCSVPGMNGIDTYFDELEDVFLLPTRDHKNPVIFGLFNTTSNIFRGHAI 341
Sema3G NKWSTFLKARLVCSVPGPGGAETHFDQLEDVFLLWPKAGKSLEVYALFSTVSAVFQGFAV 341
SEMA3G NKWSTFLKARLVCSVPGPGGAETHFDQLEDVFLLWPKAGKSLEVYALFSTVSAVFQGFAV 341
Sema3C NKWTTFLKARLVCSVTDEDGPETHFDELEDVFLLETDNPRTTLVYGIFTTSSSVFKGSAV 337
SEMA3C NKWTTFLKARLVCSVTDEDGPETHFDELEDVFLLETDNPRTTLVYGIFTTSSSVFKGSAV 337
Sema3F NKWSTFLKARLVCSVPGEDGIETHFDELQDVFVQQTQDVRNPVIYAVFTSSGSVFRGSAV 340
SEMA3F ERSAEAPQSPAVYARIGRICLNDDGGHCCLVNKWSTFLKARLVCSVPGEDGIETHFDELQ 340
       :: :   ::  : :  .    :  ..    :                       . .
```

Figure 3 (cont. 2).

```
Sema3A CMYSMSDVRRVFLGPYAHRDGPNYQWVPYQGRVPYPRPGTCPSKTFG----GFDSTKDLP 396
SEMA3A CMYSMSDVRRVFLGPYAHRDGPNYQWVPYQGRVPYPRPGTCPSKTFG----GFDSTKDLP 396
Sema3D CVYSMADIRAVFNGPYAHKESADHRWVQYDGRIPYPRPGTCPSKTYDP---LIKSTRDFP 414
SEMA3D CVYSMADIRAVFNGPYAHKESADHRWVQYDGRIPYPRPGTCPSKTYDP---LIKSTRDFP 414
Sema3B CVYSMNDVRRAFLGPFAHKEGPTHQWVSYQGRVPYPRPGMCPSKTFG----TFSSTKDFP 395
SEMA3B CVYSMNDVRRAFLGPFAHKEGPMHQWVSYQGRVPYPRPGMCPSKTFG----TFSSTKDFP 395
Sema3E CVYHMSSIREAFNGPYAHKEGPEYHWSLYEGKVPYPRPGSCASKVNG--GK-YGTTKDYP 398
SEMA3E CVYHMSSIRAAFNGPYAHKEGPEYHWSVYEGKVPYPRPGSCASKVNG--GR-YGTTKDYP 398
Sema3G CVYHMVDIWEVFNGPFAHRDGPQHQWGPYGGKVPFPRPGVCPSKMTAQPGRPFGSTKDYP 401
SEMA3G CVYHMADIWEVFNGPFAHRDGPQHQWGPYGGKVPFPRPGVCPSKMTAQPGRPFGSTKDYP 401
Sema3C CVYHLSDIQTVFNGPFAHKEGPNHQLISYQGRIPYPRPGTCPGGAFTP---NMRTTKDFP 394
SEMA3C CVYHLSDIQTVFNGPFAHKEGPNHQLISYQGRIPYPRPGTCPGGAFTP---NMRTTKEFP 394
Sema3F CVYSMADIRMVFNGPFAHKEGPNYQWMPFSGKMPYPRPGTCPGGTFTP---SMKSTKDYP 397
SEMA3F DVFVQQTQDVRNPVIYAVFTSSGSVFRGSAVCVYSMADIRMVFNGPFA---HKEGPNYQW 397
        ::            :*   ..          :                      ..

Sema3A DDVITFARSHPAMYNPVFPINNRPIMIKTDVNYQFTQIVVDRVDAEDGQYDVMFIGTDVG 456
SEMA3A DDVITFARSHPAMYNPVFPMNNRPIVIKTDVNYQFTQIVVDRVDAEDGQYDVMFIGTDVG 456
Sema3D DDVISFIRRHPVMYKSVYPVAGAPTFKRINVDYRLTQIVVDHVVAEDGQYDVMFLGTDIG 474
SEMA3D DDVISFIKRHSVMYKSVYPVAGGPTFKRINVDYRLTQIVVDHVIAEDGQYDVMFLGTDIG 474
Sema3B DDVIQFARNHPLMYNPVLPMGGRPLFLQVGAGYTFTQIAADRVAAADGHYDVLFIGTDVG 455
SEMA3B DDVIQFARNHPLMYNSVLPTGGRPLFLQVGANYTFTQIAADRVAAADGHYDVLFIGTDVG 455
Sema3E DDAIRFARMHPLMYQPIKPVHKKPILVKTDGKYNLRQLAVDRVEAEDGQYDVLFIGTDTG 458
SEMA3E DDAIRFARSHPLMYQAIKPAHKKPILVKTDGKYNLKQIAVDRVEAEDGQYDVLFIGTDNG 458
Sema3G DEVLQFVRDHPLMFQPVRPRRGRPVLVKTHLAQRLRQIVVDRVEAEDGTYDVIFLGTDSG 461
SEMA3G DEVLQFARAHPLMFWPVRPRHGRPVLVKTHLAQQLHQIVVDRVEAEDGTYDVIFLGTDSG 461
Sema3C DDVVTFIRNHPLMYNSIYPIHRRPLIVRIGTDYKYTKIAVDRVNAADGRYHVLFLGTDRG 454
SEMA3C DDVVTFIRNHPLMYNSIYPIHKRPLIVRIGTDYKYTKIAVDRVNAADGRYHVLFLGTDRG 454
Sema3F DEVINFMRTHPLMYQAVYPLQRRPLVVRTGAPYRLTTVAVDQVDAADGRYEVLFLGTDRG 457
SEMA3F MPFSGKMPYPRPGTCPGGTFTPSMKSTKDYPDEVINFMRSHPLMYQAVYPLQRRPLVVRT 457
                      .  .        :         :  . :             .

Sema3A TVLKVVSVPKETWHDLEEVLLEEMTVFREPTTISAMELSTKQQQLYIGSTAGVAQLPLHR 516
SEMA3A TVLKVVSIPKETWYDLEEVLLEEMTVFREPTAISAMELSTKQQQLYIGSTAGVAQLPLHR 516
Sema3D TVLKVVSISKEKWN-MEEVVLEELQVFKHPTAILNMELSLKQQQLYVGSWDGLVQLSLHR 533
SEMA3D TVLKVVSISKEKWN-MEEVVLEELQIFKHSSIILNMELSLKQQQLYIGSRDGLVQLSLHR 533
Sema3B TVLKVISVPKGSRPNSEGLLLEELQVFEDSAAITSMQISSKRQQLYIASRSAVAQIALHR 515
SEMA3B TVLKVISVPKGSRPSAEGLLLEELHVFEDSAAVTSMQISSKRHQLYVASRSAVAQIALHR 515
Sema3E IVLKVITIYNQETEWMEEVILEELQIFKDPAPIISMEISSKRQQLYIGSASAVAQVRFHH 518
SEMA3E IVLKVITIYNQEMESMEEVILEELQIFKDPVPIISMEISSKRQQLYIGSASAVAQVRFHH 518
Sema3G SVLKVIALQGGGLTEPEEVVLEELQVFKVPTPITEMEISVKRQTLYVGSPLGVARLQLHQ 521
SEMA3G SVLKVIALQAGGSAEPEEVVLEELQVFKVPTPITEMEISVKRQMLYVGSRLGVAQLRLHQ 521
Sema3C TVQKVVVLPTNSSA-SGELILEELEVFKNHVPITTMKISSKKQQLYVSSNEGVSQVSLHR 513
SEMA3C TVQKVVVLPTNNSV-SGELILEELEVFKNHAPITTMKISSKKQQLYVSSNEGVSQVSLHR 513
Sema3F TVQKVIVLPKDDQE-VEELMLEEVEVFKEPAPVKTMTISSKRQQLYVASAVGVTHLSLHR 516
SEMA3F GAPYRLTTIAVDQV-DAADGRYEVLFLGTDRGTVQKVIVLPKDDQELEELMLEEVEVFKD 516
        .   :                *: .:          :   :.   : .        ::
```

Figure 3 (cont. 3).

```
Sema3A CDIYGKACAECCLARDPYCAWDGSSCSRYFPT---AKRRTRRQDIRNGDPLTHCSDLQHH 573
SEMA3A CDIYGKACAECCLARDPYCAWDGSACSRYFPT---AKRRTRRQDIRNGDPLTHCSDLHHD 573
Sema3D CDTYGKACADCCLARDPYCAWDGNACSRYAPT---SKRRARRQDVKYGDPITQCWDIEDS 590
SEMA3D CDTYGKACADCCLARDPYCAWDGNACSRYAPT---SKRRARRQDVKYGDPITQCWDIEDS 590
Sema3B CTALGRACAECCLARDPYCAWDGSACTRFQPT---AKRRFRRQDIRNGDPSTLCS----G 568
SEMA3B CAAHGRVCTECCLARDPYCAWDGVACTRFQPS---AKRRFRRQDVRNGDPSTLCS----G 568
Sema3E CDMYGSACADCCLARDPYCAWDGISCSRYYPTGAHAKRRFRRQDVRHGNAAQQCFGQQFV 578
SEMA3E CDMYGSACADCCLARDPYCAWDGISCSRYYPTGTHAKRRFRRQDVRHGNAAQQCFGQQFV 578
Sema3G CETYGSACAECCLARDPYCAWDGTACARYRPS--SGKRRFRRQDIRHGNPAVQCLGQGQS 579
SEMA3G CETYGTACAECCLARDPYCAWDGASCTHYRPS--LGKRRFRRQDIRHGNPALQCLGQSQE 579
Sema3C CHIYGTACADCCLARDPYCAWDGHSCSRFYPT---GKRRSRRQDVRHGNPLTQCRG--FN 568
SEMA3C CHIYGTACADCCLARDPYCAWDGHSCSRFYPT---GKRRSRRQDVRHGNPLTQCRG--FN 568
Sema3F CQAYGAACADCCLARDPYCAWDGQACSRYTAS---SKRRSRRQDVRHGNPIRQCRG--FN 571
SEMA3F PAPVKTMTISSKRQQLYVASAVGVTHLSLHRC---QAYGAACADCCLARDPYCAWD--GQ 571
              ..   :  .: * :               *  .    .

Sema3A DNHHGPSLEERIIYGVENSSTFLECSPKSQRALVYWQFQRRNEDRKEEIRMGDHIIRTEQ 633
SEMA3A NHHGHSPEERIIYGVENSSTFLECSPKSQRALVYWQFQRRNEERKEEIRVDDHIIRTDQG 633
Sema3D ISH-ETADEKVIFGIEFNSTFLECIPKSQQASVEWYIQRSGDEHREELKPDERIIKTDYG 649
SEMA3D ISH-ETADEKVIFGIEFNSTFLECIPKSQQATIKWYIQRSGDEHREELKPDERIIKTEYG 649
Sema3B DSSHSVLLEKKVLGVESGSAFLECEPRSLQAHVQWTFQGAGEAAHTQVLAEERVERTARG 628
SEMA3B DSSRPALLEHKVFGVEGSSAFLECEPRSLQARVEWTFQRAGVTAHTQVLAEERTERTARG 628
Sema3E GDALDRTEERLAYGIESNSTLLECTPRSLQAKVIWFVQKGRDVRKEEVKTDDRVVKMDLG 638
SEMA3E GDALDKTEEHLAYGIENNSTLLECTPRSLQAKVIWFVQKGRETRKEEVKTDDRVVKMDLG 638
Sema3G QNKAASGLMTRVFGTEHNSTFLECLPKSPQAAVRWFLQRPGDKGTDQVKTDERVVQTAQG 639
SEMA3G EEAVGLVAATMVYGTEHNSTFLECLPKSPQAAVRWLLQRPGDEGPDQVKTDERVLHTERG 639
Sema3C LKAYRNAAEIVQYGVRNNSTFLECAPKSPQASIKWLLQKDK-DRRKEVKLNERIIATSQG 627
SEMA3C LKAYRNAAEIVQYGVKNNTTFLECAPKSPQASIKWLLQKDK-DRRKEVKLNERIIATSQG 627
Sema3F SNANKNAVESVQYGVAGSAAFLECQPRSPQATVKWLFQRDPSDRRREIRAEDRFLRTEQG 631
SEMA3F ACSRYTASSKRRSRRQDVRHGNPIRQCRGFNSNANKNAVESVQYGVAGSAAFLECQPRSP 631


Sema3A GLLLRSLQKKDSGNYLCHAVEHGFMQTLLKVTLEVIDTEHLEELLHKDDDGD--GSKIKE 691
SEMA3A LLLRSLQQKDSGNYLCHAVEHGFIQTLLKVTLEVIDTEHLEELLHKDDDGDG--SKTKEM 691
Sema3D LLIRSLQKKDSGMYYCKAQEHTFIHTIVKLTLNVIENEQMENTQRAEYQEG--------Q 701
SEMA3D LLIRSLQKKDSGMYYCKAQEHTFIHTIVKLTLNVIENEQMENTQRAEHEEG--------K 701
Sema3B LLLRGLRRQDSGVYLCVAVEQGFSQPLRRLVLHVLSAAQAERLARAEEAAA--------- 679
SEMA3B LLLRRLRRRDSGVYLCAAVEQGFTQPLRRLSLHVLSATQAERLARAEEAAP--------- 679
Sema3E LLFLRVRKSDAGTYFCQTVEHNFVHTVRKITLEVVEEHKVEGMFHKDHEEERHHKMPCPP 698
SEMA3E LLFLRLHKSDAGTYFCQTVEHSFVHTVRKITLEVVEEEKVEDMFNKDDEEDRHHRMPCPA 698
Sema3G LLFRRLSRHDAGNYTCTTLEHGFSQTVVRFALEVIAAVQLDSLFLRESRLE----EPSAW 695
SEMA3G LLFRRLSRFDAGTYTCTTLEHGFSQTVVRLALVVIVASQLDNLFPPEPKPE----EPPAR 695
Sema3C LLIRSVQDSDQGLYHCIATENSFKQTIAKINFKVLDSEMV--AVVTDKWSPWT------- 678
SEMA3C LLIRSVQGSDQGLYHCIATENSFKQTIAKINFKVLDSEMV--AVVTDKWSPWT------- 678
Sema3F LLLRALQLGDRGLYSCTATENNFKHIVTRVQLHVLGRDAVHAALFPPLAVSVP------- 684
SEMA3F QATVKWLFQRDPGDRRREIRAEDRFLRTEQGLLLRALQLSDRGLYSCTATENN------- 684
```

Figure 3 (cont. 4).

```
Sema3A MSSSMTPSQKVWYRDFMQLINHP---NLNTMDEFCEQVWKR---------DRKQRRQRPGH 740
SEMA3A SNSMTPSQKVWYRDFMQLINHPN---LNTMDEFCEQVWKRD---------RKQRRQRPGHT 740
Sema3D VKDLLAESRLRYKDYIQILSSP----NFSLDQYCEQMWYKE---------KRRQRNK---- 745
SEMA3D VKDLLAESRLRYKDYIQILSSP----NFSLDQYCEQMWHRE---------KRRQRNK---- 745
Sema3B --PAPPGPKLWYRDFLQLVEPGGGGGANSLRMCRPQPGHHS---------VAADSRRK--- 726
SEMA3B --AAPPGPKLWYRDFLQLVEPGGGGSANSLRMCRPQPALQS---------LPLESRRK--- 726
Sema3E LSGMSQGTKPWYKEFLQLIGYSN---FQRVEEYCEKVWCTD---------KKRKKLKM--- 744
SEMA3E QSSISQGAKPWYKEFLQLIGYSN---FQRVEEYCEKVWCTD---------RKRKKLKM--- 744
Sema3G GSLASASPKTWYKDILQLTGFAN---LPRVDEYCERVWCRGVGERSGSFRGKGKQAK--- 749
SEMA3G GGLASTPPKAWYKDILQLIGFAN---LPRVDEYCERVWCRGTTECSGCFRSRSRGKQ--- 749
Sema3C WAGSVRALPFHPKDILGAFSHSE---MQLINQYCKDTRQQQ---------QLGEEPQK--- 724
SEMA3C WASSVRALPFHPKDIMGAFSHSE---MQMINQYCKDTRQQH---------QQGDESQK--- 724
Sema3F PPPGTGPPTPPYQELAQLLAQPE---VGLIHQYCQGYWRHV---------PPRPREAP--- 730
SEMA3F FKHVVTRVQLHVLGRDAVHAALF---PPLSMSAPPPPGAGP---------PTPPYQEL--- 730

Sema3A SQGSSNKWKHMQESKKGRNRRTHEFERAPRSV------------------------- 772
SEMA3A PGNSNKWKHLQENKKGRNRRTHEFERAPRSV-------------------------- 771
Sema3D --GSPKWKHMQEMKKKRNRRHHRDLDELQRSVAT----------------------- 777
SEMA3D --GGPKWKHMQEMKKKRNRRHHRDLDELPRAVAT----------------------- 777
Sema3B --GRNRRMHVSELRAERGPRSAAHW-------------------------------- 749
SEMA3B --GRNRRTHAPEPRAERGPRSATHW-------------------------------- 749
Sema3E --SPSKWKYANPQEKRLRSKAEHFRLPRHTLLS------------------------ 775
SEMA3E --SPSKWKYANPQEKKLRSKPEHYRLPRHTLDS------------------------ 775
Sema3G --GKSWAGLELGKKMKSRVLAEHNRTPREVEAT------------------------ 780
SEMA3G --ARGKSWAGLELGKKMKSRVHAEHNRTPREVEAT---------------------- 782
Sema3C --MRGDYGKLKALINSRKSRNRRNQLPES---------------------------- 751
SEMA3C --MRGDYGKLKALINSRKSRNRRNQLPES---------------------------- 751
Sema3F --GALRPPELQDQKKPRNRRHHPPDT------------------------------- 754
SEMA3F --AQLLAQPEVGLIHQYCQGYWRHVPPSPREAPGAPRSPEPQDQKKPRNRRHHPPDT 785
```

Figure 3 (cont. 5).

B

```
SEMA3A --------------MGWLTRIVCLFWGVLLTARANYQNGKNNVPRLKLSYKEMLESNNVIT 47
SEMA3B --------------MGRAG-AAAVIPGLALLWAVGLGSAAPSPPRLRLSFQELQAWHGLQT 46
SEMA3D MNANKDERLKARSQDFHLFPALMMLSMTMLFLPVTGTLKQNIPRLKLTYKDLLLSNSCIP 60
SEMA3C ----------------MAFRTICVLVGVFICSICVKGSSQPQ-ARVYLTFDELRETKTSEY 44
                             :: .: :       .    . .*: *::.::    :

SEMA3A FNGLANSSSYHTFLLDEERSRLYVGAKDHIFSFDLVNI-KDFQKIVWPVSYTRRDECKWA 106
SEMA3B FS-LERTCCYQALLVDEERGRLFVGAENHVASLNLDNISKRAKKLAWPAPVEWREECNWA 105
SEMA3D FLGSSEGLDFQTLLLDEERGRLLLGAKDHIFLLSLVDLNKNFKKIYWPAAKERVELCKLA 120
SEMA3C FSLSHHPLDYRILLMDEDQDRIYVGSKDHILSLNINNISQEALSVFWPASTIKVEECKMA 104
       *    .    :: :*:**::.*: :*:::*:  :.: :: :   .: **..    : *: *

SEMA3A GKDILKECANFIKVLKAYNQTHLYACGTGAFHPICTYIEIGHHPEDNIFKLENSHFENGR 166
SEMA3B GKDIGTECMNFVKLLHAYNRTHLLACGTGAFHPTCAFVEVGHRAEEPVLRLDPGRIEDGK 165
SEMA3D GKDANTECANFIRVLQPYNKTHIYVCGTGAFHPICGYIDLGVYKEDIIFKLDTHNLESGR 180
SEMA3C GKDPTHGCGNFVRVIQTFNRTHLYVCGSGAFSPVCTYLNRGRRSEDQVFMIDS-KCESGK 163
       ***    * **::::::.:*:**: .**:*** * *  ::: *   *: :: ::  . *.*:

SEMA3A GKSPYDPKLLTASLLIDGELYSGTAADFMGRDFAIFRTLG---HHHPIRTEQHDSRWLND 223
SEMA3B GKSPYDPRHRAASVLVGEELYSGVAADLMGRDFTIFRSLG---QRPSLRTEPHDSRWLNE 222
SEMA3D LKCPFDPQQPFASVMTDEYLYSGTASDFLGKDTAFTRSLGPTHDHHYIRTDISEHYWLNG 240
SEMA3C GRCSFNPNVNTVSVMINEELFSGMYIDFMGTDAAIFRSLT---KRNAVRTDQHNSKWLSE 220
         :..::*.   .*:: .   *:**   *::* * :: *:*     .:  :**:  :  **.

SEMA3A PKFISAHLISESDNPEDDKVYFFFRENAIDGEHS-GKATHARIGQICKNDFGGHRSLVNK 282
SEMA3B PKFVKVFWIPESENPDDDKIYFFFRETAVEAAPALGRLSVSRVGQICRNDVGGQRSLVNK 282
SEMA3D AKFIGTFFIPDTYNPDDDKIYFFFRESSQEGSTS-DKTILSRVGRVCKNDVGGQRSLINK 299
SEMA3C PMFVDAHVIPDGTDPNDAKVYFFFKEKLTDNNRS-TKQIHSMIARICPNDTGGLRSLVNK 279
       . *: .. *.:   :*:* *:****:*.   :    :   :    : :.::* ** ** ***:**

SEMA3A WTTFLKARLICSVPGPNGIDTHFDELQDVFLMNFKDPKNPVVYGVFTTSSNIFKGSAVCM 342
SEMA3B WTTFLKARLVCSVPGVEG-DTHFDQLQDVFLLSSRDHRTPLLYAVFSTSSSIFQGSAVCV 341
SEMA3D WTTFLKARLICSIPGSDGADTYFDELQDIYLLPTRDERNPVVYGVFTTTSSIFKGSAVCV 359
SEMA3C WTTFLKARLVCSVTDEDGPETHFDELEDVFLLETDNPRTTLVYGIFTTSSSVFKGSAVCV 339
       *********:**:..  :*  :*:**:*:*::*:     :  :..::*.:*:*:*.:*:*****:

SEMA3A YSMSDVRRVFLGPYAHRDGPNYQWVPYQGRVPYPRPGTCPSKTFG-GFDSTKDLPDDVIT 401
SEMA3B YSMNDVRRAFLGPFAHKEGPMHQWVSYQGRVPYPRPGMCPSKTFG-TFSSTKDFPDDVIQ 400
SEMA3D YSMADIRAVFNGPYAHKESADHRWVQYDGRIPYPRPGTCPSKTYDPLIKSTRDFPDDVIS 419
SEMA3C YHLSDIQTVFNGPFAHKEGPNHQLISYQGRIPYPRPGTCPGGAFTPNMRTTKEFPDDVVT 399
       * : *:: .* **:**::.. :: : *:**:****** **. ::     : :*::****:

SEMA3A FARSHPAMYNPVFPMNNRPIVIKTDVNYQFTQIVVDRVDAEDGQYDVMFIGTDVGTVLKV 461
SEMA3B FARNHPLMYNSVLPTGGRPLFLQVGANYTFTQIAADRVAAADGHYDVLFIGTDVGTVLKV 460
SEMA3D FIKRHSVMYKSVYPVAGGPTFKRINVDYRLTQIVVDHVIAEDGQYDVMFLGTDIGTVLKV 479
SEMA3C FIRNHPLMYNSIYPIHKRPLIVRIGTDYKYTKIAVDRVNAADGRYHVLFLGTDRGTVQKV 459
       * : *. **:.: *     *  . :  ..:*  *:*..*:* * **:*.*:*:*** *** **

SEMA3A VSIPKETWYDLEEVLLEEMTVFREPTAISAMELSTKQQQLYIGSTAGVAQLPLHRCDIYG 521
SEMA3B ISVPKGSRPSAEGLLLEELHVFEDSAAVTSMQISSKRHQLYVASRSAVAQIALHRCAAHG 520
SEMA3D VSISKEKWN-MEEVVLEELQIFKHSSIILNMELSLKQQQLYIGSRDGLVQLSLHRCDTYG 538
SEMA3C VVLP-TNNSVSGELILEELEVFKNHAPITTMKISSKKQQLYVSSNEGVSQVSLHRCHIYG 518
       : :.  .      ::***: :*.. : :   *::* *::***:.*   .: *:.****   :*
```

Figure 3 (cont. 6).

```
SEMA3A KACAECCLARDPYCAWDGSACSRYFPTAKRRTRRQDIRNGDPLTHCSDLHHDNHHGHSPE 581
SEMA3B RVCTECCLARDPYCAWDGVACTRFQPSAKRRFRRQDVRNGDPSTLCS----GDSSRPALL 576
SEMA3D KACADCCLARDPYCAWDGNACSRYAPTSKRRARRQDVKYGDPITQCWD-IEDSISHETAD 597
SEMA3C TACADCCLARDPYCAWDGHSCSRFYPTGKRRSRRQDVRHGNPLTQCRG--FNLKAYRNAA 576
        .*::*************  :*:*: *:.*** ****:: *:* * *     .

SEMA3A ERIIYGVENSSTFLECSPKSQRALVYWQFQRRNEERKEEIRVDDHIIRTDQGLLLRSLQQ 641
SEMA3B EHKVFGVEGSSAFLECEPRSLQARVEWTFQRAGVTAHTQVLAEERTERTARGLLLRRLRR 636
SEMA3D EKVIFGIEFNSTFLECIPKSQQATIKWYIQRSGDEHREELKPDERIIKTEYGLLIRSLQK 657
SEMA3C EIVQYGVKNNTTFLECAPKSPQASIKWLLQK-DKDRRKEVKLNERIIATSQGLLIRSVQG 635
       *   :*:: .::**** *:* :* : * :*: .    : ::  :::    *   ***:* ::

SEMA3A KDSGNYLCHAVEHGFIQTLLKVTLEVIDTEHLEELLHKDDDGDGSKTKEMSNSMTPSQKV 701
SEMA3B RDSGVYLCAAVEQGFTQPLRRLSLHVLSATQAERLAR---------AEEAAPAAPPGPKL 687
SEMA3D KDSGMYYCKAQEHTFIHTIVKLTLNVIENEQMENTQR-------AEHEEGKVKDLLAESRL 711
SEMA3C SDQGLYHCIATENSFKQTIAKINFKVLDSEMVAVVTD-------KWSPWTWASSVRALPF 688
        *.* * * * *: * :.: ::.:.*:.                               .

SEMA3A WYRDFMQLINHPNLNTMDEFCEQVWKRDRKQRRQRPGHTPGNSNKWKHLQENKKGRNRRT 761
SEMA3B WYRDFLQLVEPGGGGSAN---------SLRMCRPQPALQS------LPLESRRKGRNRRT 732
SEMA3D RYKDYIQILSSPN-FSLDQYCEQMWHREKRRQRNKGGPKW------KHMQEMKKKRNRRH 764
SEMA3C HPKDIMGAFSHSEMQMINQYCK-----DTRQQHQQGDESQKMRGDYGKLKALINSRKSRN 743
         :* :  ..        :          . :  : :              ::    : *: *

SEMA3A HE----FERAPRSV--- 771
SEMA3B HAPEPRAERGPRSATHW 749
SEMA3D HR---DLDELPRAVAT- 777
SEMA3C RR-----NQLPES---- 751
       :      :. *.:
```

C

SEMA3A: 527-539
SEMA3B: 526-538
SEMA3D: 544-556
SEMA3C: 524-536

SEMA3A KACAECCLARDPYCAWDGSACSRYFPTAKRRTRRQDIRNGDPLTHCSDLHHDNHHGHSPE 581
SEMA3B RVCTECCLARDPYCAWDGVACTRFQPSAKRRFRRQDVRNGDPSTLCS----GDSSRPALL 576
SEMA3D KACADCCLARDPYCAWDGNACSRYAPTSKRRARRQDVKYGDPITQCWD-IEDSISHETAD 597
SEMA3C TACADCCLARDPYCAWDGHSCSRFYPTGKRRSRRQDVRHGNPLTQCRG--FNLKAYRNAA 576

Figure 4:
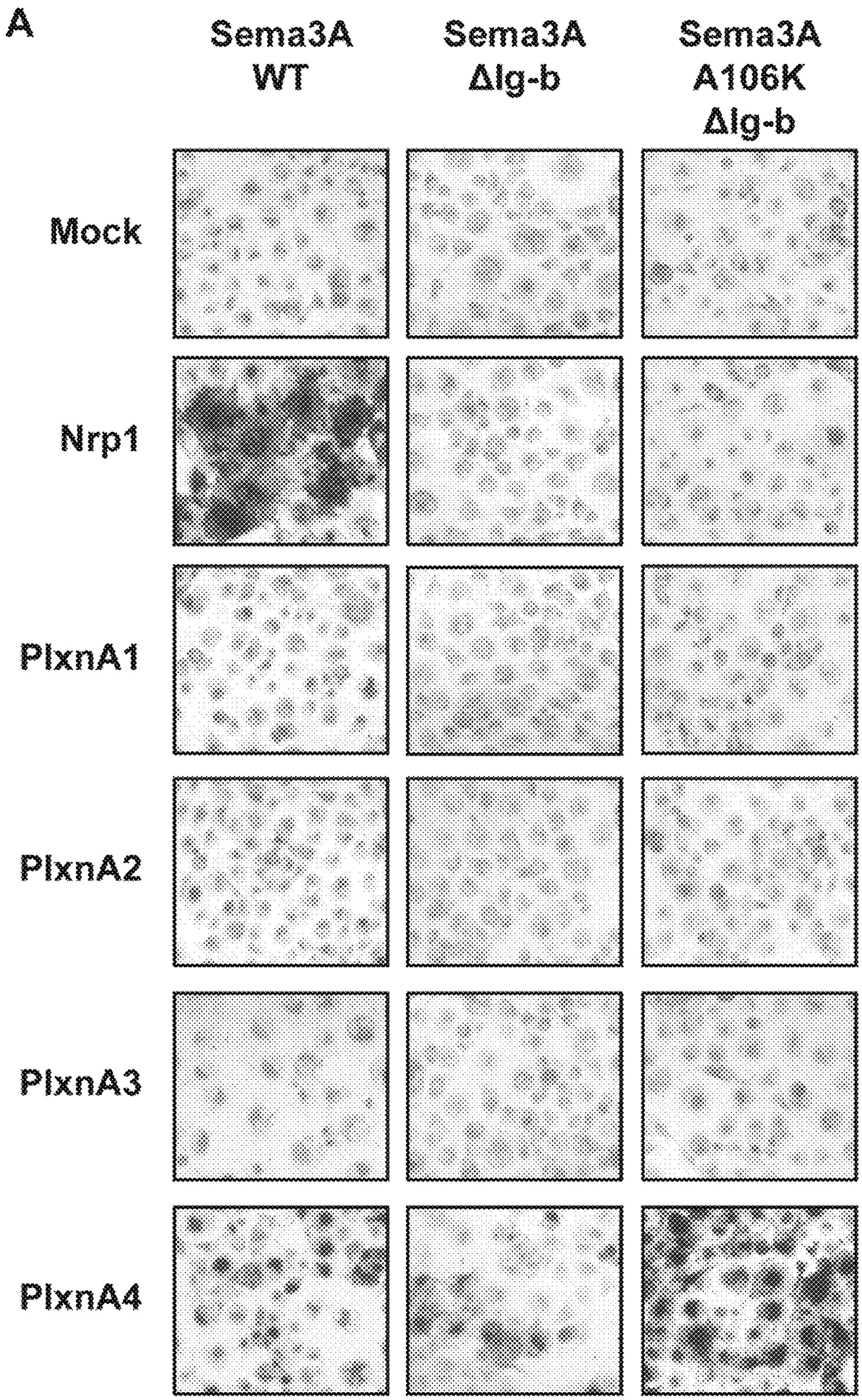

Figure 4 (cont. 1).
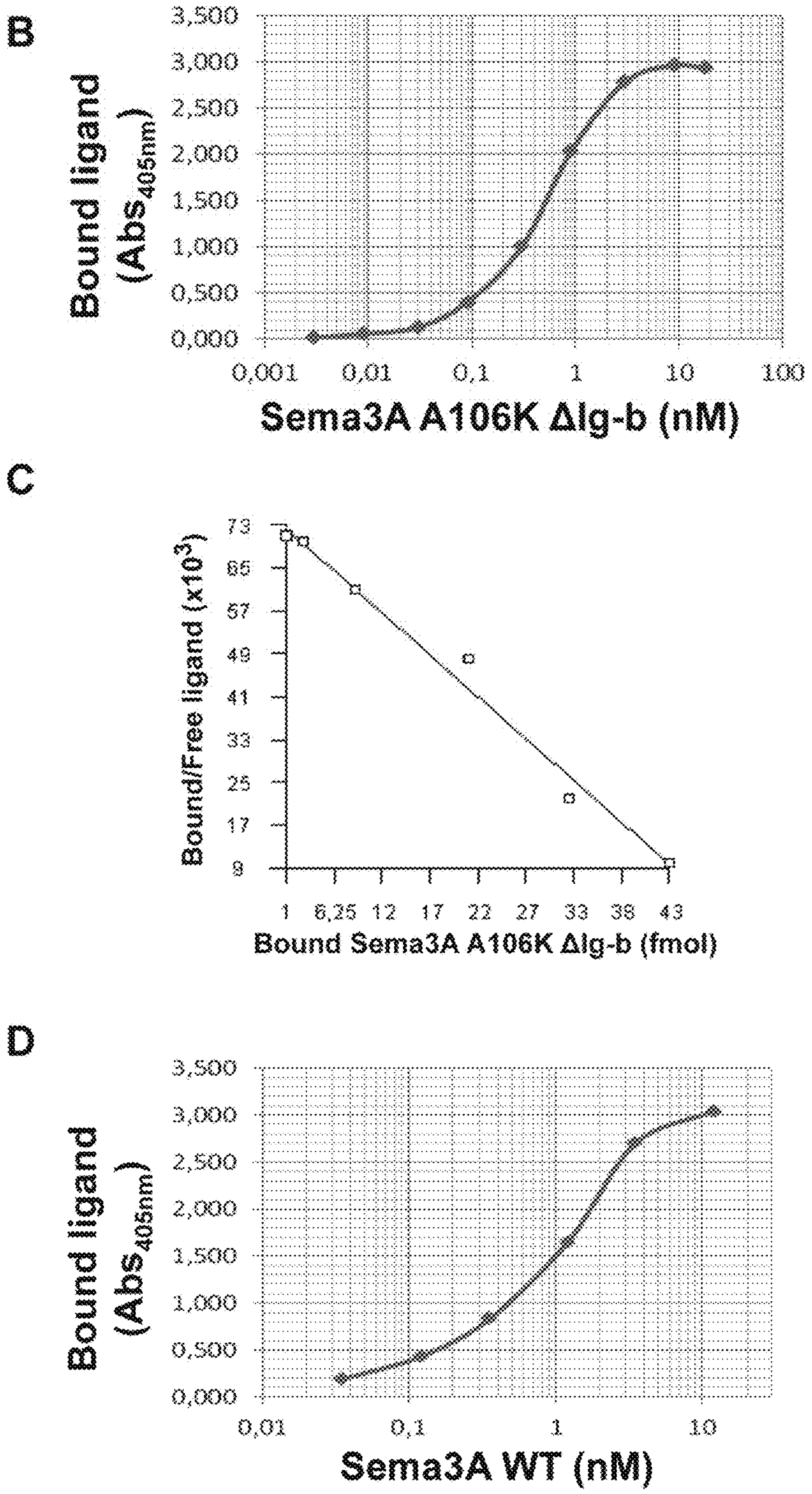

Figure 4 (cont. 2).
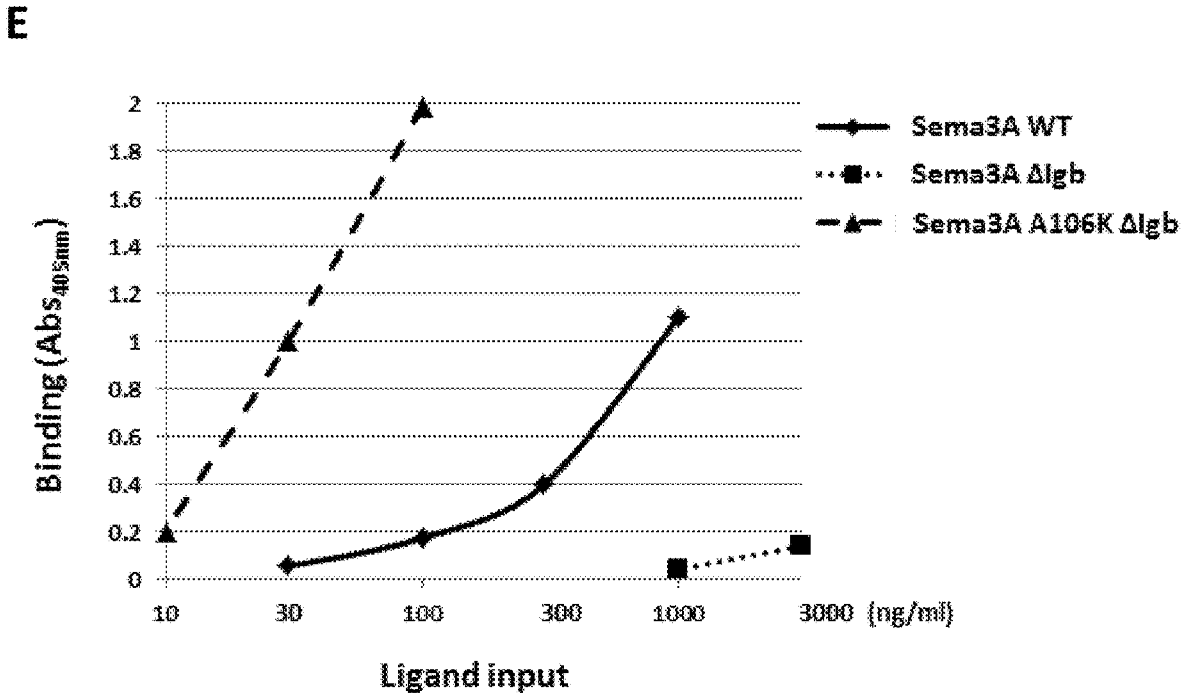
*Estimated affinity*:
Sema3A A106K ΔIgb: Kd ≈ 0.7 nM
Sema3A WT: Kd ≈ 7 nM
Sema3A ΔIgb: Kd ≈ 200 nM Figure 4 (cont. 3).
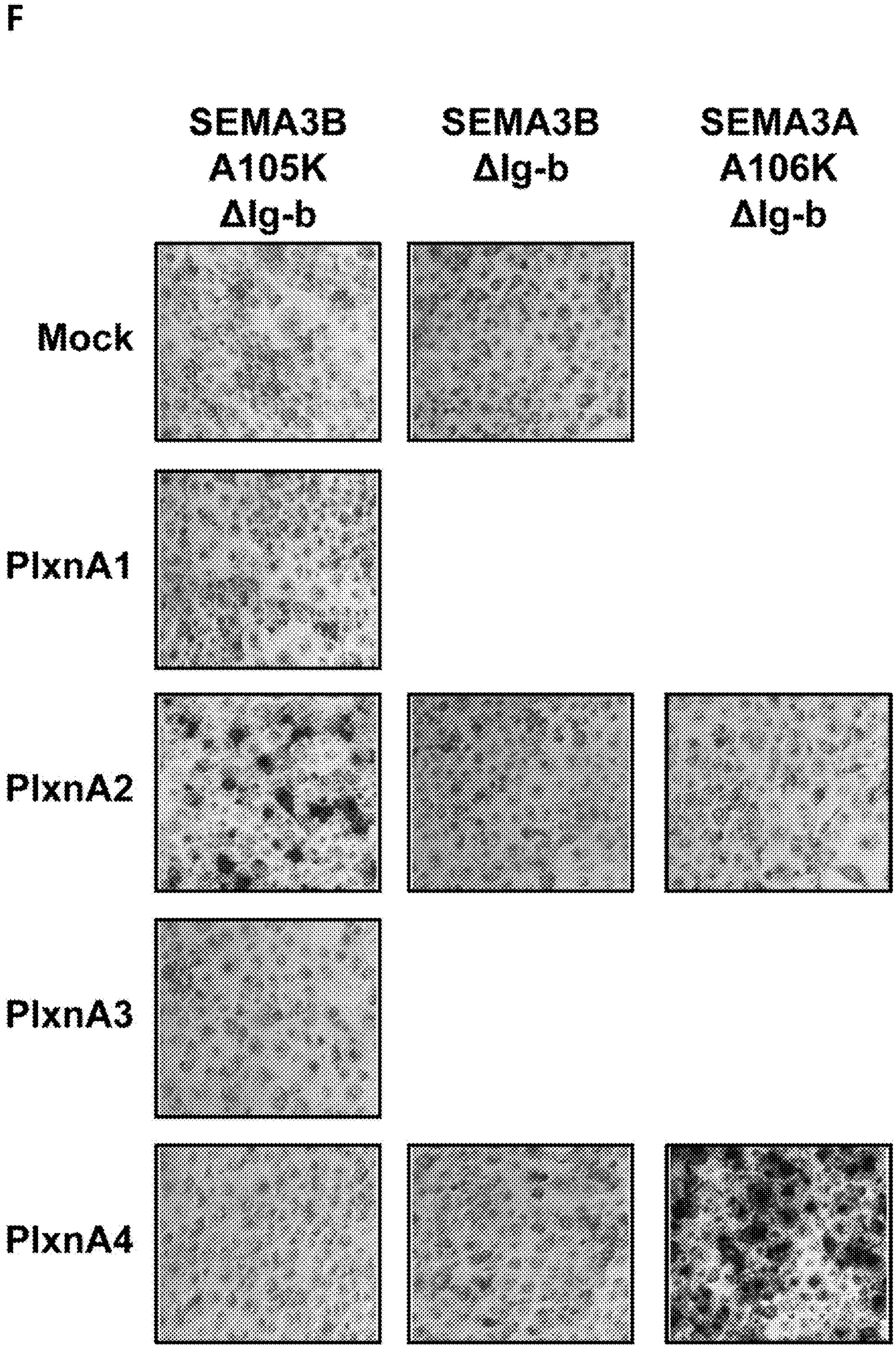

A

Figure 6:
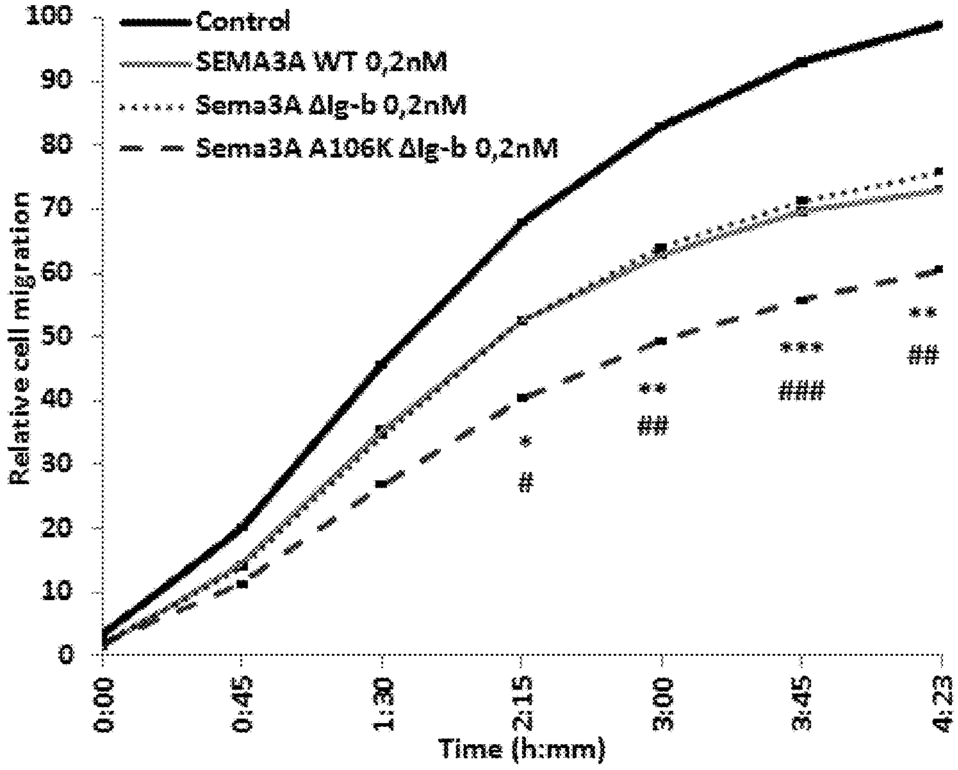

Figure 6 (cont. 1).
B
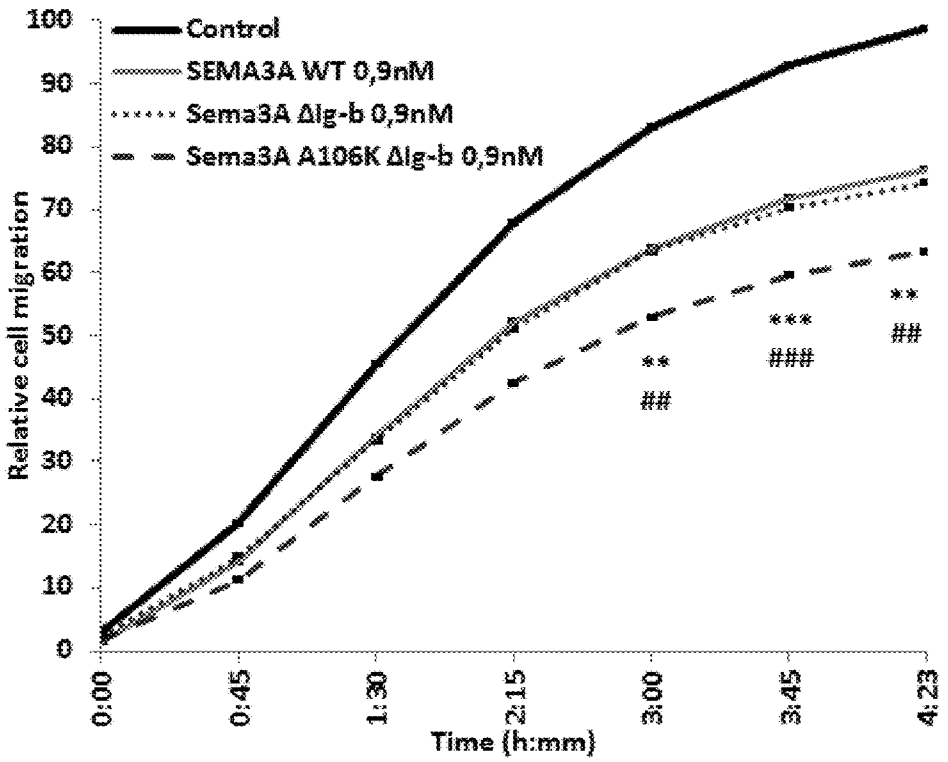

Figure 6 (cont. 2).
C
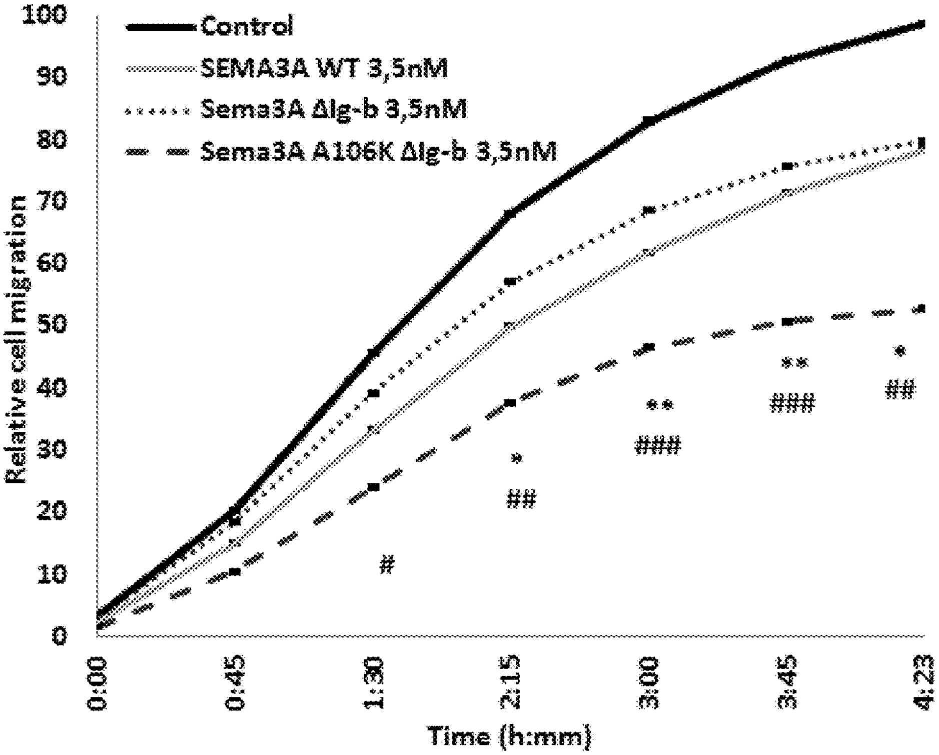

Figure 6 (cont. 3).
D
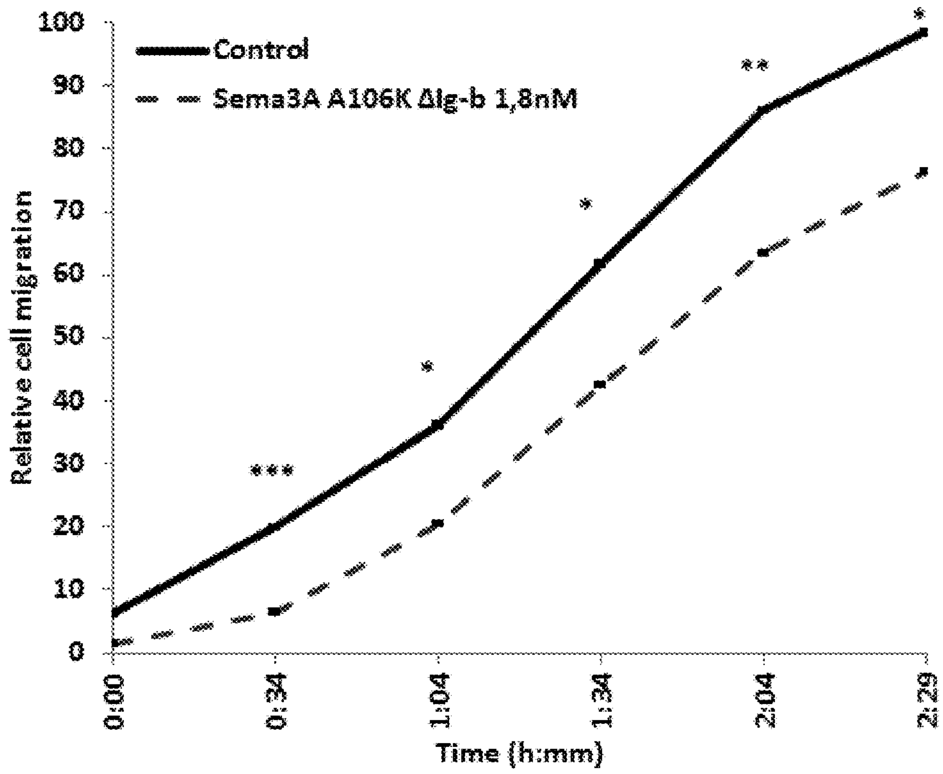

Figure 6 (cont. 4).
E
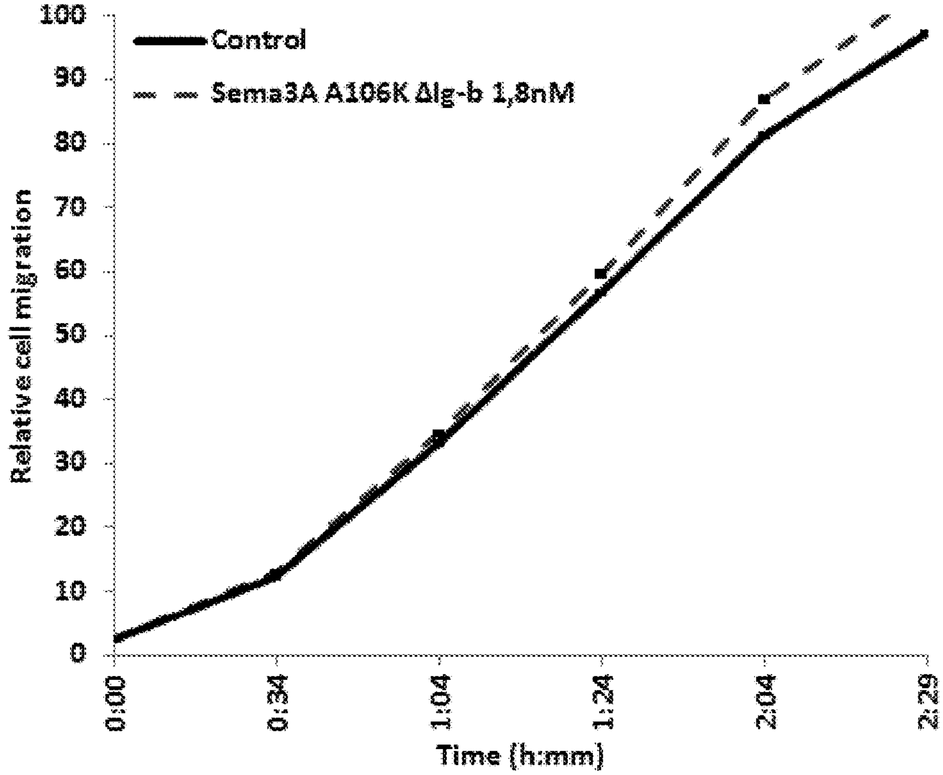

A

Figure 7:
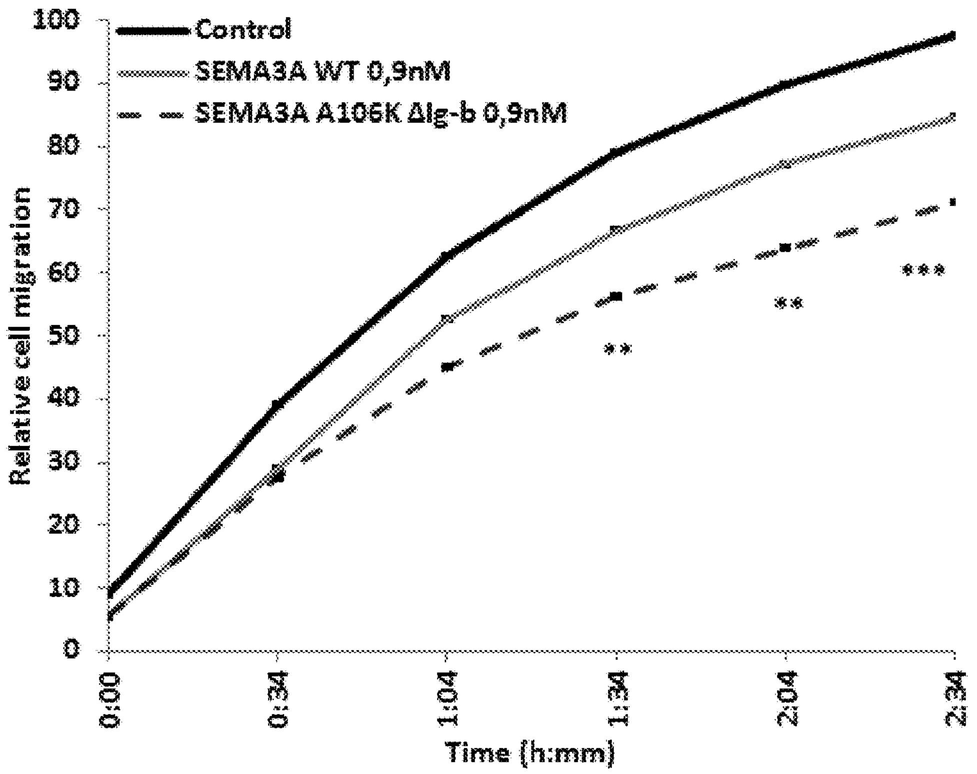

Figure 7 (cont. 1).
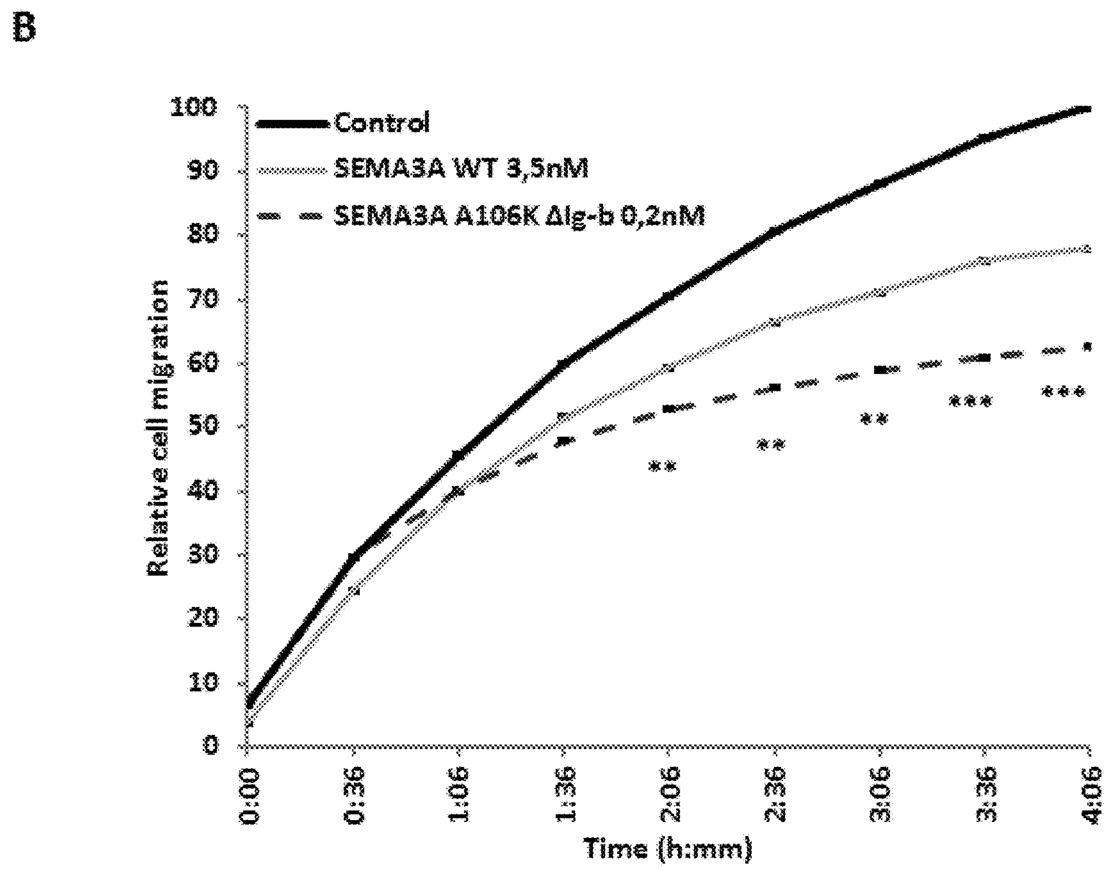

Figure 11.
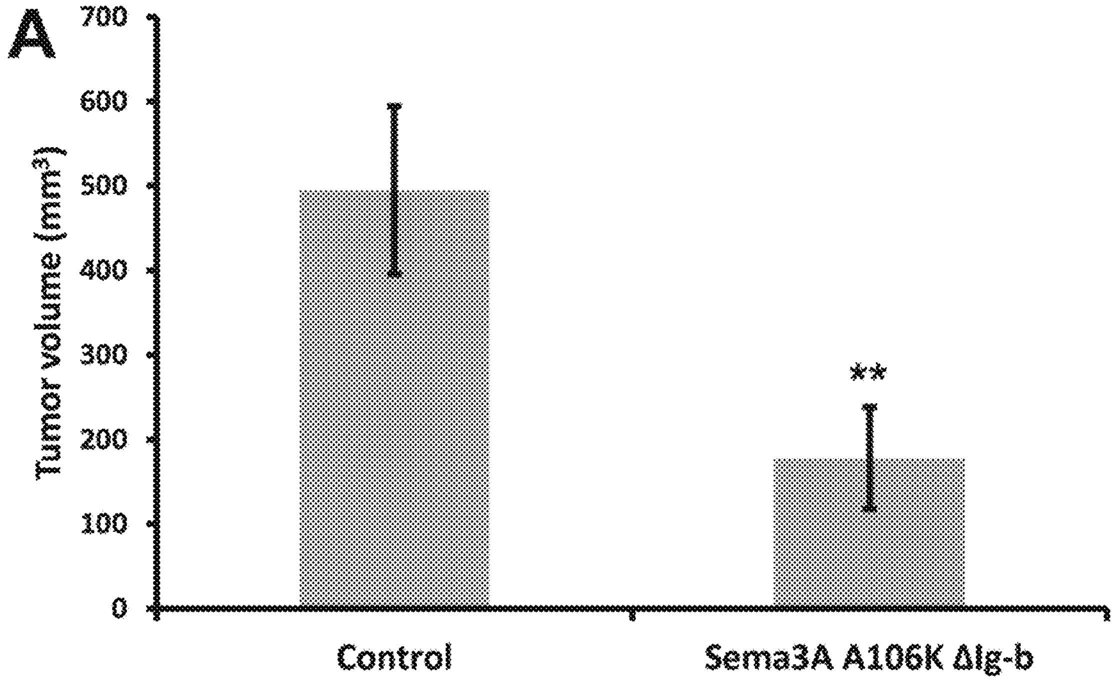
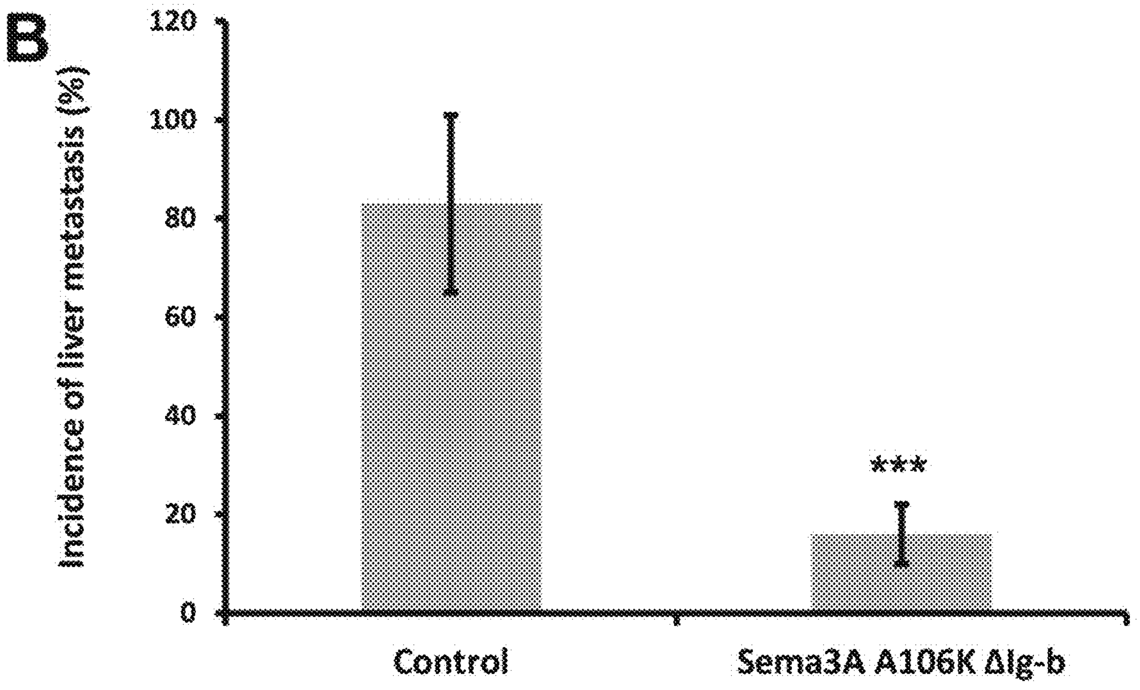

Figure 11. (cont. 1)
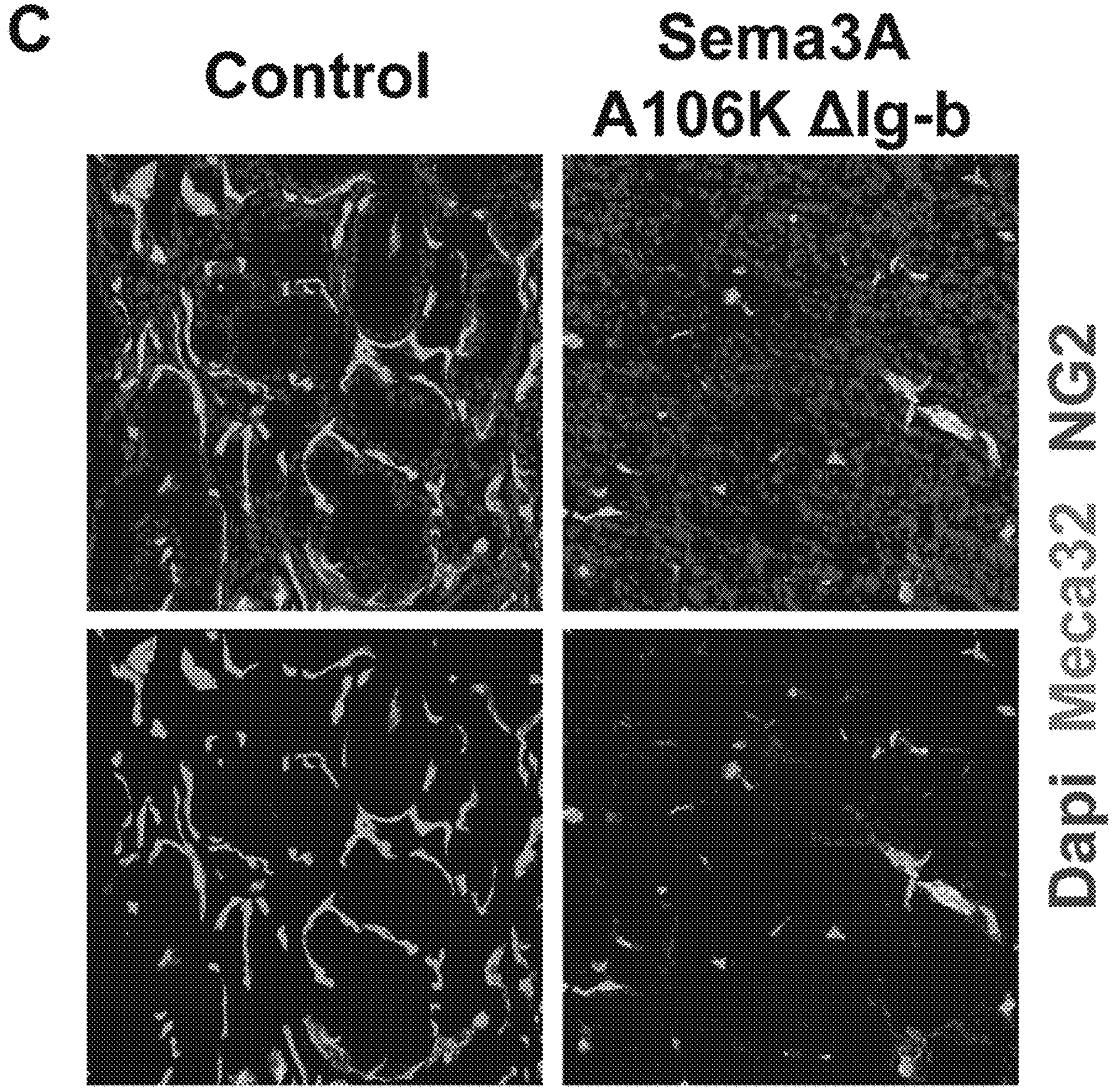

A

Figure 13:
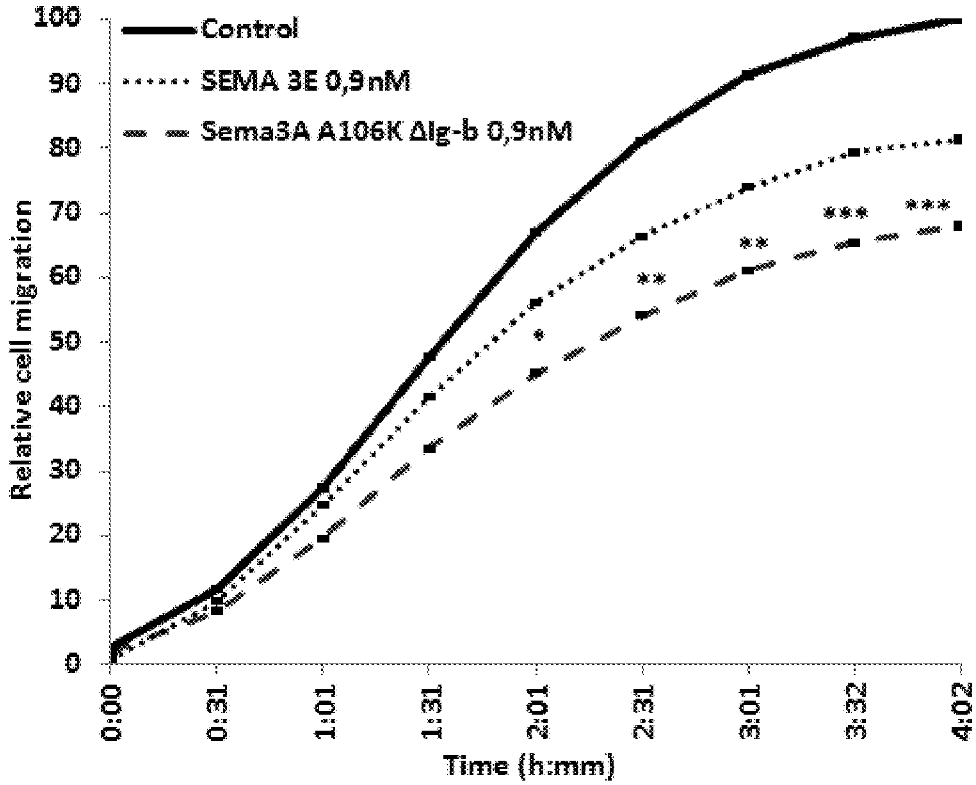

Figure 13. (cont. 1)
B
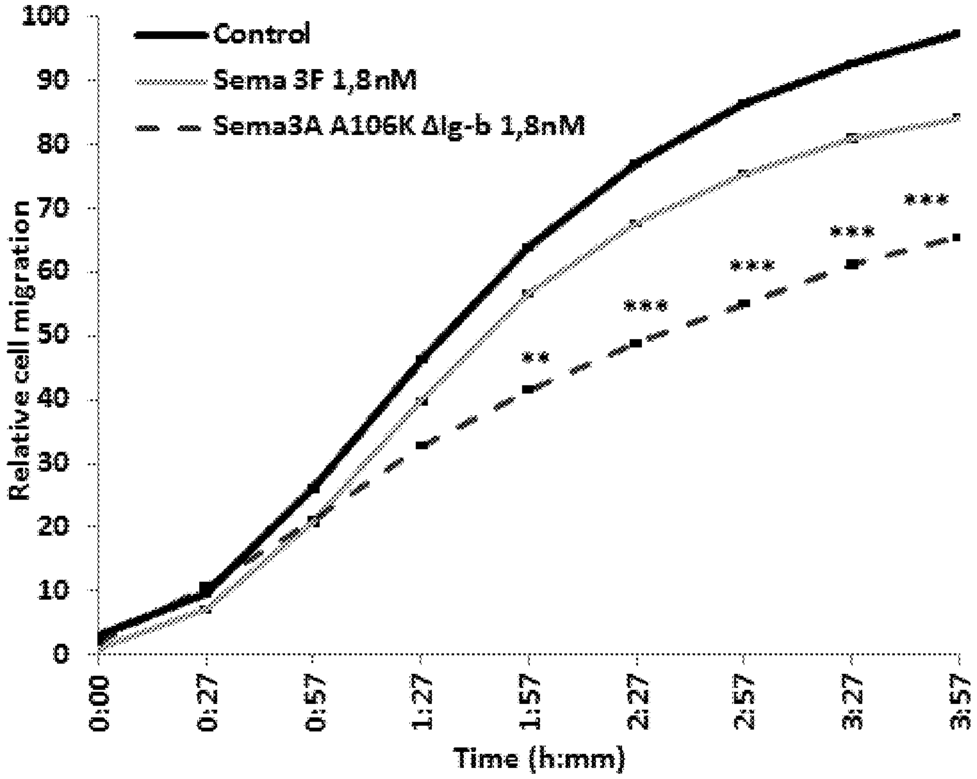

NON-NATURAL SEMAPHORINS 3 AND THEIR MEDICAL USE

CROSS-REFERENCE TO RELATED APPLICATIONS

This application is a § 371 National Stage Application of PCT/EP2016/053750 filed on Feb. 23, 2016, which claims priority to EP 15156195.8 filed on Feb. 23, 2015, which are both incorporated by reference in their entirety.

SEQUENCE LISTING

The instant application contains a Sequence Listing which has been submitted in ASCII format via EFS-Web and is hereby incorporated by reference in its entirety. Said ASCII copy, created on May 27, 2020, and is named "REPLACEMENT_SEQUENCE_LISTING_SEA-01-US_Sequence_Listing_May_2020" and is 464 KB in size.

The present invention relates to non-naturally occurring, mutated Semaphorin 3 molecules. Particularly, the invention relates to the mutated Semaphorin 3 or the functional fragment thereof that exhibit improved properties and pharmacologic effects, e.g., in the treatment of angiogenic disease and cancer. In addition, the present invention relates to nucleic acid molecules encoding such polypeptides, and vectors and hosts comprising such nucleic acids. The invention further relates to methods for producing the polypeptides of the invention, and to methods of using them in the treatment of disease, in particular in the medical intervention of angiogenic diseases, tumors and/or cancer.

Cancer development, progression, and metastatization crucially depend on angiogenesis, i.e. the formation of new blood vessels. Yet, due to abnormalities, such as tortuosity, leakiness due to weak cell-to-cell contacts among vascular endothelial cells (ECs) that upholster their walls, and lack of ensheathing mural pericytes, cancer blood vessels are structurally and functionally aberrant (Goel et al., 2011). As a result, vascular permeability is generally elevated in cancer tissues, proteins and fluids accumulate in the extravascular compartment in which interstitial pressure significantly rises, finally impairing the delivery of anti-cancer drugs (Goel et al., 2011). In addition, chronic oxygen shortage up-regulates hepatocyte growth factor/Met tyrosine kinase signaling (Michieli, 2009), which, coupled to the abnormal vascular permeability, strongly favors cancer cell intravasation, dissemination through the bloodstream, and metastatization. Normalization of cancer blood vessel architecture and function could result in a sizeable increase in the effectiveness of standard anti-cancer therapy, that instead can be impaired by improper blood vessel pruning associated with standard anti-angiogenic treatments (Van der Veldt et al., 2012). Remarkably, mounting evidence indicates how the most effective benefits of the vascular normalizing therapy result from the relief in cancers of different hypoxia-driven phenomena, such as a significant increase of cancer stem cells (Conley et al., 2012), the induction of cancer cell de-differentiation (Michieli, 2009), and the stimulation of cancer invasion and metastatization (Michieli, 2009; Sennino and McDonald, 2012). Thus, to attain the ability of converting aberrant cancer blood vessels in a quasi-normal vascular network, molecules need to be identified that support physiological vascular morphogenesis and are, therefore, of medical use in the treatment, e.g., of disorders wherein aberrant vascular morphogenesis occurs and/or wherein normal vascular morphogenesis is perturbed, like in (solid) cancers.

Semaphorin 3A (also known as Sema3A in mice and SEMA3A in human) is a physiological vascular normalizing molecule. Prior art studies identified molecules that could in principle be pharmacologically exploited for therapies aimed at normalizing the cancer vasculature/abnormal vascular genesis in cancer (Goel et al., 2011). Inhibition of pro-angiogenic factors, such as vascular endothelial growth factor (VEGF), may normalize the cancer vasculature. Yet, a major obstacle by this kind of clinical intervention is represented by the fact that these pro-angiogenic factors display a limited temporal efficacy (Goel et al., 2011). Furthermore, vascular networks are under the simultaneous and balanced control of pro-angiogenic and anti-angiogenic factors, the function of both of which is altered in cancer tissues (Maione et al., 2012; Maione et al., 2009).

During embryonic vascular development, ECs generate autocrine chemorepulsive signals of secreted class 3 Semaphorins (also known as Sema3) that, by inhibiting integrins, which are the main class of extracellular matrix (ECM) receptors in multicellular organisms endow the vascular system with the plasticity required for its reshaping (Serini et al., 2003). Different transgenic mouse models of cancer unraveled that during cancer angiogenesis Semaphorin 3A is also expressed in ECs, where it serves as an endogenous inhibitor that is present in pre-malignant lesions, but lost during cancer progression (Maione et al., 2009). Importantly, the lack of Semaphorin 3A in overt cancer lesions clearly correlated with a dramatic increase of integrin activation in ECs (Maione et al., 2009). Reintroducing Semaphorin 3A into cancers by somatic gene transfer restored physiological amounts of active endothelial integrins, finally resulting in reduced blood vessel density, structural and functional vascular normalization, inhibition of cancer growth and metastatization, and significant survival extension (Maione et al., 2012; Maione et al., 2009). Thus, Semaphorin 3A may be a physiological vascular normalizing agent (Serini et al., 2012).

Semaphorin 3A belongs to the Semaphorin (designated as Sema) family whose categorization in seven different classes relies on the similarity of unique domains located at their C-terminus (Tran et al., 2007). Their N-terminus comprise the "sema domain", a seven-blade β-propeller (Gherardi et al., 2004) followed by a Plexin-Semaphorin-integrin (PSI) domain.

Semaphorins are homo-dimeric ligands that signal through Plexins (Kumanogoh and Kikutani, 2013; Tamagnone et al., 1999), a class of sema domain-containing receptors endowed with an extracellular sema domain and a cytosolic GTPase-activating protein (GAP) activity that inhibits R-Ras (Kumanogoh and Kikutani, 2013; Tran et al., 2007) and Rap1 (Bos and Pannekoek, 2012; Wang et al., 2012), two small GTPases known for their ability to promote integrin-mediated cell adhesion to ECM proteins (Kinbara et al., 2003; Shattil et al., 2010). Semaphorin 3A signals through the activation and phosphorylation of extracellular signal-regulated kinases 1 and 2 (ERK 1/2) (Kruger et al., 2005). Sema domain homo-dimers of membrane-associated Semaphorins directly bind with high affinity to the sema domains of Plexins. This triggers Plexin dimerization and activation (Janssen et al., 2010; Nogi et al., 2010). In some Semaphorins, like Semaphorin 3A, the receptor complex is formed by neuropilin 1 (Nrp1) in association with type A Plexins (Plexin A) (Tamagnone et al., 1999) representing the ligand binding and the signal transducing subunits (Kumanogoh and Kikutani, 2013). Consistently, downstream to the sema-PSI and immunoglobulin (Ig)-like domains, Semaphorin 3A and other secreted Semaphorins comprise a C-terminal basic aminoacid stretch. While disulphide bound Ig-like domains may physically stabilize sema domain homo-dimerization, the C-terminal basic stretch is required for Semaphorin 3A high affinity binding of the b1 subdomain in the extracellular moiety of Nrp1 (FIG. 1) (Kumanogoh and Kikutani, 2013).

Semaphorin 3A comprises multiple furin protease recognition motifs that, once cleaved, can result in the release of this C-terminal portion of the molecule. This leads to an impairment of both Semaphorin 3A binding to Nrp1 as well as stabilization of Semaphorin 3A homo-dimers (Adams et al., 1997; Koppel and Raper, 1998; Parker et al., 2010; Parker et al., 2012). Since Semaphorin 3A does not directly bind Plexin with high affinity (Tamagnone et al., 1999) its furin dependent cleavage and lack of Nrp1-binding was found to result in a dramatic loss of activity in some biological settings, in particular neuron growth cone collapse (Koppel and Raper, 1998). Notably, furin proteases are widely present in tissue, which provides a built-in regulatory mechanism for Semaphorin 3A. Yet, these proteases may also lead to a short-lived activity of Semaphorin 3A.

The binding of Semaphorin 3A to Nrp1 is responsible for Semaphorin 3A-induced entry of macrophages into avascular cancer areas fostering cancer progression (Casazza et al., 2013). Therefore, the high affinity interaction of wild type Semaphorin 3A with Nrp1 limits its exploitability as an effective anti-cancer drug and even potentially favors cancer progression.

The technical problem underlying the present invention is the provision of means and methods for an improved therapy of angiogenic disorders, tumorous diseases and/or cancer.

The technical problem is solved by provision of the embodiments provided herein below and as characterized in the appended claims.

The present invention relates to a non-naturally occurring/genetically modified/mutated Semaphorin of class 3, particularly of a non-naturally occurring/genetically modified/mutated Semaphorin selected from the group consisting of Semaphorin 3A, Semaphorin 3B, Semaphorin 3C and Semaphorin 3D, most preferably of a non-naturally occurring/genetically modified/mutated Semaphorin 3A.

Accordingly, the present invention relates to a mutated Semaphorin 3 (or a functional fragment thereof functioning as an inhibitor of angiogenesis or a fusion protein/polypeptide comprising said mutated Semaphorin or said functional fragment) that (a) comprises a hydrophilic amino acid in place of the alanine corresponding to position 106 of the wild type Semaphorin 3A as shown in SEQ ID NO: 2; or (b) comprises a hydrophilic amino acid in place of the alanine at the position which corresponds in other Semaphorin 3 proteins by comparison of homology to position 106 of the wild type Semaphorin 3A as shown in SEQ ID NO: 2; and (c) wherein said Semaphorin 3 is selected from the group of Semaphorin 3A, Semaphorin 3B, Semaphorin 3C and Semaphorin 3D, wherein preferably said Semaphorin 3 is Semaphorin 3A.

Therefore, the present invention in general provides for Semaphorin 3A, 3B, 3C and 3D that are not naturally-occurring and that comprise a hydrophilic amino acid instead of the alanine at position 106 of the exemplified Semaphorin 3A shown in SEQ ID NO: 2.

Herein below corresponding positions for this mutation in other Semaphorin 3 proteins than Semaphorin 3A, namely, Semaphorins 3 B, C and D are exemplified.

Examples of these mutated Semaphorins 3 are Semaphorins comprising said hydrophilic amino acid in place of the alanine corresponding to position 106 of the wild type Semaphorin 3A as shown in SEQ ID NO: 2; said hydrophilic amino acid in place of the alanine corresponding to position 105 of the wild type Semaphorin 3B as shown in SEQ ID NO: 6; said hydrophilic amino acid in place of the alanine corresponding to position 104 of the wild type Semaphorin 3C as shown in SEQ ID NO: 10; or said hydrophilic amino acid in place of the alanine corresponding to position 120 of the wild type Semaphorin 3D as shown in SEQ ID NO: 14.

In other words, the present invention provides for a non-naturally occurring/genetically modified Semaphorin 3A, Semaphorin 3B, Semaphorin 3C and/or Semaphorin 3D, wherein said Semaphorin 3, said functional fragment thereof and/or said fusion protein/polypeptide comprises an amino acid sequence $CX_1X_2A_3GKD$, wherein:

$X_1$ is K or N;

$X_2$ is an amino acid selected from the group of W, M and L; and $A_3$ is said hydrophilic amino acid that replaces said alanine.

The herein provided consensus motif $CX_1X_2A_3GKD$ is identified for the first time in the present invention.

The present invention also relates to a nucleic acid molecule encoding the non-naturally occurring polypeptides of this invention, i.e. the mutated Semaphorin 3 selected form the group consisting of the mutated Semaphorin 3A, the mutated Semaphorin 3B, the mutated Semaphorin 3C and/or the mutated Semaphorin 3D as characterized and described herein. Also provided are nucleic acid molecules that encode the herein defined functional fragments of the non-naturally occurring Semaphorins 3 as well as nucleic acid molecules encoding fusion proteins/polypeptides comprising the inventive non-naturally occurring Semaphorins 3 or said functional fragments. As laid down herein, the functional fragments as well as the fusion polypeptides/proteins of this invention retain the surprisingly high inhibition of angiogenesis and/or are capable of surprisingly high vascular normalization of disease tissues (like in cancer tissue and/or tumors). Accordingly, the present invention provides for nucleic acids molecules that encode the polypeptides of this invention. The polypeptides of the invention are mutated Semaphorins 3 or functional fragments thereof as defined herein. The polypeptides of this invention also comprise fusion proteins that comprise a mutated Semaphorin 3 (or a functional fragment of such a mutated Semaphorin 3 as defined herein). The polypeptides of this invention, in particular the fusion proteins as defined herein, function as an inhibitors of angiogenesis and/or as vascular normalizing agents and wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

In particular, the present invention relates to nucleic acid molecules, wherein the encoded mutated Semaphorin 3 (or said functional fragment thereof or said fusion polypeptide/protein) comprises an amino acid sequence consensus motif $CX_1X_2A_3GKD$, wherein $X_1$ is an amino acid, which is K or N, $X_2$ is an amino acid selected from the group of W, M and L and wherein the alanine ($A_3$) is replaced by said hydrophilic amino acid, in particular lysine, arginine, asparagine, glutamine, serine, threonine, glutamic acid, aspartic acid or histidine, more preferably lysine or arginine, most preferably, lysine.

The herein provided non-naturally occurring/artificial/mutated Semaphorins (or their herein described functional fragments and/or fusion proteins comprising said non-naturally occurring/artificial/mutated Semaphorins or said non-naturally occurring/artificial/mutated functional fragments of said Semaphorins) have high medical potential. As is illustrated in the appended examples, the medical use of the herein provided inventive molecules is a surprising reduction of cancer progression and metastasis in in vivo cancer models. This in vivo effect is surprisingly superior over any effect documented or seen with naturally occurring Semaphorins, such as wild type Semaphorin 3A. This surprising effect is exemplified herein by certain, selected Semaphorins (Semaphorins of the class 3 selected from the group consisting of Semaphorin 3A, Semaphorin 3B, Semaphorin 3C and Semaphorin 3D) comprising an artificial replacement of the (naturally occurring) alanine ($A_3$) by a hydrophilic amino acid within the herein identified consensus motif $CX_1X_2A_3GKD$ of Semaphorin 3 as defined herein. This replacement in said Semaphorins (or in functional fragments thereof that comprise said motif) results in a surprisingly increased affinity to its Plexin receptor as compared to non-modified, naturally occurring wild type version of said Semaphorins (selected from the group consisting of Semaphorin 3A, Semaphorin 3B, Semaphorin 3C and Semaphorin 3D). In other words, the present invention provides for non-naturally occurring, mutated Semaphorins of class 3 and selected from the group consisting of mutated Semaphorin 3A, mutated Semaphorin 3B, mutated Semaphorin 3C and mutated Semaphorin 3D. Accordingly, the present invention provides for non-naturally occurring, mutated Semaphorins of class 3 that are selected from the group consisting of mutated Semaphorin 3A, mutated Semaphorin 3B, mutated Semaphorin 3C and mutated Semaphorin 3D. The herein described mutated Semaphorins 3 (or the functional fragment of these mutated Semaphorins of this invention as well as fusion proteins comprising the herein described mutated, non-naturally occurring Semaphorins or their functional fragments) bind to Plexin receptor with surprisingly high affinity. The increased binding affinity circumvents the need for involvement of the ambivalent Nrp1 protein. Furthermore, the high affinity binding between the mutated Semaphorin 3 (or the herein described functional fragment thereof or the herein described fusion proteins) and the Plexin receptor effectively triggers its downstream pathway leading to a desired vessel normalization and/or physiological, non-diseased angiogenesis. Without being bound by theory, the mutated Semaphorins 3 of this invention (or the functional fragments or the fusion proteins of this invention comprising the same) enable a high affinity binding between its Plexin receptor independent of the Ig-like domain/basic stretch region which comprises multiple furin protease recognition motifs. In certain embodiments, the invention relates to the mutated Semaphorin 3 or the fragment thereof, wherein the Ig-like domain/basic stretch region is deleted. Due to the lack of the protease (furin) cleavage sites as described herein above and as shown in the appended FIG. 2, the retention time of the proteins of the invention can be increased.

As documented in the appended in vitro and in vivo examples herein below, it was surprisingly found that the replacement of the alanine $A_3$ by a hydrophilic amino acid in the consensus motif $CX_1X_2A_3GKD$ of Semaphorin 3 (or functional fragments thereof) as selected from the group consisting of Semaphorin 3A, Semaphorin 3B, Semaphorin 3C and Semaphorin 3D results in increased binding to its Plexin receptor. Thus, the inventive, non-naturally occurring mutated Semaphorins 3 (or the functional fragments thereof or fusion polypeptides/proteins comprising said Semaphorins 3 or their functional fragments) bind with a high affinity to its Plexin receptor independently of Nrp1. It is also documented herein that the replacement of alanine by a hydrophilic amino acid in the consensus motif $CX_1X_2A_3GKD$ of Semaphorin 3 (or in functional fragments of said Semaphorin3 comprising said consensus motif with its mutation/modification) results in a surprisingly increased activation of the Plexin receptors and in a surprisingly increased inhibition of haptotactic migration of human ECs. Plexin receptor binding and activation is a critical step in the control of integrin activation, cell adhesion and migration on ECM proteins. Without being bound by theory, the activation of the Plexin receptors through Semaphorins inactivates integrins and thus impairs the motility of cells within the ECM. Cell migration is crucial for cancer cell progression and metastasis dissemination. Hence, the mutated Semaphorin 3 (and the functional fragments thereof) of this invention can be used to effectively inhibit cancer progression and metastasis. Without being bound by theory, the inventive mutated Semaphorins 3 (and/or the functional fragments thereof and/or fusion proteins/polypeptides comprising said mutated Semaphorins or the herein defined functional fragments) bind with a high affinity to the corresponding Plexin receptor, effectively activate the corresponding downstream pathway and effectively inhibit cell motility. As shown and documented in the examples, the herein defined artificially introduced modification in certain Semaphorins of the class 3 (Semaphorin 3A, Semaphorin 3B, Semaphorin 3C and Semaphorin 3D) lead to surprisingly effective molecules which show even in vivo an increased reduction of cancer progression and/or metastasis. The herein described mutated/non-naturally occurring Semaphorin-like molecules show surprisingly better in vivo and/or in vitro properties when compared to naturally occurring Semaphorins 3. It is documented herein and shown in the appended examples that the replacement of alanine in the consensus motif $CX_1X_2A_3GKD$ of Semaphorins 3 (or in functional fragments thereof or in fusion polypeptides/proteins comprising the herein defined non-naturally occurring Semaphorins 3 or comprising the herein defined functional fragments with said mutated motif) results in an increased reduction of cancer progression and metastasis. The replacement of said alanine ($A_3$) is preferably a hydrophilic amino acid, most preferably a lysine. This resulting reduction of cancer progression and metastasis in the non-naturally occurring mutated Semaphorin 3 is surprisingly superior to the effect seen with conventional or naturally occurring Semaphorins, such as wild type Semaphorin 3A. In particular, in vivo data presented herein proves a surprisingly increased inhibition of cancer growth and metastasis volume. Two mouse models for human cancer prove the beneficial pharmacologic effect.

Accordingly, as documented in the appended examples and as explained herein, the inventive Semaphorins (and/or the functional fragment thereof and/or the fusion polypeptides/proteins described herein) are superior in the therapy of angiogenic disorders and/or tumorous disease compared to conventional or naturally occurring Semaphorins.

Figure 2:
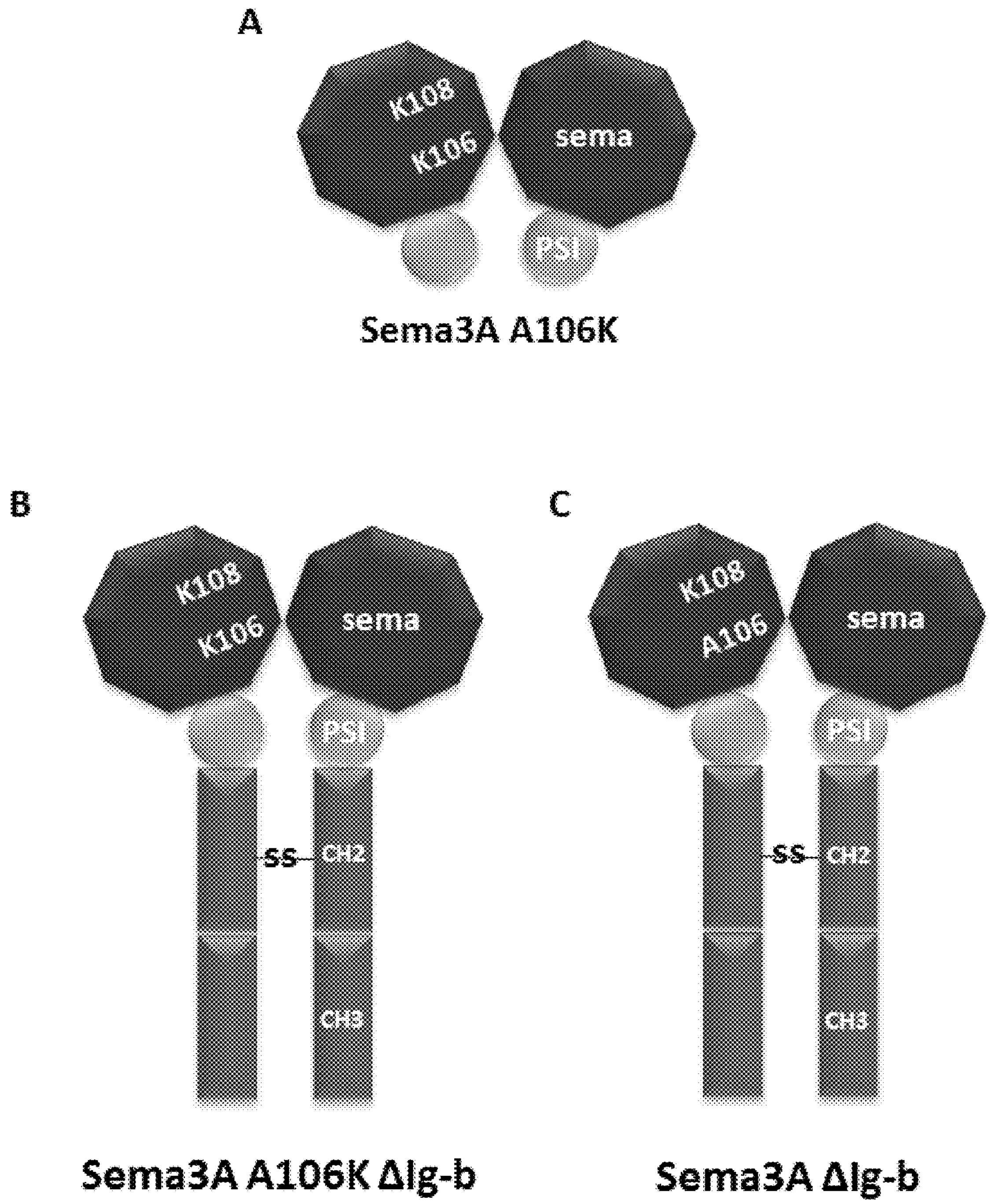
Figure 3:
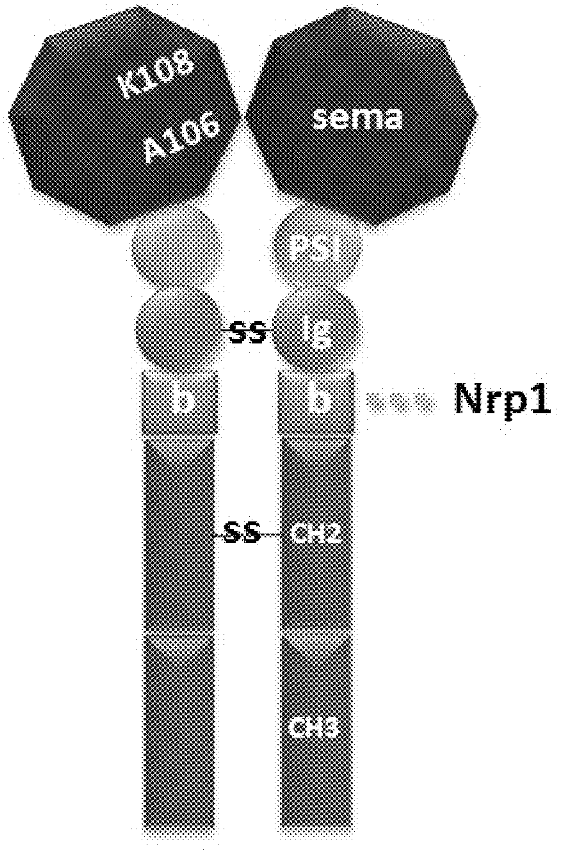

The superior effect of the inventive Semaphorins (or of the functional fragment(s) or fusion polypeptides/proteins comprising the non-naturally occurring Semaphorins of this invention or comprising said functional fragments) is due to the replacement of alanine ($A_3$) by a hydrophilic amino acid in the consensus motif $CX_1X_2A_3GKD$ like e.g., Semaphorin 3A A106K (mutation of the alanine at position 106 to lysine) in the appended examples (e.g. Semaphorin 3A A106K ΔIg-b as shown in SEQ ID NO: 18 or 20); see appended FIG. 3. As is shown in the appended examples, Semaphorin 3 constructs having the same architecture as Semaphorin 3A A106K, with the exception of lacking the point mutation in the conserved motif $CX_1X_2A_3GKD$ (Semaphorin 3A ΔIg-b, e.g. encoding nucleic acid sequences as shown in SEQ ID NO: 43 or 44), see appended FIG. 2, failed to show the beneficial pharmacologic effects. Accordingly, the surprising beneficial effect as documented in the present invention can be attributed to the herein described mutation in the $CX_1X_2A_3GKD$ of mouse and/or human Sema3A, Sema3B, Sema3C and Sema3D. Preferably, the present invention relates to human Semaphorins 3 selected form the group consisting of Sema 3A, Sema 3B, Sema 3C and Sema 3D (or functional fragments of these human Semaphorins comprising the herein defined consensus motif) comprising the herein defined mutation in alanine ($A_3$). Most preferably, the present invention relates to mutated human Sema 3A (or functional fragments of said human Sema 3A) comprising the herein defined motif with the herein described replacement of alanine ($A_3$) in the sequence motif $CX_1X_2A_3GKD$. Said replacement is a replacement with a hydrophilic amino acid, most preferably a replacement with a lysine (K). The mutated alanine ($A_3$) is part of a highly conserved sequence motif $CX_1X_2A_3GKD$ that can be found in mouse and human Sema3A, Sema3B, Sema3C and Sema3D; see appended FIG. 3. Consistently, equal beneficial effects that are shown in the appended examples are envisaged and plausible from a replacement of said alanine by a hydrophilic amino acid (like K) in (human) Sema3B, Sema3C and/or Sema3D.

Human and mouse Sema3E, Sema3G and Sema3F have a naturally occurring hydrophilic amino acid where alanine $A_3$ resides in the consensus sequence $CX_1X_2A_3GK$. Hence, they have a hydrophilic amino acid at the position corresponding to the position 106 of Semaphorin 3A as shown in SEQ ID NO: 2. Both Sema3E and Sema3G comprise a lysine and Sema3F comprise a serine at this position. Yet, Sema 3E and Sema 3F fail to show the inventive properties as demonstrated for the inventive Semaphorins 3 as explained in the following and as documented in the appended examples. The replacement of serine by lysine at the position 107 in Sema3F fails to increase the binding to the Plexin A, B, C, or D receptors. Furthermore, this mutant fails to inhibit EC migration more effectively than its wild type counterpart displaying a serine at the position 107, which is documented herein for the mutated Semaphorin 3 or the functional fragment of this invention, see appended example 2 and FIG. 12. Moreover, Fc-tagged Semaphorin 3E and Semaphorin 3F fail to inhibit EC migration as strong as the exemplary mutated Semaphorin 3A comprising the inventive replacement of alanine by a hydrophilic amino acid; see illustrative FIG. 13. Consequently, the inventive mutated Semaphorins provided herein, namely mutated Semaphorin 3A, mutated Semaphorin 3B, mutated Semaphorin 3C, and mutated Semaphorin 3D are surprisingly superior inhibitors of EC cell motility compared to Semaphorins 3 comprising a naturally occurring hydrophilic amino acid at the position corresponding to position 106 of Semaphorin 3A as given in SEQ ID NO: 2. The demonstrated strong inhibition of cell motility is an indication that the inventive mutated Semaphorin 3 proteins are superior in the therapy of angiogenic disorders and/or tumorous disease compared to naturally-occurring Semaphorins 3 (see also below).

Accordingly, the present invention does not relate to (human) Sema 3E, Sema 3F and/or Sema 3G.

The replacement of alanine ($A_3$) by, e.g., lysine in the consensus motif $CX_1X_2A_3GKD$ in Sema 3A/3B/3C or 3D (or in functional fragments thereof) (like, inter alia, in Sema3A the exchange A106K) results in increased inhibition of cancer growth and metastasis formation in two different transgenic mouse models, i.e., spontaneous pancreatic neuroendocrine cancer (RipTag2) and pancreatic ductal adenocarcinoma (PDAC); see example 2. The PDAC mouse is a model for the frequently and deadly human pancreatic cancer histotype. Most importantly and surprisingly, parenterally delivered Sema3A A106K shows a superior pharmacologic effect in PDAC mice compared to AAV8-wild type Sema3A protein. In detail, Sema3A A106K inhibited cancer growth by 64%, see appended FIG. 11A, liver metastasis incidence by 81%, see appended FIG. 11B and diminished metastasis volume by 78%. The AAV-8-delivered wild type Sema3A only inhibited cancer growth by 52%, see appended FIG. 10A and liver metastasis incidence by 59%. Furthermore, Sema3A A106K reduced vessel area and promoted cancer vessel normalization by enhancing pericyte coverage, increased blood vessel perfusion and inhibited cancer hypoxia in mouse models recapitulating human cancer, see appended FIG. 11C.

Accordingly, mutated/non-naturally occurring Semaphorins of the present invention, like Sema3A A106K exert a superior effect in reducing cancer progression and metastasis dissemination compared to conventional, non-modified Semaphorins.

Furthermore, parenterally administered Sema3A A106K extended the survival of RIP-Tag2 mice similarly to adeno-associated virus-8 (AAV8) delivered full length Sema3A. Sema3A A106K i) induced a 67% reduction of cancer volume; ii) efficiently reduced the cancer blood vessel area by 51%, see appended FIG. 9A; iii) favored the normalization of cancer blood vessels in terms of increased pericyte coverage, see appended FIG. 9B; iv) enhanced perfusion, see appended FIG. 9C and reduced tissue hypoxia, see appended FIG. 9D. Thus, the present invention demonstrates its surprising therapeutic effect, which is independent of Nrp1 binding.

Furthermore, the superior effect of the mutated Semaphorin 3 proteins (and/or the functional fragments thereof and/or the fusion proteins/polypeptides comprising said mutated Semaphorins or the therein defined fragments) is also proven in in vitro experiments, see the appended examples. The replacement of alanine ($A_3$) by a hydrophilic amino acid in the consensus motif $CX_1X_2A_3GKD$ of the Semaphorin 3 or the functional fragment thereof, such as found in the mutated Semaphorin 3A A106K results in a high affinity binding to PlexinA4 compared to wild type Sema3A and Sema3A ΔIg-b, see the appended examples. Furthermore, the mutated Semaphorin 3 or the functional fragment thereof, e.g., Sema3A A106K, shows an increased inhibition of the GTP-loading of Rap1 small GTPase, see appended FIG. 8A and an increased phosphorylation of the ERK 1/2 kinase compared to conventional Semaphorins, see appended FIG. 8B. Hence, the mutated Semaphorin 3 (or a functional fragment thereof or fusion polypeptides/proteins comprising the same) bind to Plexin subunits with an exceptionally high affinity and effectively trigger its downstream pathway leading to cancer vessel normalization compared to conventional Semaphorins, like natural human Sema3A.

Furthermore, Semaphorin 3 proteins control the cell motility via integrins, such as the haptotactic migration of ECs towards ECM proteins. Integrin-mediated cell motility on and towards ECM proteins plays crucial roles in several physiological and pathological settings, such as blood vessel formation (angiogenesis) and cancer cell dissemination throughout the body (metastatization) (Desgrosellier and Cheresh, 2010). Accordingly, the migration of cells in response to the conventional or non-naturally occurring Semaphorins 3 or the functional fragments thereof was analyzed. Surprisingly, the replacement of alanine ($A_3$) by a hydrophilic amino acid in the consensus motif $CX_1X_2A_3$GKD of the Semaphorin 3 or the functional fragment thereof results in an increased inhibition of the directional migration of human umbilical vein endothelial cells (EC) compared to conventional Semaphorins, see appended FIG. 6A-C. Commercial human wild type Semaphorin 3A and mouse Semaphorin 3A ΔIg-b impaired EC motility by only 19-25% (Table 3). Importantly, mutated Semaphorin 3 proteins (and/or the functional fragments thereof and/or the fusion proteins/polypeptides comprising said mutated Semaphorins or the therein defined fragments), such as Sema3A A106K are the most efficient inhibitors of EC motility. In particular, while the maximal (3.5 nM) dose of commercial human SEMA3A WT inhibited EC directional migration by 20%, a 17.5 times lower (0.2 nM) dose of human SEMA3A A106K (e.g., SEQ ID NO: 18) inhibited EC motility by 46% (Table 4).

Accordingly, the mutated Semaphorins 3 of the invention (or the functional fragments thereof and/or the fusion polypeptides/proteins of this invention comprising the mutated, non-naturally occurring Semaphorins or their functional fragments) are superior inhibitors of the motility of cells compared to conventional Semaphorins. The inhibition of cell motility also impairs the metastatic dissemination of cancer cells. Therefore, the inventive, mutated Semaphorins 3 (or the functional fragment thereof and/or the fusion polypeptides/proteins of this invention comprising the mutated, non-naturally occurring Semaphorins or their functional fragments) are superior inhibitors of cancer cell formation and metastatic dissemination compared to conventional Semaphorins.

Accordingly, the experimental data in the appended examples provide for a clear rationale to use the inventive mutated Semaphorins 3 (or functional fragment thereof or fusion proteins/polypeptides comprising the same) in the improved therapy of angiogenic disorders and/or tumorous disease/cancer.

The present invention has, inter alia, the following advantages over conventional antiangiogenic agents: One advantage of the present invention is the fact that the inventive compounds i.e. the mutated Semaphorins/functional fragments thereof/fusion proteins/polypeptides as described herein bind to the Plexin receptors with a high affinity, but nevertheless circumvent the Nrp-1-dependent Semaphorin induced entry of macrophages into avascular tumor areas that foster cancer progression. As a further advantage, the compounds of this invention effectively trigger Plexin receptor signaling. As a further advantageous property, the inventive compounds activate the Plexin receptor independently from Nrp1. Furthermore, the compounds of the invention inhibit EC migration more effectively compared to conventional Semaphorin 3 proteins. The compounds of this invention are not cleaved by proteases resulting in an increased retention time. As a further advantage, the compounds of this invention (proteins as well as nucleic acid molecules encoding the same) can be delivered parenterally. The compounds of the invention are superior in preventing the formation of new blood vessels, thereby stopping or slowing the growth or spread of tumors. The compounds of the invention are superior in reducing the blood vessel area, normalizing cancer blood vessel, enhancing perfusion of cancer blood vessels and/or reducing tissue hypoxia. The compounds of this invention of the invention can be used as a vascular normalizing agent, i.e., the cancer blood vessels are normalized, the perfusion of cancer blood vessels is enhanced and/or tissue hypoxia is reduced. A further advantage of the invention is that the cancer growth is inhibited more effectively. As a further advantageous property, the proteins and/or nucleic acid molecules of this invention reduce metastasis incidence and diminishes metastasis volume. Consequently, the invention has a superior effect in inhibiting cancer progression and metastasis dissemination.

As used herein the term "mutated Semaphorin 3", "genetically modified Semaphorin 3", "non-naturally occurring Semaphorin 3" or "non-natural Semaphorin 3" in accordance with the present invention refers to a mutated form of Semaphorin 3A, Semaphorin 3B, Semaphorin 3C or Semaphorin 3D as defined herein. A mutated Semaphorin 3 differs from a wild type Semaphorin 3 or a functional fragment thereof by at least one mutation that is selected from the group consisting of amino acid substitution(s), addition(s), deletions(s) and duplication(s). In particular, the mutated form of the Semaphorin 3 comprises a replacement of the alanine by a hydrophilic amino acid at the position that by comparison of homology corresponds to position 106 of the wild type Semaphorin 3A as shown in SEQ ID NO: 2. In other words, the alanine ($A_3$) in the consensus motif $CX_1X_2A_3$GKD (also shown in SEQ ID NO: 73) in the Semaphorin 3 proteins is mutated to a hydrophilic amino acid (table 1). Accordingly, the mutated Semaphorin 3A comprises an amino acid sequence, wherein the alanine at the position 106 of the wild type Semaphorin 3A as shown in SEQ ID NO: 2 or 4 is replaced by a hydrophilic amino acid. The mutated Semaphorin 3B comprises an amino acid sequence, wherein the alanine at the position 105 of the wild type Semaphorin 3B as shown in SEQ ID NO: 6 or 8 is replaced by a hydrophilic amino acid. The mutated Semaphorin 3C comprises an amino acid sequence, wherein the alanine at the position 104 of the wild type Semaphorin 3C as shown in SEQ ID NO: 10 or 12 is replaced by a hydrophilic amino acid. The mutated Semaphorin 3D comprises an amino acid sequence, wherein the alanine at the position 120 of the wild type Semaphorin 3D as shown in SEQ ID NO: 14 or 16 is replaced by a hydrophilic amino acid. Said hydrophilic amino acid can be, e.g., a lysine, arginine, asparagine, glutamine, serine, threonine, glutamic acid, aspartic acid or histidine, more preferably a lysine or arginine, most preferably a lysine. It is also envisaged herein that the hydrophilic amino acid can be a non-proteinogenic or a non-standard α-amino acid (such as, e.g., ornithine and citrulline). It is shown herein above and in the appended examples that the replacement of the alanine by a hydrophilic amino acid results in an increased inhibition of cancer growth and metastasis formation. In general, the mutation to a hydrophilic amino acid in the Semaphorins 3 results in a high binding affinity to the Plexin receptors. The increased binding of the mutated Semaphorin 3 results in an increased activation of the Plexin receptors and their downstream signaling. Plexin receptors are crucial in the control of integrin activation, cell adhesion and migration on or towards ECM proteins, which are key aspects in cancer cell progression and metastasis. Accordingly, the mutated Semaphorin 3 of the invention can be employed as inhibitor of angiogenesis and as a vascular normalizing agent.

TABLE 1

The mutated Semaphorin 3 comprises an amino acid sequence $CX_1X_2A_3GKD$, wherein the alanine $A_3$ is replaced by a hydrophilic amino acid. The amino acids that correspond to $X_1$ and $X_2$ are indicated. The positions of the amino acids of the wild type Semaphorin 3A, Semaphorin 3B, Semaphorin 3C and Semaphorin 3D as shown in SEQ ID NOs: 2, 4, 6, 8, 10, 12, 14 and 16 are indicated.

| C | $X_1$ | $X_2$ | $A_3$ | G | K | D | Semaphorin 3 and SEQ ID NO: |
|---|---|---|---|---|---|---|---|
| C | K | W | A | G | K | D | Human Semaphorin |
| 103 | 104 | 105 | 106 | 107 | 108 | 109 | 3A SEQ ID NO: 2 |
| C | N | W | A | G | K | D | Human Semaphorin |
| 102 | 103 | 104 | 105 | 106 | 107 | 108 | 3B SEQ ID NO: 6 |
| C | K | M | A | G | K | D | Human Semaphorin |
| 101 | 102 | 103 | 104 | 105 | 106 | 107 | 3C SEQ ID NO: 10 |
| C | K | L | A | G | K | D | Human Semaphorin |
| 117 | 118 | 119 | 120 | 121 | 122 | 123 | 3D SEQ ID NO: 14 |
| C | K | W | A | G | K | D | Mouse Semaphorin |
| 103 | 104 | 105 | 106 | 107 | 108 | 109 | 3A SEQ ID NO: 4 |
| C | N | W | A | G | K | D | Mouse Semaphorin |
| 102 | 103 | 104 | 105 | 106 | 107 | 108 | 3B SEQ ID NO: 8 |
| C | K | M | A | G | K | D | Mouse Semaphorin |
| 101 | 102 | 103 | 104 | 105 | 106 | 107 | 3C SEQ ID NO: 12 |
| C | K | L | A | G | K | D | Mouse Semaphorin |
| 117 | 118 | 119 | 120 | 121 | 122 | 123 | 3D SEQ ID NO: 16 |

In particular, the invention relates to mutated Semaphorin 3 proteins which mean that the mutated Semaphorins are selected from the group of Semaphorin 3A, Semaphorin 3B, Semaphorin 3C and Semaphorin 3D. Likewise, if reference is made to mutated Semaphorin 3 or mutated Semaphorin 3 proteins in the context of the present invention, this is intended to refer to mutated Semaphorin 3A, mutated Semaphorin 3B, mutated Semaphorin 3C and mutated Semaphorin 3D. In most preferred aspects of the invention the mutated Semaphorin 3 is mutated Semaphorin 3A. It is understood herein that the mutated Semaphorin 3 is not Semaphorin 3E, Semaphorin 3F or Semaphorin 3G. Furthermore, it is herein understood that mutated Semaphorin 3 according to the invention does not include Semaphorin 3B isoform $X_2$, e.g. from Equus przewalskii, or Semaphorin 3B isoform $X_6$, e.g., from Panthera tigris altaica. Such Semaphorins do not comprise the amino acid sequence $CX_1X_2A_3GKD$, wherein the alanine $A_3$ is replaced by a hydrophilic amino acid. Furthermore, the mutated Semaphorin 3 according to the invention functions as an inhibitor of angiogenesis and/or as a vascular normalizing agent.

The terms “Semaphorin 3A”, “Semaphorin 3B”, “Semaphorin 3C”, and “Semaphorin 3D”, “Sema3A”, “Sema3B”, “Sema3C” and “Sema3D”, SEMA3A", “SEMA3B”, “SEMA3C” and “SEMA3D” as used herein refer primarily to a protein. “Sema3A”, “Sema3B”, “Sema3C” and “Sema3D” as defined herein and to be used in accordance with the present invention are preferably human “Sema3A”, “Sema3B”, “Sema3C” and “Sema3D”. “Semaphorin 3A”, “Semaphorin 3B”, “Semaphorin 3C”, and “Semaphorin 3D” as defined herein and to be used in accordance with the present invention are preferably human “Sema3A”, “Sema3B”, “Sema3C” and “Sema3D”. “SEMA3A”, “SEMA3B”, “SEMA3C” and “SEMA3D” as defined herein and to be used in accordance with the present invention are preferably human “Sema3A”, “Sema3B”, “Sema3C” and “Sema3D”.

Sema3A A106K or Semaphorin 3A A106K is also designated herein and in the appended examples as Fc-tagged Sema3A A106K ΔIg-b.

The amino acid sequences and encoding nucleotide sequences of wild-type Semaphorin 3 are well known in the art. Nucleic acid sequences can be retrieved in public databases like NCBI using the following accession numbers (the following sequences have been retrieved from the NCBI database):

*Homo sapiens* SEMA3A, >gi|100913215|ref|NM_006080.2| corresponding to SEQ ID NO: 1; *Mus musculus* Sema3A, >gi|340523098|ref|NM_009152.41) corresponding to SEQ ID NO: 3; *Homo sapiens* SEMA3B, >gi|586798179|ref|NM_001290060.1| corresponding to SEQ ID NO: 5; *Mus musculus* Sema3B, >gi|615276319|ref|NM_001042779.2| corresponding to SEQ ID NO: 7; *Homo sapiens* SEMA3C>gi|335057525|ref|NM_006379.3| corresponding to SEQ ID NO: 9; *Mus musculus* Sema3C, >gi|118130842|ref|NM_013657.5| corresponding to SEQ ID NO: 11; *Homo sapiens* SEMA3D, >gi|41406085|ref|NM_152754.21 corresponding to SEQ ID NO: 13; or *Mus musculus* Sema3D>gi|282847343|ref|NM_028882.4| corresponding to SEQ ID NO: 15.

SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15 encode wild type full length Semaphorin 3 proteins.

Corresponding amino acid sequences can be retrieved in public databases like NCBI. The following sequences have been retrieved from the NCBI database.

*Homo sapiens* SEMA3A, |ref|NP_006071.1| corresponding to SEQ ID NO: 2; *Mus musculus* Sema3A, |ref|NP_033178.2| corresponding to SEQ ID NO: 4; *Homo sapiens* SEMA3B, |ref|NP_001276989.1| corresponding to SEQ ID NO: 6; *Mus musculus* Sema3B, |ref|NP_001036244.1| corresponding to SEQ ID NO: 8; *Homo sapiens* SEMA3C, |ref|NP_006370.1| corresponding to SEQ ID NO: 10; *Mus musculus* Sema3C, |ref|NP_038685.3| corresponding to SEQ ID NO: 12; *Homo sapiens* SEMA3D, c|ref|NP_689967.2| corresponding to SEQ ID NO: 14; or *Mus musculus* Sema3D, |ref|NP_083158.3| corresponding to SEQ ID NO: 16.

SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16 comprise amino acid sequences of wild type full length Semaphorin 3 proteins.

Amino acid sequences of Semaphorin 3 of the invention can also be obtained from Uniprot, e.g. for mouse and human Semaphorin 3A, Semaphorin 3B, Semaphorin 3C and Semaphorin 3D.

In one embodiment, the invention relates to a nucleic acid molecule encoding a polypeptide comprising an amino acid sequence of a mutated Semaphorin 3, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

In a further embodiment, the invention relates to a mutated Semaphorin 3, wherein said mutated Semaphorin 3 comprises an amino acid sequence, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

In a further embodiment, the invention relates to a nucleic acid molecule encoding a polypeptide comprising an amino acid sequence of a mutated Semaphorin 3 or a fragment thereof, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

In a further embodiment, the invention relates to the mutated Semaphorin 3 or fragment thereof, wherein said mutated Semaphorin 3 or said fragment thereof comprises an amino acid sequence, wherein the alanine corresponding to position 106 of the wild type Semaphorin 3A as shown in SEQ ID NO: 2 or the alanine at the position which corresponds in other Semaphorins of the Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

As explained above, a mutated Semaphorin 3 or a functional fragment thereof comprises a hydrophilic amino acid in place of the alanine corresponding to position 106 of the wild type Semaphorin 3A as shown in SEQ ID NO: 2 or comprises a hydrophilic amino acid in place of the alanine at the position which corresponds in other Semaphorin 3 proteins by comparison of homology to position 106 of the wild type Semaphorin 3A as shown in SEQ ID NO: 2 and wherein said Semaphorin 3 is selected from the group of Semaphorin 3A, Semaphorin 3B, Semaphorin 3C and Semaphorin 3D.

As explained above and as illustrated in Table 1, the alanine corresponding to position 106 of the wild type Semaphorin 3A as shown in SEQ ID NO: 2 refers to the specific alanine of Semaphorin 3A at position 106 of SEQ ID NO: 2 or the specific alanine amino acid residue in a known wild-type sequence of Semaphorin 3A, 3B, 3C or 3D, preferably Semaphorin 3A, corresponding to said specific alanine of Semaphorin 3A at position 106 of SEQ ID NO: 2. It also means a specific amino acid residue in a known wild-type sequence e.g. Semaphorin 3A, 3B, 3C or 3D that is homologous to said specific alanine at position 106 of SEQ ID NO: 2, at position 105 of SEQ ID NO: 6, at position 104 of SEQ ID NO: 10 or at position 120 of SEQ ID NO: 14. Exemplary homologous amino acids residues can be alanine, valine, isoleucine, leucine, methionine, phenylalanine, tyrosine or tryptophan. Most preferably, the specific amino acid residue is alanine.

The corresponding amino acid residue in other wild-type sequences at the corresponding position can be selected preferably by standard homology screenings or PCR-mediated screening techniques for related sequences as described below. The alanine or the corresponding alanine is replaced by or changed to a hydrophilic amino acid in the mutated Semaphorin 3 according to the invention.

As mentioned and explained herein, the alanine at the position which corresponds in other Semaphorin 3 proteins by comparison of homology to position 106 of the wild type Semaphorin 3A as shown in SEQ ID NO: 2 refers to the specific alanine amino acid residue in a known wild-type sequence of Semaphorin 3B, 3C or 3D that corresponds to said specific alanine of said Semaphorin 3A at position 106 given in SEQ ID NO: 2. The corresponding alanine is replaced by a hydrophilic amino acid in mutated Semaphorin 3B, 3C or 3D. In other words, the alanine corresponding to position 105 of the wild type Semaphorin 3B as shown in SEQ ID NO: 6, the alanine corresponding to position 104 of the wild type Semaphorin 3C as shown in SEQ ID NO: 10; or the alanine corresponding to position 120 of the wild type Semaphorin 3D as shown in SEQ ID NO: 14 is replaced by the hydrophilic amino acid.

The alanine corresponding to position 105 of the wild type Semaphorin 3B as shown in SEQ ID NO: 6 refers to the specific alanine of Semaphorin 3B at position 105 of SEQ ID NO: 6 or the specific alanine amino acid residue in a known wild-type sequence of Semaphorin 3B corresponding to said specific alanine of Semaphorin 3B at position 105 of SEQ ID NO: 6. The alanine corresponding to position 104 of the wild type Semaphorin 3C as shown in SEQ ID NO: 10 refers to the specific alanine of Semaphorin 3C at position 104 of SEQ ID NO: 10 or the specific alanine amino acid residue in a known wild-type sequence of Semaphorin 3C corresponding to said specific alanine of Semaphorin 3C at position 104 of SEQ ID NO: 10. The alanine corresponding to position 120 of the wild type Semaphorin 3D as shown in SEQ ID NO: 14 refers to the specific alanine of Semaphorin 3D at position 120 of SEQ ID NO: 14 or the specific alanine amino acid residue in a known wild-type sequence of Semaphorin 3D corresponding to said specific alanine of Semaphorin 3D at position 120 of SEQ ID NO: 14. As mentioned and detailed herein, the corresponding amino acid residue at the corresponding position can be selected preferably by comparison of homology. Homology among polypeptides or nucleotide sequences is typically inferred from their sequence similarity. Alignments of multiple sequences can herein be used to indicate which regions or specific amino acids of each sequence are homologous. The amino acid sequences of Semaphorin 3A, B, C and D can be used as (a) reference sequences. The homology exist preferably over a stretch of amino acids, e.g. 10, more preferably 20, more preferably 30, more preferably 50, or more preferably 100 amino acid residues, or most preferably the homology exist over the whole amino acid stretch. An illustrative amino acid sequence alignment of exemplary amino acid stretches of Semaphorin 3 proteins is shown in Table 1. The corresponding alanine is most preferably $A_3$ in the amino acid sequence $CX_1X_2A_3GKD$ comprised in the mutated Semaphorin 3. Thus, the inventive mutation can also be identified with the help of the amino acid sequence $CX_1X_2A_3GKD$.

As described herein, the invention relates to the mutated Semaphorin 3 or the functional fragment thereof that comprises a hydrophilic amino acid in place of the alanine corresponding to position 106 of the wild type Semaphorin 3A as shown in SEQ ID NO: 2 or comprises a hydrophilic amino acid in place of the alanine at the position which corresponds in other Semaphorin 3 proteins by comparison of homology to position 106 of the wild type Semaphorin 3A as shown in SEQ ID NO: 2 and wherein said Semaphorin 3 is selected from the group of Semaphorin 3A, Semaphorin 3B, Semaphorin 3C and Semaphorin 3D.

In other words, the mutated Semaphorin 3 or the functional fragment thereof comprises a hydrophilic amino acid in place of the alanine corresponding to position 106 of the wild type Semaphorin 3A as shown in SEQ ID NO: 2 or comprises a hydrophilic amino acid in place of the alanine at the position which corresponds in Semaphorin 3 B, C or D by comparison of homology to position 106 of the wild type Semaphorin 3A as shown in SEQ ID NO: 2; and wherein said Semaphorin 3 is selected from the group of Semaphorin 3A, Semaphorin 3B, Semaphorin 3C and Semaphorin 3D. In other words, the other Semaphorins are Semaphorin 3B, 3C and 3D.

In other words, the mutated Semaphorin 3 or the functional fragment thereof wherein said Semaphorin 3 is selected from the group consisting of Semaphorin 3A, Semaphorin 3B, Semaphorin 3C and Semaphorin 3D and wherein said mutated Semaphorin 3 comprises a hydrophilic amino acid in place of the alanine corresponding to position 106 of the wild type Semaphorin 3A as shown in SEQ ID NO: 2;

a hydrophilic amino acid in place of the alanine corresponding to position 105 of the wild type Semaphorin 3B as shown in SEQ ID NO: 6;

a hydrophilic amino acid in place of the alanine corresponding to position 104 of the wild type Semaphorin 3C as shown in SEQ ID NO: 10; or a hydrophilic amino acid in place of the alanine corresponding to position 120 of the wild type Semaphorin 3D as shown in SEQ ID NO: 14.

In most preferred embodiments of the invention, the mutated Semaphorin 3 or the functional fragment thereof comprises a hydrophilic amino acid in place of the alanine corresponding to position 106 of the wild type Semaphorin 3A as shown in SEQ ID NO: 2, and wherein said Semaphorin 3 is Semaphorin 3A. In other words, the present invention relates to a mutated Semaphorin 3 A or a functional fragment thereof, wherein said mutated Semaphorin 3A comprises a hydrophilic amino acid in place of the alanine corresponding to position 106 of the wild type Semaphorin 3A as shown in SEQ ID NO: 2.

As outlined above and as demonstrated in the appended examples, the replacement of the alanine ($A_3$) in the amino acid sequence $CX_1X_2A_3GKD$ renders Semaphorin 3A, B, C or D polypeptides to strong angiogenesis inhibitors. Therefore, in the amino acid sequence $CX_1X_2A_3GKD$ comprised in the mutated Semaphorins, the alanine ($A_3$) is mutated to the hydrophilic amino acid, i.e., the present invention relates to a mutated Semaphorin 3 or a functional fragment thereof wherein said mutated Semaphorin 3 is selected from the group consisting of Semaphorin 3A, Semaphorin 3B, Semaphorin 3C and Semaphorin 3D and wherein said mutated Semaphorin 3 or said functional fragment thereof comprises a hydrophilic amino acid in place of the alanine corresponding to position 106 of the wild type Semaphorin 3A as shown in SEQ ID NO: 2;

a hydrophilic amino acid in place of the alanine corresponding to position 105 of the wild type Semaphorin 3B as shown in SEQ ID NO: 6;

a hydrophilic amino acid in place of the alanine corresponding to position 104 of the wild type Semaphorin 3C as shown in SEQ ID NO: 10; or a hydrophilic amino acid in place of the alanine corresponding to position 120 of the wild type Semaphorin 3D as shown in SEQ ID NO: 14; and wherein said mutated Semaphorin 3 or said functional fragment thereof comprises an amino acid sequence $CX_1X_2A_3GKD$, wherein $X_1$ is an amino acid, which is K or N, $X_2$ is an amino acid selected from the group of W, M and L, and wherein the alanine ($A_3$) is replaced by said hydrophilic amino acid.

In other words, the present invention relates to a mutated Semaphorin 3 or a functional fragment thereof wherein said mutated Semaphorin 3 is selected from the group consisting of Semaphorin 3A, Semaphorin 3B, Semaphorin 3C, and Semaphorin 3D and wherein said mutated Semaphorin 3 or said functional fragment thereof comprises an amino acid sequence $CX_1X_2A_3GKD$, wherein $X_1$ is an amino acid, which is K or N, $X_2$ is an amino acid selected from the group of W, M and L, and wherein the alanine ($A_3$) is replaced by a hydrophilic amino acid; and wherein said mutated Semaphorin 3 or said functional fragment thereof comprises said hydrophilic amino acid in place of the alanine corresponding to position 106 of the wild type Semaphorin 3A as shown in SEQ ID NO: 2;

said hydrophilic amino acid in place of the alanine corresponding to position 105 of the wild type Semaphorin 3B as shown in SEQ ID NO: 6;

said hydrophilic amino acid in place of the alanine corresponding to position 104 of the wild type Semaphorin 3C as shown in SEQ ID NO: 10; or said hydrophilic amino acid in place of the alanine corresponding to position 120 of the wild type Semaphorin 3D as shown in SEQ ID NO: 14.

The following description includes all different embodiments. The following relates to the herein provided non-naturally occurring/artificial/mutated Semaphorin 3 proteins or their herein described functional fragments or the herein described functional sema domains and/or fusion proteins/polypeptides comprising said non-naturally occurring/artificial/mutated Semaphorin 3 proteins or said non-naturally occurring/artificial/mutated functional fragments or said functional sema domains of said Semaphorin 3 proteins that have primarily the activity to function as an inhibitor of angiogenesis. In other words the compounds of the invention, i.e., the mutated Semaphorin 3 proteins/functional fragments thereof/functional sema domains/fusion proteins/polypeptides as described herein have primarily the activity to function as an inhibitor of angiogenesis. In general, an inhibitor of angiogenesis prevents the formation of new blood vessels, thereby stopping or slowing the growth or spread of tumors. As shown herein, the compounds of the invention reduce the blood vessel area, normalize cancer blood vessels, i.e., increase the pericyte coverage, enhance the perfusion of cancer blood vessels and/or reduce the tissue hypoxia. Accordingly, the amino acid sequences and/or nucleic sequences of the present invention relate to a direct and/or an indirect inhibitor of angiogenesis. In general, inhibitors of angiogenesis also bind to receptors on the surface of cells, such as ECs and/or to other proteins in the downstream signaling pathways, blocking their activities. As shown in the appended examples the mutated Semaphorin 3, the functional fragment thereof, the functional sema domain, the fusion protein or the polypeptide of the invention binds to its Plexin receptor, e.g. type A Plexins such as Plexin A4 or Plexin A2, with a high affinity, i.e. displaying dissociation constant $K_D$ in the very-low-nanomolar/sub-nanomolar range. Accordingly, the amino acid sequences and/or nucleic sequences of the present invention inhibit directly and/or indirectly angiogenesis. In particular, the mutated Semaphorin 3, the functional fragment thereof or the fusion protein/polypeptide of the invention has an affinity to its Plexin receptor with a dissociation constant $K_D$ lower than 6 nM. In preferred aspects, the mutated Semaphorin 3, the functional fragment thereof or the fusion protein/polypeptide of the invention has an affinity to its Plexin receptor with a dissociation constant $K_D$ lower than 4 nM. In even more preferred aspects, the mutated Semaphorin 3, the functional fragment thereof or the fusion protein/polypeptide of the invention has an affinity to its Plexin receptor with a dissociation constant $K_D$ lower than 2 nM. In most preferred aspects, the mutated Semaphorin 3, the functional fragment thereof or the fusion protein/polypeptide of the invention has an affinity to its Plexin receptor with a dissociation constant $K_D$ lower than 1 nM. The dissociation constant $K_D$ can be measured by standard methods known in the art, such as an assay that is evident from the appended examples. It is documented in the appended examples, that the mutated Semaphorin 3A binds to Plexin A4 receptor, with a high affinity, i.e. displaying dissociation constant $K_D$ in the very-low-nanomolar/sub-nanomolar range. Furthermore, it is documented that the mutated Semaphorin 3B binds to Plexin A2 receptor, with a high affinity, i.e. displaying dissociation constant $K_D$ in the very-low-nanomolar/sub-nanomolar range.

Further, the mutated Semaphorin 3, the functional fragment thereof, the functional sema domain or the fusion protein/polypeptide of the invention inhibits Rap1 GTP loading (by 65%). Accordingly, the amino acid sequences and/or nucleic sequences of the present invention mediate downstream signaling pathways relevant in angiogenesis. Therefore, the mutated Semaphorin 3, the functional fragment thereof or the fusion protein/polypeptide of the invention inhibits directly and/or indirectly angiogenesis, as shown in the appended examples. In particular, the mutated Semaphorin 3, the functional fragment thereof or the fusion protein/polypeptide of the invention inhibits Rap1 GTP loading by at least 50%. In preferred aspects, the mutated Semaphorin 3, the functional fragment thereof or the fusion protein/polypeptide of the invention inhibits Rap1 GTP loading by at least 55%. In even more preferred aspects, the mutated Semaphorin 3, the functional fragment thereof or the fusion protein/polypeptide of the invention inhibits Rap1 GTP loading by at least 55%. In most preferred aspects, the mutated Semaphorin 3, the functional fragment thereof or the fusion protein/polypeptide of the invention inhibits Rap1 GTP loading by at least 65%. The inhibition of Rap1 GTP loading can be measured by standard methods known in the art, such as an assay that is evident from the appended examples. Further, the mutated Semaphorin 3, the functional fragment thereof, the functional sema domain or the fusion protein/polypeptide of the invention activates ERK 1/2 phosphorylation (by 3.9 fold). In particular, the mutated Semaphorin 3, the functional fragment thereof or the fusion protein/polypeptide of the invention activates ERK 1/2 phosphorylation by at least 2.5 fold. In preferred aspects, the mutated Semaphorin 3, the functional fragment thereof or the fusion protein/polypeptide of the invention activates ERK 1/2 phosphorylation by at least 3.0 fold. In even more preferred aspects, the mutated Semaphorin 3, the functional fragment thereof or the fusion protein/polypeptide of the invention activates ERK 1/2 phosphorylation by at least 3.5 fold. In most preferred aspects, the mutated Semaphorin 3, the functional fragment thereof or the fusion protein/polypeptide of the invention activates ERK 1/2 phosphorylation by at least 4.9 fold. The activation of ERK 1/2 phosphorylation can be measured by standard methods known in the art, such as an assay that is evident from the appended examples.

Further, the mutated Semaphorin 3, the functional fragment thereof, the functional sema domain, the fusion protein or the polypeptide of the invention inhibits the motility of cells, such as ECs (by 46%). Accordingly, the mutated Semaphorin 3 of the invention, the functional fragment thereof and the fusion protein/polypeptide of the invention are (superior) inhibitors of the motility of cells and/or inhibitors of the metastatic dissemination of cancer cells. Thus, the mutated Semaphorin 3, the functional fragment thereof or the fusion protein/polypeptide of the invention inhibits metastatic dissemination of cancer cells. In particular, the mutated Semaphorin 3, the functional fragment thereof or the fusion protein/polypeptide of the invention inhibits the motility of cells such as endothelial cells by at least 30%. In preferred aspects, the mutated Semaphorin 3, the functional fragment thereof or the fusion protein/polypeptide of the invention inhibits the motility of cells such as endothelial cells by at least 35%. In even more preferred aspects, the mutated Semaphorin 3, the functional fragment thereof or the fusion protein/polypeptide of the invention inhibits the motility of cells such as endothelial cells by at least 40%. In most preferred aspects, the mutated Semaphorin 3, the functional fragment thereof or the fusion protein/polypeptide of the invention inhibits the motility of cells such as endothelial cells by at least 45%. The motility of cells can be measured by standard methods known in the art, such as an assay that is evident from the appended examples.

In a further embodiment the invention relates to a nucleic acid molecule encoding a polypeptide comprising an amino acid sequence of a mutated Semaphorin 3 or a functional fragment thereof that functions as an inhibitor of angiogenesis, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

In a further embodiment, the invention relates to the mutated Semaphorin 3 or the functional fragment thereof, wherein said mutated Semaphorin 3 or said functional fragment thereof that functions as an inhibitor of angiogenesis comprises an amino acid sequence, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

In a further embodiment, the invention relates to a nucleic acid molecule encoding a polypeptide comprising an amino acid sequence of a genetically modified Semaphorin 3 or a functional fragment thereof that functions as an inhibitor of angiogenesis, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

In a further embodiment, the invention relates to the genetically modified Semaphorin 3 or functional fragment thereof, wherein said mutated Semaphorin 3 or said functional fragment thereof that functions as an inhibitor of angiogenesis comprises an amino acid sequence, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

In a further embodiment, the herein provided non-naturally occurring/artificial/mutated Semaphorin 3 proteins or their herein described functional fragments and/or fusion proteins/polypeptides comprising said non-naturally occurring/artificial/mutated Semaphorin 3 proteins or said non-naturally occurring/artificial/mutated functional fragments or said functional sema domains of said Semaphorin 3 proteins or the herein provided polypeptides have the activity to function as a vascular normalizing agent. In other words the compounds of the invention, i.e., the mutated Semaphorin 3 proteins/functional fragments thereof/functional sema domain/fusion polypeptides/proteins as described herein have the activity to function as a vascular normalizing agent, wherein the vascular normalizing agent normalizes cancer blood vessel, i.e., increases the pericyte coverage, enhances the perfusion of cancer blood vessels, reduces tissue hypoxia and/or improves drug delivery to cancer. Accordingly, the amino acid sequences and/or nucleic sequences of the present invention relate to a direct and/or indirect vascular normalizing agent.

Thus, the invention relates to a nucleic acid molecule encoding a polypeptide comprising an amino acid sequence of a mutated Semaphorin 3 or a functional fragment thereof that functions as vascular normalizing agent, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

Further, the invention relates to the mutated Semaphorin 3 or the functional fragment thereof, wherein said mutated Semaphorin 3 or said functional fragment thereof that functions as a vascular normalizing agent comprises an amino acid sequence, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

The following description relates to each one of the embodiments of the present invention as described herein above unless explicitly stated otherwise.

Mutated Semaphorin 3 proteins, genetically modified Semaphorin 3 proteins or related polypeptides (functional fragments thereof and/or fusion proteins comprising said mutated Semaphorin 3 proteins or said mutated functional fragments of said Semaphorin 3 proteins having an identity of at least 55% to the specific Semaphorin 3 proteins provided and defined herein, and the like) have primarily the activity as an angiogenesis inhibitor.

Further, mutated Semaphorin 3 proteins, genetically modified Semaphorin 3 proteins or related polypeptides (functional fragments thereof and/or fusion proteins comprising said mutated Semaphorin 3 proteins or said mutated functional fragments of said Semaphorin 3 proteins having an identity of at least 55% to the specific Semaphorin 3 proteins provided and defined herein, and the like) have primarily the activity as a vascular normalizing agent.

In preferred aspects, the nucleic acid molecule encoding for the herein provided mutated Semaphorin 3 is preferably at least 50% homologous/identical to the nucleic acid sequence as shown in SEQ ID NO: 1. It is understood that such nucleic acid sequences can also include orthologous/homologous/identical (and thus related) sequences. More preferably, the nucleic acid sequence encoding the herein provided mutated Semaphorin 3 is at least 52%, 53%, 55%, 60%, 65%, 70%, 75%, 80%, 85%, 90%, 91%, 92%, 93%, 94%, 95%, 96%, 97% or 98% homologous/identical to the nucleic acid sequence as shown in any one of SEQ ID NO: 1, wherein the higher values of sequence identity are preferred.

In certain aspects, the nucleic acid molecule encoding for the herein provided mutated Semaphorin 3 is preferably at least 48% homologous/identical to the nucleic acid sequence as shown in SEQ ID NOs: 5. It is understood that such nucleic acid sequences can also include orthologous/homologous/identical (and thus related) sequences. More preferably, the nucleic acid sequence encoding the herein provided mutated Semaphorin 3 is at least 50%, 52%, 53%, 60%, 65%, 70%, 75%, 80%, 85%, 90%, 91%, 92%, 93%, 94%, 95%, 96%, 97% or 98% homologous/identical to the nucleic acid sequence as shown in any one of SEQ ID NO: 5, wherein the higher values of sequence identity are preferred.

In certain aspects, the nucleic acid molecule encoding for the herein provided mutated Semaphorin 3 is preferably at least 55% homologous/identical to the nucleic acid sequence as shown in SEQ ID NO: 9. It is understood that such nucleic acid sequences can also include orthologous/homologous/identical (and thus related) sequences. More preferably, the nucleic acid sequence encoding the herein provided mutated Semaphorin 3 is at least 57%, 60%, 63%, 65%, 70%, 75%, 80%, 85%, 90%, 91%, 92%, 93%, 94%, 95%, 96%, 97% or 98% homologous/identical to the nucleic acid sequence as shown in any one of SEQ ID NO: 9, wherein the higher values of sequence identity are preferred.

In certain aspects, the nucleic acid molecule encoding for the herein provided mutated Semaphorin 3 is preferably at least 45% homologous/identical to the nucleic acid sequence as shown in SEQ ID NO: 13. It is understood that such nucleic acid sequences can also include orthologous/homologous/identical (and thus related) sequences. More preferably, the nucleic acid sequence encoding the herein provided mutated Semaphorin 3 is at least 48%, 50%, 53%, 55%, 60%, 65%, 70%, 75%, 80%, 85%, 90%, 91%, 92%, 93%, 94%, 95%, 96%, 97% or 98% homologous/identical to the nucleic acid sequence as shown in any one of SEQ ID NO: 13, wherein the higher values of sequence identity are preferred.

In certain aspects, the nucleic acid molecule encoding for the herein provided mutated Semaphorin 3 is preferably at least 55% homologous/identical to the nucleic acid sequence as shown in any one of SEQ ID NO: 1, 3, 5, 7, 9, 11, 13, 15, 57, 59, 61, 63, 65, 67, 69 or 71. It is understood that such nucleic acid sequences can also include orthologous/homologous/identical (and thus related) sequences. More preferably, the nucleic acid sequence encoding the herein provided mutated Semaphorin 3 is at least 56%, 58%, 60%, 65%, 70%, 75%, 80%, 85%, 90%, 91%, 92%, 93%, 94%, 95%, 96%, 97% or 98% homologous/identical to the nucleic acid sequence as shown in any one of SEQ ID NO: 1, 3, 5, 7, 9, 11, 13, 15, 57, 59, 61, 63, 65, 67, 69 or 71, wherein the higher values of sequence identity are preferred. More preferably, the nucleic acid sequence of all aspects encoding the herein provided mutated Semaphorin 3 is at least 60% homologous/identical to the nucleic acid sequence as shown in any one of SEQ ID NO: NO: 1, 3, 5, 7, 9, 11, 13, 15, 57, 59, 61, 63, 65, 67, 69 or 71. More preferably, the nucleic acid sequence encoding the herein provided mutated Semaphorin 3 is at least 70% homologous/identical to the nucleic acid sequence as shown in any one of SEQ ID NO: 1, 3, 5, 7, 9, 11, 13, 15, 57, 59, 61, 63, 65, 67, 69 or 71. Even more preferably, the nucleic acid sequence encoding the herein provided mutated Semaphorin 3 is at least 80% homologous/identical to the nucleic acid sequence as shown in any one of SEQ ID NO: 1, 3, 5, 7, 9, 11, 13, 15, 57, 59, 61, 63, 65, 67, 69 or 71. Most preferably, the nucleic acid sequence encoding the herein provided mutated Semaphorin 3 is at least 90% homologous/identical to the nucleic acid sequence as shown in any one of SEQ ID NO: 1, 3, 5, 7, 9, 11, 13, 15, 57, 59, 61, 63, 65, 67, 69 or 71. The above defined orthologous/homologous/identical sequences can also be encompassed in longer or shorter isoforms, spliced variants and fusion transcripts. The term "orthologous protein" or "orthologous gene" as used herein refers to proteins and genes, respectively, in different species that are similar to each other because they originated from a common ancestor.

Hybridization assays for the characterization of orthologs or other related sequences of known nucleic acid sequences are well known in the art; see e.g. Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989).

The term "hybridization" or "hybridizing", as used herein in connection with nucleic acids, relates to hybridizations under conditions of any degree of stringency. In general, hybridizations of nucleic acids, such as Southern or Northern hybridizations, can be performed under experimental conditions of various degrees of stringency. Usually a nucleic acid immobilized on a solid support such as a membrane is contacted with a liquid containing another, similar nucleic acid (called probe) under suitable buffer and temperature conditions in order to selectively allow the interaction of the probe with the immobilized nucleic acid, wherein the probe has a certain degree of sequence identity to the immobilized nucleic acid to be tested. Commonly the buffer used for the hybridization, in particular the washing steps after hybridization, is standard sodium citrate buffer (SSC; also referred to as saline sodium citrate buffer). A 20-fold concentrated SSC buffer contains 3 M NaCl and 0.3 M sodium citrate, adjusted to pH 7.0 using HCl, and is commercially available, e.g., from Sigma Aldrich. The $Na^+$ concentration of a corresponding 20-fold SSC buffer is 3.3 M (i.e., 3.3 mol/L), and it is 1.65 M for a 10-fold SSC buffer, 0.825 M for a 5-fold SSC buffer, 0.33 M for a 2-fold SSC buffer, 0.165 M for a 1-fold SSC buffer, and 0.0165 M for a 0.1-fold SSC buffer. Formamide or sodium dodecyl sulfate (SDS) can be added to the SSC buffer to reduce unspecific binding of the probe. The stringency of the hybridization depends on the percentage of the nucleotides G and C present in the sequence of the probe (% G+C) and the hybridization conditions, particularly the temperature, the concentration of $Na^+$ and the concentration of formamide or SDS (if present). In general, the higher the hybridization temperature and the lower the sodium (Nat) concentration, the higher will be the stringency. The stringency of the hybridization can thus be controlled by appropriately choosing the temperature for the hybridization, the concentration of the SSC buffer (and thereby the sodium concentration) and optionally the concentration of formamide (or SDS) added to the SSC buffer. If different concentrations of SSC buffer are used in different steps of the hybridization procedure, the concentrations of sodium and formamide in the most concentrated SSC buffer (which is typically the buffer used for the final washing step) are decisive.

Accordingly, at a given GC-content of the probe and at specific concentrations of sodium and formamide (if present) in the most concentrated buffer used for the washing after hybridization (typically the buffer used for the final washing step), the stringency of the hybridization can be controlled by adjusting the hybridization temperature to a specific number of degrees Celsius (e.g., 25° C. or less) below the effective melting temperature (Tm) which can be calculated using the following formula (for DNA-DNA-hybridizations):

$$Tm=81.5+16.6(\log M[Na^+])+0.41(\%\ G+C)-0.72(\%\ \text{formamide})$$

In the above formula, "Tm" is the temperature under which the sequence of the immobilized nucleic acid to be tested needs to match 100% of the sequence of the probe in order for both sequences to hybridize to each other; "log M [$Na^+$]" is the logarithm to base 10 ($\log_{10}$) of the concentration of sodium (Nat) in mol/L in the buffer; "% G+C" is the percentage of the nucleotides G and C in the sequence of the probe (GC-content); and "% formamide" is the concentration of formamide in % (volume/volume) in the buffer. As is well known, the length of the probe to be determined constitutes further parameters of the hybridization conditions.

The farther the hybridization temperature is below the Tm, the lower will be the stringency of the hybridization. In particular, for each 1.4° C. the hybridization temperature is below the calculated Tm, the hybridization will still occur in the presence of 1% sequence mismatch, i.e., a mismatch of x % of the sequences of the probe and the immobilized nucleic acid to be tested will still lead to hybridization if the hybridization temperature is at least x·1.4° C. below the calculated Tm. For example, if the Tm is calculated to be 90° C. and the hybridization experiment is conducted at 55° C. (i.e., 35° C. below the Tm), nucleic acid sequences matching at least 82.1% of the sequence of the probe will hybridize to the probe (i.e., 35° C./1.4° C.=25.0, meaning that 100%−25.0%=75.0%).

As used herein, hybridization under "stringent conditions" preferably means that the hybridization temperature is about 35° C. or less below the Tm (calculated using the formula explained above), which corresponds to a minimum sequence identity of about 75.0% required for hybridization to occur (i.e., 100%−(35° C./1.4° C.)%). More preferably, hybridization under stringent conditions means that the hybridization temperature is about 30° C. or less below the Tm (corresponding to a minimum sequence identity of about 78.6% required for hybridization), even more preferably, hybridization under stringent conditions means that the hybridization temperature is about 25° C. or less below the Tm (corresponding to a minimum sequence identity of about 82.1% required for hybridization), even more preferably, hybridization under stringent conditions means that the hybridization temperature is about 20° C. or less below the Tm (corresponding to a minimum sequence identity of about 85.7% required for hybridization), even more preferably about 15° C. or less below the Tm (corresponding to a minimum sequence identity of about 89.3% required for hybridization), even more preferably about 10° C. or less below the Tm (corresponding to a minimum sequence identity of about 92.9% required for hybridization), even more preferably about 7° C. or less below the Tm (corresponding to a minimum sequence identity of about 95.0% required for hybridization), yet even more preferably about 5° C. or less below the Tm (corresponding to a minimum sequence identity of about 96.4% required for hybridization), and still more preferably about 3° C. or less below the Tm (corresponding to a minimum sequence identity of about 97.9% required for hybridization). Conversely, hybridization under "non-stringent conditions" means that the hybridization temperature is below the above-defined temperature required for stringent hybridization. If not further specified, the conditions are preferably non-stringent. Said hybridization conditions may be established according to conventional protocols described, e.g., in Sambrook (2001) loc. cit.; Ausubel (1989) loc. cit., or Higgins and Hames (Eds.) "Nucleic acid hybridization, a practical approach" IRL Press Oxford, Washington D.C., (1985). The setting of conditions is well within the skill of the artisan and can be determined according to protocols described in the art.

In accordance with the present invention, the terms "homology" or "percent homology" or "identical" or "percent identity" or "percentage identity" or "sequence identity" in the context of two or more nucleic acid sequences refers to two or more sequences or subsequences that are the same, or that have a specified percentage of nucleotides that are the same, when compared and aligned for maximum correspondence over the window of comparison (preferably over the full length), or over a designated region (e.g., the functional sema domain) as measured using a sequence comparison algorithm as known in the art, or by manual alignment and visual inspection. Sequences having, for example, 70% to 90% or greater sequence identity may be considered to be substantially identical. Such a definition also applies to the complement of a test sequence. Preferably the described identity exists over a region that is at least about 15 to about 25 nucleotides in length, more preferably, over a region that is at least about 50 to about 100 nucleotides in length, even more preferably, over a region that is at least about 800 to about 1200 nucleotides in length and most preferably, over the full length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul, (1997) Nucl. Acids Res. 25:3389-3402; Altschul (1993) J. Mol. Evol. 36:290-300; Altschul (1990) J. Mol. Biol. 215:403-410). The BLASTN program for nucleic acid sequences uses as defaults a word length (W) of 11, an expectation (E) of 10, M=5, N=4, and a comparison of both strands. The BLOSUM62 scoring matrix (Henikoff (1989) PNAS 89:10915) uses alignments (B) of 50, expectation (E) of 10, M=5, N=4, and a comparison of both strands.

In order to determine whether a nucleotide in a nucleic acid sequence corresponds to a certain position in the nucleotide sequence of e.g. SEQ ID NO: 1, 3, 5, 7, 9, 11, 13, 15, 57, 59, 61, 63, 65, 67, 69 or 71, respectively, the skilled person can use means and methods well-known in the art, e.g., alignments, either manually or by using computer programs such as those mentioned herein. For example, BLAST 2.0, which stands for Basic Local Alignment Search Tool BLAST (Altschul (1997), loc. cit.; Altschul (1993), loc. cit.; Altschul (1990), loc. cit.), can be used to search for local sequence alignments. BLAST, as discussed above, produces alignments of nucleotide sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cut-off score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score, which is defined as:

$$\frac{\%\text{ sequence identity} \times \%\text{ maximum } BLAST \text{ score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those, which show product scores between 15 and 40, although lower scores may identify related molecules. Another example for a program capable of generating sequence alignments is the CLUSTALW computer program (Thompson (1994) Nucl. Acids Res. 2:4673-4680) or FASTDB (Brutlag (1990) Comp. App. Biosci. 6:237-245), as known in the art.

The explanations and definitions given herein above in respect of "homology/identity of nucleic acid sequences" apply, mutatis mutandis, to "amino acid sequences" of members of the mutated Semaphorin 3 or the functional fragments thereof or the polypeptide, in particular an amino acid sequence as depicted in SEQ ID NO: 2 (*Homo sapiens* SEMA3A), SEQ ID NO: 6 (*Homo sapiens* SEMA3B), SEQ ID NO: 10 (*Homo sapiens* SEMA3C), SEQ ID NO: 14 (*Homo sapiens* SEMA3D), SEQ ID NO: 4 (*Mus musculus* Sema3A), SEQ ID NO: 8 (*Mus musculus* Sema3B), SEQ ID NO: 12 (*Mus musculus* Sema3C) and SEQ ID NO: 16 (*Mus musculus* Sema3D). Exemplary sequences of the Semaphorin 3 proteins comprising a lysine at the position that by comparison of homology corresponds to position 106 of the wild type human Semaphorin 3A as shown in SEQ ID NO: 2 are given in SEQ ID NO: 58, 60, 62, 64, 66, 68, 70 or 72.

The mutated Semaphorin 3 proteins or genetically modified Semaphorin 3 proteins have of at least 55% homology/identity to a wild type Semaphorin 3 protein/polypeptide having the amino acid sequence as, for example, depicted in SEQ ID NO: 2, 4, 6, 8, 10, 12, 14 or 16 and functioning as an inhibitor angiogenesis.

In preferred aspects, the provided mutated Semaphorin 3 of the invention is preferably at least 50% homologous/identical to the amino acid sequence as shown in SEQ ID NO: 2. It is understood that such amino acid sequences can also include orthologous/homologous/identical (and thus related) sequences. More preferably, the amino acid sequence encoding the herein provided mutated Semaphorin 3 is at least 52%, 53%, 55%, 60%, 65%, 70%, 75%, 80%, 85%, 90%, 91%, 92%, 93%, 94%, 95%, 96%, 97% or 98% homologous/identical to the amino acid sequence as shown in any one of SEQ ID NO: 2, wherein the higher values of sequence identity are preferred.

In certain aspects, the herein provided mutated Semaphorin 3 of the invention is preferably at least 48% homologous/identical to the amino acid sequence as shown in SEQ ID NO: 6. It is understood that such amino acid sequences can also include orthologous/homologous/identical (and thus related) sequences. More preferably, the amino acid sequence encoding the herein provided mutated Semaphorin 3 is at least 50%, 52%, 53%, 60%, 65%, 70%, 75%, 80%, 85%, 90%, 91%, 92%, 93%, 94%, 95%, 96%, 97% or 98% homologous/identical to the amino acid sequence as shown in any one of SEQ ID NO: 6, wherein the higher values of sequence identity are preferred.

In certain aspects, the herein provided mutated Semaphorin 3 of the invention is preferably at least 55% homologous/identical to the amino acid sequence as shown in SEQ ID NO: 10. It is understood that such amino acid sequences can also include orthologous/homologous/identical (and thus related) sequences. More preferably, the amino acid sequence encoding the herein provided mutated Semaphorin 3 is at least 57%, 60%, 63%, 65%, 70%, 75%, 80%, 85%, 90%, 91%, 92%, 93%, 94%, 95%, 96%, 97% or 98% homologous/identical to the amino acid sequence as shown in any one of SEQ ID NO: 10, wherein the higher values of sequence identity are preferred.

In certain aspects, the herein provided mutated Semaphorin 3 of the invention is preferably at least 45% homologous/identical to the amino acid sequence as shown in SEQ ID NO: 14. It is understood that such amino acid sequences can also include orthologous/homologous/identical (and thus related) sequences. More preferably, the amino acid sequence encoding the herein provided mutated Semaphorin 3 is at least 48%, 50%, 53%, 55%, 60%, 65%, 70%, 75%, 80%, 85%, 90%, 91%, 92%, 93%, 94%, 95%, 96%, 97% or 98% homologous/identical to the amino acid sequence as shown in any one of SEQ ID NO: 14, wherein the higher values of sequence identity are preferred.

In certain aspects, the provided mutated Semaphorin 3 of the invention is preferably at least 55% homologous/identical to the amino acid sequence as shown in any one of SEQ ID NO: 2, 4, 6, 8, 10, 12, 14 or 16. More preferably, the mutated Semaphorin 3 has at least 57%, 60%, 65%, 70%, 75%, 80%, 85%, 90%, 91%, 92%, 93%, 94%, 95%, 96%, 97% or 98% homology/identity to a wild type Semaphorin 3 protein/polypeptide having the amino acid sequence as, for example, depicted in SEQ ID NOs: 2, 4, 6, 8, 10, 12, 14 and 16, respectively, wherein the higher values are preferred. Most preferably, the mutated Semaphorin 3 has at least 99% homology to a wild type Semaphorin 3 protein/polypeptide having the amino acid sequence as, for example, depicted in SEQ ID NO: 2, 4, 6, 8, 10, 12, 14 or 16.

The present invention comprises also polypeptides deviating from wild type amino acid sequences described herein above, wherein said deviation may be, for example, the result of amino acid and/or nucleotide substitution(s), deletion(s), addition(s), insertion(s), duplication(s), inversion(s) and/or recombination(s) either alone or in combination. Those deviations may naturally occur or be produced via recombinant DNA techniques well known in the art; see, for example, the techniques described in Sambrook (Molecular Cloning; A Laboratory Manual, 2$^{nd}$ Edition, Cold Spring Harbour Laboratory Press, Cold Spring Harbour, N.Y. (1989)) and Ausubel, "Current Protocols in Molecular Biology", Green Publishing Associates; and Wiley Interscience, N.Y. (1989). The allelic variations may be naturally occurring allelic variants as well as synthetically produced or genetically engineered variants. The polypeptides, peptides or protein fragments encoded by the various derivatives, allelic variants, homologues or analogues of the above-described nucleic acid molecules encoding mutated Semaphorin 3 and/or fragment thereof may share specific common characteristics, such as molecular weight, immunological reactivity, conformation etc., as well as physical properties, such as electrophoretic mobility, chromatographic behavior, sedimentation coefficients, pH optimum, stability, solubility, spectroscopic properties etc.

The terms "complement", "reverse complement" and "reverse sequence" referred to herein are described in the following example: For sequence 5'AGTGAAGT3', the complement is 3'TCACTTCA5', the reverse complement is 3'ACTTCACT5' and the reverse sequence is 5'TGAAGTGA3'.

The invention relates to the mutated Semaphorin 3 or the functional fragment thereof as defined herein that can be selected from the group of:

(a) a polypeptide that is encoded by a nucleic acid sequence selected from the group of SEQ ID NO: 1, SEQ ID NO: 5, SEQ ID NO: 9 and SEQ ID NO: 13,
  wherein the nucleotides GCT at position 631 to 633 of SEQ ID NO: 1 are replaced by nucleotides encoding said hydrophilic amino acid,
  wherein the nucleotides GCA at position 559 to 561 of SEQ ID NO: 5 are replaced by nucleotides encoding said hydrophilic amino acid,
  wherein the nucleotides GCT at position 872 to 874 of SEQ ID NO: 9 are replaced by nucleotides encoding said hydrophilic amino acid, and
  wherein the nucleotides GCC at position 398 to 400 of SEQ ID NO: 13 are replaced by nucleotides encoding said hydrophilic amino acid;

(b) a polypeptide having the amino acid sequence selected from the group of SEQ ID NO: 2, SEQ ID NO: 6, SEQ ID NO: 10 and SEQ ID NO: 14, wherein the alanine residue at position 106 of SEQ ID NO: 2, at position 105 of SEQ ID NO: 6, at position 104 of SEQ ID NO: 10 or at position 120 of SEQ ID NO: 14 is replaced by said hydrophilic amino acid;

(c) a polypeptide that is encoded by a nucleic acid sequence that hybridizes under stringent conditions to the complementary strand of a nucleic acid molecule encoding a polypeptide as defined in (a) or (b);

(d) a polypeptide that functions as an inhibitor of angiogenesis and has at least 55% identity to any one of the polypeptides referred to in (b).

In most preferred embodiments, the invention relates to the mutated Semaphorin 3A or the functional fragment thereof as defined herein that can be selected from the group of:

(a) a polypeptide that is encoded by a nucleic acid sequence as shown in SEQ ID NO: 1
  wherein the nucleotides GCT at position 631 to 633 of SEQ ID NO: 1 are replaced by nucleotides encoding said hydrophilic amino acid, (b) a polypeptide having the amino acid sequence of SEQ ID NO: 2, wherein the alanine residue at position 106 of SEQ ID NO: 2 is replaced by said hydrophilic amino acid;

(c) a polypeptide that is encoded by a nucleic acid sequence that hybridizes under stringent conditions to the complementary strand of a nucleic acid molecule encoding a polypeptide as defined in (a) or (b);

(d) a polypeptide that functions as an inhibitor of angiogenesis and has at least 50% identity to any one of the polypeptides referred to in (b).

In certain aspects, the mutated Semaphorin 3 or the functional fragment thereof as defined herein can be selected from the group of:

(a) a polypeptide comprising an amino acid sequence encoded by a nucleic acid molecule having the nucleic acid sequence selected from the group of SEQ ID NO: 1, SEQ ID NO: 5, SEQ ID NO: 9 and SEQ ID NO: 13,
  wherein the nucleotides GCT at position 631 to 633 of SEQ ID NO: 1 are replaced by nucleotides encoding said hydrophilic amino acid,
  wherein the nucleotides GCA at position 559 to 561 of SEQ ID NO: 5 are replaced by nucleotides encoding said hydrophilic amino acid,
  wherein the nucleotides GCT at position 872 to 874 of SEQ ID NO: 9 are replaced by nucleotides encoding said hydrophilic amino acid, and
  wherein the nucleotides GCC at position 398 to 400 of SEQ ID NO: 13 are replaced by nucleotides encoding said hydrophilic amino acid;

(b) a polypeptide having an amino acid sequence selected from the group of SEQ ID NO: 2, SEQ ID NO: 6, SEQ ID NO: 10 and SEQ ID NO: 14, wherein the alanine residue corresponding to position 106 of SEQ ID NO: 2, corresponding to position 105 of SEQ ID NO: 6, corresponding to position 104 of SEQ ID NO: 10 or corresponding to position 120 of SEQ ID NO: 14 is replaced by said hydrophilic amino acid;

(c) a polypeptide encoded by a nucleic acid molecule encoding a polypeptide having an amino acid sequence selected from the group of SEQ ID NO: 2, SEQ ID NO: 6, SEQ ID NO: 10 and SEQ ID NO: 14, wherein the alanine residue corresponding to position 106 of SEQ ID NO: 2, corresponding to position 105 of SEQ ID NO: 6, corresponding to position 104 of SEQ ID NO: 10 or corresponding to position 120 of SEQ ID NO: 14 is replaced by said hydrophilic amino acid;

(d) a polypeptide encoded by a nucleic acid molecule hybridizing under stringent conditions to the complementary strand of a nucleic acid molecule as defined in (a) or (c);

(e) a polypeptide having at least 55% identity to the polypeptide of any one of (a) to (d) and functioning as an inhibitor of angiogenesis; and (f) a polypeptide that functions as an inhibitor of angiogenesis comprising an amino acid sequence encoded by a nucleic acid molecule being degenerate as a result of the genetic code to the nucleotide sequence of a nucleic acid molecule as defined in any one of (a), (c) and (d).

In certain aspects, the mutated Semaphorin 3, the functional fragment thereof or the polypeptide comprises the amino acid sequence selected from the group of SEQ ID NO: 2, SEQ ID NO: 4, SEQ ID NO: 6, SEQ ID NO: 8, SEQ ID NO: 10, SEQ ID NO: 12, and SEQ ID NO: 14, wherein the alanine residue corresponding to position 106 of SEQ ID NO: 2; wherein the alanine residue corresponding to position 106 of SEQ ID NO: 4; wherein the alanine residue corresponding to position 105 of SEQ ID NO: 6; wherein the alanine residue corresponding to position 105 of SEQ ID NO: 8; wherein the alanine residue corresponding to position 104 of SEQ ID NO: 10; wherein the alanine residue corresponding to position 104 of SEQ ID NO: 12; wherein the alanine residue corresponding to position 120 of SEQ ID NO: 14; or wherein the alanine residue corresponding to position 120 of SEQ ID NO: 16 is replaced by an hydrophilic amino acid.

In most preferred embodiments the mutated Semaphorin 3A, the functional fragment thereof or the polypeptide comprises the amino acid sequence selected from the group of SEQ ID NO: 2, wherein the alanine residue corresponding to position 106 of SEQ ID NO: 4 is replaced by an hydrophilic amino acid.

In other words, the invention relates to a mutated Semaphorin 3 or a fragment thereof, wherein the alanine corresponding to position 106 of the wild type Semaphorin 3A as shown in SEQ ID NO: 2; the alanine corresponding to position 106 of the wild type Semaphorin 3A as shown in SEQ ID NO: 4; the alanine corresponding to position 105 of the wild type Semaphorin 3B as shown in SEQ ID NO: 6; the alanine corresponding to position 105 of the wild type Semaphorin 3B as shown in SEQ ID NO: 8; the alanine corresponding to position 104 of the wild type Semaphorin 3C as shown in SEQ ID NO: 10; the alanine corresponding to position 104 of the wild type Semaphorin 3C as shown in SEQ ID NO: 12; the alanine corresponding to position 120 of the wild type Semaphorin 3D as shown in SEQ ID NO: 14; or the alanine corresponding to position 120 of the wild type Semaphorin 3D as shown in SEQ ID NO: 16 is replaced by a hydrophilic amino acid.

Accordingly, the skilled person understands that in case the inventive mutation is defined herein by a specific position, e.g. the alanine at the position 106 of the wild type Semaphorin 3A as shown in SEQ ID NO: 2 is replaced, it is clear that also a corresponding amino acid (position) can be meant in other Semaphorin 3 proteins, such as other Semaphorin 3A polypeptides, or Semaphorin 3B, C or D polypeptides, which for instance can be found by comparison of homology. Hence, it is understood herein that for the identification of further wild-type sequences and/or for the detection of the relevant specific amino acid residue corresponding to the alanine on position 106 of wild-type Semaphorin 3A that is mutated according to the invention standard homology screenings (e.g. sequence alignments) or PCR-mediated screening techniques can be employed.

In most preferred embodiments, the invention relates to the mutated Semaphorin 3A or the functional fragment thereof, wherein the alanine corresponding to position 106 of the wild type Semaphorin 3A as shown in SEQ ID NO: 2 is replaced by a hydrophilic amino acid.

SEQ ID NO: 58, 60, 62, 64, 66, 68, 70 or 72 relates to the full length human or mouse mutated Semaphorin 3A, B, C or D, wherein lysine is in place at the position that by comparison of homology corresponds to position 106 of the wild type Semaphorin 3A as shown in SEQ ID NO: 2. Therefore, comprising a hydrophilic amino acid in place of means that the specific alanine, e.g., corresponding to position 106 shown in SEQ ID NO: 2, that is present in the naturally occurring Semaphorin 3A, B, C or D is mutated or changed to the hydrophilic amino acid, preferably lysine, in the mutated Semaphorin 3A, B, C or D.

An exemplary polypeptide comprising a human mutated Semaphorin 3A has an amino acid sequence as given in SEQ ID NO: 58, wherein a lysine is in place at the position 106.

An exemplary polypeptide comprising a mouse mutated Semaphorin 3A has an amino acid sequence as given in SEQ ID NO: 60, wherein a lysine is in place at the position 106.

An exemplary polypeptide comprising a human mutated Semaphorin 3B has an amino acid sequence as given in SEQ ID NO: 62, wherein a lysine is in place at the position 105.

An exemplary polypeptide comprising a mouse mutated Semaphorin 3B has an amino acid sequence as given in SEQ ID NO: 64, wherein a lysine is in place at the position 105.

An exemplary polypeptide comprising a human mutated Semaphorin 3C has an amino acid sequence as given in SEQ ID NO: 66, wherein a lysine is in place at the position 104.

An exemplary polypeptide comprising a mouse mutated Semaphorin 3C has an amino acid sequence as given in SEQ ID NO: 68, wherein a lysine is in place at the position 104.

An exemplary polypeptide comprising a human mutated Semaphorin 3D has an amino acid sequence as given in SEQ ID NO: 70, wherein a lysine is in place at the position 120.

An exemplary polypeptide comprising a mouse mutated Semaphorin 3D has an amino acid sequence as given in SEQ ID NO: 72, wherein a lysine is in place at the position 120.

Therefore, the invention relates to the mutated Semaphorin 3 or the functional fragment thereof wherein the mutated Semaphorin 3 comprises an amino acid sequence that is selected from the group consisting of SEQ ID NO: 58, SEQ ID NO: 60, SEQ ID NO: 62, SEQ ID NO: 64, SEQ ID NO: 66, SEQ ID NO: 68, SEQ ID NO: 70 and SEQ ID NO: 72 or a functional fragment thereof. In preferred aspects of the invention, the invention relates to the mutated Semaphorin 3A or the functional fragment thereof wherein the mutated Semaphorin 3A comprises an amino acid sequence that is SEQ ID NO: 58 or SEQ ID NO: 60. In preferred aspects, the functional fragment is the sema domain as detailed herein below.

Further, the invention relates to a nucleic acid molecule encoding the mutated Semaphorin 3 or the functional fragment thereof. The nucleic acid molecule of the invention can be selected from the group of:

(a) a nucleic acid molecule selected from the group of SEQ ID NO: 1, SEQ ID NO: 5, SEQ ID NO: 9 and SEQ ID NO: 13,
 wherein the nucleotides GCT at position 631 to 633 of SEQ ID NO: 1 are replaced by nucleotides encoding said hydrophilic amino acid,
 wherein the nucleotides GCA at position 559 to 561 of SEQ ID NO: 5 are replaced by nucleotides encoding said hydrophilic amino acid,
 wherein the nucleotides GCT at position 872 to 874 of SEQ ID NO: 9 are replaced by nucleotides encoding said hydrophilic amino acid, and
 wherein the nucleotides GCC at position 398 to 400 of SEQ ID NO: 13 are replaced by nucleotides encoding said hydrophilic amino acid;
(b) a nucleic acid molecule encoding a polypeptide selected from the group of SEQ ID NO: 2, SEQ ID NO: 6, SEQ ID NO: 10 and SEQ ID NO: 14, wherein the alanine residue at position 106 of SEQ ID NO: 2, at position 105 of SEQ ID NO: 6, at position 104 of SEQ ID NO: 10 or at position 120 of SEQ ID NO: 14 is replaced by said hydrophilic amino acid;
(c) a nucleic acid molecule hybridizing under stringent conditions to the complementary strand of a nucleic acid molecule as defined in (a) or (b);
(d) a nucleic acid molecule encoding a polypeptide that functions as an inhibitor of angiogenesis and has at least 55% identity to any one of the polypeptides referred to in (b); and
(e) a nucleic acid molecule being degenerate as a result of the genetic code to the nucleotide sequence of a nucleic acid molecule as defined in any one of (a) to (d), wherein the degenerate nucleic acid molecule encodes a polypeptide that functions as an inhibitor of angiogenesis.

In certain aspects, the encoded mutated Semaphorin 3 or the functional fragment thereof as defined herein can be selected from the group of:

(a) a nucleic acid molecule comprising a nucleic acid molecule having a DNA sequence selected from the group of SEQ ID NO: 1, SEQ ID NO: 5, SEQ ID NO: 9 and SEQ ID NO: 13,
 wherein the nucleotides GCT at position 631 to 633 of SEQ ID NO: 1 are replaced by nucleotides encoding said hydrophilic amino acid,
 wherein the nucleotides GCA at position 559 to 561 of SEQ ID NO: 5 are replaced by nucleotides encoding said hydrophilic amino acid,
 wherein the nucleotides GCT at position 872 to 874 of SEQ ID NO: 9 are replaced by nucleotides encoding said hydrophilic amino acid, and
 wherein the nucleotides GCC at position 398 to 400 of SEQ ID NO: 13 are replaced by nucleotides encoding said hydrophilic amino acid;
(b) a nucleic acid molecule comprising a nucleic acid molecule encoding a polypeptide having the amino acid sequence selected from the group of SEQ ID NO: 2, SEQ ID NO: 6, SEQ ID NO: 10 and SEQ ID NO: 14, wherein the alanine residue at position 106 of SEQ ID NO: 2, at position 105 of SEQ ID NO: 6, at position 104 of SEQ ID NO: 10 or at position 120 of SEQ ID NO: 14 is replaced by said hydrophilic amino acid;
(c) a nucleic acid molecule hybridizing under stringent conditions to the complementary strand of a nucleic acid molecule as defined in (a) or (b);
(d) a nucleic acid molecule comprising a nucleic acid molecule encoding a polypeptide that functions as an inhibitor of angiogenesis and has at least 55% identity to any one of the polypeptides referred to in (b); and
(e) a nucleic acid molecule being degenerate as a result of the genetic code to the nucleotide sequence of a nucleic acid molecule as defined in any one of (a) to (d), wherein the degenerate nucleic acid molecule encodes a polypeptide that functions as an inhibitor of angiogenesis.

In most preferred embodiments, the encoded mutated Semaphorin 3A or the functional fragment thereof as defined herein can be selected from the group of:

(a) a nucleic acid molecule as shown in SEQ ID NO: 1, wherein the nucleotides GCT at position 631 to 633 of SEQ ID NO: 1 are replaced by nucleotides encoding said hydrophilic amino acid, (b) a nucleic acid molecule encoding a polypeptide as shown in SEQ ID NO: 2, wherein the alanine residue at position 106 of SEQ ID NO: 2 is replaced by said hydrophilic amino acid;

(c) a nucleic acid molecule hybridizing under stringent conditions to the complementary strand of a nucleic acid molecule as defined in (a) or (b);

(d) a nucleic acid molecule encoding a polypeptide that functions as an inhibitor of angiogenesis and has at least 50% identity to any one of the polypeptides referred to in (b); and (e) a nucleic acid molecule being degenerate as a result of the genetic code to the nucleotide sequence of a nucleic acid molecule as defined in any one of (a) to (d), wherein the degenerate nucleic acid molecule encodes a polypeptide that functions as an inhibitor of angiogenesis.

In certain aspects, the encoded mutated Semaphorin 3 or the functional fragment thereof as defined herein can be selected from the group of:

a nucleic acid molecule comprising a nucleic acid sequence as defined in SEQ ID NO: 1, SEQ ID NO: 3, SEQ ID NO: 5, SEQ ID NO: 7, SEQ ID NO: 9, SEQ ID NO: 11, SEQ ID NO: 13 and SEQ ID NO: 15, wherein the nucleotides GCT at position 631 to 633 of SEQ ID NO: 1 are replaced by nucleotides encoding said hydrophilic amino acid, wherein the nucleotides GCT at position 965 to 967 of SEQ ID NO: 3 are replaced by nucleotides encoding said hydrophilic amino acid, wherein the nucleotides GCA at position 559 to 561 of SEQ ID NO: 5 are replaced by nucleotides encoding said hydrophilic amino acid, wherein the nucleotides GCT at position 712 to 714 of SEQ ID NO: 7 are replaced by nucleotides encoding said hydrophilic amino acid, wherein the nucleotides GCT at position 872 to 874 of SEQ ID NO: 9 are replaced by nucleotides encoding said hydrophilic amino acid, wherein the nucleotides GCT at position 498 to 500 of SEQ ID NO: 11 are replaced by nucleotides encoding said hydrophilic amino acid, wherein the nucleotides GCC at position 398 to 400 of SEQ ID NO: 13 are replaced by nucleotides encoding said hydrophilic amino acid, or wherein the nucleotides GCT at position 904 to 906 of SEQ ID NO: 15 are replaced by nucleotides encoding said hydrophilic amino acid.

SEQ ID NO: 57, 59, 61, 63, 65, 67, 69 or 71 relates to a nucleic acid sequence encoding the full length human or mouse mutated Semaphorin 3A, B, C or D, wherein lysine is in place at the position that by comparison of homology corresponds to position 106 of the wild type Semaphorin 3A as shown in SEQ ID NO: 2.

An exemplary nucleic acid molecule encoding the mutated human Semaphorin 3A comprises a nucleic acid sequence as defined in SEQ ID NO: 57, wherein the nucleotides at position 631 to 633 of SEQ ID NO: 57 encode for the amino acid lysine.

An exemplary nucleic acid molecule encoding the mutated mouse Semaphorin 3A comprises a nucleic acid sequence as defined in SEQ ID NO: 59, wherein the nucleotides at position 965 to 967 of SEQ ID NO: 59 encode for the amino acid lysine.

An exemplary nucleic acid molecule encoding the mutated human Semaphorin 3B comprises a nucleic acid sequence as defined in SEQ ID NO: 61, wherein the nucleotides at position 559 to 561 of SEQ ID NO: 61 encode for the amino acid lysine.

An exemplary nucleic acid molecule encoding the mutated mouse Semaphorin 3B comprises a nucleic acid sequence as defined in SEQ ID NO: 63, wherein the nucleotides at position 712 to 714 of SEQ ID NO: 63 encode for the amino acid lysine.

An exemplary nucleic acid molecule encoding the mutated human Semaphorin 3C comprises a nucleic acid sequence as defined in SEQ ID NO: 65, wherein the nucleotides at position 872 to 874 of SEQ ID NO: 65 encode for the amino acid lysine.

An exemplary nucleic acid molecule encoding the mutated mouse Semaphorin 3C comprises a nucleic acid sequence as defined in SEQ ID NO: 67, wherein the nucleotides at position 498 to 500 of SEQ ID NO: 67 encode for the amino acid lysine.

An exemplary nucleic acid molecule encoding the mutated human Semaphorin 3D comprises a nucleic acid sequence as defined in SEQ ID NO: 69, wherein the nucleotides at position 398 to 400 of SEQ ID NO: 69 encode for the amino acid lysine.

An exemplary nucleic acid molecule encoding the mutated mouse Semaphorin 3D comprises a nucleic acid sequence as defined in SEQ ID NO: 71, wherein the nucleotides at position 904 to 906 of SEQ ID NO: 71 encode for the amino acid lysine.

The nucleic acid given in SEQ ID NO: 57, SEQ ID NO: 59, SEQ ID NO: 61, SEQ ID NO: 63, SEQ ID NO: 65, SEQ ID NO: 67, SEQ ID NO: 69 or SEQ ID NO: 71 encodes full length mutated Semaphorin 3 proteins. Therefore, the invention relates to the mutated Semaphorin 3 or the functional fragment thereof wherein the mutated Semaphorin 3 is encoded by a nucleic acid molecule comprising the nucleic acid selected from the group consisting of SEQ ID NO: 57, SEQ ID NO: 59, SEQ ID NO: 61, SEQ ID NO: 63, SEQ ID NO: 65, SEQ ID NO: 67, SEQ ID NO: 69 and SEQ ID NO: 71. In preferred aspects of the invention, the mutated Semaphorin 3 or the functional fragment thereof is mutated Semaphorin 3A or the functional fragment thereof, wherein the mutated Semaphorin 3A is encoded by a nucleic acid molecule comprising the nucleic acid SEQ ID NO: 57 or SEQ ID NO: 59. In preferred aspects, the functional fragment is the sema domain as detailed herein below.

In certain aspects, the encoded mutated Semaphorin 3 or the functional fragment thereof as defined herein can be selected from the group of:

a nucleic acid molecule comprising a nucleic acid sequence as defined in SEQ ID NO: 1, SEQ ID NO: 5, SEQ ID NO: 9 and SEQ ID NO: 13, wherein the codon at nucleotide position 631 to 633 of SEQ ID NO: 1 is replaced by a codon encoding said hydrophilic amino acid, wherein the codon at nucleotide position 559 to 561 of SEQ ID NO: 5 is replaced by a codon encoding said hydrophilic amino acid, wherein the codon at nucleotide position 872 to 874 of SEQ ID NO: 9 is replaced by a codon encoding said hydrophilic amino acid, and wherein the codon at nucleotide position 398 to 400 of SEQ ID NO: 13 is replaced by a codon encoding said hydrophilic amino acid;

A codon encoding a hydrophilic amino acid means in accordance with the present invention, a codon, which according to the standard genetic code (as illustrated, inter alia, in Stryer (1995), "Biochemistry", Freeman and Company, ISBN 0-7167-2009-4) codes for a "hydrophilic amino acid". In certain aspects, K is encoded by a codon coding for K. In particular preferred aspects, K is encoded by the codon AAG or AAA. The degeneracy of the genetic code permits the same amino acid sequence to be encoded and translated in many different ways. For example, leucine, serine and arginine are each encoded by six different codons, while valine, proline, threonine, alanine and glycine are each encoded by four different codons. However, the frequency of use of such synonymous codons varies from genome to genome among eukaryotes and prokaryotes. For example, synonymous codon-choice patterns among mammals are very similar, while evolutionarily distant organisms such as yeast (*S. cerevisiae*), bacteria (such as *E. coli*) and insects (such as *D. melanogaster*) reveal a clearly different pattern of genomic codon use frequencies. Therefore, codon optimized genes can be used in the present invention. The design of codon optimized genes should take into account a variety of factors, including the frequency of codon usage in an organism, nearest neighbor frequencies, RNA stability, the potential for secondary structure formation, the route of synthesis and the intended future DNA manipulations of that gene. It is contemplated herein that codon optimized nucleic acid sequences can be employed. Such codon optimized genes (SEQ ID NOs: 17, 19, 43 and 44) were used in the appended examples.

As was shown herein, the replacement of alanine by a hydrophilic amino acid in the consensus motif $CX_1X_2A_3GKD$ results in beneficial pharmacologic effects.

Therefore, the amino acid sequences of the present invention relates to the mutated Semaphorin 3 or the functional fragment thereof, wherein said mutated Semaphorin 3 or said functional fragment thereof comprises an amino acid sequence $CX_1X_2A_3GKD$, wherein $X_1$ is an amino acid, which is K or N, $X_2$ is an amino acid selected from the group of W, M and L and wherein the alanine ($A_3$) is replaced by said hydrophilic amino acid.

In other words, the present invention relates to the mutated Semaphorin 3 or the functional fragment thereof, wherein said mutated Semaphorin 3 is selected from the group consisting of Semaphorin 3A, Semaphorin 3B, Semaphorin 3C, and Semaphorin 3D, wherein preferably said mutated Semaphorin is Semaphorin 3A, wherein said mutated Semaphorin 3 or said functional fragment thereof comprises an amino acid sequence $CX_1X_2A_3GKD$, wherein $X_1$ is an amino acid, which is K or N, $X_2$ is an amino acid selected from the group of W, M and L, and wherein the alanine ($A_3$) is replaced by said hydrophilic amino acid.

It is herein understood that $A_3$ refers to the alanine corresponding to position 106 of the wild type Semaphorin 3A as shown in SEQ ID NO: 2; to the alanine corresponding to position 105 of the wild type Semaphorin 3B as shown in SEQ ID NO: 6, to the alanine corresponding to position 104 of the wild type Semaphorin 3C as shown in SEQ ID NO: 10, or to the alanine corresponding to position 120 of the wild type Semaphorin 3D as shown in SEQ ID NO: 14. "$A_3$" usually refers to the specific alanine; however, "$A_3$" can also refer to an amino acid residue that is homologous to alanine, such as valine, isoleucine, leucine, methionine, phenylalanine, tyrosine or tryptophan. Most preferably, "$A_3$" is alanine. Furthermore, the amino acid residues defined by "C", "$X_1$", "$X_2$", "G", "K" and "D" can also refer to amino acid residues that are homologous to said respective defined amino acid residues as long as the mutated Semaphorin 3 is selected from the group consisting of Semaphorin 3 A, B, C and D. According to the invention the mutated Semaphorin 3 is not Semaphorin 3E, F or G. In preferred aspects of the invention, "$X_1$" is not isoleucine or valine.

Said hydrophilic amino acid is selected from the group consisting of lysine, arginine, asparagine, glutamine, serine, threonine, glutamic acid, aspartic acid and histidine. More preferably, said hydrophilic amino acid is lysine or arginine and most preferably, said hydrophilic amino acid is lysine.

The term "hydrophilic amino acid" preferably means an amino acid selected from the group consisting of N, Q, S, T, E, D, K, R and H. According to the standard three letter amino acid code and single letter code arginine can be abbreviated (Arg) or (R). Lysine can be abbreviated (Lys) or (K). Aspartic acid can be abbreviated (Asp) or (D). Glutamic acid can be abbreviated (Glu) or (E). Glutamine can be abbreviated (Gln) or (Q). Asparagine can be abbreviated (Asn) or (N). Histidine can be abbreviated (His) or (H). Serine can be abbreviated (Ser) or (S). Threonine can be abbreviated (Thr) or (T). N, Q, S and T are hydrophilic uncharged amino acids and E, D, K, R and H are hydrophilic charged amino acids. It is also envisaged herein that said hydrophilic amino acid can be a non-proteinogenic and/or non-standard $\alpha$-amino acid (such as, e.g., ornithine and citrulline).

The present invention relates to the amino acid sequences comprising the mutated Semaphorin 3 or the functional fragment thereof, wherein said hydrophilic amino acid is selected from the group of K, R, N, Q, S, T, E, D, and H. In preferred aspects, the present invention relates to the amino acid sequences comprising the mutated Semaphorin 3 or the functional fragment thereof, wherein said hydrophilic amino acid is selected from the group of K, R, E, D, and H. In even more preferred aspects, the present invention relates to the amino acid sequences comprising the mutated Semaphorin 3 or the functional fragment thereof, wherein said hydrophilic amino acid is K or R. In most preferred aspects, the present invention relates to the amino acid sequences comprising the mutated Semaphorin 3 or the functional fragment thereof, wherein said hydrophilic amino acid is K.

In certain aspects, the present invention relates to the amino acid sequences comprising the mutated Semaphorin 3 or the functional fragment thereof, wherein the alanine ($A_3$) in the amino acid sequence motif $CX_1X_2A_3GKD$ is replaced by said hydrophilic amino acid selected from the group of K, R, N, Q, S, T, E, D, and H. In certain aspects, the present invention relates to the mutated Semaphorin 3 or the functional fragment thereof, wherein the alanine ($A_3$) in the amino acid sequence motif $CX_1X_2A_3GKD$ is replaced by said hydrophilic amino acid selected from the group of K, R, E, D, and H. In preferred aspects, the present invention relates to the mutated Semaphorin 3 or the functional fragment thereof, wherein the alanine ($A_3$) in the amino acid sequence motif $CX_1X_2A_3GKD$ is replaced by said hydrophilic amino acid is K or R. In particularly preferred aspects the present invention relates to the mutated Semaphorin 3 or the functional fragment thereof, wherein the alanine ($A_3$) in the amino acid sequence motif $CX_1X_2A_3GKD$ is replaced by said hydrophilic amino acid is K.

Further, the invention relates to the polypeptides comprising the mutated Semaphorin 3 or the functional fragment thereof, wherein said mutated Semaphorin 3 or said functional fragment thereof comprises said hydrophilic amino acid at position 106 of SEQ ID NO: 2, at position 105 of SEQ ID NO: 6, at position 104 of SEQ ID NO: 10 or at position 120 of SEQ ID NO: 14. In certain aspects the polypeptides of the present invention comprises at least one additional mutation selected from the group consisting of amino acid substitution(s), addition(s), deletions(s), inversion(s) and duplication(s). Most preferred, the invention relates to the polypeptide comprising the mutated Semaphorin 3A or the functional fragment thereof, wherein said mutated Semaphorin 3A or said functional fragment thereof comprises said hydrophilic amino acid at position 106 of SEQ ID NO: 2 and comprises at least one additional mutation selected from the group consisting of amino acid substitution(s), addition(s), deletions(s), inversion(s) and duplication(s).

In other words, the amino acid sequences of the present invention relates to the mutated Semaphorin 3 or the functional fragment thereof, wherein the mutated Semaphorin 3 or the functional fragment thereof comprises said hydrophilic amino acid at position 106 of SEQ ID NO: 2, at position 105 of SEQ ID NO: 6, at position 104 of SEQ ID NO: 10 or at position 120 of SEQ ID NO: 14 and comprises at least one additional mutation selected from the group consisting of amino acid substitution(s), addition(s), deletions(s), inversion(s) and duplication(s).

In certain aspects, the amino acid sequences of the present invention relates to the mutated Semaphorin 3 or the functional fragment thereof, wherein said mutated Semaphorin 3 or said functional fragment thereof comprises said hydrophilic amino acid at position 106 of SEQ ID NO: 2; at position 106 of SEQ ID NO: 4; at position 105 of SEQ ID NO: 6; at position 105 of SEQ ID NO: 8; at position 104 of SEQ ID NO: 10; at position 104 of SEQ ID NO: 12; at position 120 of SEQ ID NO: 14; or at position 120 of SEQ ID NO: 16 acid and comprises at least one additional mutation selected from the group consisting of amino acid substitution(s), addition(s), deletions(s), inversion(s) and duplication(s).

The following relates to mutated Semaphorin 3 proteins that are encompassed in the fusion proteins/polypeptides. The mutated Semaphorin 3 protein encompassed in the fusion protein/polypeptide can also be a functional fragment of the mutated Semaphorin 3 protein. In other words, the following relates to the herein provided functional fragments of the non-naturally occurring/artificial/mutated Semaphorin 3 proteins or the herein provided functional fragments of the non-naturally occurring/artificial/mutated Semaphorin 3 proteins that are comprised in the fusion protein/polypeptide:

In most preferred embodiments, the herein provided inventive functional fragment of the mutated Semaphorin 3 comprises a functional sema domain, wherein the sema domain comprises the hydrophilic amino acid at the position that by comparison of homology corresponds to position 106 of the wild type Semaphorin 3A as shown in SEQ ID NO: 2 and wherein the sema domain has the properties of mutated Semaphorin 3A, B, C or D. The term "sema domain" refers to a structural domain of Semaphorin 3 proteins. In general, Semaphorins comprise a sema domain fold [NCBI Position-Specific Scoring Matrix (PSSM)-ID: 214747; Conserved Domain Database (CDD): smart00630 and cl15693], which is described in prior art as an about 500 amino acid long variation of the so-called β propeller topology (Chen et al., 2011; Gherardi et al., 2004). More generally, β-propeller proteins are a wide family of disc-like structures generated by circularly arranged structural modules, also known as blades, around a central channel. Each blade is a four-stranded antiparallel β sheet. The strands are designated as strand A to D starting from the N-terminal end of each (Chen et al., 2011; Gherardi et al., 2004). The inner strand of each blade (A) lines the channel at the center of the propeller, with strands B and C of the same repeat radiating outward, and strand D of the next repeat forming the outer edge of the blade. The fact that the inner strand of each sheet (strand A) runs parallel to the central axis whereas the outer one (strand D) runs perpendicular (twisting each β sheet to look like a propeller blade) combine to give the domain its propeller-like appearance. In general, the sema domain as described in prior art is a seven blade β propeller and is the largest known variant of the β propeller fold. The large size of the sema domain results from the presence of additional secondary structure elements inserted in several blades and giving rise to several long loops, mostly on the top face of the β propeller, that were termed as extrusions by Love and colleagues, when they described the first Semaphorin crystal structure (Love et al., 2003). The sema domain displays two extrusions named extrusion 1 (between blade 1 and blade 2) and extrusion 2 (inside blade 5). The sema domain uses a 'loop and hook' system to close the circle between the first and the last blades. The fold is stabilized by inter-sheet hydrophobic contacts and, in most structures, by a 'velcro'-type ring closure in which the N-terminal β strand closes the circle by providing the outermost strand (D) of the seventh (C-terminal) blade. The β propeller is further stabilized by an extension of the N terminus, providing an additional, fifth β strand on the outer edge of blade 6. For example in Semaphorin 3A: i) blade 1 has an additional strand and a helix; ii) blade 4 has an extra helix; blade 5 has the largest insertion composed of three helices and two strands (Antipenko et al., 2003). The sema domain may be characterized by a conserved set of cysteine residues, which form four disulphide bonds to stabilize the structure: Cys 103-Cys 114, Cys 132-Cys 144, Cys 269-Cys 381, and Cys 293-Cys 341. Hence, a sema domain according to the invention can comprise at least one or all of Cys 103-Cys 114, Cys 132-Cys 144, Cys 269-Cys 381, and Cys 293-Cys 341.

In Semaphorins the C-terminal β strand of blade 7 of the sema domain leads directly into an about 50 amino acid long Plexin Semaphorin Integrin (PSI) domain (NCBI PSSM-ID: 214655; smart00423), which nestles against the side of blade 6 of the sema domain β propeller (Love et al., 2003). The PSI is a domain formed by a two-stranded antiparallel β-sheet, with two flanking short a helices, connected by three disulfide bridges forming the inner domain core. This repeat motif is found in semaphorins, in several different extracellular receptors, including plexins, and in the β subunit of αβ integrin heterodimers (Xiong et al., 2004). A key difference between the plexin, semaphorin, and integrin PSI domains is a distinctively shorter interstrand AB loop in plexins and semaphorins. The overall structures of the Plexin-, Semaphorin-, and Integrin-PSI domains are different in the C-terminal half of the domain, suggesting how the function of this portion of PSI is defined by its specific structural context.

The heterodimer interface between the sema domain of a Semaphorin and the sema domain of a Plexin receptor can involve three motifs/sequences/consensus motifs included in the sema domain of Semaphorins. As described herein above, the sema domain of the Semaphorins comprises within its structural fold two extrusions named extrusion 1

(between blade 1 and blade 2) and extrusion 2 (inside blade 5). The three consensus motifs/sequences/motifs that are included in the interface between the Semaphorin and the Plexin receptor are localized in the Semaphorin 3A, B, C or D in: i) extrusion 1 herein referred as motif-1 (e.g. SEMA3A amino acids 104-113 of SEQ ID NO: 2 corresponding to SEQ ID NO: 25; SEMA3B amino acids 103-112 of SEQ ID NO: 6 corresponding to SEQ ID NO: 28; SEMA3C amino acids 102-111 of SEQ ID NO: 10 corresponding to SEQ ID NO: 31; SEMA3D amino acids 118-127 of SEQ ID NO:14 corresponding to SEQ ID NO: 34); ii) blade 3 herein referred as motif-2 (e.g. SEMA3A amino acids 214-221 of SEQ ID NO: 2 corresponding to SEQ ID NO: 26; SEMA3B amino acids 213-220 of SEQ ID NO: 6 corresponding to SEQ ID NO: 29; SEMA3C amino acids 211-218 of SEQ ID NO: 10 corresponding to SEQ ID NO: 32; SEMA3D amino acids 231-238 of SEQ ID NO:14 corresponding to SEQ ID NO: 35); and iii) blade 4 herein referred as motif-3 (e.g. SEMA3A amino acids 274-287 of SEQ ID NO: 2 corresponding to SEQ ID NO: 27; SEMA3B amino acids 274-287 of SEQ ID NO: 6 corresponding to SEQ ID NO: 30; SEMA3C amino acids 271-284 of SEQ ID NO: 10 corresponding to SEQ ID NO: 33; SEMA3D amino acids 291-304 of SEQ ID NO:14 corresponding to SEQ ID NO: 36). Accordingly, the sema domain of the invention can comprise motif-1, motif-2 and/or motif-3.

The amino acid sequence (of extrusion 1/motif-1) as illustrated in SEQ ID NO: 25, 28, 31 or 34 (corresponding to amino acid sequences of Semaphorin A, B, C or D, respectively) corresponds to the amino acid sequence $CX_1X_2A_3GKD$ (wherein $X_1$ is K or N; $X_2$ is an amino acid selected from the group of W, M and L), wherein SEQ ID NOs: 25, 28, 31 or 34 lacks the N-terminal cysteine (C) and comprises further amino acids at the C-terminus. The amino acid sequence (of extrusion 1/motif-1) as illustrated in SEQ ID NO: 25, 28, 31 or 34 is comprised in the herein described mutated Semaphorin 3, the functional fragment thereof of the invention or in the functional sema domain according to the invention, wherein the alanine at the position that by comparison of homology corresponds to position 106 of the wild type Semaphorin 3A as shown in SEQ ID NO: 2 is replaced by the hydrophilic amino acid. Thus, the functional fragment of the mutated Semaphorin 3 comprises the amino acid sequence selected from the group consisting of SEQ ID NO: 25, 28, 31 and 34, wherein the alanine at the position that by comparison of homology corresponds to position 106 of the wild type Semaphorin 3A as shown in SEQ ID NO: 2 is replaced by the hydrophilic amino acid. In preferred embodiments, the functional fragment of the mutated Semaphorin 3A comprises the amino acid sequence as shown in SEQ ID NO: 25, wherein the alanine corresponding to the position 106 of the wild type Semaphorin 3A as shown in SEQ ID NO: 2 is replaced by the hydrophilic amino acid.

The amino acid sequence as illustrated in SEQ ID NO: 53, SEQ ID NO: 54, SEQ ID NO: 55 or SEQ ID NO: 56 (corresponding to amino acid sequences of mutated Semaphorin 3 A, B, C or D, respectively) corresponds to SEQ ID NO: 25, 28, 31 or 34 (motif-1), respectively, with the difference that the amino acid sequence as shown in SEQ ID NO: 53, SEQ ID NO: 54, SEQ ID NO: 55 or SEQ ID NO: 56 has a lysine in place at the position that by comparison of homology corresponds to position 106 of the wild type Semaphorin 3A as shown in SEQ ID NO: 2. The amino acid sequence as shown in SEQ ID NO: 53, SEQ ID NO: 54, SEQ ID NO: 55 or SEQ ID NO: 56 is herein referred as "motif-1*". The herein described mutated Semaphorin 3, the functional fragment thereof or the functional sema domain of the invention comprises an amino acid sequence selected from the group consisting of SEQ ID NO: 53, SEQ ID NO: 54, SEQ ID NO: 55 and SEQ ID NO: 56. In most preferred embodiments, the functional fragment of the inventive mutated Semaphorin 3A comprises the amino acid sequence as shown in SEQ ID NO: 53.

In summary, the herein described functional fragment of the non-naturally occurring/artificial/mutated Semaphorin 3 comprises:

- the amino acid sequence $CX_1X_2A_3GKD$, wherein $X_1$ is an amino acid, which is K or N, $X_2$ is an amino acid selected from the group of W, M and L and wherein the alanine ($A_3$) is replaced by the hydrophilic amino acid;
- the amino acid sequence selected from the group consisting of SEQ ID NO: 25, 28, 31 and 34, wherein the alanine at the position that by comparison of homology corresponds to position 106 of the wild type Semaphorin 3A as shown in SEQ ID NO: 2 is replaced by the hydrophilic amino acid; or
- the amino acid sequence SEQ ID NO: 53, SEQ ID NO: 54, SEQ ID NO: 55 or SEQ ID NO: 56, and wherein the functional fragment has the properties/characteristics of mutated Semaphorin 3A, B, C or D and has not the properties/characteristics of Semaphorin 3E, F or G.

The functional fragment of the mutated Semaphorin 3 can comprise further to the amino acid sequence of motif 1* (SEQ ID NO: 53, SEQ ID NO: 54, SEQ ID NO: 55 or SEQ ID NO: 56) the amino sequence of motif-2 (SEQ ID NO: 26, SEQ ID NO: 29, SEQ ID NO: 32 or SEQ ID NO: 35) and/or the amino sequence of motif-3 (SEQ ID NO: 27, SEQ ID NO: 30, SEQ ID NO: 33 or SEQ ID NO: 36). Accordingly, the mutated Semaphorin 3 or the inventive functional fragment of the mutated Semaphorin 3 comprises further to the amino acid sequence $CX_1X_2A_3GKD$ one or more of the following amino acid sequences as defined in any one of SEQ ID NO: 26, SEQ ID NO: 27, SEQ ID NO: 29, SEQ ID NO: 30, SEQ ID NO: 32, SEQ ID NO: 33, SEQ ID NO: 35 or SEQ ID NO: 36, wherein $X_1$ is an amino acid, which is K or N, $X_2$ is an amino acid selected from the group of W, M and L and wherein the alanine ($A_3$) is replaced by the hydrophilic amino acid, and wherein the functional fragment should have the characteristics of mutated Semaphorin 3A, B, C or D. It is herein understood that the functional fragment of the mutated Semaphorin 3 of this invention should not have the characteristics of Semaphorin 3E, F or G. In preferred embodiments, the functional fragment of the mutated Semaphorin 3A comprises further to the amino acid sequence $CX_1X_2A_3GKD$ one or more of the amino acid sequences as defined in SEQ ID NO: 26 or SEQ ID NO: 27, wherein $X_1$ is K, $X_2$ is W and wherein the alanine ($A_3$) is replaced by the hydrophilic amino acid, and wherein the functional fragment should have the characteristics of mutated Semaphorin 3A.

The PSI domain stabilizes the structural conformation and/or the structural integrity of the functional sema domain, the functional fragment of the mutated Semaphorin 3 or the fusion protein/polypeptide. The functional fragment of the mutated Semaphorin 3 can comprise fragments of the PSI domain so long as the fragment of the PSI domain has the function to stabilize the mutated Semaphorin 3 or the functional fragment thereof or the fusion protein/polypeptide, more preferably, the functional sema domain. The PSI domain of Semaphorins 3A, B, C or D shares conserved amino acid sequences illustrated in the consensus motifs/sequences/motifs SEQ ID NO: 45, SEQ ID NO: 46, SEQ ID NO: 47 or SEQ ID NO: 48, respectively. Accordingly, the PSI domain of the invention comprises one or more of the following sequences SEQ ID NO: 45, SEQ ID NO: 46, SEQ ID NO: 47 or SEQ ID NO: 48. An exemplary amino acid sequence of the PSI domain of human Semaphorin 3A spans from amino acid residues 517 to 567 of SEQ ID NO: 2. As shown in the appended examples and thus more preferably, an exemplary amino acid sequence of a shorter PSI domain, which lacks furin protease cleavage sites, spans from amino acid residues 517 to 548 of SEQ ID NO: 2. Exemplary PSI domains are given in the following: an exemplary amino acid sequence of the PSI domain of human Semaphorin 3A spans from amino acid residues 517 to 548 of SEQ ID NO: 2, an exemplary amino acid sequence of the PSI domain of human Semaphorin 3B spans from amino acid residues 516 to 547 of SEQ ID NO: 6, an exemplary amino acid sequence of the PSI domain of human Semaphorin 3C spans from amino acid residues 514 to 545 of SEQ ID NO: 10, and an exemplary amino acid sequence of the PSI domain of human Semaphorin 3D spans from amino acid residues 534 to 565) of SEQ ID NO: 14.

Further, the herein provided mutated Semaphorin 3 or the functional fragment of the mutated Semaphorin 3 can comprise further to the amino acid sequence $CX_1X_2A_3GKD$ one or more of the following amino acid sequence(s) as defined in any one of SEQ ID NO: 26, SEQ ID NO: 27, SEQ ID NO: 29, SEQ ID NO: 30, SEQ ID NO: 32, SEQ ID NO: 33, SEQ ID NO: 35, SEQ ID NO: 36, SEQ ID NO: 45, SEQ ID NO: 46, SEQ ID NO: 47 or SEQ ID NO: 48, wherein $X_1$ is an amino acid, which is K or N, $X_2$ is an amino acid selected from the group of W, M and L and wherein the alanine ($A_3$) is replaced by the hydrophilic amino acid, and wherein the functional fragment should have the characteristics of mutated Semaphorin 3A, B, C or D. It is understood herein that the functional fragment of the mutated Semaphorin 3 of this invention should not have the characteristics of Semaphorin 3E, F or G. In preferred embodiments, the mutated Semaphorin 3 or the functional fragment of the mutated Semaphorin 3A comprises further to the amino acid sequence $CX_1X_2A_3GKD$ one or more of the following amino acid sequences as defined in any one of SEQ ID NO: 26, SEQ ID NO: 27 or SEQ ID NO: 45, wherein $X_1$ is K, $X_2$ is W and wherein the alanine ($A_3$) is replaced by the hydrophilic amino acid, and wherein the functional fragment should have the characteristics of mutated Semaphorin 3A. It is herein understood that the herein above given amino acid sequences, inter alia, SEQ ID NO: 53, SEQ ID NO: 54, SEQ ID NO: 55 or SEQ ID NO: 56, can be in the context of the amino acid sequence of naturally occurring Semaphorin 3 proteins. It is also herein envisaged that these amino acid sequences can be linked together with artificial amino acid linkers, e.g., serine-glycine linkers. The length of the functional fragments of the mutated Semaphorin 3 proteins is not limited as long as the functional fragments according to the invention exhibit the function e.g., as an angiogenesis inhibitor and/or as a vascular normalizing agent, as described above for the mutated Semaphorin 3, the functional fragment thereof, the fusion protein comprising the functional fragment or the functional sema domain. It is envisaged herein that such functional fragments can have a length of e.g., 10, 20, 30, 40, 50, 60, 80, 100, 200, 250, 300, 400, 500 or 600 amino acids. Preferably, such fragments have a length of about 400 to 500 amino acids. Preferably, such fragments have a length of about 300 to 400 amino acids. Preferably, such fragments have a length of about 100 to 300 amino acids. It is herein envisaged that that the amino acid sequence of the herein provided functional fragments of the non-naturally occurring/artificial/mutated Semaphorin 3 proteins can be truncated at the N-terminus, the C-terminus and/or in the body of the amino acid sequence. It is herein envisaged that, e.g., 10, 20, 30, 40, or 50 amino acids can be deleted. These deletions/modifications do not depart from the scope of the invention as long as the functional fragment has the characteristics of mutated Semaphorin 3A, B, C or D. Further, these deletions/modifications are not limited as long as the herein provided functional fragment or the fusion protein/polypeptide comprising the herein provided functional fragment, which has the hydrophilic amino acid in place of the alanine at the position which corresponds by comparison of homology to position 106 of the wild type Semaphorin 3A as shown in SEQ ID NO: 2, has the function/activity as defined herein above, e.g., as an angiogenesis inhibitor and/or as a vascular normalizing agent, of the mutated Semaphorin 3, the functional fragment thereof, the fusion protein comprising the functional fragment or the functional sema domain.

In most preferred embodiments, the functional fragment of the mutated Semaphorin 3 according to the invention comprises the functional sema domain, wherein said sema domain comprises the hydrophilic amino acid at the position that by comparison of homology corresponds to the position 106 of the wild type Semaphorin 3A as shown in SEQ ID NO: 2. In other words, the mutated Semaphorin 3 according to the invention may comprise the functional sema domain, wherein said sema domain comprises the hydrophilic amino acid at the position that by comparison of homology corresponds to the position 106 of the wild type Semaphorin 3A as shown in SEQ ID NO: 2. The functional sema domain of the invention comprises the amino acid sequence as described in motif-1* or comprises the amino acid sequence $CX_1X_2A_3GKD$, wherein $X_1$ is an amino acid, which is K or N, $X_2$ is an amino acid selected from the group of W, M and L and wherein the alanine ($A_3$) is replaced by the hydrophilic amino acid, and wherein said sema domain should have the characteristics of mutated Semaphorin 3A, B, C or D. It is herein understood that the herein described functional sema domain of the mutated Semaphorin 3 should not have the characteristics of Semaphorin 3E, F or G. Furthermore, the functional sema domain of the invention can comprise further to the amino acid sequence of motif 1* (SEQ ID NO: 53, SEQ ID NO: 54, SEQ ID NO: 55 and SEQ ID NO: 56) the amino sequence of motif-2 (SEQ ID NO: 26, SEQ ID NO: 29, SEQ ID NO: 32 or SEQ ID NO: 35) and/or the amino sequence of motif-3 (SEQ ID NO: 27, SEQ ID NO: 30, SEQ ID NO: 33, SEQ ID NO: 36, SEQ ID NO: 45, SEQ ID NO: 46, SEQ ID NO: 47 or SEQ ID NO: 48. Furthermore, the functional sema domain can comprise at least one additional mutation selected from the group consisting of amino acid substitution(s), addition(s), deletions(s), inversion(s) and duplication(s). Further, the functional sema domain can comprise additional amino acid deletion(s). It is envisaged herein that that the amino acid sequence of the functional sema domain can be truncated at the N-terminus, the C-terminus and/or in the body of the amino acid sequence. It is envisaged herein that, e.g., 10, 20, 30, 40, 50 or 100 amino acids can be deleted. These deletions/modifications do not depart from the scope of the invention as long as the functional sema domain has the characteristics of the mutated Semaphorin 3A, B, C or D as defined herein above. Further, these deletions/modifications are not limited as long as the herein provided functional sema domain or the herein provided fusion protein comprising said sema domain, which has the hydrophilic amino acid in place of the alanine at the position which corresponds by comparison of homology to position 106 of the wild type Semaphorin 3A as shown in SEQ ID NO: 2, exhibits the function/activity as defined herein above, e.g., as an angiogenesis inhibitor and/or as a vascular normalizing agent, of the mutated Semaphorin 3 or the functional fragment thereof or of the fusion protein comprising the functional fragment or the functional sema domain. It is herein understood that the functional sema domain interacts with another functional sema domain of Semaphorins and the Plexin receptor. This can occur by means of different surface exposed areas of the sema domain. Without being bound by theory a sema domain displays at least two distinct areas on its surface. The first are area supports its binding to another sema domain of a Semaphorin and the second area is involved in its binding to the Plexin receptor.

An exemplary nucleic acid molecule encoding the functional sema domain or the functional fragment of the mutated Semaphorin 3 of the present invention can comprise:

the nucleotides from 601 to 1206 of SEQ ID NO: 1, wherein the nucleotides GCT at position 631 to 633 of SEQ ID NO: 1 are replaced by nucleotides encoding the hydrophilic amino acid;

the nucleotides from 529 to 1137 of SEQ ID NO: 5, wherein the nucleotides GCA at position 559 to 561 of SEQ ID NO: 5 are replaced by nucleotides encoding the hydrophilic amino acid;

the nucleotides from 842 to 1444 of SEQ ID NO: 9, wherein the nucleotides GCT at position 872 to 874 of SEQ ID NO: 9 are replaced by nucleotides encoding the hydrophilic amino acid; or the nucleotides from 368 to 982 of SEQ ID NO: 13 wherein the nucleotides GCC at position 398 to 400 of SEQ ID NO: 13 are replaced by nucleotides encoding the hydrophilic amino acid.

SEQ ID NO: 1, SEQ ID NO: 5, SEQ ID NO: 9 or SEQ ID NO: 13 is the full-length nucleic acid sequence encoding wild type human Semaphorin 3A, B, C or D, respectively.

In preferred embodiments, the nucleic acid molecule encoding the functional sema domain or the functional fragment of the mutated Semaphorin 3A of the present invention comprises the nucleotides from 601 to 1206 of SEQ ID NO: 1, wherein the nucleotides GCT at position 631 to 633 of SEQ ID NO: 1 are replaced by nucleotides encoding the hydrophilic amino acid.

Further, an exemplary nucleic acid molecule encoding the functional sema domain or the functional fragment of the mutated Semaphorin 3 of the present invention can comprise the nucleotides from 601 to 1206 of SEQ ID NO: 57; the nucleotides from 529 to 1137 of SEQ ID NO: 61; the nucleotides from 842 to 1444 of SEQ ID NO: 65; or the nucleotides from 368 to 982 of SEQ ID NO: 69. SEQ ID NO: 57, 61, 65 or 65 comprises a nucleic acid sequence encoding the mutated Semaphorin 3A, B, C or D, respectively, wherein lysine is in place at the position that by comparison of homology corresponds to position 106 of the wild type Semaphorin 3A as shown in SEQ ID NO: 2. In preferred embodiments, the nucleic acid molecule encoding the functional sema domain or the functional fragment of the mutated Semaphorin 3A of the present invention comprises the nucleotides from 601 to 1206 of SEQ ID NO: 57.

Further, an exemplary polypeptide comprises the functional fragment of the mutated Semaphorin 3, wherein the functional fragment comprises or is the functional sema domain of the mutated Semaphorin 3 of the present invention as shown in:

In other words, the mutated Semaphorin 3 or the functional fragment thereof comprises or is the functional sema domain of the mutated Semaphorin 3 of the present invention as shown in:

SEQ ID NO: 21, wherein the alanine residue corresponding to position 106 of SEQ ID NO: 2 is replaced by the hydrophilic amino acid;

SEQ ID NO: 22, wherein the alanine residue corresponding to position 105 of SEQ ID NO: 6 is replaced by the hydrophilic amino acid;

SEQ ID NO: 23 wherein the alanine residue corresponding to position 104 of SEQ ID NO: 10 is replaced by the hydrophilic amino acid; or SEQ ID NO: 24, wherein the alanine residue corresponding to position 120 of SEQ ID NO: 14 is replaced by the hydrophilic amino acid.

In preferred embodiments, the amino acid sequence of the functional sema domain or the functional fragment of the mutated Semaphorin 3A of the present invention comprises an amino acid sequence as shown in SEQ ID NO: 21, wherein the alanine residue corresponding to position 106 of SEQ ID NO: 2 is replaced by the hydrophilic amino acid.

SEQ ID NO: 49, 50, 51 or 52 comprises an amino acid sequence of an exemplary functional sema domain or an exemplary functional fragment of the mutated Semaphorin 3A, B, C or D, respectively, wherein the alanine is replaced by a lysine at the position that by comparison of homology corresponds to position 106 of the wild type Semaphorin 3A as shown in SEQ ID NO: 2. Thus, an exemplary amino acid sequence of the functional sema domain or the functional fragment of the mutated Semaphorin 3 of the present invention can comprise the amino acid sequence that is selected from the group consisting of SEQ ID NO: 49, SEQ ID NO: 50, SEQ ID NO: 51 and SEQ ID NO: 52. In preferred embodiments, the amino acid sequence of the functional sema domain or the functional fragment of the mutated Semaphorin 3A of the present invention comprises the amino acid sequence as shown in SEQ ID NO: 49. Fragments of the functional sema domain are also envisaged herein. For example, the sema domain can also comprise shortened versions of the herein defined exemplary sema domains.

The following relates to the most preferred embodiment of the invention, the fusion protein/polypeptide. In most preferred embodiments, the polypeptide of the invention is the fusion protein. The fusion protein comprises the non-naturally occurring/artificial/mutated Semaphorin 3 protein, the non-naturally occurring/artificial/mutated functional fragment of the Semaphorin 3, the non-naturally occurring/artificial/mutated functional sema domain of the Semaphorin 3, the stabilizer domain and/or the dimerization domain. Any one of the herein above defined functional fragments of the mutated Semaphorin 3 can be comprised in the fusion protein, wherein the functional fragments have the characteristics/properties of mutated Semaphorin 3A, B, C or D and not of Semaphorin 3E, F or G. In other words, the fusion protein may comprise the mutated Semaphorin 3 or the functional fragment thereof according to the invention.

Accordingly, the fusion protein of the invention comprises the mutated Semaphorin 3 or the functional fragment thereof, wherein the mutated Semaphorin 3 or the functional fragment thereof comprises the amino acid sequence selected from the group consisting of SEQ ID NO: 25, 28, 31 and 34, wherein the alanine at the position that by comparison of homology corresponds to position 106 of the wild type Semaphorin 3A as shown in SEQ ID NO: 2 is replaced by the hydrophilic amino acid. Optionally, the fusion protein of the invention comprises the mutated Semaphorin 3 or the functional fragment thereof, wherein the mutated Semaphorin 3 or the functional fragment thereof comprises the amino acid sequence $CX_1X_2A_3GKD$, wherein $X_1$ is an amino acid, which is K or N, $X_2$ is an amino acid selected from the group of W, M and L and wherein the alanine ($A_3$) is replaced by the hydrophilic amino acid. Optionally, the fusion protein of the invention comprises the mutated Semaphorin 3 or the functional fragment thereof, wherein the mutated Semaphorin 3 or the functional fragment thereof comprises the amino acid sequence selected from the group consisting of SEQ ID NO: 53, SEQ ID NO: 54, SEQ ID NO: 55 and SEQ ID NO: 56.

In preferred embodiments, the fusion protein of the invention comprises the amino acid sequence as shown in SEQ ID NO: 25, wherein the alanine corresponding to the position 106 of the wild type Semaphorin 3A as shown in SEQ ID NO: 2 is replaced by the hydrophilic amino acid. Optionally, in preferred embodiments, the inventive fusion protein comprises the amino acid sequence as shown in SEQ ID NO: 53.

Further, the inventive fusion protein comprises the mutated Semaphorin 3 or the functional fragment thereof, wherein the mutated Semaphorin 3 or the functional fragment thereof comprises further to the amino acid sequence $CX_1X_2A_3GKD$ one or more of the following amino acid sequences as defined in any one of SEQ ID NO: 26, SEQ ID NO: 27, SEQ ID NO: 29, SEQ ID NO: 30, SEQ ID NO: 32, SEQ ID NO: 33, SEQ ID NO: 35 or SEQ ID NO: 36, wherein $X_1$ is an amino acid, which is K or N, $X_2$ is an amino acid selected from the group of W, M and L and wherein the alanine ($A_3$) is replaced by the hydrophilic amino acid, and wherein the functional fragment should have the characteristics of mutated Semaphorin 3A, B, C or D. It is herein understood that the functional fragment of the mutated Semaphorin 3 of this invention should not have the characteristics of Semaphorin 3E, F or G. In preferred embodiments, the fusion protein of the invention comprises the mutated Semaphorin 3A or the functional fragment thereof, wherein the mutated Semaphorin 3A or the functional fragment thereof comprises further to the amino acid sequence $CX_1X_2A_3GKD$ one or more of the following amino acid sequences as defined in SEQ ID NO: 26 or SEQ ID NO: 27, wherein $X_1$ is K, $X_2$ is W and wherein the alanine ($A_3$) is replaced by the hydrophilic amino acid, and wherein the functional fragment should have the characteristics of mutated Semaphorin 3A.

Further, the fusion protein of the invention comprises the mutated Semaphorin 3 or the functional fragment thereof, wherein the mutated Semaphorin 3 or the functional fragment thereof comprises further to the amino acid sequence $CX_1X_2A_3GKD$ one or more of the following amino acid sequence(s) as defined in any one of SEQ ID NO: 26, SEQ ID NO: 27, SEQ ID NO: 29, SEQ ID NO: 30, SEQ ID NO: 32, SEQ ID NO: 33, SEQ ID NO: 35, SEQ ID NO: 36, SEQ ID NO: 45, SEQ ID NO: 46, SEQ ID NO: 47 and SEQ ID NO: 48, wherein $X_1$ is an amino acid, which is K or N, $X_2$ is an amino acid selected from the group of W, M and L and wherein the alanine ($A_3$) is replaced by the hydrophilic amino acid, and wherein the functional fragment should have the characteristics of Semaphorin mutated 3A, B, C or D. It is herein understood that the functional fragment of the mutated Semaphorin 3 of this invention should not have the characteristics of Semaphorin 3E, F or G. In preferred embodiments, the fusion protein of the invention comprises the mutated Semaphorin 3A or the functional fragment thereof, wherein the mutated Semaphorin 3A or the functional fragment thereof comprises further to the amino acid sequence $CX_1X_2A_3GKD$ one or more of the following amino acid sequences as defined in any one of SEQ ID NO: 26, SEQ ID NO: 27 or SEQ ID NO: 45, wherein $X_1$ is K, $X_2$ is W and wherein the alanine ($A_3$) is replaced by the hydrophilic amino acid, and wherein the functional fragment should have the characteristics of mutated Semaphorin 3A.

In most preferred embodiments, the invention relates to the fusion protein comprising the functional sema domain, wherein within the functional sema domain of the mutated Semaphorin 3 the alanine corresponding to position 106 of the wild type Semaphorin 3A of SEQ ID NO: 2 is replaced by the hydrophilic amino acid or wherein the alanine corresponding to said alanine 106 in Semaphorin 3B, 3C or 3D is replaced by the hydrophilic amino acid. In other words, the fusion protein of the invention comprises the functional fragment of the mutated Semaphorin 3, wherein said functional fragment comprises the functional sema domain, wherein the sema domain comprises the hydrophilic amino acid at the position that by comparison of homology corresponds to the position 106 of the wild type Semaphorin 3A as shown in SEQ ID NO: 2. In other words, the fusion protein of the invention comprises the functional sema domain, wherein the sema domain comprises the hydrophilic amino acid at the position that by comparison of homology corresponds to the position 106 of the wild type Semaphorin 3A as shown in SEQ ID NO: 2.

The functional sema domain comprised in the fusion protein of the invention comprises the amino acid sequence as shown in motif-1* (SEQ ID NO: 53, SEQ ID NO: 54, SEQ ID NO: 55 and SEQ ID NO: 56) or the functional sema domain comprised in the fusion protein of the invention comprises the amino acid sequence $CX_1X_2A_3GKD$, wherein $X_1$ is an amino acid, which is K or N, $X_2$ is an amino acid selected from the group of W, M and L and wherein the alanine ($A_3$) is replaced by the hydrophilic amino acid, and wherein the functional sema domain should have the characteristics of Semaphorin 3A, B, C or D. It is herein understood that the functional sema domain of the mutated Semaphorin 3 comprised in the fusion protein of this invention should not have the characteristics of Semaphorin 3E, F or G, but should have the characteristics of mutated Semaphorin 3A, B, C or D. Further, the fusion protein comprising the inventive functional sema domain can comprise further to the amino acid sequence of motif 1* (SEQ ID NO: 53, SEQ ID NO: 54, SEQ ID NO: 55 and SEQ ID NO: 56) the amino sequence of motif-2 (SEQ ID NO: 26, SEQ ID NO: 29, SEQ ID NO: 32 or SEQ ID NO: 35) and/or the amino sequence of motif-3 (SEQ ID NO: 27, SEQ ID NO: 30, SEQ ID NO: 33 or SEQ ID NO: 36). Furthermore, the functional sema domain or the functional fragment of the mutated Semaphorin 3 comprised in the fusion protein can comprise at least one additional mutation selected from the group consisting of amino acid substitution(s), addition(s), deletions(s), inversion(s) and duplication(s). It is herein envisaged that that the amino acid sequence of the functional sema domain or the functional fragment of the mutated Semaphorin 3 comprised in the fusion protein can be truncated at the N-terminus, the C-terminus and/or in the body of the amino acid sequence. It is envisaged herein that, e.g., 10, 20, 30, 40, 50 or 100 amino acids can be deleted. These deletions/modifications do not depart from the scope of the invention as long as the functional fragment or the functional sema domain has the characteristics of mutated Semaphorin 3A, B, C or D. Further, these deletions/modifications are not limited as long as the fusion protein comprising the functional sema domain or the functional fragment of the mutated Semaphorin 3 exhibits the herein above defined function/activity of the fusion protein/polypeptide comprising said non-naturally occurring/artificial/mutated Semaphorin 3 proteins or said non-naturally occurring/artificial/mutated functional fragments or functional sema domains of said Semaphorin 3 proteins, e.g., as an angiogenesis inhibitor and/or as a vascular normalizing agent. The fusion protein can also comprise a short isoform of the mutated Semaphorin 3.

An exemplary nucleic acid molecule encoding the functional sema domain or the functional fragment of the mutated Semaphorin 3 that can be comprised in the fusion protein is given in the following:

the nucleotides from 601 to 1206 of SEQ ID NO: 1, wherein the nucleotides GCT at position 631 to 633 of SEQ ID NO: 1 are replaced by nucleotides encoding a hydrophilic amino acid;

the nucleotides from 529 to 1137 of SEQ ID NO: 5, wherein the nucleotides GCA at position 559 to 561 of SEQ ID NO: 5 are replaced by nucleotides encoding a hydrophilic amino acid;

the nucleotides from 842 to 1444 of SEQ ID NO: 9, wherein the nucleotides GCT at position 872 to 874 of SEQ ID NO: 9 are replaced by nucleotides encoding a hydrophilic amino acid;

or the nucleotides from 368 to 982 of SEQ ID NO: 13 wherein the nucleotides GCC at position 398 to 400 of SEQ ID NO: 13 are replaced by nucleotides encoding a hydrophilic amino acid.

In preferred embodiments, the fusion protein comprises the functional sema domain of the present invention, wherein the sema domain is encoded by the nucleic acid molecule that comprises the nucleotides from 601 to 1206 of SEQ ID NO: 1, wherein the nucleotides GCT at position 631 to 633 of SEQ ID NO: 1 are replaced by nucleotides encoding the hydrophilic amino acid.

An exemplary nucleic acid molecule encoding the functional sema domain or the functional fragment of the mutated Semaphorin 3 comprised in the fusion protein can comprise the nucleotides from 601 to 1206 of SEQ ID NO: 57; the nucleotides from 529 to 1137 of SEQ ID NO: 61; the nucleotides from 842 to 1444 of SEQ ID NO: 65; or the nucleotides from 368 to 982 of SEQ ID NO: 69. SEQ ID NO: 57, 61, 65 or 65 comprises a nucleic acid sequence encoding the full length mutated Semaphorin 3A, B, C or D, respectively, wherein lysine is in place at the position that by comparison of homology corresponds to position 106 of the wild type Semaphorin 3A as shown in SEQ ID NO: 2. In preferred embodiments, the nucleic acid molecule encoding the functional sema domain of the mutated Semaphorin 3A comprised in the fusion protein comprises the nucleotides from 601 to 1206 of SEQ ID NO: 57.

Further, an exemplary fusion protein/polypeptide can comprise the functional fragment of the mutated Semaphorin 3, wherein the functional fragment comprises or is the functional sema domain of mutated Semaphorin 3 as defined in:

SEQ ID NO: 21, wherein the alanine residue corresponding to position 106 of SEQ ID NO: 2 is replaced by a hydrophilic amino acid;

SEQ ID NO: 22, wherein the alanine residue corresponding to position 105 of SEQ ID NO: 6 is replaced by a hydrophilic amino acid;

SEQ ID NO: 23 wherein the alanine residue corresponding to position 104 of SEQ ID NO: 10 is replaced by a hydrophilic amino acid; or SEQ ID NO: 24, wherein the alanine residue corresponding to position 120 of SEQ ID NO: 14 is replaced by a hydrophilic amino acid.

In preferred embodiments, the amino acid sequence of the functional sema domain of the mutated Semaphorin 3A comprised in the fusion protein comprises an amino acid sequence as shown in SEQ ID NO: 21, wherein the alanine residue corresponding to position 106 of SEQ ID NO: 2 is replaced by a hydrophilic amino acid.

SEQ ID NO: 49, 50, 51 and 52 comprise amino acid sequences of exemplary functional sema domains or functional fragments of the mutated Semaphorin 3A, B, C and D, respectively, that can be comprised in the fusion protein, wherein the alanine is replaced by a lysine at the position that by comparison of homology corresponds to position 106 of the wild type Semaphorin 3A as shown in SEQ ID NO: 2. Thus, an exemplary fusion protein can comprise the functional fragment of the mutated Semaphorin 3, wherein the functional fragment comprises or is the sema domain selected from the group consisting of SEQ ID NO: 49, SEQ ID NO: 50, SEQ ID NO: 51 and SEQ ID NO: 52. In preferred embodiments, the amino acid sequence of the functional sema domain of the mutated Semaphorin 3A comprised in the fusion protein comprises the amino acid sequence as shown in SEQ ID NO: 49.

In preferred embodiments, the fusion protein comprises further to the mutated Semaphorin 3 or the functional fragment thereof a stabilizer domain. Said stabilizer domain stabilizes the structural conformation and/or the structural integrity of the non-naturally occurring/artificial/mutated Semaphorin 3 protein, the herein provided functional fragment of the non-naturally occurring/artificial/mutated Semaphorin 3 protein, or the herein provided functional sema domain. As defined herein above, such a stabilizer domain can be the PSI domain or fragments thereof. Therefore, the fusion protein comprising the mutated Semaphorin 3 or the functional fragment thereof can be stabilized by the PSI domain. The stabilizer domain can be the PSI domain or a fragment thereof, wherein said PSI domain can comprise one of the following consensus sequence motifs SEQ ID NO: 45, SEQ ID NO: 46, SEQ ID NO: 47 or SEQ ID NO: 48. An exemplary amino acid sequence of the PSI domain of human Semaphorin 3A spans from amino acid residues 517 to 567 of SEQ ID NO: 2. As shown in the appended examples and thus more preferably, an exemplary amino acid sequence of the PSI domain spans from amino acid residues 517 to 548 of SEQ ID NO: 2. Exemplary PSI domains that can be comprised in the fusion protein are given in the following: an exemplary amino acid sequence of the PSI domain of human Semaphorin 3A spans from amino acid residues 517 to 548 of SEQ ID NO: 2, an exemplary amino acid sequence of the PSI domain of human Semaphorin 3B spans from amino acid residues 516 to 547 of SEQ ID NO: 6, an exemplary amino acid sequence of the PSI domain of human Semaphorin 3C spans from amino acid residues 514 to 545 of SEQ ID NO: 10, and an exemplary amino acid sequence of the PSI domain of human Semaphorin 3D spans from amino acid residues 534 to 565 of SEQ ID NO: 14.

In preferred embodiments, the fusion protein can comprise the mutated Semaphorin 3 or the functional fragment thereof, wherein the functional fragment comprises the sema domain and the PSI domain. Therefore, an exemplary fusion protein can comprise the mutated Semaphorin 3 or the functional fragment thereof, wherein the functional fragment thereof comprise an amino acid sequence:

spanning from amino acid residues 1 to 548 of SEQ ID NO: 2, wherein the alanine residue at position 106 of SEQ ID NO: 2 is replaced by the hydrophilic amino acid;

spanning from amino acid residues 1 to 547 of SEQ ID NO: 6, wherein the alanine residue at position 105 of SEQ ID NO: 6 is replaced by the hydrophilic amino acid;

spanning from amino acid residues 1 to 565 of SEQ ID NO: 10, wherein the alanine residue at position 104 of SEQ ID NO: 10 is replaced by the hydrophilic amino acid; or spanning from amino acid residues 1 to 545 of SEQ ID NO: 14, wherein the alanine residue at position 120 of SEQ ID NO: 14 is replaced by the hydrophilic amino acid. In preferred embodiments, the functional fragment of the mutated Semaphorin 3A comprised in the fusion protein has a polypeptide spanning from amino acid residues 1 to 548 of SEQ ID NO: 2, wherein the alanine residue at position 106 of SEQ ID NO: 2 is replaced by the hydrophilic amino acid.

In other words, the fusion protein can comprise the mutated Semaphorin 3 comprising the sema domain and the PSI domain. Therefore, an exemplary fusion protein can comprise the mutated Semaphorin 3 comprising an amino acid sequence:

spanning from amino acid residues 1 to 548 of SEQ ID NO: 2, wherein the alanine residue at position 106 of SEQ ID NO: 2 is replaced by the hydrophilic amino acid;

spanning from amino acid residues 1 to 547 of SEQ ID NO: 6, wherein the alanine residue at position 105 of SEQ ID NO: 6 is replaced by the hydrophilic amino acid;

spanning from amino acid residues 1 to 565 of SEQ ID NO: 10, wherein the alanine residue at position 104 of SEQ ID NO: 10 is replaced by the hydrophilic amino acid; or spanning from amino acid residues 1 to 545 of SEQ ID NO: 14, wherein the alanine residue at position 120 of SEQ ID NO: 14 is replaced by the hydrophilic amino acid.

As indicated in the appended examples and as explained above, dimerization of the mutated Semaphorin 3 proteins increases the inhibiting effect of EC migration. Therefore, the mutated Semaphorin 3 proteins of the invention are preferably in the form of the dimer. A functional sema domain of the mutated Semaphorin 3 proteins may be responsible for the dimerization and the binding to the Plexin receptors. The binding of the Semaphorin 3 to its Plexin receptor leads to an activation of the cytoplasmic region of the Plexin receptor, which results in active downstream signaling. Without being bound by theory, the Plexin receptors are activated by the Semaphorin induced dimerization. Therefore, in most preferred embodiments of the invention, the herein provided mutated Semaphorin 3 or the functional sema domain or functional fragment of the mutated Semaphorin 3 is in the form of a dimer with another herein provided mutated Semaphorin 3 or the functional sema domain or functional fragment of the mutated Semaphorin 3. The dimerization of the non-naturally occurring/artificial/mutated Semaphorin 3 proteins or the herein provided functional fragments of the non-naturally occurring/artificial/mutated Semaphorin 3 proteins that are comprised in the fusion protein can be induced by said functional fragments, e.g. by the functional sema domain itself and/or can be induced/promoted by a dimerization domain.

In most preferred embodiments, the fusion protein comprises a dimerization domain further to the mutated Semaphorin 3, the functional fragment of the mutated Semaphorin 3 and/or the stabilizer domain. In other words, the fusion protein comprises further to the mutated Semaphorin 3 or to the functional fragment thereof a stabilizer domain stabilizing the structural integrity of the molecule and/or a dimerization domain inducing homo- or hetero-dimers. In other words, the fusion protein can comprise the stabilizer domain and/or the dimerization domain. The "dimerization domain" refers to a domain that induce/promote spatial proximity of the non-naturally occurring/artificial/mutated Semaphorin 3 proteins, the herein provided functional fragments of the non-naturally occurring/artificial/mutated Semaphorin 3 proteins, or the herein provided functional sema domains. It is herein understood that a "dimer" is an oligomer consisting of two structural similar monomers joined by bonds that can be either weak or strong, i.e., intermolecular or covalent. The two monomers that form the dimer can be comprised in the same fusion protein or in two fusion proteins. The dimerization domain can be any dimerization domain so long as the two dimerization domains have with each other a dissociation constant $K_D$ in the range of $10^{-5}$M to $10^{-6}$ M. The binding affinity of two sema domains of Semaphorin 3 was found to be in the range of $10^{-5}$ to $10^{-6}$ M (Antipenko et al., 2003). The dimerization domain can be selected from the group of a C-terminal IgG constant domain, DARPin and leucine zipper. In a preferred embodiment, the dimerization domain is an IgG constant domain. In an even more preferred embodiment, the dimerization domain is an IgG1 or IgG3 domain. In an even more preferred embodiment, the dimerization domain is an IgG1. Such exemplary amino acid and encoding nucleic acid sequences of human IgG1 are given in SEQ ID NOs: 37, 38 and 41. In a most preferred embodiment, the constant fragment of the IgG1 domain is used as a dimerization domain comprising the amino acid sequence spanning from the position 104 to 330. Such an exemplary amino acid sequence is depicted in SEQ ID NO: 41. The mouse IgG1 constant fragment can also be used corresponding amino acid and nucleic acid sequences are depicted in SEQ ID NOs: 39, 40 and 42. The affinity strength with which, for example, leucine-zippers and/or constant domains, like immunoglobulin CH3 or Fc fragments, hetero- and homo-dimerize is estimated to be at a dissociation constant $K_D$ in the range of ~$10^{-5}$ to $10^{-6}$ M. The dissociation constant of a dimer of sema domains was estimated to be in the range of $10^{-5}$ to $10^{-6}$ M (Antipenko et al., 2003). In general, the $K_D$s referred to herein (i) apply to, (ii) are at or (iii) are to be measured at a temperature of 4 to 38° C., preferably 4 to 20° C. (for example 10° C.) or 20 to 38° C. (for example 30° C.), and/or a pH of 4.5 to 8 (for example a pH of 7). As shown in the appended examples, the dimerization domains, e.g. the IgG1 domain, can be stabilized by disulphide bridges. The two monomers of the dimerization domains, e.g. the IgG1 domains, can be stabilized by disulphide bridges within the dimer.

In most preferred embodiments, the non-naturally occurring/artificial/mutated Semaphorin 3 proteins or the functional fragments thereof or the fusion proteins comprising said Semaphorin 3 protein(s) or said functional fragment(s) thereof form homo- or hetero-dimers with each other. The term "homo-dimer" means that two identical monomers are in the form of a dimer. The term "hetero-dimer" means that two different monomers are in the form of a dimer.

In certain aspects, the two monomers of the dimer can be comprised in one fusion protein. It is envisaged herein that two of the non-naturally occurring/artificial/mutated Semaphorin 3 proteins, two of the herein provided functional fragments of the non-naturally occurring/artificial/mutated Semaphorin 3 proteins or two of the herein provided functional sema domains can be comprised in one fusion protein. In further aspects, a wild type protein together with the non-naturally occurring/artificial/mutated Semaphorin 3 protein, the herein provided functional fragment of the non-naturally occurring/artificial/mutated Semaphorin 3 protein, or the herein provided functional sema domain can also form the dimer. Thus, a wild type Semaphorin 3 or the fragment thereof can be comprised together with the non-naturally occurring/artificial/mutated Semaphorin 3 protein, the herein provided functional fragment of the non-naturally occurring/artificial/mutated Semaphorin 3 protein or the herein provided functional sema domain in one fusion protein, wherein the fusion protein has the characteristics of mutated Semaphorin 3A, B, C or D. It is understood herein, that the term "first polypeptide" refers to the first monomer in the dimer. The term "second polypeptide" refers to the second monomer in the dimer. In certain aspects, the fusion protein can comprise two non-naturally occurring/artificial/mutated Semaphorin 3 proteins, two of the herein provided functional fragments of the non-naturally occurring/artificial/mutated Semaphorin 3 protein(s), or two of the herein provided functional sema domains, two stabilizer domains and/or one or two dimerization domain(s). The fusion protein can comprise mutated Semaphorin 3, the functional fragment thereof, the functional sema domains and/or the herein described polypeptides of the invention in any combination, wherein the fusion protein has the characteristics of mutated Semaphorin 3A, B, C or D. In the following aspects, such combinations are exemplified:

In certain aspects, the fusion protein of the invention comprises a first polypeptide comprising a mutated Semaphorin 3 or a functional fragment thereof that functions as an inhibitor of angiogenesis, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid and a second polypeptide comprising a Semaphorin 3 or a functional fragment thereof that functions as an inhibitor of angiogenesis, wherein said Semaphorin 3 proteins are selected from the group of Semaphorin 3A, Semaphorin 3B, Semaphorin 3C and Semaphorin 3D.

In certain aspects, the fusion protein of the invention comprises a first polypeptide comprising a mutated Semaphorin 3 or a functional fragment thereof that functions as an inhibitor of angiogenesis, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid and a second polypeptide comprising a mutated Semaphorin 3 or a functional fragment thereof that functions as an inhibitor of angiogenesis, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 proteins are selected from the group of Semaphorin 3A, Semaphorin 3B, Semaphorin 3C and Semaphorin 3D.

In certain aspects, the fusion protein of the invention comprises a first polypeptide comprising a mutated Semaphorin 3A or a functional fragment thereof that functions as an inhibitor of angiogenesis, wherein the alanine corresponding to position 106 of the wild type Semaphorin 3A as shown in SEQ ID NO: 2 is replaced by a hydrophilic amino acid and a second polypeptide comprising a Semaphorin 3 or a functional fragment thereof that functions as an inhibitor of angiogenesis, wherein said Semaphorin 3 protein is selected from the group of Semaphorin 3A, Semaphorin 3B, Semaphorin 3C and Semaphorin 3D.

In certain aspects, the fusion protein of the invention comprises a first polypeptide comprising a mutated Semaphorin 3A or a functional fragment thereof that functions as an inhibitor of angiogenesis, wherein the alanine corresponding to position 106 of the wild type Semaphorin 3A as shown in SEQ ID NO: 2 is replaced by a hydrophilic amino acid and a second polypeptide comprising a mutated Semaphorin 3A or a functional fragment thereof that functions as an inhibitor of angiogenesis, wherein the alanine corresponding to position 106 of the wild type Semaphorin 3A as shown in SEQ ID NO: 2 is replaced by a hydrophilic amino acid.

In certain aspects, the fusion protein of the invention comprises a first polypeptide comprising a mutated Semaphorin 3A or a functional fragment thereof that functions as an inhibitor of angiogenesis, wherein the alanine corresponding to position 106 of the wild type Semaphorin 3A as shown in SEQ ID NO: 2 is replaced by a hydrophilic amino acid and a second polypeptide comprising a mutated Semaphorin 3B or a functional fragment thereof that functions as an inhibitor of angiogenesis, wherein the alanine corresponding to position 105 of the wild type Semaphorin 3B as shown in SEQ ID NO: 6 is replaced by a hydrophilic amino acid.

In certain aspects, the fusion protein of the invention comprises a first polypeptide comprising a mutated Semaphorin 3A or a functional fragment thereof that functions as an inhibitor of angiogenesis, wherein the alanine corresponding to position 106 of the wild type Semaphorin 3A as shown in SEQ ID NO: 2 is replaced by a hydrophilic amino acid and a second polypeptide comprising a mutated Semaphorin 3C or a functional fragment thereof that functions as an inhibitor of angiogenesis, wherein the alanine corresponding to position 104 of the wild type Semaphorin 3C as shown in SEQ ID NO: 10 is replaced by a hydrophilic amino acid.

In certain aspects, the fusion protein of the invention comprises a first polypeptide comprising a mutated Semaphorin 3A or a functional fragment thereof that functions as an inhibitor of angiogenesis, wherein the alanine corresponding to position 106 of the wild type Semaphorin 3A as shown in SEQ ID NO: 2 is replaced by a hydrophilic amino acid and a second polypeptide comprising a mutated Semaphorin 3D or a functional fragment thereof that functions as an inhibitor of angiogenesis, wherein the alanine corresponding to position 120 of the wild type Semaphorin 3D as shown in SEQ ID NO: 14 is replaced by a hydrophilic amino acid.

In certain aspects, the fusion protein of the invention comprises a first polypeptide comprising a mutated Semaphorin 3B or a functional fragment thereof that functions as an inhibitor of angiogenesis, wherein the alanine corresponding to position 105 of the wild type Semaphorin 3B as shown in SEQ ID NO: 6 is replaced by a hydrophilic amino acid and a second polypeptide comprising a Semaphorin 3 or a functional fragment thereof, wherein said Semaphorin 3 protein is selected from the group of Semaphorin 3A, Semaphorin 3B, Semaphorin 3C and Semaphorin 3D.

In certain aspects, the fusion protein of the invention comprises a first polypeptide comprising a mutated Semaphorin 3B or a functional fragment thereof that functions as an inhibitor of angiogenesis, wherein the alanine corresponding to position 105 of the wild type Semaphorin 3B as shown in SEQ ID NO: 6 is replaced by a hydrophilic amino acid and a second polypeptide comprising a mutated Semaphorin 3B or a functional fragment thereof that functions as an inhibitor of angiogenesis, wherein the alanine corresponding to position 105 of the wild type Semaphorin 3B as shown in SEQ ID NO: 6 is replaced by a hydrophilic amino acid.

In certain aspects, the fusion protein of the invention comprises a first polypeptide comprising a mutated Semaphorin 3B or a functional fragment thereof that functions as an inhibitor of angiogenesis, wherein the alanine corresponding to position 105 of the wild type Semaphorin 3B as shown in SEQ ID NO: 6 is replaced by a hydrophilic amino acid and a second polypeptide comprising a mutated Semaphorin 3C or a functional fragment thereof that functions as an inhibitor of angiogenesis, wherein the alanine corresponding to position 104 of the wild type Semaphorin 3C as shown in SEQ ID NO: 10 is replaced by a hydrophilic amino acid.

In certain aspects, the fusion protein of the invention comprises a first polypeptide comprising a mutated Semaphorin 3B or a functional fragment thereof that functions as an inhibitor of angiogenesis, wherein the alanine corresponding to position 105 of the wild type Semaphorin 3B as shown in SEQ ID NO: 6 is replaced by a hydrophilic amino acid and a second polypeptide comprising a mutated Semaphorin 3D or a functional fragment thereof that functions as an inhibitor of angiogenesis, wherein the alanine corresponding to position 120 of the wild type Semaphorin 3D as shown in SEQ ID NO: 14 is replaced by a hydrophilic amino acid.

In certain aspects, the fusion protein of the invention comprises a first polypeptide comprising a mutated Semaphorin 3C or a functional fragment thereof that functions as an inhibitor of angiogenesis, wherein the alanine corresponding to position 104 of the wild type Semaphorin 3C as shown in SEQ ID NO: 10 is replaced by a hydrophilic amino acid and a second polypeptide comprising a Semaphorin 3 or a functional fragment thereof, wherein said Semaphorin 3 protein is selected from the group of Semaphorin 3A, Semaphorin 3B, Semaphorin 3C and Semaphorin 3D.

In certain aspects, the fusion protein of the invention comprises a first polypeptide comprising a mutated Semaphorin 3C or a functional fragment thereof that functions as an inhibitor of angiogenesis, wherein the alanine corresponding to position 104 of the wild type Semaphorin 3C as shown in SEQ ID NO: 10 is replaced by a hydrophilic amino acid and a second polypeptide comprising a mutated Semaphorin 3C or a functional fragment thereof that functions as an inhibitor of angiogenesis, wherein the alanine corresponding to position 104 of the wild type Semaphorin 3C as shown in SEQ ID NO: 10 is replaced by a hydrophilic amino acid.

In certain aspects, the fusion protein of the invention comprises a first polypeptide comprising a mutated Semaphorin 3C or a functional fragment thereof that functions as an inhibitor of angiogenesis, wherein the alanine corresponding to position 104 of the wild type Semaphorin 3C as shown in SEQ ID NO: 10 is replaced by a hydrophilic amino acid and a second polypeptide comprising a mutated Semaphorin 3D or a functional fragment thereof that functions as an inhibitor of angiogenesis, wherein the alanine corresponding to position 120 of the wild type Semaphorin 3D as shown in SEQ ID NO: 14 is replaced by a hydrophilic amino acid.

In certain aspects, the fusion protein of the invention comprises a first polypeptide comprising a mutated Semaphorin 3D or a functional fragment thereof that functions as an inhibitor of angiogenesis, wherein the alanine corresponding to position 120 of the wild type Semaphorin 3D as shown in SEQ ID NO: 14 is replaced by a hydrophilic amino acid and a second polypeptide comprising a Semaphorin 3 or a functional fragment thereof, wherein said Semaphorin 3 protein is selected from the group of Semaphorin 3A, Semaphorin 3B, Semaphorin 3C and Semaphorin 3D.

In certain aspects, the fusion protein of the invention comprises a first polypeptide comprising a mutated Semaphorin 3D or a functional fragment thereof that functions as an inhibitor of angiogenesis, wherein the alanine corresponding to position 120 of the wild type Semaphorin 3D as shown in SEQ ID NO: 14 is replaced by a hydrophilic amino acid and a second polypeptide comprising a mutated Semaphorin 3D or a functional fragment thereof that functions as an inhibitor of angiogenesis, wherein the alanine corresponding to position 120 of the wild type Semaphorin 3D as shown in SEQ ID NO: 14 is replaced by a hydrophilic amino acid It is also envisaged herein that the fusion protein of the mutated Semaphorin 3 comprises the following domains:

(i) a sema domain;

(ii) a PSI domain; and (iii) a C-terminal IgG constant domain fused to the C-terminus of the PSI domain, and is further characterized in that the alanine ($A_3$) residue comprised in the motif $CX_1X_2A_3GKD$ of the Semaphorin 3 is mutated to lysine, wherein the Semaphorin 3 is selected from the group consisting of Semaphorin 3A, B, C and D.

The fusion protein comprises the functional sema domain, wherein said sema domain comprises a hydrophilic amino acid in place of the alanine at the position that by comparison of homology corresponds to position 106 of the wild type Semaphorin 3A as shown in SEQ ID NO: 2 and a dimerization domain and/or a stabilizer domain.

In other words, the fusion protein comprises the functional sema domain, wherein said sema domain is selected from the group consisting of Semaphorin 3A, Semaphorin 3B, Semaphorin 3C and Semaphorin 3D, wherein said sema domain comprises a hydrophilic amino acid in place of the alanine corresponding to position 106 of the wild type Semaphorin 3A as shown in SEQ ID NO: 2;

a hydrophilic amino acid in place of the alanine corresponding to position 105 of the wild type Semaphorin 3B as shown in SEQ ID NO: 6;

a hydrophilic amino acid in place of the alanine corresponding to position 104 of the wild type Semaphorin 3C as shown in SEQ ID NO: 10; or a hydrophilic amino acid in place of the alanine corresponding to position 120 of the wild type Semaphorin 3D as shown in SEQ ID NO: 14;

and wherein said fusion protein further comprises a dimerization domain and/or a stabilizer domain.

Most preferably, the fusion protein comprises a functional sema domain, wherein within said functional sema domain the alanine corresponding to position 106 of the wild type Semaphorin 3A of SEQ ID NO: 2 is replaced by a hydrophilic amino acid or wherein the alanine corresponding to said alanine 106 in Semaphorin 3B, 3C or 3D is replaced by a hydrophilic amino acid and a dimerization domain, wherein the dimerization domain is IgG1 and/or a stabilizer domain, wherein the stabilizer domain is the PSI domain. In most preferred aspects, the fusion protein comprises the functional sema domain of Semaphorin 3A, wherein said sema domain comprises a hydrophilic amino acid in place of the alanine corresponding to position 106 of the wild type Semaphorin 3A as shown in SEQ ID NO: 2 and wherein said fusion protein further comprises a dimerization domain and/or a stabilizer domain.

In most preferred embodiments of the invention, the fusion proteins/polypeptides of the invention can comprise the functional sema domain that is fused to the PSI domain (as shown in the appended examples). The resulting sema-PSI domain is fused to the dimerization domain, e.g., the constant fragment of the IgG1 domain. Furthermore, such fusion proteins lack the Nrp1 binding and/or the furin cleavable Ig-like (amino acids spanning from 580-670 of SEQ ID NO: 2)/basic region (amino acids spanning from 715-771 of SEQ ID NO: 2). Such fusion proteins are herein most preferred embodiments and exemplary nucleic acid molecules of such a encoded fusion protein can comprise a nucleic acid sequence having: a nucleic acid sequence spanning from nucleotides 316 to 1959 of SEQ ID NO: 1 and a nucleic acid sequence spanning from nucleotides 295 to 990 of SEQ ID NO: 37, wherein the nucleotides GCT at position 631 to 633 of SEQ ID NO: 1 are replaced by nucleotides encoding the hydrophilic amino acid;

a nucleic acid sequence spanning from nucleotides 247 to 1887 of SEQ ID NO: 5 and a nucleic acid sequence spanning from nucleotides 295 to 990 of SEQ ID NO: 37, wherein the nucleotides GCA at position 559 to 561 of SEQ ID NO: 5 are replaced by nucleotides encoding the hydrophilic amino acid;

a nucleic acid sequence spanning from nucleotides 563 to 2197 of SEQ ID NO: 9 and a nucleic acid sequence spanning from nucleotides 295 to 990 of SEQ ID NO: 37, wherein the nucleotides GCT at position 872 to 874 of SEQ ID NO: 9 are replaced by nucleotides encoding the hydrophilic amino acid; or a nucleic acid sequence spanning from nucleotides 41 to 1735 of SEQ ID NO: 13 and a nucleic acid sequence spanning from nucleotides 295 to 990 of SEQ ID NO: 37, wherein the nucleotides GCC at position 398 to 400 of SEQ ID NO: 13 are replaced by nucleotides encoding the hydrophilic amino acid.

In most preferred embodiments, the fusion protein of the mutated Semaphorin 3A is encoded by a nucleic acid sequence spanning from nucleotides 316 to 1959 of SEQ ID NO: 1 and a nucleic acid sequence spanning from nucleotides 295 to 990 of SEQ ID NO: 37, wherein the nucleotides GCT at position 631 to 633 of SEQ ID NO: 1 are replaced by nucleotides encoding the hydrophilic amino acid.

It is contemplated herein that codon optimized nucleic acid sequences can be employed as shown in the appended examples (SEQ ID NOs: 17, 19, 43 and 44).

In most preferred embodiments, the fusion protein comprises a sema domain, a stabilizer domain and a dimerization domain. The functional sema domain is fused to the stabilizer domain, e.g., the PSI domain. The resulting sema-PSI domain is fused to the dimerization domain, e.g., the constant fragment of the IgG1 domain as shown in SEQ ID NO: 38 or 41. Such an exemplary fusion protein comprises a sema domain, a PSI and a dimerization domain, wherein the fusion protein comprises an amino acid sequence:

spanning from amino acid residues 1 to 548 of SEQ ID NO: 2 and an amino acid sequence as shown in SEQ ID NO: 41, wherein the alanine residue at position 106 of SEQ ID NO: 2 is replaced by the hydrophilic amino acid;

spanning from amino acid residues 1 to 547 of SEQ ID NO: 6 and an amino acid sequence as shown in SEQ ID NO: 41, wherein the alanine residue at position 105 of SEQ ID NO: 6 is replaced by the hydrophilic amino acid;

spanning from amino acid residues 1 to 565 of SEQ ID NO: 10 and an amino acid sequence as shown in SEQ ID NO: 41, wherein the alanine residue at position 104 of SEQ ID NO: 10 is replaced by the hydrophilic amino acid; or spanning from amino acid residues 1 to 545 of SEQ ID NO: 14 and an amino acid sequence as shown in SEQ ID NO: 41, wherein the alanine residue at position 120 of SEQ ID NO: 14 is replaced by the hydrophilic amino acid.

In most preferred embodiments, the fusion protein of the mutated Semaphorin 3A comprises a polypeptide: spanning from amino acid residues 1 to 548 of SEQ ID NO: 2 and an amino acid sequence as shown in SEQ ID NO: 41, wherein the alanine residue at position 106 of SEQ ID NO: 2 is replaced by the hydrophilic amino acid An exemplary fusion protein comprising the functional sema domain of mutated Semaphorin 3A, the PSI domain, the IgG1 domain is shown in SEQ ID NO: 18 or 20. An exemplary fusion protein comprising the functional sema domain of mutated Semaphorin 3B, mutated Semaphorin 3C, or mutated Semaphorin 3D and the PSI domain, the IgG1 domain is shown in SEQ ID NO: 76, 78 or 79, respectively. SEQ ID NO: 18 shows a fusion protein comprising the functional sema domain of the human mutated Semaphorin 3A, wherein the alanine at the position that by comparison of homology corresponds to position 106 of the wild type Semaphorin 3A as shown in SEQ ID NO:2 is replaced by lysine, the PSI domain and the human constant fragment of IgG1. The corresponding nucleic acid sequence encoding the fusion protein comprising the functional sema domain of the human mutated Semaphorin 3A, wherein the alanine at the position that by comparison of homology corresponds to position 106 of the wild type Semaphorin 3A as shown in SEQ ID NO:2 is replaced by lysine, the PSI domain and the human constant fragment of IgG1 is given in SEQ ID NO: 17. SEQ ID NOs: 74 and 75 show an amino acid sequence and the encoding nucleic acid sequence of an exemplary fusion protein of Semaphorin 3B without the inventive mutation.

SEQ ID NO: 20 shows a fusion protein comprising the functional sema domain of mouse mutated Semaphorin 3A, wherein the alanine at the position that by comparison of homology corresponds to position 106 of the wild type Semaphorin 3A as shown in SEQ ID NO:2 is replaced by lysine, the PSI domain and the human constant fragment of IgG1. The corresponding nucleic acid sequence encoding the fusion protein comprising the functional sema domain of the mouse mutated Semaphorin 3A, wherein the alanine at the position that by comparison of homology corresponds to position 106 of the wild type Semaphorin 3A as shown in SEQ ID NO:2 is replaced by lysine, the PSI domain and the mouse constant fragment of IgG1 is given in SEQ ID NO: 19.

The fusion protein as described herein can be a heterologous protein, wherein the non-naturally occurring/artificial/mutated Semaphorin 3 protein, the non-naturally occurring/artificial/mutated functional fragment of the Semaphorin 3 or the non-naturally occurring/artificial/mutated functional sema domain of the Semaphorin 3, the dimerization domain and/or the stabilization domain are from different sources, e.g. from different species.

It is understood herein that the non-naturally occurring/artificial/mutated Semaphorin 3 protein, the non-naturally occurring/artificial/mutated functional fragment of the Semaphorin 3, the non-naturally occurring/artificial/mutated functional sema domain of the Semaphorin 3, the dimerization domain and/or the stabilization domain can be linked/fused together as found in natural occurring Semaphorin 3 proteins, wherein the character of the mutated Semaphorin 3A, B, C or D is maintained. Further, the non-naturally occurring/artificial/mutated Semaphorin 3 protein, the non-naturally occurring/artificial/mutated functional fragment of the Semaphorin 3, the non-naturally occurring/artificial/mutated functional sema domain of the Semaphorin 3, the dimerization domain and/or the stabilization domain can be linked/fused together as is not found in nature. The non-naturally occurring/artificial/mutated Semaphorin 3 protein, the non-naturally occurring/artificial/mutated functional fragment of the Semaphorin 3, the non-naturally occurring/artificial/mutated functional sema domain of the Semaphorin 3, the dimerization domain and/or the stabilization domain can be conjugated/linked together via amino acid linkers, e.g., serine-glycine linkers. Such linkers are known in the art and can be for example short peptide sequences that occur between protein domains. The linkers are often composed of flexible residues like glycine and serine so that the adjacent protein domains are free to move relative to one another. Longer linkers are used when it is necessary to ensure that two adjacent domains do not sterically interfere with one another. Non-peptide bonds are also envisaged herein. Such non-peptide bonds may include disulfide bonds, e.g. between Cys side chains, thioether bonds or non-peptide covalent bonds induced by chemical cross-linkers, such as disuccinimidyl suberate (DSS) or sulfosuccinimidyl 4-[p-maleimidophenyl]butyrate (Sulfo-SMPB), metal-chelating/complexing groups, as well as non-covalent protein-protein interactions. These are merely embodiments of the present invention and it is evident for the skilled artisan that modifications can easily be made within the fusion proteins and used without deferring from the gist of the present invention.

It is also envisaged herein that the stability of the mutated Semaphorin 3 or the functional fragment thereof can be optimized by adding immunoglobulin-like domains and to simultaneously enhance pharmacokinetic properties like prolonged half-life in serum and protection from proteolytic digestion by proteases. Moreover, stability of the formats can be enhanced by optimizing the production. Since linker sequences which are utilized to covalently join domains often leads to aggregates, production lines have been established that first produce two or three polypeptides that can be easily reassembled in order to generate a functional drug. Such techniques utilize directed disulphide-bridges or cross-linking reagents to covalently join two different polypeptides. Other techniques make use of hetero- or homo-dimerization domains like leucine-zipper domains, Fc-domains and others like knob into hole technologies (see, for example, WO 2007/062466).

The present invention also relates to a vector comprising the nucleic acid sequence(s) of the present invention.

Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

Preferably said vector is a gene targeting vector and/or a gene transfer vector. Gene therapy, which is based on introducing therapeutic genes (for example for vaccination) into cells by ex vivo or in vivo techniques, is one of the most important applications of gene transfer. Suitable vectors, vector systems and methods for in vitro or in vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957, Schaper, Current Opinion in Biotechnology 7 (1996), 635-640 or Verma, Nature 389 (1997), 239-242 and references cited therein. In certain aspects, the vector is an adeno-associated-virus (AAV) vector. In particular aspects, the AAV virus is an AAV8 and thus the vector is an AAV8 vector. AAV vectors are attractive for gene therapy. The AAV system has several advantages including long-term gene expression, the inability to autonomously replicate without a helper virus, transduction of dividing and nondividing cells, and the lack of pathogenicity from wild-type infections. It is envisaged herein that AAV serotypes display different organ tropism. Accordingly, different AAV serotypes can be employed to target the proteins/polypeptides of the invention to cancers of different organs. It is envisaged herein that different AAV vectors can be employed in gene therapy according to standard protocols (Grieger et al., 2012 and Asokan et al., 2012).

The nucleic acid molecules of the invention and vectors as described herein above may be designed for direct introduction or for introduction via liposomes, or viral vectors (e.g. adenoviral, retroviral) into the cell. Additionally, baculoviral systems or systems based on vaccinia virus or Semliki Forest Virus can be used as eukaryotic expression system for the nucleic acid molecules of the invention. In addition to recombinant production, fragments of the protein, the fusion protein or antigenic fragments of the invention may be produced by direct peptide synthesis using solid-phase techniques (cf Stewart et al. (1969) Solid Phase Peptide Synthesis, WH Freeman Co, San Francisco; Merrifield, J. Am. Chem. Soc. 85 (1963), 2149-2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule.

In certain aspects, the vector comprises a nucleic acid sequence which is a regulatory sequence operably linked to said nucleic acid sequence defined herein.

The term “regulatory sequence” refers to DNA sequences, which are necessary to effect the expression of coding sequences to which they are ligated. The nature of such control sequences differs depending upon the host organism. In prokaryotes, control sequences generally include promoter, ribosomal binding site, and terminators. In eukaryotes general control sequences include promoters, terminators and, in some instances, enhancers, transactivators or transcription factors. The term “control sequence” is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

The recited vector can also be an expression vector. An "expression vector" is a construct that can be used to transform a selected host and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normal promoters ensuring initiation of transcription and optionally poly-A signals ensuring termination of transcription and stabilization of the transcript. Possible regulatory elements permitting expression in prokaryotic host cells comprise, e.g., the PL, lac, trp or tac promoter in *E. coli*, and examples of regulatory elements permitting expression in eukaryotic host cells are the $AOX_1$ or GAL1 promoter in yeast or the CMV-, SV40-, RSV-promoter (Rous sarcoma virus), CMV-enhancer, SV40-enhancer or a globin intron in mammalian and other animal cells.

Beside elements, which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the recited nucleic acid sequence and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Accordingly, such a leader sequence can also be a signal peptide. Thus, the mutated Semaphorin 3 polypeptides can comprise a signal peptide. The signal peptide is a short stretch of amino acids usually present at the N-terminus of proteins that are destined towards the secretory pathway. Such proteins include those that reside either inside certain organelles, like the endoplasmic reticulum, golgi or endosomes, or are secreted from the cell. The signal peptide is cleaved off and active polypeptides usually do not comprise signal peptides. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (Invitrogen), pEF-DHFR, pEF-ADA or pEF-neo (Mack et al. PNAS (1995) 92, 7021-7025 and Raum et al. Cancer Immunol Immunother (2001) 50(3), 141-150) or pSPORT1 (GIBCO BRL).

Preferably, the expression control sequences will be eukaryotic promoter systems in vectors capable of transforming of transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the invention may follow; see, e.g., the appended examples.

The present invention relates to a host transformed with a vector of the present invention or to a host comprising the nucleic acid molecule of this invention. Said host may be any prokaryotic or eukaryotic cell. Suitable prokaryotic/bacterial cells are those generally used for cloning like *E. coli* or *Bacillus subtilis*. Said eukaryotic host may be a mammalian cell. In a preferred embodiment said mammalian cell is a neuronal cell and/or a cultured cell like, inter alia, a HEK 293 (human embryonic kidney) cell, a CHO, HeLa, NIH3T3, BHK or a PC12 cell. In a particularly preferred embodiment, the HEK293 cell line expresses stably the Epstein-Barr virus nuclear antigen-1 (HEK293-EBNA1, or 293E). In general, this is the most commonly used cell line for large-scale transfection (CSH Protocols; 2008; doi:10.1101/pdb.prot4976).

It is particularly envisaged that the recited host may be a mammalian cell. Particularly preferred host cells comprise HEK cells, HEK293E cells, HEK293 cell line stably expressing the Epstein-Barr virus nuclear antigen-1 (HEK293-EBNA1, or 293E).

The term "cell" or "mammalian cell" as used in this context may also comprise a plurality of cells as well as cells comprised in a tissue. The cell to be used in the screening or validation method may be obtained from samples from a (transgenic) non-human animal or human suffering from a disease, e.g. angiogenic disease, cancer or a disease associated with Semaphorin dependent Plexin receptor activation. The cell (e.g. a tumor cell and the like) may also be obtained or derived from patient samples (e.g. biopsies), in particular a biopsy/biopsies from a patient/subject suffering from a disease as defined herein above or below. Accordingly, the cell may be a human cell. Again, such a cell to be used in the present screening or validation methods may be comprised in a tissue or tissue sample, like in a sample biopsy. The invention also provides for a host transformed or transfected with a vector of the invention. Said host may be produced by introducing the above described vector of the invention or the above described nucleic acid molecule of the invention into the host. The presence of at least one vector or at least one nucleic acid molecule in the host may mediate the expression of a gene encoding the above described mutated Semaphorin 3 or the fragment thereof. The described nucleic acid molecule or vector of the invention, which is introduced in the host, may either integrate into the genome of the host or it may be maintained extrachromosomally. The host can be any prokaryote or eukaryotic cell.

An alternative expression system is the insect system or the insect cell expression system. In one such system, *Autographa californica* nuclear polyhedrosis virus (AcNPV) is used as a vector to express foreign genes in *Spodoptera frugiperda* cells or in *Trichoplusia* larvae. The coding sequence of a recited nucleic acid molecule may be cloned into a nonessential region of the virus, such as the polyhedrin gene, and placed under control of the polyhedrin promoter. Successful insertion of said coding sequence will render the polyhedrin gene inactive and produce recombinant virus lacking coat protein coat. The recombinant viruses are then used to infect *S. frugiperda* cells or *Trichoplusia* larvae in which the protein of the invention is expressed (Smith, J. Virol. 46 (1983), 584; Engelhard, Proc. Nat. Acad. Sci. USA 91 (1994), 3224-3227). In certain aspects, the pFBDM vector can be used for expression. The insertion into the MultiBac baculoviral DNA is mediated via the Tn7 transposition sequence upon transformation in DH10 MultiBac *E. coli* cells (Berger et al., 2004; Fitzgerald et al., 2006). Virus amplification and expression can be performed in Sf21 (*Spodoptera frugiperda*) (Gibco, Invitrogen) and/or High Five (*Trichoplusia ni*) (Gibco, Invitrogen) cell.

Additional regulatory elements may include transcriptional as well as translational enhancers. Advantageously, the above-described vectors of the invention comprise a selectable and/or scorable marker.

Selectable marker genes useful for the selection of transformed cells and, e.g., plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule can be used alone or as part of a vector to express the polypeptide of the invention in cells, for, e.g., purification but also for gene therapy purposes. The nucleic acid molecules or vectors containing the DNA sequence(s) encoding any one of the above described polypeptide of the invention is introduced into the cells which in turn produce the polypeptide of interest. Gene therapy, which is based on introducing therapeutic genes into cells by ex vivo or in vivo techniques, is one of the most important applications of gene transfer. Suitable vectors, methods or gene-delivery systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086; Onodera, Blood 91 (1998), 30-36; Verma, Gene Ther. 5 (1998), 692-699; Nabel, Ann. N.Y. Acad. Sci. 811 (1997), 289-292; Verzeletti, Hum. Gene Ther. 9 (1998), 2243-51; Wang, Nature Medicine 2 (1996), 714-716; WO 94/29469; WO 97/00957, U.S. Pat. Nos. 5,580,859; 5,589,466; or Schaper, Current Opinion in Biotechnology 7 (1996), 635-640. The recited nucleic acid molecules and vectors may be designed for direct introduction or for introduction via liposomes, or viral vectors (e.g., adenoviral, retroviral) into the cell. Preferably, said cell is a germ line cell, embryonic cell, or egg cell or derived there from, most preferably said cell is a stem cell. An example for an embryonic stem cell can be, inter alia, a stem cell as described in Nagy, Proc. Natl. Acad. Sci. USA 90 (1993), 8424-8428.

The term "prokaryote" is meant to include all bacteria, which can be transformed or transfected with DNA or RNA molecules for the expression of a protein of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells. Depending upon the host employed in a recombinant production procedure, the protein encoded by the polynucleotide of the present invention may be glycosylated or may be non-glycosylated. Especially preferred is the use of a plasmid or a virus containing the coding sequence of the polypeptide of the invention and genetically fused thereto to a Protein A tag. An above described polynucleotide can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, loc cit.).

Herein provided is also a process for the production of a polypeptide to be used in accordance with the present invention, said process comprising culturing/raising the host of the invention under conditions allowing the expression of the polypeptide of the invention and optionally recovering/isolating the produced polypeptide from the culture.

The transformed hosts can be grown in fermenters and cultured according to techniques known in the art to achieve optimal cell growth. The polypeptide of the invention can then be isolated from the growth medium, cellular lysates, or cellular membrane fractions. The isolation and purification of the, e.g., microbially expressed polypeptides of the invention may be by any conventional means such as, for example, preparative chromatographic separations and immunological separations such as those involving the use of monoclonal or polyclonal antibodies directed, e.g., against a tag of the polypeptide of the invention or as described in the appended examples.

The conditions for the culturing of a host, which allow the expression, are known in the art to depend on the host system and the expression system/vector used in such process. The parameters to be modified in order to achieve conditions allowing the expression of a recombinant polypeptide are known in the art. Thus, suitable conditions can be determined by the person skilled in the art in the absence of further inventive input.

Once expressed, the polypeptide of the invention can be purified according to standard procedures of the art, including ammonium sulfate precipitation, affinity columns, column chromatography, gel electrophoresis and the like; see, Scopes, "Protein Purification", Springer-Verlag, N.Y. (1982). Substantially pure polypeptides of at least about 90 to 95% homogeneity are preferred, and 98 to 99% or more homogeneity are most preferred, for pharmaceutical uses. Once purified, partially or to homogeneity as desired, the polypeptide of the invention may then be used therapeutically (including extracorporeally) or in developing and performing assay procedures. Furthermore, examples for methods for the recovery of the polypeptide of the invention from a culture are described in the appended examples.

As detailed herein, the present invention also relates to an antibody specifically binding to the mutated Semaphorin 3, the functional fragment thereof or to the inventive fusion protein comprising said mutated Semaphorin 3 or the functional fragment thereof. In particular, herein provided is an antibody specifically binding to the mutated Semaphorin 3 or the functional fragment thereof, wherein said antibody specifically binds to an epitope comprising the hydrophilic amino acid which replaces the alanine corresponding to position 106 of the wild type Semaphorin 3A as shown in SEQ ID NO: 2 or the alanine at the position which corresponds in other Semaphorins 3 proteins by comparison of homology to position 106 of the wild type Semaphorin 3A as shown in SEQ ID NO: 2 is replaced by a hydrophilic amino acid, wherein the said Semaphorin 3 is selected from the group of Semaphorin 3A, Semaphorin 3B, Semaphorin 3C and Semaphorin 3D. Accordingly, the invention relates to an antibody specifically binding to the mutated Semaphorin 3 or the functional fragment thereof, wherein said antibody specifically binds to an epitope comprising a hydrophilic amino acid in place of the alanine corresponding to position 106 of the wild type Semaphorin 3A as shown in SEQ ID NO: 2; a hydrophilic amino acid in place of the alanine corresponding to position 105 of the wild type Semaphorin 3B as shown in SEQ ID NO: 6; a hydrophilic amino acid in place of the alanine corresponding to position 104 of the wild type Semaphorin 3C as shown in SEQ ID NO: 10; or a hydrophilic amino acid in place of the alanine corresponding to position 120 of the wild type Semaphorin 3D as shown in SEQ ID NO: 14, and wherein said Semaphorin 3 is selected from the group consisting of Semaphorin 3A, Semaphorin 3B, Semaphorin 3C and Semaphorin 3D.

The term "antibody", in accordance with the present invention, comprises polyclonal and monoclonal antibodies as well as derivatives or fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" in accordance with the invention also includes embodiments such as chimeric, single chain and humanized antibodies, as well as antibody fragments, like, inter alia, Fab fragments, fusion proteins consisting of Eph receptors, ephrin or phosphatase extracellular domains and Fc. Antibody fragments or derivatives further comprise $F(ab')_2$, Fv fragments, scFvs, single domain $V_H$ or V-like domains, such as VhH or V-NAR-domains, as well as multimeric formats such as minibodies, diabodies, tribodies, tetrabodies or chemically conjugated Fab'-multimers; see, for example, Harlow and Lane (1988) and (1999), Altshuler (2010) Biochemistry (Moscow) 75, 1584-605 or Holliger (2005) Nature Biotechnology 23, 1126-36. Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies specific for polypeptide(s) and fusion proteins of this invention. Also, transgenic animals may be used to express humanized antibodies specific for polypeptides and fusion proteins of this invention. Most preferably, the antibody of this invention is a monoclonal antibody. For the preparation of monoclonal antibodies, any technique, which provides antibodies produced by continuous cell line cultures, can be used. Examples for such techniques include the original hybridoma technique (Köhler and Milstein (1975) Nature 256, 495) as further developed by the art, the trioma technique, the human B-cell hybridoma technique (Kozbor (1983) Immunology Today 4, 72) and the EBV-hybridoma technique to produce human monoclonal antibodies (Cole et al. (1985) Monoclonal Antibodies and Cancer Therapy, Alan R. Liss, Inc., 77). The term antibody also relates to humanized antibodies. "Humanized" forms of non-human (e.g. murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Often, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin. For further details, see: Jones Nature 321 (1986), 522-525; Reichmann Nature 332 (1998), 323-327 and Presta Curr Op Struct Biol 2 (1992), 593-596.

A popular method for humanization of antibodies involves CDR grafting, where a functional antigen-binding site from a non-human 'donor' antibody is grafted onto a human 'acceptor' antibody. CDR grafting methods are known in the art and described, for example, in U.S. Pat. Nos. 5,225,539, 5,693,761 and 6,407,213. Another related method is the production of humanized antibodies from transgenic animals that are genetically engineered to contain one or more humanized immunoglobulin loci which are capable of undergoing gene rearrangement and gene conversion (see, for example, U.S. Pat. No. 7,129,084). Further methods for designing and producing humanized antibodies are described in U.S. Ser. No. 07/290,975, U.S. Ser. No. 07/310,252 and US 2003/0229208 or by Queen PNAS (1989), 10029-10033.

Surface plasmon resonance as employed in the BIAcore system can be used to increase the efficiency like efficiency and/or selectivity of phage antibodies which bind to an epitope of a polypeptide of the invention (Schier (1996) Human Antibodies Hybridomas 7, 97; Malmborg (1995) J. Immunol. Methods 183, 7). It is also envisaged in the context of this invention that the term "antibody" comprises antibody constructs, which may be expressed in cells, e.g. antibody constructs which may be transfected and/or transduced via, amongst others, viruses or plasmid vectors. The antibody described in the context of the invention is capable to specifically bind/interact with an epitope of the mentioned polypeptide or the mutated Semaphorin 3 as defined herein. The term "specifically binding/interacting with" as used in accordance with the present invention means that the antibody does not or essentially does not cross-react with an epitope of similar structure. Cross-reactivity of a panel of antibodies under investigation may be tested, for example, by assessing binding of said panel of antibodies under conventional conditions to the epitope of interest as well as to a number of more or less (structurally and/or functionally) closely related epitopes. Only those antibodies that bind to the epitope of interest in its relevant context (e.g. a specific motif in the structure of mutated Semaphorin 3 or the functional fragment thereof) but do not or do not essentially bind to any of the other epitopes are considered specific for the epitope of interest and thus to be antibodies in accordance with this invention. Corresponding methods are described e.g. in Harlow and Lane, 1988 and 1999, loc cit. The antibody specifically binds to/interacts with conformational or continuous epitopes, which are unique for the mentioned polypeptide, preferably mutated Semaphorin 3. A conformational or discontinuous epitope is characterized for polypeptide antigens by the presence of two or more discrete amino acid residues which are separated in the primary sequence, but come together on the surface of the molecule when the polypeptide folds into the native protein/antigen (Sela (1969) Science 166, 1365; Laver (1990) Cell 61, 553). The two or more discrete amino acid residues contributing to the epitope are present on separate sections of one or more polypeptide chain(s). These residues come together on the surface of the molecule when the polypeptide chain(s) fold(s) into a three-dimensional structure to constitute the epitope. In contrast, a continuous or linear epitope consists of two or more discrete amino acid residues, which are present in a single linear segment of a polypeptide chain.

Various techniques have been developed for the production of antibody fragments. Traditionally, these fragments were derived via proteolytic digestion of intact antibodies (see Morimoto et al (1992) Journal of Biochemical and Biophysical Methods 24:107-117; and Brennan et al (1985) Science 229:81). Antibody fragments can also be produced directly by recombinant host cells and the antibody phage libraries discussed above. Fab'-SH fragments can be directly recovered from *E. coli* and chemically coupled to form F(ab')2 fragments (Carter et al (1992) Bio/Technology 10:163-167). According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; 5,587,458. The antibody fragment may also be a "linear antibody", e.g., as described in U.S. Pat. No. 5,641,870. Such linear antibody fragments may be monospecific or bispecific.

Bispecific antibodies with binding specificities for at least two different epitopes (Millstein et al (1983), Nature 305: 537-539) may bind to two different epitopes of the mutated Semaphorin 3. Techniques for generating bispecific antibodies from antibody fragments have also been described, such as using chemical linkage wherein intact antibodies are proteolytically cleaved to generate F(ab')2 fragments (Brennan et al (1985) Science 229:81). Fab'-SH fragments can be recovered from *E. coli* and chemically coupled to form bispecific antibodies (Shalaby et al (1992) J. Exp. Med. 175:217-225. The "diabody" technology provides an alternative method for making bispecific antibody fragments (Hollinger et al (1993) Proc. Natl. Acad. Sci. USA 90:6444-6448).

A "Fab fragment" generally is comprised of one light chain and the $C_H1$ and variable regions of one heavy chain. The heavy chain of a Fab molecule cannot form a disulfide bond with another heavy chain molecule. An "Fc" region generally contains two heavy chain fragments comprising the $C_H2$ and $C_H3$ domains of an antibody. The two heavy chain fragments are held together by two or more disulfide bonds and by hydrophobic interactions of the $C_H3$ domains. A "Fab' fragment" generally contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a $F(ab')_2$ molecule. A "$F(ab')_2$ fragment" generally contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains. The "Fv region" generally comprises the variable regions from both the heavy and light chains, but lacks the constant regions. Antibodies with more than two valencies are contemplated. Multivalent, "Octopus" antibodies with three or more antigen binding sites and two or more variable domains can be readily produced by recombinant expression of nucleic acid encoding the polypeptide chains of the antibody (US 2002/0004586; WO01/77342). For example, trispecific antibodies can be prepared (Tutt et al (1991) J. Immunol. 147:60.).

Binding molecules/antibodies/antigen-binding fragments provided herein are preferably in the IgG1 or IgG3 framework, more preferred human IgG1 or IgG3 framework. Binding molecules, antibodies or antigen-binding fragments of these antibodies in the IgG1 or IgG3, preferably human IgG1 or IgG3, framework, are particularly preferred for use in vaccine therapy.

The following exemplary assay can be used to determine that a candidate antibody is indeed specifically binding to the mutated Semaphorin 3 or a functional fragment thereof in accordance with the present invention.

Antibodies that selectively and specifically bind to the epitope comprising the hydrophilic amino acid at the position that by comparison of homology corresponds to position 106 of Semaphorin 3A as shown in SEQ ID NO:2 can be identified by, e.g., capture ELISA assays. In order to perform such an assay, Corning 96 Well Clear Polystyrene High Bind Stripwell Microplate (product #2592) are coated overnight with increasing amounts (0.02 nM to 3.5 nM) of the affinity purified mutated Semaphorin 3 or (the functional fragment thereof) or the purified wild type Semaphorin 3 (or the functional fragment thereof) in 0.05 M $Na_2CO_3$ (pH 9.6) at 4° C. Subsequently, the reaction is blocked with PBS containing 0.05% Tween-20 (PBS-T) with 5% BSA for 2 hours at room temperature. Solutions containing equal amounts of generated antibodies are captured by overnight incubation at 4° C. Unbound material is removed by extensive washing with PBS-T. The binding of anti-mutated-Semaphorin 3 antibodies is detected by incubating wells with appropriate horseradish peroxidase-conjugated secondary antibodies in PBS-T containing 1% BSA for 1 h at 4° C. Following further washing, mutated Semaphorin 3-bound (or functional fragment thereof-bound) or wild type Semaphorin 3-bound (or functional fragment thereof-bound) anti-mutated-Semaphorin 3 antibodies are detected by a chromogenic reaction with ortho-phenylenediamine. Antibodies that specifically bind to the mutated Semaphorin 3 (or the functional fragment thereof), but not to the wild type Semaphorin 3 (or the functional fragment thereof) are selected.

In a further embodiment, the nucleic acid molecule, the vector, the mutated Semaphorin 3, the functional fragment thereof or the fusion protein/polypeptide according to the invention can be used as a medicament, i.e. the mutated Semaphorin 3 or the functional fragment thereof provided and described herein are for use in medicine. The terms "medicament" and "pharmaceutical composition" are used interchangeably herein. Accordingly, definitions and explanations provided herein in relation to "pharmaceutical compositions", apply, mutatis mutandis, to the term "medicament".

The term "treatment of a disorder or disease" as used herein, such as "treatment of cancer", is well known in the art. "Treatment of a disorder or disease" implies that a disorder or disease is suspected or has been diagnosed in a patient/subject. A patient/subject suspected of suffering from a disorder or disease typically shows specific clinical and/or pathological symptoms which a skilled person can attribute to a specific pathological condition (i.e., diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (e.g., the exemplary responses as described herein above). The treatment of a disorder or disease may, inter alia, comprise curative treatment (preferably leading to a complete response and eventually to healing of the disorder or disease) and palliative treatment (including symptomatic relief). Thus, the term "treatment" means obtaining a desired pharmacological and/or physiological effect. The effect may also be prophylactic in terms of completely or partially preventing a disease/medical condition/disorder or symptom thereof and/or may be therapeutic in terms of partially or completely curing a disease/medical condition/disorder and/or adverse effect attributed to the disease/medical condition/disorder. The term "prevention of a disorder or disease" as used herein, such as "prevention of cancer", is also well known in the art. For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

The present invention provides a pharmaceutical composition comprising the nucleic acid molecule of the invention, the mutated Semaphorin 3 or the functional fragment thereof of the invention, the fusion protein or the polypeptide of the invention. The pharmaceutical composition can comprise a pharmaceutical excipient. It is understood herein that said pharmaceutical excipient can comprise or is a pharmaceutical carrier, vehicle and/or diluent. In one specific embodiment, said pharmaceutical carrier is a virus. In a preferred embodiment said virus is an adeno-associated-virus (AAV), wherein the adeno-associated-virus is AAV8. AAV can be for instance employed in gene therapy. Thus, in one aspect, the invention provides a nucleotide sequence which contains elements of an adenovirus genome as well as a mutated Semaphorin 3 or fragments thereof that is under the control of a eukaryotic transcriptional promoter. This nucleic acid sequence can function as a vector allowing expression of the aforementioned heterologous gene when the vector is introduced in a cell of an individual.

Further, the invention provides the pharmaceutical composition for use as a medicament. Further, the invention provides the pharmaceutical composition for use in the treatment of an angiogenic disorder, cancer, tumor, tumorous disease, vascular retinopathy, blood-brain barrier permeability alterations, neuroinflammatory disorders, inflammatory disorders, osteoporosis, psoriasis, obesity Mycobacterial infections, and/or granulomas. Further the invention provides the pharmaceutical composition for use of the treatment of tumor, wherein the tumor is a solid tumor. In particular, the invention provides the pharmaceutical composition for use in the treatment of tumor, wherein the tumor is a pancreatic tumor. Further, the invention provides the pharmaceutical composition for use in the treatment of cancer, wherein the cancer is selected from the group consisting of pancreatic cancer, cervical cancer, breast cancer, colon cancer, melanoma, prostate cancer, bladder cancer and tongue cancer. In particular, the invention provides the pharmaceutical composition for use in the treatment of pancreatic cancer. Further, the invention provides the pharmaceutical composition, wherein vascular normalization, reduction of tumor growth, reduction of metastatization or survival extension is involved. Further, the invention provides the pharmaceutical composition, the nucleic acid molecule, the vector, the mutated Semaphorin 3, the functional fragment thereof and/or the fusion protein/polypeptide, which is to be administered in combination with a with an anti-proliferative drug, an anticancer drug, a cytostatic drug, a cytotoxic drug and/or radiotherapy. In particular preferred aspects, the pharmaceutical composition, the nucleic acid molecule, the vector, the mutated Semaphorin 3, the functional fragment thereof and/or the fusion protein/polypeptide is to be administered parenterally.

Furthermore, the invention provides the pharmaceutical composition, the mutated Semaphorin 3, the functional fragment thereof and/or the fusion protein/polypeptide or the encoding nucleic acid molecule for use in the treatment of a tumor or cancer for inhibiting cancer growth, reducing liver metastasis or metastasis volume, reducing vessel area and/or promoting cancer vessel normalization by enhancing pericyte coverage, and/or increasing blood vessel perfusion and inhibiting cancer hypoxia.

The pharmaceutical composition, the nucleic acid molecule, the vector, said mutated Semaphorin 3, the functional fragment thereof and/or the fusion protein/polypeptide can be used in combination with other therapeutic agents. When a compound of the invention is used in combination with a second therapeutic agent active against the same disease, the dose of each compound may differ from that when the compound is used alone. The combination of a compound of the present invention with a second therapeutic agent may comprise the administration of the second therapeutic agent with the compound of the invention. Such an administration may comprise simultaneous/concomitant administration. However, also sequential/separate administration is envisaged, as also explained below.

Preferably, the second therapeutic agent to be administered in combination with the compounds of this invention is an anticancer drug. The anticancer drug to be administered in combination with the pharmaceutical composition, the nucleic acid molecule, the vector, the mutated Semaphorin 3, the functional fragment thereof and/or the fusion protein/polypeptide according to the present invention may be: a tumor angiogenesis inhibitor (for example, a protease inhibitor, an epidermal growth factor receptor kinase inhibitor, or a vascular endothelial growth factor receptor kinase inhibitor); a cytotoxic drug (for example, an antimetabolite, such as purine and pyrimidine analogue antimetabolites); an antimitotic agent (for example, a microtubule stabilizing drug or an antimitotic alkaloid); a platinum coordination complex; an anti-tumor antibiotic; an alkylating agent (for example, a nitrogen mustard or a nitrosourea); an endocrine agent (for example, an adrenocorticosteroid, an androgen, an anti-androgen, an estrogen, an anti-estrogen, an aromatase inhibitor, a gonadotropin-releasing hormone agonist, or a somatostatin analogue); or a compound that targets an enzyme or receptor that is overexpressed and/or otherwise involved in a specific metabolic pathway that is misregulated in the tumor cell (for example, ATP and GTP phosphodiesterase inhibitors, histone deacetylase inhibitors, protein kinase inhibitors (such as serine, threonine and tyrosine kinase inhibitors (for example, Abelson protein tyrosine kinase)) and the various growth factors, their receptors and corresponding kinase inhibitors (such as epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors)); methionine, aminopeptidase inhibitors, proteasome inhibitors, cyclooxygenase inhibitors (for example, cyclooxygenase-1 or cyclooxygenase-2 inhibitors) and topoisomerase inhibitors (for example, topoisomerase I inhibitors or topoisomerase II inhibitors).

An alkylating agent which can be used as an anticancer drug in combination with the pharmaceutical composition, the nucleic acid, the vector, the mutated Semaphorin 3, the functional fragment thereof and/or the fusion protein/polypeptide of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazines (such as temozolomide).

A platinum coordination complex which can be used as an anticancer drug in combination with the pharmaceutical composition, the nucleic acid molecule, the vector, the mutated Semaphorin 3, the functional fragment thereof and/or the fusion protein/polypeptide of the present invention may be, for example, cisplatin, carboplatin, nedaplatin, oxaliplatin, satraplatin, or triplatin tetranitrate.

A cytotoxic drug which can be used as an anticancer drug in combination with the pharmaceutical composition, the nucleic acid molecule, the vector, the mutated Semaphorin 3, the functional fragment thereof and/or the fusion protein/polypeptide of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with the pharmaceutical composition, the nucleic acid molecule, the vector, the mutated Semaphorin 3, the functional fragment thereof and/or the fusion protein/polypeptide of the present invention may be, for example, a taxane (such as docetaxel, larotaxel, ortataxel, paclitaxel/taxol, or tesetaxel), a *Vinca* alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumor antibiotic which can be used as an anticancer drug in combination with the pharmaceutical composition, the nucleic acid molecule, the vector, the mutated Semaphorin 3, the functional fragment thereof and/or the fusion protein/polypeptide of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from *Streptomyces* (such as actinomycin (including actinomycin D), bleomycin, mitomycin (including mitomycin C), or plicamycin).

A tyrosine kinase inhibitor which can be used as an anticancer drug in combination with the pharmaceutical composition, the nucleic acid molecule, the vector, the mutated Semaphorin 3, the functional fragment thereof and/or the fusion protein/polypeptide of the present invention may be, for example, axitinib, bosutinib, cediranib, dasatinib, erlotinib, gefitinib, imatinib, lapatinib, lestaurtinib, nilotinib, semaxanib, sorafenib, sunitinib, or vandetanib.

A topoisomerase-inhibitor which can be used as an anticancer drug in combination with the pharmaceutical composition, the nucleic acid molecule, the vector, the mutated Semaphorin 3, the functional fragment thereof and/or the fusion protein/polypeptide of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

Further anticancer drugs may be used in combination with the pharmaceutical composition, the nucleic acid molecule, the vector, the mutated Semaphorin 3, the functional fragment thereof and/or the fusion protein/polypeptide of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, trastuzumab, pertuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, and vorinostat.

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in proliferative diseases can be employed in co-therapy approaches with the pharmaceutical composition, the nucleic acid molecule, the vector, the mutated Semaphorin 3, the functional fragment thereof and/or the fusion protein/polypeptide of the invention. Examples of such biological molecules are anti-HER2 antibodies (e.g. trastuzumab, Herceptin®), anti-CD20 antibodies (e.g. Rituximab, Rituxan®, MabThera®, Reditux®), anti-CD19/CD3 constructs (see, e.g., EP-B1 1071752) and anti-TNF antibodies (see, e.g., Taylor P C. Antibody therapy for rheumatoid arthritis. Curr Opin Pharmacol. 2003. 3(3):323-328). Further antibodies, antibody fragments, antibody constructs and/or modified antibodies to be used in co-therapy approaches with the pharmaceutical composition, the nucleic acid molecule, the vector, the mutated Semaphorin 3, the functional fragment thereof and/or the polypeptide of the invention can be found in Taylor P C. Curr Opin Pharmacol. 2003. 3(3):323-328; Roxana A. Maedica. 2006. 1(1):63-65.

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the pharmaceutical composition, the nucleic acid molecule, the vector, the mutated Semaphorin 3, the functional fragment thereof and/or the fusion protein/polypeptide of the present invention or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately, they may be provided in any convenient formulation.

The pharmaceutical composition, the nucleic acid molecule, the vector, the mutated Semaphorin 3, the functional fragment thereof and/or the fusion protein/polypeptide can also be administered in combination with physical therapy, such as radiotherapy. Radiotherapy may commence before, after, or simultaneously with administration of the compounds of the invention. For example, radiotherapy may commence 1-10 minutes, 1-10 hours or 24-72 hours after administration of the compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens.

The present invention thus relates to a nucleic acid molecule, a mutated Semaphorin 3, a functional fragment thereof, a fusion protein or a polypeptide and/or a pharmaceutically acceptable salt, solvate, or prodrug thereof, or a pharmaceutical composition comprising any of the aforementioned entities in combination with a pharmaceutically acceptable excipient, for use in the treatment or prevention of cancer, in particular the treatment or prevention of pancreatic cancer, wherein the compound or the pharmaceutical composition is to be administered in combination with an anticancer drug and/or in combination with radiotherapy.

In other words, the invention provides the nucleic acid molecule of the invention, the vector of the invention and/or the mutated Semaphorin 3 or the functional fragment thereof, the fusion protein of the invention or the polypeptide of the invention for use as a medicament. Further the invention provides the nucleic acid molecule of the invention, the vector of the invention and/or the mutated Semaphorin 3 or the functional fragment thereof of the invention or the fusion protein/polypeptide of the invention for use in the treatment of an angiogenic disorder, cancer, tumorous disease, vascular retinopathy, blood-brain barrier permeability alterations, neuroinflammatory disorders, osteoporosis, obesity Mycobacterial infections, and/or granulomas. Further the invention provides the nucleic acid molecule of the invention, the vector of the invention and/or the mutated Semaphorin 3 or the functional fragment thereof of the invention or the fusion protein/polypeptide of the invention for use in the treatment of tumor, wherein the tumor is a solid tumor. Further the invention provides the nucleic acid molecule of the invention, the vector of the invention and/or the mutated Semaphorin 3 or the functional fragment thereof of the invention or the fusion protein/polypeptide of the invention for use in the treatment of tumor selected from the group consisting of pancreatic tumor, cervical cancer, breast cancer, colon cancer, melanoma, prostate cancer, bladder cancer and tongue cancer. In particular the invention provides the nucleic acid molecule of the invention, the vector of the invention and/or the mutated Semaphorin 3 or the functional fragment thereof of the invention or the fusion protein/polypeptide of the invention for use in the treatment of pancreatic cancer. Further the invention provides the nucleic acid molecule of the invention, the vector of the invention and/or the mutated Semaphorin 3 or the functional fragment thereof of the invention or the fusion protein/polypeptide of the invention, wherein vascular normalization, reduction of tumor growth, reduction of metastatization or survival extension is involved.

The term "Angiogenesis" means that a vascular EC germinates from a pre-existing vessel and a capillary vessel is formed in a way that goes into a tissue. A formative process is the digestion of the vascular basement membrane by a protease, the migration/growth of a vascular EC, and the lumen formation. "Angiogenic disorder" is a vascular disease such as arterial sclerosis, hypertonia, angina pectoris, obstructive arteriosclerosis, myocardial infarction, cerebral infarction, diabetic angiopathy or vascular malformation; inflammatory disease such as hepatitis, pneumonitis, glomerular nephritis, thyroiditis, osteitis, arthromeningitis, osteoclasia, chondrolysis, rheumatism, bronchial asthma, sarcoidosis, Crow-Fukase syndrome, pannus, allergic oedema, ulcers, hydroperitoneum, peritoneal sclerosis or tissular conglutination; entoptic neovascular disease such as diabetic retinopathy, occlusion of retinal vein or aging macular degeneration; reproductive system disease such as uterus dysfunction, placental dysfunction, ovarian hyperergasia or follicle cyst; central nervous system disease such as retinosis, cerebral apoplexy, vascular dementia or Alzheimer disease; cancer such as solid cancer, angiomatous, hemangioendothelioma, sarcomas, Kaposi's sarcoma or hematopoietic organic ulcer.

"Cancer", in accordance with the present invention, refers to a class of diseases or disorders characterized by uncontrolled division of cells and the ability of these to spread, either by direct growth into adjacent tissue through invasion, or by implantation into distant sites by metastasis, where cancer cells are transported through the bloodstream or lymphatic system. The tumorous disease can be any form of a cancer, a tumor or is chosen from pancreas cancer, breast cancer, epithelial cancer, hepatocellular carcinoma, cholangiocellular cancer, stomach cancer, colon cancer, prostate cancer, bladder cancer, tongue cancer, head and neck cancer, skin cancer (melanoma), a cancer of the urogenital tract, e.g., ovarian cancer, endometrial cancer, cervix cancer, and kidney cancer; lung cancer, gastric cancer, a cancer of the small intestine, liver cancer, gall bladder cancer, a cancer of the bile duct, esophagus cancer, a cancer of the salivary glands or a cancer of the thyroid gland.

The angiogenesis inhibitor can be used as a preventive or therapeutic agent for a disease whose condition can become serious by angiogenesis in the above diseases. The disease on which the angiogenesis inhibitor has effect is vascular disease, inflammatory disease, entoptic neovascular disease, reproductive system disease, central nervous system disease, cancer or the like. A form of formulation of a vector of this invention (a gene therapy agent) can be one of different forms according to the above each form of administration. For example, when it is an injection comprising DNA of this invention which is an active ingredient, the injection can be prepared by a usual method. A base ingredient for a gene therapy agent is not especially restricted as long as it is a base ingredient usually used for an injection. It is, for example, distilled water, sodium chloride, a salt solution such as mixture of sodium chloride and mineral salts, a solution such as mannitol, lactose, dextran or glucose, an amino acid solution such as glycine or arginine, or mixture of an organic acid solution or a salt solution and a glucose solution. An injection can be prepared with an auxiliary such as an osmotic adjustment agent, pH adjustment agent, plant oil such as sesame oil or soybean oil, surfactant such as lecithin or nonionic surfactant or the like according to a usual method as a solution, suspension or dispersion. The injection as above can be a preparation dissolved in use by manipulation such as disintegration or lyophilization.

Further, the invention provides the use of the mutated Semaphorin 3 or the functional fragment thereof, of the nucleic acid molecule, of the fusion protein, of the polypeptide or of the host according to the invention.

Further, the invention provides a method of treatment for angiogenic disorder and/or tumorous disease and/or cancer comprising the step of administering to a subject in need of such treatment a pharmaceutical active amount of the nucleic acid molecule of the present invention, or the mutated Semaphorin 3 or the functional fragment thereof according to the present invention, the fusion protein, the polypeptide of the invention, the pharmaceutical composition of the present invention or as produced by the method as described herein.

The subject or patient to be treated in accordance with the invention may be an animal (e.g., a non-human animal), a vertebrate animal, a mammal, a rodent (e.g., a guinea pig, a hamster, a rat, a mouse), a murine (e.g., a mouse), a canine (e.g., a dog), a feline (e.g., a cat), a porcine (e.g., a pig), an equine (e.g., a horse), a primate, a simian (e.g., a monkey or ape), a monkey (e.g., a marmoset, a baboon), an ape (e.g., a gorilla, chimpanzee, orangutan, gibbon), or a human. In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melanogaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal; more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig); most preferably, the subject/patient is a human.

The pharmaceutical effective amount can be higher than 10 mg/kg of body weight. Further, the pharmaceutical effective amount can be lower than 0.5 mg/kg of body weight. In particular preferred aspects, the invention provides a method of treatment according to the invention, wherein the pharmaceutical effective amount is the range of 0.5 to 10 mg/kg of body weight.

It is envisaged herein that the content of DNA of a preparation is different depending on a disease of therapeutic purpose, administration site, number of doses, desired duration of therapy, an age or body weight of a patient or the like and can be suitably adjusted. It is usually about 0.01-2000 mg and preferably 0.1-100 mg of DNA encoding a protein of this invention for a patient (the body weight is 60 kg).

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations.

The skilled person knows that the effective amount of pharmaceutical composition administered to an individual will, inter alia, depend on the nature of the compound.

The administration of the herein provided compositions may, inter alia, comprise an administration twice daily, every day, every other day, every third day, every fourth day, every fifth day, once a week, once every second week, once every third week, once every month, etc.

For example, if said compound is a (poly)peptide or protein the total pharmaceutically effective amount of pharmaceutical composition administered parenterally per dose will be in the range of about 1 μg protein/kg/day to 15 mg protein/kg/day of patient body weight, although, as noted above, this will be subject to therapeutic discretion. More preferably, this dose is at least 0.01 mg protein/kg/day, and most preferably for humans between about 0.01 and 1 mg protein/kg/day. If given continuously, the pharmaceutical composition is typically administered at a dose rate of about 1 μg/kg/hour to about 50 μg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect. The particular amounts may be determined by conventional tests which are well known to the person skilled in the art.

Pharmaceutical compositions of the invention may be administered parenterally, orally, rectally, intracistemally, intravaginally, intraperitoneally, topically (as by powders, ointments, drops or transdermal patch) or bucally. In particular preferred embodiments, the pharmaceutical composition is administered parenterally.

Pharmaceutical compositions of the invention preferably comprise a pharmaceutically acceptable carrier. By "pharmaceutically acceptable carrier" is meant a virus, a non-toxic solid, semisolid or liquid filler, diluent, encapsulating material or formulation auxiliary of any type. The term "parenteral" as used herein refers to modes of administration which include intravenous, intramuscular, intraperitoneal, intratracheal, intranasal, intrasternal, subcutaneous and intraarticular injection and infusion.

The pharmaceutical composition is also suitably administered by sustained release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained release pharmaceutical composition also include liposomally entrapped compound. Liposomes containing the pharmaceutical composition are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

The invention further relates to kit comprising the mutated Semaphorin 3 or the functional fragment thereof, the fusion protein, the nucleic acid molecule, the antibody and/or the pharmaceutical composition as defined herein. Such a kit can be used, for example, in the treatment of cancer, tumor and/or tumorous disease, wherein said tumor cancer, tumorous disease is a solid tumor, in particular a pancreatic tumor/cancer.

The term "nucleic acid molecule" in accordance with the present invention comprises coding and, wherever applicable, non-coding sequences (like promoters, enhancers etc.).

The terms "polypeptide", "(poly)peptide", "peptide" and "protein" are used herein interchangeably and refer to a polymer of two or more amino acids linked via amide bonds that are formed between an amino group of one amino acid and a carboxyl group of another amino acid. The amino acids comprised in the peptide or protein, which are also referred to as amino acid residues, may be selected from the 20 standard proteinogenic α-amino acids (i.e., Ala, Arg, Asn, Asp, Cys, Glu, Gln, Gly, His, Ile, Leu, Lys, Met, Phe, Pro, Ser, Thr, Trp, Tyr, and Val) but also from non-proteinogenic and/or non-standard α-amino acids (such as, e.g., ornithine, citrulline, homolysine, pyrrolysine, or 4-hydroxyproline) as well as β-amino acids (e.g., β-alanine), γ-amino acids and δ-amino acids. Preferably, the amino acid residues comprised in the peptide or protein are selected from α-amino acids, more preferably from the 20 standard proteinogenic α-amino acids (which can be present as the L-isomer or the D-isomer, and are preferably all present as the L-isomer). The peptide or protein may be unmodified or may be modified, e.g., at its N-terminus, at its C-terminus and/or at a functional group in the side chain of any of its amino acid residues (particularly at the side chain functional group of one or more Lys, His, Ser, Thr, Tyr, Cys, Asp, Glu, and/or Arg residues). Such modifications may include, e.g., the attachment of any of the protecting groups described for the corresponding functional groups in: Wuts P G & Greene T W, Greene's protective groups in organic synthesis, John Wiley & Sons, 2006. Such modifications may also include the covalent attachment of one or more polyethylene glycol (PEG) chains (forming a PEGylated peptide or protein), the glycosylation and/or the acylation with one or more fatty acids (e.g., one or more C8-30 alkanoic or alkenoic acids; forming a fatty acid acylated peptide or protein). The amino acid residues comprised in the peptide or protein may, e.g., be present as a linear molecular chain (forming a linear peptide or protein) or may form one or more rings (corresponding to a cyclic peptide or protein). The peptide or protein may also form oligomers consisting of two or more identical or different molecules. As used herein, the term "domain" relates to any region/part of an amino acid sequence that is capable of autonomously adopting a specific structure and/or function. In the context of the present invention, accordingly, a "domain" may represent a functional domain or a structural domain.

The term "consensus sequence" or "consensus sequence motif" is the calculated order of most frequent residues, either nucleotide or amino acid, found at each position in a sequence alignment. It represents the results of a multiple sequence alignments in which related sequences are compared to each other and similar sequence motifs are calculated.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of."

Thus, the terms "comprising"/"including"/"having" mean that any further component (or likewise features, integers, steps and the like) can/may be present.

The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means those specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

The term "about" preferably refers to ±10% of the indicated numerical value, more preferably to ±5% of the indicated numerical value, and in particular to the exact numerical value indicated.

As used herein, the term "about" refers to ±10% of the indicated numerical value, and in particular to ±5% of the indicated numerical value. Whenever the term "about" is used, a specific reference to the exact numerical value indicated is also included. If the term "about" is used in connection with a parameter that is quantified in integers, such as the number of nucleotides in a given nucleic acid, the numbers corresponding to ±10% or ±5% of the indicated numerical value are to be rounded to the nearest integer. For example, the expression "about 25 nucleotides" refers to the range of 23 to 28 nucleotides, in particular the range of 24 to 26 nucleotides, and preferably refers to the specific value of 25 nucleotides.

The present invention is further described by reference to the following non-limiting figures and examples. Unless otherwise indicated, established methods of recombinant gene technology were used as described, for example, in Sambrook, Russell "Molecular Cloning, A Laboratory Manual", Cold Spring Harbor Laboratory, N.Y. (2001)) which is incorporated herein by reference in its entirety.

As used herein, the term "isolated" refers to a composition that has been removed from its in-vivo location. Preferably the isolated compositions or compounds of the present invention are substantially free from other substances (e.g., other proteins or other compounds) that are present in their in-vivo location (i.e. purified or semi-purified compositions or compounds.)

The given definitions and explanations are also applicable to these items and apply mutatis mutandis. In accordance with the above, the present invention relates to the following items in certain embodiments.

1. A nucleic acid molecule encoding a polypeptide comprising an amino acid sequence of a mutated Semaphorin 3 or a functional fragment thereof that functions as an inhibitor of angiogenesis, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.
2. The nucleic acid molecule of item 1, wherein said mutated Semaphorin 3 or said functional fragment thereof functions as an inhibitor of angiogenesis.
3. The nucleic acid molecule of item 1 or 2, wherein said mutated Semaphorin 3 or said functional fragment thereof comprises an amino acid sequence $CX_1X_2A_3GKD$, wherein
   $X_1$ is K or N,
   $X_2$ is an amino acid selected from the group of W, M and L and wherein the alanine ($A_3$) is replaced by said hydrophilic amino acid.
4. The nucleic acid molecule of any one of items 1 to 3, which is selected from the group of:
   (a) a nucleic acid molecule selected from the group of SEQ ID NO: 1, SEQ ID NO: 5, SEQ ID NO: 9 and SEQ ID NO: 13,
      wherein the nucleotides GCT at position 631 to 633 of SEQ ID NO: 1 are replaced by nucleotides encoding said hydrophilic amino acid,
      wherein the nucleotides GCA at position 559 to 561 of SEQ ID NO: 5 are replaced by nucleotides encoding said hydrophilic amino acid,
      wherein the nucleotides GCT at position 872 to 874 of SEQ ID NO: 9 are replaced by nucleotides encoding said hydrophilic amino acid, and
      wherein the nucleotides GCC at position 398 to 400 of SEQ ID NO: 13 are replaced by nucleotides encoding said hydrophilic amino acid;

(b) a nucleic acid molecule encoding a polypeptide selected from the group of SEQ ID NO: 2, SEQ ID NO: 6, SEQ ID NO: 10 and SEQ ID NO: 14, wherein the alanine residue at position 106 of SEQ ID NO: 2, at position 105 of SEQ ID NO: 6, at position 104 of SEQ ID NO: 10 or at position 120 of SEQ ID NO: 14 is replaced by said hydrophilic amino acid;

(c) a nucleic acid molecule hybridizing under stringent conditions to the complementary strand of a nucleic acid molecule as defined in (a) or (b);

(d) a nucleic acid molecule encoding a polypeptide that functions as an inhibitor of angiogenesis and has at least 55% identity to any one of the polypeptides referred to in (b); and (e) a nucleic acid molecule being degenerate as a result of the genetic code to the nucleotide sequence of a nucleic acid molecule as defined in any one of (a) to (d), wherein the degenerate nucleic acid molecule encodes a polypeptide that functions as an inhibitor of angiogenesis.

5. The nucleic acid molecule of any one of items 1 to 4, wherein said mutated Semaphorin 3 or said functional fragment thereof comprises said hydrophilic amino acid at position 106 of SEQ ID NO: 2, at position 105 of SEQ ID NO: 6, at position 104 of SEQ ID NO: 10 or at position 120 of SEQ ID NO: 14.

6. The nucleic acid molecule of any one of items 1 to 5, wherein said mutated Semaphorin 3 or functional fragment thereof comprises at least one additional mutation selected from the group consisting of amino acid substitution(s), addition(s), deletions(s) and duplication(s).

7. The nucleic acid molecule of any one of items 1 to 6, wherein said hydrophilic amino acid is selected from the group of K, R, N, Q, S, T, E, D, and H.

8. The nucleic acid molecule of item 7, wherein said hydrophilic amino acid is selected from the group of K, R, E, D, and H.

9. The nucleic acid molecule of item 7, wherein said hydrophilic amino acid residue is K or R.

10. The nucleic acid molecule of item 7, wherein said hydrophilic amino acid residue is K.

11. The nucleic acid molecule of any one of items 1 to 10, wherein K is encoded by a codon AAG or AAA.

12. The nucleic acid molecule of any one of items 1 to 11, wherein said mutated Semaphorin 3 or said functional fragment thereof is a mutated human or mouse Semaphorin 3 or a functional fragment thereof 13. The nucleic acid molecule of any one of items 1 to 12, wherein said mutated Semaphorin 3 or said functional fragment thereof comprises one or more of the following sequence(s) as defined in any one of SEQ ID NO: 26, SEQ ID NO: 27, SEQ ID NO: 29, SEQ ID NO: 30, SEQ ID NO: 32, SEQ ID NO: 33, SEQ ID NO: 35, SEQ ID NO: 36, SEQ ID NO: 45, SEQ ID NO: 46, SEQ ID NO: 47 and SEQ ID NO: 48.

14. The nucleic acid molecule of any one of items 1 to 13, wherein said nucleic acid molecule comprises:

(a) the nucleotides from 601 to 1206 of SEQ ID NO: 1, wherein the nucleotides GCT at position 631 to 633 of SEQ ID NO: 1 are replaced by nucleotides encoding a hydrophilic amino acid;

(b) the nucleotides from 529 to 1137 of SEQ ID NO: 5, wherein the nucleotides GCA at position 559 to 561 of SEQ ID NO: 5 are replaced by nucleotides encoding a hydrophilic amino acid;

(c) the nucleotides from 842 to 1444 of SEQ ID NO: 9, wherein the nucleotides GCT at position 872 to 874 of SEQ ID NO: 9 are replaced by nucleotides encoding a hydrophilic amino acid; or (d) the nucleotides from 368 to 982 of SEQ ID NO: 13 wherein the nucleotides GCC at position 398 to 400 of SEQ ID NO: 13 are replaced by nucleotides encoding a hydrophilic amino acid.

15. The nucleic acid molecule of any one of items 1 to 14, wherein said nucleic acid molecule comprises the nucleotides from 601 to 1206 of SEQ ID NO: 57; the nucleotides from 529 to 1137 of SEQ ID NO: 61; the nucleotides from 842 to 1444 of SEQ ID NO: 65; or the nucleotides from 368 to 982 of SEQ ID NO: 69.

16. The nucleic acid molecule of any one of items 1 to 15, wherein said mutated Semaphorin 3 or said functional fragment thereof comprises an amino acid sequence as shown in:

(a) SEQ ID NO: 21, wherein the alanine residue corresponding to position 106 of SEQ ID NO: 2 is replaced by a hydrophilic amino acid;

(b) SEQ ID NO: 22, wherein the alanine residue corresponding to position 105 of SEQ ID NO: 6 is replaced by a hydrophilic amino acid;

(c) SEQ ID NO: 23 wherein the alanine residue corresponding to position 104 of SEQ ID NO: 10 is replaced by a hydrophilic amino acid; or (d) SEQ ID NO: 24, wherein the alanine residue corresponding to position 120 of SEQ ID NO: 14 is replaced by a hydrophilic amino acid.

17. The nucleic acid molecule of any one of items 1 to 16, wherein said mutated Semaphorin 3 or said functional fragment thereof comprises an amino acid sequence that is selected from the group of SEQ ID NO: 49, SEQ ID NO: 50, SEQ ID NO: 51 and SEQ ID NO: 52.

18. The nucleic acid molecule of any one of items 1 to 17, wherein said polypeptide is a fusion protein.

19. The nucleic acid molecule of item 18, wherein said polypeptide comprises said mutated Semaphorin 3 or said functional fragment thereof, a stabilizer domain and/or a dimerization domain.

20. The nucleic acid molecule of item 18 or 19, wherein said stabilizer domain is a Plexin Semaphorin Integrin (PSI) domain, wherein said PSI domain comprises one or more of the following sequences SEQ ID NO: 45, SEQ ID NO: 46, SEQ ID NO: 47 or SEQ ID NO: 48.

21. The nucleic acid molecule of any one of items 18 to 20, wherein said dimerization domain has a dissociation constant $K_D$ in the range of $10^{-5}$ M to $10^{-6}$ M with another such dimerization domain.

22. The nucleic acid molecule of any one of items 18 to 21, wherein said dimerization domain is selected from the group of a C-terminal IgG constant domain, DARPin and leucine zipper.

23. The nucleic acid molecule of item 22, wherein the IgG constant domain is IgG1 or IgG3.

24. The nucleic acid molecule of any one of items 1 to 23, wherein said nucleic acid molecule comprises a nucleic acid sequence having:

(a) a nucleic acid sequence spanning from nucleotides 316 to 1959 of SEQ ID NO: 1 and a nucleic acid sequence spanning from nucleotides 295 to 990 of SEQ ID NO: 37, wherein the nucleotides GCT at position 631 to 633 of SEQ ID NO: 1 are replaced by nucleotides encoding a hydrophilic amino acid;

(b) a nucleic acid sequence spanning from nucleotides 247 to 1887 of SEQ ID NO: 5 and a nucleic acid sequence spanning from nucleotides 295 to 990 of SEQ ID NO: 37, wherein the nucleotides GCA at position 559 to 561 of SEQ ID NO: 5 are replaced by nucleotides encoding a hydrophilic amino acid;

(c) a nucleic acid sequence spanning from nucleotides 563 to 2197 of SEQ ID NO: 9 and a nucleic acid sequence spanning from nucleotides 295 to 990 of SEQ ID NO: 37, wherein the nucleotides GCT at position 872 to 874 of SEQ ID NO: 9 are replaced by nucleotides encoding a hydrophilic amino acid; or (d) a nucleic acid sequence spanning from nucleotides 41 to 1735 of SEQ ID NO: 13 and a nucleic acid sequence spanning from nucleotides 295 to 990 of SEQ ID NO: 37, wherein the nucleotides GCC at position 398 to 400 of SEQ ID NO: 13 are replaced by nucleotides encoding a hydrophilic amino acid.

25. The nucleic acid molecule of any one of items 1 to 24, wherein said polypeptide comprises an amino acid sequence:

(a) spanning from amino acid residues 1 to 548 of SEQ ID NO: 2 and an amino acid sequence as shown in SEQ ID NO: 41, wherein the alanine residue at position 106 of SEQ ID NO: 2 is replaced by a hydrophilic amino acid;

(b) spanning from amino acid residues 1 to 547 of SEQ ID NO: 6 and an amino acid sequence as shown in SEQ ID NO: 41, wherein the alanine residue at position 105 of SEQ ID NO: 6 is replaced by a hydrophilic amino acid;

(c) spanning from amino acid residues 1 to 565 of SEQ ID NO: 10 and an amino acid sequence as shown in SEQ ID NO: 41, wherein the alanine residue at position 104 of SEQ ID NO: 10 is replaced by a hydrophilic amino acid; or (d) spanning from amino acid residues 1 to 545 of SEQ ID NO: 14 and an amino acid sequence as shown in SEQ ID NO: 41, wherein the alanine residue at position 120 of SEQ ID NO: 14 is replaced by said hydrophilic amino acid.

26. A vector comprising the nucleic acid molecule of any one of items 1 to 25.

27. The vector of item 26, wherein said vector is a gene targeting vector or a gene transfer vector.

28. The vector of item 26 or 27, wherein said vector is an adeno-associated-virus (AAV) vector.

29. The vector of any one of items 26 to 28, wherein the adeno-associated-virus is AAV8 vector.

30. A host transformed with a vector of any one of items 26 to 29 or comprising the nucleic acid molecule of item 1 to 22.

31. The host of item 30 which is a mammalian cell.

32. The host of item 30 or 31, wherein the mammalian cell is a HEK cell.

33. The host of any one of items 30 to 32, wherein the HEK cell is a HEK293-EBNA1 or a HEK293E cell.

34. A method for producing said polypeptide, said mutated Semaphorin 3 or said functional fragment thereof encoded by the nucleic acid molecule of any one of items 1 to 25 said method comprising culturing/raising the host of any one of items 30 to 33 and optionally isolating the produced polypeptide.

35. A polypeptide which is encoded by the nucleic acid molecule of any one of items 1 to 25.

36. A mutated Semaphorin 3 or a functional fragment thereof, wherein said mutated Semaphorin 3 or said functional fragment thereof that functions as an inhibitor of angiogenesis comprises an amino acid sequence, wherein the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

37. The mutated Semaphorin 3 or the functional fragment thereof according to item 36, wherein said mutated Semaphorin 3 or said functional fragment thereof functions as an inhibitor of angiogenesis.

38. The mutated Semaphorin 3 or the functional fragment thereof according to any one of items 36 to 37, wherein said mutated Semaphorin 3 or said functional fragment thereof comprises an amino acid sequence $CX_1X_2A_3GKD$, wherein $X_1$ is K or N, $X_2$ is an amino acid selected from the group of W, M and L and wherein the alanine ($A_3$) is replaced by said hydrophilic amino acid.

39. The mutated Semaphorin 3 or the functional fragment thereof according to any one of items 36 to 38, wherein said mutated Semaphorin 3 is selected from the group of:

(a) a polypeptide encoded by a nucleic acid molecule selected from the group of SEQ ID NO: 1, SEQ ID NO: 5, SEQ ID NO: 9 and SEQ ID NO: 13, wherein the nucleotides GCT at position 631 to 633 of SEQ ID NO: 1 are replaced by nucleotides encoding said hydrophilic amino acid, wherein the nucleotides GCA at position 559 to 561 of SEQ ID NO: 5 are replaced by nucleotides encoding said hydrophilic amino acid, wherein the nucleotides GCT at position 872 to 874 of SEQ ID NO: 9 are replaced by nucleotides encoding said hydrophilic amino acid, and wherein the nucleotides GCC at position 398 to 400 of SEQ ID NO: 13 are replaced by nucleotides encoding said hydrophilic amino acid;

(b) a polypeptide selected from the group of SEQ ID NO: 2, SEQ ID NO: 6, SEQ ID NO: 10 and SEQ ID NO: 14, wherein the alanine residue corresponding to position 106 of SEQ ID NO: 2, corresponding to position 105 of SEQ ID NO: 6, corresponding to position 104 of SEQ ID NO: 10 or corresponding to position 120 of SEQ ID NO: 14 is replaced by said hydrophilic amino acid;

(c) a polypeptide encoded by a nucleic acid molecule hybridizing under stringent conditions to the complementary strand of a nucleic acid molecule as defined in (a) or (c);

(d) a polypeptide having at least 55% identity to the polypeptide of any one of (a) to (d) and functioning as an inhibitor of angiogenesis; and (e) a polypeptide that functions as an inhibitor of angiogenesis comprising an amino acid sequence encoded by a nucleic acid molecule being degenerate as a result of the genetic code to the nucleotide sequence of a nucleic acid molecule as defined in any one of (a), (c) and (d).

40. The mutated Semaphorin 3 or the functional fragment thereof according to any one of items 36 to 39, wherein said mutated Semaphorin 3 or said functional fragment thereof comprises said hydrophilic amino acid at position 106 of SEQ ID NO: 2, at position 105 of SEQ ID NO: 6, at position 104 of SEQ ID NO: 10 or at position 120 of SEQ ID NO: 14.

41. The mutated Semaphorin 3 or the functional fragment thereof according to any one of items 36 to 40, wherein the mutated Semaphorin 3 or the functional fragment thereof comprises at least one additional mutation selected from the group consisting of amino acid substitution(s), addition(s), deletions(s) and duplication(s).

42. The mutated Semaphorin 3 or the functional fragment thereof according to any one of items 36 to 41, wherein said hydrophilic amino acid is selected from the group of K, R, N, Q, S, T, E, D, and H.

43. The mutated Semaphorin 3 or the functional fragment thereof according to item 42, wherein said hydrophilic amino acid is selected from the group of K, R, E, D, and H.

44. The mutated Semaphorin 3 or the functional fragment thereof according to item 42, wherein said hydrophilic amino acid is K or R.

45. The mutated Semaphorin 3 or the functional fragment thereof according to item 42, wherein said hydrophilic amino acid is K.

46. The mutated Semaphorin 3 or the functional fragment thereof according to any one of items 36 to 45, wherein said mutated Semaphorin 3 or said functional fragment thereof is a mutated human or mouse Semaphorin 3 or a functional fragment thereof 47. The mutated Semaphorin 3 or the functional fragment thereof according to any one of items 36 to 46, wherein said mutated Semaphorin 3 or said functional fragment thereof comprises one or more of the following sequence(s) as defined in any one of SEQ ID NO: 26, SEQ ID NO: 27, SEQ ID NO: 29, SEQ ID NO: 30, SEQ ID NO: 32, SEQ ID NO: 33, SEQ ID NO: 35, SEQ ID NO: 36, SEQ ID NO: 45, SEQ ID NO: 46, SEQ ID NO: 47 and SEQ ID NO: 48.

48. The mutated Semaphorin 3 or the functional fragment thereof according to any one of items 36 to 47, wherein said mutated Semaphorin 3 or said functional fragment thereof is encoded by a nucleic acid molecule comprising:
   (a) the nucleotides from 601 to 1206 of SEQ ID NO: 1, wherein the nucleotides GCT at position 631 to 633 of SEQ ID NO: 1 are replaced by nucleotides encoding a hydrophilic amino acid;
   (b) the nucleotides from 529 to 1137 of SEQ ID NO: 5, wherein the nucleotides GCA at position 559 to 561 of SEQ ID NO: 5 are replaced by nucleotides encoding a hydrophilic amino acid;
   (c) the nucleotides from 842 to 1444 of SEQ ID NO: 9, wherein the nucleotides GCT at position 872 to 874 of SEQ ID NO: 9 are replaced by nucleotides encoding a hydrophilic amino acid; or
   (d) the nucleotides from 368 to 982 of SEQ ID NO: 13, wherein the nucleotides GCC at position 398 to 400 of SEQ ID NO: 13 are replaced by nucleotides encoding a hydrophilic amino acid.

49. The mutated Semaphorin 3 or the functional fragment thereof according to any one of items 36 to 48, wherein said mutated Semaphorin 3 or said functional fragment thereof is encoded by a nucleic acid molecule comprising the nucleotides from 601 to 1206 of SEQ ID NO: 57; the nucleotides from 529 to 1137 of SEQ ID NO: 61; the nucleotides from 842 to 1444 of SEQ ID NO: 65; or the nucleotides from 368 to 982 of SEQ ID NO: 69.

50. The mutated Semaphorin 3 or the functional fragment thereof according to any one of items 36 to 49, wherein said mutated Semaphorin 3 or said functional fragment thereof comprises an amino acid sequence as shown in:
   (a) SEQ ID NO: 21, wherein the alanine residue corresponding to position 106 of SEQ ID NO: 2 is replaced by a hydrophilic amino acid;
   (b) SEQ ID NO: 22, wherein the alanine residue corresponding to position 105 of SEQ ID NO: 6 is replaced by a hydrophilic amino acid;
   (c) SEQ ID NO: 23 wherein the alanine residue corresponding to position 104 of SEQ ID NO: 10 is replaced by a hydrophilic amino acid; or
   (d) SEQ ID NO: 24, wherein the alanine residue corresponding to position 120 of SEQ ID NO: 14 is replaced by a hydrophilic amino acid.

51. The mutated Semaphorin 3 or the functional fragment thereof according to any one of items 36 to 50, wherein said mutated Semaphorin 3 or said functional fragment thereof comprises an amino acid sequence that is selected from the group of SEQ ID NO: 49, SEQ ID NO: 50, SEQ ID NO: 51 and SEQ ID NO: 52.

52. A polypeptide, wherein the polypeptide comprises the mutated Semaphorin 3 or the functional fragment thereof according to any one of items 36 to 51.

53. The polypeptide according to item 52, wherein said polypeptide is a fusion protein.

54. The polypeptide of item 52 or 53, wherein said polypeptide comprises said mutated Semaphorin 3 or said functional fragment thereof, a stabilizer domain and/or a dimerization domain.

55. The polypeptide according to any one of items 52 to 54, wherein said stabilizer domain is a Plexin Semaphorin Integrin (PSI) domain, wherein said PSI domain comprises one or more of the following sequences SEQ ID NO: 45, SEQ ID NO: 46, SEQ ID NO: 47 or SEQ ID NO: 48.

56. The polypeptide according to any one of items 52 to 55, wherein said dimerization domain has a dissociation constant $K_D$ in the range of $10^{-5}$ M to $10^{-6}$ M with another such dimerization domain.

57. The polypeptide according to any one of items 52 to 56, wherein said dimerization domain is selected from the group of a C-terminal IgG constant domain, DARPin and leucine zippers.

58. The polypeptide according to item 57, wherein the IgG constant domain is IgG1 or IgG3.

59. The polypeptide according to any one of items 52 to 58, wherein said polypeptide is encoded by a nucleic acid molecule comprising a nucleic acid sequence having:
   (a) a nucleic acid sequence spanning from nucleotides 316 to 1959 of SEQ ID NO: 1 and a nucleic acid sequence spanning from nucleotides 295 to 990 of SEQ ID NO: 37, wherein the nucleotides GCT at position 631 to 633 of SEQ ID NO: 1 are replaced by nucleotides encoding a hydrophilic amino acid;
   (b) a nucleic acid sequence spanning from nucleotides 247 to 1887 of SEQ ID NO: 5 and a nucleic acid sequence spanning from nucleotides 295 to 990 of SEQ ID NO: 37, wherein the nucleotides GCA at position 559 to 561 of SEQ ID NO: 5 are replaced by nucleotides encoding a hydrophilic amino acid;
   (c) a nucleic acid sequence spanning from nucleotides 563 to 2197 of SEQ ID NO: 9 and a nucleic acid sequence spanning from nucleotides 295 to 990 of SEQ ID NO: 37, wherein the nucleotides GCT at position 872 to 874 of SEQ ID NO: 9 are replaced by nucleotides encoding a hydrophilic amino acid; or
   (d) a nucleic acid sequence spanning from nucleotides 41 to 1735 of SEQ ID NO: 13 and a nucleic acid sequence spanning from nucleotides 295 to 990 of SEQ ID NO: 37, wherein the nucleotides GCC at position 398 to 400 of SEQ ID NO: 13 are replaced by nucleotides encoding a hydrophilic amino acid.

60. The polypeptide according to any one of items 52 to 59, wherein said polypeptide comprises an amino acid sequence:
(a) spanning from amino acid residues 1 to 548 of SEQ ID NO: 2 and an amino acid sequence as shown in SEQ ID NO: 41, wherein the alanine residue at position 106 of SEQ ID NO: 2 is replaced by a hydrophilic amino acid;
(b) spanning from amino acid residues 1 to 547 of SEQ ID NO: 6 and an amino acid sequence as shown in SEQ ID NO: 41, wherein the alanine residue at position 105 of SEQ ID NO: 6 is replaced by a hydrophilic amino acid;
(c) spanning from amino acid residues 1 to 565 of SEQ ID NO: 10 and an amino acid sequence as shown in SEQ ID NO: 41, wherein the alanine residue at position 104 of SEQ ID NO: 10 is replaced by a hydrophilic amino acid; or
(d) spanning from amino acid residues 1 to 545 of SEQ ID NO: 14 and an amino acid sequence as shown in SEQ ID NO: 41, wherein the alanine residue at position 120 of SEQ ID NO: 14 is replaced by said hydrophilic amino acid.

61. An antibody specifically binding to the mutated Semaphorin 3 or the functional fragment thereof according to any one of items 36 to 51, wherein said antibody specifically binds to an epitope comprising the hydrophilic amino acid which replaces the alanine corresponding to position 106 of the wild type Semaphorin 3A as shown in SEQ ID NO: 2 or the alanine at the position which corresponds in other Semaphorin 3 proteins by comparison of homology to position 106 of the wild type Semaphorin 3A as shown in SEQ ID NO: 2 is replaced by a hydrophilic amino acid, wherein said Semaphorin 3 is selected from the group of Semaphorin 3A, Semaphorin 3B, Semaphorin 3C and Semaphorin 3D.

62. A pharmaceutical composition comprising the nucleic acid molecule of any one of items 1 to 25 or the mutated Semaphorin 3 or the functional fragment thereof according to any one of items 36 to 51 or the polypeptide according to any one of items 52 to 60 optionally comprising a pharmaceutical excipient.

63. The pharmaceutical composition of item 62, wherein the composition comprises the mutated Semaphorin 3 or the functional fragment thereof according to any one of items 36 to 51 or the polypeptide according to any one of items of 52 to 60 optionally comprising a pharmaceutical excipient.

64. The pharmaceutical composition of item 62 or 63, wherein the pharmaceutical excipient is a pharmaceutical carrier, which is a virus.

65. The pharmaceutical composition of any one of items 62 to 64, wherein said virus is an adeno-associated-virus (AAV).

66. The pharmaceutical composition of any one of items 62 to 65, wherein the adeno-associated-virus is AAV8.

67. The nucleic acid molecule of any one of items 1 to 25, the vector of any one of items 26 or 29, the mutated Semaphorin 3 or the functional fragment thereof according to any one of items 36 to 51, the polypeptide according to any one of items of 52 to 60 or the pharmaceutical composition of any one of items 62 to 66 for use as a medicament.

68. The nucleic acid molecule of any one of items 1 to 25, the vector of any one of items 26 or 29, the mutated Semaphorin 3 or the functional fragment thereof according to any one of items 36 to 51, the polypeptide according to any one of items of 52 to 60 or the pharmaceutical composition of any one of items 62 to 66 for use in the treatment of an angiogenic disorder, cancer, tumor, tumorous disease, vascular retinopathies, blood-brain barrier permeability alterations, neuroinflammatory disorder, osteoporosis, obesity, mycobacterial infection, and/or granuloma.

69. The nucleic acid molecule of any one of items 1 to 25 for use according to item 68, the vector of any one of items 26 or 29 for use according to item 68, the mutated Semaphorin 3 or the functional fragment thereof according to any one of items 36 to 51 for use according to item 68, the polypeptide of any one of items 52 to 60 for use according to item 68 or the pharmaceutical composition of any one of items 62 to 66 for use according to item 68, wherein the tumor is a solid tumor.

70. The nucleic acid molecule of any one of items 1 to 25 for use according to item 68 or 69, the vector of any one of items 26 or 29 for use according to item 68 or 69, the mutated Semaphorin 3 or the functional fragment thereof according to any one of items 36 to 51 for use according to item 68 or 69, the polypeptide of any one of items 52 to 60 for use according to item 68 or 69 or the pharmaceutical composition of any one of items 62 to 66 for use according to item 68 or 69, wherein the tumor is pancreatic tumor.

71. The nucleic acid molecule of any one of items 1 to 25 for use according to any one of items 68 to 70, the vector of any one of items 26 or 29 for use according to any one of items 68 to 70, the mutated Semaphorin 3 or the functional fragment thereof according to any one of items 36 to 51 for use according to any one of items 68 to 70, the polypeptide of any one of items 52 to 60 for use according to any one of items 68 to 70 or the pharmaceutical composition of any one of items 62 to 66 for use according to any one of items 68 to 70, wherein the cancer is selected from the group consisting of pancreatic cancer, cervical cancer, breast cancer, colon cancer, melanoma, prostate cancer, bladder cancer and tongue cancer.

72. The nucleic acid molecule of any one of items 1 to 25 for use according to any one of items 68 to 71, the vector of any one of items 26 or 29 for use according to any one of items 68 to 71, the mutated Semaphorin 3 or the functional fragment thereof according to any one of items 36 to 51 for use according to any one of items 68 to 71, the polypeptide of any one of items 52 to 60 for use according to any one of items 68 to 71 or the pharmaceutical composition of any one of items 62 to 66 for use according to any one of items 68 to 71, wherein vascular normalization, reduction of tumor growth, reduction of metastatization or survival extension is involved.

73. The nucleic acid molecule of any one of items 1 to 25 for use according to any one of items 68 to 72, the vector of any one of items 26 or 29 for use according to item 68, the mutated Semaphorin 3 or the functional fragment thereof according to any one of items 36 to 51 for use according to any one of items 68 to 72, the polypeptide of any one of items 52 to 60 for use according to any one of items 68 to 72 or the pharmaceutical composition of any one of items 62 to 66 for use according to any one of items 68 to 72, wherein said nucleic acid molecule, said vector, said mutated Semaphorin 3, said functional fragment thereof, said polypeptide or said pharmaceutical composition is to be administered in combination with a with an anti-proliferative drug, an anticancer drug, a cytostatic drug, a cytotoxic drug and/or radiotherapy.

74. The nucleic acid molecule of any one of items 1 to 25 for use according to any one of items 68 to 72, the vector of any one of items 26 or 29 for use according to item 68, the mutated Semaphorin 3 or the functional fragment thereof according to any one of items 36 to 51 for use according to any one of items 68 to 72, the polypeptide of any one of items 52 to 60 for use according to any one of items 68 to 72 or the pharmaceutical composition of any one of items 62 to 66 for use according to any one of items 68 to 72, wherein said nucleic acid molecule, said vector, said mutated Semaphorin 3, said functional fragment thereof, said polypeptide or said pharmaceutical composition is to be administered parenterally.

75. Use of the mutated Semaphorin 3 or the functional fragment thereof as encoded by the nucleic acid molecule of any one of items 1 to 25 or of the mutated Semaphorin 3 or the functional fragment thereof according to any one of items 36 to 51 or of the polypeptide according to any one of items 52 to 60 or of the host of any one of items 30 to 33.

76. A method of treatment for angiogenic disorder, tumorous disease and/or cancer comprising the step of administering to a subject in need of such treatment a pharmaceutical effective amount of the nucleic acid molecule of any one of items 1 to 23, or the mutated Semaphorin 3 or the functional fragment thereof according to any one of items 36 to 51, the polypeptide according to any one of items 52 to 60, the pharmaceutical composition of any one of items 62 to 68 or as produced by the method of item 34.

77. The method of treatment according to item 76, wherein the subject is a human.

78. The method of treatment according to item 76 or 77, wherein the pharmaceutical effective amount is the range of 0.5 to 10 mg/kg of body weight.

The present invention is further described by reference to the following non-limiting figures and examples.

Unless otherwise indicated, established methods of recombinant gene technology were used as described, for example, in Sambrook, Russell "Molecular Cloning, A Laboratory Manual", Cold Spring Harbor Laboratory, N.Y. (2001)) which is incorporated herein by reference in its entirety.

The Figures show:

FIG. 1. The Sema3A-Nrp1-PlexinA4 signaling complex. Sema3A is characterized by the presence of a sema domain at its $NH_2$-terminal end, followed by a PSI domain, an Ig-like domain, and an additional short C-terminal basic stretch (b). The extracellular moiety of Nrp1 contains two repeated complement-binding domains (a1-a2 domains), two coagulation factor-like domains (b1-b2 domains), and a juxtamembrane meprin/A5/mu-phosphatase (MAM; c) homology domain. Plexin A4 is characterized by an extracellular sema domain, followed by multiple PSI and integrin-plexin-transcription factor (IPT) domains, while intracellularly displays a half-split GAP domain. The C-terminal basic stretch of Sema3A binds with high affinity (black border double arrow) the b1 domain of Nrp1, which acts as a co-receptor that keeps dimeric Sema3A close to Plexin A4. Without being bound by theory, Sema3A is thought to drive Plexin A4 dimerization and activation via a very low affinity sema domain-sema domain interaction (grey border double arrows), which results in the inhibition of R-Ras and Rapt GTP-loading and in the phosphorylation of ERK 1/2.

FIG. 2. Schematic representation of Sema3A protein constructs. Representatives of Sema3A mutants are depicted: (A) Sema3A domain comprising the A106K mutation with or without an additional PSI domain or a domain that can stabilize the structure of the functional sema domain (stabilizer domain); (B) Sema3A A106K ΔIg-b; (C) Sema3A ΔIg-b, and (D) full length SEMA3A WT (R&D Systems).

FIG. 3. Alignment of amino acidic sequences of mouse Sema3A, Sema3B, Sema3C, Sema3D, Sema3E, Sema3F and Sema3G. The protein sequences of mouse Sema3A (SEQ ID NO: 4), Sema3B (SEQ ID NO: 8), Sema3C (SEQ ID NO: 12), Sema3D (SEQ ID NO: 16), Sema3E (SEQ ID NO: 81), Sema3F (SEQ ID NO: 83) and Sema3G (SEQ ID NO: 85) and human SEMA3A (SEQ ID NO: 2), SEMA3B (SEQ ID NO: 6), SEMA3C (SEQ ID NO: 10). SEMA3D (SEQ ID NO: 14), SEMA3E (SEQ ID NO:80), and SEMA3F (SEQ ID NO:82) are depicted in the single letter amino acid code. (A) The $CX_1X_2A_3GKD$ peptide motif is highlighted (bold). (B) Three consensus sequence motifs of human SEMA3A (SEQ ID NO: 2). SEMA3B (SEQ ID NO:6) SEMA3C (SEQ ID NO: 10), and SEMA3D (SEQ ID NO: 14) are highlighted in bold that are predicted to allow for a strong interaction of the sema domain with the sema domain of Plexins. (C) One consensus sequence motif of human SEMA3A (SEQ ID NO: 45) SEMA38 (SEQ ID NO: 46). SEMA3C (SEQ ID NO: 47), and SEMA3D (SEQ ID NO: 48) is highlighted in bold in the PSI domain. The conservation is indicated with ClustalW consensus symbols: an asterisk (*) indicates positions which have a single, fully conserved residue; a colon (:) indicates conservation between groups of strongly similar properties—scoring >0.5 in the Gonnet PAM 250 matrix; a period (.) indicates conservation between groups of weakly similar properties—scoring=<0.5 in the Gonnet PAM 250 matrix.

FIG. 4. Analysis of Semaphorin 3 and mutated Semaphorin 3 proteins binding to type A Plexin and Nrp1 receptors. (A) cDNAs of alkaline phosphatase (AP) and full-length Sema3A WT, mutant Sema3A ΔIg-b or mutant Sema3A A106K ΔIg-b were fused to generate the corresponding AP-conjugated Sema3A ligands. In an in situ binding assay, COS-7 cells were transfected with different candidate receptors. Ligand binding to cells expressing specific receptors was revealed by phosphatase substrate nitroblue tetrazolium. (B-D) Binding curves (B, D) and Scatchard analysis (C) of Plexin A4 (B, C) or Nrp1 (D) binding at different concentrations of ligands (B, C, Sema3A A106K ΔIg-b; D, Sema3A WT) was independently quantified by spectrometry of chromogenic conversion of AP substrate p-nitrophenyl phosphate. (E). Estimated affinities of Sema3A WT, Sema3A ΔIg-b, and Sema3A A106K ΔIg-b for Plexin A4 receptor. Ligand binding curves of AP-conjugated Sema3A WT, mutant Sema3A ΔIg-b or mutant Sema3A A106K ΔIg-b to COS-7 cells expressing Plexin A4 receptor was independently quantified by spectrometry of chromogenic conversion of AP substrate p-nitrophenyl phosphate. The binding of Sema3A WT, mutant Sema3A ΔIg-b or mutant Sema3A A106K ΔIg-b to Plexin A4 respectively display an estimated $K_d$ of 7 nM, 200 nM, and 0.7 nM. (F). In an in situ binding assay, COS-7 cells were transfected with different type A Plexin receptors or green fluorescent protein (Mock), for control purposes. Binding of human Fc-tagged SEMA3B ΔIg-b, SEMA3B A105K ΔIg-b, and SEMA3A A106K ΔIg-b to cells expressing different type A Plexin receptors was revealed in immunocytochemistry by means of an alkaline phosphatase (AP) conjugated goat anti-human IgG Fc secondary antibody. A combination of nitro-blue tetrazolium chloride (NBT) and 5-bromo-4-chloro-3'-indolyphosphate p-toluidine salt (BCIP) was employed as AP substrate to yield an insoluble black-purple-colored product at locations where AP-conjugated goat anti-human IgG Fc secondary antibody was bound to human Fc tagged recombinant SEMA3 proteins.

Figure 5:
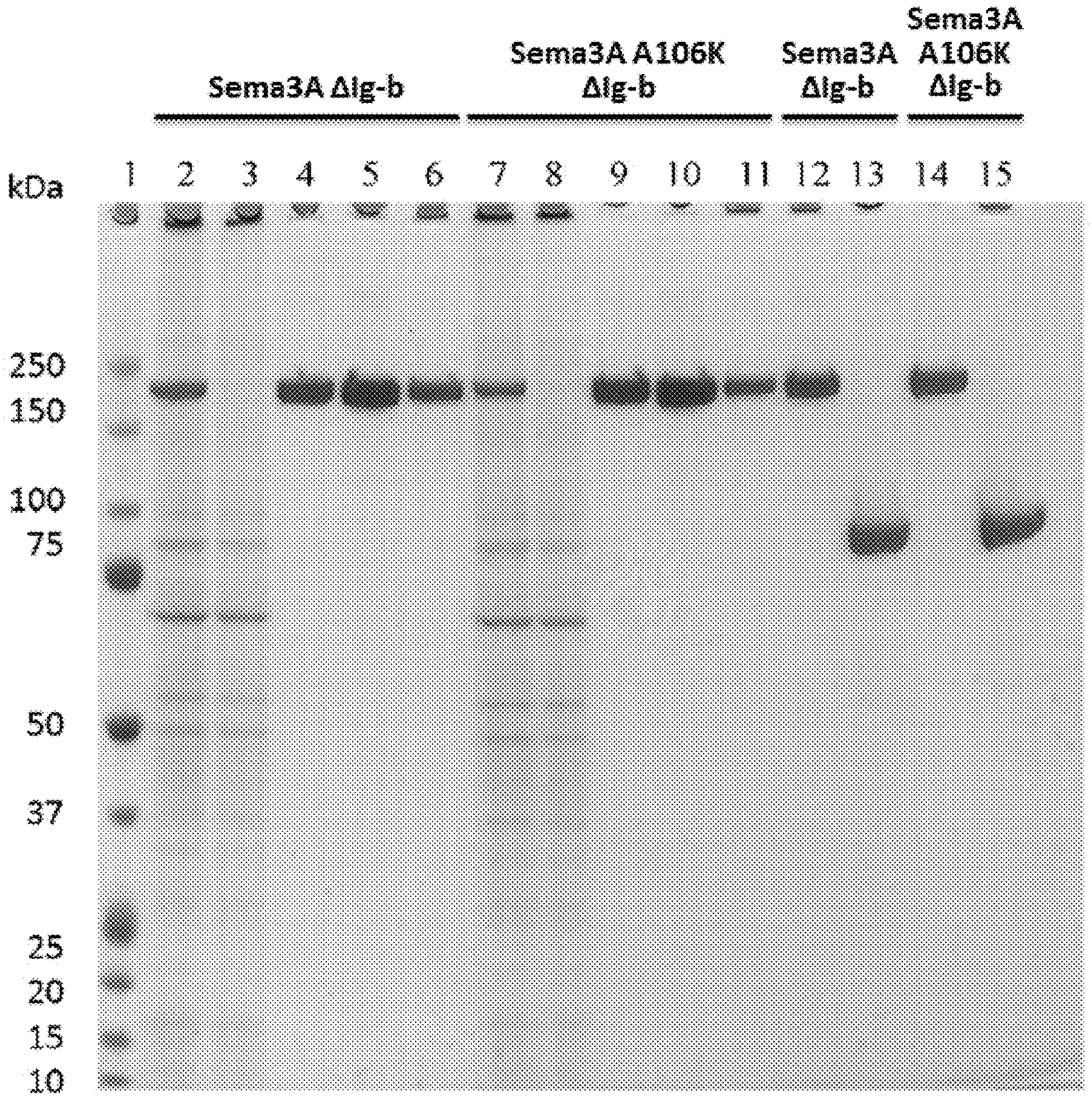

FIG. 5. Purification of Fc-tagged Sema3A Mg-b and Sema3A A106K Mg-b recombinant proteins. Proteins were produced in human HEK 293 cells, purified from supernatant on protein A-Sepharose, eluted and analyzed by NuPAGE 4-12% gel under non-reducing or reducing conditions. Lanes: 1) Mol. weight markers; 2) Fc-tagged Sema3A ΔIg-b cell culture medium; 3) Unbound protein A; 4) Fc-tagged Sema3A ΔIg-b Fraction 1; 5) Fc-tagged Sema3A ΔIg-b Fraction 2; 6) Fc-tagged Sema3A ΔIg-b Fraction 3; 7) Fc-tagged Sema3A A106K ΔIg-b cell culture medium; 8) Unbound protein A; 9) Fc-tagged Sema3A A106K ΔIg-b Fraction 1; 10) Fc-tagged Sema3A A106K ΔIg-b Fraction 2; 11) Fc-tagged Sema3A A106K ΔIg-b Fraction 3; 12) Fc-tagged Sema3A ΔIg-b, pool Fractions 1, 2 and 3; 13) Fc-tagged Sema3A ΔIg-b, pool Fractions 1, 2 and 3 (reduced); 14) Fc-tagged Sema3A A106K ΔIg-b, pool Fractions 1, 2 and 3; 15) Fc-tagged Sema3A A106K ΔIg-b, pool Fractions 1, 2 and 3 (reduced). In non-reducing conditions, both Fc-tagged Sema3A ΔIg-b and Fc-tagged Sema3A A106K ΔIg-b appear as a ~200 kDa dimer without degradation products.

FIG. 6. Fe-tagged Sema3A A106K Mg-b is more effective than commercially available Fe-tagged SEMA3A WT in inhibiting EC directional migration. Directional EC migration towards type I collagen (1 μg/ml) was analyzed by real time analysis. (A-C) The migration of ECs was tracked over a 4 hour-long period in CIM-Plates 16 of an xCELLigence system platform either in the absence (Control, black solid line) or the presence of 0.2 nM (A), 0.9 nM (B), and 3.5 nM (C) Fc-tagged SEMA3A WT (grey solid line) or Fc-tagged Sema3A ΔIg-b (black dotted line) or Fc-tagged Sema3A A106K ΔIg-b (black dashed line). Each curve is the average of four technical replicates±SD. Statistical analysis: results were analyzed by a two-tailed heteroscedastic Student's t-test; * Fc-tagged Sema3A A106K ΔIg-b vs. Fc-tagged SEMA3A WT; #Fc-tagged Sema3A A106K ΔIg-b vs. Fc-tagged Sema3A ΔIg-b; *, #p<0.05, , ##p<0.01, *, ###p<0.001. (D, E) Control silenced (D) or Plexin A4 silenced (E) ECs were left to migrate over a 2 hours and half-long period either in the absence (Control, black solid line) or the presence of 1.8 nM Fc-tagged Sema3A A106K ΔIg-b (black dashed line); *, p<0.05; , p<0.01; * p<0.001.

FIG. 7. Human Fe-tagged SEMA3A A106K Mg-b protein is more effective than commercially available Fe-tagged SEMA3A WT in inhibiting EC directional migration. Directional EC migration towards type I collagen (1 μg/ml) was analyzed by real time analysis. The migration of ECs was tracked over a 4 hour long period in CIM-Plates 16 of an xCELLigence system platform either in the absence (Control, black solid line) or the presence of: (A) equimolar (0.9 nM) amounts of commercial Fc-tagged SEMA3A WT (grey solid line) or Fc-tagged human SEMA3A A106K ΔIg-b (black dashed line); (B) 3.5 nM commercial Fc-tagged SEMA3A WT (grey solid line) or 0.2 nM Fc-tagged human SEMA3A A106K ΔIg-b (black dashed line). Each curve is the average of four technical replicates±SD. Statistical analysis: results were analyzed by a two-tailed heteroscedastic Student's t-test; * Fc-tagged SEMA3A A106K ΔIg-b vs. Fc-tagged SEMA3A WT; *, p<0.05; , p<0.01; * p<0.001.

Figure 8:
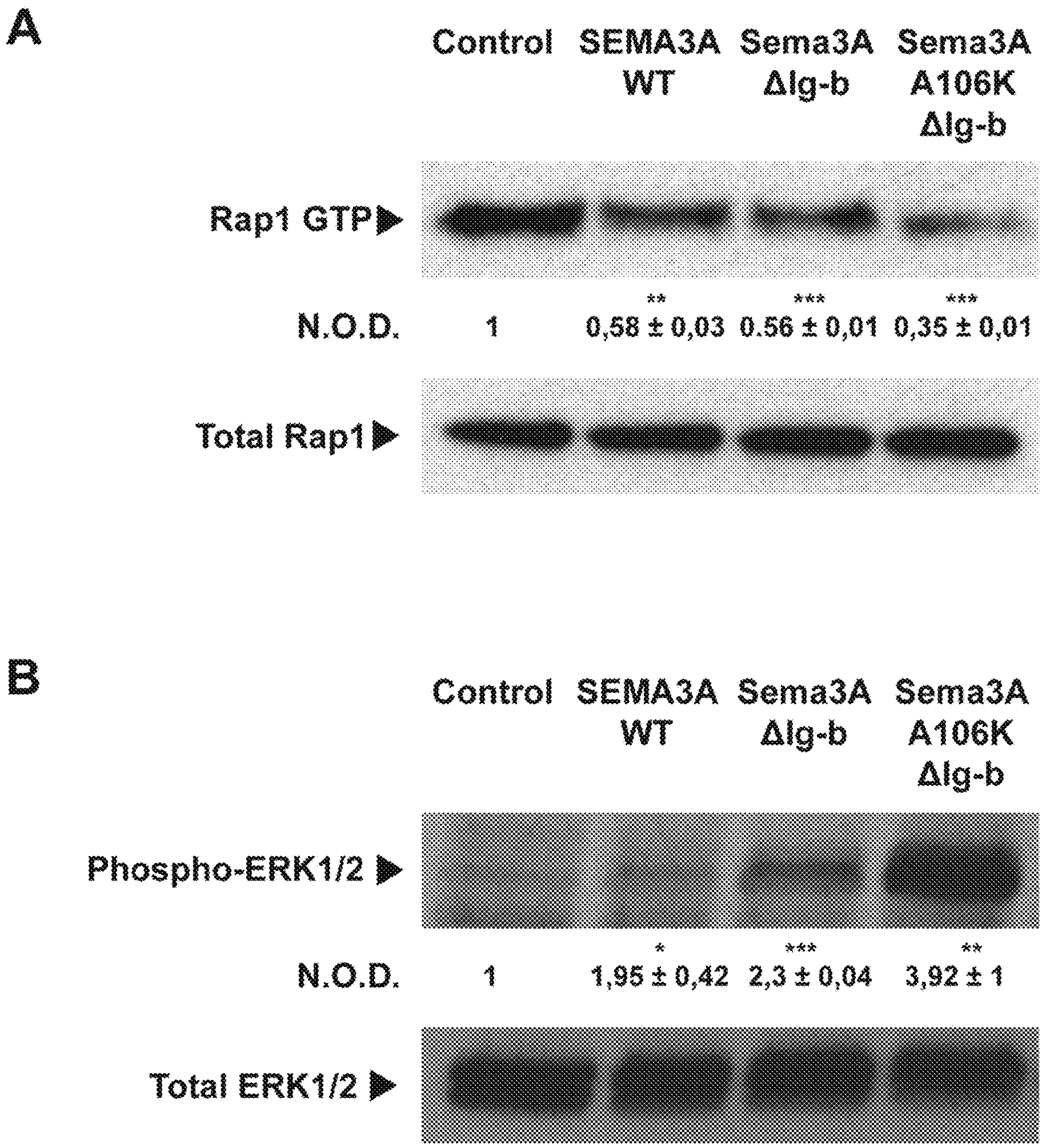

FIG. 8. Fe-tagged Sema3A A106K Mg-b protein is much more effective than commercially available Fe-tagged SEMA3A WT in eliciting biochemical signaling in ECs. (A) Pull-down assay of active Rap1 GTP in ECs that were treated or not for 1 minute with 0.02 nM Fc-tagged SEMA3A WT, Sema3A ΔIg-b or Sema3A A106K ΔIg-b. Total Rap1, detected in the input fractions, was used to calculate the normalized optical density (N.O.D.) of active Rap1. (B) Western blot analysis of activated phospho-ERK1/2 in ECs that were treated or not for 15 minutes with 0.2 nM Fc-tagged SEMA3A WT or Sema3A ΔIg-b or Sema3A A106K ΔIg-b. Western blot analysis of total ERK1/2 was used to calculate the N.O.D. of active ERK 1/2. A representative of three independent assays with similar results is shown. Bands were quantified and N.O.D.s were calculated relative to control (Values are means±SD; n=3 separate assays). Statistical analysis: results were analyzed by a two-tailed heteroscedastic Student's t-test; * p<0.05,  p<0.01, * p<0.001.

Figure 9:
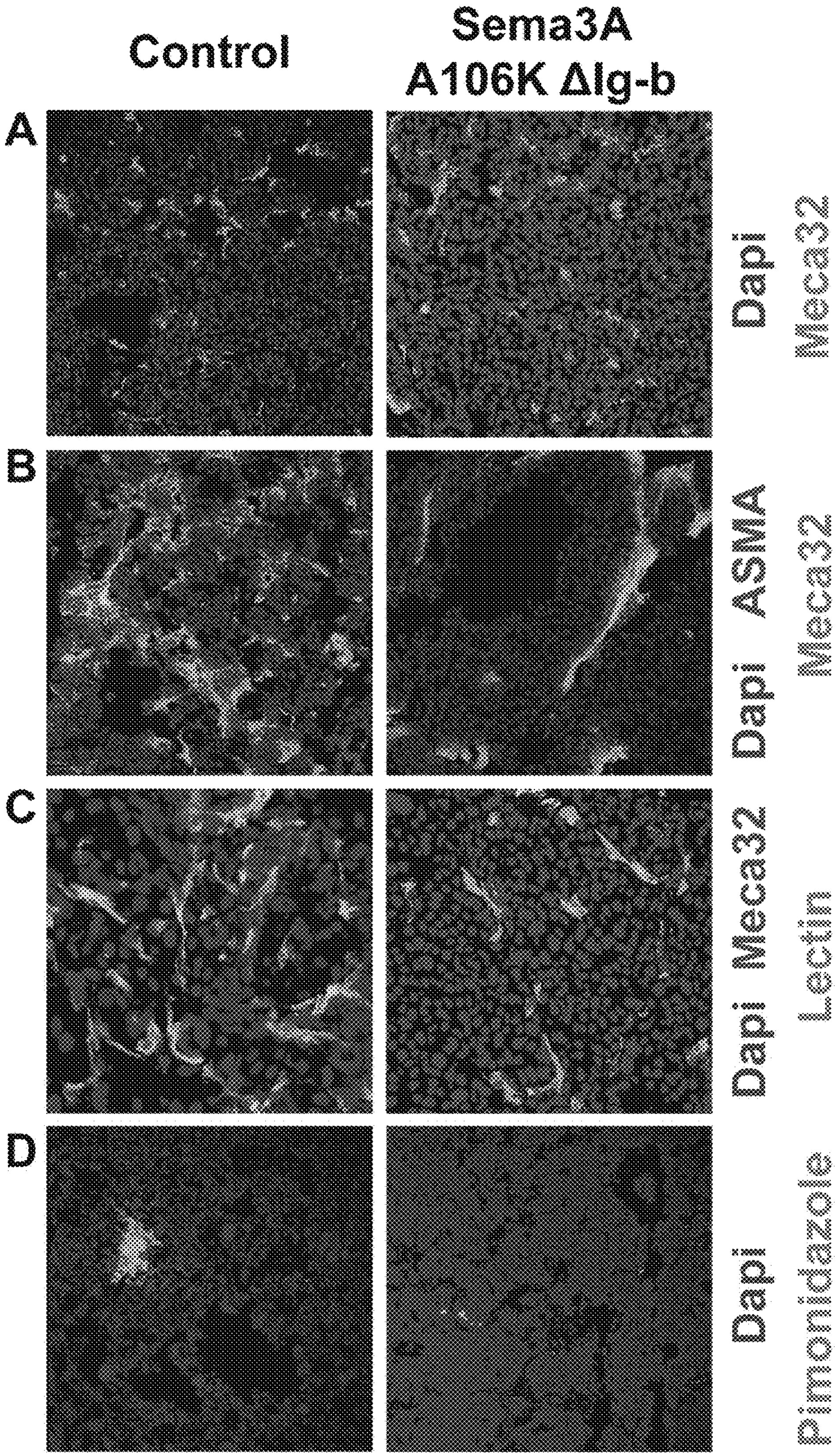

FIG. 9. Sema3A A106K Mg-b impairs angiogenesis and normalizes the cancer vasculature of RIP-Tag2 mice. Immunofluorescence analysis of control and Sema3A A106K ΔIg-b-treated cancer tissues were stained as indicated. Confocal images are representative of 7 mice per group and of five fields per cancers. (A) An anti-Meca32 Ab (green) was employed to stain vascular ECs. Sema3A A106K ΔIg-b significantly reduced blood vessel area by 51%. (B) An anti-α-smooth muscle actin (ASMA) was used to detect pericytes (red) in combination with an anti-Meca32 (green). Sema3A A106K ΔIg-b strongly enhanced blood vessel pericytes. (C) Control and Sema3A A106K ΔIg-b-treated mice were heart-perfused with FITC-lectin (green) and cancer tissues were then stained with an anti-Meca32 Ab (red). While control cancers display a poorly perfused vasculature, Sema3A A106K ΔIg-b enhanced the perfusion of cancer blood vessels. (D) Sema3A A106K ΔIg-b efficiently inhibited cancer hypoxia that was detected by injecting mice before sacrifice with pimonidazole (Maione et al 2012).

Figure 10:
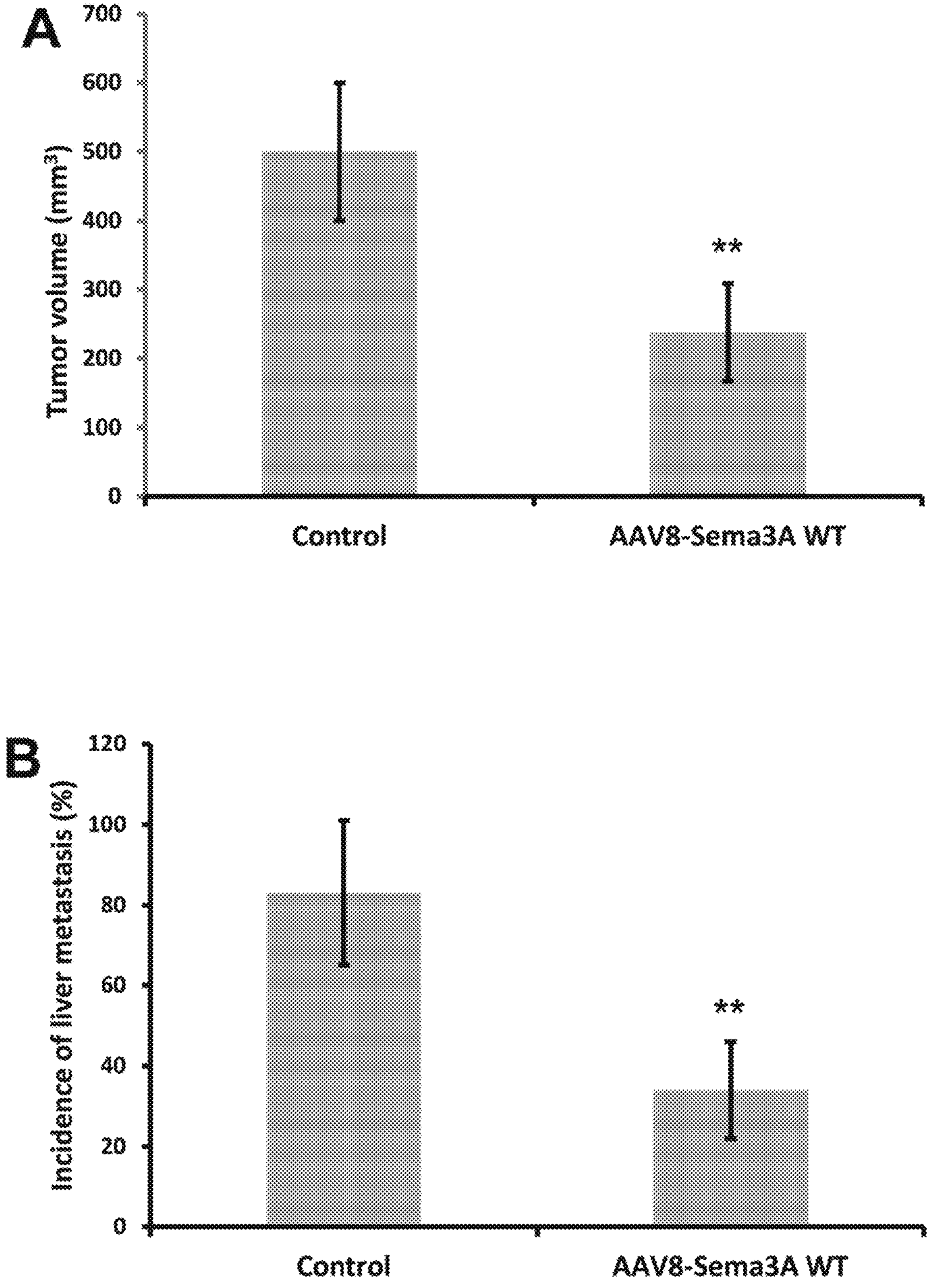

FIG. 10. AAV8-full length SEMA3A WT inhibits cancer growth and metastasis formation in a PDAC mouse model. Full length SEMA3A WT was transduced in the pancreas of PDAC mice by AAV-8-mediated somatic gene transfer, as previously described (Maione et. al 2009, 2012). AAV8-LacZ was transduced as a control. After three weeks of SEMA3A WT gene therapy mice were sacrificed and analyzed. AAV8-SEMA3A WT inhibited cancer volume by 52% (A) and reduced liver metastasis incidence by 59% (B). Number of mice per group (n=10). Statistical analysis: Mann-Whitney U test was used, **p<0.01.

FIG. 11. Sema3A A106K Mg-b inhibits cancer growth, impairs metastasis formation and increases blood vessel coverage by pericytes in a PDAC mouse model. (A, B) Cancer-bearing PDAC mice were treated with 3 mg/kg (i.p.) of Sema3A A106K ΔIg-b for three weeks. Sema3A A106K ΔIg-b shrinks cancer volume by 64% (A) and inhibits liver metastasis incidence by 81% (B); number of mice per group (n=10); statistical analysis: Mann-Whitney U test was used, p<0.01, *p<0.001. (C) Confocal images of immunofluorescence analysis of Sema3A A106K ΔIg-b-treated and control cancer tissues stained with an anti-NG2 (red, to label pericytes), and an anti-Meca32 Ab (green). Sema3A A106K ΔIg-b strongly enhanced vessel pericyte, compared to controls. Images a representative of 7 mice per group and of five fields per cancer.

Figure 12:
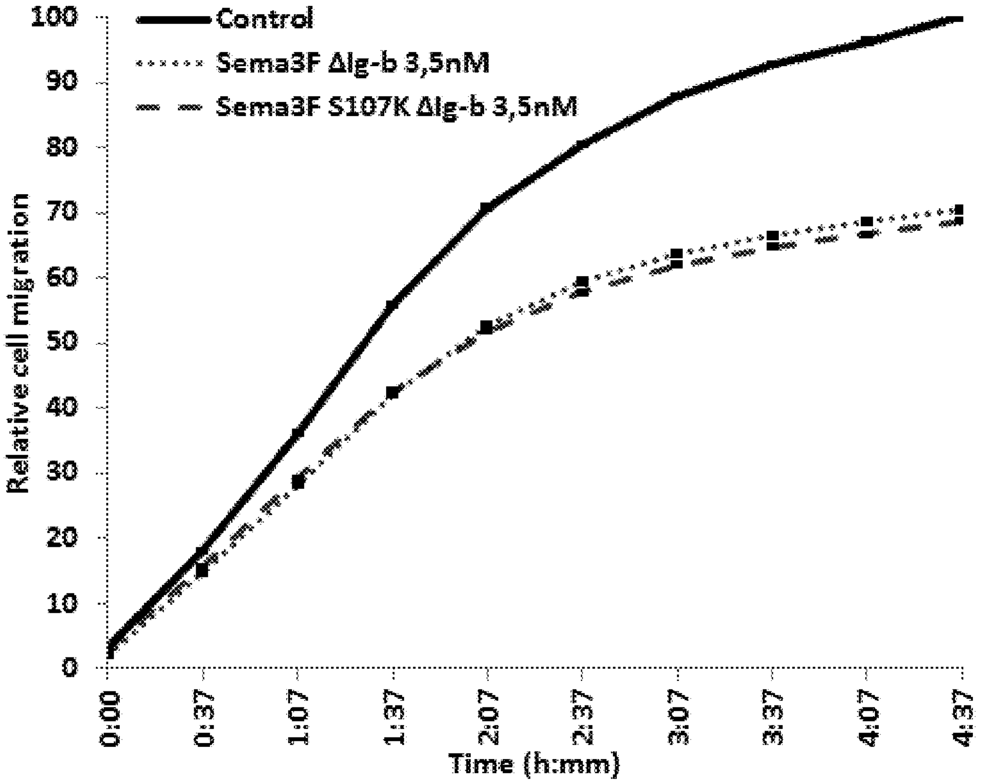

FIG. 12. Sema3F A106K fails to increase the inhibition of endothelial cell migration. Directional EC migration towards type I collagen (1 μg/ml) was analyzed by real time analysis. The migration of ECs was tracked over a 4 hour-long period in CIM-Plates 16 of an xCELLigence system platform either in the absence (Control, black solid line) or the presence of 3.5 nM Fc-tagged Sema3F ΔIg-b (black dotted line) or Fc-tagged Sema3F S107K ΔIg-b (dashed). Each curve is the average of four technical replicates±SD. Statistical analysis: results were analyzed by a two-tailed heteroscedastic Student's t-test; * Fc-tagged Sema3F ΔIg-b vs. Control; *, $p<0.05$; , $p<0.01$; * $p<0.001$.

FIG. 13. Fc-tagged Sema3A A106K Mg-b is more effective than commercially available Fc-tagged SEMA3E and SEMA3F in inhibiting EC directional migration. Directional EC migration towards type I collagen (1 μg/ml) was analyzed by real time analysis. (A-B) The migration of ECs was tracked over a 4 hour-long period in CIM-Plates 16 of an xCELLigence system platform either in the absence (Control, black solid line) or the presence of equimolar amounts of Fc-tagged Sema3A A106K ΔIg-b (A-B, black dashed line) or commercially available Fc-tagged SEMA3E WT (black dotted line) or commercially available Fc-tagged Sema3F WT (grey solid line). Each curve is the average of four technical replicates±SD. Statistical analysis: results were analyzed by a two-tailed heteroscedastic Student's t-test; * Fc-tagged Sema3A A106K ΔIg-b vs. Fc-tagged SEMA3E WT or Fc-tagged Sema3F WT; *, $p<0.05$, , $p<0.01$, *, $p<0.001$.

The following non-binding Examples illustrate the invention.

EXAMPLE 1—SEMA3A A106K MG-B IS A SPECIFIC BINDER, POWERFUL ACTIVATOR OF PLEXINA4 AND INHIBITOR OF HAPTOTACTIC MIGRATION OF ECS

Materials and Methods

Cell-Binding Assays and Scatchard Analysis.

In situ binding assays were performed with a modification of the protocol described previously (Tamagnone et al 1999). In particular, COST cells transfected with cDNA constructs expressing different semaphorin receptors were seeded in wells of 48-well cluster dishes. They were then incubated for 1 hour at 37° C. with complete medium containing recombinant semaphorin molecules fused with secreted placental Alkaline Phosphatase (e.g. Sema3A-AP). After five washes, cells were fixed, heated for 10 min at 65° C. to inactivate endogenous phosphatases, and incubated with NBT-BCIP (nitro blue tetrazolium-5-bromo-4-chloro-3-indolyl-phosphate) AP substrate (Promega, Catalog #S3771) for in situ cell staining. For a quantitative assessment of ligand binding, receptor-expressing cells were incubated with increasing concentrations of AP-conjugated ligands (with predetermined specific activity/μg); cell-bound AP activity was eventually revealed by incubation with the chromogenic soluble substrate p-nitrophenylphosphate (Sigma-Aldrich, Catalog #P7998) and measured by a multiwell spectrophotometer (absorbance at 405 nm). Scatchard plot analysis was performed using Prism 6 (GraphPad Software Inc.).

Haptotactic Endothelial Cell Migration Assays

Real-time directional migration of human umbilical vein ECs was monitored by means of xCELLigence (Acea Biosciences Inc.), an electrical impedance-based system in which microelectronic sensor arrays are integrated microplate wells. The impedance-based xCELLigence system is based on the Real-Time Cell Analyzer (RTCA) instrument. The core of the instrument is the E-plate. E-Plates 16 are single-use plates and each individual well on an E-Plate 16 has incorporated a sensor electrode array that allows cells in the well to be constantly monitored. Set up the experiment file using the RTCA Software 1.2.: this software converts impedance values to obtain parameters such as: cell index (CI), average values, maximum and minimum values, standard deviation (SD), half maximum effect of concentration (EC50), half maximum inhibition of concentration (IC50). Data expressed in CI units can then be exported for any type of mathematical and statistical analyses.

In this assay, we monitored the directional migration of ECs in real-time by using the CIM-Plate 16 of the xCELLigence RTCA DP instrument. The bottom side of the upper chamber (the side facing the lower chamber) of the CIM-Plate was coated with 30 μl of type I collagen (1 μg/ml) for 30 minutes inside the tissue culture hood. Each lower chamber well was first filled with 160 μl of serum-free M199 medium (containing or not Sema3A) and then assembled to the upper chamber. The assembled plate was incubated at 37° C. for one hour to equilibrate (30 μl of serum free media was added in each well of the upper chamber). ECs were detached and resuspended to a final concentration of 30000 cells/100 μl. The BLANCK step was started to measure the background impedance of cell culture medium, which was then used as reference impedance for calculating CI values. 100 μl of cell suspension (30,000 cells) were then added to each well of the upper chamber. The CIM-Plate 16 was placed in the RTCA DP Instrument equilibrated in a $CO_2$ incubator. ECs migration was continuously monitored using the RTCA DP Instrument.

For statistical evaluation, results were analyzed by a two-tailed heteroscedastic Student's t-test. The average, standard deviation and p value have been calculated on the CI data exported from RTCA instrument for the technical replicates of each experimental condition in the time. Migration data are represented as a percentage considering the control samples as 100%.

Rap1-GTP Pull-Down Assay

ECs were first starved for 3 hours and then treated or not with 0.02 nM of SEMA3A, for 1 minute at 37° C. Active Rap1-GTP was then pulled-down on a glutathione-S-transferase-fusion protein of the Rap1-binding domain (RBD) of human Ral guanine nucleotide dissociation stimulator (RalGDS) isolated by means of a glutathione agarose resin. We proceeded with the active Rap1 Pull-down assay according to the manufacturer's guideline and detection kit (Thermo Scientific, Product Cat. #16120). Total Rap1, detected in the input fractions, was used to calculate the normalized optical density (N.O.D.) of active Rap1-GTP. A representative of three independent pull-down assays with similar results is shown. Bands were quantified and N.O.D.s were calculated relative to control (Values are means±SD; n=3 separate assays). For statistical evaluation, results were analyzed by a two-tailed heteroscedastic Student's t-test.

ERK 1/2 Phosphorylation

ECs were first starved for 3 hours and then treated or not with SEMA3A [0.225 nM] for 15' at 37° C. We lysed cells and proceeded to protein analysis through WB with anti-phopsho ERK 1/2 [Mouse anti-phospho-p44/42 MAPK (ERK1/2; Thr202/Tyr204) (clone E10); dilution 1:1000; Cell Signaling Technology, Product Cat #91061 and anti-Tot ERK [Rabbit anti-p44/42 MAPK (ERK1/2) (clone 137F5); dilution 1:1000; Cell Signaling Technology, Product Cat #4695] antibodies. The total protein amount was determined using the bicinchoninic acid (BCA) protein assay reagent (Thermo Scientific). Equivalent amounts of protein separated by SDS-PAGE with precast Bolt 4-12% Bis-Tris gel (Invitrogen). Proteins were then transferred to a Trans-Blot Turbo™ Mini Nitrocellulose Transfer (Biorad), probed with either goat anti-rabbit IgG (H+L) secondary antibody, HRP conjugate (Invitrogen, Catalog #: 65-6120) or goat anti-mouse IgG (H+L) secondary antibody, HRP conjugate, (Jackson ImmunoResearch Inc. Catalog #: 11-035-062) and detected by enhanced chemiluminescence technique (Western Lightning Plus-ECL, Enhanced Chemiluminescence Substrate; Perkin Elmer, Catalog #NEL105001EA). Total ERK1/2, detected in the input fractions, was used to calculate the N.O.D. of phospho-ERK1/2. A representative of three independent pull-down assays with similar results is shown. Bands were quantified and N.O.D.s were calculated relative to control (Values are means±SD; n=3 separate assays). For statistical evaluation, results were analyzed by a two-tailed heteroscedastic Student's t-test.

Human and mouse Semaphorin 3 proteins are conserved proteins. Human Semaphorin 3A as shown in SEQ ID NO: 1 is at least 52% homologous/identical to human Semaphorin 3B as shown in SEQ ID NO: 5. Further, human Semaphorin 3A as shown in SEQ ID NO: 1 is at least 45% homologous/identical to human Semaphorin 3C as shown in SEQ ID NO: 9. Further, human Semaphorin 3A as shown in SEQ ID NO: 1 is at least 53% homologous/identical to human Semaphorin 3D as shown in SEQ ID NO: 13. Further, mouse Semaphorin 3A as shown in SEQ ID NO: 3 is at least 53% homologous/identical to human or mouse Semaphorin 3A as shown in SEQ ID NO: 13 or SEQ ID NO: 15. Further, mouse Semaphorin 3A as shown in SEQ ID NO: 3 is at least 45% homologous/identical to mouse Semaphorin 3C as shown in SEQ ID NO: 11.

Results

We developed a strategy in order to provide a novel, easy to purify and parenterally deliverable mutant synthetic protein derived from Sema3A WT. This mutant should comprise the following features: i) is unable to bind to Nrp1; ii) lacks any furin protease cleavage site; iii) is stably dimeric; and iv) is able to bind to Plexins with high affinity. Therefore, a novel recombinant mouse Sema3A mutant protein was generated. This exemplary mutant Sema3A was designed in the format of a fusion protein. This mutant Semaphorin 3A comprises the features summarized in table 2 and is designated Sema3A A106K ΔIg-b (Table 2 and FIG. 2). Exemplary, amino acid sequences are illustrated in SEQ ID NO: 18 or 20. Furthermore, corresponding fusion proteins of mutated Semaphorin 3B, C and D were also generated. These mutants are herein designated Sema3B A105K-Fc, Sema3C A104K-Fc and Sema3D A120K-Fc (shown in SEQ ID NO 76, 78 or 79, respectively). A mutant of Semaphorin 3A retaining the alanine at position 106 but comprising the same architecture as Sema3A A106K ΔIg-b is designated Sema3A ΔIg-b, the nucleic acid sequence of such a molecule is given in SEQ ID NO: 43 or 44 (human and mouse Sema3A ΔIg-b, respectively).

TABLE 2

Molecular features of the novel Sema3A A106K ΔIg-b

| Aim | Wild type Sema3A modifications |
|---|---|
| To abolish mutant Sema3A binding to Nrp1 | Deletion of the basic stretch |
| To abolish furin cleavage of mutant Sema3A | Deletion of the Ig-like domain and basic stretch |
| To render mutant Sema3A stably dimeric | Fusion of the remaining sema-PSI domain with IgG1 Fc |
| To allow high affinity binding of mutant Sema3A to PlexinA4 | Mutation of Ala 106 into Lys |

The Sema3A A106K ΔIg-b mutant is characterized by the following features and advantages:

1) the Nrp1 binding and the furin cleavable Ig-like/basic region of Sema3A WT (e.g., amino acids 549-772) is deleted;

2) the remaining Sema-PSI domain region (e.g., amino acids 1-548) of the mutant mouse Sema3A is fused with its C-terminus to the IgG1 constant fragment (e.g., from mouse) (Fc, formed by hinge, CH2, and CH3 domains) to induce dimerization. The IgG1 Fc allowed easy and large scale purification on Sepharose protein A of the mutant Sema3A protein;

3) the $Ala_{106}$ residue of Sema3A WT was substituted with a Lys (A106K) endowing the mutant form a high ($K_d$=0.7 nM) affinity to type A plexin PlexinA4.

Mutated and wild-type Semaphorin 3 A, B, C, D, E, and F were produced using standard protein purification. In particular, human and mouse Fc-tagged Sema3A A106K ΔIg-b (given in SEQ ID NO: 18 or 20, respectively) as well as mouse Fc-tagged Sema3A ΔIg-b, were produced using routine protein purification by a service. SEMA3A WT full-length was purchased from R&D Systems Inc., Minneapolis, Minn.; catalog #1250-S3-025. The Sema3A A106K ΔIg-b coding cDNA designated as SEQ ID NO:19 was generated by synthetic gene design (GeneArt® Gene Synthesis, Life-Technologies/Thermo Fisher Scientific Inc.). The Sema3A A106K ΔIg-b coding cDNA (SEQ ID NO:19) was then subcloned in the pUPE expression vector. A transfection grade preparation of pUPE expression vector carrying the Sema3A A106K ΔIg-b coding cDNA (Sema3A A106K ΔIg-b pUPE) was then transiently transfected into suspension growing HEK293 cell line stably expressing the Epstein-Barr virus nuclear antigen-1 (HEK293-EBNA1, or 293E), i.e. the cell line that is most commonly employed for large-scale transfections. After one week the medium of Sema3A A106K ΔIg-b pUPE HEK293E suspension cultures was harvested, by centrifugation. The fusion proteins were bound batch-wise to protein A-Sepharose. The beads were collected and transferred into a gravity-flow column. Specifically bound proteins were removed by washing the column with phosphate buffered saline (PBS). The bound fusion proteins were eluted using 20 mM citrate, 150 mM NaCl pH 2.7 and 0.9 ml fractions were collected in Eppendorf tubes containing 0.1 ml 1M KH2PO4/K2HPO4 pH 8.0 for neutralization.

To pinpoint the function of the A106K mutation in Sema3A, a Sema3A ΔIg-b recombinant protein was generated. Sema3A ΔIg-b lacked the Ig-like/basic region but preserved the wild type residue $Ala_{106}$ (FIG. 2). The biochemical and biological activities of both Sema3A ΔIg-b and Sema3A A106K ΔIg-b mutants were compared with that of the commercially available full-length SEMA3A WT (from R&D Systems Inc., Minneapolis, Minn.; catalog #1250-S3-025).

A ligand-receptor in situ binding assay (Flanagan et al., 2000; Tamagnone et al., 1999) confirmed that alkaline phosphatase (AP)-conjugated Sema3A WT was interacting with Nrp1 in COS cells. However, neither Sema3A ΔIg-b nor Sema3A A106K ΔIg-b mutants interacted with Nrp1 (FIG. 4A).

The Semaphorin proteins are ligands that signal through Plexins (Kumanogoh and Kikutani, 2013; Tamagnone et al., 1999). Therefore, the ability of these constructs to directly bind to Plexin family members was screened. Importantly, Sema3A A106K ΔIg-b bound to PlexinA4 with high affinity compared to Sema3A WT or the Sema3A ΔIg-b mutant (FIGS. 4 A and B). The binding affinity of Sema3A A106K ΔIg-b to PlexinA4 was increased to a $K_d$ of 0.7 nM, as evaluated by Scatchard plot analysis (FIG. 4C). In comparison, the $K_d$ of Sema3A WT binding to Nrp1 was 1.1 nM (FIG. 4D), which is consistent with previous data (Takahashi et al., 1999). Furthermore, no other type-A Plexin displayed detectable binding to Sema3A A106K ΔIg-b (FIG. 4A). Accordingly, the binding of Sema3A A106K ΔIg-b was highly specific for PlexinA4. Finally, ligand binding assays allowed to estimate the affinity range of Sema3A WT, Sema3A ΔIg-b, and Sema3A A106K ΔIg-b for Plexin A4 receptor and to reveal how the binding of Sema3A WT, mutant Sema3A ΔIg-b or mutant Sema3A A106K ΔIg-b to Plexin A4 respectively displays an estimated $K_d$ of 7 nM, 200 nM, and 0.7 nM (FIG. 4E). Furthermore, the binding affinity of mutated Semaphorin 3B to Plexins was analyzed (FIG. 4F). For example, illustrative Sema3B A105K-Fc demonstrated binding to Plexin A2 with a high binding affinity. Semaphorin 3B that has the same construct design as Sema3B A105K-Fc, but lacking the alanine to lysine mutation at position 105 (SEMA3B ΔIg-b), showed no increased binding in comparison to the mutated version. As described herein above, the strong interaction of the Semaphorin 3 proteins with its Plexin receptor is important for receptor activation and Semaphorin 3 downstream signaling. Therefore, these data provide evidence that mutated Semaphorin 3A, B, C and D can be employed in the improved anti-angiogenesis and/or anti-vasculogenesis therapy. The further analysis in in vitro as well as in vivo systems is herein exemplified on mutated Semaphorin 3A.

In order to assess the haptotactic migration of human umbilical vein endothelial cells (HUVECs or ECs) towards ECM proteins, we generated and purified Fc-tagged Sema3A ΔIg-b and Sema3A A106K ΔIg-b proteins (FIGS. 2, 3, 5). Equimolar amounts of Fc-tagged Sema3A Sema3A A106K ΔIg-b proteins and SEMA3A WT were compared in inhibiting the haptotactic migration of ECs towards ECM proteins, such as type I Collagen in a xCELLigence system platform (Acea Biosciences Inc., San Diego, Calif.) (FIG. 6). Fc-tagged Sema3A A106K ΔIg-b was always much more effective than Fc-tagged Sema3A ΔIg-b or commercial Fc-tagged SEMA3A WT in inhibiting EC directional migration over a wide range of concentrations (0.2-3.5 nM) (FIG. 6A-C). As detailed in Table 3, while mouse Fc-tagged Sema3A A106K ΔIg-b inhibited EC directional migration by 36-45%, commercial human Fc-tagged SEMA3A WT and mouse Fc-tagged Sema3A A106K ΔIg-b impaired EC motility by only 23-25% and 19-24%, respectively. Furthermore, gene silencing experiments of PlexinA4 increased the migration of ECs in response to Sema3A A106K ΔIg-b to control levels. Accordingly, the inhibitory activity on EC haptotaxis of Fc-tagged Sema3A A106K ΔIg-b is dependent on PlexinA4 (FIG. 6D, E), which is consistent with its type A Plexin receptor binding profile (FIG. 4A).

TABLE 3

Additional quantitative details concerning the ability of Fc-tagged SEMA3A WT, mouse Fc-tagged Sema3A ΔIg-b, and mouse Fc-tagged Sema3A A106K ΔIg-b in inhibiting EC directional migration. Raw numeric data corresponding to the experimental time point 3 hours and 45 minutes of the representative directional migration experiment depicted in FIG. 6 are reported here.

| Time point: 3 h:45 m | Relative migration | p value Sema3A A106K ΔIg-b vs. SEMA3A WT | p value Sema3A A106K ΔIg-b vs. Sema3A ΔIg-b |
|---|---|---|---|
| Control | 100 ± 0.01 | | |
| SEMA3A WT 0.2 nM | 75 ± 0.01 | | |
| Sema3A ΔIg-b 0.2 nM | 77 ± 0.01 | | |
| Sema3A A106K ΔIg-b 0.2 nM | 60 ± 0.001 | 0.0009 | 0.0007 |

TABLE 3-continued

Additional quantitative details concerning the ability of Fc-tagged SEMA3A WT, mouse Fc-tagged Sema3A ΔIg-b, and mouse Fc-tagged Sema3A A106K ΔIg-b in inhibiting EC directional migration. Raw numeric data corresponding to the experimental time point 3 hours and 45 minutes of the representative directional migration experiment depicted in FIG. 6 are reported here.

| Time point: 3 h:45 m | Relative migration | p value Sema3A A106K ΔIg-b vs. SEMA3A WT | p value Sema3A A106K ΔIg-b vs. Sema3A ΔIg-b |
|---|---|---|---|
| SEMA3A WT 0.9 nM | 77 ± 0.004 | | |
| Sema3A ΔIg-b 0.9 nM | 76 ± 0.06 | | |
| Sema3A A106K ΔIg-b 0.9 nM | 64 ± 0.02 | 0.001 | 0.001 |
| SEMA3A WT 3.5 nM | 77 ± 0.02 | | |
| Sema3A ΔIg-b 3.5 nM | 81 ± 0.007 | | |
| Sema3A A106K ΔIg-b 3.5 nM | 55 ± 0.01 | 0.003 | 0.0001 |

TABLE 4

Additional quantitative details concerning the ability of Fc-tagged SEMA3A WT and human Fc-tagged SEMA3A A106K ΔIg-b in inhibiting EC directional migration. Raw numeric data corresponding to the experimental time point 3 hours and 36 minutes of the representative directional migration experiment depicted in FIG. 7 are reported here.

| Time point: 3 h:36 m | Relative migration | p value SEMA3A A106K ΔIg-b vs. SEMA3A WT |
|---|---|---|
| Control | 100 ± 0.01 | |
| SEMA3A WT 3.5 nM | 80 ± 0.01 | |
| SEMA3A A106K ΔIg-b 0.2 nM | 64 ± 0.01 | 0.00009 |

We generated and tested a human Fc-tagged SEMA3A A106K ΔIg-b, whose biological activity was essentially superimposable to that of its murine counterpart (FIG. 7). As detailed in Table 4, while the maximal (3.5 nM) dose of commercial human Fc-tagged SEMA3A WT inhibited EC directional migration by 20%, a 17.5 times lower (0.2 nM) dose of human Fc-tagged SEMA3A A106K ΔIg-b inhibited EC motility by 46%. Furthermore, dimerization of SEMA3A A106K induced by the Fc-tag further increased the inhibition of EC directional migration (data not shown).

Sema3F possess a polar amino acid, i.e. serine ($Ser_{107}$) at the position that corresponds by comparison of homology to the position 106 of Sema3A. This is in contrast to Sema3A, Sema3B, Sema3C and Sema3D, which comprise a hydrophobic alanine at the corresponding position. Therefore, for control purposes, we investigated whether mutating the polar $Ser_{107}$ into a positively charged Lys (Sema3F S107K) results in a significant increase of Sema3F affinity for Plexin(s) and an ability to inhibit EC migration towards ECM proteins. By means of ligand-receptor in situ binding assays in COS cells, we found how AP-conjugated Sema3F ΔIg-b and Sema3F S107K ΔIg-b mutants failed to bind at high affinity to any type of A, B, C, or D Plexin family members. Accordingly, we observed how the ability of inhibiting EC migration towards ECM proteins of equimolar (3.5 nM) amounts of Sema3F ΔIg-b and Sema3F S107K ΔIg-b was largely superimposable (FIG. 12). Similarly, SEMA3A A106K ΔIg-b showed an increased inhibition of EC directional migration compared to Fc-tagged SEMA 3E (R&D Systems) or Sema 3F (R&D Systems) (FIG. 13). The EC migration assay was performed with equimolar amounts of protein, respectively. Therefore, without being bound by theory, we concluded that the synthetic introduction of positively charged amino acids into Sema3 proteins is more likely increasing their affinity for Plexin receptor(s) and chemorepulsive activity, if the substituted amino acid is hydrophobic, such as in the case of Sema3A A106. In other words, the herein described artificial introduction of the hydrophilic amino acid in the context of Sema 3 A, B, C or D increases the anti-angiogenic and/or vasculogenic properties.

In order to test the effect of the Sema3A constructs on downstream signaling, pull-down assays of Sema3A binding partners were performed. The Fc-tagged Sema3A A106K ΔIg-b was significantly more powerful than Fc-tagged Sema3A ΔIg-b and commercial Fc-tagged SEMA3A WT in inhibiting the GTP-loading of Rap1 small GTPase (FIG. 8A) as well as in triggering the phosphorylation of ERK 1/2 kinase (FIG. 8B). In particular, commercial Fc-tagged SEMA3A WT, Fc-tagged Sema3A ΔIg-b, and Fc-tagged Sema3A A106K ΔIg-b respectively: i) inhibited Rap1 GTP loading by 42%, 44%, and 65%; ii) activated ERK 1/2 phosphorylation by 1.95 fold, 2.3 fold, and 3.9 fold.

Therefore, it could be concluded that the novel Fc-tagged Sema3A A106K ΔIg-b mutant i.) bound specifically with a high affinity to the receptor PlexinA4; ii.) was a much more powerful activator of Plexin signaling; iii.) was a much more powerful inhibitor of EC function; iv.) did not interact with Nrp1; and v.) could not be cleaved.

This renders Sema3A A106K ΔIg-b as a specific binder, powerful activator of PlexinA4 and inhibitor of haptotactic migration of ECs

EXAMPLE 2—SEMA3A A106K MG-B EFFECTIVELY INHIBITS CANCER GROWTH AND METASTATIZATION IN PANCREAS CANCER

Considering the present in vitro data and the pre-clinical experience with the mouse model of spontaneous pancreatic neuroendocrine cancer (RIP-Tag2) (Maione et al., 2012; Maione et al., 2009), the ability of a wide range [0.5-5 mg/kg/mouse, delivered by means of either osmotic mini-pumps or intra-peritoneal (i.p.) for 4 weeks] of Fc-tagged Sema3A ΔIg-b and Sema3A A106K ΔIg-b in halting cancer progression and extending RIP-Tag2 mice survival was assessed at least up to 16 weeks of age, as we previously observed by means of Adeno-Associated Virus (AAV)-8-mediated gene transfer (Maione et al., 2012; Maione et al., 2009). We found that no dose of Sema3A ΔIg-b delivered by any therapeutic method was able to extend RIP-Tag2 mice survival as AAV-8 full length Sema3A did (Maione et al., 2012; Maione et al., 2009). On the contrary, Sema3A A106K ΔIg-b displayed a pro-survival activity similar to AAV-8 full length Sema3A, thus indicating how the increased Plexin A4-binding activity endowed Sema3A A106K ΔIg-b with a powerful Nrp1-independent anti-cancer effect. In particular, the delivery of 3 mg/kg of Sema3A A106K ΔIg-b by i.p. injection three times a week was the most effective and non-toxic therapeutic regimen to impair cancer progression, normalize the cancer vasculature, and extend RIP-Tag2 mice survival. In fact, compared to saline-treated controls, one month of treatment of RIP-Tag2 with Sema3A A106K ΔIg-b (3 mg/kg, i.p, three times a week): i) induced a 67% reduction of cancer volume; ii) efficiently reduced the cancer blood vessel area by 51% (FIG. 9A); iii) favored the normalization of cancer blood vessels in terms of increased pericyte coverage (FIG. 9B); iv) enhanced perfusion (FIG. 9C) and reduced tissue hypoxia (FIG. 9D).

Furthermore, the effect of Sema3A A106K ΔIg-b was analyzed in a mouse model of a significantly more frequent and deadly human pancreatic cancer histotype, namely a syngeneic K-Ras$^{G12D}$; Ink4a/Arf$^{-/-}$; p53$^{R172H}$ orthotopic mouse model of pancreatic ductal adenocarcinoma (PDAC). The full length SEMA3A WT was delivered in the orthotopic Ras$^{G12D}$; Ink4a/Arf$^{-/-}$; p53$^{R172H}$ PDAC mouse model by means AAV-8-mediated gene transfer (Maione et al., 2009). The treatment with full length SEMA3A WT resulted in an inhibition of both cancer growth (by 52%) and liver metastasis (by 59%) (FIG. 10A, B) after 3 weeks. Stemming from the previous promising data, we then treated cancer-bearing PDAC mice with purified Sema3A A106K ΔIg-b mutant protein (3 mg/kg, i.p., three times a week) and assessed its pharmacological effect on cancer growth and metastasis formation. Sema3A A106K ΔIg-b protein strongly inhibited cancer growth (by 64%) (FIG. 11A), reduced the incidence of liver metastasis by 81% (FIG. 11B) and diminished metastasis volume by 78%. Most importantly and surprisingly, Sema3A A106K ΔIg-b exerted a stronger effect in reducing cancer progression and metastasis dissemination compared with Sema3A full length in PDAC mice. Consistent with the treatment of RIP-tag2 mice, Sema3A A106K ΔIg-b reduced vessel area (data not shown) and promoted cancer vessel normalization also in the PDAC mouse model by enhancing pericyte coverage (FIG. 11C), increasing blood vessel perfusion and inhibiting cancer hypoxia.

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

Adams et al., (1997) *EMBO J.* 16:6077-6086.
Bos et al., (2012) *Sci Signal.* 5:pe6.
Casazza et al., (2013) *Cancer Cell.* 24:695-709.
Cleaver et al., (2003) *Nat Med.* 9:661-668.
Conley et al., (2012) *Proc Natl Acad Sci USA.*
Gherardi et al., (2004) *Curr Opin Struct Biol.* 14:669-678.
Goel et al., (2011) *Physiol Rev.* 91:1071-1121.
Hahn et al., (2009) *Nat Rev Mol Cell Biol.* 10:53-62.
Janssen et al., (2010) *Nature.* 467:1118-1122.
Kinbara et al., (2003) *Nat Rev Mol Cell Biol.* 4:767-776.
Koppel et al., (1998) *J Biol Chem.* 273:15708-15713.
Kruger et al., (2005) *Nat Rev Mol Cell Biol.* 6:789-800.
Kumanogoh et al., (2013) *Nat Rev Immunol.* 13:802-814.
Lucitti et al., (2007) *Development.* 134:3317-3326.
Maione et al., (2012) *J Clin Invest.* 122:1832-1848.
Maione et al., (2009) *J Clin Invest.* 119:3356-3372.
Michieli et al., (2009) *Cell Cycle.* 8:3291-3296.
Nogi et al., (2010) *Nature.* 467:1123-1127.
Parker et al., (2010) *Biochemistry.* 49:4068-4075.
Parker et al., (2012) *J Biol Chem.*
Sennino et al., (2012) *Nat Rev Cancer.* 12:699-709.
Serini et al., (2013) *Journal of Internal Medicine.*
Serini et al., (2003) *Nature.* 424:391-397.
Shattil et al., (2010) *Nat Rev Mol Cell Biol.* 11:288-300.
Takahashi et al., (1999) *Cell.* 99:59-69.
Tamagnone et al., (1999) *Cell.* 99:71-80.
Tran et al., (2007) *Annu. Rev. Cell Dev. Biol.* 23::263-292.
Tzima et al., (2001) *EMBO J.* 20:4639-4647.
Van der Veldt et al., (2012) *Cancer Cell.* 21:82-91.
Wang et al., (2012) *Sci Signal.* 5:ra6.

Flanagan Methods Enzymol. 2000; 327:198-210.
Gherardi et al., (2004) Curr Opin Struct Biol 14:669-678.
Love et al., (2003) Nat Struct Biol 10: 843-848.
Xiong J et al., (2004) J Biol Chem 279:40252-40254.
Rein FEBS Letters 513 (2002) 141-144, October 2001
Antipenko et al., (2003) *Neuron.* 39:589-598.
Chen et al., (2011) *Trends Biochem Sci.* 36:553-561.
Conley et al., (2012) *Proc Natl Acad Sci USA.*
Desgrosellier et al., (2010) *Nat Rev Cancer.* 10:9-22.
Flanagan et al., (2000) *Methods Enzymol.* 327:19-35.
Gherardi et al., (2004) *Curr Opin Struct Biol.* 14:669-678.
Love et al., (2003) *Nat Struct Biol.* 10:843-848.
Sennino et al., (2012) *Nat Rev Cancer.* 12:699-709.
Xiong et al., (2004) *J Biol Chem.* 279:40252-40254.

The invention claimed is:

1. A mutated Semaphorin 3 or a functional fragment thereof wherein said mutated Semaphorin 3 is derived Semaphorin 3A, Semaphorin 3B, Semaphorin 3C, and Semaphorin 3D and wherein said mutated Semaphorin 3 or said functional fragment thereof comprises the amino acid sequence $CX_1X_2A_3GKD$ (SEQ ID NO:73), wherein $X_1$ is an amino acid, which is K or N, $X_2$ is an amino acid selected from the group of W, M and L, and wherein the alanine (A3) is replaced by a hydrophilic amino acid.

2. The mutated Semaphorin 3 or the functional fragment thereof of claim 1, wherein said mutated Semaphorin 3 or said functional fragment thereof comprises said hydrophilic amino acid in place of the alanine corresponding to position 106 of the wild type Semaphorin 3A as shown in SEQ ID NO: 2;

said hydrophilic amino acid in place of the alanine corresponding to position 105 of the wild type Semaphorin 3B as shown in SEQ ID NO: 6;

said hydrophilic amino acid in place of the alanine corresponding to position 104 of the wild type Semaphorin 3C as shown in SEQ ID NO: 10; or said hydrophilic amino acid in place of the alanine corresponding to position 120 of the wild type Semaphorin 3D as shown in SEQ ID NO: 14.

3. The mutated Semaphorin 3 or the functional fragment thereof of claim 1, wherein said mutated Semaphorin 3 is selected from the group of:

(a) a polypeptide that is encoded by a nucleic acid sequence selected from the group of SEQ ID NO: 1, SEQ ID NO: 5, SEQ ID NO: 9 and SEQ ID NO: 13, wherein the nucleotides GCT at position 631 to 633 of SEQ ID NO: 1 are replaced by nucleotides encoding said hydrophilic amino acid, wherein the nucleotides GCA at position 559 to 561 of SEQ ID NO: 5 are replaced by nucleotides encoding said hydrophilic amino acid, wherein the nucleotides GCT at position 872 to 874 of SEQ ID NO: 9 are replaced by nucleotides encoding said hydrophilic amino acid, and wherein the nucleotides GCC at position 398 to 400 of SEQ ID NO: 13 are replaced by nucleotides encoding said hydrophilic amino acid;

(b) a polypeptide having the amino acid sequence selected from the group of SEQ ID NO: 2, SEQ ID NO: 6, SEQ ID NO: 10 and SEQ ID NO: 14, wherein the alanine residue at position 106 of SEQ ID NO: 2, at position 105 of SEQ ID NO: 6, at position 104 of SEQ ID NO: 10 or at position 120 of SEQ ID NO: 14 is replaced by said hydrophilic amino acid;

(c) a polypeptide that is encoded by a nucleic acid sequence that hybridizes under stringent conditions to the complementary strand of a nucleic acid molecule encoding a polypeptide as defined in (a) or (b); or (d) a polypeptide that functions as an inhibitor of angiogenesis and has at least 55% identity to any one of the polypeptides referred to in (b).

4. The mutated Semaphorin 3 or the functional fragment thereof of claim 1, wherein said mutated Semaphorin 3 or said functional fragment thereof comprises a hydrophilic amino acid (a) at position 106 of SEQ ID NO: 2;

(b) at position 105 of SEQ ID NO: 6;

(c) at position 104 of SEQ ID NO: 10; or (d) at position 120 of SEQ ID NO: 14.

5. The mutated Semaphorin 3 or the functional fragment thereof of claim 1, wherein said mutated Semaphorin 3 or said functional fragment thereof comprises a functional sema domain and comprises at least one additional mutation selected from the group consisting of amino acid substitution(s), addition(s), deletions(s) and duplication(s).

6. The mutated Semaphorin 3 or the functional fragment thereof of claim 1, wherein said hydrophilic amino acid is selected from the group of K, R, N, Q, S, T, E, D, and H.

7. The mutated Semaphorin 3 or the functional fragment thereof of claim 6, wherein said hydrophilic amino acid is K or R.

8. The mutated Semaphorin 3 or the functional fragment thereof of claim 6, wherein said hydrophilic amino acid replacing said alanine is K.

9. The mutated Semaphorin 3 or the functional fragment thereof of claim 1, wherein said mutated Semaphorin 3 or said functional fragment thereof comprises one or more of the following sequence(s) as defined in any one of SEQ ID NO: 26, SEQ ID NO: 27, SEQ ID NO: 29, SEQ ID NO: 30, SEQ ID NO: 32, SEQ ID NO: 33, SEQ ID NO: 35, SEQ ID NO: 36, SEQ ID NO: 45, SEQ ID NO: 46, SEQ ID NO: 47 or SEQ ID NO: 48.

10. The mutated Semaphorin 3 or the functional fragment thereof of claim 1, wherein a nucleic acid molecule encoding said mutated Semaphorin 3 or said functional fragment thereof comprises:

(a) the nucleotides from 601 to 1206 of SEQ ID NO: 1 and wherein the nucleotides GCT at position 631 to 633 of SEQ ID NO: 1 are replaced by nucleotides encoding a hydrophilic amino acid;

(b) the nucleotides from 529 to 1137 of SEQ ID NO: 5 and wherein the nucleotides GCA at position 559 to 561 of SEQ ID NO: 5 are replaced by nucleotides encoding a hydrophilic amino acid;

(c) the nucleotides from 842 to 1444 of SEQ ID NO: 9 and wherein the nucleotides GCT at position 872 to 874 of SEQ ID NO: 9 are replaced by nucleotides encoding a hydrophilic amino acid; or (d) the nucleotides from 368 to 982 of SEQ ID NO: 13 and wherein the nucleotides GCC at position 398 to 400 of SEQ ID NO: 13 are replaced by nucleotides encoding a hydrophilic amino acid.

11. The mutated Semaphorin 3 or the functional fragment thereof of claim 1, wherein said mutated Semaphorin 3 or said functional fragment thereof comprises a functional sema domain, wherein said sema domain is selected from an amino acid sequence as shown in:

(a) SEQ ID NO: 21, wherein the alanine residue corresponding to position 106 of SEQ ID NO: 2 is replaced by a hydrophilic amino acid;

(b) SEQ ID NO: 22, wherein the alanine residue corresponding to position 105 of SEQ ID NO: 6 is replaced by a hydrophilic amino acid;

(c) SEQ ID NO: 23, wherein the alanine residue corresponding to position 104 of SEQ ID NO: 10 is replaced by a hydrophilic amino acid; or (d) SEQ ID NO: 24, wherein the alanine residue corresponding to position 120 of SEQ ID NO: 14 is replaced by a hydrophilic amino acid.

12. The mutated Semaphorin 3 or the functional fragment thereof of claim 1, wherein the mutated Semaphorin 3 comprises an amino acid sequence that is selected from the group consisting of SEQ ID NO: 58, SEQ ID NO: 60, SEQ ID NO: 62, SEQ ID NO: 64, SEQ ID NO: 66, SEQ ID NO: 68, SEQ ID NO: 70 and SEQ ID NO: 72.

13. The mutated Semaphorin 3 or the functional fragment thereof of claim 1, wherein said mutated Semaphorin 3 or function fragment thereof is part of a fusion protein.

14. The mutated Semaphorin 3 or functional fragment thereof of claim 13, wherein said mutated Semaphorin 3 or said functional fragment thereof comprises a functional sema domain, and wherein said functional sema domain comprises a polypeptide selected from:

(a) SEQ ID NO: 21, wherein the alanine residue corresponding to position 106 of SEQ ID NO: 2 is replaced by a hydrophilic amino acid;

(b) SEQ ID NO: 22, wherein the alanine residue corresponding to position 105 of SEQ ID NO: 6 is replaced by a hydrophilic amino acid;

(c) SEQ ID NO: 23, wherein the alanine residue corresponding to position 104 of SEQ ID NO: 10 is replaced by a hydrophilic amino acid; or (d) SEQ ID NO: 24, wherein the alanine residue corresponding to position 120 of SEQ ID NO: 14 is replaced by a hydrophilic amino acid.

15. The mutated Semaphorin 3 or said functional fragment thereof of claim 13, wherein said fusion protein further comprises:

(a) a stabilizer domain; and/or (b) a dimerization domain.

16. The mutated Semaphorin 3 or said functional fragment thereof of claim 15, wherein (a) said stabilizer domain is a Plexin Semaphorin Integrin (PSI) domain, wherein said PSI domain comprises one or more of the following sequences SEQ ID NO: 45, SEQ ID NO: 46, SEQ ID NO: 47 or SEQ ID NO: 48; and/or (b) said dimerization domain has a dissociation constant $K_D$ in the range of $10^{-5}$ M to $10^{-6}$ M with another such dimerization domain and/or wherein said dimerization domain is selected from the group of a C-terminal IgG constant domain, DARPin and leucine zipper.

17. The mutated Semaphorin 3 or said functional fragment thereof of claim 16, wherein the IgG constant domain is IgG1 or IgG3.

18. The mutated Semaphorin 3 or said functional fragment thereof of claim 13, wherein said fusion protein is encoded by a nucleic acid molecule comprising a nucleic acid sequence having:

a nucleic acid sequence spanning from nucleotides 316 to 1959 of SEQ ID NO: 1 and a nucleic acid sequence spanning from nucleotides 295 to 990 of SEQ ID NO: 37, wherein the nucleotides GCT at position 631 to 633 of SEQ ID NO: 1 are replaced by nucleotides encoding a hydrophilic amino acid;

a nucleic acid sequence spanning from nucleotides 247 to 1887 of SEQ ID NO: 5 and a nucleic acid sequence spanning from nucleotides 295 to 990 of SEQ ID NO: 37, wherein the nucleotides GCA at position 559 to 561 of SEQ ID NO: 5 are replaced by nucleotides encoding a hydrophilic amino acid;

a nucleic acid sequence spanning from nucleotides 563 to 2197 of SEQ ID NO: 9 and a nucleic acid sequence spanning from nucleotides 295 to 990 of SEQ ID NO: 37, wherein the nucleotides GCT at position 872 to 874 of SEQ ID NO: 9 are replaced by nucleotides encoding a hydrophilic amino acid; or a nucleic acid sequence spanning from nucleotides 41 to 1735 of SEQ ID NO: 13 and a nucleic acid sequence spanning from nucleotides 295 to 990 of SEQ ID NO: 37, wherein the nucleotides GCC at position 398 to 400 of SEQ ID NO: 13 are replaced by nucleotides encoding a hydrophilic amino acid.

19. The mutated Semaphorin 3 or said functional fragment thereof of claim 13, wherein said fusion protein comprises an amino acid sequence:

spanning from amino acid residues 1 to 548 of SEQ ID NO: 2 and an amino acid sequence as shown in SEQ ID NO: 41, wherein the alanine residue at position 106 of SEQ ID NO: 2 is replaced by a hydrophilic amino acid;

spanning from amino acid residues 1 to 547 of SEQ ID NO: 6 and an amino acid sequence as shown in SEQ ID NO: 41, wherein the alanine residue at position 105 of SEQ ID NO: 6 is replaced by a hydrophilic amino acid;

spanning from amino acid residues 1 to 565 of SEQ ID NO: 10 and an amino acid sequence as shown in SEQ ID NO: 41, wherein the alanine residue at position 104 of SEQ ID NO: 10 is replaced by a hydrophilic amino acid; or spanning from amino acid residues 1 to 545 of SEQ ID NO: 14 and an amino acid sequence as shown in SEQ ID NO: 41, wherein the alanine residue at position 120 of SEQ ID NO: 14 is replaced by said hydrophilic amino acid.

20. The mutated Semaphorin 3 or said functional fragment thereof of claim 13, wherein the fusion protein comprises an amino acid sequence selected from the group consisting of SEQ ID NO: 18, SEQ ID NO: 76, SEQ ID NO: 78 and SEQ ID NO: 79.

21. A pharmaceutical composition comprising the mutated Semaphorin 3 or the functional fragment thereof according to claim 1; and optionally comprising a pharmaceutical excipient.

22. The pharmaceutical composition of claim 21, wherein the pharmaceutical excipient is a pharmaceutical carrier.

* * * * *

UNITED STATES PATENT AND TRADEMARK OFFICE

CERTIFICATE OF CORRECTION

PATENT NO. : 10,906,948 B2
APPLICATION NO. : 15/552511
DATED : February 2, 2021
INVENTOR(S) : Guido Serini, Enrico Giraudo and Luca Tamagnone It is certified that error appears in the above-identified patent and that said Letters Patent is hereby corrected as shown below:

In the Claims

Column 381, Line 4, the word "from" is missing. Claim 1 should read:
--A mutated Semaphorin 3 or a functional fragment thereof wherein said mutated Semaphorin 3 is derived from Semaphorin 3A, Semaphorin 3B, Semaphorin 3C, and Semaphorin 3D and wherein said mutated Semaphorin 3 or said functional fragment thereof comprises the amino acid sequence $CX_1X_2A_3GKD$ (SEQ ID NO:73), wherein
$X_1$ is an amino acid, which is K or N,
$X_2$ is an amino acid selected from the group of W, M and L,
and wherein the alanine ($A_3$) is replaced by a hydrophilic amino acid.--

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 85

<210> SEQ ID NO 1
<211> LENGTH: 5672
<212> TYPE: DNA
<213> ORGANISM: Homo sapiens
<220> FEATURE:
<223> OTHER INFORMATION: wildtype full length SEMA3A
      (>gi|100913215|ref|NM_006080.2|)
<220> FEATURE:
<221> NAME/KEY: CDS
<222> LOCATION: 316..2631
<223> OTHER INFORMATION: /transl_table=1

<400> SEQUENCE: 1

aagcaccact gcagcagacc ttgttaattt tttttttttt tctttccaca caacagttgt      60

gcctcattat ccggtgcctg gctcggaatt tttttttttt tttttctttt tggagggttt     120

gaagtttctg tgcttcagtg actgttacag aagaagaggt gttagtgttg ccatgaggtc     180

ttgattgtct gcatttatga atgaaactga cctaaatcac ctgttacctc cagtttccag     240

attgtttgaa cttctctggc cgcacaatac aggaaggaag actaaagcag caaagggacc     300

tacagcgtct gcagc atg ggc tgg tta act agg att gtc tgt ctt ttc tgg      351
                 Met Gly Trp Leu Thr Arg Ile Val Cys Leu Phe Trp
                 1               5                   10

gga gta tta ctt aca gca aga gca aac tat cag aat ggg aag aac aat      399
Gly Val Leu Leu Thr Ala Arg Ala Asn Tyr Gln Asn Gly Lys Asn Asn
        15                  20                  25

gtg cca agg ctg aaa tta tcc tac aaa gaa atg ttg gaa tcc aac aat      447
Val Pro Arg Leu Lys Leu Ser Tyr Lys Glu Met Leu Glu Ser Asn Asn
    30                  35                  40

gtg atc act ttc aat ggc ttg gcc aac agc tcc agt tat cat acc ttc      495
Val Ile Thr Phe Asn Gly Leu Ala Asn Ser Ser Ser Tyr His Thr Phe
45                  50                  55                  60

ctt ttg gat gag gaa cgg agt agg ctg tat gtt gga gca aag gat cac      543
Leu Leu Asp Glu Glu Arg Ser Arg Leu Tyr Val Gly Ala Lys Asp His
                65                  70                  75

ata ttt tca ttc gac ctg gtt aat atc aag gat ttt caa aag att gtg      591
Ile Phe Ser Phe Asp Leu Val Asn Ile Lys Asp Phe Gln Lys Ile Val
            80                  85                  90

tgg cca gta tct tac acc aga aga gat gaa tgc aag tgg gct gga aaa      639
Trp Pro Val Ser Tyr Thr Arg Arg Asp Glu Cys Lys Trp Ala Gly Lys
        95                  100                 105

gac atc ctg aaa gaa tgt gct aat ttc atc aag gta ctt aag gca tat      687
Asp Ile Leu Lys Glu Cys Ala Asn Phe Ile Lys Val Leu Lys Ala Tyr
    110                 115                 120

aat cag act cac ttg tac gcc tgt gga acg ggg gct ttt cat cca att      735
Asn Gln Thr His Leu Tyr Ala Cys Gly Thr Gly Ala Phe His Pro Ile
125                 130                 135                 140

tgc acc tac att gaa att gga cat cat cct gag gac aat att ttt aag      783
Cys Thr Tyr Ile Glu Ile Gly His His Pro Glu Asp Asn Ile Phe Lys
                145                 150                 155

ctg gag aac tca cat ttt gaa aac ggc cgt ggg aag agt cca tat gac      831
Leu Glu Asn Ser His Phe Glu Asn Gly Arg Gly Lys Ser Pro Tyr Asp
```

-continued

```
            160                 165                 170

cct aag ctg ctg aca gca tcc ctt tta ata gat gga gaa tta tac tct      879
Pro Lys Leu Leu Thr Ala Ser Leu Leu Ile Asp Gly Glu Leu Tyr Ser
        175                 180                 185

gga act gca gct gat ttt atg ggg cga gac ttt gct atc ttc cga act      927
Gly Thr Ala Ala Asp Phe Met Gly Arg Asp Phe Ala Ile Phe Arg Thr
    190                 195                 200

ctt ggg cac cac cac cca atc agg aca gag cag cat gat tcc agg tgg      975
Leu Gly His His His Pro Ile Arg Thr Glu Gln His Asp Ser Arg Trp
205                 210                 215                 220

ctc aat gat cca aag ttc att agt gcc cac ctc atc tca gag agt gac     1023
Leu Asn Asp Pro Lys Phe Ile Ser Ala His Leu Ile Ser Glu Ser Asp
                225                 230                 235

aat cct gaa gat gac aaa gta tac ttt ttc ttc cgt gaa aat gca ata     1071
Asn Pro Glu Asp Asp Lys Val Tyr Phe Phe Phe Arg Glu Asn Ala Ile
            240                 245                 250

gat gga gaa cac tct gga aaa gct act cac gct aga ata ggt cag ata     1119
Asp Gly Glu His Ser Gly Lys Ala Thr His Ala Arg Ile Gly Gln Ile
        255                 260                 265

tgc aag aat gac ttt gga ggg cac aga agt ctg gtg aat aaa tgg aca     1167
Cys Lys Asn Asp Phe Gly Gly His Arg Ser Leu Val Asn Lys Trp Thr
    270                 275                 280

aca ttc ctc aaa gct cgt ctg att tgc tca gtg cca ggt cca aat ggc     1215
Thr Phe Leu Lys Ala Arg Leu Ile Cys Ser Val Pro Gly Pro Asn Gly
285                 290                 295                 300

att gac act cat ttt gat gaa ctg cag gat gta ttc cta atg aac ttt     1263
Ile Asp Thr His Phe Asp Glu Leu Gln Asp Val Phe Leu Met Asn Phe
                305                 310                 315

aaa gat cct aaa aat cca gtt gta tat gga gtg ttt acg act tcc agt     1311
Lys Asp Pro Lys Asn Pro Val Val Tyr Gly Val Phe Thr Thr Ser Ser
            320                 325                 330

aac att ttc aag gga tca gcc gtg tgt atg tat agc atg agt gat gtg     1359
Asn Ile Phe Lys Gly Ser Ala Val Cys Met Tyr Ser Met Ser Asp Val
        335                 340                 345

aga agg gtg ttc ctt ggt cca tat gcc cac agg gat gga ccc aac tat     1407
Arg Arg Val Phe Leu Gly Pro Tyr Ala His Arg Asp Gly Pro Asn Tyr
    350                 355                 360

caa tgg gtg cct tat caa gga aga gtc ccc tat cca cgg cca gga act     1455
Gln Trp Val Pro Tyr Gln Gly Arg Val Pro Tyr Pro Arg Pro Gly Thr
365                 370                 375                 380

tgt ccc agc aaa aca ttt ggt ggt ttt gac tct aca aag gac ctt cct     1503
Cys Pro Ser Lys Thr Phe Gly Gly Phe Asp Ser Thr Lys Asp Leu Pro
                385                 390                 395

gat gat gtt ata acc ttt gca aga agt cat cca gcc atg tac aat cca     1551
Asp Asp Val Ile Thr Phe Ala Arg Ser His Pro Ala Met Tyr Asn Pro
            400                 405                 410

gtg ttt cct atg aac aat cgc cca ata gtg atc aaa acg gat gta aat     1599
Val Phe Pro Met Asn Asn Arg Pro Ile Val Ile Lys Thr Asp Val Asn
        415                 420                 425

tat caa ttt aca caa att gtc gta gac cga gtg gat gca gaa gat gga     1647
Tyr Gln Phe Thr Gln Ile Val Val Asp Arg Val Asp Ala Glu Asp Gly
    430                 435                 440

cag tat gat gtt atg ttt atc gga aca gat gtt ggg acc gtt ctt aaa     1695
Gln Tyr Asp Val Met Phe Ile Gly Thr Asp Val Gly Thr Val Leu Lys
445                 450                 455                 460

gta gtt tca att cct aag gag act tgg tat gat tta gaa gag gtt ctg     1743
Val Val Ser Ile Pro Lys Glu Thr Trp Tyr Asp Leu Glu Glu Val Leu
                465                 470                 475

ctg gaa gaa atg aca gtt ttt cgg gaa ccg act gct att tca gca atg     1791
```

```
                                                                    -continued

Leu Glu Glu Met Thr Val Phe Arg Glu Pro Thr Ala Ile Ser Ala Met
            480                 485                 490

gag ctt tcc act aag cag caa caa cta tat att ggt tca acg gct ggg    1839
Glu Leu Ser Thr Lys Gln Gln Gln Leu Tyr Ile Gly Ser Thr Ala Gly
            495                 500                 505

gtt gcc cag ctc cct tta cac cgg tgt gat att tac ggg aaa gcg tgt    1887
Val Ala Gln Leu Pro Leu His Arg Cys Asp Ile Tyr Gly Lys Ala Cys
            510                 515                 520

gct gag tgt tgc ctc gcc cga gac cct tac tgt gct tgg gat ggt tct    1935
Ala Glu Cys Cys Leu Ala Arg Asp Pro Tyr Cys Ala Trp Asp Gly Ser
525                 530                 535                 540

gca tgt tct cgc tat ttt ccc act gca aag aga cgc aca aga cga caa    1983
Ala Cys Ser Arg Tyr Phe Pro Thr Ala Lys Arg Arg Thr Arg Arg Gln
            545                 550                 555

gat ata aga aat gga gac cca ctg act cac tgt tca gac tta cac cat    2031
Asp Ile Arg Asn Gly Asp Pro Leu Thr His Cys Ser Asp Leu His His
            560                 565                 570

gat aat cac cat ggc cac agc cct gaa gag aga atc atc tat ggt gta    2079
Asp Asn His His Gly His Ser Pro Glu Glu Arg Ile Ile Tyr Gly Val
            575                 580                 585

gag aat agt agc aca ttt ttg gaa tgc agt ccg aag tcg cag aga gcg    2127
Glu Asn Ser Ser Thr Phe Leu Glu Cys Ser Pro Lys Ser Gln Arg Ala
            590                 595                 600

ctg gtc tat tgg caa ttc cag agg cga aat gaa gag cga aaa gaa gag    2175
Leu Val Tyr Trp Gln Phe Gln Arg Arg Asn Glu Glu Arg Lys Glu Glu
605                 610                 615                 620

atc aga gtg gat gat cat atc atc agg aca gat caa ggc ctt ctg cta    2223
Ile Arg Val Asp Asp His Ile Ile Arg Thr Asp Gln Gly Leu Leu Leu
            625                 630                 635

cgt agt cta caa cag aag gat tca ggc aat tac ctc tgc cat gcg gtg    2271
Arg Ser Leu Gln Gln Lys Asp Ser Gly Asn Tyr Leu Cys His Ala Val
            640                 645                 650

gaa cat ggg ttc ata caa act ctt ctt aag gta acc ctg gaa gtc att    2319
Glu His Gly Phe Ile Gln Thr Leu Leu Lys Val Thr Leu Glu Val Ile
            655                 660                 665

gac aca gag cat ttg gaa gaa ctt ctt cat aaa gat gat gat gga gat    2367
Asp Thr Glu His Leu Glu Glu Leu Leu His Lys Asp Asp Asp Gly Asp
            670                 675                 680

ggc tct aag acc aaa gaa atg tcc aat agc atg aca cct agc cag aag    2415
Gly Ser Lys Thr Lys Glu Met Ser Asn Ser Met Thr Pro Ser Gln Lys
685                 690                 695                 700

gtc tgg tac aga gac ttc atg cag ctc atc aac cac ccc aat ctc aac    2463
Val Trp Tyr Arg Asp Phe Met Gln Leu Ile Asn His Pro Asn Leu Asn
            705                 710                 715

aca atg gat gag ttc tgt gaa caa gtt tgg aaa agg gac cga aaa caa    2511
Thr Met Asp Glu Phe Cys Glu Gln Val Trp Lys Arg Asp Arg Lys Gln
            720                 725                 730

cgt cgg caa agg cca gga cat acc cca ggg aac agt aac aaa tgg aag    2559
Arg Arg Gln Arg Pro Gly His Thr Pro Gly Asn Ser Asn Lys Trp Lys
            735                 740                 745

cac tta caa gaa aat aag aaa ggt aga aac agg agg acc cac gaa ttt    2607
His Leu Gln Glu Asn Lys Lys Gly Arg Asn Arg Arg Thr His Glu Phe
            750                 755                 760

gag agg gca ccc agg agt gtc tga gctgcattac ctctagaaac ctcaaacaag    2661
Glu Arg Ala Pro Arg Ser Val
765                 770

tagaaacttg cctagacaat aactggaaaa acaaatgcaa tatacatgaa cttttttcat    2721

ggcattatgt ggatgtttac aatggtggga aattcagctg agttccacca attataaatt    2781
```

-continued

```
aaatccatga gtaactttcc taataggctt tttttcctaa taccaccacc taacagagaa   2841
cacaggtgaa tgcagatgtt cactttagca gacttaatgt ttcctatgag atttcactgt   2901
acaggtttgt ctttcttctt tgcctgagaa ataaaaatgt catttgccat attgccatct   2961
aaaggagaaa aactgcatca gcaaagccat tgtattgaac taaaagttta aaatgaactg   3021
catggattta ctaagctgat gaatattcca aaacgtggtt ggattcaagg atatattttg   3081
tctaccggcc ctcatgtttg tatgtacttg aggagtaaaa tgagtaaaat gatactgaat   3141
gaaatgttct gtggaaatat taaaaaaaaa aaaaaacata agccatccat catccagaag   3201
aaaaatggaa tacactgatc tactactgat gtcttctttc agctttgatc taaagatgta   3261
ttttattaaa actataattt aaatgtacca tgaaaaatat gcagtaaaaa ttagttgttt   3321
tctaagctag agtaggattt gtcttacaat tattgtgcta tgtagttttt gttttaaaaa   3381
ttccaatggt gtgctgcttt ctttggacat tttattttca attctataag agggatagat   3441
gacattgttc tagaaacaca tatacatcat taagagtgaa tctctaaaac caggatataa   3501
attatgcttt atttctctga gaaaatcaaa caaatggaag ctgttcacac ctccccttct   3561
ttaagcatta tctaaattaa tttttacttg cataatgttc ttagaaaaaa aaacagaaca   3621
tttaagcagg aaaaaaggaa gaaacaagtt gatttttaag tgcattttac tataatgaat   3681
caatgaaggg aaaaggaact gcatatttca tgaaaataat aagcattgtc ttaatatact   3741
gttaatagaa aatgtgtctt aattccgtgc ttgaatccct gcatgatatt tgagactaag   3801
atctctctta tgattctacc aagaattata tctgtgtcac ttaatttttt taaaagagag   3861
agatcaataa ctattcagag caacatgtta aaggcaaagt ttccaatcat ttacatctgt   3921
atcaggtgcc tcttaccttt ccttatttaa gacaattatt tgtacaagaa acacatgact   3981
cttttcatat caatgggagg gacttttcta caaagtattt tccaggatgc aacccacatt   4041
taaacaatgt aaaattcttt gtttcctgca acaacttaca aaataaggta aaagactaaa   4101
attcaagatt tgcttccttc attgtcctaa gacgattcgt tgagaatcac tgactttgag   4161
atatttaaaa ctttcagcat tatactgtgg tttcttttgc actgcactca cctattcagg   4221
actcctcccc caggttcctc atcatgcaca aaaatgcaaa gaaaacatct tattagtaat   4281
taatgaagca acattgaaat tctaactcta gctgtctttg gattctaatt aactcagcat   4341
caatttctca cctcagacta cagtgaattt ttatttccta tcagctgaaa tatttcacag   4401
atggaagctc atgtttcagt tttaatgact gccttgaata aacaagttgt tgccacttgt   4461
ttcaaacaaa agcctaaaaa taatctacat tcaattttag gctccattga ctaatatggt   4521
gttgcttttg gaagtactgt atatcctcac atggaagcca aattgttaaa ttatttgaag   4581
gacacaccac tgtacagaaa gtagtgtttc aaatataaat cgaagaacaa agagtgctcc   4641
aaaaaatagg tcattctttt attttcataa agtatctaaa ctgtactaac attcagtgtt   4701
gtgtttcatt ctaaatttgc agctgaaata aatttatttg cgatagcaga aatatcttat   4761
tattcatcct cagaaataaa ggatttgaag ggatagagat tatatgataa atttatagaa   4821
gactttcaga atttgaatgc attttgttta gtgttatgaa atgacaatag aaaaaagtct   4881
cgacttcaat taaaagttac acaaacaaac aaatctacag gcatgtcttt atataccatc   4941
aggtctaagt tttcaaagaa aattgtagat ataacttgca gataactcat tacagtcata   5001
atctctgccc atgtgtattg agagggggca gtttgcacga aaaagaatta ttggcccatt   5061
taataattca gctttaaata gactttgtca tatgcatgaa tcatcagaga tgaaactgtt   5121
tgagagactc atgtgacctt acgaaaatta caacagcagt cttaaagtat gaaaaagatg   5181
```

```
catcacagca gagacattat ggcccagttg atatcaaatg taaaatgtaa atgcatgtaa   5241

atgcacactt cattttatgt attatttagt aatttgcagt ggtatgtgtt taatattttt   5301

gctacctaca cattaggcaa aaaaaagatg taaataattt gggagaaaaa gaggaagaac   5361

agtgtaaaat aaaactttct ataagtactc catttcaatg tgttcaacat catcctaaaa   5421

ggcaagattt tcccacgcag gtgacaaggt ggtttatgta ctatttaagg gcggaaggtg   5481

cgtgcccgtt caataagcat gtttttttgcc aggtaggaaa tatgttccat atctttactt   5541

atcattgcat ttcagatggg aactagaaaa actggagaga aaaatgtaat gaaactgctg   5601

ctgtaaatta ttcctttttag catgtattca cttgctaaat acacatttct tcaaaataaa   5661

aaaaaaaaaa a                                                         5672
```

<210> SEQ ID NO 2
<211> LENGTH: 771
<212> TYPE: PRT
<213> ORGANISM: Homo sapiens
<220> FEATURE:
<223> OTHER INFORMATION: wildtype full length SEMA3A
(>gi|100913215|ref|NM_006080.2|)

<400> SEQUENCE: 2

```
Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Lys Phe Ile Ser Ala His Leu Ile Ser Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
```

```
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Phe Lys Asp Pro Lys
305                 310                 315                 320

Asn Pro Val Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Met
                405                 410                 415

Asn Asn Arg Pro Ile Val Ile Lys Thr Asp Val Asn Tyr Gln Phe Thr
            420                 425                 430

Gln Ile Val Val Asp Arg Val Asp Ala Glu Asp Gly Gln Tyr Asp Val
        435                 440                 445

Met Phe Ile Gly Thr Asp Val Gly Thr Val Leu Lys Val Val Ser Ile
    450                 455                 460

Pro Lys Glu Thr Trp Tyr Asp Leu Glu Glu Val Leu Leu Glu Glu Met
465                 470                 475                 480

Thr Val Phe Arg Glu Pro Thr Ala Ile Ser Ala Met Glu Leu Ser Thr
                485                 490                 495

Lys Gln Gln Gln Leu Tyr Ile Gly Ser Thr Ala Gly Val Ala Gln Leu
            500                 505                 510

Pro Leu His Arg Cys Asp Ile Tyr Gly Lys Ala Cys Ala Glu Cys Cys
        515                 520                 525

Leu Ala Arg Asp Pro Tyr Cys Ala Trp Asp Gly Ser Ala Cys Ser Arg
    530                 535                 540

Tyr Phe Pro Thr Ala Lys Arg Arg Thr Arg Arg Gln Asp Ile Arg Asn
545                 550                 555                 560

Gly Asp Pro Leu Thr His Cys Ser Asp Leu His His Asp Asn His His
                565                 570                 575

Gly His Ser Pro Glu Glu Arg Ile Ile Tyr Gly Val Glu Asn Ser Ser
            580                 585                 590

Thr Phe Leu Glu Cys Ser Pro Lys Ser Gln Arg Ala Leu Val Tyr Trp
        595                 600                 605

Gln Phe Gln Arg Arg Asn Glu Glu Arg Lys Glu Glu Ile Arg Val Asp
    610                 615                 620

Asp His Ile Ile Arg Thr Asp Gln Gly Leu Leu Leu Arg Ser Leu Gln
625                 630                 635                 640

Gln Lys Asp Ser Gly Asn Tyr Leu Cys His Ala Val Glu His Gly Phe
                645                 650                 655

Ile Gln Thr Leu Leu Lys Val Thr Leu Glu Val Ile Asp Thr Glu His
            660                 665                 670

Leu Glu Glu Leu Leu His Lys Asp Asp Asp Gly Asp Gly Ser Lys Thr
        675                 680                 685
```

```
Lys Glu Met Ser Asn Ser Met Thr Pro Ser Gln Lys Val Trp Tyr Arg
    690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Arg Gln Arg
                725                 730                 735

Pro Gly His Thr Pro Gly Asn Ser Asn Lys Trp Lys His Leu Gln Glu
            740                 745                 750

Asn Lys Lys Gly Arg Asn Arg Arg Thr His Glu Phe Glu Arg Ala Pro
        755                 760                 765

Arg Ser Val
    770


<210> SEQ ID NO 3
<211> LENGTH: 6850
<212> TYPE: DNA
<213> ORGANISM: Mus musculus
<220> FEATURE:
<223> OTHER INFORMATION: wildtype full length Sema3A transcript variant
      1 (>gi| 340523098|ref| NM_009152.4|)
<220> FEATURE:
<221> NAME/KEY: CDS
<222> LOCATION: 650..2968
<223> OTHER INFORMATION: /transl_table=1

<400> SEQUENCE: 3

gtgacaagag ggaaggggag tgggttgagc tcgctcctct cccattgtca gcgcgtctag     60

tgagtgttgg gaaaacctgt ccgcgggatc ctgtgtcatc tctccctgct tgtgcacagg    120

aaaagtccgc gctgctctgc tcacggctgc tcgcaccccc tctctctcct ctctctcttt    180

ctctgtttcc ctttcattct gcttcctcgg agccgaatga agcagggaga gggagcagga    240

ttagagtcag ccaccggcta tcagcggagc ggagataaaa ggaactgctt cttaagcgcc    300

actgccgcag cccttgttaa ttttttttctt cttcttcttc ttctttccac acaacagttg    360

tgcctcatta tccggtgcct ggctcgattt ttttcttttct tttttctttt tttcttttct    420

ttcttccttt ttttttttt tcttttttttg agggtttgaa gtttctgtga ttccgtgact    480

gttacagaag agacgttagt gttgccatga ggtcttgatt gtctgcattt atgaatgaaa    540

ctgacctaaa tcacctgtta cctccagttt ccagattgtt tgaacttctc tggccgcaca    600

atacaggaag gaaggctgcc gcagctcagg gacctccagc gtctgcagc atg ggc tgg    658
                                                      Met Gly Trp
                                                      1

ttc act ggg att gcc tgt ctt ttc tgg ggt gta tta ctt aca gcc aga      706
Phe Thr Gly Ile Ala Cys Leu Phe Trp Gly Val Leu Leu Thr Ala Arg
    5                   10                  15

gca aac tat gca aac gga aag aac aat gtg cca aga ctg aaa tta tcg      754
Ala Asn Tyr Ala Asn Gly Lys Asn Asn Val Pro Arg Leu Lys Leu Ser
20                  25                  30                  35

tac aaa gaa atg ttg gaa tcc aac aat gtg atc act ttt aat ggc ttg      802
Tyr Lys Glu Met Leu Glu Ser Asn Asn Val Ile Thr Phe Asn Gly Leu
                40                  45                  50

gcc aac agc tcc agt tac cac acc ttc ctt ctg gat gaa gaa cgg agt      850
Ala Asn Ser Ser Ser Tyr His Thr Phe Leu Leu Asp Glu Glu Arg Ser
            55                  60                  65

aga cta tat gtt gga gca aaa gat cat ata ttt tca ttc aac ttg gtg      898
Arg Leu Tyr Val Gly Ala Lys Asp His Ile Phe Ser Phe Asn Leu Val
        70                  75                  80
```

-continued

```
aac att aaa gat ttt caa aag att gtg tgg cca gta tct tac aca agg      946
Asn Ile Lys Asp Phe Gln Lys Ile Val Trp Pro Val Ser Tyr Thr Arg
    85                  90                  95

aga gat gaa tgc aaa tgg gct gga aaa gat atc ctg aaa gaa tgt gcc      994
Arg Asp Glu Cys Lys Trp Ala Gly Lys Asp Ile Leu Lys Glu Cys Ala
100                 105                 110                 115

aat ttc atc aag gtc ctg gag gct tat aat cag act cac ttg tat gcc     1042
Asn Phe Ile Lys Val Leu Glu Ala Tyr Asn Gln Thr His Leu Tyr Ala
                120                 125                 130

tgt gga act ggg gct ttc cat cca atc tgc acc tat att gaa gtt gga     1090
Cys Gly Thr Gly Ala Phe His Pro Ile Cys Thr Tyr Ile Glu Val Gly
            135                 140                 145

cat cat cct gag gac aac att ttt aag ctg cag gac tca cat ttt gaa     1138
His His Pro Glu Asp Asn Ile Phe Lys Leu Gln Asp Ser His Phe Glu
        150                 155                 160

aac ggt cgt ggg aag agc cct tat gat ccc aaa cta ctg act gcc tct     1186
Asn Gly Arg Gly Lys Ser Pro Tyr Asp Pro Lys Leu Leu Thr Ala Ser
    165                 170                 175

ctt cta ata gac ggt gag ttg tac tct gga act gct gcg gac ttc atg     1234
Leu Leu Ile Asp Gly Glu Leu Tyr Ser Gly Thr Ala Ala Asp Phe Met
180                 185                 190                 195

gga cgg gac ttc gct atc ttc aga aca ctg ggg cac cat cac ccc atc     1282
Gly Arg Asp Phe Ala Ile Phe Arg Thr Leu Gly His His His Pro Ile
                200                 205                 210

agg acg gag cag cat gac tcc cgg tgg ctc aat gat cct aga ttc atc     1330
Arg Thr Glu Gln His Asp Ser Arg Trp Leu Asn Asp Pro Arg Phe Ile
            215                 220                 225

agt gcc cat ctc atc cca gag agt gac aac cct gaa gat gac aaa gta     1378
Ser Ala His Leu Ile Pro Glu Ser Asp Asn Pro Glu Asp Asp Lys Val
        230                 235                 240

tat ttt ttc ttc cga gaa aat gca ata gac gga gaa cac tct gga aaa     1426
Tyr Phe Phe Phe Arg Glu Asn Ala Ile Asp Gly Glu His Ser Gly Lys
    245                 250                 255

gcc act cat gct aga ata ggt cag ata tgc aag aat gac ttt ggt gga     1474
Ala Thr His Ala Arg Ile Gly Gln Ile Cys Lys Asn Asp Phe Gly Gly
260                 265                 270                 275

cac aga agt ctt gtg aat aaa tgg aca aca ttc cta aaa gca cgc ctg     1522
His Arg Ser Leu Val Asn Lys Trp Thr Thr Phe Leu Lys Ala Arg Leu
                280                 285                 290

att tgc tct gtg ccc ggt ccc aat ggc att gac acc cat ttt gat gaa     1570
Ile Cys Ser Val Pro Gly Pro Asn Gly Ile Asp Thr His Phe Asp Glu
            295                 300                 305

ttg cag gat gta ttc cta atg aac tct aaa gat cct aaa aat ccg atc     1618
Leu Gln Asp Val Phe Leu Met Asn Ser Lys Asp Pro Lys Asn Pro Ile
        310                 315                 320

gtc tat gga gtg ttc aca aca tca agc aac atc ttt aag gga tct gct     1666
Val Tyr Gly Val Phe Thr Thr Ser Ser Asn Ile Phe Lys Gly Ser Ala
    325                 330                 335

gtg tgc atg tac agc atg agt gat gta aga agg gtg ttc ctt ggt cca     1714
Val Cys Met Tyr Ser Met Ser Asp Val Arg Arg Val Phe Leu Gly Pro
340                 345                 350                 355

tat gct cac aga gat ggt ccc aac tat cag tgg gtg cct tac caa gga     1762
Tyr Ala His Arg Asp Gly Pro Asn Tyr Gln Trp Val Pro Tyr Gln Gly
                360                 365                 370

aga gtc cct tat cca cgg cca gga act tgt ccc agt aaa aca ttt ggc     1810
Arg Val Pro Tyr Pro Arg Pro Gly Thr Cys Pro Ser Lys Thr Phe Gly
            375                 380                 385

gga ttt gac tcc aca aag gac ctt cct gat gat gtc ata act ttt gca     1858
Gly Phe Asp Ser Thr Lys Asp Leu Pro Asp Asp Val Ile Thr Phe Ala
        390                 395                 400
```

-continued

```
aga agt cat cca gcc atg tac aac cca gtg ttt cct ata aat aat cgc      1906
Arg Ser His Pro Ala Met Tyr Asn Pro Val Phe Pro Ile Asn Asn Arg
    405                 410                 415

ccg atc atg atc aaa aca gat gta aat tat cag ttc aca caa att gtt      1954
Pro Ile Met Ile Lys Thr Asp Val Asn Tyr Gln Phe Thr Gln Ile Val
420                 425                 430                 435

gta gac cga gtg gat gca gaa gat ggc cag tat gat gtt atg ttc atc      2002
Val Asp Arg Val Asp Ala Glu Asp Gly Gln Tyr Asp Val Met Phe Ile
                440                 445                 450

gga aca gat gtt gga acc gtt ctt aaa gtg gtt tca gtc ccc aag gag      2050
Gly Thr Asp Val Gly Thr Val Leu Lys Val Val Ser Val Pro Lys Glu
            455                 460                 465

act tgg cat gac cta gaa gaa gtt ctt ctg gaa gaa atg acc gtc ttc      2098
Thr Trp His Asp Leu Glu Glu Val Leu Leu Glu Glu Met Thr Val Phe
        470                 475                 480

cgg gaa cca aca act att tcg gca atg gag ctt tct act aaa cag caa      2146
Arg Glu Pro Thr Thr Ile Ser Ala Met Glu Leu Ser Thr Lys Gln Gln
    485                 490                 495

cag ctg tac att ggc tca act gcg gga gtg gca cag ctt cct cta cac      2194
Gln Leu Tyr Ile Gly Ser Thr Ala Gly Val Ala Gln Leu Pro Leu His
500                 505                 510                 515

cgc tgt gac atc tat ggc aaa gcc tgt gca gaa tgc tgc ctc gct cgg      2242
Arg Cys Asp Ile Tyr Gly Lys Ala Cys Ala Glu Cys Cys Leu Ala Arg
                520                 525                 530

gac cct tac tgt gcc tgg gat ggg tcc tca tgc tca cgc tat ttt cct      2290
Asp Pro Tyr Cys Ala Trp Asp Gly Ser Ser Cys Ser Arg Tyr Phe Pro
            535                 540                 545

act gca aag agg cgc aca aga cga caa gat ata agg aat gga gac cca      2338
Thr Ala Lys Arg Arg Thr Arg Arg Gln Asp Ile Arg Asn Gly Asp Pro
        550                 555                 560

ctg act cac tgc tct gac ttg cag cac cat gat aat cat cat ggg ccc      2386
Leu Thr His Cys Ser Asp Leu Gln His His Asp Asn His His Gly Pro
    565                 570                 575

agc ctt gaa gag aga atc atc tat gga gtg gaa aac agt agt aca ttc      2434
Ser Leu Glu Glu Arg Ile Ile Tyr Gly Val Glu Asn Ser Ser Thr Phe
580                 585                 590                 595

ttg gaa tgc agt ccg aag tca cag aga gcc ttg gta tat tgg caa ttt      2482
Leu Glu Cys Ser Pro Lys Ser Gln Arg Ala Leu Val Tyr Trp Gln Phe
                600                 605                 610

cag agg aga aat gaa gat cga aaa gag gag atc aga atg ggt gat cat      2530
Gln Arg Arg Asn Glu Asp Arg Lys Glu Glu Ile Arg Met Gly Asp His
            615                 620                 625

atc atc agg aca gaa caa ggg ctc ctg ctc cgt agc ctg cag aag aag      2578
Ile Ile Arg Thr Glu Gln Gly Leu Leu Leu Arg Ser Leu Gln Lys Lys
        630                 635                 640

gat tca ggc aat tac ctg tgt cac gct gtg gaa cac gga ttc atg caa      2626
Asp Ser Gly Asn Tyr Leu Cys His Ala Val Glu His Gly Phe Met Gln
    645                 650                 655

act ctt ctt aag gta acc ctg gaa gtc att gac aca gaa cat ttg gaa      2674
Thr Leu Leu Lys Val Thr Leu Glu Val Ile Asp Thr Glu His Leu Glu
660                 665                 670                 675

gaa ctt ctt cat aaa gat gac gat gga gat ggc tct aag ata aaa gaa      2722
Glu Leu Leu His Lys Asp Asp Asp Gly Asp Gly Ser Lys Ile Lys Glu
                680                 685                 690

atg tcg agc agc atg acg ccc agc cag aaa gtc tgg tac cga gac ttc      2770
Met Ser Ser Ser Met Thr Pro Ser Gln Lys Val Trp Tyr Arg Asp Phe
            695                 700                 705

atg cag ctc att aac cac ccc aac ctg aac acg atg gat gag ttc tgt      2818
Met Gln Leu Ile Asn His Pro Asn Leu Asn Thr Met Asp Glu Phe Cys
```

-continued

```
        710                 715                 720

gaa caa gtg tgg aaa agg gac cga aag caa cgc cga caa agg ccg ggg      2866
Glu Gln Val Trp Lys Arg Asp Arg Lys Gln Arg Arg Gln Arg Pro Gly
    725                 730                 735

cac tct caa ggg agc agc aac aag tgg aag cac atg caa gag agc aag      2914
His Ser Gln Gly Ser Ser Asn Lys Trp Lys His Met Gln Glu Ser Lys
740                 745                 750                 755

aaa ggt aga aac agg agg acc cac gag ttt gag cgg gca ccc aga agt      2962
Lys Gly Arg Asn Arg Arg Thr His Glu Phe Glu Arg Ala Pro Arg Ser
                760                 765                 770

gtc tga gctgcgccac ctcccaaaac ctcaaacaag tacaaacttg cttagataat      3018
Val

aactggaaaa aatgcaatac acatgaacat ttcatggcat tatgtggatg tttacaatga   3078

tgggaagttc aaccgggttc caccaattta agtccgtgag gaactttccc agcaggcttt   3138

cttcagtata ccaacgcttg acagagatca caggtgagca tagatgttca cgtccgctga   3198

cttagtgttt cctctgaaag ttcattttgc ttccttcttt gcctgagaaa taaaaatgtc   3258

atttgccatc gaaaggagaa aaactgcatc agcaaagcca ttttattgaa gcaagagttg   3318

aaaataaact gcatggattt agtaagcaga tgaatattcc aaaacgtgat tggattcaag   3378

gatgttttgt ctaccagcac tcgtgtttgt atgtactgga gaagtaaaat aaggagaatg   3438

acactgagtg aaatagtcta tggagatata aaaacacaaa ccacccatca tccagagtaa   3498

tggagtacat tgatctacta ctgatgtctt ctttcagctt tgatctaaag atgtatttta   3558

ttaaagttat aatttaaatg taccatggca aatatgcagt aaagattagc tgtttcctaa   3618

gctagagtag gtcttgtctt gcagttacca tgctatatcg tttgtttaaa aattccaact   3678

gtgtgctgct tttttacatt gtgttttcag ttctgtaaga ggcagtatat cactttaggt   3738

ccctactcac tgtactatta cttactgaca ccaagaatta tggtcttccc ctttgaagaa   3798

accaaacaga tagaaggtta tcaccctgac ttgcaaaggt attatctaag ttaactctca   3858

catacataat gttttcagtc aaccaaaaat taagacagca caaagagaag aaaacagtca   3918

ttagaggcat cctgaaggat caagagcaaa attaaattca tgtgtctcat gaaaagaaca   3978

ttgtcttaac agagtgttga taaaatgtct ttccctcttg gcttgaatat ttgcatgatg   4038

tgtgaggcat aggactcgct catgattcca catcccacca aagattctat tttcagtcac   4098

ttaatgattt ccaaagcaga gagaaagagc gggggtgggg ggaatcagtg acattcagga   4158

catgttctaa caacaaaatg acacatttct caactatttc tttgtgaatc aactaaattt   4218

tacccaccct gtatgataca attatttgtc tgaacaactt ataagtgttt tatctcaatg   4278

agagtgaaac tatacacttc acctagaaag tgcaaaattc tttgttttat gaataaaata   4338

taagataaca caaaatgttt cagaatgtat agcctttgtt ggttggagat gatttcctaa   4398

gaatcattga gttcaaaatg cttaataaat tcaacattat agaccagttc attggtgcta   4458

caggcctcac ttcaggaatt tttttcttcg atccttcagc atgcacaaaa atgcaaagta   4518

aatatcttct tgctaagaaa tgaagtggcg ttgatatttt aactccagtt gtctcctaat   4578

tctaattaac tcagtattaa cttctcacct caactacacc aaattgtcat tccctcgcca   4638

ctgaaatagt tcacagatgg aagcttctgt ttcagtttta atgattattt aaataaaaaa   4698

acaatttgtt gacatgtctt tcatataaaa gcctaaaatc atcctacatc tgattttagg   4758

ctcattgact aatggtgttg cttttggaaa tatgtcttca aaggcaagct gaatggatga   4818

attatttgag atcacactct gaacagaaaa tattgtcagg aacattaagt gagagaaaga   4878
```

```
gggatgctcc aaataagcca ttctctcatt taatagggtc ttaactgtcc aaacatttaa   4938

tgttatattt cattctaaat ttgcatctga tacaagtata ttggcaatta cataactctc   4998

ccatttcttt ctagctctta acaataaagg atctaatgga aggaaggttg tttaataact   5058

ttatggatgc ctttcaaaat cggaatgcat tttgtttagc actaagaaat agcaatagaa   5118

aactgcttag gtttcaatta aaagtgttaa aaacaagcaa atatattaac atgtctcaat   5178

caatcaccat gtctaagttt caaagaaagt tattgattaa ctagggaata aataaataaa   5238

tacacacata catacataaa tcttatgaca gttataacct cccattgtgt attgagagag   5298

gacagtttgc acgaagaaga atgtcccatt tactaagtaa tttagatgga ctttggcata   5358

tgcatgtatc atcacaggta agacctgcct aagagatgca tgtgacctta agcaaattac   5418

cacagcagtc tcacaatagt ctcaagttga aaaagataca tcacagtgga gagagcaggc   5478

cccgctgata gcaactgtaa agtgtaaatg catgcaaatg cacacttatt gcttctttta   5538

tgtataattt agtgatttat aatggtatgt gtttaatatt tttgctacct acacattaga   5598

caaaggtgta aataattttg aaaagagtag aaagagcact gtaaattaca agtttctata   5658

gatgctccat tccagtttgt tcaccatcat cctcaagtgc aagatttccc atacaagtga   5718

tgcggtggct tatgtactac ttaagggcag agagggtgtg cccctcgaag agcatgcttt   5778

ttgccaggtc gtaaattgtt ccgtatctgt atttatcatt gcatttcaga tgggaactag   5838

aaaactggag agaaaaatgt aacgatattg ctgctgtaaa ttattccttt ttagcatgta   5898

ttcagttgct aaatacacat ttcttcaaaa tatttgaatt cagatgtctt tactgttcca   5958

tataacatat ggtattgagg aagataagct tcgaagcctt cgagaaccag agtcaggaat   6018

cagcataatt agctaacaga tttcttcatt gtagtattct gtaaactgtg ttctatattt   6078

atagtgatga tgtgaatttt ttgcccttta aactaaatgc tgttctcttt atgtcatacc   6138

tggaaagaac acatggatga aagtctttaa tcagtggatt atgatgtgaa gcatcataat   6198

tcaagatcaa taccgattcc agatgattgg catctagagg cctgtcctgc agctcatggg   6258

caagcactgc attaatatgg atttatttct gtaatgtgtt caagtccttc tcttataaat   6318

actattttaa acacatattt aattcactga aagtctgtca gagtttattt gcttcaaaga   6378

cacatttgac aaacaggtct tagcactatt atatactaac atgatggtta caaactggcc   6438

tggtgccaaa gaatccaaag cttttaattt taacttggta ataattattt aagtcaatgt   6498

taatatttac agtatatctt tccttaaaga agcaaacatt attttcaaaa gtatggaaat   6558

tctattagct ttattttaaa aactttccta tactagctaa ttcaaaaatc acacatttgt   6618

atattaatag ataaagacaa acccaaagtg aaagttgccc cagaaatggg ttttcttata   6678

actggtcaac tttcttgatt aacctaacca aagaaaaatc ttatttcttc atttccaaca   6738

cccaagtgca caaacacagt ctatggtaga aataaaacca aattaataaa agaggaatga   6798

ttttaagtta tgatattagg acccagacgt gacagcatca acctacaatt cc           6850


<210> SEQ ID NO 4
<211> LENGTH: 772
<212> TYPE: PRT
<213> ORGANISM: Mus musculus
<220> FEATURE:
<223> OTHER INFORMATION: wildtype full length Sema3A transcript variant
      1 (>gi| 340523098|ref| NM_009152.4|)

<400> SEQUENCE: 4

Met Gly Trp Phe Thr Gly Ile Ala Cys Leu Phe Trp Gly Val Leu Leu
1               5                   10                  15
```

-continued

```
Thr Ala Arg Ala Asn Tyr Ala Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asn Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Glu Ala Tyr Asn Gln Thr His
        115                 120                 125

Leu Tyr Ala Cys Gly Thr Gly Ala Phe His Pro Ile Cys Thr Tyr Ile
    130                 135                 140

Glu Val Gly His His Pro Glu Asp Asn Ile Phe Lys Leu Gln Asp Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Arg Phe Ile Ser Ala His Leu Ile Pro Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Ser Lys Asp Pro Lys
305                 310                 315                 320

Asn Pro Ile Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Ile
                405                 410                 415

Asn Asn Arg Pro Ile Met Ile Lys Thr Asp Val Asn Tyr Gln Phe Thr
            420                 425                 430
```

```
Gln Ile Val Val Asp Arg Val Asp Ala Glu Asp Gly Gln Tyr Asp Val
        435                 440                 445

Met Phe Ile Gly Thr Asp Val Gly Thr Val Leu Lys Val Val Ser Val
    450                 455                 460

Pro Lys Glu Thr Trp His Asp Leu Glu Glu Val Leu Leu Glu Glu Met
465                 470                 475                 480

Thr Val Phe Arg Glu Pro Thr Thr Ile Ser Ala Met Glu Leu Ser Thr
                485                 490                 495

Lys Gln Gln Gln Leu Tyr Ile Gly Ser Thr Ala Gly Val Ala Gln Leu
            500                 505                 510

Pro Leu His Arg Cys Asp Ile Tyr Gly Lys Ala Cys Ala Glu Cys Cys
        515                 520                 525

Leu Ala Arg Asp Pro Tyr Cys Ala Trp Asp Gly Ser Ser Cys Ser Arg
    530                 535                 540

Tyr Phe Pro Thr Ala Lys Arg Arg Thr Arg Arg Gln Asp Ile Arg Asn
545                 550                 555                 560

Gly Asp Pro Leu Thr His Cys Ser Asp Leu Gln His His Asp Asn His
                565                 570                 575

His Gly Pro Ser Leu Glu Glu Arg Ile Ile Tyr Gly Val Glu Asn Ser
            580                 585                 590

Ser Thr Phe Leu Glu Cys Ser Pro Lys Ser Gln Arg Ala Leu Val Tyr
        595                 600                 605

Trp Gln Phe Gln Arg Arg Asn Glu Asp Arg Lys Glu Glu Ile Arg Met
    610                 615                 620

Gly Asp His Ile Ile Arg Thr Glu Gln Gly Leu Leu Leu Arg Ser Leu
625                 630                 635                 640

Gln Lys Lys Asp Ser Gly Asn Tyr Leu Cys His Ala Val Glu His Gly
                645                 650                 655

Phe Met Gln Thr Leu Leu Lys Val Thr Leu Glu Val Ile Asp Thr Glu
            660                 665                 670

His Leu Glu Glu Leu Leu His Lys Asp Asp Asp Gly Asp Gly Ser Lys
        675                 680                 685

Ile Lys Glu Met Ser Ser Ser Met Thr Pro Ser Gln Lys Val Trp Tyr
    690                 695                 700

Arg Asp Phe Met Gln Leu Ile Asn His Pro Asn Leu Asn Thr Met Asp
705                 710                 715                 720

Glu Phe Cys Glu Gln Val Trp Lys Arg Asp Arg Lys Gln Arg Arg Gln
                725                 730                 735

Arg Pro Gly His Ser Gln Gly Ser Ser Asn Lys Trp Lys His Met Gln
            740                 745                 750

Glu Ser Lys Lys Gly Arg Asn Arg Arg Thr His Glu Phe Glu Arg Ala
        755                 760                 765

Pro Arg Ser Val
    770
```

```
<210> SEQ ID NO 5
<211> LENGTH: 2981
<212> TYPE: DNA
<213> ORGANISM: Homo sapiens
<220> FEATURE:
<223> OTHER INFORMATION: wildtype full length SEMA3B, transcript variant
      3, (>gi| 586798179|ref| NM_001290060.1|)
<220> FEATURE:
<221> NAME/KEY: CDS
<222> LOCATION: 247..2496
<223> OTHER INFORMATION: /transl_table=1
```

```
<400> SEQUENCE: 5

gcgtgggtgt gtctgtgatt gtggccaggc ggggcaccct cggaggggag ggttcggaag     60

tggaatgcga ccccccagcc tctttcccct aggggctgta atctgatccc tggggactcc    120

ccccctagcc tcccgccctc gccctcactg ctgactcctc ttccagatcc tggggcagag    180

tccagggcag ctcaaggctc ctccacacac acacccgctg aaccctgagc accctgagct    240

gctgag atg ggg cgg gcc ggg gct gcc gcc gtg atc ccg ggc ctg gcc       288
       Met Gly Arg Ala Gly Ala Ala Ala Val Ile Pro Gly Leu Ala
       1               5                   10

ctg ctc tgg gca gtg ggg ctg ggg agt gcc gcc ccc agc ccc cca cgc      336
Leu Leu Trp Ala Val Gly Leu Gly Ser Ala Ala Pro Ser Pro Pro Arg
15                  20                  25                  30

ctt cgg ctc tcc ttc caa gag ctc cag gcc tgg cat ggt ctc cag act      384
Leu Arg Leu Ser Phe Gln Glu Leu Gln Ala Trp His Gly Leu Gln Thr
                35                  40                  45

ttc agc ctg gag cga acc tgc tgc tac cag gcc ttg ctg gtg gat gag      432
Phe Ser Leu Glu Arg Thr Cys Cys Tyr Gln Ala Leu Leu Val Asp Glu
            50                  55                  60

gag cgt gga cgc ctg ttt gtg ggt gcc gag aac cat gtg gcc tcc ctc      480
Glu Arg Gly Arg Leu Phe Val Gly Ala Glu Asn His Val Ala Ser Leu
        65                  70                  75

aac ctg gac aac atc agc aag cgg gcc aag aag ctg gcc tgg ccg gcc      528
Asn Leu Asp Asn Ile Ser Lys Arg Ala Lys Lys Leu Ala Trp Pro Ala
    80                  85                  90

cct gtg gaa tgg cga gag gag tgc aac tgg gca ggg aag gac att ggt      576
Pro Val Glu Trp Arg Glu Glu Cys Asn Trp Ala Gly Lys Asp Ile Gly
95                  100                 105                 110

act gag tgc atg aac ttc gtg aag ttg ctg cat gcc tac aac cgc acc      624
Thr Glu Cys Met Asn Phe Val Lys Leu Leu His Ala Tyr Asn Arg Thr
                115                 120                 125

cat ttg ctg gcc tgt ggc acg gga gcc ttc cac cca acc tgt gcc ttt      672
His Leu Leu Ala Cys Gly Thr Gly Ala Phe His Pro Thr Cys Ala Phe
            130                 135                 140

gtg gaa gtg ggc cac cgg gca gag gag ccc gtc ctc cgg ctg gac cca      720
Val Glu Val Gly His Arg Ala Glu Glu Pro Val Leu Arg Leu Asp Pro
        145                 150                 155

gga agg ata gag gat ggc aag ggg aag agt cct tat gac ccc agg cat      768
Gly Arg Ile Glu Asp Gly Lys Gly Lys Ser Pro Tyr Asp Pro Arg His
    160                 165                 170

cgg gct gcc tcc gtg ctg gtg ggg gag gag cta tac tca ggg gtg gca      816
Arg Ala Ala Ser Val Leu Val Gly Glu Glu Leu Tyr Ser Gly Val Ala
175                 180                 185                 190

gca gac ctc atg gga cga gac ttt acc atc ttt cgc agc cta ggg caa      864
Ala Asp Leu Met Gly Arg Asp Phe Thr Ile Phe Arg Ser Leu Gly Gln
                195                 200                 205

cgt cca agt ctc cga aca gag cca cac gac tcc cgc tgg ctc aat gag      912
Arg Pro Ser Leu Arg Thr Glu Pro His Asp Ser Arg Trp Leu Asn Glu
            210                 215                 220

ccc aag ttt gtc aag gta ttt tgg atc ccg gag agc gag aac cca gac      960
Pro Lys Phe Val Lys Val Phe Trp Ile Pro Glu Ser Glu Asn Pro Asp
        225                 230                 235

gac gac aaa atc tac ttc ttc ttt cgt gag acg gcg gta gag gcg gcg     1008
Asp Asp Lys Ile Tyr Phe Phe Phe Arg Glu Thr Ala Val Glu Ala Ala
    240                 245                 250

ccg gca ctg gga cgc ctg tcc gtg tcc cgc gtt ggc cag atc tgc cgg     1056
Pro Ala Leu Gly Arg Leu Ser Val Ser Arg Val Gly Gln Ile Cys Arg
255                 260                 265                 270

aac gac gtg ggc ggc cag cgc agc ctg gtc aac aag tgg acg acg ttc     1104
```

```
Asn Asp Val Gly Gly Gln Arg Ser Leu Val Asn Lys Trp Thr Thr Phe
                275                 280                 285

ctg aag gcg cgg ctg gtg tgc tcg gtg ccc ggc gtc gag ggc gac acc      1152
Leu Lys Ala Arg Leu Val Cys Ser Val Pro Gly Val Glu Gly Asp Thr
            290                 295                 300

cac ttc gat cag ctc cag gat gtg ttt ctg ttg tcc tcg cgg gac cac      1200
His Phe Asp Gln Leu Gln Asp Val Phe Leu Leu Ser Ser Arg Asp His
        305                 310                 315

cgg acc ccg ctg ctc tat gcc gtc ttc tcc acg tcc agc agc atc ttc      1248
Arg Thr Pro Leu Leu Tyr Ala Val Phe Ser Thr Ser Ser Ser Ile Phe
    320                 325                 330

cag ggc tct gcg gtg tgc gtg tac agc atg aac gac gtg cgc cgg gcc      1296
Gln Gly Ser Ala Val Cys Val Tyr Ser Met Asn Asp Val Arg Arg Ala
335                 340                 345                 350

ttc ttg gga ccc ttt gca cac aag gag ggg ccc atg cac cag tgg gtg      1344
Phe Leu Gly Pro Phe Ala His Lys Glu Gly Pro Met His Gln Trp Val
                355                 360                 365

tca tac cag ggt cgc gtc ccc tac ccg cgg cca ggc atg tgc ccc agc      1392
Ser Tyr Gln Gly Arg Val Pro Tyr Pro Arg Pro Gly Met Cys Pro Ser
            370                 375                 380

aag acc ttt ggc acc ttc agt tcc acc aag gac ttc cca gac gat gtc      1440
Lys Thr Phe Gly Thr Phe Ser Ser Thr Lys Asp Phe Pro Asp Asp Val
        385                 390                 395

atc cag ttt gcg cgg aac cac ccc ctc atg tac aac tct gtc ctg ccc      1488
Ile Gln Phe Ala Arg Asn His Pro Leu Met Tyr Asn Ser Val Leu Pro
    400                 405                 410

act ggg ggg cgc cct ctt ttc cta caa gtt gga gcc aat tac acc ttc      1536
Thr Gly Gly Arg Pro Leu Phe Leu Gln Val Gly Ala Asn Tyr Thr Phe
415                 420                 425                 430

act caa att gcc gcg gac cgg gtt gca gcc gct gac gga cac tat gac      1584
Thr Gln Ile Ala Ala Asp Arg Val Ala Ala Ala Asp Gly His Tyr Asp
                435                 440                 445

gtc ctc ttc att ggc aca gac gtt ggc acg gtg ctg aag gtg atc tcg      1632
Val Leu Phe Ile Gly Thr Asp Val Gly Thr Val Leu Lys Val Ile Ser
            450                 455                 460

gtc ccc aag ggc agt agg ccc agc gca gag ggg ctg ctc ctg gag gag      1680
Val Pro Lys Gly Ser Arg Pro Ser Ala Glu Gly Leu Leu Leu Glu Glu
        465                 470                 475

ctg cac gtg ttt gag gac tcg gcc gct gtc acc agc atg caa att tct      1728
Leu His Val Phe Glu Asp Ser Ala Ala Val Thr Ser Met Gln Ile Ser
    480                 485                 490

tcc aag agg cac cag ctg tac gta gcc tcg cgg agc gcg gtg gcc cag      1776
Ser Lys Arg His Gln Leu Tyr Val Ala Ser Arg Ser Ala Val Ala Gln
495                 500                 505                 510

atc gcg ttg cac cgc tgc gct gcc cac ggc cgc gtc tgc acc gaa tgc      1824
Ile Ala Leu His Arg Cys Ala Ala His Gly Arg Val Cys Thr Glu Cys
                515                 520                 525

tgt ctg gcg cgt gac ccc tac tgc gcc tgg gac ggg gtc gcg tgc acg      1872
Cys Leu Ala Arg Asp Pro Tyr Cys Ala Trp Asp Gly Val Ala Cys Thr
            530                 535                 540

cgc ttc cag ccc agt gcc aag agg cgg ttc cgg cgg caa gac gta agg      1920
Arg Phe Gln Pro Ser Ala Lys Arg Arg Phe Arg Arg Gln Asp Val Arg
        545                 550                 555

aat ggc gac ccc agc acg ttg tgc tcc gga gac tcg tct cgt ccc gcg      1968
Asn Gly Asp Pro Ser Thr Leu Cys Ser Gly Asp Ser Ser Arg Pro Ala
    560                 565                 570

ctg ctg gaa cac aag gtg ttc ggc gtg gag ggc agc agc gcc ttt ctg      2016
Leu Leu Glu His Lys Val Phe Gly Val Glu Gly Ser Ser Ala Phe Leu
575                 580                 585                 590
```

```
gag tgt gag ccc cgc tcg ctg cag gcg cgc gtg gag tgg act ttc cag     2064
Glu Cys Glu Pro Arg Ser Leu Gln Ala Arg Val Glu Trp Thr Phe Gln
                595                 600                 605

cgc gca ggg gtg aca gcc cac acc cag gtg ctg gca gag gag cgc acc     2112
Arg Ala Gly Val Thr Ala His Thr Gln Val Leu Ala Glu Glu Arg Thr
            610                 615                 620

gag cgc acc gcc cgg gga cta ctg ctg cgc agg ctg cgg cgc cgg gac     2160
Glu Arg Thr Ala Arg Gly Leu Leu Leu Arg Arg Leu Arg Arg Arg Asp
        625                 630                 635

tcg ggc gtg tac ttg tgc gcc gcc gtc gag cag ggc ttt acg caa ccg     2208
Ser Gly Val Tyr Leu Cys Ala Ala Val Glu Gln Gly Phe Thr Gln Pro
    640                 645                 650

ctg cgt cgc ctg tcg ctg cac gtg ttg agt gct acg cag gcc gaa cga     2256
Leu Arg Arg Leu Ser Leu His Val Leu Ser Ala Thr Gln Ala Glu Arg
655                 660                 665                 670

ctg gcg cgg gcc gag gag gct gcg ccc gcc gcg ccg ccg ggc ccc aaa     2304
Leu Ala Arg Ala Glu Glu Ala Ala Pro Ala Ala Pro Pro Gly Pro Lys
                675                 680                 685

ctc tgg tac cgg gac ttt ctg cag ctg gtg gag ccg ggc gga ggt ggc     2352
Leu Trp Tyr Arg Asp Phe Leu Gln Leu Val Glu Pro Gly Gly Gly Gly
            690                 695                 700

agc gcg aac tcc ctg cgc atg tgc cgc ccg cag cct gcg ctg cag tca     2400
Ser Ala Asn Ser Leu Arg Met Cys Arg Pro Gln Pro Ala Leu Gln Ser
        705                 710                 715

ctg ccc ctg gag tcg cgg aga aag ggc cgt aac cgg agg acc cac gcc     2448
Leu Pro Leu Glu Ser Arg Arg Lys Gly Arg Asn Arg Arg Thr His Ala
    720                 725                 730

cct gag cct cgc gct gag cgg ggg ccg cgc agc gca acg cac tgg tga     2496
Pro Glu Pro Arg Ala Glu Arg Gly Pro Arg Ser Ala Thr His Trp
735                 740                 745

ccagactgtc cccacgccgg gaaccaagca ggagacgaca ggcgagagag gagccagaca   2556

gaccctgaaa agaaggacgg gttggggccg ggcacattgg gggtcaccgg ccgatggaga   2616

caccaaccga caggccctgg ctgagggcag ctgcgcgggc ttatttatta acaggataac   2676

ccttgaatgt agcagccccg ggagggcggc acaggtcggg cgcaggattc agccggaggg   2736

aagggacggg gaagccgagc tccagagcaa cgaccagggc cgaggaggtg cctggagtgc   2796

ccaccctggg agacagaccc cacctccttg ggtagtgagc agtgagcaga aagctgtgaa   2856

caggctgggc tgctggaggt ggggcgaggc aggccgactg tactaaagta acgcaataaa   2916

cgcattatca gccaaagctg gaatggcccc agcagaaaac cccagaaaaa aaaaaaaaaa   2976

aaaaa                                                               2981


<210> SEQ ID NO 6
<211> LENGTH: 749
<212> TYPE: PRT
<213> ORGANISM: Homo sapiens
<220> FEATURE:
<223> OTHER INFORMATION: wildtype full length SEMA3B, transcript variant
      3, (>gi| 586798179|ref| NM_001290060.1|)

<400> SEQUENCE: 6

Met Gly Arg Ala Gly Ala Ala Ala Val Ile Pro Gly Leu Ala Leu Leu
1               5                   10                  15

Trp Ala Val Gly Leu Gly Ser Ala Ala Pro Ser Pro Pro Arg Leu Arg
            20                  25                  30

Leu Ser Phe Gln Glu Leu Gln Ala Trp His Gly Leu Gln Thr Phe Ser
        35                  40                  45

Leu Glu Arg Thr Cys Cys Tyr Gln Ala Leu Leu Val Asp Glu Glu Arg
```

```
    50                  55                  60

Gly Arg Leu Phe Val Gly Ala Glu Asn His Val Ala Ser Leu Asn Leu
65                  70                  75                  80

Asp Asn Ile Ser Lys Arg Ala Lys Lys Leu Ala Trp Pro Ala Pro Val
                85                  90                  95

Glu Trp Arg Glu Glu Cys Asn Trp Ala Gly Lys Asp Ile Gly Thr Glu
            100                 105                 110

Cys Met Asn Phe Val Lys Leu Leu His Ala Tyr Asn Arg Thr His Leu
        115                 120                 125

Leu Ala Cys Gly Thr Gly Ala Phe His Pro Thr Cys Ala Phe Val Glu
    130                 135                 140

Val Gly His Arg Ala Glu Glu Pro Val Leu Arg Leu Asp Pro Gly Arg
145                 150                 155                 160

Ile Glu Asp Gly Lys Gly Lys Ser Pro Tyr Asp Pro Arg His Arg Ala
                165                 170                 175

Ala Ser Val Leu Val Gly Glu Glu Leu Tyr Ser Gly Val Ala Ala Asp
            180                 185                 190

Leu Met Gly Arg Asp Phe Thr Ile Phe Arg Ser Leu Gly Gln Arg Pro
        195                 200                 205

Ser Leu Arg Thr Glu Pro His Asp Ser Arg Trp Leu Asn Glu Pro Lys
    210                 215                 220

Phe Val Lys Val Phe Trp Ile Pro Glu Ser Glu Asn Pro Asp Asp Asp
225                 230                 235                 240

Lys Ile Tyr Phe Phe Phe Arg Glu Thr Ala Val Glu Ala Ala Pro Ala
                245                 250                 255

Leu Gly Arg Leu Ser Val Ser Arg Val Gly Gln Ile Cys Arg Asn Asp
            260                 265                 270

Val Gly Gly Gln Arg Ser Leu Val Asn Lys Trp Thr Thr Phe Leu Lys
        275                 280                 285

Ala Arg Leu Val Cys Ser Val Pro Gly Val Glu Gly Asp Thr His Phe
    290                 295                 300

Asp Gln Leu Gln Asp Val Phe Leu Leu Ser Ser Arg Asp His Arg Thr
305                 310                 315                 320

Pro Leu Leu Tyr Ala Val Phe Ser Thr Ser Ser Ser Ile Phe Gln Gly
                325                 330                 335

Ser Ala Val Cys Val Tyr Ser Met Asn Asp Val Arg Arg Ala Phe Leu
            340                 345                 350

Gly Pro Phe Ala His Lys Glu Gly Pro Met His Gln Trp Val Ser Tyr
        355                 360                 365

Gln Gly Arg Val Pro Tyr Pro Arg Pro Gly Met Cys Pro Ser Lys Thr
    370                 375                 380

Phe Gly Thr Phe Ser Ser Thr Lys Asp Phe Pro Asp Asp Val Ile Gln
385                 390                 395                 400

Phe Ala Arg Asn His Pro Leu Met Tyr Asn Ser Val Leu Pro Thr Gly
                405                 410                 415

Gly Arg Pro Leu Phe Leu Gln Val Gly Ala Asn Tyr Thr Phe Thr Gln
            420                 425                 430

Ile Ala Ala Asp Arg Val Ala Ala Ala Asp Gly His Tyr Asp Val Leu
        435                 440                 445

Phe Ile Gly Thr Asp Val Gly Thr Val Leu Lys Val Ile Ser Val Pro
    450                 455                 460

Lys Gly Ser Arg Pro Ser Ala Glu Gly Leu Leu Leu Glu Glu Leu His
465                 470                 475                 480
```

-continued

```
Val Phe Glu Asp Ser Ala Ala Val Thr Ser Met Gln Ile Ser Ser Lys
                485                 490                 495

Arg His Gln Leu Tyr Val Ala Ser Arg Ser Ala Val Ala Gln Ile Ala
            500                 505                 510

Leu His Arg Cys Ala Ala His Gly Arg Val Cys Thr Glu Cys Cys Leu
        515                 520                 525

Ala Arg Asp Pro Tyr Cys Ala Trp Asp Gly Val Ala Cys Thr Arg Phe
    530                 535                 540

Gln Pro Ser Ala Lys Arg Arg Phe Arg Arg Gln Asp Val Arg Asn Gly
545                 550                 555                 560

Asp Pro Ser Thr Leu Cys Ser Gly Asp Ser Ser Arg Pro Ala Leu Leu
                565                 570                 575

Glu His Lys Val Phe Gly Val Glu Gly Ser Ser Ala Phe Leu Glu Cys
            580                 585                 590

Glu Pro Arg Ser Leu Gln Ala Arg Val Glu Trp Thr Phe Gln Arg Ala
        595                 600                 605

Gly Val Thr Ala His Thr Gln Val Leu Ala Glu Glu Arg Thr Glu Arg
    610                 615                 620

Thr Ala Arg Gly Leu Leu Leu Arg Arg Leu Arg Arg Arg Asp Ser Gly
625                 630                 635                 640

Val Tyr Leu Cys Ala Ala Val Glu Gln Gly Phe Thr Gln Pro Leu Arg
                645                 650                 655

Arg Leu Ser Leu His Val Leu Ser Ala Thr Gln Ala Glu Arg Leu Ala
            660                 665                 670

Arg Ala Glu Glu Ala Ala Pro Ala Ala Pro Pro Gly Pro Lys Leu Trp
        675                 680                 685

Tyr Arg Asp Phe Leu Gln Leu Val Glu Pro Gly Gly Gly Gly Ser Ala
    690                 695                 700

Asn Ser Leu Arg Met Cys Arg Pro Gln Pro Ala Leu Gln Ser Leu Pro
705                 710                 715                 720

Leu Glu Ser Arg Arg Lys Gly Arg Asn Arg Arg Thr His Ala Pro Glu
                725                 730                 735

Pro Arg Ala Glu Arg Gly Pro Arg Ser Ala Thr His Trp
            740                 745


<210> SEQ ID NO 7
<211> LENGTH: 3746
<212> TYPE: DNA
<213> ORGANISM: Mus musculus
<220> FEATURE:
<223> OTHER INFORMATION: wildtype full-length Sema3B, transcript variant
      1, (>gi| 615276319|ref| NM_001042779.2|)
<220> FEATURE:
<221> NAME/KEY: CDS
<222> LOCATION: 400..2649
<223> OTHER INFORMATION: /transl_table=1

<400> SEQUENCE: 7

agtgaaaggc ccaaggctcc tggtggtggc ccctcctgcc acccctccac ctcagctctg      60

acatggccca ctgaagggaa gggcaagagg caaggagggg aggaactgat ctttccaaaa     120

gctcctggga cctgagcttg ctgtggagtg tacagtcatc ccttagctgt ggagggacag     180

caactgcttt gctctttgca cttggtgccc tctggaatga ccacaggatc tgactctcat     240

ctgtcggctc ttcgcccttt actgcctggg gaccttgtcc gcatcatcag tatccttgtc     300

tctgccccag gctggcatga aatcctgggg cagagtccag gactgctgaa ggctcctcca     360
```

-continued

```
cacacgcctg ctgaaccctg agcgccctga gctgccggc atg ggg cgg gct gag       414
                                           Met Gly Arg Ala Glu
                                           1               5

gcc gcc gcc atg atc cca ggc ctg gcc ctt ctc tgg gta gca ggg cta      462
Ala Ala Ala Met Ile Pro Gly Leu Ala Leu Leu Trp Val Ala Gly Leu
                10                  15                  20

ggg gat act gcc cct aac ctt ccc cgc ctt cgg ctc tcc ttt caa gaa      510
Gly Asp Thr Ala Pro Asn Leu Pro Arg Leu Arg Leu Ser Phe Gln Glu
            25                  30                  35

tta cag gcc cgg cat ggt gtc cga acc ttc agg ctg gag cgg acc tgc      558
Leu Gln Ala Arg His Gly Val Arg Thr Phe Arg Leu Glu Arg Thr Cys
        40                  45                  50

tgt tat gaa gcc ttg ctg gtg gat gag gag cgt gga cgc ctg ttt gtg      606
Cys Tyr Glu Ala Leu Leu Val Asp Glu Glu Arg Gly Arg Leu Phe Val
    55                  60                  65

ggt gct gag aac cac gtg gct tcc ctc agc ctg gac aac atc agc aag      654
Gly Ala Glu Asn His Val Ala Ser Leu Ser Leu Asp Asn Ile Ser Lys
70                  75                  80                  85

cga gcc aag aag ctg gcc tgg ccc gcc ccc gtg gaa tgg cgt gaa gaa      702
Arg Ala Lys Lys Leu Ala Trp Pro Ala Pro Val Glu Trp Arg Glu Glu
                90                  95                  100

tgc aac tgg gca ggg aag gac att ggt acc gag tgc atg aac ttc gtg      750
Cys Asn Trp Ala Gly Lys Asp Ile Gly Thr Glu Cys Met Asn Phe Val
            105                 110                 115

aag ctg ctg cac acc tac aac cac acc cac ttg ctg gcc tgt ggc aca      798
Lys Leu Leu His Thr Tyr Asn His Thr His Leu Leu Ala Cys Gly Thr
        120                 125                 130

ggg gct ttc cac cca acc tgt gcc ttt gtg gag gtg ggc cac cgg ctg      846
Gly Ala Phe His Pro Thr Cys Ala Phe Val Glu Val Gly His Arg Leu
    135                 140                 145

gag gaa ccc atg ctt caa ctg gac cgg agg aaa ctt gag gac ggc aag      894
Glu Glu Pro Met Leu Gln Leu Asp Arg Arg Lys Leu Glu Asp Gly Lys
150                 155                 160                 165

ggg aag act cct tat gac cca agg cat cgg gct gcc tcg gtg ctg gtg      942
Gly Lys Thr Pro Tyr Asp Pro Arg His Arg Ala Ala Ser Val Leu Val
                170                 175                 180

ggg gaa gaa ctg tat tct ggg gtg aca gca gac ctt atg ggc cgg gac      990
Gly Glu Glu Leu Tyr Ser Gly Val Thr Ala Asp Leu Met Gly Arg Asp
            185                 190                 195

ttt acc atc ttt cga agc ctt ggt cag aat ccg agt ctc cga aca gag     1038
Phe Thr Ile Phe Arg Ser Leu Gly Gln Asn Pro Ser Leu Arg Thr Glu
        200                 205                 210

ccc cat gat tcc cgc tgg ctc aat gaa ccc aag ttt gtc aag gtc ttt     1086
Pro His Asp Ser Arg Trp Leu Asn Glu Pro Lys Phe Val Lys Val Phe
    215                 220                 225

tgg atc cca gag agt gag aac cct gat gac gat aaa atc tat ttc ttc     1134
Trp Ile Pro Glu Ser Glu Asn Pro Asp Asp Asp Lys Ile Tyr Phe Phe
230                 235                 240                 245

ttc cgc gag tcc gct gtg gaa gca gca cca gca atg ggg cgc atg tct     1182
Phe Arg Glu Ser Ala Val Glu Ala Ala Pro Ala Met Gly Arg Met Ser
                250                 255                 260

gtg tct cgt gtt ggc cag atc tgc agg aat gac ctg ggt ggc cag cgg     1230
Val Ser Arg Val Gly Gln Ile Cys Arg Asn Asp Leu Gly Gly Gln Arg
            265                 270                 275

agc ttg gtc aac aaa tgg acc aca ttt ctg aag gcg cgg ctt gtg tgc     1278
Ser Leu Val Asn Lys Trp Thr Thr Phe Leu Lys Ala Arg Leu Val Cys
        280                 285                 290

tca gta cct gga gtt gag ggt gac acc cac ttt gac caa ctt cag gat     1326
Ser Val Pro Gly Val Glu Gly Asp Thr His Phe Asp Gln Leu Gln Asp
    295                 300                 305
```

-continued

```
gtt ttc ctt ctg tcc tcc cga gac cgc cag aca cct ctt ctc tat gct     1374
Val Phe Leu Leu Ser Ser Arg Asp Arg Gln Thr Pro Leu Leu Tyr Ala
310                 315                 320                 325

gtc ttc tcc acc tcc agt ggt gtc ttc cag ggc tct gct gtg tgc gtg     1422
Val Phe Ser Thr Ser Ser Gly Val Phe Gln Gly Ser Ala Val Cys Val
                330                 335                 340

tac agc atg aac gat gtg cgc cga gcc ttc ttg gga cct ttt gct cac     1470
Tyr Ser Met Asn Asp Val Arg Arg Ala Phe Leu Gly Pro Phe Ala His
            345                 350                 355

aaa gag ggg cct aca cac cag tgg gtg tcc tac cag ggt cgt gtc ccc     1518
Lys Glu Gly Pro Thr His Gln Trp Val Ser Tyr Gln Gly Arg Val Pro
        360                 365                 370

tac cca aga cct ggc atg tgc ccc agc aag acc ttt ggc acc ttc agc     1566
Tyr Pro Arg Pro Gly Met Cys Pro Ser Lys Thr Phe Gly Thr Phe Ser
    375                 380                 385

tcc acc aag gac ttc cca gat gac gtt atc cag ttt gct cgg aac cac     1614
Ser Thr Lys Asp Phe Pro Asp Asp Val Ile Gln Phe Ala Arg Asn His
390                 395                 400                 405

cct ctc atg tac aac cca gtc ctg ccc atg ggg ggg cgc cct ctc ttc     1662
Pro Leu Met Tyr Asn Pro Val Leu Pro Met Gly Gly Arg Pro Leu Phe
                410                 415                 420

cta caa gtg gga gct ggg tac acc ttc acc caa atc gcc gca gac cga     1710
Leu Gln Val Gly Ala Gly Tyr Thr Phe Thr Gln Ile Ala Ala Asp Arg
            425                 430                 435

gta gca gct gcc gat gga cac tac gat gtt ctc ttc att ggt aca gat     1758
Val Ala Ala Ala Asp Gly His Tyr Asp Val Leu Phe Ile Gly Thr Asp
        440                 445                 450

gtg ggc aca gtg ctg aaa gtg atc tca gtc ccc aaa ggc agc cga cct     1806
Val Gly Thr Val Leu Lys Val Ile Ser Val Pro Lys Gly Ser Arg Pro
    455                 460                 465

aat tct gaa gga ctt ctc ctg gaa gag ctg cag gtg ttc gag gac tct     1854
Asn Ser Glu Gly Leu Leu Leu Glu Glu Leu Gln Val Phe Glu Asp Ser
470                 475                 480                 485

gcc gct atc acc agc atg caa atc tcc tct aaa agg caa caa ctc tac     1902
Ala Ala Ile Thr Ser Met Gln Ile Ser Ser Lys Arg Gln Gln Leu Tyr
                490                 495                 500

ata gca tcg cgc agc gca gtg gcc cag att gct ttg cat cgc tgc act     1950
Ile Ala Ser Arg Ser Ala Val Ala Gln Ile Ala Leu His Arg Cys Thr
            505                 510                 515

gcc cta ggc cgc gcc tgc gca gaa tgc tgc ttg gcc cgt gat cct tac     1998
Ala Leu Gly Arg Ala Cys Ala Glu Cys Cys Leu Ala Arg Asp Pro Tyr
        520                 525                 530

tgc gcc tgg gat gga tca gct tgc aca cgc ttc cag cct acg gcc aag     2046
Cys Ala Trp Asp Gly Ser Ala Cys Thr Arg Phe Gln Pro Thr Ala Lys
    535                 540                 545

aga cgg ttc cgg agg caa gac ata agg aat ggc gac ccc agc acc cta     2094
Arg Arg Phe Arg Arg Gln Asp Ile Arg Asn Gly Asp Pro Ser Thr Leu
550                 555                 560                 565

tgc tct gga gac tct tct cac tct gtg ctg ctg gag aag aag gtg ttg     2142
Cys Ser Gly Asp Ser Ser His Ser Val Leu Leu Glu Lys Lys Val Leu
                570                 575                 580

ggt gtg gag agc ggc agc gcg ttt ctg gag tgt gag ccc cgc tcg ctc     2190
Gly Val Glu Ser Gly Ser Ala Phe Leu Glu Cys Glu Pro Arg Ser Leu
            585                 590                 595

cag gcg cat gtg cag tgg acc ttc caa ggt gca ggg gag gca gct cac     2238
Gln Ala His Val Gln Trp Thr Phe Gln Gly Ala Gly Glu Ala Ala His
        600                 605                 610

acc cag gtg ctg gct gag gag aga gta gag cgc act gcg cgg ggg ctg     2286
Thr Gln Val Leu Ala Glu Glu Arg Val Glu Arg Thr Ala Arg Gly Leu
```

```
    615                 620                 625

ctg ttg cgg ggg ctg cgg cgc cag gac tct ggc gtg tat ctt tgc gtc     2334
Leu Leu Arg Gly Leu Arg Arg Gln Asp Ser Gly Val Tyr Leu Cys Val
630                 635                 640                 645

gcg gtt gaa caa ggc ttt tca caa cca ctg cgt cgc ctg gtg ctg cat     2382
Ala Val Glu Gln Gly Phe Ser Gln Pro Leu Arg Arg Leu Val Leu His
                650                 655                 660

gtg ttg agt gcg gcg cag gct gaa cga ctg gca cgg gca gag gaa gca     2430
Val Leu Ser Ala Ala Gln Ala Glu Arg Leu Ala Arg Ala Glu Glu Ala
            665                 670                 675

gcc gct cct gca cct cct ggc cct aaa ctc tgg tac cgg gac ttt ctg     2478
Ala Ala Pro Ala Pro Pro Gly Pro Lys Leu Trp Tyr Arg Asp Phe Leu
        680                 685                 690

cag ttg gtg gag cca ggc ggt ggc gga ggt gca aac tcc ctg cga atg     2526
Gln Leu Val Glu Pro Gly Gly Gly Gly Gly Ala Asn Ser Leu Arg Met
    695                 700                 705

tgc cgc ccg cag ccc ggg cac cac tct gtg gca gca gat tca cgt cgt     2574
Cys Arg Pro Gln Pro Gly His His Ser Val Ala Ala Asp Ser Arg Arg
710                 715                 720                 725

aag ggt cgc aac aga cgg atg cat gtc tct gag ctc cgt gct gag cgt     2622
Lys Gly Arg Asn Arg Arg Met His Val Ser Glu Leu Arg Ala Glu Arg
                730                 735                 740

gga cca cgt agt gca gct cac tgg tga ctcggctgtc cccacaatgg           2669
Gly Pro Arg Ser Ala Ala His Trp
            745

gacgaggctg aatatgacac tccaaagagg ggcagacaga tgccaggaag acaaatgagt   2729

tatggctggg ccacactgag gtccttgggc caacagagac acctaaccct tacataggcc   2789

ctggccaaag ggtagcttat ttattaacaa gataacccgt ggatgtagcc tcaaagagtg   2849

gcctaagctc aattcaggat ctaaccagga gggaggggac agagacgtgg ggttccagag   2909

tggaccagga ccagagagtt gtcttgggtg gcagccctgg ggaaagaatt ctctttcttg   2969

ggcagcaagc agcaagctgt gaacagatta gaccgttggg tatggggtga ggcaggccaa   3029

ctgtactaaa gtaacgcaat aaacacatta tcagctgaca ttggaatggc cccagcagac   3089

aacaggtagt cctagacctt gctgggggct cttgggtatc gccctagggg tctcaagacc   3149

tgcattttcc tcatccaaga atgctaaagt gaagattaaa cgtgttagta gacgactacg   3209

ctggttccag tgagcctctg ggtactggc aatacacagt gcattagtgg caggaccaag    3269

ctctctgaag taaaaccaat actggctgtt gtgggcaagg atgtattaat tcactgaacg   3329

ggtggtgttt gagctgaata agaaggagcc aatcaccaat gtctggtgac agaacattcc   3389

gggatagaag aaccagggca acaacgtcgt ggagcagggg acagaccctc caagtctgcg   3449

gaacaaccag gaggctgata tggtgttatg gcactatgga ctcctgatgg tttggaaggt   3509

agatcccacc agccctgctt ttcaccgttg agaaacagaa cagagtccac ccagactaag   3569

gcctgcaagc tggaccagca cccttcaaga gagccacgtg cctctctctc cgtggcctgt   3629

caagcccttg tgaagaggag agggaggacc caaaacctct taagtgcttt agccatgctt   3689

cttcattttt attctcagta cagttggcca ggaacctttg ttcctgtttt acagatg      3746


<210> SEQ ID NO 8
<211> LENGTH: 749
<212> TYPE: PRT
<213> ORGANISM: Mus musculus
<220> FEATURE:
<223> OTHER INFORMATION: wildtype full-length Sema3B, transcript variant
      1, (>gi| 615276319|ref| NM_001042779.2|)
```

<400> SEQUENCE: 8

Met Gly Arg Ala Glu Ala Ala Ala Met Ile Pro Gly Leu Ala Leu Leu
1               5                   10                  15

Trp Val Ala Gly Leu Gly Asp Thr Ala Pro Asn Leu Pro Arg Leu Arg
            20                  25                  30

Leu Ser Phe Gln Glu Leu Gln Ala Arg His Gly Val Arg Thr Phe Arg
        35                  40                  45

Leu Glu Arg Thr Cys Cys Tyr Glu Ala Leu Leu Val Asp Glu Glu Arg
    50                  55                  60

Gly Arg Leu Phe Val Gly Ala Glu Asn His Val Ala Ser Leu Ser Leu
65                  70                  75                  80

Asp Asn Ile Ser Lys Arg Ala Lys Lys Leu Ala Trp Pro Ala Pro Val
                85                  90                  95

Glu Trp Arg Glu Glu Cys Asn Trp Ala Gly Lys Asp Ile Gly Thr Glu
            100                 105                 110

Cys Met Asn Phe Val Lys Leu Leu His Thr Tyr Asn His Thr His Leu
        115                 120                 125

Leu Ala Cys Gly Thr Gly Ala Phe His Pro Thr Cys Ala Phe Val Glu
    130                 135                 140

Val Gly His Arg Leu Glu Glu Pro Met Leu Gln Leu Asp Arg Arg Lys
145                 150                 155                 160

Leu Glu Asp Gly Lys Gly Lys Thr Pro Tyr Asp Pro Arg His Arg Ala
                165                 170                 175

Ala Ser Val Leu Val Gly Glu Glu Leu Tyr Ser Gly Val Thr Ala Asp
            180                 185                 190

Leu Met Gly Arg Asp Phe Thr Ile Phe Arg Ser Leu Gly Gln Asn Pro
        195                 200                 205

Ser Leu Arg Thr Glu Pro His Asp Ser Arg Trp Leu Asn Glu Pro Lys
    210                 215                 220

Phe Val Lys Val Phe Trp Ile Pro Glu Ser Glu Asn Pro Asp Asp Asp
225                 230                 235                 240

Lys Ile Tyr Phe Phe Phe Arg Glu Ser Ala Val Glu Ala Ala Pro Ala
                245                 250                 255

Met Gly Arg Met Ser Val Ser Arg Val Gly Gln Ile Cys Arg Asn Asp
            260                 265                 270

Leu Gly Gly Gln Arg Ser Leu Val Asn Lys Trp Thr Thr Phe Leu Lys
        275                 280                 285

Ala Arg Leu Val Cys Ser Val Pro Gly Val Glu Gly Asp Thr His Phe
    290                 295                 300

Asp Gln Leu Gln Asp Val Phe Leu Leu Ser Ser Arg Asp Arg Gln Thr
305                 310                 315                 320

Pro Leu Leu Tyr Ala Val Phe Ser Thr Ser Ser Gly Val Phe Gln Gly
                325                 330                 335

Ser Ala Val Cys Val Tyr Ser Met Asn Asp Val Arg Arg Ala Phe Leu
            340                 345                 350

Gly Pro Phe Ala His Lys Glu Gly Pro Thr His Gln Trp Val Ser Tyr
        355                 360                 365

Gln Gly Arg Val Pro Tyr Pro Arg Pro Gly Met Cys Pro Ser Lys Thr
    370                 375                 380

Phe Gly Thr Phe Ser Ser Thr Lys Asp Phe Pro Asp Asp Val Ile Gln
385                 390                 395                 400

Phe Ala Arg Asn His Pro Leu Met Tyr Asn Pro Val Leu Pro Met Gly
                405                 410                 415

```
Gly Arg Pro Leu Phe Leu Gln Val Gly Ala Gly Tyr Thr Phe Thr Gln
            420                 425                 430

Ile Ala Ala Asp Arg Val Ala Ala Ala Asp Gly His Tyr Asp Val Leu
        435                 440                 445

Phe Ile Gly Thr Asp Val Gly Thr Val Leu Lys Val Ile Ser Val Pro
    450                 455                 460

Lys Gly Ser Arg Pro Asn Ser Glu Gly Leu Leu Leu Glu Glu Leu Gln
465                 470                 475                 480

Val Phe Glu Asp Ser Ala Ala Ile Thr Ser Met Gln Ile Ser Ser Lys
                485                 490                 495

Arg Gln Gln Leu Tyr Ile Ala Ser Arg Ser Ala Val Ala Gln Ile Ala
            500                 505                 510

Leu His Arg Cys Thr Ala Leu Gly Arg Ala Cys Ala Glu Cys Cys Leu
        515                 520                 525

Ala Arg Asp Pro Tyr Cys Ala Trp Asp Gly Ser Ala Cys Thr Arg Phe
    530                 535                 540

Gln Pro Thr Ala Lys Arg Arg Phe Arg Arg Gln Asp Ile Arg Asn Gly
545                 550                 555                 560

Asp Pro Ser Thr Leu Cys Ser Gly Asp Ser Ser His Ser Val Leu Leu
                565                 570                 575

Glu Lys Lys Val Leu Gly Val Glu Ser Gly Ser Ala Phe Leu Glu Cys
            580                 585                 590

Glu Pro Arg Ser Leu Gln Ala His Val Gln Trp Thr Phe Gln Gly Ala
        595                 600                 605

Gly Glu Ala Ala His Thr Gln Val Leu Ala Glu Glu Arg Val Glu Arg
    610                 615                 620

Thr Ala Arg Gly Leu Leu Leu Arg Gly Leu Arg Arg Gln Asp Ser Gly
625                 630                 635                 640

Val Tyr Leu Cys Val Ala Val Glu Gln Gly Phe Ser Gln Pro Leu Arg
                645                 650                 655

Arg Leu Val Leu His Val Leu Ser Ala Ala Gln Ala Glu Arg Leu Ala
            660                 665                 670

Arg Ala Glu Glu Ala Ala Ala Pro Ala Pro Pro Gly Pro Lys Leu Trp
        675                 680                 685

Tyr Arg Asp Phe Leu Gln Leu Val Glu Pro Gly Gly Gly Gly Gly Ala
    690                 695                 700

Asn Ser Leu Arg Met Cys Arg Pro Gln Pro Gly His His Ser Val Ala
705                 710                 715                 720

Ala Asp Ser Arg Arg Lys Gly Arg Asn Arg Arg Met His Val Ser Glu
                725                 730                 735

Leu Arg Ala Glu Arg Gly Pro Arg Ser Ala Ala His Trp
            740                 745
```

<210> SEQ ID NO 9
<211> LENGTH: 5189
<212> TYPE: DNA
<213> ORGANISM: Homo sapiens
<220> FEATURE:
<223> OTHER INFORMATION: wildtype full-length SEMA3C
(>gi| 335057525|ref| NM_006379.3|)
<220> FEATURE:
<221> NAME/KEY: CDS
<222> LOCATION: 563..2818
<223> OTHER INFORMATION: /transl_table=1

<400> SEQUENCE: 9

-continued

```
ggactgcgaa aggagcaggg ttgcggagct agggctccag cctgcggccg cgcattcttg     60

cgtctggcca gccgcgagct ctaagggtcg gccccgcccg gtccgccccc gcggctccct    120

gccaggctct cgcgggcgcg ctcggggtgg ggcctcgcgg ctggcggaga tgcggccggg    180

gctgcgcggt ggtgatgcga gcctgctggg cggcgcgccg gggcagccgg agccgcgcgc    240

cgcggcgctg taatcggaca ccaagagcgc tcgcccccgg cctccggcca ctttccattc    300

actccgaggt gcttgattga gcgacgcgga gaagagctcc gggtgccgcg gcactgcagc    360

gctgagattc ctttacaaag aaactcagag gaccgggaag aaagaatttc acctttgcga    420

cgtgctagaa aataaggtcg tctgggaaaa ggactggaga cacaagcgca tccaaccccg    480

gtagcaaact gatgactttt ccgtgctgat ttctttcaac ctcggtattt tcccttggat    540

attaacttgc atatctgaag aa atg gca ttc cgg aca att tgc gtg ttg gtt     592
                         Met Ala Phe Arg Thr Ile Cys Val Leu Val
                         1               5                   10

gga gta ttt att tgt tct atc tgt gtg aaa gga tct tcc cag ccc caa      640
Gly Val Phe Ile Cys Ser Ile Cys Val Lys Gly Ser Ser Gln Pro Gln
                15                  20                  25

gca aga gtt tat tta aca ttt gat gaa ctt cga gaa acc aag acc tct      688
Ala Arg Val Tyr Leu Thr Phe Asp Glu Leu Arg Glu Thr Lys Thr Ser
            30                  35                  40

gaa tac ttc agc ctt tcc cac cat cct tta gac tac agg att tta tta      736
Glu Tyr Phe Ser Leu Ser His His Pro Leu Asp Tyr Arg Ile Leu Leu
        45                  50                  55

atg gat gaa gat cag gac cgg ata tat gtg gga agc aaa gat cac att      784
Met Asp Glu Asp Gln Asp Arg Ile Tyr Val Gly Ser Lys Asp His Ile
    60                  65                  70

ctt tcc ctg aat att aac aat ata agt caa gaa gct ttg agt gtt ttc      832
Leu Ser Leu Asn Ile Asn Asn Ile Ser Gln Glu Ala Leu Ser Val Phe
75                  80                  85                  90

tgg cca gca tct aca atc aaa gtt gaa gaa tgc aaa atg gct ggc aaa      880
Trp Pro Ala Ser Thr Ile Lys Val Glu Glu Cys Lys Met Ala Gly Lys
                95                  100                 105

gat ccc aca cac ggc tgt ggg aac ttt gtc cgt gta att cag act ttc      928
Asp Pro Thr His Gly Cys Gly Asn Phe Val Arg Val Ile Gln Thr Phe
            110                 115                 120

aat cgc aca cat ttg tat gtc tgt ggg agt ggc gct ttc agt cct gtc      976
Asn Arg Thr His Leu Tyr Val Cys Gly Ser Gly Ala Phe Ser Pro Val
        125                 130                 135

tgt act tac ttg aac aga ggg agg aga tca gag gac caa gtt ttc atg     1024
Cys Thr Tyr Leu Asn Arg Gly Arg Arg Ser Glu Asp Gln Val Phe Met
    140                 145                 150

att gac tcc aag tgt gaa tct gga aaa gga cgc tgc tct ttc aac ccc     1072
Ile Asp Ser Lys Cys Glu Ser Gly Lys Gly Arg Cys Ser Phe Asn Pro
155                 160                 165                 170

aac gtg aac acg gtg tct gtt atg atc aat gag gag ctt ttc tct gga     1120
Asn Val Asn Thr Val Ser Val Met Ile Asn Glu Glu Leu Phe Ser Gly
                175                 180                 185

atg tat ata gat ttc atg ggg aca gat gct gct att ttt cga agt tta     1168
Met Tyr Ile Asp Phe Met Gly Thr Asp Ala Ala Ile Phe Arg Ser Leu
            190                 195                 200

acc aag agg aat gcg gtc aga act gat caa cat aat tcc aaa tgg cta     1216
Thr Lys Arg Asn Ala Val Arg Thr Asp Gln His Asn Ser Lys Trp Leu
        205                 210                 215

agt gaa cct atg ttt gta gat gca cat gtc atc cca gat ggt act gat     1264
Ser Glu Pro Met Phe Val Asp Ala His Val Ile Pro Asp Gly Thr Asp
    220                 225                 230

cca aat gat gct aag gtg tac ttc ttc ttc aaa gaa aaa ctg act gac     1312
```

-continued

```
Pro Asn Asp Ala Lys Val Tyr Phe Phe Phe Lys Glu Lys Leu Thr Asp
235                 240                 245                 250

aat aac agg agc acg aaa cag att cat tcc atg att gct cga ata tgt      1360
Asn Asn Arg Ser Thr Lys Gln Ile His Ser Met Ile Ala Arg Ile Cys
                255                 260                 265

cct aat gac act ggt gga ctg cgt agc ctt gtc aac aag tgg acc act      1408
Pro Asn Asp Thr Gly Gly Leu Arg Ser Leu Val Asn Lys Trp Thr Thr
            270                 275                 280

ttc tta aag gcg agg ctg gtg tgc tcg gta aca gat gaa gac ggc cca      1456
Phe Leu Lys Ala Arg Leu Val Cys Ser Val Thr Asp Glu Asp Gly Pro
        285                 290                 295

gaa aca cac ttt gat gaa tta gag gat gtg ttt ctg ctg gaa act gat      1504
Glu Thr His Phe Asp Glu Leu Glu Asp Val Phe Leu Leu Glu Thr Asp
    300                 305                 310

aac ccg agg aca aca cta gtg tat ggc att ttt aca aca tca agc tca      1552
Asn Pro Arg Thr Thr Leu Val Tyr Gly Ile Phe Thr Thr Ser Ser Ser
315                 320                 325                 330

gtt ttc aaa gga tca gcc gtg tgt gtg tat cat tta tct gat ata cag      1600
Val Phe Lys Gly Ser Ala Val Cys Val Tyr His Leu Ser Asp Ile Gln
                335                 340                 345

act gtg ttt aat ggg cct ttt gcc cac aaa gaa ggg ccc aat cat cag      1648
Thr Val Phe Asn Gly Pro Phe Ala His Lys Glu Gly Pro Asn His Gln
            350                 355                 360

ctg att tcc tat cag ggc aga att cca tat cct cgc cct gga act tgt      1696
Leu Ile Ser Tyr Gln Gly Arg Ile Pro Tyr Pro Arg Pro Gly Thr Cys
        365                 370                 375

cca gga gga gca ttt aca ccc aat atg cga acc acc aag gag ttc cca      1744
Pro Gly Gly Ala Phe Thr Pro Asn Met Arg Thr Thr Lys Glu Phe Pro
    380                 385                 390

gat gat gtt gtc act ttt att cgg aac cat cct ctc atg tac aat tcc      1792
Asp Asp Val Val Thr Phe Ile Arg Asn His Pro Leu Met Tyr Asn Ser
395                 400                 405                 410

atc tac cca atc cac aaa agg cct ttg att gtt cgt att ggc act gac      1840
Ile Tyr Pro Ile His Lys Arg Pro Leu Ile Val Arg Ile Gly Thr Asp
                415                 420                 425

tac aag tat aca aag ata gct gtg gat cga gtg aac gct gct gat ggg      1888
Tyr Lys Tyr Thr Lys Ile Ala Val Asp Arg Val Asn Ala Ala Asp Gly
            430                 435                 440

aga tac cat gtc ctg ttt ctc gga aca gat cgg ggt act gtg caa aaa      1936
Arg Tyr His Val Leu Phe Leu Gly Thr Asp Arg Gly Thr Val Gln Lys
        445                 450                 455

gtg gtt gtt ctt cct act aac aac tct gtc agt ggc gag ctc att ctg      1984
Val Val Val Leu Pro Thr Asn Asn Ser Val Ser Gly Glu Leu Ile Leu
    460                 465                 470

gag gag ctg gaa gtc ttt aag aat cat gct cct ata aca aca atg aaa      2032
Glu Glu Leu Glu Val Phe Lys Asn His Ala Pro Ile Thr Thr Met Lys
475                 480                 485                 490

att tca tct aaa aag caa cag ttg tat gtg agt tcc aat gaa ggg gtt      2080
Ile Ser Ser Lys Lys Gln Gln Leu Tyr Val Ser Ser Asn Glu Gly Val
                495                 500                 505

tcc cag gta tct ctg cac cgc tgc cac atc tat ggt aca gcc tgt gct      2128
Ser Gln Val Ser Leu His Arg Cys His Ile Tyr Gly Thr Ala Cys Ala
            510                 515                 520

gac tgc tgc ctg gcg cgg gac cct tat tgc gcc tgg gat ggc cat tcc      2176
Asp Cys Cys Leu Ala Arg Asp Pro Tyr Cys Ala Trp Asp Gly His Ser
        525                 530                 535

tgt tcc aga ttc tac cca act ggg aaa cgg agg agc cga aga caa gat      2224
Cys Ser Arg Phe Tyr Pro Thr Gly Lys Arg Arg Ser Arg Arg Gln Asp
    540                 545                 550
```

-continued

```
gtg aga cat gga aac cca ctg act caa tgc aga gga ttt aat cta aaa     2272
Val Arg His Gly Asn Pro Leu Thr Gln Cys Arg Gly Phe Asn Leu Lys
555                 560                 565                 570

gca tac aga aat gca gct gaa att gtc cag tat gga gta aaa aat aac     2320
Ala Tyr Arg Asn Ala Ala Glu Ile Val Gln Tyr Gly Val Lys Asn Asn
                575                 580                 585

acc act ttt ctg gag tgt gcc ccc aag tct ccg cag gca tct atc aag     2368
Thr Thr Phe Leu Glu Cys Ala Pro Lys Ser Pro Gln Ala Ser Ile Lys
            590                 595                 600

tgg ctg tta cag aaa gac aaa gac agg agg aaa gag gtt aag ctg aat     2416
Trp Leu Leu Gln Lys Asp Lys Asp Arg Arg Lys Glu Val Lys Leu Asn
        605                 610                 615

gaa cga ata ata gcc act tca cag gga ctc ctg atc cgc tct gtt cag     2464
Glu Arg Ile Ile Ala Thr Ser Gln Gly Leu Leu Ile Arg Ser Val Gln
    620                 625                 630

ggt tct gac caa gga ctt tat cac tgc att gct aca gaa aat agt ttc     2512
Gly Ser Asp Gln Gly Leu Tyr His Cys Ile Ala Thr Glu Asn Ser Phe
635                 640                 645                 650

aag cag acc ata gcc aag atc aac ttc aaa gtt tta gat tca gaa atg     2560
Lys Gln Thr Ile Ala Lys Ile Asn Phe Lys Val Leu Asp Ser Glu Met
                655                 660                 665

gtg gct gtt gtg acg gac aaa tgg tcc cca tgg acc tgg gcc agc tct     2608
Val Ala Val Val Thr Asp Lys Trp Ser Pro Trp Thr Trp Ala Ser Ser
            670                 675                 680

gtg agg gct tta ccc ttc cac ccg aag gac atc atg ggg gca ttc agc     2656
Val Arg Ala Leu Pro Phe His Pro Lys Asp Ile Met Gly Ala Phe Ser
        685                 690                 695

cac tca gaa atg cag atg att aac caa tat tgc aaa gac act cgg cag     2704
His Ser Glu Met Gln Met Ile Asn Gln Tyr Cys Lys Asp Thr Arg Gln
    700                 705                 710

caa cat cag cag gga gat gaa tca cag aaa atg aga ggg gac tat ggc     2752
Gln His Gln Gln Gly Asp Glu Ser Gln Lys Met Arg Gly Asp Tyr Gly
715                 720                 725                 730

aag tta aag gcc ctc atc aat agt cgg aaa agt aga aac agg agg aat     2800
Lys Leu Lys Ala Leu Ile Asn Ser Arg Lys Ser Arg Asn Arg Arg Asn
                735                 740                 745

cag ttg cca gag tca taa tattttctta tgtgggtctt atgcttccat            2848
Gln Leu Pro Glu Ser
            750

taacaaatgc tctgtcttca atgatcaaat tttgagcaaa gaaacttgtg ctttaccaag   2908

gggaattact gaaaaaggtg attactcctg aagtgagttt tacacgaact gaaatgagca   2968

tgcattttct tgtatgatag tgactagcac tagacatgtc atggtcctca tggtgcatat   3028

aaatatattt aacttaaccc agattttatt tatatcttta ttcacctttt cttcaaaatc   3088

gatatggtgg ctgcaaaact agaattgttg catccctcaa ttgaatgagg gccatatccc   3148

tgtggtattc ctttcctgct ttggggcttt agaattctaa ttgtcagtga ttttgtatat   3208

gaaaacaagt tccaaatcca cagcttttac gtagtaaaag tcataaatgc atatgacaga   3268

atggctatca aaagaaatag aaaaggaaga cagcatttaa agttgtataa aaacatgagt   3328

tattcataaa gagaaaatga tgagttttta tggttccaat gaaatatgtt ggggtttttt   3388

taagattgta aaaataatca gttactggta tctgtcactg acctttgttt ccttattcag   3448

gaagataaaa atcagtaacc taccccatga agatatttgg tgggagttat atcagtgaag   3508

cagtttggtt tatattctta tgttatcacc ttccaaacaa aagcacttac ttttttttgga  3568

agttatttat tttagactca aagaatataa tctggcacta ctcagttatt actgtttgtt   3628

ctcttattcc ctagtctgtg tggcaaatta aacaatataa gaaggaaaaa tttgaagtat   3688
```

```
tagacttcta aataaggtgt gaaatcatca aaaagaaaaa tcaaagtaga aactactaat   3748

tttttaagag gaatttataa caaatatggc tagttttcaa cttcagtact caaattcaat   3808

gattcttcct tttattaaaa ccagtctcag atatcatact gatttttaag tcaacactat   3868

atattttatg atcttttcag tgtgatggca aggtgcttgt tatgtctaga aagtaagaaa   3928

acaatatgag gagacattct gtctttcaaa aggtaatggt acatacgttc actggtctct   3988

aagtgtaaaa gtagtaaatt ttgtgatgaa taaaataatt atctcctaat tgtatgttag   4048

aataatttta ttagaataat ttcatactga aattattttc tccaaataaa aattagatgg   4108

aaaaatgtga aaaaaattat tcatgctctc atatatattt taaaaacact actttttgctt   4168

ttttatttac cttttaagac attttcatgc ttccaggtaa aaacagatat tgtaccatgt   4228

acctaatcca aatatcatat aaacatttta tttatagtta ataatctatg atgaaggtaa   4288

ttaaagtaga ttatggcctt tttaagtatt gcagtctaaa acttcaaaaa ctaaaatcat   4348

tgtcaaaatt aatatgatta ttaatcagaa tatcagaata tgattcacta tttaaactat   4408

gataaattat gataatatat gaggaggcct cgctatagca aaaatagtta aaatgctgac   4468

ataacaccaa acttcatttt ttaaaaaatc tgttgttcca aatgtgtata attttaaagt   4528

aatttctaaa gcagtttatt ataatggttt gcctgcttaa aaggtataat taaacttctt   4588

ttctcttcta cattgacaca cagaaatgtg tcaatgtaaa gccaaaacca tcttctgtgt   4648

ttatggccaa tctattctca aagttaaaag taaaattgtt tcagagtcac agttcccttt   4708

atttcacata agcccaaact gatagacagt aacggtgttt agttttatac tatatttgtg   4768

ctatttaatt ctttctattt tcacaattat taaattgtgt acactttcat tacttttaaa   4828

aatgtagaaa ttcttcatga acataactct gctgaatgta aaagaaaatt ttttttcaaa   4888

aatgctgtta atgtatacta ctggtggttg attggtttta ttttatgtag cttgacaatt   4948

cagtgactta atatctattc catttgtatt gtacataaaa ttttctagaa atacactttt   5008

ttccaaagtg taagtttgtg aatagatttt agcatgatga aactgtcata atggtgaatg   5068

ttcaatctgt gtaagaaaac aaactaaatg tagttgtcac actaaaattt aattggatat   5128

tgatgaaatc attggcctgg caaaataaaa catgttgaat tccccaaaaa aaaaaaaaaa   5188

a                                                                   5189
```

```
<210> SEQ ID NO 10
<211> LENGTH: 751
<212> TYPE: PRT
<213> ORGANISM: Homo sapiens
<220> FEATURE:
<223> OTHER INFORMATION: wildtype full-length SEMA3C
      (>gi| 335057525|ref| NM_006379.3|)

<400> SEQUENCE: 10

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80
```

-continued

```
Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
        355                 360                 365

Arg Ile Pro Tyr Pro Arg Pro Gly Thr Cys Pro Gly Gly Ala Phe Thr
    370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445

Leu Gly Thr Asp Arg Gly Thr Val Gln Lys Val Val Val Leu Pro Thr
    450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
```

```
            500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
    530                 535                 540

Thr Gly Lys Arg Arg Ser Arg Arg Gln Asp Val Arg His Gly Asn Pro
545                 550                 555                 560

Leu Thr Gln Cys Arg Gly Phe Asn Leu Lys Ala Tyr Arg Asn Ala Ala
                565                 570                 575

Glu Ile Val Gln Tyr Gly Val Lys Asn Asn Thr Thr Phe Leu Glu Cys
            580                 585                 590

Ala Pro Lys Ser Pro Gln Ala Ser Ile Lys Trp Leu Leu Gln Lys Asp
        595                 600                 605

Lys Asp Arg Arg Lys Glu Val Lys Leu Asn Glu Arg Ile Ile Ala Thr
    610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Val Thr Asp
            660                 665                 670

Lys Trp Ser Pro Trp Thr Trp Ala Ser Ser Val Arg Ala Leu Pro Phe
        675                 680                 685

His Pro Lys Asp Ile Met Gly Ala Phe Ser His Ser Glu Met Gln Met
    690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser Arg Lys Ser Arg Asn Arg Arg Asn Gln Leu Pro Glu Ser
            740                 745                 750


<210> SEQ ID NO 11
<211> LENGTH: 4956
<212> TYPE: DNA
<213> ORGANISM: Mus musculus
<220> FEATURE:
<223> OTHER INFORMATION: wildtype full-length Sema3C
      (>gi| 118130842|ref| NM_013657.5|)
<220> FEATURE:
<221> NAME/KEY: CDS
<222> LOCATION: 189..2444
<223> OTHER INFORMATION: /transl_table=1

<400> SEQUENCE: 11

ctgctacaaa gaaactcagc accggccggc aggaatccca ccctccggac tcactaagtc      60

tttaaaggtc ttctggggaa aggacctagg ggactggaaa tccaagcccg gagcaagtgg     120

ctgacttctc ctggatcttt tcccacctcg gtattttccc ttggatatta attcccaaat     180

cagaagaa atg gca ttc cgg gcg att tgt gtg ttg gtt gga gta ttt att      230
         Met Ala Phe Arg Ala Ile Cys Val Leu Val Gly Val Phe Ile
         1               5                   10

tgt tcc att tgt gta cga gga tct tcc cag ccc caa gca aga gtt tat       278
Cys Ser Ile Cys Val Arg Gly Ser Ser Gln Pro Gln Ala Arg Val Tyr
15                  20                  25                  30

tta aca ttt gat gag ctt cga gaa acc aaa acc tct gag tac ttt agt       326
Leu Thr Phe Asp Glu Leu Arg Glu Thr Lys Thr Ser Glu Tyr Phe Ser
                35                  40                  45
```

```
ctg tcc cac cag cag tta gac tac aga ata ttg ctg atg gat gaa gat      374
Leu Ser His Gln Gln Leu Asp Tyr Arg Ile Leu Leu Met Asp Glu Asp
            50                  55                  60

caa gac cgg ata tat gtg ggg agc aaa gac cac atc ctg tct ttg aat      422
Gln Asp Arg Ile Tyr Val Gly Ser Lys Asp His Ile Leu Ser Leu Asn
        65                  70                  75

atc aac aat atc agt caa gaa cct ttg agt gtt ttc tgg cca gca tca      470
Ile Asn Asn Ile Ser Gln Glu Pro Leu Ser Val Phe Trp Pro Ala Ser
    80                  85                  90

aca atc aaa gtt gaa gag tgc aaa atg gct ggc aaa gat cct aca cat      518
Thr Ile Lys Val Glu Glu Cys Lys Met Ala Gly Lys Asp Pro Thr His
95                  100                 105                 110

ggc tgt gga aat ttc gtc cgg gtg att cag aca ttc aac cgt act cac      566
Gly Cys Gly Asn Phe Val Arg Val Ile Gln Thr Phe Asn Arg Thr His
                115                 120                 125

ctg tat gtc tgt ggg agt gga gcg ttc agc cca gtg tgc acc tac ctg      614
Leu Tyr Val Cys Gly Ser Gly Ala Phe Ser Pro Val Cys Thr Tyr Leu
            130                 135                 140

aac cgg gga agg agg tca gag gac cag gta ttc atg atc gac tct aag      662
Asn Arg Gly Arg Arg Ser Glu Asp Gln Val Phe Met Ile Asp Ser Lys
        145                 150                 155

tgt gaa tct ggc aaa gga cga tgc tct ttc aac ccg aat gtg aac act      710
Cys Glu Ser Gly Lys Gly Arg Cys Ser Phe Asn Pro Asn Val Asn Thr
    160                 165                 170

gtg tct gtt atg atc aat gag gaa ctc ttc tca gga atg tat ata gac      758
Val Ser Val Met Ile Asn Glu Glu Leu Phe Ser Gly Met Tyr Ile Asp
175                 180                 185                 190

ttc atg gga aca gat gct gct att ttc cga agt tta act aag agg aat      806
Phe Met Gly Thr Asp Ala Ala Ile Phe Arg Ser Leu Thr Lys Arg Asn
                195                 200                 205

gca gtt cga act gat caa cat aat tca aaa tgg ctg agt gaa ccc atg      854
Ala Val Arg Thr Asp Gln His Asn Ser Lys Trp Leu Ser Glu Pro Met
            210                 215                 220

ttt gtg gac gca cat gtg atc cca gat ggc act gat cca aat gat gct      902
Phe Val Asp Ala His Val Ile Pro Asp Gly Thr Asp Pro Asn Asp Ala
        225                 230                 235

aag gtc tat ttc ttc ttc aaa gaa aga ctg act gac aac aat agg agc      950
Lys Val Tyr Phe Phe Phe Lys Glu Arg Leu Thr Asp Asn Asn Arg Ser
    240                 245                 250

aca aaa cag att cat tcc atg att gca aga ata tgc cct aat gac act      998
Thr Lys Gln Ile His Ser Met Ile Ala Arg Ile Cys Pro Asn Asp Thr
255                 260                 265                 270

ggt gga caa cgt agt ctt gtc aac aag tgg acc aca ttc tta aag gca     1046
Gly Gly Gln Arg Ser Leu Val Asn Lys Trp Thr Thr Phe Leu Lys Ala
                275                 280                 285

aga ctt gta tgc tca gtc aca gat gaa gat ggc cca gag aca cat ttt     1094
Arg Leu Val Cys Ser Val Thr Asp Glu Asp Gly Pro Glu Thr His Phe
            290                 295                 300

gat gaa cta gag gat gtc ttt ctg ctg gaa act gac aat cca agg aca     1142
Asp Glu Leu Glu Asp Val Phe Leu Leu Glu Thr Asp Asn Pro Arg Thr
        305                 310                 315

aca ctc gtg tat ggc atc ttc acc aca tca agc tct gtt ttt aag gga     1190
Thr Leu Val Tyr Gly Ile Phe Thr Thr Ser Ser Ser Val Phe Lys Gly
    320                 325                 330

tcg gca gtg tgt gtg tat cat tta tct gat ata cag act gta ttc aat     1238
Ser Ala Val Cys Val Tyr His Leu Ser Asp Ile Gln Thr Val Phe Asn
335                 340                 345                 350

ggg ccc ttt gcc cac aag gaa ggg ccc aat cac cag ctg atc tcc tat     1286
Gly Pro Phe Ala His Lys Glu Gly Pro Asn His Gln Leu Ile Ser Tyr
```

```
                355                 360                 365

caa ggt aga atc cca tat cct cgc cca gga act tgc cca gga ggg gcc      1334
Gln Gly Arg Ile Pro Tyr Pro Arg Pro Gly Thr Cys Pro Gly Gly Ala
            370                 375                 380

ttt aca ccc aat atg aga acc acc aag gac ttc cca gat gac gtt gtc      1382
Phe Thr Pro Asn Met Arg Thr Thr Lys Asp Phe Pro Asp Asp Val Val
        385                 390                 395

act ttt att cgg aac cac cct ctc atg tac aat tcc atc tac ccc atc      1430
Thr Phe Ile Arg Asn His Pro Leu Met Tyr Asn Ser Ile Tyr Pro Ile
    400                 405                 410

cac aga agg cct ctg ata gtc cgc ata ggc act gac tac aag tac aca      1478
His Arg Arg Pro Leu Ile Val Arg Ile Gly Thr Asp Tyr Lys Tyr Thr
415                 420                 425                 430

aag att gct gtg gac cgt gtc aac gct gct gat ggg aga tac cac gtt      1526
Lys Ile Ala Val Asp Arg Val Asn Ala Ala Asp Gly Arg Tyr His Val
                435                 440                 445

ctg ttt ctg ggc aca gat cgg ggc acc gtg cag aag gtc gta gtc ctt      1574
Leu Phe Leu Gly Thr Asp Arg Gly Thr Val Gln Lys Val Val Val Leu
            450                 455                 460

cct acc aat agc tct gcc agt ggg gaa ctc atc ctg gag gag ctg gaa      1622
Pro Thr Asn Ser Ser Ala Ser Gly Glu Leu Ile Leu Glu Glu Leu Glu
        465                 470                 475

gtc ttc aag aat cat gtt ccc ata aca aca atg aaa atc tca tcc aaa      1670
Val Phe Lys Asn His Val Pro Ile Thr Thr Met Lys Ile Ser Ser Lys
    480                 485                 490

aag caa cag ttg tac gtg agc tcc aat gag ggg gtt tcc caa gtc tct      1718
Lys Gln Gln Leu Tyr Val Ser Ser Asn Glu Gly Val Ser Gln Val Ser
495                 500                 505                 510

ctg cat cgc tgc cat atc tac ggc aca gcc tgt gcg gac tgc tgc ttg      1766
Leu His Arg Cys His Ile Tyr Gly Thr Ala Cys Ala Asp Cys Cys Leu
                515                 520                 525

gcg agg gat cca tac tgt gcc tgg gat ggc cac tct tgc tct agg ttc      1814
Ala Arg Asp Pro Tyr Cys Ala Trp Asp Gly His Ser Cys Ser Arg Phe
            530                 535                 540

tac ccc act ggg aag cgg agg agc cga aga caa gat gtg aga cat gga      1862
Tyr Pro Thr Gly Lys Arg Arg Ser Arg Arg Gln Asp Val Arg His Gly
        545                 550                 555

aac cca ctg aca caa tgc cga ggg ttc aat ctg aaa gca tac aga aat      1910
Asn Pro Leu Thr Gln Cys Arg Gly Phe Asn Leu Lys Ala Tyr Arg Asn
    560                 565                 570

gca gct gaa att gtt cag tat gga gta aga aat aac agc act ttc ctt      1958
Ala Ala Glu Ile Val Gln Tyr Gly Val Arg Asn Asn Ser Thr Phe Leu
575                 580                 585                 590

gag tgt gct ccc aag tct cca cag gca tct atc aag tgg ttg ctg cag      2006
Glu Cys Ala Pro Lys Ser Pro Gln Ala Ser Ile Lys Trp Leu Leu Gln
                595                 600                 605

aaa gac aaa gac agg agg aag gag gtt aaa ctg aac gag cgc att ata      2054
Lys Asp Lys Asp Arg Arg Lys Glu Val Lys Leu Asn Glu Arg Ile Ile
            610                 615                 620

gct act tcc caa gga cta ctg att cgc tct gtt caa gat tct gac caa      2102
Ala Thr Ser Gln Gly Leu Leu Ile Arg Ser Val Gln Asp Ser Asp Gln
        625                 630                 635

gga ctc tac cac tgc att gcc act gag aac agc ttc aaa cag acc ata      2150
Gly Leu Tyr His Cys Ile Ala Thr Glu Asn Ser Phe Lys Gln Thr Ile
    640                 645                 650

gcc aag atc aac ttc aaa gtt tta gat tca gaa atg gtg gcc gtt gtg      2198
Ala Lys Ile Asn Phe Lys Val Leu Asp Ser Glu Met Val Ala Val Val
655                 660                 665                 670

aca gac aag tgg tcc ccg tgg aca tgg gct ggc tct gtg agg gct cta      2246
```

-continued

```
Thr Asp Lys Trp Ser Pro Trp Thr Trp Ala Gly Ser Val Arg Ala Leu
                675                 680                 685

ccc ttc cat cca aag gac atc ctg ggg gca ttc agc cac tcg gaa atg     2294
Pro Phe His Pro Lys Asp Ile Leu Gly Ala Phe Ser His Ser Glu Met
            690                 695                 700

cag ctc atc aat cag tac tgc aaa gac acc cgg cag cag cag cag ctg     2342
Gln Leu Ile Asn Gln Tyr Cys Lys Asp Thr Arg Gln Gln Gln Gln Leu
        705                 710                 715

ggg gaa gaa cca cag aag atg aga ggg gac tat ggc aag ctg aag gct     2390
Gly Glu Glu Pro Gln Lys Met Arg Gly Asp Tyr Gly Lys Leu Lys Ala
    720                 725                 730

ctc atc aac agc agg aaa agc aga aac agg agg aat cag ctt cca gag     2438
Leu Ile Asn Ser Arg Lys Ser Arg Asn Arg Arg Asn Gln Leu Pro Glu
735                 740                 745                 750

tca taa aacattcatc catgaagttt tgcttccagg aacaaatgct ctgtcttcac      2494
Ser

tagtcaacta ttaaataaaa tcttgtgctt tacccatgag aaatttctga caaaagctgg   2554

agactcactc taaagtgtgt tctctgtgaa ctgaaaagag catgcatttt cttgtatgat   2614

acagactagc actagacatg tcatggtcct tgtggtgcat aaaaaatatt taacttatcc   2674

cagattttat ttatatcttt atgtgtcttt tcttcaaaat caatgcgaca acagaagcag   2734

aactgttaca gcctcggttg agcgagggcc ataaatttcc ctgtgctctt ccttccgtgc   2794

tctaggggtt tagctttcta attgtcactg gcttttatac atgaaaaaga attccagttc   2854

acaattttca catagtaaat gtcatataaa tgtgtgtgac atccagtgtc atgtaggtta   2914

cacaaatgac agggaagaga gcatccagat gttacgtaaa gtcaagagtg actcataaag   2974

agcaagtgat gagttcatat gcttccagtg atttatcttc ttgcttgttc ctttgtttaa   3034

gattgtaaga tgtgtcggct gctgatagct gccatcaatg tttgttctct tgttttagaa   3094

aaacaaaaga aatggcctgt accatccaag gcctttgatg ggagatctat cagtgagcca   3154

ttgacgtttc tactgttatg ttatcatctt ccaaacaaaa gtgctttgtt tttttggaag   3214

ttatttaagt tattatagac ttacataaac tattgcatta tttaattgat ttactgtttt   3274

ggttttaatc ccctagtcta cctggaaaat taaagacaac aaggatgcag tattattaaa   3334

gcattcaact tttccatgca gagtgaagct atccaaaggg aaaaggaaga ttaaaaaaaa   3394

agcatacaat ttgtcatgta aaggaattag taacatgtag tttgttttct accttagtaa   3454

tcaaattcta ggagtaattt gtacatccaa ggaaccagtt tcacaaagca taatgatttt   3514

tcaggcaagg tttcatgatt tgtaaacata tctgtgatgg gaaagttatt attacatcaa   3574

gaaagaaaat ctcaacacat tttaaacaaa acagacttct tttaaagact atctattttc   3634

acccagatat tttttccact tgataatact tctttaggaa tgttgataca catgtttaac   3694

tattggaaaa ttttagcact atcttctaat tatatacttg gattgtttaa tgagaaaagt   3754

ataatactaa aattagtttc tccaatttaa atgaataaaa tataggagat tttcttatat   3814

gtcttttaat tatacaactt tcattttatt taattttatt ttaatatgtt tatattttca   3874

gataaaaaga gaagttttac taaaacacca ttgaaacata cttcttatta acagttcatc   3934

tagaatgtaa ctacagggga tctacatcat tttataatgc tgtggaaaaa cctgcaggaa   3994

gtaaaactat ggataggagt gtaagttggt agtagactac gtgtttagca tgcacaaaga   4054

cctgggctca aacagaaaga aaggaagaaa gacaccaagg aaggagggca agcaggaaaa   4114

agaacagact gactggagag aagaagggca ggaaagtggt aaagaaggca aagaaagatg   4174

gagggaatac attcattatc agaagattaa aaaatggtag ttaaatgatg gtcaattctg   4234
```

-continued

```
gtgttcttaa gagtgcacct cagtgttgta gaaaacacca gttaaaatag cataaatgta   4294

cccaaatgtg tacagtgcta caataatcta tggggttagc atatggttaa aatgtttggt   4354

tagcatgttt aaaatgttca cactttgggt tttcttatac atataaaaat agccatgcgt   4414

tcacgtgtga tgctaacacc atcctctttc tgtgtttgta attaatctat tgtatggaaa   4474

cagctacttc cccttgctcc acttaccttc aaactgccag ccacttggct attatttgtt   4534

ctatttagta cctcctgggt tggtttttaa ccataattac atttcaaatc ttcatttctt   4594

tttctttaaa gatatagaaa ttgctgtgca gcatagcccg gccaaaacta aaacatatat   4654

ctctcaaaag cataactaat acatattgag tatgggtgat tactcggttt tattttgttt   4714

acttgggaaa attaataatt aaacatgttt ttcttttgta ttgtacataa aattacctag   4774

aaatgcactt ttcctccaaa atgtaggttc gtgaatagac ttagcatgat gaagctgtct   4834

ttacagtgaa tgcttaccct gtgtagagaa agcaaactag atgtagttac cacatgagaa   4894

tttaattaga tgttgaaaaa aataatttgt ctggaaaaat aaagcattca attcccctga   4954

aa                                                                  4956
```

```
<210> SEQ ID NO 12
<211> LENGTH: 751
<212> TYPE: PRT
<213> ORGANISM: Mus musculus
<220> FEATURE:
<223> OTHER INFORMATION: wildtype full-length Sema3C
      (>gi| 118130842|ref| NM_013657.5|)

<400> SEQUENCE: 12

Met Ala Phe Arg Ala Ile Cys Val Leu Val Gly Val Phe Ile Cys Ser
1               5                   10                  15

Ile Cys Val Arg Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His Gln Gln Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Pro Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220
```

-continued

```
Asp Ala His Val Ile Pro Asp Gly Thr Asp Pro Asn Asp Ala Lys Val
225                 230                 235                 240

Tyr Phe Phe Phe Lys Glu Arg Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Gln Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
        355                 360                 365

Arg Ile Pro Tyr Pro Arg Pro Gly Thr Cys Pro Gly Gly Ala Phe Thr
    370                 375                 380

Pro Asn Met Arg Thr Thr Lys Asp Phe Pro Asp Asp Val Val Thr Phe
385                 390                 395                 400

Ile Arg Asn His Pro Leu Met Tyr Asn Ser Ile Tyr Pro Ile His Arg
                405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445

Leu Gly Thr Asp Arg Gly Thr Val Gln Lys Val Val Val Leu Pro Thr
    450                 455                 460

Asn Ser Ser Ala Ser Gly Glu Leu Ile Leu Glu Glu Leu Glu Val Phe
465                 470                 475                 480

Lys Asn His Val Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
    530                 535                 540

Thr Gly Lys Arg Arg Ser Arg Arg Gln Asp Val Arg His Gly Asn Pro
545                 550                 555                 560

Leu Thr Gln Cys Arg Gly Phe Asn Leu Lys Ala Tyr Arg Asn Ala Ala
                565                 570                 575

Glu Ile Val Gln Tyr Gly Val Arg Asn Asn Ser Thr Phe Leu Glu Cys
            580                 585                 590

Ala Pro Lys Ser Pro Gln Ala Ser Ile Lys Trp Leu Leu Gln Lys Asp
        595                 600                 605

Lys Asp Arg Arg Lys Glu Val Lys Leu Asn Glu Arg Ile Ile Ala Thr
    610                 615                 620

Ser Gln Gly Leu Leu Ile Arg Ser Val Gln Asp Ser Asp Gln Gly Leu
625                 630                 635                 640
```

```
Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Val Thr Asp
            660                 665                 670

Lys Trp Ser Pro Trp Thr Trp Ala Gly Ser Val Arg Ala Leu Pro Phe
        675                 680                 685

His Pro Lys Asp Ile Leu Gly Ala Phe Ser His Ser Glu Met Gln Leu
    690                 695                 700

Ile Asn Gln Tyr Cys Lys Asp Thr Arg Gln Gln Gln Gln Leu Gly Glu
705                 710                 715                 720

Glu Pro Gln Lys Met Arg Gly Asp Tyr Gly Lys Leu Lys Ala Leu Ile
                725                 730                 735

Asn Ser Arg Lys Ser Arg Asn Arg Arg Asn Gln Leu Pro Glu Ser
            740                 745                 750


<210> SEQ ID NO 13
<211> LENGTH: 6276
<212> TYPE: DNA
<213> ORGANISM: Homo sapiens
<220> FEATURE:
<223> OTHER INFORMATION: wildtype full-length SEMA3D
      (>gi| 41406085|ref| NM_152754.2|)
<220> FEATURE:
<221> NAME/KEY: CDS
<222> LOCATION: 41..2374
<223> OTHER INFORMATION: /transl_table=1

<400> SEQUENCE: 13

attaaattaa caccatttga aagagaacat tgttttcatc atg aat gct aat aaa       55
                                            Met Asn Ala Asn Lys
                                            1               5

gat gaa aga ctt aaa gcc aga agc caa gat ttt cac ctt ttt cct gct      103
Asp Glu Arg Leu Lys Ala Arg Ser Gln Asp Phe His Leu Phe Pro Ala
                10                  15                  20

ttg atg atg cta agc atg acc atg ttg ttt ctt cca gtc act ggc act      151
Leu Met Met Leu Ser Met Thr Met Leu Phe Leu Pro Val Thr Gly Thr
            25                  30                  35

ttg aag caa aat att cca aga ctc aag cta acc tac aaa gac ttg ctg      199
Leu Lys Gln Asn Ile Pro Arg Leu Lys Leu Thr Tyr Lys Asp Leu Leu
        40                  45                  50

ctt tca aat agc tgt att ccc ttt ttg ggt tca tca gaa gga ctg gat      247
Leu Ser Asn Ser Cys Ile Pro Phe Leu Gly Ser Ser Glu Gly Leu Asp
    55                  60                  65

ttt caa act ctt ctc tta gat gag gaa aga ggc agg ctg ctc ttg gga      295
Phe Gln Thr Leu Leu Leu Asp Glu Glu Arg Gly Arg Leu Leu Leu Gly
70                  75                  80                  85

gcc aaa gac cac atc ttt cta ctc agt ctg gtt gac tta aac aaa aat      343
Ala Lys Asp His Ile Phe Leu Leu Ser Leu Val Asp Leu Asn Lys Asn
                90                  95                  100

ttt aag aag att tat tgg cct gct gca aag gaa cgg gtg gaa tta tgt      391
Phe Lys Lys Ile Tyr Trp Pro Ala Ala Lys Glu Arg Val Glu Leu Cys
            105                 110                 115

aaa tta gct ggg aaa gat gcc aat aca gaa tgt gca aat ttc atc aga      439
Lys Leu Ala Gly Lys Asp Ala Asn Thr Glu Cys Ala Asn Phe Ile Arg
        120                 125                 130

gta ctt cag ccc tat aac aaa act cac ata tat gtg tgt gga act gga      487
Val Leu Gln Pro Tyr Asn Lys Thr His Ile Tyr Val Cys Gly Thr Gly
    135                 140                 145

gca ttt cat cca ata tgt ggg tat att gat ctt gga gtc tac aag gag      535
Ala Phe His Pro Ile Cys Gly Tyr Ile Asp Leu Gly Val Tyr Lys Glu
150                 155                 160                 165
```

```
gat att ata ttc aaa cta gac aca cat aat ttg gag tct ggc aga ctg      583
Asp Ile Ile Phe Lys Leu Asp Thr His Asn Leu Glu Ser Gly Arg Leu
                170                 175                 180

aaa tgt cct ttc gat cct cag cag cct ttt gct tca gta atg aca gat      631
Lys Cys Pro Phe Asp Pro Gln Gln Pro Phe Ala Ser Val Met Thr Asp
            185                 190                 195

gag tac ctc tac tct gga aca gct tct gat ttc ctt ggc aaa gat act      679
Glu Tyr Leu Tyr Ser Gly Thr Ala Ser Asp Phe Leu Gly Lys Asp Thr
        200                 205                 210

gca ttc act cga tcc ctt ggg cct act cat gac cac cac tac atc aga      727
Ala Phe Thr Arg Ser Leu Gly Pro Thr His Asp His His Tyr Ile Arg
    215                 220                 225

act gac att tca gag cac tac tgg ctc aat gga gca aaa ttt att gga      775
Thr Asp Ile Ser Glu His Tyr Trp Leu Asn Gly Ala Lys Phe Ile Gly
230                 235                 240                 245

act ttc ttc ata cca gac acc tac aat cca gat gat gat aaa ata tat      823
Thr Phe Phe Ile Pro Asp Thr Tyr Asn Pro Asp Asp Asp Lys Ile Tyr
                250                 255                 260

ttc ttc ttt cgt gaa tca tct caa gaa ggc agt acc tcc gat aaa acc      871
Phe Phe Phe Arg Glu Ser Ser Gln Glu Gly Ser Thr Ser Asp Lys Thr
            265                 270                 275

atc ctt tct cga gtt gga aga gtt tgt aag aat gat gta gga gga caa      919
Ile Leu Ser Arg Val Gly Arg Val Cys Lys Asn Asp Val Gly Gly Gln
        280                 285                 290

cgc agc ctg ata aac aag tgg acg act ttt ctt aag gcc aga ctg att      967
Arg Ser Leu Ile Asn Lys Trp Thr Thr Phe Leu Lys Ala Arg Leu Ile
    295                 300                 305

tgc tca att cct gga agt gat ggg gca gat act tac ttt gat gag ctt     1015
Cys Ser Ile Pro Gly Ser Asp Gly Ala Asp Thr Tyr Phe Asp Glu Leu
310                 315                 320                 325

caa gat att tat tta ctc ccc aca aga gat gaa aga aat cct gta gta     1063
Gln Asp Ile Tyr Leu Leu Pro Thr Arg Asp Glu Arg Asn Pro Val Val
                330                 335                 340

tat gga gtc ttt act aca acc agc tcc atc ttc aaa ggc tct gct gtt     1111
Tyr Gly Val Phe Thr Thr Thr Ser Ser Ile Phe Lys Gly Ser Ala Val
            345                 350                 355

tgt gtg tat agc atg gct gac atc aga gca gtt ttt aat ggt cca tat     1159
Cys Val Tyr Ser Met Ala Asp Ile Arg Ala Val Phe Asn Gly Pro Tyr
        360                 365                 370

gct cat aag gaa agt gca gac cat cgt tgg gtg cag tat gat ggg aga     1207
Ala His Lys Glu Ser Ala Asp His Arg Trp Val Gln Tyr Asp Gly Arg
    375                 380                 385

att cct tat cca cgg cct ggt aca tgt cca agc aaa acc tat gac cca     1255
Ile Pro Tyr Pro Arg Pro Gly Thr Cys Pro Ser Lys Thr Tyr Asp Pro
390                 395                 400                 405

ctg att aag tcc acc cga gat ttt cca gat gat gtc atc agt ttc ata     1303
Leu Ile Lys Ser Thr Arg Asp Phe Pro Asp Asp Val Ile Ser Phe Ile
                410                 415                 420

aag cgg cac tct gtg atg tat aag tcc gta tac cca gtt gca gga gga     1351
Lys Arg His Ser Val Met Tyr Lys Ser Val Tyr Pro Val Ala Gly Gly
            425                 430                 435

cca acg ttc aag aga atc aat gtg gat tac aga ctg aca cag ata gtg     1399
Pro Thr Phe Lys Arg Ile Asn Val Asp Tyr Arg Leu Thr Gln Ile Val
        440                 445                 450

gtg gat cat gtc att gca gaa gat ggc cag tac gat gta atg ttt ctt     1447
Val Asp His Val Ile Ala Glu Asp Gly Gln Tyr Asp Val Met Phe Leu
    455                 460                 465

gga aca gac att gga act gtc ctc aaa gtt gtc agc att tca aag gaa     1495
Gly Thr Asp Ile Gly Thr Val Leu Lys Val Val Ser Ile Ser Lys Glu
```

-continued

```
470                 475                 480                 485

aag tgg aat atg gaa gag gta gtg ctg gag gag ttg cag ata ttc aag      1543
Lys Trp Asn Met Glu Glu Val Val Leu Glu Glu Leu Gln Ile Phe Lys
                490                 495                 500

cac tca tca atc atc ttg aac atg gaa ttg tct ctg aag cag caa caa      1591
His Ser Ser Ile Ile Leu Asn Met Glu Leu Ser Leu Lys Gln Gln Gln
            505                 510                 515

ttg tac att ggt tcc cga gat gga ttg gtt cag ctc tcc ttg cac aga      1639
Leu Tyr Ile Gly Ser Arg Asp Gly Leu Val Gln Leu Ser Leu His Arg
        520                 525                 530

tgc gac act tat ggg aaa gct tgc gca gac tgt tgt ctt gcc aga gac      1687
Cys Asp Thr Tyr Gly Lys Ala Cys Ala Asp Cys Cys Leu Ala Arg Asp
    535                 540                 545

ccc tac tgt gcc tgg gat gga aat gca tgc tct cga tat gct cct act      1735
Pro Tyr Cys Ala Trp Asp Gly Asn Ala Cys Ser Arg Tyr Ala Pro Thr
550                 555                 560                 565

tct aaa agg aga gct aga cgc caa gat gta aaa tat ggc gac cca atc      1783
Ser Lys Arg Arg Ala Arg Arg Gln Asp Val Lys Tyr Gly Asp Pro Ile
                570                 575                 580

acc cag tgc tgg gac atc gaa gac agc att agt cat gaa act gct gat      1831
Thr Gln Cys Trp Asp Ile Glu Asp Ser Ile Ser His Glu Thr Ala Asp
            585                 590                 595

gaa aag gtg att ttt ggc att gaa ttt aac tca acc ttt ctg gaa tgt      1879
Glu Lys Val Ile Phe Gly Ile Glu Phe Asn Ser Thr Phe Leu Glu Cys
        600                 605                 610

ata cct aaa tcc caa caa gca act att aaa tgg tat atc cag agg tca      1927
Ile Pro Lys Ser Gln Gln Ala Thr Ile Lys Trp Tyr Ile Gln Arg Ser
    615                 620                 625

ggg gat gag cat cga gag gag ttg aag ccc gat gaa aga atc atc aaa      1975
Gly Asp Glu His Arg Glu Glu Leu Lys Pro Asp Glu Arg Ile Ile Lys
630                 635                 640                 645

acg gaa tat ggg cta ctg att cga agt ttg cag aag aag gat tct ggg      2023
Thr Glu Tyr Gly Leu Leu Ile Arg Ser Leu Gln Lys Lys Asp Ser Gly
                650                 655                 660

atg tat tac tgc aaa gcc cag gag cac act ttc atc cac acc ata gtg      2071
Met Tyr Tyr Cys Lys Ala Gln Glu His Thr Phe Ile His Thr Ile Val
            665                 670                 675

aag ctg act ttg aat gtc att gag aat gaa cag atg gaa aat acc cag      2119
Lys Leu Thr Leu Asn Val Ile Glu Asn Glu Gln Met Glu Asn Thr Gln
        680                 685                 690

agg gca gag cat gag gag ggg aag gtc aag gat cta ttg gct gag tca      2167
Arg Ala Glu His Glu Glu Gly Lys Val Lys Asp Leu Leu Ala Glu Ser
    695                 700                 705

cgg ttg aga tac aaa gac tac atc caa atc ctt agc agc cca aac ttc      2215
Arg Leu Arg Tyr Lys Asp Tyr Ile Gln Ile Leu Ser Ser Pro Asn Phe
710                 715                 720                 725

agc ctc gac cag tac tgc gaa cag atg tgg cac agg gag aag cgg aga      2263
Ser Leu Asp Gln Tyr Cys Glu Gln Met Trp His Arg Glu Lys Arg Arg
                730                 735                 740

cag aga aac aag ggg ggc cca aag tgg aag cac atg cag gaa atg aag      2311
Gln Arg Asn Lys Gly Gly Pro Lys Trp Lys His Met Gln Glu Met Lys
            745                 750                 755

aag aaa cga aat cga aga cat cac aga gac ctg gat gag ctc cct aga      2359
Lys Lys Arg Asn Arg Arg His His Arg Asp Leu Asp Glu Leu Pro Arg
        760                 765                 770

gct gta gcc acg tag ttttctactt aatttaaaga aaagaattcc ttacctataa      2414
Ala Val Ala Thr
    775

aaacattgcc ttctgttttg tatatccctt atagtaattc ataaatgctt cccatggagt    2474
```

```
tttgctaagg cacaagacaa taatctgaat aagacaatat gtgatgaata taagaaaggg   2534
caaaaaattc atttgaacca gttttccaag aacaaatctt gcacaagcaa agtataagaa   2594
ttatcctaaa aatagggggt ttacagttgt aaatgtttta tgttttgagt tttggaattt   2654
attgtcatgt aaatagttga gctaagcaag ccccgaattt gatagtgtat aaggtgcttt   2714
attccctcga atgtccatta agcatggaat ttaccatgca gttgtgctat gttcttatga   2774
acagatatat cattcctatt gagaaccagc taccttgtgg tagggaataa gaggtcagac   2834
acaaattaag acaactccca ttatcaacag gaactttctc agtgagccat tcactcctgg   2894
agaatggtat aggaatttgg agaggtgcat tatttctttc tggccactgg ggttaaattt   2954
agtgtactac aacattgatt tactgaaggg cactaatgtt tcccccagga tttctattga   3014
ctagtcagga gtaacaggtt cacagagaga agttggtgct tagttatgtg ttttttagag   3074
tatatactaa gctctacagg gacagaatgc ttaataaata ctttaataag atatgggaaa   3134
atattttaat aaaacaagga aaacataatg atgtataatg catcctgatg ggaaggcatg   3194
cagatgggat ttgttagaag acagaaggaa agacagccat aaattctggc tttggggaaa   3254
actcatatcc ccatgaaaag gaagaacaat cacaaataaa gtgagagtaa tgtaatggag   3314
ctcttttcac tagggtataa gtagctgcca atttgtaatt catctgttaa aaaaaatcta   3374
gattataaca aactgctagc aaaatctgag gaaacataaa ttcttctgaa gaatcatagg   3434
aagagtagac attttattta taaccaatga tatttcagta tatattttct ctcttttaaa   3494
aaatatttat catactctgt atattatttc tttttactgc ctttattctc tcctgtatat   3554
tggattttgt gattatattt gagtgaatag gagaaaacaa tatataacac acagagaatt   3614
aagaaaatga catttctggg gagtggggat atatatttgt tgaataacag aacgagtgta   3674
aaattttaac aacggaaagg gttaaattaa ctctttgaca tcttcactca accttttctc   3734
attgctgagt taatctgttg taattgtagt attgtttttg taatttaaca ataaataagc   3794
ctgctacatg taaaaagaac caaactcaca atattaacat aaacatcttt catattttgt   3854
tagtactttc aaatgttttc aatttgactt tccctctgaa tatgcatggt gtgtttcctg   3914
tctgtttaag cagaactcac ctttccttct tgtaacacag aacccttagc cttcttctgt   3974
tttgcctttt cacgcccttt atagtgtgaa atgaaaaatt agtcacttcc tcacatggaa   4034
ggcagctttt cagaaaataa cagacattgc tcgtttctca tgcattctac atatcttgaa   4094
agaaaagtct gtgagaaaac cctgtgatta gagggcaact taatgcaaga tctgtggctc   4154
tatgttgaga gcattctctc tctgttattt ttattttatt tgcattgctt acctatctca   4214
aagtagtcaa actgatatat gagattgagt actccctttt gatattatac tgatgaatat   4274
ttgtaggtgt ttcactataa ggaacagcta aggaataatt ttaataaaag tgaaccagaa   4334
caaatcactc atttaaaaag taattcagaa gaacagtgtg gcatgatcag acttctaatt   4394
gaatagcgta acaacagtgt ttgtaattat agatttgctt ggacaaaata ttccaggaac   4454
tcatagcgag ctcaaagcaa ttaagtggga acatttttaa tttaaaaaaa atttccaaat   4514
atttgtgggt ccgacagtaa tgatcaaaat atgaatgact ttggaaaatt tacatgaagc   4574
tcaagtgtta ggattgactt atgaaaataa attttatttc tatccaaatt tgaatgtcca   4634
aaccattttt tagttacttc tttctaatcc tagttattca gacaaaattt ggaaacttat   4694
tttatgacca catctaatat tctggctgct ttggatacaa tactcttgat ttatgataat   4754
tagttaaaat atattaaaaa tattattagt aaaataaaat ttcacacaat aaaaaacaac   4814
```

atagagtaca catatttata tgtattttta aagataaaga atatctaaaa tgtgtttttt 4874 tcttagcttt ttagttgtct agaacattta gagaaagagt atgaatatat taaatccaca 4934 aacacactat atacttcctc accactgact attttatcaa atttgcctta aaataatgaa 4994 aaagaaaagt atagttaatg gtttcaaata tgctaagaaa ttgactctgc ggaggggatc 5054 ttaaaatgcc tgtttactca tgttttcgta tttttcttgt ctctaatact tttgtctttg 5114 tctgccttgt gtgttctttt ctgaatttca tttcagcaat ttatgctgct aaatagaatc 5174 ccgcatgtct gcattcattt acattcaact tattgtaaat tttgagattt tatttagaaa 5234 tgaattgtct aattaattta tgtagagtcc ttttttccaa agagctcaaa acactacatc 5294 cacattattg acttttggaa accaaccaaa ttacttaaga aatggaaaag tagtcacaga 5354 gaaatttagt aatttgcaaa agccacaaca gtagtggaag aattaaaatt cataaagtct 5414 catcattctg ttggctaaaa taatgctctt tacaatatgc tggctacaaa atggtcttac 5474 tcttgaattt tgcttttggt tcatattttg gttcttcata ttctagtatg ttttgttcct 5534 gctgaatttt acagactcag ctaaacaata agttattagt agtcacttgt tttcattatc 5594 ataattgaat ttccaagaac aacttgatat cattcagctg tccaaaaaat aataagagca 5654 ttcattaaat actgattttc ttaaacttaa atgttgtatt tcatatttat ttatataata 5714 caaatggaaa tcaaaactga aatagcctcc ctttagaatg tcacattttt cttagaaaac 5774 attttggaat tggttaacct tattgggaat ggataattta gaaacaaacc aaaaaaaaaa 5834 aaagatattt gaagtgtttt tataggagat gtatttttat catagtaaat gatcacaatt 5894 ttaaataatt catcttacaa gtcaggtaaa ataaaatcga ttcccagatt ccatacatta 5954 ggagtgcaaa gacaggatca tacacatgac ttatacctct catttaaata ttttatagta 6014 taaagtattt atggaaaggg tttgagatag atgatttttg ggaaagggca aaatgtgtca 6074 gatgccctag ttaatcatgt aatttaattc tggtattgtg agtggttagc aatcaatttt 6134 gaatttataa ttctgctatt ttaaaagaaa tgtagtcttg tagtatgaaa taattaaaaa 6194 ttgttaaatg tatattttgg ttgtattata ataaaatgca aacatgactg ttctatgatt 6254 ataaaaaaaa aaaaaaaaaa aa 6276

<210> SEQ ID NO 14
<211> LENGTH: 777
<212> TYPE: PRT
<213> ORGANISM: Homo sapiens
<220> FEATURE:
<223> OTHER INFORMATION: wildtype full-length SEMA3D
(>gi| 41406085|ref| NM_152754.2|)

<400> SEQUENCE: 14

```
Met Asn Ala Asn Lys Asp Glu Arg Leu Lys Ala Arg Ser Gln Asp Phe
1               5                   10                  15

His Leu Phe Pro Ala Leu Met Met Leu Ser Met Thr Met Leu Phe Leu
            20                  25                  30

Pro Val Thr Gly Thr Leu Lys Gln Asn Ile Pro Arg Leu Lys Leu Thr
        35                  40                  45

Tyr Lys Asp Leu Leu Leu Ser Asn Ser Cys Ile Pro Phe Leu Gly Ser
    50                  55                  60

Ser Glu Gly Leu Asp Phe Gln Thr Leu Leu Leu Asp Glu Glu Arg Gly
65                  70                  75                  80

Arg Leu Leu Leu Gly Ala Lys Asp His Ile Phe Leu Leu Ser Leu Val
                85                  90                  95
```

-continued

```
Asp Leu Asn Lys Asn Phe Lys Lys Ile Tyr Trp Pro Ala Ala Lys Glu
            100                 105                 110

Arg Val Glu Leu Cys Lys Leu Ala Gly Lys Asp Ala Asn Thr Glu Cys
        115                 120                 125

Ala Asn Phe Ile Arg Val Leu Gln Pro Tyr Asn Lys Thr His Ile Tyr
    130                 135                 140

Val Cys Gly Thr Gly Ala Phe His Pro Ile Cys Gly Tyr Ile Asp Leu
145                 150                 155                 160

Gly Val Tyr Lys Glu Asp Ile Ile Phe Lys Leu Asp Thr His Asn Leu
                165                 170                 175

Glu Ser Gly Arg Leu Lys Cys Pro Phe Asp Pro Gln Gln Pro Phe Ala
            180                 185                 190

Ser Val Met Thr Asp Glu Tyr Leu Tyr Ser Gly Thr Ala Ser Asp Phe
        195                 200                 205

Leu Gly Lys Asp Thr Ala Phe Thr Arg Ser Leu Gly Pro Thr His Asp
    210                 215                 220

His His Tyr Ile Arg Thr Asp Ile Ser Glu His Tyr Trp Leu Asn Gly
225                 230                 235                 240

Ala Lys Phe Ile Gly Thr Phe Phe Ile Pro Asp Thr Tyr Asn Pro Asp
                245                 250                 255

Asp Asp Lys Ile Tyr Phe Phe Phe Arg Glu Ser Ser Gln Glu Gly Ser
            260                 265                 270

Thr Ser Asp Lys Thr Ile Leu Ser Arg Val Gly Arg Val Cys Lys Asn
        275                 280                 285

Asp Val Gly Gly Gln Arg Ser Leu Ile Asn Lys Trp Thr Thr Phe Leu
    290                 295                 300

Lys Ala Arg Leu Ile Cys Ser Ile Pro Gly Ser Asp Gly Ala Asp Thr
305                 310                 315                 320

Tyr Phe Asp Glu Leu Gln Asp Ile Tyr Leu Leu Pro Thr Arg Asp Glu
                325                 330                 335

Arg Asn Pro Val Val Tyr Gly Val Phe Thr Thr Thr Ser Ser Ile Phe
            340                 345                 350

Lys Gly Ser Ala Val Cys Val Tyr Ser Met Ala Asp Ile Arg Ala Val
        355                 360                 365

Phe Asn Gly Pro Tyr Ala His Lys Glu Ser Ala Asp His Arg Trp Val
    370                 375                 380

Gln Tyr Asp Gly Arg Ile Pro Tyr Pro Arg Pro Gly Thr Cys Pro Ser
385                 390                 395                 400

Lys Thr Tyr Asp Pro Leu Ile Lys Ser Thr Arg Asp Phe Pro Asp Asp
                405                 410                 415

Val Ile Ser Phe Ile Lys Arg His Ser Val Met Tyr Lys Ser Val Tyr
            420                 425                 430

Pro Val Ala Gly Gly Pro Thr Phe Lys Arg Ile Asn Val Asp Tyr Arg
        435                 440                 445

Leu Thr Gln Ile Val Val Asp His Val Ile Ala Glu Asp Gly Gln Tyr
    450                 455                 460

Asp Val Met Phe Leu Gly Thr Asp Ile Gly Thr Val Leu Lys Val Val
465                 470                 475                 480

Ser Ile Ser Lys Glu Lys Trp Asn Met Glu Glu Val Val Leu Glu Glu
                485                 490                 495

Leu Gln Ile Phe Lys His Ser Ser Ile Ile Leu Asn Met Glu Leu Ser
            500                 505                 510

Leu Lys Gln Gln Gln Leu Tyr Ile Gly Ser Arg Asp Gly Leu Val Gln
```

-continued

```
        515                 520                 525

Leu Ser Leu His Arg Cys Asp Thr Tyr Gly Lys Ala Cys Ala Asp Cys
    530                 535                 540

Cys Leu Ala Arg Asp Pro Tyr Cys Ala Trp Asp Gly Asn Ala Cys Ser
545                 550                 555                 560

Arg Tyr Ala Pro Thr Ser Lys Arg Arg Ala Arg Arg Gln Asp Val Lys
                565                 570                 575

Tyr Gly Asp Pro Ile Thr Gln Cys Trp Asp Ile Glu Asp Ser Ile Ser
            580                 585                 590

His Glu Thr Ala Asp Glu Lys Val Ile Phe Gly Ile Glu Phe Asn Ser
        595                 600                 605

Thr Phe Leu Glu Cys Ile Pro Lys Ser Gln Gln Ala Thr Ile Lys Trp
    610                 615                 620

Tyr Ile Gln Arg Ser Gly Asp Glu His Arg Glu Glu Leu Lys Pro Asp
625                 630                 635                 640

Glu Arg Ile Ile Lys Thr Glu Tyr Gly Leu Leu Ile Arg Ser Leu Gln
                645                 650                 655

Lys Lys Asp Ser Gly Met Tyr Tyr Cys Lys Ala Gln Glu His Thr Phe
            660                 665                 670

Ile His Thr Ile Val Lys Leu Thr Leu Asn Val Ile Glu Asn Glu Gln
        675                 680                 685

Met Glu Asn Thr Gln Arg Ala Glu His Glu Glu Gly Lys Val Lys Asp
    690                 695                 700

Leu Leu Ala Glu Ser Arg Leu Arg Tyr Lys Asp Tyr Ile Gln Ile Leu
705                 710                 715                 720

Ser Ser Pro Asn Phe Ser Leu Asp Gln Tyr Cys Glu Gln Met Trp His
                725                 730                 735

Arg Glu Lys Arg Arg Gln Arg Asn Lys Gly Gly Pro Lys Trp Lys His
            740                 745                 750

Met Gln Glu Met Lys Lys Lys Arg Asn Arg Arg His His Arg Asp Leu
        755                 760                 765

Asp Glu Leu Pro Arg Ala Val Ala Thr
    770                 775
```

<210> SEQ ID NO 15
<211> LENGTH: 6521
<212> TYPE: DNA
<213> ORGANISM: Mus musculus
<220> FEATURE:
<223> OTHER INFORMATION: wildtype full-length Sema3D
(>gi| 282847343|ref| NM_028882.4|)
<220> FEATURE:
<221> NAME/KEY: CDS
<222> LOCATION: 547..2880
<223> OTHER INFORMATION: /transl_table=1

<400> SEQUENCE: 15

```
aaacccaccc tggacagcgc ggccgagaca gggaaggttt gctcgctctg agggattgcc      60

agcacatcag aagtggccgg gagctggggg aggagactga agggagaggt aatccctggc     120

gttttgagca tccccttttt agaaagaagg agtctctccc aggacagctg ctgcggtcac     180

accacaaact taaaagccgc cctcctgctt ggagcgtgcc tttcctcacc acgctcgctg     240

gcctaagcgc caactggtgg gtcactgtcc gagagagagg cgctgcgctc gggggacagg     300

agcgccccct gccttcccgc ttggccgtag ccgcggcctc attgctctgc cagggccgcc     360

tgtgcggggt tcagccccgg ctgccgctcc gaagaactcg cgcctgtgcc cgcggtcgcc     420
```

```
atcctcttgg cttccttggg ctgtcctttc ctctctcctg agcctgcgac gtaaggaaag    480

gaaaagcgac aagagttgct agcaggaagg gtgaactaac agtgtttgaa aaacaaaatt    540

ttcatc atg aat gtt act aaa gat gag aac cca aga tcc aga agt caa       588
       Met Asn Val Thr Lys Asp Glu Asn Pro Arg Ser Arg Ser Gln
       1               5                   10

gat ctt cac ctt ttt cat gct tgg atg atg tta atc atg acg gtg ctc      636
Asp Leu His Leu Phe His Ala Trp Met Met Leu Ile Met Thr Val Leu
15                  20                  25                  30

ttt ctt cct gtc act gaa acg tct aaa caa aat att cca aga ctc aag      684
Phe Leu Pro Val Thr Glu Thr Ser Lys Gln Asn Ile Pro Arg Leu Lys
                35                  40                  45

cta acc tac aaa gac ttg ctg ctt tca aac acc tgt atc ccc ttt ttg      732
Leu Thr Tyr Lys Asp Leu Leu Leu Ser Asn Thr Cys Ile Pro Phe Leu
            50                  55                  60

ggt tca tca gaa gga ttg gat ttc cag act ctt ctt ttg gat gag gag      780
Gly Ser Ser Glu Gly Leu Asp Phe Gln Thr Leu Leu Leu Asp Glu Glu
        65                  70                  75

agg ggc ata ctg ctc cta gga gcc aaa gac cat gtc ttc ctg ctc agt      828
Arg Gly Ile Leu Leu Leu Gly Ala Lys Asp His Val Phe Leu Leu Ser
    80                  85                  90

ctg gtt gac ttg aac aag aat ttt aag aag att tat tgg cct gct gca      876
Leu Val Asp Leu Asn Lys Asn Phe Lys Lys Ile Tyr Trp Pro Ala Ala
95                  100                 105                 110

aaa gaa cga gtg gag cta tgt aaa tta gct ggg aaa gat gcc aat gca      924
Lys Glu Arg Val Glu Leu Cys Lys Leu Ala Gly Lys Asp Ala Asn Ala
                115                 120                 125

gaa tgt gca aat ttc atc cgt gtg ctt caa ccc tat aat aag act cac      972
Glu Cys Ala Asn Phe Ile Arg Val Leu Gln Pro Tyr Asn Lys Thr His
            130                 135                 140

gtt tac gtg tgt gga act gga gcg ttt cat ccg ctg tgt ggg tac att     1020
Val Tyr Val Cys Gly Thr Gly Ala Phe His Pro Leu Cys Gly Tyr Ile
        145                 150                 155

gat ctc ggc gcc aac aag gag gaa ctc ata ttt aaa cta gac acg cac     1068
Asp Leu Gly Ala Asn Lys Glu Glu Leu Ile Phe Lys Leu Asp Thr His
    160                 165                 170

aac ctg gag tct ggc aga ctg aaa tgt ccc ttt gat cct cag cag cct     1116
Asn Leu Glu Ser Gly Arg Leu Lys Cys Pro Phe Asp Pro Gln Gln Pro
175                 180                 185                 190

ttt gct tca gta atg aca gat gag cac ctc tac tct gga aca gct tct     1164
Phe Ala Ser Val Met Thr Asp Glu His Leu Tyr Ser Gly Thr Ala Ser
                195                 200                 205

gat ttc ctt ggc aaa gac act gca ttc aca agg tct ctg ggg cta atg     1212
Asp Phe Leu Gly Lys Asp Thr Ala Phe Thr Arg Ser Leu Gly Leu Met
            210                 215                 220

cag gac cac cat tcc atc aga act gac att tca gag cac cac tgg ctc     1260
Gln Asp His His Ser Ile Arg Thr Asp Ile Ser Glu His His Trp Leu
        225                 230                 235

aat gga gca aaa ttt atc gga aca ttc ccc att cca gac acc tat aat     1308
Asn Gly Ala Lys Phe Ile Gly Thr Phe Pro Ile Pro Asp Thr Tyr Asn
    240                 245                 250

cca gat gat gat aaa ata tat ttc ttc ttt cga gaa tca tcc cag gaa     1356
Pro Asp Asp Asp Lys Ile Tyr Phe Phe Phe Arg Glu Ser Ser Gln Glu
255                 260                 265                 270

ggc agt act tct gac aga agc att ctt tca aga gtt gga aga gtt tgt     1404
Gly Ser Thr Ser Asp Arg Ser Ile Leu Ser Arg Val Gly Arg Val Cys
                275                 280                 285

aag aat gat gta ggt ggg caa cga agt ctg ata aac aaa tgg aca act     1452
Lys Asn Asp Val Gly Gly Gln Arg Ser Leu Ile Asn Lys Trp Thr Thr
            290                 295                 300
```

```
ttt cta aag gca aga ctg att tgc tcg att cct gga agc gat ggg gca      1500
Phe Leu Lys Ala Arg Leu Ile Cys Ser Ile Pro Gly Ser Asp Gly Ala
        305                 310                 315

gat acc cat ttt gat gaa ctc caa gat att tac tta ctc cct acg aga      1548
Asp Thr His Phe Asp Glu Leu Gln Asp Ile Tyr Leu Leu Pro Thr Arg
    320                 325                 330

gat gaa aga aat cct gta gta tat gga gtc ttt acc aca acc agc tcc      1596
Asp Glu Arg Asn Pro Val Val Tyr Gly Val Phe Thr Thr Thr Ser Ser
335                 340                 345                 350

atc ttc aaa ggc tct gct gtc tgt gtg tac agc atg gct gat atc cga      1644
Ile Phe Lys Gly Ser Ala Val Cys Val Tyr Ser Met Ala Asp Ile Arg
                355                 360                 365

gca gtc ttt aat ggt ccc tat gct cat aag gaa agt gct gac cat cgc      1692
Ala Val Phe Asn Gly Pro Tyr Ala His Lys Glu Ser Ala Asp His Arg
            370                 375                 380

tgg gtg caa tat gat gga agg ata cct tac ccc cga cct gga acg tgt      1740
Trp Val Gln Tyr Asp Gly Arg Ile Pro Tyr Pro Arg Pro Gly Thr Cys
        385                 390                 395

cca agc aaa acc tat gac cca ctg att aag tcc acc cga gac ttt cca      1788
Pro Ser Lys Thr Tyr Asp Pro Leu Ile Lys Ser Thr Arg Asp Phe Pro
    400                 405                 410

gac gat gtt atc agt ttc ata agg cgg cac cct gtg atg tat aag tcc      1836
Asp Asp Val Ile Ser Phe Ile Arg Arg His Pro Val Met Tyr Lys Ser
415                 420                 425                 430

gtg tac cca gtg gca gga gca ccg acc ttc aag aga atc aac gtg gat      1884
Val Tyr Pro Val Ala Gly Ala Pro Thr Phe Lys Arg Ile Asn Val Asp
                435                 440                 445

tac aga ctg acg cag ata gtg gtg gat cac gtg gtc gct gaa gac ggg      1932
Tyr Arg Leu Thr Gln Ile Val Val Asp His Val Val Ala Glu Asp Gly
            450                 455                 460

cag tat gat gtc atg ttt ctc gga aca gac att gga aca gtc ctg aaa      1980
Gln Tyr Asp Val Met Phe Leu Gly Thr Asp Ile Gly Thr Val Leu Lys
        465                 470                 475

gtt gtg agc atc tcc aag gag aag tgg aat atg gaa gag gtc gta ctg      2028
Val Val Ser Ile Ser Lys Glu Lys Trp Asn Met Glu Glu Val Val Leu
    480                 485                 490

gag gag ctt cag gta ttc aag cac cca aca gct atc ttg aac atg gag      2076
Glu Glu Leu Gln Val Phe Lys His Pro Thr Ala Ile Leu Asn Met Glu
495                 500                 505                 510

ttg tcg ctg aag cag caa cag ttg tac gtt ggt tcc tgg gat gga ttg      2124
Leu Ser Leu Lys Gln Gln Gln Leu Tyr Val Gly Ser Trp Asp Gly Leu
                515                 520                 525

gtc cag ctc tcc ttg cac aga tgc gac act tac ggg aaa gca tgt gca      2172
Val Gln Leu Ser Leu His Arg Cys Asp Thr Tyr Gly Lys Ala Cys Ala
            530                 535                 540

gac tgc tgt ctc gcc aga gac cct tac tgt gcc tgg gat gga aat gct      2220
Asp Cys Cys Leu Ala Arg Asp Pro Tyr Cys Ala Trp Asp Gly Asn Ala
        545                 550                 555

tgc tcc aga tat gca ccc acg tct aaa agg cga gct aga cgc cag gat      2268
Cys Ser Arg Tyr Ala Pro Thr Ser Lys Arg Arg Ala Arg Arg Gln Asp
    560                 565                 570

gta aaa tat ggg gac cca atc act cag tgc tgg gac ata gaa gac agc      2316
Val Lys Tyr Gly Asp Pro Ile Thr Gln Cys Trp Asp Ile Glu Asp Ser
575                 580                 585                 590

att agt cat gaa aca gct gat gaa aag gtg att ttt gga att gaa ttt      2364
Ile Ser His Glu Thr Ala Asp Glu Lys Val Ile Phe Gly Ile Glu Phe
                595                 600                 605

aat tca acc ttt ttg gag tgt ata cct aaa tcc caa caa gcc tct gtt      2412
Asn Ser Thr Phe Leu Glu Cys Ile Pro Lys Ser Gln Gln Ala Ser Val
```

-continued

```
            610                 615                 620

gag tgg tac atc cag cgg tca gga gat gag cat cga gag gag ttg aaa      2460
Glu Trp Tyr Ile Gln Arg Ser Gly Asp Glu His Arg Glu Glu Leu Lys
        625                 630                 635

cct gat gaa agg atc atc aaa act gac tat ggg cta ctg att cga agt      2508
Pro Asp Glu Arg Ile Ile Lys Thr Asp Tyr Gly Leu Leu Ile Arg Ser
    640                 645                 650

ctg cag aag aag gat tct ggg atg tat tac tgc aaa gca cag gag cac      2556
Leu Gln Lys Lys Asp Ser Gly Met Tyr Tyr Cys Lys Ala Gln Glu His
655                 660                 665                 670

act ttc atc cac acc ata gtg aag ctg act ttg aat gtc att gag aat      2604
Thr Phe Ile His Thr Ile Val Lys Leu Thr Leu Asn Val Ile Glu Asn
                675                 680                 685

gaa cag atg gaa aat acc cag agg gca gaa tac cag gag ggg cag gtc      2652
Glu Gln Met Glu Asn Thr Gln Arg Ala Glu Tyr Gln Glu Gly Gln Val
            690                 695                 700

aag gat ctg ttg gct gag tca cgg ttg aga tac aaa gac tac atc caa      2700
Lys Asp Leu Leu Ala Glu Ser Arg Leu Arg Tyr Lys Asp Tyr Ile Gln
        705                 710                 715

atc ctt agc agc ccg aac ttc agc ctg gac cag tac tgt gag cag atg      2748
Ile Leu Ser Ser Pro Asn Phe Ser Leu Asp Gln Tyr Cys Glu Gln Met
    720                 725                 730

tgg tac aag gag aag cgg aga cag cgc aac aag ggc agc cca aag tgg      2796
Trp Tyr Lys Glu Lys Arg Arg Gln Arg Asn Lys Gly Ser Pro Lys Trp
735                 740                 745                 750

aag cac atg cag gaa atg aag aag aaa cga aat cga cga cat cac aga      2844
Lys His Met Gln Glu Met Lys Lys Lys Arg Asn Arg Arg His His Arg
                755                 760                 765

gac ctc gat gag ctc cag aga tca gta gct aca tag ttttctattt           2890
Asp Leu Asp Glu Leu Gln Arg Ser Val Ala Thr
            770                 775

aatttaaaga gggaattatt tacctgcctg cacaaataat gtcttctgtt ttgtacatcc   2950

cttatactaa ctcatacatg cttcccatgg agtctcacgg aggcacagga tgctatgctg   3010

agtaagacta tataggacat catctgaacc agctttccaa gaacaaaatc tgtatcagca   3070

aagttaagaa ttgtcttaaa aataggggcc ttatgtttgt aaatgtctca tagtttgaat   3130

ttaatgtcat gtaaataatc aagttaaatg aacccaggtc cacttagtaa gggcgttatt   3190

cccgtgcatg tccattaagc atggactttc ccatgctgct ggctatgtgc ttaatcattc   3250

cattctagaa caggtgatca tgtaggaact ggagaaaagg cacactttaa aacagcttat   3310

gttagcaaaa aaaaaacttt ctcaaggagc caacaggcca cacttggagt caggcgtggg   3370

aatttagaaa ggcatgttcc ctctttgtgg accaggctac atctagtgta ctgcagtaat   3430

gctctgtgag agggtagtaa tgatcctcac caatttcctt ttgattgctc aagcacagca   3490

tcatggacag aaccccatgg tgtgctctag agtacagaca atggaactta gtacacactt   3550

cctgtgctct ttgggaagca tggtaaaaga tcttaatata ataataaggg tgacatgata   3610

tacactgtat cctaatctgt agatgggaat tatttggaga cagacaagat agctgtaaat   3670

tctgtctctg agaaaaactt atattgccat aaaaaaggag aaagccacaa agtagataga   3730

atgtaatgga attctttcca ctggagtata aatatctgcc aacttataat gttttggtta   3790

aaaataattt agattatagc aaattgttag caaaaatgca agtgaaagta aaatttgtaa   3850

aaaaaattat gggatggcaa tatattattt ataaccaatg tatttctgtg ttctcttttt   3910

ttctaagtat ttatcgtatt ctgtatattg tttgcattta catccttttt tttattatat   3970

ttgagtaaat aggagaaagc aatacgtaat acatagagat aattgagtag atgaccaagg   4030
```

tggggagtgg ggctatatat ttgttgaatg gatggataat ggcaaaattt tgatgacggg 4090
aagggttaaa ttaactcttc gacatcctct cgttacataa actttcaagc agtgttgttt 4150
tcagcagttt cacaaggaag tcttcaacat ctaaagaaaa cactcacacc gttagcataa 4210
gtaccatttg tattttgcta gcctgtgtca aattcaactt tgcctttgaa cagtgttttc 4270
ctgccagtct ctccagaaat caactttcct tcctgtagca caaaaccctt agccttcctc 4330
tgttttgcct tttcacgctc tttatagtgt gaaatgaaca attagtcact tcctcacaaa 4390
gaatgcagct ttttagaaaa ccaacagacc ttgtttgttt ctcatgcatt ctacatgttt 4450
tgaaagattc tgtgagaagc ctgtgtgatt aaaaagcagt tttacagagt caagcaatct 4510
atctcttcaa agtagcatca gtattttaca ttcatttaat ttgcattggg tacctatctc 4570
aagggcataa cattatctgc aagggactag tataataatg aatatttgtt gatgtttcac 4630
tcttggaaaa agcaaaaatg aaggaacaat tttaatttgt aaaccagaat gaatcacatc 4690
tccagcagaa gtgcatacaa atccttgtgt catggttaga ctactaatca tagatcacac 4750
aataatgttt atctactggc ttactgagtc ctgcaaagtc acagcaaaca tgtcagtggg 4810
tgcatgcttc attcaaaaaa tgctttcaga tagctgtgca tcagagagta atactcaaat 4870
atcagtagta ttgaaagatt gcacaagatt ctactctttg tattgacatc tgaaaattaa 4930
ttttatatag ataataatgt ccaaactatt ttctaattac ttatgtaatt agaaatgtaa 4990
tgttttatca acattctgta aatctatttt acatcttaga tttaaaattt tggctgtttt 5050
gggcataaaa cttctaatta tgattaaata tattataaac attattagga aaatatgatt 5110
ccataataaa ggtagggcta tggtttattt tgaaatgcag actatagcta agcagcattc 5170
attcttattc aaaagactta gaagagtgtt gtgaaagatc agttgacaaa tgtaatgtgt 5230
agttccttac cattgaggat gaacaactct gttttgaaat aataaaaagc agaatattgc 5290
tcaaagttta aatattaaag gtaccagatc ccccagaagc aactctgaac tatgtagtta 5350
ttcatttttt tttaaatcta tttttctgtc ttcagtacaa gtctctagct tctgtgagtg 5410
tttttgctgc atttttattc agtcctttgt gctgctaaat agtagtatgc ctgaatgagt 5470
taatttacat ttaatttatt gggaatttta agagtttgtt tagaaatgga taatctaaat 5530
aagcaattta tgtaaaatcc tttgtttttc tttcccaaaa gagttcataa tcatatatca 5590
cacgacagag taaacatttc agaagaaaca gtcaagttac ttaaaaaact gcaaagtagt 5650
catagaaaaa ctgagcacac tgcagaatcc acaatagctc tcggatgcac aattccagga 5710
tgatttgttt aaagcaagac ttacttacaa catgcctgca atatgatggt cacgcttttg 5770
gacgtttcct ttgtgctata ctttgattct ttgcatatat taattattac atgctattcc 5830
tactgaattg gtgatcttac ctagaggcta acaagagtga ctacttgtta gactaacata 5890
accaagaata atttcccagg acaacttgtg tcatttcatt cacatgaaaa aataaaatta 5950
aacaagacca ctcagtaaac attgattctt cttaaacata tgtctaagat gtattgtaca 6010
tattttactg aaacagaata aagttaactt gggaatccct tctcttcata ataccacatt 6070
gttgcagtca gtgtgtttca actaacaagc cattttgagg gatgggtaac tttttaaaaa 6130
tagaaatgta tattttctca taatagatga tcacaatatt tcaatttaca gtatgtaagg 6190
ttaaaaatac ataagactta aattttccag acttgttaaa ctgaaaatcc atgtacacaa 6250
taaatctcac gctttgtaac tcttgcttaa atcttttgta atgtaaggta tttatgaaaa 6310
tttgaagcat acctttttgg gaaagaaaaa taaaacctgt cagaagccac agttggtctt 6370

```
cacttcttag cattgtcagt ggtgggtatc aatgaatttg aataatttta cttttaaaaa   6430

actgtagtct tgtagtatag catacttaaa attgttaaat gtatattttg tttgtattat   6490

aataaaacaa gtatcagtgt tctattatta t                                  6521


<210> SEQ ID NO 16
<211> LENGTH: 777
<212> TYPE: PRT
<213> ORGANISM: Mus musculus
<220> FEATURE:
<223> OTHER INFORMATION: wildtype full-length Sema3D
      (>gi| 282847343|ref| NM_028882.4|)

<400> SEQUENCE: 16

Met Asn Val Thr Lys Asp Glu Asn Pro Arg Ser Arg Ser Gln Asp Leu
1               5                   10                  15

His Leu Phe His Ala Trp Met Met Leu Ile Met Thr Val Leu Phe Leu
            20                  25                  30

Pro Val Thr Glu Thr Ser Lys Gln Asn Ile Pro Arg Leu Lys Leu Thr
        35                  40                  45

Tyr Lys Asp Leu Leu Leu Ser Asn Thr Cys Ile Pro Phe Leu Gly Ser
    50                  55                  60

Ser Glu Gly Leu Asp Phe Gln Thr Leu Leu Leu Asp Glu Glu Arg Gly
65                  70                  75                  80

Ile Leu Leu Leu Gly Ala Lys Asp His Val Phe Leu Leu Ser Leu Val
                85                  90                  95

Asp Leu Asn Lys Asn Phe Lys Lys Ile Tyr Trp Pro Ala Ala Lys Glu
            100                 105                 110

Arg Val Glu Leu Cys Lys Leu Ala Gly Lys Asp Ala Asn Ala Glu Cys
        115                 120                 125

Ala Asn Phe Ile Arg Val Leu Gln Pro Tyr Asn Lys Thr His Val Tyr
    130                 135                 140

Val Cys Gly Thr Gly Ala Phe His Pro Leu Cys Gly Tyr Ile Asp Leu
145                 150                 155                 160

Gly Ala Asn Lys Glu Glu Leu Ile Phe Lys Leu Asp Thr His Asn Leu
                165                 170                 175

Glu Ser Gly Arg Leu Lys Cys Pro Phe Asp Pro Gln Gln Pro Phe Ala
            180                 185                 190

Ser Val Met Thr Asp Glu His Leu Tyr Ser Gly Thr Ala Ser Asp Phe
        195                 200                 205

Leu Gly Lys Asp Thr Ala Phe Thr Arg Ser Leu Gly Leu Met Gln Asp
    210                 215                 220

His His Ser Ile Arg Thr Asp Ile Ser Glu His His Trp Leu Asn Gly
225                 230                 235                 240

Ala Lys Phe Ile Gly Thr Phe Pro Ile Pro Asp Thr Tyr Asn Pro Asp
                245                 250                 255

Asp Asp Lys Ile Tyr Phe Phe Phe Arg Glu Ser Ser Gln Glu Gly Ser
            260                 265                 270

Thr Ser Asp Arg Ser Ile Leu Ser Arg Val Gly Arg Val Cys Lys Asn
        275                 280                 285

Asp Val Gly Gly Gln Arg Ser Leu Ile Asn Lys Trp Thr Thr Phe Leu
    290                 295                 300

Lys Ala Arg Leu Ile Cys Ser Ile Pro Gly Ser Asp Gly Ala Asp Thr
305                 310                 315                 320

His Phe Asp Glu Leu Gln Asp Ile Tyr Leu Leu Pro Thr Arg Asp Glu
                325                 330                 335
```

```
Arg Asn Pro Val Val Tyr Gly Val Phe Thr Thr Thr Ser Ser Ile Phe
            340                 345                 350

Lys Gly Ser Ala Val Cys Val Tyr Ser Met Ala Asp Ile Arg Ala Val
        355                 360                 365

Phe Asn Gly Pro Tyr Ala His Lys Glu Ser Ala Asp His Arg Trp Val
    370                 375                 380

Gln Tyr Asp Gly Arg Ile Pro Tyr Pro Arg Pro Gly Thr Cys Pro Ser
385                 390                 395                 400

Lys Thr Tyr Asp Pro Leu Ile Lys Ser Thr Arg Asp Phe Pro Asp Asp
                405                 410                 415

Val Ile Ser Phe Ile Arg Arg His Pro Val Met Tyr Lys Ser Val Tyr
            420                 425                 430

Pro Val Ala Gly Ala Pro Thr Phe Lys Arg Ile Asn Val Asp Tyr Arg
        435                 440                 445

Leu Thr Gln Ile Val Val Asp His Val Val Ala Glu Asp Gly Gln Tyr
    450                 455                 460

Asp Val Met Phe Leu Gly Thr Asp Ile Gly Thr Val Leu Lys Val Val
465                 470                 475                 480

Ser Ile Ser Lys Glu Lys Trp Asn Met Glu Glu Val Val Leu Glu Glu
                485                 490                 495

Leu Gln Val Phe Lys His Pro Thr Ala Ile Leu Asn Met Glu Leu Ser
            500                 505                 510

Leu Lys Gln Gln Gln Leu Tyr Val Gly Ser Trp Asp Gly Leu Val Gln
        515                 520                 525

Leu Ser Leu His Arg Cys Asp Thr Tyr Gly Lys Ala Cys Ala Asp Cys
    530                 535                 540

Cys Leu Ala Arg Asp Pro Tyr Cys Ala Trp Asp Gly Asn Ala Cys Ser
545                 550                 555                 560

Arg Tyr Ala Pro Thr Ser Lys Arg Arg Ala Arg Arg Gln Asp Val Lys
                565                 570                 575

Tyr Gly Asp Pro Ile Thr Gln Cys Trp Asp Ile Glu Asp Ser Ile Ser
            580                 585                 590

His Glu Thr Ala Asp Glu Lys Val Ile Phe Gly Ile Glu Phe Asn Ser
        595                 600                 605

Thr Phe Leu Glu Cys Ile Pro Lys Ser Gln Gln Ala Ser Val Glu Trp
    610                 615                 620

Tyr Ile Gln Arg Ser Gly Asp Glu His Arg Glu Glu Leu Lys Pro Asp
625                 630                 635                 640

Glu Arg Ile Ile Lys Thr Asp Tyr Gly Leu Leu Ile Arg Ser Leu Gln
                645                 650                 655

Lys Lys Asp Ser Gly Met Tyr Tyr Cys Lys Ala Gln Glu His Thr Phe
            660                 665                 670

Ile His Thr Ile Val Lys Leu Thr Leu Asn Val Ile Glu Asn Glu Gln
        675                 680                 685

Met Glu Asn Thr Gln Arg Ala Glu Tyr Gln Glu Gly Gln Val Lys Asp
    690                 695                 700

Leu Leu Ala Glu Ser Arg Leu Arg Tyr Lys Asp Tyr Ile Gln Ile Leu
705                 710                 715                 720

Ser Ser Pro Asn Phe Ser Leu Asp Gln Tyr Cys Glu Gln Met Trp Tyr
                725                 730                 735

Lys Glu Lys Arg Arg Gln Arg Asn Lys Gly Ser Pro Lys Trp Lys His
            740                 745                 750
```

```
Met Gln Glu Met Lys Lys Lys Arg Asn Arg Arg His His Arg Asp Leu
        755                 760                 765

Asp Glu Leu Gln Arg Ser Val Ala Thr
    770                 775


<210> SEQ ID NO 17
<211> LENGTH: 2328
<212> TYPE: DNA
<213> ORGANISM: Homo sapiens
<220> FEATURE:
<223> OTHER INFORMATION: Codon optimized cDNA sequence Human SEMA3A
      A106K delta Ig-b
<220> FEATURE:
<221> NAME/KEY: CDS
<222> LOCATION: 1..2328
<223> OTHER INFORMATION: /transl_table=1

<400> SEQUENCE: 17

atg gga tgg ctg acc aga atc gtg tgc ctg ttc tgg ggc gtg ctg ctg       48
Met Gly Trp Leu Thr Arg Ile Val Cys Leu Phe Trp Gly Val Leu Leu
1               5                   10                  15

acc gcc aga gcc aac tac cag aac ggc aag aac aac gtg ccc cgg ctg       96
Thr Ala Arg Ala Asn Tyr Gln Asn Gly Lys Asn Asn Val Pro Arg Leu
            20                  25                  30

aag ctg agc tac aaa gag atg ctg gaa agc aac aac gtg atc acc ttc      144
Lys Leu Ser Tyr Lys Glu Met Leu Glu Ser Asn Asn Val Ile Thr Phe
        35                  40                  45

aac ggc ctg gcc aac agc agc agc tac cac acc ttt ctg ctg gac gag      192
Asn Gly Leu Ala Asn Ser Ser Ser Tyr His Thr Phe Leu Leu Asp Glu
    50                  55                  60

gaa cgg tcc cgg ctg tac gtg gga gcc aag gac cac atc ttc agc ttc      240
Glu Arg Ser Arg Leu Tyr Val Gly Ala Lys Asp His Ile Phe Ser Phe
65                  70                  75                  80

gac ctc gtg aac atc aag gac ttc cag aaa atc gtg tgg ccc gtg tcc      288
Asp Leu Val Asn Ile Lys Asp Phe Gln Lys Ile Val Trp Pro Val Ser
                85                  90                  95

tac acc aga cgg gac gag tgc aag tgg aag ggc aag gac atc ctg aaa      336
Tyr Thr Arg Arg Asp Glu Cys Lys Trp Lys Gly Lys Asp Ile Leu Lys
            100                 105                 110

gag tgc gcc aac ttc atc aag gtg ctg aag gcc tac aac cag acc cac      384
Glu Cys Ala Asn Phe Ile Lys Val Leu Lys Ala Tyr Asn Gln Thr His
        115                 120                 125

ctg tac gcc tgt ggc acc ggc gcc ttc cac cct atc tgc acc tac atc      432
Leu Tyr Ala Cys Gly Thr Gly Ala Phe His Pro Ile Cys Thr Tyr Ile
    130                 135                 140

gag atc ggc cac cac ccc gag gac aat atc ttc aag ctg gaa aac agc      480
Glu Ile Gly His His Pro Glu Asp Asn Ile Phe Lys Leu Glu Asn Ser
145                 150                 155                 160

cac ttc gag aac ggc aga ggc aag agc ccc tac gac ccc aag ctg ctg      528
His Phe Glu Asn Gly Arg Gly Lys Ser Pro Tyr Asp Pro Lys Leu Leu
                165                 170                 175

aca gcc tcc ctg ctg atc gac ggc gag ctg tac tct ggc aca gcc gcc      576
Thr Ala Ser Leu Leu Ile Asp Gly Glu Leu Tyr Ser Gly Thr Ala Ala
            180                 185                 190

gac ttc atg ggc cgg gac ttc gcc atc ttc aga acc ctg gga cac cac      624
Asp Phe Met Gly Arg Asp Phe Ala Ile Phe Arg Thr Leu Gly His His
        195                 200                 205

cac cca atc cgg acc gag cag cac gac agc aga tgg ctg aac gac cct      672
His Pro Ile Arg Thr Glu Gln His Asp Ser Arg Trp Leu Asn Asp Pro
    210                 215                 220

aag ttc atc agc gcc cac ctg atc agc gag agc gac aac cct gag gac      720
Lys Phe Ile Ser Ala His Leu Ile Ser Glu Ser Asp Asn Pro Glu Asp
```

-continued

```
225                 230                 235                 240

gac aag gtg tac ttc ttc ttc cgg gaa aac gcc atc gac ggg gag cac      768
Asp Lys Val Tyr Phe Phe Phe Arg Glu Asn Ala Ile Asp Gly Glu His
                245                 250                 255

agc gga aag gcc aca cac gcc aga atc ggc cag atc tgc aag aac gac      816
Ser Gly Lys Ala Thr His Ala Arg Ile Gly Gln Ile Cys Lys Asn Asp
            260                 265                 270

ttc ggc ggc cac cgg tcc ctc gtg aac aag tgg acc acc ttc ctg aag     864
Phe Gly Gly His Arg Ser Leu Val Asn Lys Trp Thr Thr Phe Leu Lys
        275                 280                 285

gcc cgg ctg atc tgt agc gtg cca ggc ccc aat ggc atc gac acc cac      912
Ala Arg Leu Ile Cys Ser Val Pro Gly Pro Asn Gly Ile Asp Thr His
    290                 295                 300

ttc gac gag ctg cag gac gtg ttc ctg atg aat ttc aag gac ccc aag      960
Phe Asp Glu Leu Gln Asp Val Phe Leu Met Asn Phe Lys Asp Pro Lys
305                 310                 315                 320

aac ccc gtg gtg tac ggc gtg ttc acc acc agc agc aac atc ttc aag     1008
Asn Pro Val Val Tyr Gly Val Phe Thr Thr Ser Ser Asn Ile Phe Lys
                325                 330                 335

ggc agc gcc gtg tgc atg tac agc atg agc gac gtg cgg cgg gtg ttc     1056
Gly Ser Ala Val Cys Met Tyr Ser Met Ser Asp Val Arg Arg Val Phe
            340                 345                 350

ctg gga cct tac gcc cat aga gat ggc ccc aat tac cag tgg gtg ccc     1104
Leu Gly Pro Tyr Ala His Arg Asp Gly Pro Asn Tyr Gln Trp Val Pro
        355                 360                 365

tac cag ggc aga gtg cct tac ccc aga cct ggc acc tgt ccc agc aag     1152
Tyr Gln Gly Arg Val Pro Tyr Pro Arg Pro Gly Thr Cys Pro Ser Lys
    370                 375                 380

acc ttt ggc ggc ttc gac agc acc aag gac ctg ccc gac gat gtg att     1200
Thr Phe Gly Gly Phe Asp Ser Thr Lys Asp Leu Pro Asp Asp Val Ile
385                 390                 395                 400

acc ttc gcc aga tcc cac ccc gcc atg tac aac ccc gtg ttc ccc atg     1248
Thr Phe Ala Arg Ser His Pro Ala Met Tyr Asn Pro Val Phe Pro Met
                405                 410                 415

aac aac cgg ccc atc gtg atc aag acc gac gtg aac tac cag ttc acc     1296
Asn Asn Arg Pro Ile Val Ile Lys Thr Asp Val Asn Tyr Gln Phe Thr
            420                 425                 430

cag atc gtg gtg gac aga gtg gac gcc gag gac ggc cag tac gac gtg     1344
Gln Ile Val Val Asp Arg Val Asp Ala Glu Asp Gly Gln Tyr Asp Val
        435                 440                 445

atg ttc atc ggc acc gac gtg ggc acc gtg ctg aaa gtg gtg tcc atc     1392
Met Phe Ile Gly Thr Asp Val Gly Thr Val Leu Lys Val Val Ser Ile
    450                 455                 460

ccc aaa gag act tgg tac gac ctg gaa gag gtg ctg ctg gaa gag atg     1440
Pro Lys Glu Thr Trp Tyr Asp Leu Glu Glu Val Leu Leu Glu Glu Met
465                 470                 475                 480

acc gtg ttc aga gag ccc acc gcc atc tcc gcc atg gaa ctg agc aca     1488
Thr Val Phe Arg Glu Pro Thr Ala Ile Ser Ala Met Glu Leu Ser Thr
                485                 490                 495

aag cag cag cag ctg tac atc ggc agc aca gct ggc gtg gca cag ctg     1536
Lys Gln Gln Gln Leu Tyr Ile Gly Ser Thr Ala Gly Val Ala Gln Leu
            500                 505                 510

cct ctg cac aga tgc gac atc tac ggc aag gcc tgc gcc gag tgt tgc     1584
Pro Leu His Arg Cys Asp Ile Tyr Gly Lys Ala Cys Ala Glu Cys Cys
        515                 520                 525

ctg gcc aga gat cct tac tgc gcc tgg gat ggc agc gcc tgc agc aga     1632
Leu Ala Arg Asp Pro Tyr Cys Ala Trp Asp Gly Ser Ala Cys Ser Arg
    530                 535                 540

tac ttc ccc acc gac aag acc cac aca tgc ccc cct tgt cct gcc cct     1680
```

```
Tyr Phe Pro Thr Asp Lys Thr His Thr Cys Pro Pro Cys Pro Ala Pro
545                 550                 555                 560

gaa ctg ctg gga ggc ccc tcc gtg ttt ctg ttc ccc cca aag ccc aag     1728
Glu Leu Leu Gly Gly Pro Ser Val Phe Leu Phe Pro Pro Lys Pro Lys
                565                 570                 575

gat acc ctg atg atc agc aga acc ccc gaa gtg acc tgc gtg gtg gtg     1776
Asp Thr Leu Met Ile Ser Arg Thr Pro Glu Val Thr Cys Val Val Val
            580                 585                 590

gac gtg tcc cac gag gac cct gaa gtg aag ttc aat tgg tac gtg gac     1824
Asp Val Ser His Glu Asp Pro Glu Val Lys Phe Asn Trp Tyr Val Asp
        595                 600                 605

ggc gtg gaa gtg cac aac gcc aag acc aag ccc aga gag gaa cag tac     1872
Gly Val Glu Val His Asn Ala Lys Thr Lys Pro Arg Glu Glu Gln Tyr
    610                 615                 620

aac agc acc tac cgc gtg gtg tcc gtg ctg acc gtg ctg cac cag gac     1920
Asn Ser Thr Tyr Arg Val Val Ser Val Leu Thr Val Leu His Gln Asp
625                 630                 635                 640

tgg ctg aat ggc aaa gag tac aag tgc aag gtg tcc aac aag gcc ctg     1968
Trp Leu Asn Gly Lys Glu Tyr Lys Cys Lys Val Ser Asn Lys Ala Leu
                645                 650                 655

cct gcc ccc atc gag aaa acc atc agc aag gcc aag ggc cag ccc cgc     2016
Pro Ala Pro Ile Glu Lys Thr Ile Ser Lys Ala Lys Gly Gln Pro Arg
            660                 665                 670

gaa ccc cag gtg tac aca ctg ccc cct agc agg gac gag ctg acc aag     2064
Glu Pro Gln Val Tyr Thr Leu Pro Pro Ser Arg Asp Glu Leu Thr Lys
        675                 680                 685

aac cag gtg tcc ctg acc tgt ctc gtg aag ggc ttc tac ccc tcc gat     2112
Asn Gln Val Ser Leu Thr Cys Leu Val Lys Gly Phe Tyr Pro Ser Asp
    690                 695                 700

atc gcc gtg gaa tgg gag agc aac ggc cag ccc gag aac aac tac aag     2160
Ile Ala Val Glu Trp Glu Ser Asn Gly Gln Pro Glu Asn Asn Tyr Lys
705                 710                 715                 720

acc acc ccc cct gtg ctg gac agc gac ggc tca ttc ttc ctg tac agc     2208
Thr Thr Pro Pro Val Leu Asp Ser Asp Gly Ser Phe Phe Leu Tyr Ser
                725                 730                 735

aag ctg aca gtg gac aag agc cgg tgg cag cag ggc aac gtg ttc agc     2256
Lys Leu Thr Val Asp Lys Ser Arg Trp Gln Gln Gly Asn Val Phe Ser
            740                 745                 750

tgc agc gtg atg cac gag gcc ctg cac aac cac tac acc cag aag tcc     2304
Cys Ser Val Met His Glu Ala Leu His Asn His Tyr Thr Gln Lys Ser
        755                 760                 765

ctg agc ctg agc ccc ggc aaa tga                                     2328
Leu Ser Leu Ser Pro Gly Lys
    770                 775


<210> SEQ ID NO 18
<211> LENGTH: 775
<212> TYPE: PRT
<213> ORGANISM: Homo sapiens
<220> FEATURE:
<223> OTHER INFORMATION: Translation of codon optimized cDNA sequence
      Human SEMA3A A106K delta Ig-b

<400> SEQUENCE: 18

Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45
```

-continued

```
Asn Gly Leu Ala Asn Ser Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Lys Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Lys Phe Ile Ser Ala His Leu Ile Ser Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Phe Lys Asp Pro Lys
305                 310                 315                 320

Asn Pro Val Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Met
                405                 410                 415

Asn Asn Arg Pro Ile Val Ile Lys Thr Asp Val Asn Tyr Gln Phe Thr
            420                 425                 430

Gln Ile Val Val Asp Arg Val Asp Ala Glu Asp Gly Gln Tyr Asp Val
        435                 440                 445

Met Phe Ile Gly Thr Asp Val Gly Thr Val Leu Lys Val Val Ser Ile
    450                 455                 460

Pro Lys Glu Thr Trp Tyr Asp Leu Glu Glu Val Leu Leu Glu Glu Met
```

```
465                 470                 475                 480

Thr Val Phe Arg Glu Pro Thr Ala Ile Ser Ala Met Glu Leu Ser Thr
                485                 490                 495

Lys Gln Gln Gln Leu Tyr Ile Gly Ser Thr Ala Gly Val Ala Gln Leu
            500                 505                 510

Pro Leu His Arg Cys Asp Ile Tyr Gly Lys Ala Cys Ala Glu Cys Cys
        515                 520                 525

Leu Ala Arg Asp Pro Tyr Cys Ala Trp Asp Gly Ser Ala Cys Ser Arg
    530                 535                 540

Tyr Phe Pro Thr Asp Lys Thr His Thr Cys Pro Pro Cys Pro Ala Pro
545                 550                 555                 560

Glu Leu Leu Gly Gly Pro Ser Val Phe Leu Phe Pro Pro Lys Pro Lys
                565                 570                 575

Asp Thr Leu Met Ile Ser Arg Thr Pro Glu Val Thr Cys Val Val Val
            580                 585                 590

Asp Val Ser His Glu Asp Pro Glu Val Lys Phe Asn Trp Tyr Val Asp
        595                 600                 605

Gly Val Glu Val His Asn Ala Lys Thr Lys Pro Arg Glu Glu Gln Tyr
    610                 615                 620

Asn Ser Thr Tyr Arg Val Val Ser Val Leu Thr Val Leu His Gln Asp
625                 630                 635                 640

Trp Leu Asn Gly Lys Glu Tyr Lys Cys Lys Val Ser Asn Lys Ala Leu
                645                 650                 655

Pro Ala Pro Ile Glu Lys Thr Ile Ser Lys Ala Lys Gly Gln Pro Arg
            660                 665                 670

Glu Pro Gln Val Tyr Thr Leu Pro Pro Ser Arg Asp Glu Leu Thr Lys
        675                 680                 685

Asn Gln Val Ser Leu Thr Cys Leu Val Lys Gly Phe Tyr Pro Ser Asp
    690                 695                 700

Ile Ala Val Glu Trp Glu Ser Asn Gly Gln Pro Glu Asn Asn Tyr Lys
705                 710                 715                 720

Thr Thr Pro Pro Val Leu Asp Ser Asp Gly Ser Phe Phe Leu Tyr Ser
                725                 730                 735

Lys Leu Thr Val Asp Lys Ser Arg Trp Gln Gln Gly Asn Val Phe Ser
            740                 745                 750

Cys Ser Val Met His Glu Ala Leu His Asn His Tyr Thr Gln Lys Ser
        755                 760                 765

Leu Ser Leu Ser Pro Gly Lys
    770                 775


<210> SEQ ID NO 19
<211> LENGTH: 2313
<212> TYPE: DNA
<213> ORGANISM: Mus musculus
<220> FEATURE:
<223> OTHER INFORMATION: Codon optimized cDNA sequence Mouse Sema3A
      A106K delta Ig-b
<220> FEATURE:
<221> NAME/KEY: CDS
<222> LOCATION: 1..2313
<223> OTHER INFORMATION: /transl_table=1

<400> SEQUENCE: 19

atg gga tgg ttt act gga att gcc tgt ctg ttt tgg gga gtg ctt ctg       48
Met Gly Trp Phe Thr Gly Ile Ala Cys Leu Phe Trp Gly Val Leu Leu
1               5                   10                  15

act gcc aga gca aat tac gcc aat ggc aag aac aac gtc ccc aga ctg       96
```

-continued

```
Thr Ala Arg Ala Asn Tyr Ala Asn Gly Lys Asn Asn Val Pro Arg Leu
            20                  25                  30

aag ctc tct tac aag gag atg ctg gag tct aac aat gtg att aca ttc      144
Lys Leu Ser Tyr Lys Glu Met Leu Glu Ser Asn Asn Val Ile Thr Phe
        35                  40                  45

aat ggc ctt gcc aac tct tcc tca tac cac acc ttt ctg ctg gat gag      192
Asn Gly Leu Ala Asn Ser Ser Ser Tyr His Thr Phe Leu Leu Asp Glu
    50                  55                  60

gag cgc tca cgg ctg tat gtg gga gcc aag gac cat att ttc agt ttt      240
Glu Arg Ser Arg Leu Tyr Val Gly Ala Lys Asp His Ile Phe Ser Phe
65                  70                  75                  80

aat ctc gtg aat atc aag gat ttt cag aag atc gta tgg cct gtc tca      288
Asn Leu Val Asn Ile Lys Asp Phe Gln Lys Ile Val Trp Pro Val Ser
                85                  90                  95

tat acc cgc aga gac gag tgc aaa tgg aag ggc aaa gat ata ctg aag      336
Tyr Thr Arg Arg Asp Glu Cys Lys Trp Lys Gly Lys Asp Ile Leu Lys
            100                 105                 110

gaa tgc gca aat ttc att aag gtg ctc gag gca tac aac cag aca cac      384
Glu Cys Ala Asn Phe Ile Lys Val Leu Glu Ala Tyr Asn Gln Thr His
        115                 120                 125

ttg tat gcc tgt ggg act ggc gcg ttc cat cct att tgt aca tac atc      432
Leu Tyr Ala Cys Gly Thr Gly Ala Phe His Pro Ile Cys Thr Tyr Ile
    130                 135                 140

gag gtg gga cat cat ccg gag gac aac atc ttc aag ttg cag gat agc      480
Glu Val Gly His His Pro Glu Asp Asn Ile Phe Lys Leu Gln Asp Ser
145                 150                 155                 160

cac ttc gag aac ggc agg gga aag tca cct tac gac cca aaa ctc ctg      528
His Phe Glu Asn Gly Arg Gly Lys Ser Pro Tyr Asp Pro Lys Leu Leu
                165                 170                 175

act gct tcc ctg ctt atc gac ggt gaa ctc tac tct ggc acc gca gcc      576
Thr Ala Ser Leu Leu Ile Asp Gly Glu Leu Tyr Ser Gly Thr Ala Ala
            180                 185                 190

gac ttt atg ggc aga gac ttt gct ata ttc agg acc ctc gga cat cat      624
Asp Phe Met Gly Arg Asp Phe Ala Ile Phe Arg Thr Leu Gly His His
        195                 200                 205

cat ccg att cgg acc gag caa cac gac tca cgc tgg ctg aat gac ccc      672
His Pro Ile Arg Thr Glu Gln His Asp Ser Arg Trp Leu Asn Asp Pro
    210                 215                 220

aga ttc att tca gcc cac ctg atc ccc gaa agt gat aac cca gag gac      720
Arg Phe Ile Ser Ala His Leu Ile Pro Glu Ser Asp Asn Pro Glu Asp
225                 230                 235                 240

gac aaa gta tac ttc ttc ttt cgc gag aat gct ata gac ggc gag cac      768
Asp Lys Val Tyr Phe Phe Phe Arg Glu Asn Ala Ile Asp Gly Glu His
                245                 250                 255

agc gga aag gct act cat gct cgg atc ggg caa atc tgt aaa aac gat      816
Ser Gly Lys Ala Thr His Ala Arg Ile Gly Gln Ile Cys Lys Asn Asp
            260                 265                 270

ttt gga ggc cat cga tca ttg gtt aac aag tgg acc aca ttt ctt aaa      864
Phe Gly Gly His Arg Ser Leu Val Asn Lys Trp Thr Thr Phe Leu Lys
        275                 280                 285

gca aga ctt atc tgc tct gtg cct ggt cca aac ggg ata gat act cat      912
Ala Arg Leu Ile Cys Ser Val Pro Gly Pro Asn Gly Ile Asp Thr His
    290                 295                 300

ttc gac gag ctg cag gac gtg ttc ctt atg aac agt aag gac ccg aag      960
Phe Asp Glu Leu Gln Asp Val Phe Leu Met Asn Ser Lys Asp Pro Lys
305                 310                 315                 320

aac cct atc gtg tac gga gtt ttt acg acg tcc tcc aac atc ttc aag     1008
Asn Pro Ile Val Tyr Gly Val Phe Thr Thr Ser Ser Asn Ile Phe Lys
                325                 330                 335
```

-continued

```
ggc tca gca gtc tgc atg tat agc atg agc gac gtc cgg agg gtc ttc      1056
Gly Ser Ala Val Cys Met Tyr Ser Met Ser Asp Val Arg Arg Val Phe
            340                 345                 350

ctc gga ccc tac gca cac cgc gat ggc ccc aat tat cag tgg gtt cct      1104
Leu Gly Pro Tyr Ala His Arg Asp Gly Pro Asn Tyr Gln Trp Val Pro
        355                 360                 365

tat caa ggg aga gta cct tac cct aga cca ggg aca tgt cca tcc aag      1152
Tyr Gln Gly Arg Val Pro Tyr Pro Arg Pro Gly Thr Cys Pro Ser Lys
    370                 375                 380

aca ttc gga ggt ttt gat tca acc aag gac ttg cca gac gat gtc ata      1200
Thr Phe Gly Gly Phe Asp Ser Thr Lys Asp Leu Pro Asp Asp Val Ile
385                 390                 395                 400

acc ttc gcc aga tca cac ccc gcc atg tac aat cct gtt ttt ccg att      1248
Thr Phe Ala Arg Ser His Pro Ala Met Tyr Asn Pro Val Phe Pro Ile
                405                 410                 415

aac aac cgc ccc att atg atc aaa act gat gtg aac tat caa ttc acc      1296
Asn Asn Arg Pro Ile Met Ile Lys Thr Asp Val Asn Tyr Gln Phe Thr
            420                 425                 430

cag att gtt gta gat aga gtt gat gct gag gat ggc cag tat gat gtc      1344
Gln Ile Val Val Asp Arg Val Asp Ala Glu Asp Gly Gln Tyr Asp Val
        435                 440                 445

atg ttc atc ggt aca gac gtg gga aca gtc ttg aaa gtc gtt tct gtc      1392
Met Phe Ile Gly Thr Asp Val Gly Thr Val Leu Lys Val Val Ser Val
    450                 455                 460

cct aaa gag acc tgg cac gac ctg gaa gag gtc ctc ctg gag gag atg      1440
Pro Lys Glu Thr Trp His Asp Leu Glu Glu Val Leu Leu Glu Glu Met
465                 470                 475                 480

aca gtg ttc cgg gag ccc acc aca atc agc gcc atg gaa ctc tct acc      1488
Thr Val Phe Arg Glu Pro Thr Thr Ile Ser Ala Met Glu Leu Ser Thr
                485                 490                 495

aag cag cag cag ctc tac atc ggt tcc aca gct ggg gtg gct cag ctt      1536
Lys Gln Gln Gln Leu Tyr Ile Gly Ser Thr Ala Gly Val Ala Gln Leu
            500                 505                 510

ccc ctc cac aga tgc gac ata tac ggg aag gcc tgt gct gag tgc tgc      1584
Pro Leu His Arg Cys Asp Ile Tyr Gly Lys Ala Cys Ala Glu Cys Cys
        515                 520                 525

ctg gcc aga gat ccc tac tgc gcg tgg gat ggt tca agt tgc agt cga      1632
Leu Ala Arg Asp Pro Tyr Cys Ala Trp Asp Gly Ser Ser Cys Ser Arg
    530                 535                 540

tac ttc ccc aca ggg tgc aag cct tgt att tgt act gtg ccc gaa gtg      1680
Tyr Phe Pro Thr Gly Cys Lys Pro Cys Ile Cys Thr Val Pro Glu Val
545                 550                 555                 560

tcc tcc gtg ttc atc ttt cca ccc aag cct aag gac gtt ttg aca ata      1728
Ser Ser Val Phe Ile Phe Pro Pro Lys Pro Lys Asp Val Leu Thr Ile
                565                 570                 575

acg ctg acc cca aag gtg acg tgc gtt gtg gtc gat atc agc aag gac      1776
Thr Leu Thr Pro Lys Val Thr Cys Val Val Val Asp Ile Ser Lys Asp
            580                 585                 590

gat cca gaa gtc cag ttt tct tgg ttt gtt gat gat gtg gaa gta cac      1824
Asp Pro Glu Val Gln Phe Ser Trp Phe Val Asp Asp Val Glu Val His
        595                 600                 605

act gcg caa aca cag cct agg gaa gag cag ttt aac tct act ttt agg      1872
Thr Ala Gln Thr Gln Pro Arg Glu Glu Gln Phe Asn Ser Thr Phe Arg
    610                 615                 620

agc gta agc gag ctg ccg att atg cat cag gac tgg ttg aat ggg aag      1920
Ser Val Ser Glu Leu Pro Ile Met His Gln Asp Trp Leu Asn Gly Lys
625                 630                 635                 640

gag ttc aaa tgt cgc gtt aac tcc gca gcc ttc ccc gca cct atc gaa      1968
Glu Phe Lys Cys Arg Val Asn Ser Ala Ala Phe Pro Ala Pro Ile Glu
                645                 650                 655
```

-continued

```
aaa acg atc tca aag act aag ggt agg cca aaa gcg cca cag gta tac     2016
Lys Thr Ile Ser Lys Thr Lys Gly Arg Pro Lys Ala Pro Gln Val Tyr
            660                 665                 670

acc att cct cca ccg aag gaa cag atg gca aaa gat aag gtt tca ctg     2064
Thr Ile Pro Pro Pro Lys Glu Gln Met Ala Lys Asp Lys Val Ser Leu
        675                 680                 685

aca tgc atg att act gac ttt ttc ccc gag gat atc acc gtg gaa tgg     2112
Thr Cys Met Ile Thr Asp Phe Phe Pro Glu Asp Ile Thr Val Glu Trp
    690                 695                 700

cag tgg aat ggc caa ccc gca gag aac tat aag aac act caa cca att     2160
Gln Trp Asn Gly Gln Pro Ala Glu Asn Tyr Lys Asn Thr Gln Pro Ile
705                 710                 715                 720

atg gac aca gac ggc tca tat ttc gtg tac tct aag ctg aat gtc cag     2208
Met Asp Thr Asp Gly Ser Tyr Phe Val Tyr Ser Lys Leu Asn Val Gln
                725                 730                 735

aag tca aat tgg gaa gct gga aac acg ttt acc tgt agt gtg ttg cat     2256
Lys Ser Asn Trp Glu Ala Gly Asn Thr Phe Thr Cys Ser Val Leu His
            740                 745                 750

gag gga ctg cac aac cat cat acc gaa aag tca ttg tcc cat agc cca     2304
Glu Gly Leu His Asn His His Thr Glu Lys Ser Leu Ser His Ser Pro
        755                 760                 765

gga aag tga                                                         2313
Gly Lys
    770


<210> SEQ ID NO 20
<211> LENGTH: 770
<212> TYPE: PRT
<213> ORGANISM: Mus musculus
<220> FEATURE:
<223> OTHER INFORMATION: Translation of codon optimized cDNA sequence
      Mouse Sema3A A106K delta Ig-b

<400> SEQUENCE: 20

Met Gly Trp Phe Thr Gly Ile Ala Cys Leu Phe Trp Gly Val Leu Leu
1               5                   10                  15

Thr Ala Arg Ala Asn Tyr Ala Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asn Leu Val Asn Ile Lys Asp Phe Gln Lys Ile Val Trp Pro Val Ser
                85                  90                  95

Tyr Thr Arg Arg Asp Glu Cys Lys Trp Lys Gly Lys Asp Ile Leu Lys
            100                 105                 110

Glu Cys Ala Asn Phe Ile Lys Val Leu Glu Ala Tyr Asn Gln Thr His
        115                 120                 125

Leu Tyr Ala Cys Gly Thr Gly Ala Phe His Pro Ile Cys Thr Tyr Ile
    130                 135                 140

Glu Val Gly His His Pro Glu Asp Asn Ile Phe Lys Leu Gln Asp Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190
```

```
Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Arg Phe Ile Ser Ala His Leu Ile Pro Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Ser Lys Asp Pro Lys
305                 310                 315                 320

Asn Pro Ile Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Ile
                405                 410                 415

Asn Asn Arg Pro Ile Met Ile Lys Thr Asp Val Asn Tyr Gln Phe Thr
            420                 425                 430

Gln Ile Val Val Asp Arg Val Asp Ala Glu Asp Gly Gln Tyr Asp Val
        435                 440                 445

Met Phe Ile Gly Thr Asp Val Gly Thr Val Leu Lys Val Val Ser Val
    450                 455                 460

Pro Lys Glu Thr Trp His Asp Leu Glu Glu Val Leu Leu Glu Glu Met
465                 470                 475                 480

Thr Val Phe Arg Glu Pro Thr Thr Ile Ser Ala Met Glu Leu Ser Thr
                485                 490                 495

Lys Gln Gln Gln Leu Tyr Ile Gly Ser Thr Ala Gly Val Ala Gln Leu
            500                 505                 510

Pro Leu His Arg Cys Asp Ile Tyr Gly Lys Ala Cys Ala Glu Cys Cys
        515                 520                 525

Leu Ala Arg Asp Pro Tyr Cys Ala Trp Asp Gly Ser Ser Cys Ser Arg
    530                 535                 540

Tyr Phe Pro Thr Gly Cys Lys Pro Cys Ile Cys Thr Val Pro Glu Val
545                 550                 555                 560

Ser Ser Val Phe Ile Phe Pro Pro Lys Pro Lys Asp Val Leu Thr Ile
                565                 570                 575

Thr Leu Thr Pro Lys Val Thr Cys Val Val Val Asp Ile Ser Lys Asp
            580                 585                 590

Asp Pro Glu Val Gln Phe Ser Trp Phe Val Asp Asp Val Glu Val His
        595                 600                 605
```

-continued

```
Thr Ala Gln Thr Gln Pro Arg Glu Glu Gln Phe Asn Ser Thr Phe Arg
    610                 615                 620

Ser Val Ser Glu Leu Pro Ile Met His Gln Asp Trp Leu Asn Gly Lys
625                 630                 635                 640

Glu Phe Lys Cys Arg Val Asn Ser Ala Ala Phe Pro Ala Pro Ile Glu
                645                 650                 655

Lys Thr Ile Ser Lys Thr Lys Gly Arg Pro Lys Ala Pro Gln Val Tyr
            660                 665                 670

Thr Ile Pro Pro Pro Lys Glu Gln Met Ala Lys Asp Lys Val Ser Leu
        675                 680                 685

Thr Cys Met Ile Thr Asp Phe Phe Pro Glu Asp Ile Thr Val Glu Trp
    690                 695                 700

Gln Trp Asn Gly Gln Pro Ala Glu Asn Tyr Lys Asn Thr Gln Pro Ile
705                 710                 715                 720

Met Asp Thr Asp Gly Ser Tyr Phe Val Tyr Ser Lys Leu Asn Val Gln
                725                 730                 735

Lys Ser Asn Trp Glu Ala Gly Asn Thr Phe Thr Cys Ser Val Leu His
            740                 745                 750

Glu Gly Leu His Asn His His Thr Glu Lys Ser Leu Ser His Ser Pro
        755                 760                 765

Gly Lys
    770


<210> SEQ ID NO 21
<211> LENGTH: 202
<212> TYPE: PRT
<213> ORGANISM: Homo sapiens
<220> FEATURE:
<223> OTHER INFORMATION: SEMA3A 96-297

<400> SEQUENCE: 21

Ser Tyr Thr Arg Arg Asp Glu Cys Lys Trp Ala Gly Lys Asp Ile Leu
1               5                   10                  15

Lys Glu Cys Ala Asn Phe Ile Lys Val Leu Lys Ala Tyr Asn Gln Thr
            20                  25                  30

His Leu Tyr Ala Cys Gly Thr Gly Ala Phe His Pro Ile Cys Thr Tyr
        35                  40                  45

Ile Glu Ile Gly His His Pro Glu Asp Asn Ile Phe Lys Leu Glu Asn
    50                  55                  60

Ser His Phe Glu Asn Gly Arg Gly Lys Ser Pro Tyr Asp Pro Lys Leu
65                  70                  75                  80

Leu Thr Ala Ser Leu Leu Ile Asp Gly Glu Leu Tyr Ser Gly Thr Ala
                85                  90                  95

Ala Asp Phe Met Gly Arg Asp Phe Ala Ile Phe Arg Thr Leu Gly His
            100                 105                 110

His His Pro Ile Arg Thr Glu Gln His Asp Ser Arg Trp Leu Asn Asp
        115                 120                 125

Pro Lys Phe Ile Ser Ala His Leu Ile Ser Glu Ser Asp Asn Pro Glu
    130                 135                 140

Asp Asp Lys Val Tyr Phe Phe Phe Arg Glu Asn Ala Ile Asp Gly Glu
145                 150                 155                 160

His Ser Gly Lys Ala Thr His Ala Arg Ile Gly Gln Ile Cys Lys Asn
                165                 170                 175

Asp Phe Gly Gly His Arg Ser Leu Val Asn Lys Trp Thr Thr Phe Leu
            180                 185                 190
```

```
Lys Ala Arg Leu Ile Cys Ser Val Pro Gly
        195                 200


<210> SEQ ID NO 22
<211> LENGTH: 203
<212> TYPE: PRT
<213> ORGANISM: Homo sapiens
<220> FEATURE:
<223> OTHER INFORMATION: SEMA3B 95-297

<400> SEQUENCE: 22

Pro Val Glu Trp Arg Glu Glu Cys Asn Trp Ala Gly Lys Asp Ile Gly
1               5                   10                  15

Thr Glu Cys Met Asn Phe Val Lys Leu Leu His Ala Tyr Asn Arg Thr
            20                  25                  30

His Leu Leu Ala Cys Gly Thr Gly Ala Phe His Pro Thr Cys Ala Phe
        35                  40                  45

Val Glu Val Gly His Arg Ala Glu Glu Pro Val Leu Arg Leu Asp Pro
    50                  55                  60

Gly Arg Ile Glu Asp Gly Lys Gly Lys Ser Pro Tyr Asp Pro Arg His
65                  70                  75                  80

Arg Ala Ala Ser Val Leu Val Gly Glu Glu Leu Tyr Ser Gly Val Ala
                85                  90                  95

Ala Asp Leu Met Gly Arg Asp Phe Thr Ile Phe Arg Ser Leu Gly Gln
            100                 105                 110

Arg Pro Ser Leu Arg Thr Glu Pro His Asp Ser Arg Trp Leu Asn Glu
        115                 120                 125

Pro Lys Phe Val Lys Val Phe Trp Ile Pro Glu Ser Glu Asn Pro Asp
    130                 135                 140

Asp Asp Lys Ile Tyr Phe Phe Phe Arg Glu Thr Ala Val Glu Ala Ala
145                 150                 155                 160

Pro Ala Leu Gly Arg Leu Ser Val Ser Arg Val Gly Gln Ile Cys Arg
                165                 170                 175

Asn Asp Val Gly Gly Gln Arg Ser Leu Val Asn Lys Trp Thr Thr Phe
            180                 185                 190

Leu Lys Ala Arg Leu Val Cys Ser Val Pro Gly
        195                 200


<210> SEQ ID NO 23
<211> LENGTH: 201
<212> TYPE: PRT
<213> ORGANISM: Homo sapiens
<220> FEATURE:
<223> OTHER INFORMATION: SEMA3C 94-294

<400> SEQUENCE: 23

Ser Thr Ile Lys Val Glu Glu Cys Lys Met Ala Gly Lys Asp Pro Thr
1               5                   10                  15

His Gly Cys Gly Asn Phe Val Arg Val Ile Gln Thr Phe Asn Arg Thr
            20                  25                  30

His Leu Tyr Val Cys Gly Ser Gly Ala Phe Ser Pro Val Cys Thr Tyr
        35                  40                  45

Leu Asn Arg Gly Arg Arg Ser Glu Asp Gln Val Phe Met Ile Asp Ser
    50                  55                  60

Lys Cys Glu Ser Gly Lys Gly Arg Cys Ser Phe Asn Pro Asn Val Asn
65                  70                  75                  80

Thr Val Ser Val Met Ile Asn Glu Glu Leu Phe Ser Gly Met Tyr Ile
                85                  90                  95
```

Asp Phe Met Gly Thr Asp Ala Ala Ile Phe Arg Ser Leu Thr Lys Arg
100 105 110

Asn Ala Val Arg Thr Asp Gln His Asn Ser Lys Trp Leu Ser Glu Pro
115 120 125

Met Phe Val Asp Ala His Val Ile Pro Asp Gly Thr Asp Pro Asn Asp
130 135 140

Ala Lys Val Tyr Phe Phe Phe Lys Glu Lys Leu Thr Asp Asn Asn Arg
145 150 155 160

Ser Thr Lys Gln Ile His Ser Met Ile Ala Arg Ile Cys Pro Asn Asp
165 170 175

Thr Gly Gly Leu Arg Ser Leu Val Asn Lys Trp Thr Thr Phe Leu Lys
180 185 190

Ala Arg Leu Val Cys Ser Val Thr Asp
195 200

<210> SEQ ID NO 24
<211> LENGTH: 205
<212> TYPE: PRT
<213> ORGANISM: Homo sapiens
<220> FEATURE:
<223> OTHER INFORMATION: SEMA3D 110-314

<400> SEQUENCE: 24

Ala Lys Glu Arg Val Glu Leu Cys Lys Leu Ala Gly Lys Asp Ala Asn
1 5 10 15

Thr Glu Cys Ala Asn Phe Ile Arg Val Leu Gln Pro Tyr Asn Lys Thr
20 25 30

His Ile Tyr Val Cys Gly Thr Gly Ala Phe His Pro Ile Cys Gly Tyr
35 40 45

Ile Asp Leu Gly Val Tyr Lys Glu Asp Ile Ile Phe Lys Leu Asp Thr
50 55 60

His Asn Leu Glu Ser Gly Arg Leu Lys Cys Pro Phe Asp Pro Gln Gln
65 70 75 80

Pro Phe Ala Ser Val Met Thr Asp Glu Tyr Leu Tyr Ser Gly Thr Ala
85 90 95

Ser Asp Phe Leu Gly Lys Asp Thr Ala Phe Thr Arg Ser Leu Gly Pro
100 105 110

Thr His Asp His His Tyr Ile Arg Thr Asp Ile Ser Glu His Tyr Trp
115 120 125

Leu Asn Gly Ala Lys Phe Ile Gly Thr Phe Phe Ile Pro Asp Thr Tyr
130 135 140

Asn Pro Asp Asp Asp Lys Ile Tyr Phe Phe Phe Arg Glu Ser Ser Gln
145 150 155 160

Glu Gly Ser Thr Ser Asp Lys Thr Ile Leu Ser Arg Val Gly Arg Val
165 170 175

Cys Lys Asn Asp Val Gly Gly Gln Arg Ser Leu Ile Asn Lys Trp Thr
180 185 190

Thr Phe Leu Lys Ala Arg Leu Ile Cys Ser Ile Pro Gly
195 200 205

<210> SEQ ID NO 25
<211> LENGTH: 10
<212> TYPE: PRT
<213> ORGANISM: Homo sapiens
<220> FEATURE:
<223> OTHER INFORMATION: SEMA3A 104-113

<400> SEQUENCE: 25

Lys Trp Ala Gly Lys Asp Ile Leu Lys Glu
1 5 10

<210> SEQ ID NO 26
<211> LENGTH: 8
<212> TYPE: PRT
<213> ORGANISM: Homo sapiens
<220> FEATURE:
<223> OTHER INFORMATION: SEMA3A 214-221

<400> SEQUENCE: 26

Glu Gln His Asp Ser Arg Trp Leu
1 5

<210> SEQ ID NO 27
<211> LENGTH: 14
<212> TYPE: PRT
<213> ORGANISM: Homo sapiens
<220> FEATURE:
<223> OTHER INFORMATION: SEMA3A 274-287

<400> SEQUENCE: 27

Gly Gly His Arg Ser Leu Val Asn Lys Trp Thr Thr Phe Leu
1 5 10

<210> SEQ ID NO 28
<211> LENGTH: 10
<212> TYPE: PRT
<213> ORGANISM: Homo sapiens
<220> FEATURE:
<223> OTHER INFORMATION: SEMA3B 103-112

<400> SEQUENCE: 28

Asn Trp Ala Gly Lys Asp Ile Gly Thr Glu
1 5 10

<210> SEQ ID NO 29
<211> LENGTH: 8
<212> TYPE: PRT
<213> ORGANISM: Homo sapiens
<220> FEATURE:
<223> OTHER INFORMATION: SEMA3B 213-220

<400> SEQUENCE: 29

Glu Pro His Asp Ser Arg Trp Leu
1 5

<210> SEQ ID NO 30
<211> LENGTH: 14
<212> TYPE: PRT
<213> ORGANISM: Homo sapiens
<220> FEATURE:
<223> OTHER INFORMATION: SEMA3B 274-287

<400> SEQUENCE: 30

Gly Gly Gln Arg Ser Leu Val Asn Lys Trp Thr Thr Phe Leu
1 5 10

<210> SEQ ID NO 31
<211> LENGTH: 10
<212> TYPE: PRT
<213> ORGANISM: Homo sapiens
<220> FEATURE:
<223> OTHER INFORMATION: SEMA3C 102-111

<400> SEQUENCE: 31

Lys Met Ala Gly Lys Asp Pro Thr His Gly
1 5 10

<210> SEQ ID NO 32
<211> LENGTH: 8
<212> TYPE: PRT
<213> ORGANISM: Homo sapiens
<220> FEATURE:
<223> OTHER INFORMATION: SEMA3C 211-218

<400> SEQUENCE: 32

Asp Gln His Asn Ser Lys Trp Leu
1 5

<210> SEQ ID NO 33
<211> LENGTH: 14
<212> TYPE: PRT
<213> ORGANISM: Homo sapiens
<220> FEATURE:
<223> OTHER INFORMATION: SEMA3C 271-284

<400> SEQUENCE: 33

Gly Gly Leu Arg Ser Leu Val Asn Lys Trp Thr Thr Phe Leu
1 5 10

<210> SEQ ID NO 34
<211> LENGTH: 10
<212> TYPE: PRT
<213> ORGANISM: Homo sapiens
<220> FEATURE:
<223> OTHER INFORMATION: SEMA3D 118-127

<400> SEQUENCE: 34

Lys Leu Ala Gly Lys Asp Ala Asn Thr Glu
1 5 10

<210> SEQ ID NO 35
<211> LENGTH: 8
<212> TYPE: PRT
<213> ORGANISM: Homo sapiens
<220> FEATURE:
<223> OTHER INFORMATION: SEMA3D 231-238

<400> SEQUENCE: 35

Asp Ile Ser Glu His Tyr Trp Leu
1 5

<210> SEQ ID NO 36
<211> LENGTH: 14
<212> TYPE: PRT
<213> ORGANISM: Homo sapiens
<220> FEATURE:
<223> OTHER INFORMATION: SEMA3D 291-304

<400> SEQUENCE: 36

Gly Gly Gln Arg Ser Leu Ile Asn Lys Trp Thr Thr Phe Leu
1 5 10

<210> SEQ ID NO 37
<211> LENGTH: 990
<212> TYPE: DNA
<213> ORGANISM: Homo sapiens
<220> FEATURE:
<223> OTHER INFORMATION: immunoglobulin heavy chain constant region
gamma 1 (IGHG1 gene) (>gi| 12054071|ref| AJ294730.1|)
<220> FEATURE:
<221> NAME/KEY: CDS

```
<222> LOCATION: 1..990
<223> OTHER INFORMATION: /transl_table=1

<400> SEQUENCE: 37

gca agc ttc aag ggc cca tcg gtc ttc ccc ctg gca ccc tcc tcc aag       48
Ala Ser Phe Lys Gly Pro Ser Val Phe Pro Leu Ala Pro Ser Ser Lys
1               5                   10                  15

agc acc tct ggg ggc aca gcg gcc ctg ggc tgc ctg gtc aag gac tac       96
Ser Thr Ser Gly Gly Thr Ala Ala Leu Gly Cys Leu Val Lys Asp Tyr
            20                  25                  30

ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
        35                  40                  45

ggc gtg cac acc ttc ccg gct gtc cta cag tcc tca gga ctc tac tcc      192
Gly Val His Thr Phe Pro Ala Val Leu Gln Ser Ser Gly Leu Tyr Ser
    50                  55                  60

ctc agc agc gtg gtg acc gtg ccc tcc agc agc ttg ggc acc cag acc      240
Leu Ser Ser Val Val Thr Val Pro Ser Ser Ser Leu Gly Thr Gln Thr
65                  70                  75                  80

tac atc tgc aac gtg aat cac aag ccc agc aac acc aag gtg gac aag      288
Tyr Ile Cys Asn Val Asn His Lys Pro Ser Asn Thr Lys Val Asp Lys
                85                  90                  95

aaa gtt gag ccc aaa tct tgt gac aaa act cac aca tgc cca ccg tgc      336
Lys Val Glu Pro Lys Ser Cys Asp Lys Thr His Thr Cys Pro Pro Cys
            100                 105                 110

cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
        115                 120                 125

aaa ccc aag gac acc ctc atg atc tcc cgg acc cct gag gtc aca tgc      432
Lys Pro Lys Asp Thr Leu Met Ile Ser Arg Thr Pro Glu Val Thr Cys
    130                 135                 140

gtg gtg gtg gac gtg agc cac gaa gac cct gag gtc aag ttc aac tgg      480
Val Val Val Asp Val Ser His Glu Asp Pro Glu Val Lys Phe Asn Trp
145                 150                 155                 160

tac gtg gac ggc gtg gag gtg cat aat gcc aag aca aag ccg cgg gag      528
Tyr Val Asp Gly Val Glu Val His Asn Ala Lys Thr Lys Pro Arg Glu
                165                 170                 175

gag cag tac aac agc acg tac cgt gtg gtc agc gtc ctc acc gtc ctg      576
Glu Gln Tyr Asn Ser Thr Tyr Arg Val Val Ser Val Leu Thr Val Leu
            180                 185                 190

cac cag gac tgg ctg aat ggc aag gag tac aag tgc aag gtc tcc aac      624
His Gln Asp Trp Leu Asn Gly Lys Glu Tyr Lys Cys Lys Val Ser Asn
        195                 200                 205

aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
    210                 215                 220

cag ccc cga gaa cca cag gtg tac acc ctg ccc cca tcc cgg gat gag      720
Gln Pro Arg Glu Pro Gln Val Tyr Thr Leu Pro Pro Ser Arg Asp Glu
225                 230                 235                 240

ctg acc aag aac cag gtc agc ctg acc tgc ctg gtc aaa ggc ttc tat      768
Leu Thr Lys Asn Gln Val Ser Leu Thr Cys Leu Val Lys Gly Phe Tyr
                245                 250                 255

ccc agc gac atc gcc gtg gag tgg gag agc aat ggg cag ccg gag aac      816
Pro Ser Asp Ile Ala Val Glu Trp Glu Ser Asn Gly Gln Pro Glu Asn
            260                 265                 270

aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285

ctc tac agc aag ctc acc gtg gac aag agc agg tgg cag cag ggg aac      912
Leu Tyr Ser Lys Leu Thr Val Asp Lys Ser Arg Trp Gln Gln Gly Asn
```

```
    290                 295                 300

gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320

cag aag agc ctc tcc ctg tct ccg ggt aaa                              990
Gln Lys Ser Leu Ser Leu Ser Pro Gly Lys
                325                 330


<210> SEQ ID NO 38
<211> LENGTH: 330
<212> TYPE: PRT
<213> ORGANISM: Homo sapiens
<220> FEATURE:
<223> OTHER INFORMATION: immunoglobulin heavy chain constant region
      gamma 1 (IGHG1 gene) (>gi| 12054071|ref| AJ294730.1|)

<400> SEQUENCE: 38

Ala Ser Phe Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

-continued

```
305                 310                 315                 320

Gln Lys Ser Leu Ser Leu Ser Pro Gly Lys
                325                 330


<210> SEQ ID NO 39
<211> LENGTH: 1047
<212> TYPE: DNA
<213> ORGANISM: Mus musculus
<220> FEATURE:
<223> OTHER INFORMATION: hybridoma 36-35 immunoglobulin heavy chain
      constant region, partial cds (>gi| 195165|ref| M60435.1|)
<220> FEATURE:
<221> NAME/KEY: CDS
<222> LOCATION: 1..975
<223> OTHER INFORMATION: /transl_table=1

<400> SEQUENCE: 39

gcc aaa acg aca ccc cca tct gtc tat cca ctg gcc cct gga tct gct       48
Ala Lys Thr Thr Pro Pro Ser Val Tyr Pro Leu Ala Pro Gly Ser Ala
1               5                   10                  15

gcc caa act aac tcc atg gtg acc ctg gga tgc ctg gtc aag ggc tat       96
Ala Gln Thr Asn Ser Met Val Thr Leu Gly Cys Leu Val Lys Gly Tyr
            20                  25                  30

ttc cct gag cca gtg aca gtg acc tgg aac tct gga tcc ctg tcc agc      144
Phe Pro Glu Pro Val Thr Val Thr Trp Asn Ser Gly Ser Leu Ser Ser
        35                  40                  45

ggt gtg cac acc ttc cca gct gtc ctg cag tct gac ctc tac act ctg      192
Gly Val His Thr Phe Pro Ala Val Leu Gln Ser Asp Leu Tyr Thr Leu
    50                  55                  60

agc agc tca gtg act gtc ccc tcc agc acc tgg ccc agc gag acc gtc      240
Ser Ser Ser Val Thr Val Pro Ser Ser Thr Trp Pro Ser Glu Thr Val
65                  70                  75                  80

acc tgc aac gtt gcc cac ccg gcc agc agc acc aag gtg gac aag aaa      288
Thr Cys Asn Val Ala His Pro Ala Ser Ser Thr Lys Val Asp Lys Lys
                85                  90                  95

att gtg ccc agg gat tgt ggt tgt aag cct tgc ata tgt aca gtc cca      336
Ile Val Pro Arg Asp Cys Gly Cys Lys Pro Cys Ile Cys Thr Val Pro
            100                 105                 110

gaa gta tca tct gtc ttc atc ttc ccc cca aag ccc aag gat gtg ctc      384
Glu Val Ser Ser Val Phe Ile Phe Pro Pro Lys Pro Lys Asp Val Leu
        115                 120                 125

acc att act ctg act cct aag gtc acg tgt gtt gtg gta gac atc agc      432
Thr Ile Thr Leu Thr Pro Lys Val Thr Cys Val Val Val Asp Ile Ser
    130                 135                 140

aag gat gat ccc gag gtc cag ttc agc tgg ttt gta gat gat gtg gag      480
Lys Asp Asp Pro Glu Val Gln Phe Ser Trp Phe Val Asp Asp Val Glu
145                 150                 155                 160

gtg cac aca gct cag acg caa ccc cgg gag gag cag ttc aac agc act      528
Val His Thr Ala Gln Thr Gln Pro Arg Glu Glu Gln Phe Asn Ser Thr
                165                 170                 175

ttc cgc tca gtc agt gaa ctt ccc atc atg cac cag gac tgg ctc aat      576
Phe Arg Ser Val Ser Glu Leu Pro Ile Met His Gln Asp Trp Leu Asn
            180                 185                 190

ggc aag gag ttc aaa tgc agg gtc aac agt gca gct ttc cct gcc ccc      624
Gly Lys Glu Phe Lys Cys Arg Val Asn Ser Ala Ala Phe Pro Ala Pro
        195                 200                 205

atc gag aaa acc atc tcc aaa acc aaa ggc aga ccg aag gct cca cag      672
Ile Glu Lys Thr Ile Ser Lys Thr Lys Gly Arg Pro Lys Ala Pro Gln
    210                 215                 220

gtg tac acc att cca cct ccc aag gag cag atg gcc aag gat aaa gtc      720
Val Tyr Thr Ile Pro Pro Pro Lys Glu Gln Met Ala Lys Asp Lys Val
225                 230                 235                 240
```

```
agt ctg acc tgc atg ata aca gac ttc ttc cct gaa gac att act gtg      768
Ser Leu Thr Cys Met Ile Thr Asp Phe Phe Pro Glu Asp Ile Thr Val
                245                 250                 255

gag tgg cag tgg aat ggg cag cca gcg gag aac tac aag aac act cag      816
Glu Trp Gln Trp Asn Gly Gln Pro Ala Glu Asn Tyr Lys Asn Thr Gln
            260                 265                 270

ccc atc atg gac aca gat ggc tct tac ttc gtc tac agc aag ctc aat      864
Pro Ile Met Asp Thr Asp Gly Ser Tyr Phe Val Tyr Ser Lys Leu Asn
        275                 280                 285

gtg cag aag agc aac tgg gag gca gga aat act ttc acc tgc tct gtg      912
Val Gln Lys Ser Asn Trp Glu Ala Gly Asn Thr Phe Thr Cys Ser Val
    290                 295                 300

tta cat gag ggc ctg cac aac cac cat act gag aag agc ctc tcc cac      960
Leu His Glu Gly Leu His Asn His His Thr Glu Lys Ser Leu Ser His
305                 310                 315                 320

tct cct ggt aaa tga tctcagtgtc cttggagccc tctggtccta caggactctg     1015
Ser Pro Gly Lys

acacctacct ccacccctcc ctgtgtaaat aa                                 1047


<210> SEQ ID NO 40
<211> LENGTH: 324
<212> TYPE: PRT
<213> ORGANISM: Mus musculus
<220> FEATURE:
<223> OTHER INFORMATION: hybridoma 36-35 immunoglobulin heavy chain
      constant region, partial cds (>gi| 195165|ref| M60435.1|)

<400> SEQUENCE: 40

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220
```

```
Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys


<210> SEQ ID NO 41
<211> LENGTH: 232
<212> TYPE: PRT
<213> ORGANISM: Homo sapiens
<220> FEATURE:
<223> OTHER INFORMATION: Human immunoglobulin heavy chain constant
      region gamma 1, aa 104-330 encoded by nucleotides 295-990 of
      gi|12054071|ref|AJ294730.1|

<400> SEQUENCE: 41

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 42
```

<211> LENGTH: 222
<212> TYPE: PRT
<213> ORGANISM: Mus musculus
<220> FEATURE:
<223> OTHER INFORMATION: Mouse immunoglobulin heavy chain constant region gamma 1, aa 103-324 encoded by nucleotides 307-975 of gi|195165|ref|M60435.1|

<400> SEQUENCE: 42

```
Gly Cys Lys Pro Cys Ile Cys Thr Val Pro Glu Val Ser Ser Val Phe
1               5                   10                  15

Ile Phe Pro Pro Lys Pro Lys Asp Val Leu Thr Ile Thr Leu Thr Pro
            20                  25                  30

Lys Val Thr Cys Val Val Val Asp Ile Ser Lys Asp Asp Pro Glu Val
        35                  40                  45

Gln Phe Ser Trp Phe Val Asp Asp Val Glu Val His Thr Ala Gln Thr
    50                  55                  60

Gln Pro Arg Glu Glu Gln Phe Asn Ser Thr Phe Arg Ser Val Ser Glu
65                  70                  75                  80

Leu Pro Ile Met His Gln Asp Trp Leu Asn Gly Lys Glu Phe Lys Cys
                85                  90                  95

Arg Val Asn Ser Ala Ala Phe Pro Ala Pro Ile Glu Lys Thr Ile Ser
            100                 105                 110

Lys Thr Lys Gly Arg Pro Lys Ala Pro Gln Val Tyr Thr Ile Pro Pro
        115                 120                 125

Pro Lys Glu Gln Met Ala Lys Asp Lys Val Ser Leu Thr Cys Met Ile
    130                 135                 140

Thr Asp Phe Phe Pro Glu Asp Ile Thr Val Glu Trp Gln Trp Asn Gly
145                 150                 155                 160

Gln Pro Ala Glu Asn Tyr Lys Asn Thr Gln Pro Ile Met Asp Thr Asp
                165                 170                 175

Gly Ser Tyr Phe Val Tyr Ser Lys Leu Asn Val Gln Lys Ser Asn Trp
            180                 185                 190

Glu Ala Gly Asn Thr Phe Thr Cys Ser Val Leu His Glu Gly Leu His
        195                 200                 205

Asn His His Thr Glu Lys Ser Leu Ser His Ser Pro Gly Lys
    210                 215                 220
```

<210> SEQ ID NO 43
<211> LENGTH: 2328
<212> TYPE: DNA
<213> ORGANISM: Homo sapiens
<220> FEATURE:
<223> OTHER INFORMATION: Human SEMA3A-delta Ig-b

<400> SEQUENCE: 43

```
atgggatggc tgaccagaat cgtgtgcctg ttctggggcg tgctgctgac cgccagagcc      60

aactaccaga acggcaagaa caacgtgccc cggctgaagc tgagctacaa agagatgctg     120

gaaagcaaca acgtgatcac cttcaacggc ctggccaaca gcagcagcta ccacaccttt     180

ctgctggacg aggaacggtc ccggctgtac gtgggagcca aggaccacat cttcagcttc     240

gacctcgtga acatcaagga cttccagaaa atcgtgtggc ccgtgtccta caccagacgg     300

gacgagtgca agtgggccgg caaggacatc ctgaaagagt gcgccaactt catcaaggtg     360

ctgaaggcct acaaccagac ccacctgtac gcctgtggca ccggcgcctt ccaccctatc     420

tgcacctaca tcgagatcgg ccaccacccc gaggacaata tcttcaagct ggaaaacagc     480

cacttcgaga acggcagagg caagagcccc tacgacccca agctgctgac agcctccctg     540
```

ctgatcgacg gcgagctgta ctctggcaca gccgccgact tcatgggccg ggacttcgcc 600
atcttcagaa ccctgggaca ccaccaccca atccggaccg agcagcacga cagcagatgg 660
ctgaacgacc ctaagttcat cagcgcccac ctgatcagcg agagcgacaa ccctgaggac 720
gacaaggtgt acttcttctt ccgggaaaac gccatcgacg gggagcacag cggaaaggcc 780
acacacgcca gaatcggcca gatctgcaag aacgacttcg gcggccaccg gtccctcgtg 840
aacaagtgga ccaccttcct gaaggcccgg ctgatctgta gcgtgccagg ccccaatggc 900
atcgacaccc acttcgacga gctgcaggac gtgttcctga tgaatttcaa ggaccccaag 960
aaccccgtgg tgtacggcgt gttcaccacc agcagcaaca tcttcaaggg cagcgccgtg 1020
tgcatgtaca gcatgagcga cgtgcggcgg gtgttcctgg gaccttacgc ccatagagat 1080
ggccccaatt accagtgggt gccctaccag ggcagagtgc cttaccccag acctggcacc 1140
tgtcccagca agacctttgg cggcttcgac agcaccaagg acctgcccga cgatgtgatt 1200
accttcgcca gatcccaccc cgccatgtac aaccccgtgt tccccatgaa caaccggccc 1260
atcgtgatca agaccgacgt gaactaccag ttcacccaga tcgtggtgga cagagtggac 1320
gccgaggacg gccagtacga cgtgatgttc atcggcaccg acgtgggcac cgtgctgaaa 1380
gtggtgtcca tccccaaaga gacttggtac gacctggaag aggtgctgct ggaagagatg 1440
accgtgttca gagagcccac cgccatctcc gccatggaac tgagcacaaa gcagcagcag 1500
ctgtacatcg gcagcacagc tggcgtggca cagctgcctc tgcacagatg cgacatctac 1560
ggcaaggcct gcgccgagtg ttgcctggcc agagatcctt actgcgcctg ggatggcagc 1620
gcctgcagca gatacttccc caccgacaag acccacacat gcccccccttg tcctgcccct 1680 gaactgctgg gaggcccctc cgtgtttctg ttcccccccaa agcccaagga taccctgatg 1740
atcagcagaa cccccgaagt gacctgcgtg gtggtggacg tgtcccacga ggaccctgaa 1800
gtgaagttca attggtacgt ggacggcgtg gaagtgcaca acgccaagac caagcccaga 1860
gaggaacagt acaacagcac ctaccgcgtg gtgtccgtgc tgaccgtgct gcaccaggac 1920
tggctgaatg gcaaagagta caagtgcaag gtgtccaaca aggccctgcc tgcccccatc 1980
gagaaaacca tcagcaaggc caagggccag ccccgcgaac cccaggtgta cacactgccc 2040
cctagcaggg acgagctgac caagaaccag gtgtccctga cctgtctcgt gaagggcttc 2100 taccccctccg atatcgccgt ggaatgggag agcaacggcc agcccgagaa caactacaag 2160
accacccccc ctgtgctgga cagcgacggc tcattcttcc tgtacagcaa gctgacagtg 2220
gacaagagcc ggtggcagca gggcaacgtg ttcagctgca gcgtgatgca cgaggccctg 2280
cacaaccact acacccagaa gtccctgagc ctgagccccg gcaaatga 2328

<210> SEQ ID NO 44
<211> LENGTH: 2313
<212> TYPE: DNA
<213> ORGANISM: Mus musculus
<220> FEATURE:
<223> OTHER INFORMATION: Mouse Sema3A-delta Ig-b

<400> SEQUENCE: 44
atgggatggt ttactggaat tgcctgtctg ttttggggag tgcttctgac tgccagagca 60
aattacgcca atggcaagaa caacgtcccc agactgaagc tctcttacaa ggagatgctg 120
gagtctaaca atgtgattac attcaatggc cttgccaact cttcctcata ccacaccttt 180
ctgctggatg aggagcgctc acggctgtat gtgggagcca aggaccatat tttcagtttt 240

-continued

```
aatctcgtga atatcaagga ttttcagaag atcgtatggc ctgtctcata tacccgcaga    300

gacgagtgca aatgggcagg caaagatata ctgaaggaat gcgcaaattt cattaaggtg    360

ctcgaggcat acaaccagac acacttgtat gcctgtggga ctggcgcgtt ccatcctatt    420

tgtacataca tcgaggtggg acatcatccg gaggacaaca tcttcaagtt gcaggatagc    480

cacttcgaga acggcagggg aaagtcacct tacgacccaa aactcctgac tgcttccctg    540

cttatcgacg gtgaactcta ctctggcacc gcagccgact ttatgggcag agactttgct    600

atattcagga ccctcggaca tcatcatccg attcggaccg agcaacacga ctcacgctgg    660

ctgaatgacc ccagattcat ttcagcccac ctgatccccg aaagtgataa cccagaggac    720

gacaaagtat acttcttctt tcgcgagaat gctatagacg gcgagcacag cggaaaggct    780

actcatgctc ggatcgggca aatctgtaaa aacgattttg gaggccatcg atcattggtt    840

aacaagtgga ccacatttct taaagcaaga cttatctgct ctgtgcctgg tccaaacggg    900

atagatactc atttcgacga gctgcaggac gtgttcctta tgaacagtaa ggacccgaag    960

aaccctatcg tgtacggagt ttttacgacg tcctccaaca tcttcaaggg ctcagcagtc   1020

tgcatgtata gcatgagcga cgtccggagg gtcttcctcg gaccctacgc acaccgcgat   1080

ggccccaatt atcagtgggt tccttatcaa gggagagtac cttaccctag accagggaca   1140

tgtccatcca agacattcgg aggttttgat tcaaccaagg acttgccaga cgatgtcata   1200

accttcgcca gatcacaccc cgccatgtac aatcctgttt ttccgattaa caaccgcccc   1260

attatgatca aaactgatgt gaactatcaa ttcacccaga ttgttgtaga tagagttgat   1320

gctgaggatg gccagtatga tgtcatgttc atcggtacag acgtgggaac agtcttgaaa   1380

gtcgtttctg tccctaaaga gacctggcac gacctggaag aggtcctcct ggaggagatg   1440

acagtgttcc gggagcccac cacaatcagc gccatggaac tctctaccaa gcagcagcag   1500

ctctacatcg gttccacagc tggggtggct cagcttcccc tccacagatg cgacatatac   1560

gggaaggcct gtgctgagtg ctgcctggcc agagatccct actgcgcgtg ggatggttca   1620

agttgcagtc gatacttccc cacagggtgc aagccttgta tttgtactgt gcccgaagtg   1680

tcctccgtgt tcatctttcc acccaagcct aaggacgttt tgacaataac gctgacccca   1740

aaggtgacgt gcgttgtggt cgatatcagc aaggacgatc cagaagtcca gttttcttgg   1800

tttgttgatg atgtggaagt acacactgcg caaacacagc ctagggaaga gcagtttaac   1860

tctactttta ggagcgtaag cgagctgccg attatgcatc aggactggtt gaatgggaag   1920

gagttcaaat gtcgcgttaa ctccgcagcc ttccccgcac ctatcgaaaa aacgatctca   1980

aagactaagg gtaggccaaa agcgccacag gtatacacca ttcctccacc gaaggaacag   2040

atggcaaaag ataaggtttc actgacatgc atgattactg actttttccc cgaggatatc   2100

accgtggaat ggcagtggaa tggccaaccc gcagagaact ataagaacac tcaaccaatt   2160

atggacacag acggctcata tttcgtgtac tctaagctga atgtccagaa gtcaaattgg   2220

gaagctggaa acacgtttac ctgtagtgtg ttgcatgagg gactgcacaa ccatcatacc   2280

gaaaagtcat tgtcccatag cccaggaaag tga                                2313
```

<210> SEQ ID NO 45
<211> LENGTH: 13
<212> TYPE: PRT
<213> ORGANISM: Homo sapiens
<220> FEATURE:
<223> OTHER INFORMATION: SEMA3A 527-539

<400> SEQUENCE: 45

Cys Cys Leu Ala Arg Asp Pro Tyr Cys Ala Trp Asp Gly
1 5 10

<210> SEQ ID NO 46
<211> LENGTH: 13
<212> TYPE: PRT
<213> ORGANISM: Homo sapiens
<220> FEATURE:
<223> OTHER INFORMATION: SEMA3B 526-538

<400> SEQUENCE: 46

Cys Cys Leu Ala Arg Asp Pro Tyr Cys Ala Trp Asp Gly
1 5 10

<210> SEQ ID NO 47
<211> LENGTH: 13
<212> TYPE: PRT
<213> ORGANISM: Homo sapiens
<220> FEATURE:
<223> OTHER INFORMATION: SEMA3C 524-536

<400> SEQUENCE: 47

Cys Cys Leu Ala Arg Asp Pro Tyr Cys Ala Trp Asp Gly
1 5 10

<210> SEQ ID NO 48
<211> LENGTH: 13
<212> TYPE: PRT
<213> ORGANISM: Homo sapiens
<220> FEATURE:
<223> OTHER INFORMATION: SEMA3D 544-556

<400> SEQUENCE: 48

Cys Cys Leu Ala Arg Asp Pro Tyr Cys Ala Trp Asp Gly
1 5 10

<210> SEQ ID NO 49
<211> LENGTH: 202
<212> TYPE: PRT
<213> ORGANISM: Homo sapiens
<220> FEATURE:
<223> OTHER INFORMATION: SEMA3A 96-297

<400> SEQUENCE: 49

Ser Tyr Thr Arg Arg Asp Glu Cys Lys Trp Lys Gly Lys Asp Ile Leu
1 5 10 15

Lys Glu Cys Ala Asn Phe Ile Lys Val Leu Lys Ala Tyr Asn Gln Thr
20 25 30

His Leu Tyr Ala Cys Gly Thr Gly Ala Phe His Pro Ile Cys Thr Tyr
35 40 45

Ile Glu Ile Gly His His Pro Glu Asp Asn Ile Phe Lys Leu Glu Asn
50 55 60

Ser His Phe Glu Asn Gly Arg Gly Lys Ser Pro Tyr Asp Pro Lys Leu
65 70 75 80

Leu Thr Ala Ser Leu Leu Ile Asp Gly Glu Leu Tyr Ser Gly Thr Ala
85 90 95

Ala Asp Phe Met Gly Arg Asp Phe Ala Ile Phe Arg Thr Leu Gly His
100 105 110

His His Pro Ile Arg Thr Glu Gln His Asp Ser Arg Trp Leu Asn Asp
115 120 125

Pro Lys Phe Ile Ser Ala His Leu Ile Ser Glu Ser Asp Asn Pro Glu
130 135 140

```
Asp Asp Lys Val Tyr Phe Phe Phe Arg Glu Asn Ala Ile Asp Gly Glu
145                 150                 155                 160

His Ser Gly Lys Ala Thr His Ala Arg Ile Gly Gln Ile Cys Lys Asn
                165                 170                 175

Asp Phe Gly Gly His Arg Ser Leu Val Asn Lys Trp Thr Thr Phe Leu
            180                 185                 190

Lys Ala Arg Leu Ile Cys Ser Val Pro Gly
        195                 200


<210> SEQ ID NO 50
<211> LENGTH: 203
<212> TYPE: PRT
<213> ORGANISM: Homo sapiens
<220> FEATURE:
<223> OTHER INFORMATION: SEMA3B 95-297

<400> SEQUENCE: 50

Pro Val Glu Trp Arg Glu Glu Cys Asn Trp Lys Gly Lys Asp Ile Gly
1               5                   10                  15

Thr Glu Cys Met Asn Phe Val Lys Leu Leu His Ala Tyr Asn Arg Thr
            20                  25                  30

His Leu Leu Ala Cys Gly Thr Gly Ala Phe His Pro Thr Cys Ala Phe
        35                  40                  45

Val Glu Val Gly His Arg Ala Glu Glu Pro Val Leu Arg Leu Asp Pro
    50                  55                  60

Gly Arg Ile Glu Asp Gly Lys Gly Lys Ser Pro Tyr Asp Pro Arg His
65                  70                  75                  80

Arg Ala Ala Ser Val Leu Val Gly Glu Glu Leu Tyr Ser Gly Val Ala
                85                  90                  95

Ala Asp Leu Met Gly Arg Asp Phe Thr Ile Phe Arg Ser Leu Gly Gln
            100                 105                 110

Arg Pro Ser Leu Arg Thr Glu Pro His Asp Ser Arg Trp Leu Asn Glu
        115                 120                 125

Pro Lys Phe Val Lys Val Phe Trp Ile Pro Glu Ser Glu Asn Pro Asp
    130                 135                 140

Asp Asp Lys Ile Tyr Phe Phe Phe Arg Glu Thr Ala Val Glu Ala Ala
145                 150                 155                 160

Pro Ala Leu Gly Arg Leu Ser Val Ser Arg Val Gly Gln Ile Cys Arg
                165                 170                 175

Asn Asp Val Gly Gly Gln Arg Ser Leu Val Asn Lys Trp Thr Thr Phe
            180                 185                 190

Leu Lys Ala Arg Leu Val Cys Ser Val Pro Gly
        195                 200


<210> SEQ ID NO 51
<211> LENGTH: 201
<212> TYPE: PRT
<213> ORGANISM: Homo sapiens
<220> FEATURE:
<223> OTHER INFORMATION: SEMA3C 94-294

<400> SEQUENCE: 51

Ser Thr Ile Lys Val Glu Glu Cys Lys Met Lys Gly Lys Asp Pro Thr
1               5                   10                  15

His Gly Cys Gly Asn Phe Val Arg Val Ile Gln Thr Phe Asn Arg Thr
            20                  25                  30

His Leu Tyr Val Cys Gly Ser Gly Ala Phe Ser Pro Val Cys Thr Tyr
```

```
        35                  40                  45

Leu Asn Arg Gly Arg Arg Ser Glu Asp Gln Val Phe Met Ile Asp Ser
    50                  55                  60

Lys Cys Glu Ser Gly Lys Gly Arg Cys Ser Phe Asn Pro Asn Val Asn
65                  70                  75                  80

Thr Val Ser Val Met Ile Asn Glu Glu Leu Phe Ser Gly Met Tyr Ile
                85                  90                  95

Asp Phe Met Gly Thr Asp Ala Ala Ile Phe Arg Ser Leu Thr Lys Arg
            100                 105                 110

Asn Ala Val Arg Thr Asp Gln His Asn Ser Lys Trp Leu Ser Glu Pro
        115                 120                 125

Met Phe Val Asp Ala His Val Ile Pro Asp Gly Thr Asp Pro Asn Asp
    130                 135                 140

Ala Lys Val Tyr Phe Phe Phe Lys Glu Lys Leu Thr Asp Asn Asn Arg
145                 150                 155                 160

Ser Thr Lys Gln Ile His Ser Met Ile Ala Arg Ile Cys Pro Asn Asp
                165                 170                 175

Thr Gly Gly Leu Arg Ser Leu Val Asn Lys Trp Thr Thr Phe Leu Lys
            180                 185                 190

Ala Arg Leu Val Cys Ser Val Thr Asp
        195                 200
```

<210> SEQ ID NO 52
<211> LENGTH: 205
<212> TYPE: PRT
<213> ORGANISM: Homo sapiens
<220> FEATURE:
<223> OTHER INFORMATION: SEMA3D 110-314

<400> SEQUENCE: 52

```
Ala Lys Glu Arg Val Glu Leu Cys Lys Leu Lys Gly Lys Asp Ala Asn
1               5                   10                  15

Thr Glu Cys Ala Asn Phe Ile Arg Val Leu Gln Pro Tyr Asn Lys Thr
            20                  25                  30

His Ile Tyr Val Cys Gly Thr Gly Ala Phe His Pro Ile Cys Gly Tyr
        35                  40                  45

Ile Asp Leu Gly Val Tyr Lys Glu Asp Ile Ile Phe Lys Leu Asp Thr
    50                  55                  60

His Asn Leu Glu Ser Gly Arg Leu Lys Cys Pro Phe Asp Pro Gln Gln
65                  70                  75                  80

Pro Phe Ala Ser Val Met Thr Asp Glu Tyr Leu Tyr Ser Gly Thr Ala
                85                  90                  95

Ser Asp Phe Leu Gly Lys Asp Thr Ala Phe Thr Arg Ser Leu Gly Pro
            100                 105                 110

Thr His Asp His His Tyr Ile Arg Thr Asp Ile Ser Glu His Tyr Trp
        115                 120                 125

Leu Asn Gly Ala Lys Phe Ile Gly Thr Phe Phe Ile Pro Asp Thr Tyr
    130                 135                 140

Asn Pro Asp Asp Asp Lys Ile Tyr Phe Phe Phe Arg Glu Ser Ser Gln
145                 150                 155                 160

Glu Gly Ser Thr Ser Asp Lys Thr Ile Leu Ser Arg Val Gly Arg Val
                165                 170                 175

Cys Lys Asn Asp Val Gly Gly Gln Arg Ser Leu Ile Asn Lys Trp Thr
            180                 185                 190

Thr Phe Leu Lys Ala Arg Leu Ile Cys Ser Ile Pro Gly
```

195 200 205

<210> SEQ ID NO 53
<211> LENGTH: 10
<212> TYPE: PRT
<213> ORGANISM: Homo sapiens
<220> FEATURE:
<223> OTHER INFORMATION: SEMA3A 104-113

<400> SEQUENCE: 53

Lys Trp Lys Gly Lys Asp Ile Leu Lys Glu
1 5 10

<210> SEQ ID NO 54
<211> LENGTH: 10
<212> TYPE: PRT
<213> ORGANISM: Homo sapiens
<220> FEATURE:
<223> OTHER INFORMATION: SEMA3B 103-112

<400> SEQUENCE: 54

Asn Trp Lys Gly Lys Asp Ile Gly Thr Glu
1 5 10

<210> SEQ ID NO 55
<211> LENGTH: 10
<212> TYPE: PRT
<213> ORGANISM: Homo sapiens
<220> FEATURE:
<223> OTHER INFORMATION: SEMA3C 102-111

<400> SEQUENCE: 55

Lys Met Lys Gly Lys Asp Pro Thr His Gly
1 5 10

<210> SEQ ID NO 56
<211> LENGTH: 10
<212> TYPE: PRT
<213> ORGANISM: Homo sapiens
<220> FEATURE:
<223> OTHER INFORMATION: SEMA3D 118-127

<400> SEQUENCE: 56

Lys Leu Lys Gly Lys Asp Ala Asn Thr Glu
1 5 10

<210> SEQ ID NO 57
<211> LENGTH: 5672
<212> TYPE: DNA
<213> ORGANISM: Artificial Sequence
<220> FEATURE:
<223> OTHER INFORMATION: full-length human SEMA3A A106K
<220> FEATURE:
<221> NAME/KEY: CDS
<222> LOCATION: 316..2631
<223> OTHER INFORMATION: /transl_table=1

<400> SEQUENCE: 57
aagcaccact gcagcagacc ttgttaattt tttttttttt tctttccaca caacagttgt 60
gcctcattat ccggtgcctg gctcggaatt tttttttttt tttttctttt tggagggttt 120
gaagtttctg tgcttcagtg actgttacag aagaagaggt gttagtgttg ccatgaggtc 180
ttgattgtct gcatttatga atgaaactga cctaaatcac ctgttacctc cagtttccag 240
attgtttgaa cttctctggc cgcacaatac aggaaggaag actaaagcag caaagggacc 300
tacagcgtct gcagc atg ggc tgg tta act agg att gtc tgt ctt ttc tgg 351

-continued

```
                 Met Gly Trp Leu Thr Arg Ile Val Cys Leu Phe Trp
                 1               5                   10

gga gta tta ctt aca gca aga gca aac tat cag aat ggg aag aac aat      399
Gly Val Leu Leu Thr Ala Arg Ala Asn Tyr Gln Asn Gly Lys Asn Asn
        15                  20                  25

gtg cca agg ctg aaa tta tcc tac aaa gaa atg ttg gaa tcc aac aat      447
Val Pro Arg Leu Lys Leu Ser Tyr Lys Glu Met Leu Glu Ser Asn Asn
    30                  35                  40

gtg atc act ttc aat ggc ttg gcc aac agc tcc agt tat cat acc ttc      495
Val Ile Thr Phe Asn Gly Leu Ala Asn Ser Ser Ser Tyr His Thr Phe
45                  50                  55                  60

ctt ttg gat gag gaa cgg agt agg ctg tat gtt gga gca aag gat cac      543
Leu Leu Asp Glu Glu Arg Ser Arg Leu Tyr Val Gly Ala Lys Asp His
                65                  70                  75

ata ttt tca ttc gac ctg gtt aat atc aag gat ttt caa aag att gtg      591
Ile Phe Ser Phe Asp Leu Val Asn Ile Lys Asp Phe Gln Lys Ile Val
            80                  85                  90

tgg cca gta tct tac acc aga aga gat gaa tgc aag tgg aag gga aaa      639
Trp Pro Val Ser Tyr Thr Arg Arg Asp Glu Cys Lys Trp Lys Gly Lys
        95                  100                 105

gac atc ctg aaa gaa tgt gct aat ttc atc aag gta ctt aag gca tat      687
Asp Ile Leu Lys Glu Cys Ala Asn Phe Ile Lys Val Leu Lys Ala Tyr
    110                 115                 120

aat cag act cac ttg tac gcc tgt gga acg ggg gct ttt cat cca att      735
Asn Gln Thr His Leu Tyr Ala Cys Gly Thr Gly Ala Phe His Pro Ile
125                 130                 135                 140

tgc acc tac att gaa att gga cat cat cct gag gac aat att ttt aag      783
Cys Thr Tyr Ile Glu Ile Gly His His Pro Glu Asp Asn Ile Phe Lys
                145                 150                 155

ctg gag aac tca cat ttt gaa aac ggc cgt ggg aag agt cca tat gac      831
Leu Glu Asn Ser His Phe Glu Asn Gly Arg Gly Lys Ser Pro Tyr Asp
            160                 165                 170

cct aag ctg ctg aca gca tcc ctt tta ata gat gga gaa tta tac tct      879
Pro Lys Leu Leu Thr Ala Ser Leu Leu Ile Asp Gly Glu Leu Tyr Ser
        175                 180                 185

gga act gca gct gat ttt atg ggg cga gac ttt gct atc ttc cga act      927
Gly Thr Ala Ala Asp Phe Met Gly Arg Asp Phe Ala Ile Phe Arg Thr
    190                 195                 200

ctt ggg cac cac cac cca atc agg aca gag cag cat gat tcc agg tgg      975
Leu Gly His His His Pro Ile Arg Thr Glu Gln His Asp Ser Arg Trp
205                 210                 215                 220

ctc aat gat cca aag ttc att agt gcc cac ctc atc tca gag agt gac     1023
Leu Asn Asp Pro Lys Phe Ile Ser Ala His Leu Ile Ser Glu Ser Asp
                225                 230                 235

aat cct gaa gat gac aaa gta tac ttt ttc ttc cgt gaa aat gca ata     1071
Asn Pro Glu Asp Asp Lys Val Tyr Phe Phe Phe Arg Glu Asn Ala Ile
            240                 245                 250

gat gga gaa cac tct gga aaa gct act cac gct aga ata ggt cag ata     1119
Asp Gly Glu His Ser Gly Lys Ala Thr His Ala Arg Ile Gly Gln Ile
        255                 260                 265

tgc aag aat gac ttt gga ggg cac aga agt ctg gtg aat aaa tgg aca     1167
Cys Lys Asn Asp Phe Gly Gly His Arg Ser Leu Val Asn Lys Trp Thr
    270                 275                 280

aca ttc ctc aaa gct cgt ctg att tgc tca gtg cca ggt cca aat ggc     1215
Thr Phe Leu Lys Ala Arg Leu Ile Cys Ser Val Pro Gly Pro Asn Gly
285                 290                 295                 300

att gac act cat ttt gat gaa ctg cag gat gta ttc cta atg aac ttt     1263
Ile Asp Thr His Phe Asp Glu Leu Gln Asp Val Phe Leu Met Asn Phe
                305                 310                 315
```

-continued

```
aaa gat cct aaa aat cca gtt gta tat gga gtg ttt acg act tcc agt     1311
Lys Asp Pro Lys Asn Pro Val Val Tyr Gly Val Phe Thr Thr Ser Ser
            320                 325                 330

aac att ttc aag gga tca gcc gtg tgt atg tat agc atg agt gat gtg      1359
Asn Ile Phe Lys Gly Ser Ala Val Cys Met Tyr Ser Met Ser Asp Val
        335                 340                 345

aga agg gtg ttc ctt ggt cca tat gcc cac agg gat gga ccc aac tat      1407
Arg Arg Val Phe Leu Gly Pro Tyr Ala His Arg Asp Gly Pro Asn Tyr
    350                 355                 360

caa tgg gtg cct tat caa gga aga gtc ccc tat cca cgg cca gga act      1455
Gln Trp Val Pro Tyr Gln Gly Arg Val Pro Tyr Pro Arg Pro Gly Thr
365                 370                 375                 380

tgt ccc agc aaa aca ttt ggt ggt ttt gac tct aca aag gac ctt cct      1503
Cys Pro Ser Lys Thr Phe Gly Gly Phe Asp Ser Thr Lys Asp Leu Pro
                385                 390                 395

gat gat gtt ata acc ttt gca aga agt cat cca gcc atg tac aat cca      1551
Asp Asp Val Ile Thr Phe Ala Arg Ser His Pro Ala Met Tyr Asn Pro
            400                 405                 410

gtg ttt cct atg aac aat cgc cca ata gtg atc aaa acg gat gta aat      1599
Val Phe Pro Met Asn Asn Arg Pro Ile Val Ile Lys Thr Asp Val Asn
        415                 420                 425

tat caa ttt aca caa att gtc gta gac cga gtg gat gca gaa gat gga      1647
Tyr Gln Phe Thr Gln Ile Val Val Asp Arg Val Asp Ala Glu Asp Gly
    430                 435                 440

cag tat gat gtt atg ttt atc gga aca gat gtt ggg acc gtt ctt aaa      1695
Gln Tyr Asp Val Met Phe Ile Gly Thr Asp Val Gly Thr Val Leu Lys
445                 450                 455                 460

gta gtt tca att cct aag gag act tgg tat gat tta gaa gag gtt ctg      1743
Val Val Ser Ile Pro Lys Glu Thr Trp Tyr Asp Leu Glu Glu Val Leu
                465                 470                 475

ctg gaa gaa atg aca gtt ttt cgg gaa ccg act gct att tca gca atg      1791
Leu Glu Glu Met Thr Val Phe Arg Glu Pro Thr Ala Ile Ser Ala Met
            480                 485                 490

gag ctt tcc act aag cag caa caa cta tat att ggt tca acg gct ggg      1839
Glu Leu Ser Thr Lys Gln Gln Gln Leu Tyr Ile Gly Ser Thr Ala Gly
        495                 500                 505

gtt gcc cag ctc cct tta cac cgg tgt gat att tac ggg aaa gcg tgt      1887
Val Ala Gln Leu Pro Leu His Arg Cys Asp Ile Tyr Gly Lys Ala Cys
    510                 515                 520

gct gag tgt tgc ctc gcc cga gac cct tac tgt gct tgg gat ggt tct      1935
Ala Glu Cys Cys Leu Ala Arg Asp Pro Tyr Cys Ala Trp Asp Gly Ser
525                 530                 535                 540

gca tgt tct cgc tat ttt ccc act gca aag aga cgc aca aga cga caa      1983
Ala Cys Ser Arg Tyr Phe Pro Thr Ala Lys Arg Arg Thr Arg Arg Gln
                545                 550                 555

gat ata aga aat gga gac cca ctg act cac tgt tca gac tta cac cat      2031
Asp Ile Arg Asn Gly Asp Pro Leu Thr His Cys Ser Asp Leu His His
            560                 565                 570

gat aat cac cat ggc cac agc cct gaa gag aga atc atc tat ggt gta      2079
Asp Asn His His Gly His Ser Pro Glu Glu Arg Ile Ile Tyr Gly Val
        575                 580                 585

gag aat agt agc aca ttt ttg gaa tgc agt ccg aag tcg cag aga gcg      2127
Glu Asn Ser Ser Thr Phe Leu Glu Cys Ser Pro Lys Ser Gln Arg Ala
    590                 595                 600

ctg gtc tat tgg caa ttc cag agg cga aat gaa gag cga aaa gaa gag      2175
Leu Val Tyr Trp Gln Phe Gln Arg Arg Asn Glu Glu Arg Lys Glu Glu
605                 610                 615                 620

atc aga gtg gat gat cat atc atc agg aca gat caa ggc ctt ctg cta      2223
Ile Arg Val Asp Asp His Ile Ile Arg Thr Asp Gln Gly Leu Leu Leu
                625                 630                 635
```

```
cgt agt cta caa cag aag gat tca ggc aat tac ctc tgc cat gcg gtg      2271
Arg Ser Leu Gln Gln Lys Asp Ser Gly Asn Tyr Leu Cys His Ala Val
            640                 645                 650

gaa cat ggg ttc ata caa act ctt ctt aag gta acc ctg gaa gtc att      2319
Glu His Gly Phe Ile Gln Thr Leu Leu Lys Val Thr Leu Glu Val Ile
        655                 660                 665

gac aca gag cat ttg gaa gaa ctt ctt cat aaa gat gat gat gga gat      2367
Asp Thr Glu His Leu Glu Glu Leu Leu His Lys Asp Asp Asp Gly Asp
    670                 675                 680

ggc tct aag acc aaa gaa atg tcc aat agc atg aca cct agc cag aag      2415
Gly Ser Lys Thr Lys Glu Met Ser Asn Ser Met Thr Pro Ser Gln Lys
685                 690                 695                 700

gtc tgg tac aga gac ttc atg cag ctc atc aac cac ccc aat ctc aac      2463
Val Trp Tyr Arg Asp Phe Met Gln Leu Ile Asn His Pro Asn Leu Asn
                705                 710                 715

aca atg gat gag ttc tgt gaa caa gtt tgg aaa agg gac cga aaa caa      2511
Thr Met Asp Glu Phe Cys Glu Gln Val Trp Lys Arg Asp Arg Lys Gln
            720                 725                 730

cgt cgg caa agg cca gga cat acc cca ggg aac agt aac aaa tgg aag      2559
Arg Arg Gln Arg Pro Gly His Thr Pro Gly Asn Ser Asn Lys Trp Lys
        735                 740                 745

cac tta caa gaa aat aag aaa ggt aga aac agg agg acc cac gaa ttt      2607
His Leu Gln Glu Asn Lys Lys Gly Arg Asn Arg Arg Thr His Glu Phe
    750                 755                 760

gag agg gca ccc agg agt gtc tga gctgcattac ctctagaaac ctcaaacaag     2661
Glu Arg Ala Pro Arg Ser Val
765                 770

tagaaacttg cctagacaat aactggaaaa acaaatgcaa tatacatgaa ctttttcat    2721

ggcattatgt ggatgtttac aatggtggga aattcagctg agttccacca attataaatt   2781

aaatccatga gtaactttcc taataggctt tttttcctaa taccaccacc taacagagaa   2841

cacaggtgaa tgcagatgtt cactttagca gacttaatgt ttcctatgag atttcactgt   2901

acaggtttgt ctttcttctt tgcctgagaa ataaaaatgt catttgccat attgccatct   2961

aaaggagaaa aactgcatca gcaaagccat tgtattgaac taaaagttta aaatgaactg   3021

catggattta ctaagctgat gaatattcca aaacgtggtt ggattcaagg atatattttg   3081

tctaccggcc ctcatgtttg tatgtacttg aggagtaaaa tgagtaaaat gatactgaat   3141

gaaatgttct gtggaaatat taaaaaaaaa aaaaaacata agccatccat catccagaag   3201

aaaaatggaa tacactgatc tactactgat gtcttctttc agctttgatc taaagatgta   3261

ttttattaaa actataattt aaatgtacca tgaaaaatat gcagtaaaaa ttagttgttt   3321

tctaagctag agtaggattt gtcttacaat tattgtgcta tgtagttttt gttttaaaaa   3381

ttccaatggt gtgctgcttt ctttggacat tttattttca attctataag agggatagat   3441

gacattgttc tagaaacaca tatacatcat taagagtgaa tctctaaaac caggatataa   3501

attatgcttt atttctctga gaaaatcaaa caaatggaag ctgttcacac ctccccttct   3561

ttaagcatta tctaaattaa tttttacttg cataatgttc ttagaaaaaa aaacagaaca   3621

tttaagcagg aaaaaaggaa gaaacaagtt gatttttaag tgcattttac tataatgaat   3681

caatgaaggg aaaaggaact gcatatttca tgaaaataat aagcattgtc ttaatatact   3741

gttaatagaa aatgtgtctt aattccgtgc ttgaatccct gcatgatatt tgagactaag   3801

atctctctta tgattctacc aagaattata tctgtgtcac ttaatttttt taaaagagag   3861

agatcaataa ctattcagag caacatgtta aaggcaaagt ttccaatcat ttacatctgt   3921
```

atcaggtgcc tcttaccttt ccttatttaa gacaattatt tgtacaagaa acacatgact 3981 cttttcatat caatgggagg gacttttcta caaagtattt tccaggatgc aacccacatt 4041 taaacaatgt aaaattcttt gtttcctgca acaacttaca aaataaggta aaagactaaa 4101 attcaagatt tgcttccttc attgtcctaa gacgattcgt tgagaatcac tgactttgag 4161 atatttaaaa ctttcagcat tatactgtgg tttcttttgc actgcactca cctattcagg 4221 actcctcccc caggttcctc atcatgcaca aaaatgcaaa gaaaacatct tattagtaat 4281 taatgaagca acattgaaat tctaactcta gctgtctttg gattctaatt aactcagcat 4341 caatttctca cctcagacta cagtgaattt ttatttccta tcagctgaaa tatttcacag 4401 atggaagctc atgtttcagt tttaatgact gccttgaata aacaagttgt tgccacttgt 4461 ttcaaacaaa agcctaaaaa taatctacat tcaattttag gctccattga ctaatatggt 4521 gttgcttttg gaagtactgt atatcctcac atggaagcca aattgttaaa ttatttgaag 4581 gacacaccac tgtacagaaa gtagtgtttc aaatataaat cgaagaacaa agagtgctcc 4641 aaaaaatagg tcattctttt attttcataa agtatctaaa ctgtactaac attcagtgtt 4701 gtgtttcatt ctaaatttgc agctgaaata aatttatttg cgatagcaga aatatcttat 4761 tattcatcct cagaaataaa ggatttgaag ggatagagat tatatgataa atttatagaa 4821 gactttcaga atttgaatgc attttgttta gtgttatgaa atgacaatag aaaaaagtct 4881 cgacttcaat taaaagttac acaaacaaac aaatctacag gcatgtcttt atataccatc 4941 aggtctaagt tttcaaagaa aattgtagat ataacttgca gataactcat tacagtcata 5001 atctctgccc atgtgtattg agagggggca gtttgcacga aaaagaatta ttggcccatt 5061 taataattca gctttaaata gactttgtca tatgcatgaa tcatcagaga tgaaactgtt 5121 tgagagactc atgtgacctt acgaaaatta caacagcagt cttaaagtat gaaaaagatg 5181 catcacagca gagacattat ggcccagttg atatcaaatg taaaatgtaa atgcatgtaa 5241 atgcacactt cattttatgt attatttagt aatttgcagt ggtatgtgtt taatattttt 5301 gctacctaca cattaggcaa aaaaaagatg taaataattt gggagaaaaa gaggaagaac 5361 agtgtaaaat aaaactttct ataagtactc catttcaatg tgttcaacat catcctaaaa 5421 ggcaagattt tcccacgcag gtgacaaggt ggtttatgta ctatttaagg gcggaaggtg 5481 cgtgcccgtt caataagcat gttttttgcc aggtaggaaa tatgttccat atctttactt 5541 atcattgcat ttcagatggg aactagaaaa actggagaga aaaatgtaat gaaactgctg 5601 ctgtaaatta ttcctttttag catgtattca cttgctaaat acacatttct tcaaaataaa 5661 aaaaaaaaaa a 5672

<210> SEQ ID NO 58
<211> LENGTH: 771
<212> TYPE: PRT
<213> ORGANISM: Artificial Sequence
<220> FEATURE:
<223> OTHER INFORMATION: full-length human SEMA3A A106K

<400> SEQUENCE: 58

Met Gly Trp Leu Thr Arg Ile Val Cys Leu Phe Trp Gly Val Leu Leu
1 5 10 15

Thr Ala Arg Ala Asn Tyr Gln Asn Gly Lys Asn Asn Val Pro Arg Leu
20 25 30

Lys Leu Ser Tyr Lys Glu Met Leu Glu Ser Asn Asn Val Ile Thr Phe
35 40 45

-continued

```
Asn Gly Leu Ala Asn Ser Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Lys Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Lys Phe Ile Ser Ala His Leu Ile Ser Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Phe Lys Asp Pro Lys
305                 310                 315                 320

Asn Pro Val Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Met
                405                 410                 415

Asn Asn Arg Pro Ile Val Ile Lys Thr Asp Val Asn Tyr Gln Phe Thr
            420                 425                 430

Gln Ile Val Val Asp Arg Val Asp Ala Glu Asp Gly Gln Tyr Asp Val
        435                 440                 445

Met Phe Ile Gly Thr Asp Val Gly Thr Val Leu Lys Val Val Ser Ile
    450                 455                 460

Pro Lys Glu Thr Trp Tyr Asp Leu Glu Glu Val Leu Leu Glu Glu Met
```

465 470 475 480

Thr Val Phe Arg Glu Pro Thr Ala Ile Ser Ala Met Glu Leu Ser Thr
485 490 495

Lys Gln Gln Gln Leu Tyr Ile Gly Ser Thr Ala Gly Val Ala Gln Leu
500 505 510

Pro Leu His Arg Cys Asp Ile Tyr Gly Lys Ala Cys Ala Glu Cys Cys
515 520 525

Leu Ala Arg Asp Pro Tyr Cys Ala Trp Asp Gly Ser Ala Cys Ser Arg
530 535 540

Tyr Phe Pro Thr Ala Lys Arg Arg Thr Arg Arg Gln Asp Ile Arg Asn
545 550 555 560

Gly Asp Pro Leu Thr His Cys Ser Asp Leu His His Asp Asn His His
565 570 575

Gly His Ser Pro Glu Glu Arg Ile Ile Tyr Gly Val Glu Asn Ser Ser
580 585 590

Thr Phe Leu Glu Cys Ser Pro Lys Ser Gln Arg Ala Leu Val Tyr Trp
595 600 605

Gln Phe Gln Arg Arg Asn Glu Glu Arg Lys Glu Glu Ile Arg Val Asp
610 615 620

Asp His Ile Ile Arg Thr Asp Gln Gly Leu Leu Leu Arg Ser Leu Gln
625 630 635 640

Gln Lys Asp Ser Gly Asn Tyr Leu Cys His Ala Val Glu His Gly Phe
645 650 655

Ile Gln Thr Leu Leu Lys Val Thr Leu Glu Val Ile Asp Thr Glu His
660 665 670

Leu Glu Glu Leu Leu His Lys Asp Asp Asp Gly Asp Gly Ser Lys Thr
675 680 685

Lys Glu Met Ser Asn Ser Met Thr Pro Ser Gln Lys Val Trp Tyr Arg
690 695 700

Asp Phe Met Gln Leu Ile Asn His Pro Asn Leu Asn Thr Met Asp Glu
705 710 715 720

Phe Cys Glu Gln Val Trp Lys Arg Asp Arg Lys Gln Arg Arg Gln Arg
725 730 735

Pro Gly His Thr Pro Gly Asn Ser Asn Lys Trp Lys His Leu Gln Glu
740 745 750

Asn Lys Lys Gly Arg Asn Arg Arg Thr His Glu Phe Glu Arg Ala Pro
755 760 765

Arg Ser Val
770

<210> SEQ ID NO 59
<211> LENGTH: 6850
<212> TYPE: DNA
<213> ORGANISM: Artificial Sequence
<220> FEATURE:
<223> OTHER INFORMATION: full-length mouse Sema3A A106K, transcript variant 1
<220> FEATURE:
<221> NAME/KEY: CDS
<222> LOCATION: 650..2968
<223> OTHER INFORMATION: /transl_table=1

<400> SEQUENCE: 59
gtgacaagag ggaaggggag tgggttgagc tcgctcctct cccattgtca gcgcgtctag 60
tgagtgttgg gaaaacctgt ccgcgggatc ctgtgtcatc tctccctgct tgtgcacagg 120
aaaagtccgc gctgctctgc tcacggctgc tcgcaccccc tctctctcct ctctctcttt 180

```
ctctgtttcc ctttcattct gcttcctcgg agccgaatga agcagggaga gggagcagga    240

ttagagtcag ccaccggcta tcagcggagc ggagataaaa ggaactgctt cttaagcgcc    300

actgccgcag cccttgttaa tttttttctt cttcttcttc ttctttccac acaacagttg    360

tgcctcatta tccggtgcct ggctcgattt ttttctttct tttttctttt tttcttttct    420

ttcttccttt tttttttttt tcttttttttg agggtttgaa gtttctgtga ttccgtgact    480

gttacagaag agacgttagt gttgccatga ggtcttgatt gtctgcattt atgaatgaaa    540

ctgacctaaa tcacctgtta cctccagttt ccagattgtt tgaacttctc tggccgcaca    600

atacaggaag gaaggctgcc gcagctcagg gacctccagc gtctgcagc atg ggc tgg    658
                                                      Met Gly Trp
                                                      1

ttc act ggg att gcc tgt ctt ttc tgg ggt gta tta ctt aca gcc aga      706
Phe Thr Gly Ile Ala Cys Leu Phe Trp Gly Val Leu Leu Thr Ala Arg
    5                   10                  15

gca aac tat gca aac gga aag aac aat gtg cca aga ctg aaa tta tcg      754
Ala Asn Tyr Ala Asn Gly Lys Asn Asn Val Pro Arg Leu Lys Leu Ser
20                  25                  30                  35

tac aaa gaa atg ttg gaa tcc aac aat gtg atc act ttt aat ggc ttg      802
Tyr Lys Glu Met Leu Glu Ser Asn Asn Val Ile Thr Phe Asn Gly Leu
                40                  45                  50

gcc aac agc tcc agt tac cac acc ttc ctt ctg gat gaa gaa cgg agt      850
Ala Asn Ser Ser Ser Tyr His Thr Phe Leu Leu Asp Glu Glu Arg Ser
            55                  60                  65

aga cta tat gtt gga gca aaa gat cat ata ttt tca ttc aac ttg gtg      898
Arg Leu Tyr Val Gly Ala Lys Asp His Ile Phe Ser Phe Asn Leu Val
        70                  75                  80

aac att aaa gat ttt caa aag att gtg tgg cca gta tct tac aca agg      946
Asn Ile Lys Asp Phe Gln Lys Ile Val Trp Pro Val Ser Tyr Thr Arg
    85                  90                  95

aga gat gaa tgc aaa tgg aag gga aaa gat atc ctg aaa gaa tgt gcc      994
Arg Asp Glu Cys Lys Trp Lys Gly Lys Asp Ile Leu Lys Glu Cys Ala
100                 105                 110                 115

aat ttc atc aag gtc ctg gag gct tat aat cag act cac ttg tat gcc     1042
Asn Phe Ile Lys Val Leu Glu Ala Tyr Asn Gln Thr His Leu Tyr Ala
                120                 125                 130

tgt gga act ggg gct ttc cat cca atc tgc acc tat att gaa gtt gga     1090
Cys Gly Thr Gly Ala Phe His Pro Ile Cys Thr Tyr Ile Glu Val Gly
            135                 140                 145

cat cat cct gag gac aac att ttt aag ctg cag gac tca cat ttt gaa     1138
His His Pro Glu Asp Asn Ile Phe Lys Leu Gln Asp Ser His Phe Glu
        150                 155                 160

aac ggt cgt ggg aag agc cct tat gat ccc aaa cta ctg act gcc tct     1186
Asn Gly Arg Gly Lys Ser Pro Tyr Asp Pro Lys Leu Leu Thr Ala Ser
    165                 170                 175

ctt cta ata gac ggt gag ttg tac tct gga act gct gcg gac ttc atg     1234
Leu Leu Ile Asp Gly Glu Leu Tyr Ser Gly Thr Ala Ala Asp Phe Met
180                 185                 190                 195

gga cgg gac ttc gct atc ttc aga aca ctg ggg cac cat cac ccc atc     1282
Gly Arg Asp Phe Ala Ile Phe Arg Thr Leu Gly His His His Pro Ile
                200                 205                 210

agg acg gag cag cat gac tcc cgg tgg ctc aat gat cct aga ttc atc     1330
Arg Thr Glu Gln His Asp Ser Arg Trp Leu Asn Asp Pro Arg Phe Ile
            215                 220                 225

agt gcc cat ctc atc cca gag agt gac aac cct gaa gat gac aaa gta     1378
Ser Ala His Leu Ile Pro Glu Ser Asp Asn Pro Glu Asp Asp Lys Val
        230                 235                 240
```

-continued

```
tat ttt ttc ttc cga gaa aat gca ata gac gga gaa cac tct gga aaa     1426
Tyr Phe Phe Phe Arg Glu Asn Ala Ile Asp Gly Glu His Ser Gly Lys
    245                 250                 255

gcc act cat gct aga ata ggt cag ata tgc aag aat gac ttt ggt gga     1474
Ala Thr His Ala Arg Ile Gly Gln Ile Cys Lys Asn Asp Phe Gly Gly
260                 265                 270                 275

cac aga agt ctt gtg aat aaa tgg aca aca ttc cta aaa gca cgc ctg     1522
His Arg Ser Leu Val Asn Lys Trp Thr Thr Phe Leu Lys Ala Arg Leu
                280                 285                 290

att tgc tct gtg ccc ggt ccc aat ggc att gac acc cat ttt gat gaa     1570
Ile Cys Ser Val Pro Gly Pro Asn Gly Ile Asp Thr His Phe Asp Glu
            295                 300                 305

ttg cag gat gta ttc cta atg aac tct aaa gat cct aaa aat ccg atc     1618
Leu Gln Asp Val Phe Leu Met Asn Ser Lys Asp Pro Lys Asn Pro Ile
        310                 315                 320

gtc tat gga gtg ttc aca aca tca agc aac atc ttt aag gga tct gct     1666
Val Tyr Gly Val Phe Thr Thr Ser Ser Asn Ile Phe Lys Gly Ser Ala
    325                 330                 335

gtg tgc atg tac agc atg agt gat gta aga agg gtg ttc ctt ggt cca     1714
Val Cys Met Tyr Ser Met Ser Asp Val Arg Arg Val Phe Leu Gly Pro
340                 345                 350                 355

tat gct cac aga gat ggt ccc aac tat cag tgg gtg cct tac caa gga     1762
Tyr Ala His Arg Asp Gly Pro Asn Tyr Gln Trp Val Pro Tyr Gln Gly
                360                 365                 370

aga gtc cct tat cca cgg cca gga act tgt ccc agt aaa aca ttt ggc     1810
Arg Val Pro Tyr Pro Arg Pro Gly Thr Cys Pro Ser Lys Thr Phe Gly
            375                 380                 385

gga ttt gac tcc aca aag gac ctt cct gat gat gtc ata act ttt gca     1858
Gly Phe Asp Ser Thr Lys Asp Leu Pro Asp Asp Val Ile Thr Phe Ala
        390                 395                 400

aga agt cat cca gcc atg tac aac cca gtg ttt cct ata aat aat cgc     1906
Arg Ser His Pro Ala Met Tyr Asn Pro Val Phe Pro Ile Asn Asn Arg
    405                 410                 415

ccg atc atg atc aaa aca gat gta aat tat cag ttc aca caa att gtt     1954
Pro Ile Met Ile Lys Thr Asp Val Asn Tyr Gln Phe Thr Gln Ile Val
420                 425                 430                 435

gta gac cga gtg gat gca gaa gat ggc cag tat gat gtt atg ttc atc     2002
Val Asp Arg Val Asp Ala Glu Asp Gly Gln Tyr Asp Val Met Phe Ile
                440                 445                 450

gga aca gat gtt gga acc gtt ctt aaa gtg gtt tca gtc ccc aag gag     2050
Gly Thr Asp Val Gly Thr Val Leu Lys Val Val Ser Val Pro Lys Glu
            455                 460                 465

act tgg cat gac cta gaa gaa gtt ctt ctg gaa gaa atg acc gtc ttc     2098
Thr Trp His Asp Leu Glu Glu Val Leu Leu Glu Glu Met Thr Val Phe
        470                 475                 480

cgg gaa cca aca act att tcg gca atg gag ctt tct act aaa cag caa     2146
Arg Glu Pro Thr Thr Ile Ser Ala Met Glu Leu Ser Thr Lys Gln Gln
    485                 490                 495

cag ctg tac att ggc tca act gcg gga gtg gca cag ctt cct cta cac     2194
Gln Leu Tyr Ile Gly Ser Thr Ala Gly Val Ala Gln Leu Pro Leu His
500                 505                 510                 515

cgc tgt gac atc tat ggc aaa gcc tgt gca gaa tgc tgc ctc gct cgg     2242
Arg Cys Asp Ile Tyr Gly Lys Ala Cys Ala Glu Cys Cys Leu Ala Arg
                520                 525                 530

gac cct tac tgt gcc tgg gat ggg tcc tca tgc tca cgc tat ttt cct     2290
Asp Pro Tyr Cys Ala Trp Asp Gly Ser Ser Cys Ser Arg Tyr Phe Pro
            535                 540                 545

act gca aag agg cgc aca aga cga caa gat ata agg aat gga gac cca     2338
Thr Ala Lys Arg Arg Thr Arg Arg Gln Asp Ile Arg Asn Gly Asp Pro
        550                 555                 560
```

```
ctg act cac tgc tct gac ttg cag cac cat gat aat cat cat ggg ccc     2386
Leu Thr His Cys Ser Asp Leu Gln His His Asp Asn His His Gly Pro
    565                 570                 575

agc ctt gaa gag aga atc atc tat gga gtg gaa aac agt agt aca ttc     2434
Ser Leu Glu Glu Arg Ile Ile Tyr Gly Val Glu Asn Ser Ser Thr Phe
580                 585                 590                 595

ttg gaa tgc agt ccg aag tca cag aga gcc ttg gta tat tgg caa ttt     2482
Leu Glu Cys Ser Pro Lys Ser Gln Arg Ala Leu Val Tyr Trp Gln Phe
                600                 605                 610

cag agg aga aat gaa gat cga aaa gag gag atc aga atg ggt gat cat     2530
Gln Arg Arg Asn Glu Asp Arg Lys Glu Glu Ile Arg Met Gly Asp His
            615                 620                 625

atc atc agg aca gaa caa ggg ctc ctg ctc cgt agc ctg cag aag aag     2578
Ile Ile Arg Thr Glu Gln Gly Leu Leu Leu Arg Ser Leu Gln Lys Lys
        630                 635                 640

gat tca ggc aat tac ctg tgt cac gct gtg gaa cac gga ttc atg caa     2626
Asp Ser Gly Asn Tyr Leu Cys His Ala Val Glu His Gly Phe Met Gln
    645                 650                 655

act ctt ctt aag gta acc ctg gaa gtc att gac aca gaa cat ttg gaa     2674
Thr Leu Leu Lys Val Thr Leu Glu Val Ile Asp Thr Glu His Leu Glu
660                 665                 670                 675

gaa ctt ctt cat aaa gat gac gat gga gat ggc tct aag ata aaa gaa     2722
Glu Leu Leu His Lys Asp Asp Asp Gly Asp Gly Ser Lys Ile Lys Glu
                680                 685                 690

atg tcg agc agc atg acg ccc agc cag aaa gtc tgg tac cga gac ttc     2770
Met Ser Ser Ser Met Thr Pro Ser Gln Lys Val Trp Tyr Arg Asp Phe
            695                 700                 705

atg cag ctc att aac cac ccc aac ctg aac acg atg gat gag ttc tgt     2818
Met Gln Leu Ile Asn His Pro Asn Leu Asn Thr Met Asp Glu Phe Cys
        710                 715                 720

gaa caa gtg tgg aaa agg gac cga aag caa cgc cga caa agg ccg ggg     2866
Glu Gln Val Trp Lys Arg Asp Arg Lys Gln Arg Arg Gln Arg Pro Gly
    725                 730                 735

cac tct caa ggg agc agc aac aag tgg aag cac atg caa gag agc aag     2914
His Ser Gln Gly Ser Ser Asn Lys Trp Lys His Met Gln Glu Ser Lys
740                 745                 750                 755

aaa ggt aga aac agg agg acc cac gag ttt gag cgg gca ccc aga agt     2962
Lys Gly Arg Asn Arg Arg Thr His Glu Phe Glu Arg Ala Pro Arg Ser
                760                 765                 770

gtc tga gctgcgccac ctcccaaaac ctcaaacaag tacaaacttg cttagataat      3018

Val

aactggaaaa aatgcaatac acatgaacat ttcatggcat tatgtggatg tttacaatga   3078

tgggaagttc aaccgggttc caccaattta agtccgtgag gaactttccc agcaggcttt   3138

cttcagtata ccaacgcttg acagagatca caggtgagca tagatgttca cgtccgctga   3198

cttagtgttt cctctgaaag ttcattttgc ttccttcttt gcctgagaaa taaaaatgtc   3258

atttgccatc gaaaggagaa aaactgcatc agcaaagcca ttttattgaa gcaagagttg   3318

aaaataaact gcatggattt agtaagcaga tgaatattcc aaaacgtgat tggattcaag   3378

gatgttttgt ctaccagcac tcgtgtttgt atgtactgga gaagtaaaat aaggagaatg   3438

acactgagtg aaatagtcta tggagatata aaaacacaaa ccacccatca tccagagtaa   3498

tggagtacat tgatctacta ctgatgtctt ctttcagctt tgatctaaag atgtatttta   3558

ttaaagttat aatttaaatg taccatggca aatatgcagt aaagattagc tgtttcctaa   3618

gctagagtag gtcttgtctt gcagttacca tgctatatcg tttgtttaaa aattccaact   3678
```

-continued

```
gtgtgctgct tttttacatt gtgttttcag ttctgtaaga ggcagtatat cactttaggt   3738
ccctactcac tgtactatta cttactgaca ccaagaatta tggtcttccc ctttgaagaa   3798
accaaacaga tagaaggtta tcaccctgac ttgcaaaggt attatctaag ttaactctca   3858
catacataat gttttcagtc aaccaaaaat taagacagca caaagagaag aaaacagtca   3918
ttagaggcat cctgaaggat caagagcaaa attaaattca tgtgtctcat gaaaagaaca   3978
ttgtcttaac agagtgttga taaaatgtct ttccctcttg gcttgaatat ttgcatgatg   4038
tgtgaggcat aggactcgct catgattcca catcccacca aagattctat tttcagtcac   4098
ttaatgattt ccaaagcaga gagaaagagc gggggtgggg ggaatcagtg acattcagga   4158
catgttctaa caacaaaatg acacatttct caactatttc tttgtgaatc aactaaattt   4218
tacccaccct gtatgataca attatttgtc tgaacaactt ataagtgttt tatctcaatg   4278
agagtgaaac tatacacttc acctagaaag tgcaaaattc tttgttttat gaataaaata   4338
taagataaca caaaatgttt cagaatgtat agcctttgtt ggttggagat gatttcctaa   4398
gaatcattga gttcaaaatg cttaataaat tcaacattat agaccagttc attggtgcta   4458
caggcctcac ttcaggaatt tttttcttcg atccttcagc atgcacaaaa atgcaaagta   4518
aatatcttct tgctaagaaa tgaagtggcg ttgatatttt aactccagtt gtctcctaat   4578
tctaattaac tcagtattaa cttctcacct caactacacc aaattgtcat tccctcgcca   4638
ctgaaatagt tcacagatgg aagcttctgt ttcagtttta atgattattt aaataaaaaa   4698
acaatttgtt gacatgtctt tcatataaaa gcctaaaatc atcctacatc tgattttagg   4758
ctcattgact aatggtgttg cttttggaaa tatgtcttca aaggcaagct gaatggatga   4818
attatttgag atcacactct gaacagaaaa tattgtcagg aacattaagt gagagaaaga   4878
gggatgctcc aaataagcca ttctctcatt taatagggtc ttaactgtcc aaacatttaa   4938
tgttatattt cattctaaat ttgcatctga tacaagtata ttggcaatta cataactctc   4998
ccatttcttt ctagctctta acaataaagg atctaatgga aggaaggttg tttaataact   5058
ttatggatgc ctttcaaaat cggaatgcat tttgtttagc actaagaaat agcaatagaa   5118
aactgcttag gtttcaatta aaagtgttaa aaacaagcaa atatattaac atgtctcaat   5178
caatcaccat gtctaagttt caaagaaagt tattgattaa ctagggaata aataaataaa   5238
tacacacata catacataaa tcttatgaca gttataacct cccattgtgt attgagagag   5298
gacagtttgc acgaagaaga atgtcccatt tactaagtaa tttagatgga ctttggcata   5358
tgcatgtatc atcacaggta agacctgcct aagagatgca tgtgacctta agcaaattac   5418
cacagcagtc tcacaatagt ctcaagttga aaaagataca tcacagtgga gagagcaggc   5478
cccgctgata gcaactgtaa agtgtaaatg catgcaaatg cacacttatt gcttctttta   5538
tgtataattt agtgatttat aatggtatgt gtttaatatt tttgctacct acacattaga   5598
caaaggtgta aataattttg aaaagagtag aaagagcact gtaaattaca agtttctata   5658
gatgctccat tccagtttgt tcaccatcat cctcaagtgc aagatttccc atacaagtga   5718
tgcggtggct tatgtactac ttaagggcag agagggtgtg cccctcgaag agcatgcttt   5778
ttgccaggtc gtaaattgtt ccgtatctgt atttatcatt gcatttcaga tgggaactag   5838
aaaactggag agaaaaatgt aacgatattg ctgctgtaaa ttattccttt ttagcatgta   5898
ttcagttgct aaatacacat ttcttcaaaa tatttgaatt cagatgtctt tactgttcca   5958
tataacatat ggtattgagg aagataagct tcgaagcctt cgagaaccag agtcaggaat   6018
cagcataatt agctaacaga tttcttcatt gtagtattct gtaaactgtg ttctatattt   6078
```

```
atagtgatga tgtgaatttt ttgcccttta aactaaatgc tgttctcttt atgtcatacc   6138

tggaaagaac acatggatga aagtctttaa tcagtggatt atgatgtgaa gcatcataat   6198

tcaagatcaa taccgattcc agatgattgg catctagagg cctgtcctgc agctcatggg   6258

caagcactgc attaatatgg atttatttct gtaatgtgtt caagtccttc tcttataaat   6318

actattttaa acacatattt aattcactga aagtctgtca gagtttattt gcttcaaaga   6378

cacatttgac aaacaggtct tagcactatt atatactaac atgatggtta caaactggcc   6438

tggtgccaaa gaatccaaag cttttaattt taacttggta ataattattt aagtcaatgt   6498

taatatttac agtatatctt tccttaaaga agcaaacatt attttcaaaa gtatggaaat   6558

tctattagct ttattttaaa aactttccta tactagctaa ttcaaaaatc acacatttgt   6618

atattaatag ataaagacaa acccaaagtg aaagttgccc cagaaatggg ttttcttata   6678

actggtcaac tttcttgatt aacctaacca aagaaaaatc ttatttcttc atttccaaca   6738

cccaagtgca caaacacagt ctatggtaga aataaaacca aattaataaa agaggaatga   6798

ttttaagtta tgatattagg acccagacgt gacagcatca acctacaatt cc           6850


<210> SEQ ID NO 60
<211> LENGTH: 772
<212> TYPE: PRT
<213> ORGANISM: Artificial Sequence
<220> FEATURE:
<223> OTHER INFORMATION: full-length mouse Sema3A A106K, transcript
      variant 1

<400> SEQUENCE: 60

Met Gly Trp Phe Thr Gly Ile Ala Cys Leu Phe Trp Gly Val Leu Leu
1               5                   10                  15

Thr Ala Arg Ala Asn Tyr Ala Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asn Leu Val Asn Ile Lys Asp Phe Gln Lys Ile Val Trp Pro Val Ser
                85                  90                  95

Tyr Thr Arg Arg Asp Glu Cys Lys Trp Lys Gly Lys Asp Ile Leu Lys
            100                 105                 110

Glu Cys Ala Asn Phe Ile Lys Val Leu Glu Ala Tyr Asn Gln Thr His
        115                 120                 125

Leu Tyr Ala Cys Gly Thr Gly Ala Phe His Pro Ile Cys Thr Tyr Ile
    130                 135                 140

Glu Val Gly His His Pro Glu Asp Asn Ile Phe Lys Leu Gln Asp Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220
```

-continued

```
Arg Phe Ile Ser Ala His Leu Ile Pro Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Ser Lys Asp Pro Lys
305                 310                 315                 320

Asn Pro Ile Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Ile
                405                 410                 415

Asn Asn Arg Pro Ile Met Ile Lys Thr Asp Val Asn Tyr Gln Phe Thr
            420                 425                 430

Gln Ile Val Val Asp Arg Val Asp Ala Glu Asp Gly Gln Tyr Asp Val
        435                 440                 445

Met Phe Ile Gly Thr Asp Val Gly Thr Val Leu Lys Val Val Ser Val
    450                 455                 460

Pro Lys Glu Thr Trp His Asp Leu Glu Glu Val Leu Leu Glu Glu Met
465                 470                 475                 480

Thr Val Phe Arg Glu Pro Thr Thr Ile Ser Ala Met Glu Leu Ser Thr
                485                 490                 495

Lys Gln Gln Gln Leu Tyr Ile Gly Ser Thr Ala Gly Val Ala Gln Leu
            500                 505                 510

Pro Leu His Arg Cys Asp Ile Tyr Gly Lys Ala Cys Ala Glu Cys Cys
        515                 520                 525

Leu Ala Arg Asp Pro Tyr Cys Ala Trp Asp Gly Ser Ser Cys Ser Arg
    530                 535                 540

Tyr Phe Pro Thr Ala Lys Arg Arg Thr Arg Arg Gln Asp Ile Arg Asn
545                 550                 555                 560

Gly Asp Pro Leu Thr His Cys Ser Asp Leu Gln His His Asp Asn His
                565                 570                 575

His Gly Pro Ser Leu Glu Glu Arg Ile Ile Tyr Gly Val Glu Asn Ser
            580                 585                 590

Ser Thr Phe Leu Glu Cys Ser Pro Lys Ser Gln Arg Ala Leu Val Tyr
        595                 600                 605

Trp Gln Phe Gln Arg Arg Asn Glu Asp Arg Lys Glu Glu Ile Arg Met
    610                 615                 620

Gly Asp His Ile Ile Arg Thr Glu Gln Gly Leu Leu Leu Arg Ser Leu
625                 630                 635                 640
```

```
Gln Lys Lys Asp Ser Gly Asn Tyr Leu Cys His Ala Val Glu His Gly
                645                 650                 655

Phe Met Gln Thr Leu Leu Lys Val Thr Leu Glu Val Ile Asp Thr Glu
            660                 665                 670

His Leu Glu Glu Leu Leu His Lys Asp Asp Asp Gly Asp Gly Ser Lys
        675                 680                 685

Ile Lys Glu Met Ser Ser Ser Met Thr Pro Ser Gln Lys Val Trp Tyr
    690                 695                 700

Arg Asp Phe Met Gln Leu Ile Asn His Pro Asn Leu Asn Thr Met Asp
705                 710                 715                 720

Glu Phe Cys Glu Gln Val Trp Lys Arg Asp Arg Lys Gln Arg Arg Gln
                725                 730                 735

Arg Pro Gly His Ser Gln Gly Ser Ser Asn Lys Trp Lys His Met Gln
            740                 745                 750

Glu Ser Lys Lys Gly Arg Asn Arg Arg Thr His Glu Phe Glu Arg Ala
        755                 760                 765

Pro Arg Ser Val
    770


<210> SEQ ID NO 61
<211> LENGTH: 2981
<212> TYPE: DNA
<213> ORGANISM: Artificial Sequence
<220> FEATURE:
<223> OTHER INFORMATION: full-length human SEMA3B A105K, transcript
      variant 3
<220> FEATURE:
<221> NAME/KEY: CDS
<222> LOCATION: 247..2496
<223> OTHER INFORMATION: /transl_table=1

<400> SEQUENCE: 61

gcgtgggtgt gtctgtgatt gtggccaggc ggggcaccct cggaggggag ggttcggaag      60

tggaatgcga ccccccagcc tctttcccct aggggctgta atctgatccc tggggactcc     120

ccccctagcc tcccgccctc gccctcactg ctgactcctc ttccagatcc tggggcagag     180

tccagggcag ctcaaggctc ctccacacac acacccgctg aaccctgagc accctgagct     240

gctgag atg ggg cgg gcc ggg gct gcc gcc gtg atc ccg ggc ctg gcc       288
       Met Gly Arg Ala Gly Ala Ala Ala Val Ile Pro Gly Leu Ala
       1               5                   10

ctg ctc tgg gca gtg ggg ctg ggg agt gcc gcc ccc agc ccc cca cgc      336
Leu Leu Trp Ala Val Gly Leu Gly Ser Ala Ala Pro Ser Pro Pro Arg
15                  20                  25                  30

ctt cgg ctc tcc ttc caa gag ctc cag gcc tgg cat ggt ctc cag act      384
Leu Arg Leu Ser Phe Gln Glu Leu Gln Ala Trp His Gly Leu Gln Thr
                35                  40                  45

ttc agc ctg gag cga acc tgc tgc tac cag gcc ttg ctg gtg gat gag      432
Phe Ser Leu Glu Arg Thr Cys Cys Tyr Gln Ala Leu Leu Val Asp Glu
            50                  55                  60

gag cgt gga cgc ctg ttt gtg ggt gcc gag aac cat gtg gcc tcc ctc      480
Glu Arg Gly Arg Leu Phe Val Gly Ala Glu Asn His Val Ala Ser Leu
        65                  70                  75

aac ctg gac aac atc agc aag cgg gcc aag aag ctg gcc tgg ccg gcc      528
Asn Leu Asp Asn Ile Ser Lys Arg Ala Lys Lys Leu Ala Trp Pro Ala
    80                  85                  90

cct gtg gaa tgg cga gag gag tgc aac tgg aag ggg aag gac att ggt      576
Pro Val Glu Trp Arg Glu Glu Cys Asn Trp Lys Gly Lys Asp Ile Gly
95                  100                 105                 110

act gag tgc atg aac ttc gtg aag ttg ctg cat gcc tac aac cgc acc      624
```

-continued

```
Thr Glu Cys Met Asn Phe Val Lys Leu Leu His Ala Tyr Asn Arg Thr
                115                 120                 125

cat ttg ctg gcc tgt ggc acg gga gcc ttc cac cca acc tgt gcc ttt      672
His Leu Leu Ala Cys Gly Thr Gly Ala Phe His Pro Thr Cys Ala Phe
            130                 135                 140

gtg gaa gtg ggc cac cgg gca gag gag ccc gtc ctc cgg ctg gac cca      720
Val Glu Val Gly His Arg Ala Glu Glu Pro Val Leu Arg Leu Asp Pro
        145                 150                 155

gga agg ata gag gat ggc aag ggg aag agt cct tat gac ccc agg cat      768
Gly Arg Ile Glu Asp Gly Lys Gly Lys Ser Pro Tyr Asp Pro Arg His
    160                 165                 170

cgg gct gcc tcc gtg ctg gtg ggg gag gag cta tac tca ggg gtg gca      816
Arg Ala Ala Ser Val Leu Val Gly Glu Glu Leu Tyr Ser Gly Val Ala
175                 180                 185                 190

gca gac ctc atg gga cga gac ttt acc atc ttt cgc agc cta ggg caa      864
Ala Asp Leu Met Gly Arg Asp Phe Thr Ile Phe Arg Ser Leu Gly Gln
                195                 200                 205

cgt cca agt ctc cga aca gag cca cac gac tcc cgc tgg ctc aat gag      912
Arg Pro Ser Leu Arg Thr Glu Pro His Asp Ser Arg Trp Leu Asn Glu
            210                 215                 220

ccc aag ttt gtc aag gta ttt tgg atc ccg gag agc gag aac cca gac      960
Pro Lys Phe Val Lys Val Phe Trp Ile Pro Glu Ser Glu Asn Pro Asp
        225                 230                 235

gac gac aaa atc tac ttc ttc ttt cgt gag acg gcg gta gag gcg gcg     1008
Asp Asp Lys Ile Tyr Phe Phe Phe Arg Glu Thr Ala Val Glu Ala Ala
    240                 245                 250

ccg gca ctg gga cgc ctg tcc gtg tcc cgc gtt ggc cag atc tgc cgg     1056
Pro Ala Leu Gly Arg Leu Ser Val Ser Arg Val Gly Gln Ile Cys Arg
255                 260                 265                 270

aac gac gtg ggc ggc cag cgc agc ctg gtc aac aag tgg acg acg ttc     1104
Asn Asp Val Gly Gly Gln Arg Ser Leu Val Asn Lys Trp Thr Thr Phe
                275                 280                 285

ctg aag gcg cgg ctg gtg tgc tcg gtg ccc ggc gtc gag ggc gac acc     1152
Leu Lys Ala Arg Leu Val Cys Ser Val Pro Gly Val Glu Gly Asp Thr
            290                 295                 300

cac ttc gat cag ctc cag gat gtg ttt ctg ttg tcc tcg cgg gac cac     1200
His Phe Asp Gln Leu Gln Asp Val Phe Leu Leu Ser Ser Arg Asp His
        305                 310                 315

cgg acc ccg ctg ctc tat gcc gtc ttc tcc acg tcc agc agc atc ttc     1248
Arg Thr Pro Leu Leu Tyr Ala Val Phe Ser Thr Ser Ser Ser Ile Phe
    320                 325                 330

cag ggc tct gcg gtg tgc gtg tac agc atg aac gac gtg cgc cgg gcc     1296
Gln Gly Ser Ala Val Cys Val Tyr Ser Met Asn Asp Val Arg Arg Ala
335                 340                 345                 350

ttc ttg gga ccc ttt gca cac aag gag ggg ccc atg cac cag tgg gtg     1344
Phe Leu Gly Pro Phe Ala His Lys Glu Gly Pro Met His Gln Trp Val
                355                 360                 365

tca tac cag ggt cgc gtc ccc tac ccg cgg cca ggc atg tgc ccc agc     1392
Ser Tyr Gln Gly Arg Val Pro Tyr Pro Arg Pro Gly Met Cys Pro Ser
            370                 375                 380

aag acc ttt ggc acc ttc agt tcc acc aag gac ttc cca gac gat gtc     1440
Lys Thr Phe Gly Thr Phe Ser Ser Thr Lys Asp Phe Pro Asp Asp Val
        385                 390                 395

atc cag ttt gcg cgg aac cac ccc ctc atg tac aac tct gtc ctg ccc     1488
Ile Gln Phe Ala Arg Asn His Pro Leu Met Tyr Asn Ser Val Leu Pro
    400                 405                 410

act ggg ggg cgc cct ctt ttc cta caa gtt gga gcc aat tac acc ttc     1536
Thr Gly Gly Arg Pro Leu Phe Leu Gln Val Gly Ala Asn Tyr Thr Phe
415                 420                 425                 430
```

-continued

```
act caa att gcc gcg gac cgg gtt gca gcc gct gac gga cac tat gac      1584
Thr Gln Ile Ala Ala Asp Arg Val Ala Ala Ala Asp Gly His Tyr Asp
                435                 440                 445

gtc ctc ttc att ggc aca gac gtt ggc acg gtg ctg aag gtg atc tcg      1632
Val Leu Phe Ile Gly Thr Asp Val Gly Thr Val Leu Lys Val Ile Ser
            450                 455                 460

gtc ccc aag ggc agt agg ccc agc gca gag ggg ctg ctc ctg gag gag      1680
Val Pro Lys Gly Ser Arg Pro Ser Ala Glu Gly Leu Leu Leu Glu Glu
        465                 470                 475

ctg cac gtg ttt gag gac tcg gcc gct gtc acc agc atg caa att tct      1728
Leu His Val Phe Glu Asp Ser Ala Ala Val Thr Ser Met Gln Ile Ser
    480                 485                 490

tcc aag agg cac cag ctg tac gta gcc tcg cgg agc gcg gtg gcc cag      1776
Ser Lys Arg His Gln Leu Tyr Val Ala Ser Arg Ser Ala Val Ala Gln
495                 500                 505                 510

atc gcg ttg cac cgc tgc gct gcc cac ggc cgc gtc tgc acc gaa tgc      1824
Ile Ala Leu His Arg Cys Ala Ala His Gly Arg Val Cys Thr Glu Cys
                515                 520                 525

tgt ctg gcg cgt gac ccc tac tgc gcc tgg gac ggg gtc gcg tgc acg      1872
Cys Leu Ala Arg Asp Pro Tyr Cys Ala Trp Asp Gly Val Ala Cys Thr
            530                 535                 540

cgc ttc cag ccc agt gcc aag agg cgg ttc cgg cgg caa gac gta agg      1920
Arg Phe Gln Pro Ser Ala Lys Arg Arg Phe Arg Arg Gln Asp Val Arg
        545                 550                 555

aat ggc gac ccc agc acg ttg tgc tcc gga gac tcg tct cgt ccc gcg      1968
Asn Gly Asp Pro Ser Thr Leu Cys Ser Gly Asp Ser Ser Arg Pro Ala
    560                 565                 570

ctg ctg gaa cac aag gtg ttc ggc gtg gag ggc agc agc gcc ttt ctg      2016
Leu Leu Glu His Lys Val Phe Gly Val Glu Gly Ser Ser Ala Phe Leu
575                 580                 585                 590

gag tgt gag ccc cgc tcg ctg cag gcg cgc gtg gag tgg act ttc cag      2064
Glu Cys Glu Pro Arg Ser Leu Gln Ala Arg Val Glu Trp Thr Phe Gln
                595                 600                 605

cgc gca ggg gtg aca gcc cac acc cag gtg ctg gca gag gag cgc acc      2112
Arg Ala Gly Val Thr Ala His Thr Gln Val Leu Ala Glu Glu Arg Thr
            610                 615                 620

gag cgc acc gcc cgg gga cta ctg ctg cgc agg ctg cgg cgc cgg gac      2160
Glu Arg Thr Ala Arg Gly Leu Leu Leu Arg Arg Leu Arg Arg Arg Asp
        625                 630                 635

tcg ggc gtg tac ttg tgc gcc gcc gtc gag cag ggc ttt acg caa ccg      2208
Ser Gly Val Tyr Leu Cys Ala Ala Val Glu Gln Gly Phe Thr Gln Pro
    640                 645                 650

ctg cgt cgc ctg tcg ctg cac gtg ttg agt gct acg cag gcc gaa cga      2256
Leu Arg Arg Leu Ser Leu His Val Leu Ser Ala Thr Gln Ala Glu Arg
655                 660                 665                 670

ctg gcg cgg gcc gag gag gct gcg ccc gcc gcg ccg ccg ggc ccc aaa      2304
Leu Ala Arg Ala Glu Glu Ala Ala Pro Ala Ala Pro Pro Gly Pro Lys
                675                 680                 685

ctc tgg tac cgg gac ttt ctg cag ctg gtg gag ccg ggc gga ggt ggc      2352
Leu Trp Tyr Arg Asp Phe Leu Gln Leu Val Glu Pro Gly Gly Gly Gly
            690                 695                 700

agc gcg aac tcc ctg cgc atg tgc cgc ccg cag cct gcg ctg cag tca      2400
Ser Ala Asn Ser Leu Arg Met Cys Arg Pro Gln Pro Ala Leu Gln Ser
        705                 710                 715

ctg ccc ctg gag tcg cgg aga aag ggc cgt aac cgg agg acc cac gcc      2448
Leu Pro Leu Glu Ser Arg Arg Lys Gly Arg Asn Arg Arg Thr His Ala
    720                 725                 730

cct gag cct cgc gct gag cgg ggg ccg cgc agc gca acg cac tgg tga      2496
Pro Glu Pro Arg Ala Glu Arg Gly Pro Arg Ser Ala Thr His Trp
735                 740                 745
```

```
ccagactgtc cccacgccgg gaaccaagca ggagacgaca ggcgagagag gagccagaca   2556

gaccctgaaa agaaggacgg gttggggccg ggcacattgg gggtcaccgg ccgatggaga   2616

caccaaccga caggccctgg ctgagggcag ctgcgcgggc ttatttatta acaggataac   2676

ccttgaatgt agcagccccg ggagggcggc acaggtcggg cgcaggattc agccggaggg   2736

aagggacggg gaagccgagc tccagagcaa cgaccagggc cgaggaggtg cctggagtgc   2796

ccaccctggg agacagaccc cacctccttg ggtagtgagc agtgagcaga aagctgtgaa   2856

caggctgggc tgctggaggt ggggcgaggc aggccgactg tactaaagta acgcaataaa   2916

cgcattatca gccaaagctg gaatggcccc agcagaaaac cccagaaaaa aaaaaaaaaa   2976

aaaaa                                                               2981
```

```
<210> SEQ ID NO 62
<211> LENGTH: 749
<212> TYPE: PRT
<213> ORGANISM: Artificial Sequence
<220> FEATURE:
<223> OTHER INFORMATION: full-length human SEMA3B A105K, transcript
      variant 3

<400> SEQUENCE: 62

Met Gly Arg Ala Gly Ala Ala Ala Val Ile Pro Gly Leu Ala Leu Leu
1               5                   10                  15

Trp Ala Val Gly Leu Gly Ser Ala Ala Pro Ser Pro Pro Arg Leu Arg
            20                  25                  30

Leu Ser Phe Gln Glu Leu Gln Ala Trp His Gly Leu Gln Thr Phe Ser
        35                  40                  45

Leu Glu Arg Thr Cys Cys Tyr Gln Ala Leu Leu Val Asp Glu Glu Arg
    50                  55                  60

Gly Arg Leu Phe Val Gly Ala Glu Asn His Val Ala Ser Leu Asn Leu
65                  70                  75                  80

Asp Asn Ile Ser Lys Arg Ala Lys Lys Leu Ala Trp Pro Ala Pro Val
                85                  90                  95

Glu Trp Arg Glu Glu Cys Asn Trp Lys Gly Lys Asp Ile Gly Thr Glu
            100                 105                 110

Cys Met Asn Phe Val Lys Leu Leu His Ala Tyr Asn Arg Thr His Leu
        115                 120                 125

Leu Ala Cys Gly Thr Gly Ala Phe His Pro Thr Cys Ala Phe Val Glu
    130                 135                 140

Val Gly His Arg Ala Glu Glu Pro Val Leu Arg Leu Asp Pro Gly Arg
145                 150                 155                 160

Ile Glu Asp Gly Lys Gly Lys Ser Pro Tyr Asp Pro Arg His Arg Ala
                165                 170                 175

Ala Ser Val Leu Val Gly Glu Glu Leu Tyr Ser Gly Val Ala Ala Asp
            180                 185                 190

Leu Met Gly Arg Asp Phe Thr Ile Phe Arg Ser Leu Gly Gln Arg Pro
        195                 200                 205

Ser Leu Arg Thr Glu Pro His Asp Ser Arg Trp Leu Asn Glu Pro Lys
    210                 215                 220

Phe Val Lys Val Phe Trp Ile Pro Glu Ser Glu Asn Pro Asp Asp Asp
225                 230                 235                 240

Lys Ile Tyr Phe Phe Phe Arg Glu Thr Ala Val Glu Ala Ala Pro Ala
                245                 250                 255

Leu Gly Arg Leu Ser Val Ser Arg Val Gly Gln Ile Cys Arg Asn Asp
```

-continued

```
            260                 265                 270

Val Gly Gly Gln Arg Ser Leu Val Asn Lys Trp Thr Thr Phe Leu Lys
        275                 280                 285

Ala Arg Leu Val Cys Ser Val Pro Gly Val Glu Gly Asp Thr His Phe
    290                 295                 300

Asp Gln Leu Gln Asp Val Phe Leu Leu Ser Ser Arg Asp His Arg Thr
305                 310                 315                 320

Pro Leu Leu Tyr Ala Val Phe Ser Thr Ser Ser Ser Ile Phe Gln Gly
                325                 330                 335

Ser Ala Val Cys Val Tyr Ser Met Asn Asp Val Arg Arg Ala Phe Leu
            340                 345                 350

Gly Pro Phe Ala His Lys Glu Gly Pro Met His Gln Trp Val Ser Tyr
        355                 360                 365

Gln Gly Arg Val Pro Tyr Pro Arg Pro Gly Met Cys Pro Ser Lys Thr
    370                 375                 380

Phe Gly Thr Phe Ser Ser Thr Lys Asp Phe Pro Asp Asp Val Ile Gln
385                 390                 395                 400

Phe Ala Arg Asn His Pro Leu Met Tyr Asn Ser Val Leu Pro Thr Gly
                405                 410                 415

Gly Arg Pro Leu Phe Leu Gln Val Gly Ala Asn Tyr Thr Phe Thr Gln
            420                 425                 430

Ile Ala Ala Asp Arg Val Ala Ala Ala Asp Gly His Tyr Asp Val Leu
        435                 440                 445

Phe Ile Gly Thr Asp Val Gly Thr Val Leu Lys Val Ile Ser Val Pro
    450                 455                 460

Lys Gly Ser Arg Pro Ser Ala Glu Gly Leu Leu Leu Glu Glu Leu His
465                 470                 475                 480

Val Phe Glu Asp Ser Ala Ala Val Thr Ser Met Gln Ile Ser Ser Lys
                485                 490                 495

Arg His Gln Leu Tyr Val Ala Ser Arg Ser Ala Val Ala Gln Ile Ala
            500                 505                 510

Leu His Arg Cys Ala Ala His Gly Arg Val Cys Thr Glu Cys Cys Leu
        515                 520                 525

Ala Arg Asp Pro Tyr Cys Ala Trp Asp Gly Val Ala Cys Thr Arg Phe
    530                 535                 540

Gln Pro Ser Ala Lys Arg Arg Phe Arg Arg Gln Asp Val Arg Asn Gly
545                 550                 555                 560

Asp Pro Ser Thr Leu Cys Ser Gly Asp Ser Ser Arg Pro Ala Leu Leu
                565                 570                 575

Glu His Lys Val Phe Gly Val Glu Gly Ser Ser Ala Phe Leu Glu Cys
            580                 585                 590

Glu Pro Arg Ser Leu Gln Ala Arg Val Glu Trp Thr Phe Gln Arg Ala
        595                 600                 605

Gly Val Thr Ala His Thr Gln Val Leu Ala Glu Glu Arg Thr Glu Arg
    610                 615                 620

Thr Ala Arg Gly Leu Leu Leu Arg Arg Leu Arg Arg Arg Asp Ser Gly
625                 630                 635                 640

Val Tyr Leu Cys Ala Ala Val Glu Gln Gly Phe Thr Gln Pro Leu Arg
                645                 650                 655

Arg Leu Ser Leu His Val Leu Ser Ala Thr Gln Ala Glu Arg Leu Ala
            660                 665                 670

Arg Ala Glu Glu Ala Ala Pro Ala Ala Pro Pro Gly Pro Lys Leu Trp
        675                 680                 685
```

```
Tyr Arg Asp Phe Leu Gln Leu Val Glu Pro Gly Gly Gly Gly Ser Ala
    690                 695                 700

Asn Ser Leu Arg Met Cys Arg Pro Gln Pro Ala Leu Gln Ser Leu Pro
705                 710                 715                 720

Leu Glu Ser Arg Arg Lys Gly Arg Asn Arg Arg Thr His Ala Pro Glu
                725                 730                 735

Pro Arg Ala Glu Arg Gly Pro Arg Ser Ala Thr His Trp
            740                 745


<210> SEQ ID NO 63
<211> LENGTH: 3746
<212> TYPE: DNA
<213> ORGANISM: Artificial Sequence
<220> FEATURE:
<223> OTHER INFORMATION: full-length mouse Sema3B A105K, transcript
      variant 1
<220> FEATURE:
<221> NAME/KEY: CDS
<222> LOCATION: 400..2649
<223> OTHER INFORMATION: /transl_table=1

<400> SEQUENCE: 63

agtgaaaggc ccaaggctcc tggtggtggc ccctcctgcc acccctccac ctcagctctg      60

acatggccca ctgaagggaa gggcaagagg caaggagggg aggaactgat ctttccaaaa     120

gctcctggga cctgagcttg ctgtggagtg tacagtcatc ccttagctgt ggagggacag     180

caactgcttt gctctttgca cttggtgccc tctggaatga ccacaggatc tgactctcat     240

ctgtcggctc ttcgcccttt actgcctggg gaccttgtcc gcatcatcag tatccttgtc     300

tctgccccag gctggcatga aatcctgggg cagagtccag gactgctgaa ggctcctcca     360

cacacgcctg ctgaaccctg agcgccctga gctgccggc atg ggg cgg gct gag        414
                                          Met Gly Arg Ala Glu
                                          1               5

gcc gcc gcc atg atc cca ggc ctg gcc ctt ctc tgg gta gca ggg cta       462
Ala Ala Ala Met Ile Pro Gly Leu Ala Leu Leu Trp Val Ala Gly Leu
                10                  15                  20

ggg gat act gcc cct aac ctt ccc cgc ctt cgg ctc tcc ttt caa gaa       510
Gly Asp Thr Ala Pro Asn Leu Pro Arg Leu Arg Leu Ser Phe Gln Glu
            25                  30                  35

tta cag gcc cgg cat ggt gtc cga acc ttc agg ctg gag cgg acc tgc       558
Leu Gln Ala Arg His Gly Val Arg Thr Phe Arg Leu Glu Arg Thr Cys
        40                  45                  50

tgt tat gaa gcc ttg ctg gtg gat gag gag cgt gga cgc ctg ttt gtg       606
Cys Tyr Glu Ala Leu Leu Val Asp Glu Glu Arg Gly Arg Leu Phe Val
    55                  60                  65

ggt gct gag aac cac gtg gct tcc ctc agc ctg gac aac atc agc aag       654
Gly Ala Glu Asn His Val Ala Ser Leu Ser Leu Asp Asn Ile Ser Lys
70                  75                  80                  85

cga gcc aag aag ctg gcc tgg ccc gcc ccc gtg gaa tgg cgt gaa gaa       702
Arg Ala Lys Lys Leu Ala Trp Pro Ala Pro Val Glu Trp Arg Glu Glu
                90                  95                  100

tgc aac tgg aag ggg aag gac att ggt acc gag tgc atg aac ttc gtg       750
Cys Asn Trp Lys Gly Lys Asp Ile Gly Thr Glu Cys Met Asn Phe Val
            105                 110                 115

aag ctg ctg cac acc tac aac cac acc cac ttg ctg gcc tgt ggc aca       798
Lys Leu Leu His Thr Tyr Asn His Thr His Leu Leu Ala Cys Gly Thr
        120                 125                 130

ggg gct ttc cac cca acc tgt gcc ttt gtg gag gtg ggc cac cgg ctg       846
Gly Ala Phe His Pro Thr Cys Ala Phe Val Glu Val Gly His Arg Leu
    135                 140                 145
```

```
gag gaa ccc atg ctt caa ctg gac cgg agg aaa ctt gag gac ggc aag      894
Glu Glu Pro Met Leu Gln Leu Asp Arg Arg Lys Leu Glu Asp Gly Lys
150                 155                 160                 165

ggg aag act cct tat gac cca agg cat cgg gct gcc tcg gtg ctg gtg      942
Gly Lys Thr Pro Tyr Asp Pro Arg His Arg Ala Ala Ser Val Leu Val
                170                 175                 180

ggg gaa gaa ctg tat tct ggg gtg aca gca gac ctt atg ggc cgg gac      990
Gly Glu Glu Leu Tyr Ser Gly Val Thr Ala Asp Leu Met Gly Arg Asp
            185                 190                 195

ttt acc atc ttt cga agc ctt ggt cag aat ccg agt ctc cga aca gag     1038
Phe Thr Ile Phe Arg Ser Leu Gly Gln Asn Pro Ser Leu Arg Thr Glu
        200                 205                 210

ccc cat gat tcc cgc tgg ctc aat gaa ccc aag ttt gtc aag gtc ttt     1086
Pro His Asp Ser Arg Trp Leu Asn Glu Pro Lys Phe Val Lys Val Phe
    215                 220                 225

tgg atc cca gag agt gag aac cct gat gac gat aaa atc tat ttc ttc     1134
Trp Ile Pro Glu Ser Glu Asn Pro Asp Asp Asp Lys Ile Tyr Phe Phe
230                 235                 240                 245

ttc cgc gag tcc gct gtg gaa gca gca cca gca atg ggg cgc atg tct     1182
Phe Arg Glu Ser Ala Val Glu Ala Ala Pro Ala Met Gly Arg Met Ser
                250                 255                 260

gtg tct cgt gtt ggc cag atc tgc agg aat gac ctg ggt ggc cag cgg     1230
Val Ser Arg Val Gly Gln Ile Cys Arg Asn Asp Leu Gly Gly Gln Arg
            265                 270                 275

agc ttg gtc aac aaa tgg acc aca ttt ctg aag gcg cgg ctt gtg tgc     1278
Ser Leu Val Asn Lys Trp Thr Thr Phe Leu Lys Ala Arg Leu Val Cys
        280                 285                 290

tca gta cct gga gtt gag ggt gac acc cac ttt gac caa ctt cag gat     1326
Ser Val Pro Gly Val Glu Gly Asp Thr His Phe Asp Gln Leu Gln Asp
    295                 300                 305

gtt ttc ctt ctg tcc tcc cga gac cgc cag aca cct ctt ctc tat gct     1374
Val Phe Leu Leu Ser Ser Arg Asp Arg Gln Thr Pro Leu Leu Tyr Ala
310                 315                 320                 325

gtc ttc tcc acc tcc agt ggt gtc ttc cag ggc tct gct gtg tgc gtg     1422
Val Phe Ser Thr Ser Ser Gly Val Phe Gln Gly Ser Ala Val Cys Val
                330                 335                 340

tac agc atg aac gat gtg cgc cga gcc ttc ttg gga cct ttt gct cac     1470
Tyr Ser Met Asn Asp Val Arg Arg Ala Phe Leu Gly Pro Phe Ala His
            345                 350                 355

aaa gag ggg cct aca cac cag tgg gtg tcc tac cag ggt cgt gtc ccc     1518
Lys Glu Gly Pro Thr His Gln Trp Val Ser Tyr Gln Gly Arg Val Pro
        360                 365                 370

tac cca aga cct ggc atg tgc ccc agc aag acc ttt ggc acc ttc agc     1566
Tyr Pro Arg Pro Gly Met Cys Pro Ser Lys Thr Phe Gly Thr Phe Ser
    375                 380                 385

tcc acc aag gac ttc cca gat gac gtt atc cag ttt gct cgg aac cac     1614
Ser Thr Lys Asp Phe Pro Asp Asp Val Ile Gln Phe Ala Arg Asn His
390                 395                 400                 405

cct ctc atg tac aac cca gtc ctg ccc atg ggg ggg cgc cct ctc ttc     1662
Pro Leu Met Tyr Asn Pro Val Leu Pro Met Gly Gly Arg Pro Leu Phe
                410                 415                 420

cta caa gtg gga gct ggg tac acc ttc acc caa atc gcc gca gac cga     1710
Leu Gln Val Gly Ala Gly Tyr Thr Phe Thr Gln Ile Ala Ala Asp Arg
            425                 430                 435

gta gca gct gcc gat gga cac tac gat gtt ctc ttc att ggt aca gat     1758
Val Ala Ala Ala Asp Gly His Tyr Asp Val Leu Phe Ile Gly Thr Asp
        440                 445                 450

gtg ggc aca gtg ctg aaa gtg atc tca gtc ccc aaa ggc agc cga cct     1806
Val Gly Thr Val Leu Lys Val Ile Ser Val Pro Lys Gly Ser Arg Pro
```

-continued

```
    455                 460                 465

aat tct gaa gga ctt ctc ctg gaa gag ctg cag gtg ttc gag gac tct     1854
Asn Ser Glu Gly Leu Leu Leu Glu Glu Leu Gln Val Phe Glu Asp Ser
470                 475                 480                 485

gcc gct atc acc agc atg caa atc tcc tct aaa agg caa caa ctc tac     1902
Ala Ala Ile Thr Ser Met Gln Ile Ser Ser Lys Arg Gln Gln Leu Tyr
                490                 495                 500

ata gca tcg cgc agc gca gtg gcc cag att gct ttg cat cgc tgc act     1950
Ile Ala Ser Arg Ser Ala Val Ala Gln Ile Ala Leu His Arg Cys Thr
            505                 510                 515

gcc cta ggc cgc gcc tgc gca gaa tgc tgc ttg gcc cgt gat cct tac     1998
Ala Leu Gly Arg Ala Cys Ala Glu Cys Cys Leu Ala Arg Asp Pro Tyr
        520                 525                 530

tgc gcc tgg gat gga tca gct tgc aca cgc ttc cag cct acg gcc aag     2046
Cys Ala Trp Asp Gly Ser Ala Cys Thr Arg Phe Gln Pro Thr Ala Lys
    535                 540                 545

aga cgg ttc cgg agg caa gac ata agg aat ggc gac ccc agc acc cta     2094
Arg Arg Phe Arg Arg Gln Asp Ile Arg Asn Gly Asp Pro Ser Thr Leu
550                 555                 560                 565

tgc tct gga gac tct tct cac tct gtg ctg ctg gag aag aag gtg ttg     2142
Cys Ser Gly Asp Ser Ser His Ser Val Leu Leu Glu Lys Lys Val Leu
                570                 575                 580

ggt gtg gag agc ggc agc gcg ttt ctg gag tgt gag ccc cgc tcg ctc     2190
Gly Val Glu Ser Gly Ser Ala Phe Leu Glu Cys Glu Pro Arg Ser Leu
            585                 590                 595

cag gcg cat gtg cag tgg acc ttc caa ggt gca ggg gag gca gct cac     2238
Gln Ala His Val Gln Trp Thr Phe Gln Gly Ala Gly Glu Ala Ala His
        600                 605                 610

acc cag gtg ctg gct gag gag aga gta gag cgc act gcg cgg ggg ctg     2286
Thr Gln Val Leu Ala Glu Glu Arg Val Glu Arg Thr Ala Arg Gly Leu
    615                 620                 625

ctg ttg cgg ggg ctg cgg cgc cag gac tct ggc gtg tat ctt tgc gtc     2334
Leu Leu Arg Gly Leu Arg Arg Gln Asp Ser Gly Val Tyr Leu Cys Val
630                 635                 640                 645

gcg gtt gaa caa ggc ttt tca caa cca ctg cgt cgc ctg gtg ctg cat     2382
Ala Val Glu Gln Gly Phe Ser Gln Pro Leu Arg Arg Leu Val Leu His
                650                 655                 660

gtg ttg agt gcg gcg cag gct gaa cga ctg gca cgg gca gag gaa gca     2430
Val Leu Ser Ala Ala Gln Ala Glu Arg Leu Ala Arg Ala Glu Glu Ala
            665                 670                 675

gcc gct cct gca cct cct ggc cct aaa ctc tgg tac cgg gac ttt ctg     2478
Ala Ala Pro Ala Pro Pro Gly Pro Lys Leu Trp Tyr Arg Asp Phe Leu
        680                 685                 690

cag ttg gtg gag cca ggc ggt ggc gga ggt gca aac tcc ctg cga atg     2526
Gln Leu Val Glu Pro Gly Gly Gly Gly Gly Ala Asn Ser Leu Arg Met
    695                 700                 705

tgc cgc ccg cag ccc ggg cac cac tct gtg gca gca gat tca cgt cgt     2574
Cys Arg Pro Gln Pro Gly His His Ser Val Ala Ala Asp Ser Arg Arg
710                 715                 720                 725

aag ggt cgc aac aga cgg atg cat gtc tct gag ctc cgt gct gag cgt     2622
Lys Gly Arg Asn Arg Arg Met His Val Ser Glu Leu Arg Ala Glu Arg
                730                 735                 740

gga cca cgt agt gca gct cac tgg tga ctcggctgtc cccacaatgg           2669
Gly Pro Arg Ser Ala Ala His Trp
            745

gacgaggctg aatatgacac tccaaagagg ggcagacaga tgccaggaag acaaatgagt   2729

tatggctggg ccacactgag gtccttgggc caacagagac acctaaccct tacataggcc   2789

ctggccaaag ggtagcttat ttattaacaa gataacccgt ggatgtagcc tcaaagagtg   2849
```

-continued

```
gcctaagctc aattcaggat ctaaccagga gggaggggac agagacgtgg ggttccagag   2909

tggaccagga ccagagagtt gtcttgggtg gcagccctgg ggaaagaatt ctctttcttg   2969

ggcagcaagc agcaagctgt gaacagatta gaccgttggg tatggggtga ggcaggccaa   3029

ctgtactaaa gtaacgcaat aaacacatta tcagctgaca ttggaatggc cccagcagac   3089

aacaggtagt cctagacctt gctgggggct cttgggtatc gccctagggg tctcaagacc   3149

tgcattttcc tcatccaaga atgctaaagt gaagattaaa cgtgttagta gacgactacg   3209

ctggttccag tgagcctctg ggtactggc aatacacagt gcattagtgg caggaccaag   3269

ctctctgaag taaaaccaat actggctgtt gtgggcaagg atgtattaat tcactgaacg   3329

ggtggtgttt gagctgaata agaaggagcc aatcaccaat gtctggtgac agaacattcc   3389

gggatagaag aaccagggca acaacgtcgt ggagcagggg acagaccctc caagtctgcg   3449

gaacaaccag gaggctgata tggtgttatg gcactatgga ctcctgatgg tttggaaggt   3509

agatcccacc agccctgctt ttcaccgttg agaaacagaa cagagtccac ccagactaag   3569

gcctgcaagc tggaccagca cccttcaaga gagccacgtg cctctctctc cgtggcctgt   3629

caagcccttg tgaagaggag agggaggacc caaaacctct taagtgcttt agccatgctt   3689

cttcattttt attctcagta cagttggcca ggaacctttg ttcctgtttt acagatg      3746
```

<210> SEQ ID NO 64
<211> LENGTH: 749
<212> TYPE: PRT
<213> ORGANISM: Artificial Sequence
<220> FEATURE:
<223> OTHER INFORMATION: full-length mouse Sema3B A105K, transcript variant 1

<400> SEQUENCE: 64

```
Met Gly Arg Ala Glu Ala Ala Ala Met Ile Pro Gly Leu Ala Leu Leu
1               5                   10                  15

Trp Val Ala Gly Leu Gly Asp Thr Ala Pro Asn Leu Pro Arg Leu Arg
            20                  25                  30

Leu Ser Phe Gln Glu Leu Gln Ala Arg His Gly Val Arg Thr Phe Arg
        35                  40                  45

Leu Glu Arg Thr Cys Cys Tyr Glu Ala Leu Leu Val Asp Glu Glu Arg
    50                  55                  60

Gly Arg Leu Phe Val Gly Ala Glu Asn His Val Ala Ser Leu Ser Leu
65                  70                  75                  80

Asp Asn Ile Ser Lys Arg Ala Lys Lys Leu Ala Trp Pro Ala Pro Val
                85                  90                  95

Glu Trp Arg Glu Glu Cys Asn Trp Lys Gly Lys Asp Ile Gly Thr Glu
            100                 105                 110

Cys Met Asn Phe Val Lys Leu Leu His Thr Tyr Asn His Thr His Leu
        115                 120                 125

Leu Ala Cys Gly Thr Gly Ala Phe His Pro Thr Cys Ala Phe Val Glu
    130                 135                 140

Val Gly His Arg Leu Glu Glu Pro Met Leu Gln Leu Asp Arg Arg Lys
145                 150                 155                 160

Leu Glu Asp Gly Lys Gly Lys Thr Pro Tyr Asp Pro Arg His Arg Ala
                165                 170                 175

Ala Ser Val Leu Val Gly Glu Glu Leu Tyr Ser Gly Val Thr Ala Asp
            180                 185                 190

Leu Met Gly Arg Asp Phe Thr Ile Phe Arg Ser Leu Gly Gln Asn Pro
```

-continued

```
        195                 200                 205

Ser Leu Arg Thr Glu Pro His Asp Ser Arg Trp Leu Asn Glu Pro Lys
    210                 215                 220

Phe Val Lys Val Phe Trp Ile Pro Glu Ser Glu Asn Pro Asp Asp Asp
225                 230                 235                 240

Lys Ile Tyr Phe Phe Phe Arg Glu Ser Ala Val Glu Ala Ala Pro Ala
                245                 250                 255

Met Gly Arg Met Ser Val Ser Arg Val Gly Gln Ile Cys Arg Asn Asp
            260                 265                 270

Leu Gly Gly Gln Arg Ser Leu Val Asn Lys Trp Thr Thr Phe Leu Lys
        275                 280                 285

Ala Arg Leu Val Cys Ser Val Pro Gly Val Glu Gly Asp Thr His Phe
    290                 295                 300

Asp Gln Leu Gln Asp Val Phe Leu Leu Ser Ser Arg Asp Arg Gln Thr
305                 310                 315                 320

Pro Leu Leu Tyr Ala Val Phe Ser Thr Ser Ser Gly Val Phe Gln Gly
                325                 330                 335

Ser Ala Val Cys Val Tyr Ser Met Asn Asp Val Arg Arg Ala Phe Leu
            340                 345                 350

Gly Pro Phe Ala His Lys Glu Gly Pro Thr His Gln Trp Val Ser Tyr
        355                 360                 365

Gln Gly Arg Val Pro Tyr Pro Arg Pro Gly Met Cys Pro Ser Lys Thr
    370                 375                 380

Phe Gly Thr Phe Ser Ser Thr Lys Asp Phe Pro Asp Asp Val Ile Gln
385                 390                 395                 400

Phe Ala Arg Asn His Pro Leu Met Tyr Asn Pro Val Leu Pro Met Gly
                405                 410                 415

Gly Arg Pro Leu Phe Leu Gln Val Gly Ala Gly Tyr Thr Phe Thr Gln
            420                 425                 430

Ile Ala Ala Asp Arg Val Ala Ala Ala Asp Gly His Tyr Asp Val Leu
        435                 440                 445

Phe Ile Gly Thr Asp Val Gly Thr Val Leu Lys Val Ile Ser Val Pro
    450                 455                 460

Lys Gly Ser Arg Pro Asn Ser Glu Gly Leu Leu Leu Glu Glu Leu Gln
465                 470                 475                 480

Val Phe Glu Asp Ser Ala Ala Ile Thr Ser Met Gln Ile Ser Ser Lys
                485                 490                 495

Arg Gln Gln Leu Tyr Ile Ala Ser Arg Ser Ala Val Ala Gln Ile Ala
            500                 505                 510

Leu His Arg Cys Thr Ala Leu Gly Arg Ala Cys Ala Glu Cys Cys Leu
        515                 520                 525

Ala Arg Asp Pro Tyr Cys Ala Trp Asp Gly Ser Ala Cys Thr Arg Phe
    530                 535                 540

Gln Pro Thr Ala Lys Arg Arg Phe Arg Arg Gln Asp Ile Arg Asn Gly
545                 550                 555                 560

Asp Pro Ser Thr Leu Cys Ser Gly Asp Ser Ser His Ser Val Leu Leu
                565                 570                 575

Glu Lys Lys Val Leu Gly Val Glu Ser Gly Ser Ala Phe Leu Glu Cys
            580                 585                 590

Glu Pro Arg Ser Leu Gln Ala His Val Gln Trp Thr Phe Gln Gly Ala
        595                 600                 605

Gly Glu Ala Ala His Thr Gln Val Leu Ala Glu Glu Arg Val Glu Arg
    610                 615                 620
```

```
Thr Ala Arg Gly Leu Leu Leu Arg Gly Leu Arg Arg Gln Asp Ser Gly
625                 630                 635                 640

Val Tyr Leu Cys Val Ala Val Glu Gln Gly Phe Ser Gln Pro Leu Arg
                645                 650                 655

Arg Leu Val Leu His Val Leu Ser Ala Ala Gln Ala Glu Arg Leu Ala
            660                 665                 670

Arg Ala Glu Glu Ala Ala Ala Pro Ala Pro Pro Gly Pro Lys Leu Trp
        675                 680                 685

Tyr Arg Asp Phe Leu Gln Leu Val Glu Pro Gly Gly Gly Gly Gly Ala
    690                 695                 700

Asn Ser Leu Arg Met Cys Arg Pro Gln Pro Gly His His Ser Val Ala
705                 710                 715                 720

Ala Asp Ser Arg Arg Lys Gly Arg Asn Arg Arg Met His Val Ser Glu
                725                 730                 735

Leu Arg Ala Glu Arg Gly Pro Arg Ser Ala Ala His Trp
            740                 745


<210> SEQ ID NO 65
<211> LENGTH: 5189
<212> TYPE: DNA
<213> ORGANISM: Artificial Sequence
<220> FEATURE:
<223> OTHER INFORMATION: full-length human SEMA3C A104K
<220> FEATURE:
<221> NAME/KEY: CDS
<222> LOCATION: 563..2818
<223> OTHER INFORMATION: /transl_table=1

<400> SEQUENCE: 65

ggactgcgaa aggagcaggg ttgcggagct agggctccag cctgcggccg cgcattcttg      60

cgtctggcca gccgcgagct ctaagggtcg gccccgcccg gtccgccccc gcggctccct     120

gccaggctct cgcgggcgcg ctcggggtgg ggcctcgcgg ctggcggaga tgcggccggg     180

gctgcgcggt ggtgatgcga gcctgctggg cggcgcgccg gggcagccgg agccgcgcgc     240

cgcggcgctg taatcggaca ccaagagcgc tcgcccccgg cctccggcca ctttccattc     300

actccgaggt gcttgattga gcgacgcgga gaagagctcc gggtgccgcg gcactgcagc     360

gctgagattc ctttacaaag aaactcagag gaccgggaag aaagaatttc acctttgcga     420

cgtgctagaa aataaggtcg tctgggaaaa ggactggaga cacaagcgca tccaaccccg     480

gtagcaaact gatgactttt ccgtgctgat ttctttcaac ctcggtattt tcccttggat     540

attaacttgc atatctgaag aa atg gca ttc cgg aca att tgc gtg ttg gtt      592
                         Met Ala Phe Arg Thr Ile Cys Val Leu Val
                         1               5                   10

gga gta ttt att tgt tct atc tgt gtg aaa gga tct tcc cag ccc caa      640
Gly Val Phe Ile Cys Ser Ile Cys Val Lys Gly Ser Ser Gln Pro Gln
                15                  20                  25

gca aga gtt tat tta aca ttt gat gaa ctt cga gaa acc aag acc tct      688
Ala Arg Val Tyr Leu Thr Phe Asp Glu Leu Arg Glu Thr Lys Thr Ser
            30                  35                  40

gaa tac ttc agc ctt tcc cac cat cct tta gac tac agg att tta tta      736
Glu Tyr Phe Ser Leu Ser His His Pro Leu Asp Tyr Arg Ile Leu Leu
        45                  50                  55

atg gat gaa gat cag gac cgg ata tat gtg gga agc aaa gat cac att      784
Met Asp Glu Asp Gln Asp Arg Ile Tyr Val Gly Ser Lys Asp His Ile
    60                  65                  70

ctt tcc ctg aat att aac aat ata agt caa gaa gct ttg agt gtt ttc      832
Leu Ser Leu Asn Ile Asn Asn Ile Ser Gln Glu Ala Leu Ser Val Phe
```

-continued

```
75                  80                  85                  90

tgg cca gca tct aca atc aaa gtt gaa gaa tgc aaa atg aag ggc aaa       880
Trp Pro Ala Ser Thr Ile Lys Val Glu Glu Cys Lys Met Lys Gly Lys
                95                  100                 105

gat ccc aca cac ggc tgt ggg aac ttt gtc cgt gta att cag act ttc       928
Asp Pro Thr His Gly Cys Gly Asn Phe Val Arg Val Ile Gln Thr Phe
            110                 115                 120

aat cgc aca cat ttg tat gtc tgt ggg agt ggc gct ttc agt cct gtc       976
Asn Arg Thr His Leu Tyr Val Cys Gly Ser Gly Ala Phe Ser Pro Val
        125                 130                 135

tgt act tac ttg aac aga ggg agg aga tca gag gac caa gtt ttc atg      1024
Cys Thr Tyr Leu Asn Arg Gly Arg Arg Ser Glu Asp Gln Val Phe Met
    140                 145                 150

att gac tcc aag tgt gaa tct gga aaa gga cgc tgc tct ttc aac ccc      1072
Ile Asp Ser Lys Cys Glu Ser Gly Lys Gly Arg Cys Ser Phe Asn Pro
155                 160                 165                 170

aac gtg aac acg gtg tct gtt atg atc aat gag gag ctt ttc tct gga      1120
Asn Val Asn Thr Val Ser Val Met Ile Asn Glu Glu Leu Phe Ser Gly
                175                 180                 185

atg tat ata gat ttc atg ggg aca gat gct gct att ttt cga agt tta      1168
Met Tyr Ile Asp Phe Met Gly Thr Asp Ala Ala Ile Phe Arg Ser Leu
            190                 195                 200

acc aag agg aat gcg gtc aga act gat caa cat aat tcc aaa tgg cta      1216
Thr Lys Arg Asn Ala Val Arg Thr Asp Gln His Asn Ser Lys Trp Leu
        205                 210                 215

agt gaa cct atg ttt gta gat gca cat gtc atc cca gat ggt act gat      1264
Ser Glu Pro Met Phe Val Asp Ala His Val Ile Pro Asp Gly Thr Asp
    220                 225                 230

cca aat gat gct aag gtg tac ttc ttc ttc aaa gaa aaa ctg act gac      1312
Pro Asn Asp Ala Lys Val Tyr Phe Phe Phe Lys Glu Lys Leu Thr Asp
235                 240                 245                 250

aat aac agg agc acg aaa cag att cat tcc atg att gct cga ata tgt      1360
Asn Asn Arg Ser Thr Lys Gln Ile His Ser Met Ile Ala Arg Ile Cys
                255                 260                 265

cct aat gac act ggt gga ctg cgt agc ctt gtc aac aag tgg acc act      1408
Pro Asn Asp Thr Gly Gly Leu Arg Ser Leu Val Asn Lys Trp Thr Thr
            270                 275                 280

ttc tta aag gcg agg ctg gtg tgc tcg gta aca gat gaa gac ggc cca      1456
Phe Leu Lys Ala Arg Leu Val Cys Ser Val Thr Asp Glu Asp Gly Pro
        285                 290                 295

gaa aca cac ttt gat gaa tta gag gat gtg ttt ctg ctg gaa act gat      1504
Glu Thr His Phe Asp Glu Leu Glu Asp Val Phe Leu Leu Glu Thr Asp
    300                 305                 310

aac ccg agg aca aca cta gtg tat ggc att ttt aca aca tca agc tca      1552
Asn Pro Arg Thr Thr Leu Val Tyr Gly Ile Phe Thr Thr Ser Ser Ser
315                 320                 325                 330

gtt ttc aaa gga tca gcc gtg tgt gtg tat cat tta tct gat ata cag      1600
Val Phe Lys Gly Ser Ala Val Cys Val Tyr His Leu Ser Asp Ile Gln
                335                 340                 345

act gtg ttt aat ggg cct ttt gcc cac aaa gaa ggg ccc aat cat cag      1648
Thr Val Phe Asn Gly Pro Phe Ala His Lys Glu Gly Pro Asn His Gln
            350                 355                 360

ctg att tcc tat cag ggc aga att cca tat cct cgc cct gga act tgt      1696
Leu Ile Ser Tyr Gln Gly Arg Ile Pro Tyr Pro Arg Pro Gly Thr Cys
        365                 370                 375

cca gga gga gca ttt aca ccc aat atg cga acc acc aag gag ttc cca      1744
Pro Gly Gly Ala Phe Thr Pro Asn Met Arg Thr Thr Lys Glu Phe Pro
    380                 385                 390

gat gat gtt gtc act ttt att cgg aac cat cct ctc atg tac aat tcc      1792
```

-continued

```
Asp Asp Val Val Thr Phe Ile Arg Asn His Pro Leu Met Tyr Asn Ser
395                 400                 405                 410

atc tac cca atc cac aaa agg cct ttg att gtt cgt att ggc act gac     1840
Ile Tyr Pro Ile His Lys Arg Pro Leu Ile Val Arg Ile Gly Thr Asp
                415                 420                 425

tac aag tat aca aag ata gct gtg gat cga gtg aac gct gct gat ggg     1888
Tyr Lys Tyr Thr Lys Ile Ala Val Asp Arg Val Asn Ala Ala Asp Gly
            430                 435                 440

aga tac cat gtc ctg ttt ctc gga aca gat cgg ggt act gtg caa aaa     1936
Arg Tyr His Val Leu Phe Leu Gly Thr Asp Arg Gly Thr Val Gln Lys
        445                 450                 455

gtg gtt gtt ctt cct act aac aac tct gtc agt ggc gag ctc att ctg     1984
Val Val Val Leu Pro Thr Asn Asn Ser Val Ser Gly Glu Leu Ile Leu
    460                 465                 470

gag gag ctg gaa gtc ttt aag aat cat gct cct ata aca aca atg aaa     2032
Glu Glu Leu Glu Val Phe Lys Asn His Ala Pro Ile Thr Thr Met Lys
475                 480                 485                 490

att tca tct aaa aag caa cag ttg tat gtg agt tcc aat gaa ggg gtt     2080
Ile Ser Ser Lys Lys Gln Gln Leu Tyr Val Ser Ser Asn Glu Gly Val
                495                 500                 505

tcc cag gta tct ctg cac cgc tgc cac atc tat ggt aca gcc tgt gct     2128
Ser Gln Val Ser Leu His Arg Cys His Ile Tyr Gly Thr Ala Cys Ala
            510                 515                 520

gac tgc tgc ctg gcg cgg gac cct tat tgc gcc tgg gat ggc cat tcc     2176
Asp Cys Cys Leu Ala Arg Asp Pro Tyr Cys Ala Trp Asp Gly His Ser
        525                 530                 535

tgt tcc aga ttc tac cca act ggg aaa cgg agg agc cga aga caa gat     2224
Cys Ser Arg Phe Tyr Pro Thr Gly Lys Arg Arg Ser Arg Arg Gln Asp
    540                 545                 550

gtg aga cat gga aac cca ctg act caa tgc aga gga ttt aat cta aaa     2272
Val Arg His Gly Asn Pro Leu Thr Gln Cys Arg Gly Phe Asn Leu Lys
555                 560                 565                 570

gca tac aga aat gca gct gaa att gtc cag tat gga gta aaa aat aac     2320
Ala Tyr Arg Asn Ala Ala Glu Ile Val Gln Tyr Gly Val Lys Asn Asn
                575                 580                 585

acc act ttt ctg gag tgt gcc ccc aag tct ccg cag gca tct atc aag     2368
Thr Thr Phe Leu Glu Cys Ala Pro Lys Ser Pro Gln Ala Ser Ile Lys
            590                 595                 600

tgg ctg tta cag aaa gac aaa gac agg agg aaa gag gtt aag ctg aat     2416
Trp Leu Leu Gln Lys Asp Lys Asp Arg Arg Lys Glu Val Lys Leu Asn
        605                 610                 615

gaa cga ata ata gcc act tca cag gga ctc ctg atc cgc tct gtt cag     2464
Glu Arg Ile Ile Ala Thr Ser Gln Gly Leu Leu Ile Arg Ser Val Gln
    620                 625                 630

ggt tct gac caa gga ctt tat cac tgc att gct aca gaa aat agt ttc     2512
Gly Ser Asp Gln Gly Leu Tyr His Cys Ile Ala Thr Glu Asn Ser Phe
635                 640                 645                 650

aag cag acc ata gcc aag atc aac ttc aaa gtt tta gat tca gaa atg     2560
Lys Gln Thr Ile Ala Lys Ile Asn Phe Lys Val Leu Asp Ser Glu Met
                655                 660                 665

gtg gct gtt gtg acg gac aaa tgg tcc cca tgg acc tgg gcc agc tct     2608
Val Ala Val Val Thr Asp Lys Trp Ser Pro Trp Thr Trp Ala Ser Ser
            670                 675                 680

gtg agg gct tta ccc ttc cac ccg aag gac atc atg ggg gca ttc agc     2656
Val Arg Ala Leu Pro Phe His Pro Lys Asp Ile Met Gly Ala Phe Ser
        685                 690                 695

cac tca gaa atg cag atg att aac caa tat tgc aaa gac act cgg cag     2704
His Ser Glu Met Gln Met Ile Asn Gln Tyr Cys Lys Asp Thr Arg Gln
    700                 705                 710
```

```
caa cat cag cag gga gat gaa tca cag aaa atg aga ggg gac tat ggc     2752
Gln His Gln Gln Gly Asp Glu Ser Gln Lys Met Arg Gly Asp Tyr Gly
715                 720                 725                 730

aag tta aag gcc ctc atc aat agt cgg aaa agt aga aac agg agg aat     2800
Lys Leu Lys Ala Leu Ile Asn Ser Arg Lys Ser Arg Asn Arg Arg Asn
                735                 740                 745

cag ttg cca gag tca taa tattttctta tgtgggtctt atgcttccat            2848
Gln Leu Pro Glu Ser
            750

taacaaatgc tctgtcttca atgatcaaat tttgagcaaa gaaacttgtg ctttaccaag   2908

gggaattact gaaaaaggtg attactcctg aagtgagttt tacacgaact gaaatgagca   2968

tgcattttct tgtatgatag tgactagcac tagacatgtc atggtcctca tggtgcatat   3028

aaatatattt aacttaaccc agattttatt tatatcttta ttcacctttt cttcaaaatc   3088

gatatggtgg ctgcaaaact agaattgttg catccctcaa ttgaatgagg gccatatccc   3148

tgtggtattc ctttcctgct ttggggcttt agaattctaa ttgtcagtga ttttgtatat   3208

gaaaacaagt tccaaatcca cagcttttac gtagtaaaag tcataaatgc atatgacaga   3268

atggctatca aaagaaatag aaaaggaaga cagcatttaa agttgtataa aaacatgagt   3328

tattcataaa gagaaaatga tgagttttta tggttccaat gaaatatgtt ggggtttttt   3388

taagattgta aaaataatca gttactggta tctgtcactg acctttgttt ccttattcag   3448

gaagataaaa atcagtaacc taccccatga agatatttgg tgggagttat atcagtgaag   3508

cagtttggtt tatattctta tgttatcacc ttccaaacaa aagcacttac ttttttttgga   3568

agttatttat tttagactca aagaatataa tctggcacta ctcagttatt actgtttgtt   3628

ctcttattcc ctagtctgtg tggcaaatta aacaatataa gaaggaaaaa tttgaagtat   3688

tagacttcta aataaggtgt gaaatcatca aaaagaaaaa tcaaagtaga aactactaat   3748

tttttaagag gaatttataa caaatatggc tagttttcaa cttcagtact caaattcaat   3808

gattcttcct tttattaaaa ccagtctcag atatcatact gatttttaag tcaacactat   3868

atattttatg atcttttcag tgtgatggca aggtgcttgt tatgtctaga aagtaagaaa   3928

acaatatgag gagacattct gtctttcaaa aggtaatggt acatacgttc actggtctct   3988

aagtgtaaaa gtagtaaatt ttgtgatgaa taaaataatt atctcctaat tgtatgttag   4048

aataatttta ttagaataat ttcatactga aattattttc tccaaataaa aattagatgg   4108

aaaaatgtga aaaaaattat tcatgctctc atatatattt taaaaacact acttttgctt   4168

ttttatttac cttttaagac attttcatgc ttccaggtaa aaacagatat tgtaccatgt   4228

acctaatcca aatatcatat aaacatttta tttatagtta ataatctatg atgaaggtaa   4288

ttaaagtaga ttatggcctt tttaagtatt gcagtctaaa acttcaaaaa ctaaaatcat   4348

tgtcaaaatt aatatgatta ttaatcagaa tatcagaata tgattcacta tttaaactat   4408

gataaattat gataatatat gaggaggcct cgctatagca aaaatagtta aaatgctgac   4468

ataacaccaa acttcatttt ttaaaaaatc tgttgttcca aatgtgtata attttaaagt   4528

aatttctaaa gcagtttatt ataatggttt gcctgcttaa aaggtataat taaacttctt   4588

ttctcttcta cattgacaca cagaaatgtg tcaatgtaaa gccaaaacca tcttctgtgt   4648

ttatggccaa tctattctca aagttaaaag taaaattgtt tcagagtcac agttcccttt   4708

atttcacata agcccaaact gatagacagt aacggtgttt agttttatac tatatttgtg   4768

ctatttaatt ctttctattt tcacaattat taaattgtgt acactttcat tacttttaaa   4828

aatgtagaaa ttcttcatga acataactct gctgaatgta aaagaaaatt ttttttcaaa   4888
```

```
aatgctgtta atgtatacta ctggtggttg attggtttta ttttatgtag cttgacaatt   4948

cagtgactta atatctattc catttgtatt gtacataaaa ttttctagaa atacactttt   5008

ttccaaagtg taagtttgtg aatagatttt agcatgatga aactgtcata atggtgaatg   5068

ttcaatctgt gtaagaaaac aaactaaatg tagttgtcac actaaaattt aattggatat   5128

tgatgaaatc attggcctgg caaaataaaa catgttgaat tccccaaaaa aaaaaaaaaa   5188

a                                                                   5189


<210> SEQ ID NO 66
<211> LENGTH: 751
<212> TYPE: PRT
<213> ORGANISM: Artificial Sequence
<220> FEATURE:
<223> OTHER INFORMATION: full-length human SEMA3C A104K

<400> SEQUENCE: 66

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Lys Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
    290                 295                 300
```

```
Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
        355                 360                 365

Arg Ile Pro Tyr Pro Arg Pro Gly Thr Cys Pro Gly Gly Ala Phe Thr
    370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445

Leu Gly Thr Asp Arg Gly Thr Val Gln Lys Val Val Val Leu Pro Thr
    450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
    530                 535                 540

Thr Gly Lys Arg Arg Ser Arg Arg Gln Asp Val Arg His Gly Asn Pro
545                 550                 555                 560

Leu Thr Gln Cys Arg Gly Phe Asn Leu Lys Ala Tyr Arg Asn Ala Ala
                565                 570                 575

Glu Ile Val Gln Tyr Gly Val Lys Asn Asn Thr Thr Phe Leu Glu Cys
            580                 585                 590

Ala Pro Lys Ser Pro Gln Ala Ser Ile Lys Trp Leu Leu Gln Lys Asp
        595                 600                 605

Lys Asp Arg Arg Lys Glu Val Lys Leu Asn Glu Arg Ile Ile Ala Thr
    610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Val Thr Asp
            660                 665                 670

Lys Trp Ser Pro Trp Thr Trp Ala Ser Ser Val Arg Ala Leu Pro Phe
        675                 680                 685

His Pro Lys Asp Ile Met Gly Ala Phe Ser His Ser Glu Met Gln Met
    690                 695                 700

Ile Asn Gln Tyr Cys Lys Asp Thr Arg Gln Gln His Gln Gln Gly Asp
705                 710                 715                 720
```

```
Glu Ser Gln Lys Met Arg Gly Asp Tyr Gly Lys Leu Lys Ala Leu Ile
            725                 730                 735

Asn Ser Arg Lys Ser Arg Asn Arg Arg Asn Gln Leu Pro Glu Ser
        740                 745                 750


<210> SEQ ID NO 67
<211> LENGTH: 4956
<212> TYPE: DNA
<213> ORGANISM: Artificial Sequence
<220> FEATURE:
<223> OTHER INFORMATION: full-length mouse Sema3C A104K
<220> FEATURE:
<221> NAME/KEY: CDS
<222> LOCATION: 189..2444
<223> OTHER INFORMATION: /transl_table=1

<400> SEQUENCE: 67

ctgctacaaa gaaactcagc accggccggc aggaatccca ccctccggac tcactaagtc      60

tttaaaggtc ttctggggaa aggacctagg ggactggaaa tccaagcccg gagcaagtgg     120

ctgacttctc ctggatcttt tcccacctcg gtattttccc ttggatatta attcccaaat     180

cagaagaa atg gca ttc cgg gcg att tgt gtg ttg gtt gga gta ttt att      230
         Met Ala Phe Arg Ala Ile Cys Val Leu Val Gly Val Phe Ile
         1               5                   10

tgt tcc att tgt gta cga gga tct tcc cag ccc caa gca aga gtt tat      278
Cys Ser Ile Cys Val Arg Gly Ser Ser Gln Pro Gln Ala Arg Val Tyr
15                  20                  25                  30

tta aca ttt gat gag ctt cga gaa acc aaa acc tct gag tac ttt agt      326
Leu Thr Phe Asp Glu Leu Arg Glu Thr Lys Thr Ser Glu Tyr Phe Ser
            35                  40                  45

ctg tcc cac cag cag tta gac tac aga ata ttg ctg atg gat gaa gat      374
Leu Ser His Gln Gln Leu Asp Tyr Arg Ile Leu Leu Met Asp Glu Asp
        50                  55                  60

caa gac cgg ata tat gtg ggg agc aaa gac cac atc ctg tct ttg aat      422
Gln Asp Arg Ile Tyr Val Gly Ser Lys Asp His Ile Leu Ser Leu Asn
    65                  70                  75

atc aac aat atc agt caa gaa cct ttg agt gtt ttc tgg cca gca tca      470
Ile Asn Asn Ile Ser Gln Glu Pro Leu Ser Val Phe Trp Pro Ala Ser
    80                  85                  90

aca atc aaa gtt gaa gag tgc aaa atg aag ggc aaa gat cct aca cat      518
Thr Ile Lys Val Glu Glu Cys Lys Met Lys Gly Lys Asp Pro Thr His
95                  100                 105                 110

ggc tgt gga aat ttc gtc cgg gtg att cag aca ttc aac cgt act cac      566
Gly Cys Gly Asn Phe Val Arg Val Ile Gln Thr Phe Asn Arg Thr His
            115                 120                 125

ctg tat gtc tgt ggg agt gga gcg ttc agc cca gtg tgc acc tac ctg      614
Leu Tyr Val Cys Gly Ser Gly Ala Phe Ser Pro Val Cys Thr Tyr Leu
        130                 135                 140

aac cgg gga agg agg tca gag gac cag gta ttc atg atc gac tct aag      662
Asn Arg Gly Arg Arg Ser Glu Asp Gln Val Phe Met Ile Asp Ser Lys
    145                 150                 155

tgt gaa tct ggc aaa gga cga tgc tct ttc aac ccg aat gtg aac act      710
Cys Glu Ser Gly Lys Gly Arg Cys Ser Phe Asn Pro Asn Val Asn Thr
    160                 165                 170

gtg tct gtt atg atc aat gag gaa ctc ttc tca gga atg tat ata gac      758
Val Ser Val Met Ile Asn Glu Glu Leu Phe Ser Gly Met Tyr Ile Asp
175                 180                 185                 190

ttc atg gga aca gat gct gct att ttc cga agt tta act aag agg aat      806
Phe Met Gly Thr Asp Ala Ala Ile Phe Arg Ser Leu Thr Lys Arg Asn
            195                 200                 205

gca gtt cga act gat caa cat aat tca aaa tgg ctg agt gaa ccc atg      854
```

-continued

```
Ala Val Arg Thr Asp Gln His Asn Ser Lys Trp Leu Ser Glu Pro Met
            210                 215                 220

ttt gtg gac gca cat gtg atc cca gat ggc act gat cca aat gat gct      902
Phe Val Asp Ala His Val Ile Pro Asp Gly Thr Asp Pro Asn Asp Ala
        225                 230                 235

aag gtc tat ttc ttc ttc aaa gaa aga ctg act gac aac aat agg agc      950
Lys Val Tyr Phe Phe Phe Lys Glu Arg Leu Thr Asp Asn Asn Arg Ser
    240                 245                 250

aca aaa cag att cat tcc atg att gca aga ata tgc cct aat gac act      998
Thr Lys Gln Ile His Ser Met Ile Ala Arg Ile Cys Pro Asn Asp Thr
255                 260                 265                 270

ggt gga caa cgt agt ctt gtc aac aag tgg acc aca ttc tta aag gca     1046
Gly Gly Gln Arg Ser Leu Val Asn Lys Trp Thr Thr Phe Leu Lys Ala
                275                 280                 285

aga ctt gta tgc tca gtc aca gat gaa gat ggc cca gag aca cat ttt     1094
Arg Leu Val Cys Ser Val Thr Asp Glu Asp Gly Pro Glu Thr His Phe
            290                 295                 300

gat gaa cta gag gat gtc ttt ctg ctg gaa act gac aat cca agg aca     1142
Asp Glu Leu Glu Asp Val Phe Leu Leu Glu Thr Asp Asn Pro Arg Thr
        305                 310                 315

aca ctc gtg tat ggc atc ttc acc aca tca agc tct gtt ttt aag gga     1190
Thr Leu Val Tyr Gly Ile Phe Thr Thr Ser Ser Ser Val Phe Lys Gly
    320                 325                 330

tcg gca gtg tgt gtg tat cat tta tct gat ata cag act gta ttc aat     1238
Ser Ala Val Cys Val Tyr His Leu Ser Asp Ile Gln Thr Val Phe Asn
335                 340                 345                 350

ggg ccc ttt gcc cac aag gaa ggg ccc aat cac cag ctg atc tcc tat     1286
Gly Pro Phe Ala His Lys Glu Gly Pro Asn His Gln Leu Ile Ser Tyr
                355                 360                 365

caa ggt aga atc cca tat cct cgc cca gga act tgc cca gga ggg gcc     1334
Gln Gly Arg Ile Pro Tyr Pro Arg Pro Gly Thr Cys Pro Gly Gly Ala
            370                 375                 380

ttt aca ccc aat atg aga acc acc aag gac ttc cca gat gac gtt gtc     1382
Phe Thr Pro Asn Met Arg Thr Thr Lys Asp Phe Pro Asp Asp Val Val
        385                 390                 395

act ttt att cgg aac cac cct ctc atg tac aat tcc atc tac ccc atc     1430
Thr Phe Ile Arg Asn His Pro Leu Met Tyr Asn Ser Ile Tyr Pro Ile
    400                 405                 410

cac aga agg cct ctg ata gtc cgc ata ggc act gac tac aag tac aca     1478
His Arg Arg Pro Leu Ile Val Arg Ile Gly Thr Asp Tyr Lys Tyr Thr
415                 420                 425                 430

aag att gct gtg gac cgt gtc aac gct gct gat ggg aga tac cac gtt     1526
Lys Ile Ala Val Asp Arg Val Asn Ala Ala Asp Gly Arg Tyr His Val
                435                 440                 445

ctg ttt ctg ggc aca gat cgg ggc acc gtg cag aag gtc gta gtc ctt     1574
Leu Phe Leu Gly Thr Asp Arg Gly Thr Val Gln Lys Val Val Val Leu
            450                 455                 460

cct acc aat agc tct gcc agt ggg gaa ctc atc ctg gag gag ctg gaa     1622
Pro Thr Asn Ser Ser Ala Ser Gly Glu Leu Ile Leu Glu Glu Leu Glu
        465                 470                 475

gtc ttc aag aat cat gtt ccc ata aca aca atg aaa atc tca tcc aaa     1670
Val Phe Lys Asn His Val Pro Ile Thr Thr Met Lys Ile Ser Ser Lys
    480                 485                 490

aag caa cag ttg tac gtg agc tcc aat gag ggg gtt tcc caa gtc tct    1718
Lys Gln Gln Leu Tyr Val Ser Ser Asn Glu Gly Val Ser Gln Val Ser
495                 500                 505                 510

ctg cat cgc tgc cat atc tac ggc aca gcc tgt gcg gac tgc tgc ttg     1766
Leu His Arg Cys His Ile Tyr Gly Thr Ala Cys Ala Asp Cys Cys Leu
                515                 520                 525
```

-continued

```
gcg agg gat cca tac tgt gcc tgg gat ggc cac tct tgc tct agg ttc      1814
Ala Arg Asp Pro Tyr Cys Ala Trp Asp Gly His Ser Cys Ser Arg Phe
            530                 535                 540

tac ccc act ggg aag cgg agg agc cga aga caa gat gtg aga cat gga      1862
Tyr Pro Thr Gly Lys Arg Arg Ser Arg Arg Gln Asp Val Arg His Gly
        545                 550                 555

aac cca ctg aca caa tgc cga ggg ttc aat ctg aaa gca tac aga aat      1910
Asn Pro Leu Thr Gln Cys Arg Gly Phe Asn Leu Lys Ala Tyr Arg Asn
    560                 565                 570

gca gct gaa att gtt cag tat gga gta aga aat aac agc act ttc ctt      1958
Ala Ala Glu Ile Val Gln Tyr Gly Val Arg Asn Asn Ser Thr Phe Leu
575                 580                 585                 590

gag tgt gct ccc aag tct cca cag gca tct atc aag tgg ttg ctg cag      2006
Glu Cys Ala Pro Lys Ser Pro Gln Ala Ser Ile Lys Trp Leu Leu Gln
                595                 600                 605

aaa gac aaa gac agg agg aag gag gtt aaa ctg aac gag cgc att ata      2054
Lys Asp Lys Asp Arg Arg Lys Glu Val Lys Leu Asn Glu Arg Ile Ile
            610                 615                 620

gct act tcc caa gga cta ctg att cgc tct gtt caa gat tct gac caa      2102
Ala Thr Ser Gln Gly Leu Leu Ile Arg Ser Val Gln Asp Ser Asp Gln
        625                 630                 635

gga ctc tac cac tgc att gcc act gag aac agc ttc aaa cag acc ata      2150
Gly Leu Tyr His Cys Ile Ala Thr Glu Asn Ser Phe Lys Gln Thr Ile
    640                 645                 650

gcc aag atc aac ttc aaa gtt tta gat tca gaa atg gtg gcc gtt gtg      2198
Ala Lys Ile Asn Phe Lys Val Leu Asp Ser Glu Met Val Ala Val Val
655                 660                 665                 670

aca gac aag tgg tcc ccg tgg aca tgg gct ggc tct gtg agg gct cta      2246
Thr Asp Lys Trp Ser Pro Trp Thr Trp Ala Gly Ser Val Arg Ala Leu
                675                 680                 685

ccc ttc cat cca aag gac atc ctg ggg gca ttc agc cac tcg gaa atg      2294
Pro Phe His Pro Lys Asp Ile Leu Gly Ala Phe Ser His Ser Glu Met
            690                 695                 700

cag ctc atc aat cag tac tgc aaa gac acc cgg cag cag cag cag ctg      2342
Gln Leu Ile Asn Gln Tyr Cys Lys Asp Thr Arg Gln Gln Gln Gln Leu
        705                 710                 715

ggg gaa gaa cca cag aag atg aga ggg gac tat ggc aag ctg aag gct      2390
Gly Glu Glu Pro Gln Lys Met Arg Gly Asp Tyr Gly Lys Leu Lys Ala
    720                 725                 730

ctc atc aac agc agg aaa agc aga aac agg agg aat cag ctt cca gag      2438
Leu Ile Asn Ser Arg Lys Ser Arg Asn Arg Arg Asn Gln Leu Pro Glu
735                 740                 745                 750

tca taa aacattcatc catgaagttt tgcttccagg aacaaatgct ctgtcttcac      2494
Ser

tagtcaacta ttaaataaaa tcttgtgctt tacccatgag aaatttctga caaaagctgg   2554

agactcactc taaagtgtgt tctctgtgaa ctgaaaagag catgcatttt cttgtatgat   2614

acagactagc actagacatg tcatggtcct tgtggtgcat aaaaaatatt taacttatcc   2674

cagattttat ttatatcttt atgtgtcttt tcttcaaaat caatgcgaca acagaagcag   2734

aactgttaca gcctcggttg agcgagggcc ataaatttcc ctgtgctctt ccttccgtgc   2794

tctaggggtt tagctttcta attgtcactg gcttttatac atgaaaaaga attccagttc   2854

acaattttca catagtaaat gtcatataaa tgtgtgtgac atccagtgtc atgtaggtta   2914

cacaaatgac agggaagaga gcatccagat gttacgtaaa gtcaagagtg actcataaag   2974

agcaagtgat gagttcatat gcttccagtg atttatcttc ttgcttgttc ctttgtttaa   3034

gattgtaaga tgtgtcggct gctgatagct gccatcaatg tttgttctct tgttttagaa   3094
```

aaacaaaaga aatggcctgt accatccaag gcctttgatg ggagatctat cagtgagcca 3154 ttgacgtttc tactgttatg ttatcatctt ccaaacaaaa gtgctttgtt tttttggaag 3214 ttatttaagt tattatagac ttacataaac tattgcatta tttaattgat ttactgtttt 3274 ggttttaatc ccctagtcta cctggaaaat taaagacaac aaggatgcag tattattaaa 3334 gcattcaact tttccatgca gagtgaagct atccaaaggg aaaaggaaga ttaaaaaaaa 3394 agcatacaat ttgtcatgta aaggaattag taacatgtag tttgttttct accttagtaa 3454 tcaaattcta ggagtaattt gtacatccaa ggaaccagtt tcacaaagca taatgatttt 3514 tcaggcaagg tttcatgatt tgtaaacata tctgtgatgg gaaagttatt attacatcaa 3574 gaaagaaaat ctcaacacat tttaaacaaa acagacttct tttaaagact atctattttc 3634 acccagatat tttttccact tgataatact tctttaggaa tgttgataca catgtttaac 3694 tattggaaaa ttttagcact atcttctaat tatatacttg gattgtttaa tgagaaaagt 3754 ataatactaa aattagtttc tccaatttaa atgaataaaa tataggagat tttcttatat 3814 gtcttttaat tatacaactt tcattttatt taattttatt ttaatatgtt tatattttca 3874 gataaaaaga gaagttttac taaaacacca ttgaaacata cttcttatta acagttcatc 3934 tagaatgtaa ctacagggga tctacatcat tttataatgc tgtggaaaaa cctgcaggaa 3994 gtaaaactat ggataggagt gtaagttggt agtagactac gtgtttagca tgcacaaaga 4054 cctgggctca aacagaaaga aaggaagaaa gacaccaagg aaggagggca agcaggaaaa 4114 agaacagact gactggagag aagaagggca ggaaagtggt aaagaaggca aagaaagatg 4174 gagggaatac attcattatc agaagattaa aaaatggtag ttaaatgatg gtcaattctg 4234 gtgttcttaa gagtgcacct cagtgttgta gaaaacacca gttaaaatag cataaatgta 4294 cccaaatgtg tacagtgcta caataatcta tggggttagc atatggttaa aatgtttggt 4354 tagcatgttt aaaatgttca cactttgggt tttcttatac atataaaaat agccatgcgt 4414 tcacgtgtga tgctaacacc atcctctttc tgtgtttgta attaatctat tgtatggaaa 4474 cagctacttc cccttgctcc acttaccttc aaactgccag ccacttggct attatttgtt 4534 ctatttagta cctcctgggt tggtttttaa ccataattac atttcaaatc ttcatttctt 4594 tttctttaaa gatatagaaa ttgctgtgca gcatagcccg gccaaaacta aaacatatat 4654 ctctcaaaag cataactaat acatattgag tatgggtgat tactcggttt tattttgttt 4714 acttgggaaa attaataatt aaacatgttt ttcttttgta ttgtacataa aattacctag 4774 aaatgcactt ttcctccaaa atgtaggttc gtgaatagac ttagcatgat gaagctgtct 4834 ttacagtgaa tgcttaccct gtgtagagaa agcaaactag atgtagttac cacatgagaa 4894 tttaattaga tgttgaaaaa aataatttgt ctggaaaaat aaagcattca attcccctga 4954 aa 4956

<210> SEQ ID NO 68
<211> LENGTH: 751
<212> TYPE: PRT
<213> ORGANISM: Artificial Sequence
<220> FEATURE:
<223> OTHER INFORMATION: full-length mouse Sema3C A104K

<400> SEQUENCE: 68

Met Ala Phe Arg Ala Ile Cys Val Leu Val Gly Val Phe Ile Cys Ser
1 5 10 15

Ile Cys Val Arg Gly Ser Ser Gln Pro Gln Ala Arg Val Tyr Leu Thr

-continued

```
            20                  25                  30

Phe Asp Glu Leu Arg Glu Thr Lys Thr Ser Glu Tyr Phe Ser Leu Ser
        35                  40                  45

His Gln Gln Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Pro Leu Ser Val Phe Trp Pro Ala Ser Thr Ile
                85                  90                  95

Lys Val Glu Glu Cys Lys Met Lys Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
225                 230                 235                 240

Tyr Phe Phe Phe Lys Glu Arg Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Gln Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
        355                 360                 365

Arg Ile Pro Tyr Pro Arg Pro Gly Thr Cys Pro Gly Gly Ala Phe Thr
    370                 375                 380

Pro Asn Met Arg Thr Thr Lys Asp Phe Pro Asp Asp Val Val Thr Phe
385                 390                 395                 400

Ile Arg Asn His Pro Leu Met Tyr Asn Ser Ile Tyr Pro Ile His Arg
                405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445
```

```
Leu Gly Thr Asp Arg Gly Thr Val Gln Lys Val Val Val Leu Pro Thr
    450                 455                 460

Asn Ser Ser Ala Ser Gly Glu Leu Ile Leu Glu Glu Leu Glu Val Phe
465                 470                 475                 480

Lys Asn His Val Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
    530                 535                 540

Thr Gly Lys Arg Arg Ser Arg Arg Gln Asp Val Arg His Gly Asn Pro
545                 550                 555                 560

Leu Thr Gln Cys Arg Gly Phe Asn Leu Lys Ala Tyr Arg Asn Ala Ala
                565                 570                 575

Glu Ile Val Gln Tyr Gly Val Arg Asn Asn Ser Thr Phe Leu Glu Cys
            580                 585                 590

Ala Pro Lys Ser Pro Gln Ala Ser Ile Lys Trp Leu Leu Gln Lys Asp
        595                 600                 605

Lys Asp Arg Arg Lys Glu Val Lys Leu Asn Glu Arg Ile Ile Ala Thr
    610                 615                 620

Ser Gln Gly Leu Leu Ile Arg Ser Val Gln Asp Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Val Thr Asp
            660                 665                 670

Lys Trp Ser Pro Trp Thr Trp Ala Gly Ser Val Arg Ala Leu Pro Phe
        675                 680                 685

His Pro Lys Asp Ile Leu Gly Ala Phe Ser His Ser Glu Met Gln Leu
    690                 695                 700

Ile Asn Gln Tyr Cys Lys Asp Thr Arg Gln Gln Gln Gln Leu Gly Glu
705                 710                 715                 720

Glu Pro Gln Lys Met Arg Gly Asp Tyr Gly Lys Leu Lys Ala Leu Ile
                725                 730                 735

Asn Ser Arg Lys Ser Arg Asn Arg Arg Asn Gln Leu Pro Glu Ser
            740                 745                 750


<210> SEQ ID NO 69
<211> LENGTH: 6276
<212> TYPE: DNA
<213> ORGANISM: Artificial Sequence
<220> FEATURE:
<223> OTHER INFORMATION: full-length human SEMA3D A120K
<220> FEATURE:
<221> NAME/KEY: CDS
<222> LOCATION: 41..2374
<223> OTHER INFORMATION: /transl_table=1

<400> SEQUENCE: 69

attaaattaa caccatttga aagagaacat tgttttcatc atg aat gct aat aaa       55
                                            Met Asn Ala Asn Lys
                                            1               5

gat gaa aga ctt aaa gcc aga agc caa gat ttt cac ctt ttt cct gct      103
Asp Glu Arg Leu Lys Ala Arg Ser Gln Asp Phe His Leu Phe Pro Ala
                10                  15                  20
```

```
ttg atg atg cta agc atg acc atg ttg ttt ctt cca gtc act ggc act      151
Leu Met Met Leu Ser Met Thr Met Leu Phe Leu Pro Val Thr Gly Thr
            25                  30                  35

ttg aag caa aat att cca aga ctc aag cta acc tac aaa gac ttg ctg      199
Leu Lys Gln Asn Ile Pro Arg Leu Lys Leu Thr Tyr Lys Asp Leu Leu
        40                  45                  50

ctt tca aat agc tgt att ccc ttt ttg ggt tca tca gaa gga ctg gat      247
Leu Ser Asn Ser Cys Ile Pro Phe Leu Gly Ser Ser Glu Gly Leu Asp
    55                  60                  65

ttt caa act ctt ctc tta gat gag gaa aga ggc agg ctg ctc ttg gga      295
Phe Gln Thr Leu Leu Leu Asp Glu Glu Arg Gly Arg Leu Leu Leu Gly
70                  75                  80                  85

gcc aaa gac cac atc ttt cta ctc agt ctg gtt gac tta aac aaa aat      343
Ala Lys Asp His Ile Phe Leu Leu Ser Leu Val Asp Leu Asn Lys Asn
                90                  95                  100

ttt aag aag att tat tgg cct gct gca aag gaa cgg gtg gaa tta tgt      391
Phe Lys Lys Ile Tyr Trp Pro Ala Ala Lys Glu Arg Val Glu Leu Cys
            105                 110                 115

aaa tta aag ggg aaa gat gcc aat aca gaa tgt gca aat ttc atc aga      439
Lys Leu Lys Gly Lys Asp Ala Asn Thr Glu Cys Ala Asn Phe Ile Arg
        120                 125                 130

gta ctt cag ccc tat aac aaa act cac ata tat gtg tgt gga act gga      487
Val Leu Gln Pro Tyr Asn Lys Thr His Ile Tyr Val Cys Gly Thr Gly
    135                 140                 145

gca ttt cat cca ata tgt ggg tat att gat ctt gga gtc tac aag gag      535
Ala Phe His Pro Ile Cys Gly Tyr Ile Asp Leu Gly Val Tyr Lys Glu
150                 155                 160                 165

gat att ata ttc aaa cta gac aca cat aat ttg gag tct ggc aga ctg      583
Asp Ile Ile Phe Lys Leu Asp Thr His Asn Leu Glu Ser Gly Arg Leu
                170                 175                 180

aaa tgt cct ttc gat cct cag cag cct ttt gct tca gta atg aca gat      631
Lys Cys Pro Phe Asp Pro Gln Gln Pro Phe Ala Ser Val Met Thr Asp
            185                 190                 195

gag tac ctc tac tct gga aca gct tct gat ttc ctt ggc aaa gat act      679
Glu Tyr Leu Tyr Ser Gly Thr Ala Ser Asp Phe Leu Gly Lys Asp Thr
        200                 205                 210

gca ttc act cga tcc ctt ggg cct act cat gac cac cac tac atc aga      727
Ala Phe Thr Arg Ser Leu Gly Pro Thr His Asp His His Tyr Ile Arg
    215                 220                 225

act gac att tca gag cac tac tgg ctc aat gga gca aaa ttt att gga      775
Thr Asp Ile Ser Glu His Tyr Trp Leu Asn Gly Ala Lys Phe Ile Gly
230                 235                 240                 245

act ttc ttc ata cca gac acc tac aat cca gat gat gat aaa ata tat      823
Thr Phe Phe Ile Pro Asp Thr Tyr Asn Pro Asp Asp Asp Lys Ile Tyr
                250                 255                 260

ttc ttc ttt cgt gaa tca tct caa gaa ggc agt acc tcc gat aaa acc      871
Phe Phe Phe Arg Glu Ser Ser Gln Glu Gly Ser Thr Ser Asp Lys Thr
            265                 270                 275

atc ctt tct cga gtt gga aga gtt tgt aag aat gat gta gga gga caa      919
Ile Leu Ser Arg Val Gly Arg Val Cys Lys Asn Asp Val Gly Gly Gln
        280                 285                 290

cgc agc ctg ata aac aag tgg acg act ttt ctt aag gcc aga ctg att      967
Arg Ser Leu Ile Asn Lys Trp Thr Thr Phe Leu Lys Ala Arg Leu Ile
    295                 300                 305

tgc tca att cct gga agt gat ggg gca gat act tac ttt gat gag ctt     1015
Cys Ser Ile Pro Gly Ser Asp Gly Ala Asp Thr Tyr Phe Asp Glu Leu
310                 315                 320                 325

caa gat att tat tta ctc ccc aca aga gat gaa aga aat cct gta gta     1063
Gln Asp Ile Tyr Leu Leu Pro Thr Arg Asp Glu Arg Asn Pro Val Val
```

```
                330                 335                 340

tat gga gtc ttt act aca acc agc tcc atc ttc aaa ggc tct gct gtt      1111
Tyr Gly Val Phe Thr Thr Thr Ser Ser Ile Phe Lys Gly Ser Ala Val
            345                 350                 355

tgt gtg tat agc atg gct gac atc aga gca gtt ttt aat ggt cca tat      1159
Cys Val Tyr Ser Met Ala Asp Ile Arg Ala Val Phe Asn Gly Pro Tyr
        360                 365                 370

gct cat aag gaa agt gca gac cat cgt tgg gtg cag tat gat ggg aga      1207
Ala His Lys Glu Ser Ala Asp His Arg Trp Val Gln Tyr Asp Gly Arg
    375                 380                 385

att cct tat cca cgg cct ggt aca tgt cca agc aaa acc tat gac cca      1255
Ile Pro Tyr Pro Arg Pro Gly Thr Cys Pro Ser Lys Thr Tyr Asp Pro
390                 395                 400                 405

ctg att aag tcc acc cga gat ttt cca gat gat gtc atc agt ttc ata      1303
Leu Ile Lys Ser Thr Arg Asp Phe Pro Asp Asp Val Ile Ser Phe Ile
                410                 415                 420

aag cgg cac tct gtg atg tat aag tcc gta tac cca gtt gca gga gga      1351
Lys Arg His Ser Val Met Tyr Lys Ser Val Tyr Pro Val Ala Gly Gly
            425                 430                 435

cca acg ttc aag aga atc aat gtg gat tac aga ctg aca cag ata gtg      1399
Pro Thr Phe Lys Arg Ile Asn Val Asp Tyr Arg Leu Thr Gln Ile Val
        440                 445                 450

gtg gat cat gtc att gca gaa gat ggc cag tac gat gta atg ttt ctt      1447
Val Asp His Val Ile Ala Glu Asp Gly Gln Tyr Asp Val Met Phe Leu
    455                 460                 465

gga aca gac att gga act gtc ctc aaa gtt gtc agc att tca aag gaa      1495
Gly Thr Asp Ile Gly Thr Val Leu Lys Val Val Ser Ile Ser Lys Glu
470                 475                 480                 485

aag tgg aat atg gaa gag gta gtg ctg gag gag ttg cag ata ttc aag      1543
Lys Trp Asn Met Glu Glu Val Val Leu Glu Glu Leu Gln Ile Phe Lys
                490                 495                 500

cac tca tca atc atc ttg aac atg gaa ttg tct ctg aag cag caa caa      1591
His Ser Ser Ile Ile Leu Asn Met Glu Leu Ser Leu Lys Gln Gln Gln
            505                 510                 515

ttg tac att ggt tcc cga gat gga ttg gtt cag ctc tcc ttg cac aga      1639
Leu Tyr Ile Gly Ser Arg Asp Gly Leu Val Gln Leu Ser Leu His Arg
        520                 525                 530

tgc gac act tat ggg aaa gct tgc gca gac tgt tgt ctt gcc aga gac      1687
Cys Asp Thr Tyr Gly Lys Ala Cys Ala Asp Cys Cys Leu Ala Arg Asp
    535                 540                 545

ccc tac tgt gcc tgg gat gga aat gca tgc tct cga tat gct cct act      1735
Pro Tyr Cys Ala Trp Asp Gly Asn Ala Cys Ser Arg Tyr Ala Pro Thr
550                 555                 560                 565

tct aaa agg aga gct aga cgc caa gat gta aaa tat ggc gac cca atc      1783
Ser Lys Arg Arg Ala Arg Arg Gln Asp Val Lys Tyr Gly Asp Pro Ile
                570                 575                 580

acc cag tgc tgg gac atc gaa gac agc att agt cat gaa act gct gat      1831
Thr Gln Cys Trp Asp Ile Glu Asp Ser Ile Ser His Glu Thr Ala Asp
            585                 590                 595

gaa aag gtg att ttt ggc att gaa ttt aac tca acc ttt ctg gaa tgt      1879
Glu Lys Val Ile Phe Gly Ile Glu Phe Asn Ser Thr Phe Leu Glu Cys
        600                 605                 610

ata cct aaa tcc caa caa gca act att aaa tgg tat atc cag agg tca      1927
Ile Pro Lys Ser Gln Gln Ala Thr Ile Lys Trp Tyr Ile Gln Arg Ser
    615                 620                 625

ggg gat gag cat cga gag gag ttg aag ccc gat gaa aga atc atc aaa      1975
Gly Asp Glu His Arg Glu Glu Leu Lys Pro Asp Glu Arg Ile Ile Lys
630                 635                 640                 645

acg gaa tat ggg cta ctg att cga agt ttg cag aag aag gat tct ggg      2023
```

```
Thr Glu Tyr Gly Leu Leu Ile Arg Ser Leu Gln Lys Lys Asp Ser Gly
                650                 655                 660

atg tat tac tgc aaa gcc cag gag cac act ttc atc cac acc ata gtg     2071
Met Tyr Tyr Cys Lys Ala Gln Glu His Thr Phe Ile His Thr Ile Val
            665                 670                 675

aag ctg act ttg aat gtc att gag aat gaa cag atg gaa aat acc cag     2119
Lys Leu Thr Leu Asn Val Ile Glu Asn Glu Gln Met Glu Asn Thr Gln
        680                 685                 690

agg gca gag cat gag gag ggg aag gtc aag gat cta ttg gct gag tca     2167
Arg Ala Glu His Glu Glu Gly Lys Val Lys Asp Leu Leu Ala Glu Ser
    695                 700                 705

cgg ttg aga tac aaa gac tac atc caa atc ctt agc agc cca aac ttc     2215
Arg Leu Arg Tyr Lys Asp Tyr Ile Gln Ile Leu Ser Ser Pro Asn Phe
710                 715                 720                 725

agc ctc gac cag tac tgc gaa cag atg tgg cac agg gag aag cgg aga     2263
Ser Leu Asp Gln Tyr Cys Glu Gln Met Trp His Arg Glu Lys Arg Arg
                730                 735                 740

cag aga aac aag ggg ggc cca aag tgg aag cac atg cag gaa atg aag     2311
Gln Arg Asn Lys Gly Gly Pro Lys Trp Lys His Met Gln Glu Met Lys
            745                 750                 755

aag aaa cga aat cga aga cat cac aga gac ctg gat gag ctc cct aga     2359
Lys Lys Arg Asn Arg Arg His His Arg Asp Leu Asp Glu Leu Pro Arg
        760                 765                 770

gct gta gcc acg tag ttttctactt aatttaaaga aaagaattcc ttacctataa     2414
Ala Val Ala Thr
    775

aaacattgcc ttctgttttg tatatccctt atagtaattc ataaatgctt cccatggagt   2474

tttgctaagg cacaagacaa taatctgaat aagacaatat gtgatgaata taagaaaggg   2534

caaaaaattc atttgaacca gttttccaag aacaaatctt gcacaagcaa agtataagaa   2594

ttatcctaaa aatagggggt ttacagttgt aaatgtttta tgttttgagt tttggaattt   2654

attgtcatgt aaatagttga gctaagcaag ccccgaattt gatagtgtat aaggtgcttt   2714

attccctcga atgtccatta agcatggaat ttaccatgca gttgtgctat gttcttatga   2774

acagatatat cattcctatt gagaaccagc taccttgtgg tagggaataa gaggtcagac   2834

acaaattaag acaactccca ttatcaacag gaactttctc agtgagccat tcactcctgg   2894

agaatggtat aggaatttgg agaggtgcat tatttctttc tggccactgg ggttaaattt   2954

agtgtactac aacattgatt tactgaaggg cactaatgtt tcccccagga tttctattga   3014

ctagtcagga gtaacaggtt cacagagaga agttggtgct tagttatgtg tttttttagag  3074

tatatactaa gctctacagg gacagaatgc ttaataaata ctttaataag atatgggaaa   3134

atattttaat aaaacaagga aaacataatg atgtataatg catcctgatg ggaaggcatg   3194

cagatgggat ttgttagaag acagaaggaa agacagccat aaattctggc tttggggaaa   3254

actcatatcc ccatgaaaag gaagaacaat cacaaataaa gtgagagtaa tgtaatggag   3314

ctcttttcac tagggtataa gtagctgcca atttgtaatt catctgttaa aaaaaatcta   3374

gattataaca aactgctagc aaaatctgag gaaacataaa ttcttctgaa gaatcatagg   3434

aagagtagac attttattta taaccaatga tatttcagta tatattttct ctcttttaaa   3494

aaatatttat catactctgt atattatttc tttttactgc ctttattctc tcctgtatat   3554

tggattttgt gattatattt gagtgaatag gagaaaacaa tatataacac acagagaatt   3614

aagaaaatga catttctggg gagtggggat atatatttgt tgaataacag aacgagtgta   3674

aaattttaac aacggaaagg gttaaattaa ctctttgaca tcttcactca accttttctc   3734
```

```
attgctgagt taatctgttg taattgtagt attgtttttg taatttaaca ataaataagc   3794
ctgctacatg taaaaagaac caaactcaca atattaacat aaacatcttt catattttgt   3854
tagtactttc aaatgttttc aatttgactt tccctctgaa tatgcatggt gtgtttcctg   3914
tctgtttaag cagaactcac ctttccttct tgtaacacag aacccttagc cttcttctgt   3974
tttgcctttt cacgcccttt atagtgtgaa atgaaaaatt agtcacttcc tcacatggaa   4034
ggcagctttt cagaaaataa cagacattgc tcgtttctca tgcattctac atatcttgaa   4094
agaaaagtct gtgagaaaac cctgtgatta gagggcaact taatgcaaga tctgtggctc   4154
tatgttgaga gcattctctc tctgttattt ttattttatt tgcattgctt acctatctca   4214
aagtagtcaa actgatatat gagattgagt actccctttt gatattatac tgatgaatat   4274
ttgtaggtgt ttcactataa ggaacagcta aggaataatt ttaataaaag tgaaccagaa   4334
caaatcactc atttaaaaag taattcagaa gaacagtgtg gcatgatcag acttctaatt   4394
gaatagcgta acaacagtgt ttgtaattat agatttgctt ggacaaaata ttccaggaac   4454
tcatagcgag ctcaaagcaa ttaagtggga acatttttaa tttaaaaaaa atttccaaat   4514
atttgtgggt ccgacagtaa tgatcaaaat atgaatgact ttggaaaatt tacatgaagc   4574
tcaagtgtta ggattgactt atgaaaataa attttatttc tatccaaatt tgaatgtcca   4634
aaccattttt tagttacttc tttctaatcc tagttattca gacaaaattt ggaaacttat   4694
tttatgacca catctaatat tctggctgct ttggatacaa tactcttgat ttatgataat   4754
tagttaaaat atattaaaaa tattattagt aaaataaaat ttcacacaat aaaaaacaac   4814
atagagtaca catatttata tgtattttta aagataaaga atatctaaaa tgtgtttttt   4874
tcttagcttt ttagttgtct agaacattta gagaaagagt atgaatatat taaatccaca   4934
aacacactat atacttcctc accactgact attttatcaa atttgcctta aaataatgaa   4994
aaagaaaagt atagttaatg gtttcaaata tgctaagaaa ttgactctgc ggaggggatc   5054
ttaaaatgcc tgtttactca tgttttcgta tttttcttgt ctctaatact tttgtctttg   5114
tctgccttgt gtgttctttt ctgaatttca tttcagcaat ttatgctgct aaatagaatc   5174
ccgcatgtct gcattcattt acattcaact tattgtaaat tttgagattt tatttagaaa   5234
tgaattgtct aattaattta tgtagagtcc ttttttccaa agagctcaaa acactacatc   5294
cacattattg acttttggaa accaaccaaa ttacttaaga aatggaaaag tagtcacaga   5354
gaaatttagt aatttgcaaa agccacaaca gtagtggaag aattaaaatt cataaagtct   5414
catcattctg ttggctaaaa taatgctctt tacaatatgc tggctacaaa atggtcttac   5474
tcttgaattt tgcttttggt tcatattttg gttcttcata ttctagtatg ttttgttcct   5534
gctgaatttt acagactcag ctaaacaata agttattagt agtcacttgt tttcattatc   5594
ataattgaat ttccaagaac aacttgatat cattcagctg tccaaaaaat aataagagca   5654
ttcattaaat actgatttc ttaaacttaa atgttgtatt tcatatttat ttatataata    5714
caaatggaaa tcaaaactga aatagcctcc ctttagaatg tcacattttt cttagaaaac   5774
attttggaat tggttaacct tattgggaat ggataattta gaaacaaacc aaaaaaaaaa   5834
aaagatattt gaagtgtttt tataggagat gtatttttat catagtaaat gatcacaatt   5894
ttaaataatt catcttacaa gtcaggtaaa ataaaatcga ttcccagatt ccatacatta   5954
ggagtgcaaa gacaggatca tacacatgac ttatacctct catttaaata ttttatagta   6014
taaagtattt atggaaaggg tttgagatag atgatttttg ggaaagggca aaatgtgtca   6074
gatgccctag ttaatcatgt aatttaattc tggtattgtg agtggttagc aatcaatttt   6134
```

```
gaatttataa ttctgctatt ttaaaagaaa tgtagtcttg tagtatgaaa taattaaaaa   6194

ttgttaaatg tatattttgg ttgtattata ataaaatgca aacatgactg ttctatgatt   6254

ataaaaaaaa aaaaaaaaaa aa                                            6276


<210> SEQ ID NO 70
<211> LENGTH: 777
<212> TYPE: PRT
<213> ORGANISM: Artificial Sequence
<220> FEATURE:
<223> OTHER INFORMATION: full-length human SEMA3D A120K

<400> SEQUENCE: 70

Met Asn Ala Asn Lys Asp Glu Arg Leu Lys Ala Arg Ser Gln Asp Phe
1               5                   10                  15

His Leu Phe Pro Ala Leu Met Met Leu Ser Met Thr Met Leu Phe Leu
            20                  25                  30

Pro Val Thr Gly Thr Leu Lys Gln Asn Ile Pro Arg Leu Lys Leu Thr
        35                  40                  45

Tyr Lys Asp Leu Leu Leu Ser Asn Ser Cys Ile Pro Phe Leu Gly Ser
    50                  55                  60

Ser Glu Gly Leu Asp Phe Gln Thr Leu Leu Leu Asp Glu Glu Arg Gly
65                  70                  75                  80

Arg Leu Leu Leu Gly Ala Lys Asp His Ile Phe Leu Leu Ser Leu Val
                85                  90                  95

Asp Leu Asn Lys Asn Phe Lys Lys Ile Tyr Trp Pro Ala Ala Lys Glu
            100                 105                 110

Arg Val Glu Leu Cys Lys Leu Lys Gly Lys Asp Ala Asn Thr Glu Cys
        115                 120                 125

Ala Asn Phe Ile Arg Val Leu Gln Pro Tyr Asn Lys Thr His Ile Tyr
    130                 135                 140

Val Cys Gly Thr Gly Ala Phe His Pro Ile Cys Gly Tyr Ile Asp Leu
145                 150                 155                 160

Gly Val Tyr Lys Glu Asp Ile Ile Phe Lys Leu Asp Thr His Asn Leu
                165                 170                 175

Glu Ser Gly Arg Leu Lys Cys Pro Phe Asp Pro Gln Gln Pro Phe Ala
            180                 185                 190

Ser Val Met Thr Asp Glu Tyr Leu Tyr Ser Gly Thr Ala Ser Asp Phe
        195                 200                 205

Leu Gly Lys Asp Thr Ala Phe Thr Arg Ser Leu Gly Pro Thr His Asp
    210                 215                 220

His His Tyr Ile Arg Thr Asp Ile Ser Glu His Tyr Trp Leu Asn Gly
225                 230                 235                 240

Ala Lys Phe Ile Gly Thr Phe Phe Ile Pro Asp Thr Tyr Asn Pro Asp
                245                 250                 255

Asp Asp Lys Ile Tyr Phe Phe Phe Arg Glu Ser Ser Gln Glu Gly Ser
            260                 265                 270

Thr Ser Asp Lys Thr Ile Leu Ser Arg Val Gly Arg Val Cys Lys Asn
        275                 280                 285

Asp Val Gly Gly Gln Arg Ser Leu Ile Asn Lys Trp Thr Thr Phe Leu
    290                 295                 300

Lys Ala Arg Leu Ile Cys Ser Ile Pro Gly Ser Asp Gly Ala Asp Thr
305                 310                 315                 320

Tyr Phe Asp Glu Leu Gln Asp Ile Tyr Leu Leu Pro Thr Arg Asp Glu
                325                 330                 335
```

```
Arg Asn Pro Val Val Tyr Gly Val Phe Thr Thr Thr Ser Ser Ile Phe
            340                 345                 350

Lys Gly Ser Ala Val Cys Val Tyr Ser Met Ala Asp Ile Arg Ala Val
        355                 360                 365

Phe Asn Gly Pro Tyr Ala His Lys Glu Ser Ala Asp His Arg Trp Val
    370                 375                 380

Gln Tyr Asp Gly Arg Ile Pro Tyr Pro Arg Pro Gly Thr Cys Pro Ser
385                 390                 395                 400

Lys Thr Tyr Asp Pro Leu Ile Lys Ser Thr Arg Asp Phe Pro Asp Asp
                405                 410                 415

Val Ile Ser Phe Ile Lys Arg His Ser Val Met Tyr Lys Ser Val Tyr
            420                 425                 430

Pro Val Ala Gly Gly Pro Thr Phe Lys Arg Ile Asn Val Asp Tyr Arg
        435                 440                 445

Leu Thr Gln Ile Val Val Asp His Val Ile Ala Glu Asp Gly Gln Tyr
    450                 455                 460

Asp Val Met Phe Leu Gly Thr Asp Ile Gly Thr Val Leu Lys Val Val
465                 470                 475                 480

Ser Ile Ser Lys Glu Lys Trp Asn Met Glu Glu Val Val Leu Glu Glu
                485                 490                 495

Leu Gln Ile Phe Lys His Ser Ser Ile Ile Leu Asn Met Glu Leu Ser
            500                 505                 510

Leu Lys Gln Gln Gln Leu Tyr Ile Gly Ser Arg Asp Gly Leu Val Gln
        515                 520                 525

Leu Ser Leu His Arg Cys Asp Thr Tyr Gly Lys Ala Cys Ala Asp Cys
    530                 535                 540

Cys Leu Ala Arg Asp Pro Tyr Cys Ala Trp Asp Gly Asn Ala Cys Ser
545                 550                 555                 560

Arg Tyr Ala Pro Thr Ser Lys Arg Arg Ala Arg Arg Gln Asp Val Lys
                565                 570                 575

Tyr Gly Asp Pro Ile Thr Gln Cys Trp Asp Ile Glu Asp Ser Ile Ser
            580                 585                 590

His Glu Thr Ala Asp Glu Lys Val Ile Phe Gly Ile Glu Phe Asn Ser
        595                 600                 605

Thr Phe Leu Glu Cys Ile Pro Lys Ser Gln Gln Ala Thr Ile Lys Trp
    610                 615                 620

Tyr Ile Gln Arg Ser Gly Asp Glu His Arg Glu Glu Leu Lys Pro Asp
625                 630                 635                 640

Glu Arg Ile Ile Lys Thr Glu Tyr Gly Leu Leu Ile Arg Ser Leu Gln
                645                 650                 655

Lys Lys Asp Ser Gly Met Tyr Tyr Cys Lys Ala Gln Glu His Thr Phe
            660                 665                 670

Ile His Thr Ile Val Lys Leu Thr Leu Asn Val Ile Glu Asn Glu Gln
        675                 680                 685

Met Glu Asn Thr Gln Arg Ala Glu His Glu Glu Gly Lys Val Lys Asp
    690                 695                 700

Leu Leu Ala Glu Ser Arg Leu Arg Tyr Lys Asp Tyr Ile Gln Ile Leu
705                 710                 715                 720

Ser Ser Pro Asn Phe Ser Leu Asp Gln Tyr Cys Glu Gln Met Trp His
                725                 730                 735

Arg Glu Lys Arg Arg Gln Arg Asn Lys Gly Gly Pro Lys Trp Lys His
            740                 745                 750
```

```
Met Gln Glu Met Lys Lys Lys Arg Asn Arg Arg His His Arg Asp Leu
        755                 760                 765

Asp Glu Leu Pro Arg Ala Val Ala Thr
    770                 775


<210> SEQ ID NO 71
<211> LENGTH: 6521
<212> TYPE: DNA
<213> ORGANISM: Artificial Sequence
<220> FEATURE:
<223> OTHER INFORMATION: full-length mouse Sema3D A120K
<220> FEATURE:
<221> NAME/KEY: CDS
<222> LOCATION: 547..2880
<223> OTHER INFORMATION: /transl_table=1

<400> SEQUENCE: 71

aaacccaccc tggacagcgc ggccgagaca gggaaggttt gctcgctctg agggattgcc      60

agcacatcag aagtggccgg gagctggggg aggagactga agggagaggt aatccctggc     120

gttttgagca tccccttttt agaaagaagg agtctctccc aggacagctg ctgcggtcac     180

accacaaact taaaagccgc cctcctgctt ggagcgtgcc tttcctcacc acgctcgctg     240

gcctaagcgc caactggtgg gtcactgtcc gagagagagg cgctgcgctc gggggacagg     300


agcgccccct gccttcccgc ttggccgtag ccgcggcctc attgctctgc cagggccgcc     360

tgtgcggggt tcagccccgg ctgccgctcc gaagaactcg cgcctgtgcc cgcggtcgcc     420

atcctcttgg cttccttggg ctgtcctttc ctctctcctg agcctgcgac gtaaggaaag     480

gaaaagcgac aagagttgct agcaggaagg gtgaactaac agtgtttgaa aaacaaaatt     540

ttcatc atg aat gtt act aaa gat gag aac cca aga tcc aga agt caa        588
       Met Asn Val Thr Lys Asp Glu Asn Pro Arg Ser Arg Ser Gln
       1               5                   10

gat ctt cac ctt ttt cat gct tgg atg atg tta atc atg acg gtg ctc       636
Asp Leu His Leu Phe His Ala Trp Met Met Leu Ile Met Thr Val Leu
15                  20                  25                  30

ttt ctt cct gtc act gaa acg tct aaa caa aat att cca aga ctc aag       684
Phe Leu Pro Val Thr Glu Thr Ser Lys Gln Asn Ile Pro Arg Leu Lys
                35                  40                  45

cta acc tac aaa gac ttg ctg ctt tca aac acc tgt atc ccc ttt ttg       732
Leu Thr Tyr Lys Asp Leu Leu Leu Ser Asn Thr Cys Ile Pro Phe Leu
            50                  55                  60

ggt tca tca gaa gga ttg gat ttc cag act ctt ctt ttg gat gag gag       780
Gly Ser Ser Glu Gly Leu Asp Phe Gln Thr Leu Leu Leu Asp Glu Glu
        65                  70                  75

agg ggc ata ctg ctc cta gga gcc aaa gac cat gtc ttc ctg ctc agt       828
Arg Gly Ile Leu Leu Leu Gly Ala Lys Asp His Val Phe Leu Leu Ser
    80                  85                  90

ctg gtt gac ttg aac aag aat ttt aag aag att tat tgg cct gct gca       876
Leu Val Asp Leu Asn Lys Asn Phe Lys Lys Ile Tyr Trp Pro Ala Ala
95                  100                 105                 110

aaa gaa cga gtg gag cta tgt aaa tta aag ggg aaa gat gcc aat gca       924
Lys Glu Arg Val Glu Leu Cys Lys Leu Lys Gly Lys Asp Ala Asn Ala
                115                 120                 125

gaa tgt gca aat ttc atc cgt gtg ctt caa ccc tat aat aag act cac       972
Glu Cys Ala Asn Phe Ile Arg Val Leu Gln Pro Tyr Asn Lys Thr His
            130                 135                 140

gtt tac gtg tgt gga act gga gcg ttt cat ccg ctg tgt ggg tac att      1020
Val Tyr Val Cys Gly Thr Gly Ala Phe His Pro Leu Cys Gly Tyr Ile
        145                 150                 155
```

-continued

```
gat ctc ggc gcc aac aag gag gaa ctc ata ttt aaa cta gac acg cac      1068
Asp Leu Gly Ala Asn Lys Glu Glu Leu Ile Phe Lys Leu Asp Thr His
    160                 165                 170

aac ctg gag tct ggc aga ctg aaa tgt ccc ttt gat cct cag cag cct      1116
Asn Leu Glu Ser Gly Arg Leu Lys Cys Pro Phe Asp Pro Gln Gln Pro
175                 180                 185                 190

ttt gct tca gta atg aca gat gag cac ctc tac tct gga aca gct tct      1164
Phe Ala Ser Val Met Thr Asp Glu His Leu Tyr Ser Gly Thr Ala Ser
                195                 200                 205

gat ttc ctt ggc aaa gac act gca ttc aca agg tct ctg ggg cta atg      1212
Asp Phe Leu Gly Lys Asp Thr Ala Phe Thr Arg Ser Leu Gly Leu Met
            210                 215                 220

cag gac cac cat tcc atc aga act gac att tca gag cac cac tgg ctc      1260
Gln Asp His His Ser Ile Arg Thr Asp Ile Ser Glu His His Trp Leu
        225                 230                 235

aat gga gca aaa ttt atc gga aca ttc ccc att cca gac acc tat aat      1308
Asn Gly Ala Lys Phe Ile Gly Thr Phe Pro Ile Pro Asp Thr Tyr Asn
    240                 245                 250

cca gat gat gat aaa ata tat ttc ttc ttt cga gaa tca tcc cag gaa      1356
Pro Asp Asp Asp Lys Ile Tyr Phe Phe Phe Arg Glu Ser Ser Gln Glu
255                 260                 265                 270

ggc agt act tct gac aga agc att ctt tca aga gtt gga aga gtt tgt      1404
Gly Ser Thr Ser Asp Arg Ser Ile Leu Ser Arg Val Gly Arg Val Cys
                275                 280                 285

aag aat gat gta ggt ggg caa cga agt ctg ata aac aaa tgg aca act      1452
Lys Asn Asp Val Gly Gly Gln Arg Ser Leu Ile Asn Lys Trp Thr Thr
            290                 295                 300

ttt cta aag gca aga ctg att tgc tcg att cct gga agc gat ggg gca      1500
Phe Leu Lys Ala Arg Leu Ile Cys Ser Ile Pro Gly Ser Asp Gly Ala
        305                 310                 315

gat acc cat ttt gat gaa ctc caa gat att tac tta ctc cct acg aga      1548
Asp Thr His Phe Asp Glu Leu Gln Asp Ile Tyr Leu Leu Pro Thr Arg
    320                 325                 330

gat gaa aga aat cct gta gta tat gga gtc ttt acc aca acc agc tcc      1596
Asp Glu Arg Asn Pro Val Val Tyr Gly Val Phe Thr Thr Thr Ser Ser
335                 340                 345                 350

atc ttc aaa ggc tct gct gtc tgt gtg tac agc atg gct gat atc cga      1644
Ile Phe Lys Gly Ser Ala Val Cys Val Tyr Ser Met Ala Asp Ile Arg
                355                 360                 365

gca gtc ttt aat ggt ccc tat gct cat aag gaa agt gct gac cat cgc      1692
Ala Val Phe Asn Gly Pro Tyr Ala His Lys Glu Ser Ala Asp His Arg
            370                 375                 380

tgg gtg caa tat gat gga agg ata cct tac ccc cga cct gga acg tgt      1740
Trp Val Gln Tyr Asp Gly Arg Ile Pro Tyr Pro Arg Pro Gly Thr Cys
        385                 390                 395

cca agc aaa acc tat gac cca ctg att aag tcc acc cga gac ttt cca      1788
Pro Ser Lys Thr Tyr Asp Pro Leu Ile Lys Ser Thr Arg Asp Phe Pro
    400                 405                 410

gac gat gtt atc agt ttc ata agg cgg cac cct gtg atg tat aag tcc      1836
Asp Asp Val Ile Ser Phe Ile Arg Arg His Pro Val Met Tyr Lys Ser
415                 420                 425                 430

gtg tac cca gtg gca gga gca ccg acc ttc aag aga atc aac gtg gat      1884
Val Tyr Pro Val Ala Gly Ala Pro Thr Phe Lys Arg Ile Asn Val Asp
                435                 440                 445

tac aga ctg acg cag ata gtg gtg gat cac gtg gtc gct gaa gac ggg      1932
Tyr Arg Leu Thr Gln Ile Val Val Asp His Val Val Ala Glu Asp Gly
            450                 455                 460

cag tat gat gtc atg ttt ctc gga aca gac att gga aca gtc ctg aaa      1980
Gln Tyr Asp Val Met Phe Leu Gly Thr Asp Ile Gly Thr Val Leu Lys
        465                 470                 475
```

```
gtt gtg agc atc tcc aag gag aag tgg aat atg gaa gag gtc gta ctg     2028
Val Val Ser Ile Ser Lys Glu Lys Trp Asn Met Glu Glu Val Val Leu
    480                 485                 490

gag gag ctt cag gta ttc aag cac cca aca gct atc ttg aac atg gag     2076
Glu Glu Leu Gln Val Phe Lys His Pro Thr Ala Ile Leu Asn Met Glu
495                 500                 505                 510

ttg tcg ctg aag cag caa cag ttg tac gtt ggt tcc tgg gat gga ttg     2124
Leu Ser Leu Lys Gln Gln Gln Leu Tyr Val Gly Ser Trp Asp Gly Leu
                515                 520                 525

gtc cag ctc tcc ttg cac aga tgc gac act tac ggg aaa gca tgt gca     2172
Val Gln Leu Ser Leu His Arg Cys Asp Thr Tyr Gly Lys Ala Cys Ala
            530                 535                 540

gac tgc tgt ctc gcc aga gac cct tac tgt gcc tgg gat gga aat gct     2220
Asp Cys Cys Leu Ala Arg Asp Pro Tyr Cys Ala Trp Asp Gly Asn Ala
        545                 550                 555

tgc tcc aga tat gca ccc acg tct aaa agg cga gct aga cgc cag gat     2268
Cys Ser Arg Tyr Ala Pro Thr Ser Lys Arg Arg Ala Arg Arg Gln Asp
    560                 565                 570

gta aaa tat ggg gac cca atc act cag tgc tgg gac ata gaa gac agc     2316
Val Lys Tyr Gly Asp Pro Ile Thr Gln Cys Trp Asp Ile Glu Asp Ser
575                 580                 585                 590

att agt cat gaa aca gct gat gaa aag gtg att ttt gga att gaa ttt     2364
Ile Ser His Glu Thr Ala Asp Glu Lys Val Ile Phe Gly Ile Glu Phe
                595                 600                 605

aat tca acc ttt ttg gag tgt ata cct aaa tcc caa caa gcc tct gtt     2412
Asn Ser Thr Phe Leu Glu Cys Ile Pro Lys Ser Gln Gln Ala Ser Val
            610                 615                 620

gag tgg tac atc cag cgg tca gga gat gag cat cga gag gag ttg aaa     2460
Glu Trp Tyr Ile Gln Arg Ser Gly Asp Glu His Arg Glu Glu Leu Lys
        625                 630                 635

cct gat gaa agg atc atc aaa act gac tat ggg cta ctg att cga agt     2508
Pro Asp Glu Arg Ile Ile Lys Thr Asp Tyr Gly Leu Leu Ile Arg Ser
    640                 645                 650

ctg cag aag aag gat tct ggg atg tat tac tgc aaa gca cag gag cac     2556
Leu Gln Lys Lys Asp Ser Gly Met Tyr Tyr Cys Lys Ala Gln Glu His
655                 660                 665                 670

act ttc atc cac acc ata gtg aag ctg act ttg aat gtc att gag aat     2604
Thr Phe Ile His Thr Ile Val Lys Leu Thr Leu Asn Val Ile Glu Asn
                675                 680                 685

gaa cag atg gaa aat acc cag agg gca gaa tac cag gag ggg cag gtc     2652
Glu Gln Met Glu Asn Thr Gln Arg Ala Glu Tyr Gln Glu Gly Gln Val
            690                 695                 700

aag gat ctg ttg gct gag tca cgg ttg aga tac aaa gac tac atc caa     2700
Lys Asp Leu Leu Ala Glu Ser Arg Leu Arg Tyr Lys Asp Tyr Ile Gln
        705                 710                 715

atc ctt agc agc ccg aac ttc agc ctg gac cag tac tgt gag cag atg     2748
Ile Leu Ser Ser Pro Asn Phe Ser Leu Asp Gln Tyr Cys Glu Gln Met
    720                 725                 730

tgg tac aag gag aag cgg aga cag cgc aac aag ggc agc cca aag tgg     2796
Trp Tyr Lys Glu Lys Arg Arg Gln Arg Asn Lys Gly Ser Pro Lys Trp
735                 740                 745                 750

aag cac atg cag gaa atg aag aag aaa cga aat cga cga cat cac aga     2844
Lys His Met Gln Glu Met Lys Lys Lys Arg Asn Arg Arg His His Arg
                755                 760                 765

gac ctc gat gag ctc cag aga tca gta gct aca tag ttttctattt          2890
Asp Leu Asp Glu Leu Gln Arg Ser Val Ala Thr
            770                 775

aatttaaaga gggaattatt tacctgcctg cacaaataat gtcttctgtt ttgtacatcc   2950
```

-continued

```
cttatactaa ctcatacatg cttcccatgg agtctcacgg aggcacagga tgctatgctg   3010
agtaagacta tataggacat catctgaacc agctttccaa gaacaaaatc tgtatcagca   3070
aagttaagaa ttgtcttaaa aataggggcc ttatgtttgt aaatgtctca tagtttgaat   3130
ttaatgtcat gtaaataatc aagttaaatg aacccaggtc cacttagtaa gggcgttatt   3190
cccgtgcatg tccattaagc atggactttc ccatgctgct ggctatgtgc ttaatcattc   3250
cattctagaa caggtgatca tgtaggaact ggagaaaagg cacactttaa aacagcttat   3310
gttagcaaaa aaaaaacttt ctcaaggagc caacaggcca cacttggagt caggcgtggg   3370
aatttagaaa ggcatgttcc ctctttgtgg accaggctac atctagtgta ctgcagtaat   3430
gctctgtgag agggtagtaa tgatcctcac caatttcctt ttgattgctc aagcacagca   3490
tcatggacag aaccccatgg tgtgctctag agtacagaca atggaactta gtacacactt   3550
cctgtgctct ttgggaagca tggtaaaaga tcttaatata ataataaggg tgacatgata   3610
tacactgtat cctaatctgt agatgggaat tatttggaga cagacaagat agctgtaaat   3670
tctgtctctg agaaaaactt atattgccat aaaaaaggag aaagccacaa agtagataga   3730
atgtaatgga attctttcca ctggagtata aatatctgcc aacttataat gttttggtta   3790
aaaataattt agattatagc aaattgttag caaaaatgca agtgaaagta aaatttgtaa   3850
aaaaaattat gggatggcaa tatattattt ataaccaatg tatttctgtg ttctcttttt   3910
ttctaagtat ttatcgtatt ctgtatattg tttgcattta catccttttt tttattatat   3970
ttgagtaaat aggagaaagc aatacgtaat acatagagat aattgagtag atgaccaagg   4030
tggggagtgg ggctatatat ttgttgaatg gatggataat ggcaaaattt tgatgacggg   4090
aagggttaaa ttaactcttc gacatcctct cgttacataa actttcaagc agtgttgttt   4150
tcagcagttt cacaaggaag tcttcaacat ctaaagaaaa cactcacacc gttagcataa   4210
gtaccatttg tattttgcta gcctgtgtca aattcaactt tgcctttgaa cagtgttttc   4270
ctgccagtct ctccagaaat caactttcct tcctgtagca caaaaccctt agccttcctc   4330
tgttttgcct tttcacgctc tttatagtgt gaaatgaaca attagtcact tcctcacaaa   4390
gaatgcagct ttttagaaaa ccaacagacc ttgtttgttt ctcatgcatt ctacatgttt   4450
tgaaagattc tgtgagaagc ctgtgtgatt aaaaagcagt tttacagagt caagcaatct   4510
atctcttcaa agtagcatca gtattttaca ttcatttaat ttgcattggg tacctatctc   4570
aagggcataa cattatctgc aagggactag tataataatg aatatttgtt gatgtttcac   4630
tcttggaaaa agcaaaaatg aaggaacaat tttaatttgt aaaccagaat gaatcacatc   4690
tccagcagaa gtgcatacaa atccttgtgt catggttaga ctactaatca tagatcacac   4750
aataatgttt atctactggc ttactgagtc ctgcaaagtc acagcaaaca tgtcagtggg   4810
tgcatgcttc attcaaaaaa tgctttcaga tagctgtgca tcagagagta atactcaaat   4870
atcagtagta ttgaaagatt gcacaagatt ctactctttg tattgacatc tgaaaattaa   4930
ttttatatag ataataatgt ccaaactatt ttctaattac ttatgtaatt agaaatgtaa   4990
tgttttatca acattctgta aatctatttt acatcttaga tttaaaattt tggctgtttt   5050
gggcataaaa cttctaatta tgattaaata tattataaac attattagga aaatatgatt   5110
ccataataaa ggtagggcta tggtttattt tgaaatgcag actatagcta agcagcattc   5170
attcttattc aaaagactta gaagagtgtt gtgaaagatc agttgacaaa tgtaatgtgt   5230
agttccttac cattgaggat gaacaactct gttttgaaat aataaaaagc agaatattgc   5290
tcaaagttta aatattaaag gtaccagatc ccccagaagc aactctgaac tatgtagtta   5350
```

```
ttcattttt tttaaatcta tttttctgtc ttcagtacaa gtctctagct tctgtgagtg   5410

tttttgctgc atttttattc agtcctttgt gctgctaaat agtagtatgc ctgaatgagt   5470

taatttacat ttaatttatt gggaatttta agagtttgtt tagaaatgga taatctaaat   5530

aagcaattta tgtaaaatcc tttgtttttc tttcccaaaa gagttcataa tcatatatca   5590

cacgacagag taaacatttc agaagaaaca gtcaagttac ttaaaaaact gcaaagtagt   5650

catagaaaaa ctgagcacac tgcagaatcc acaatagctc tcggatgcac aattccagga   5710

tgatttgttt aaagcaagac ttacttacaa catgcctgca atatgatggt cacgcttttg   5770

gacgtttcct ttgtgctata ctttgattct ttgcatatat taattattac atgctattcc   5830

tactgaattg gtgatcttac ctagaggcta acaagagtga ctacttgtta gactaacata   5890

accaagaata atttcccagg acaacttgtg tcatttcatt cacatgaaaa aataaaatta   5950

aacaagacca ctcagtaaac attgattctt cttaaacata tgtctaagat gtattgtaca   6010

tattttactg aaacagaata aagttaactt gggaatccct tctcttcata ataccacatt   6070

gttgcagtca gtgtgtttca actaacaagc cattttgagg gatgggtaac tttttaaaaa   6130

tagaaatgta tattttctca taatagatga tcacaatatt tcaatttaca gtatgtaagg   6190

ttaaaaatac ataagactta aattttccag acttgttaaa ctgaaaatcc atgtacacaa   6250

taaatctcac gctttgtaac tcttgcttaa atcttttgta atgtaaggta tttatgaaaa   6310

tttgaagcat accttttgg gaaagaaaaa taaaacctgt cagaagccac agttggtctt   6370

cacttcttag cattgtcagt ggtgggtatc aatgaatttg aataatttta cttttaaaaa   6430

actgtagtct tgtagtatag catacttaaa attgttaaat gtatattttg tttgtattat   6490

aataaaacaa gtatcagtgt tctattatta t                                  6521
```

<210> SEQ ID NO 72
<211> LENGTH: 777
<212> TYPE: PRT
<213> ORGANISM: Artificial Sequence
<220> FEATURE:
<223> OTHER INFORMATION: full-length mouse Sema3D A120K

<400> SEQUENCE: 72

```
Met Asn Val Thr Lys Asp Glu Asn Pro Arg Ser Arg Ser Gln Asp Leu
1               5                   10                  15

His Leu Phe His Ala Trp Met Met Leu Ile Met Thr Val Leu Phe Leu
            20                  25                  30

Pro Val Thr Glu Thr Ser Lys Gln Asn Ile Pro Arg Leu Lys Leu Thr
        35                  40                  45

Tyr Lys Asp Leu Leu Leu Ser Asn Thr Cys Ile Pro Phe Leu Gly Ser
    50                  55                  60

Ser Glu Gly Leu Asp Phe Gln Thr Leu Leu Leu Asp Glu Glu Arg Gly
65                  70                  75                  80

Ile Leu Leu Leu Gly Ala Lys Asp His Val Phe Leu Leu Ser Leu Val
                85                  90                  95

Asp Leu Asn Lys Asn Phe Lys Lys Ile Tyr Trp Pro Ala Ala Lys Glu
            100                 105                 110

Arg Val Glu Leu Cys Lys Leu Lys Gly Lys Asp Ala Asn Ala Glu Cys
        115                 120                 125

Ala Asn Phe Ile Arg Val Leu Gln Pro Tyr Asn Lys Thr His Val Tyr
    130                 135                 140

Val Cys Gly Thr Gly Ala Phe His Pro Leu Cys Gly Tyr Ile Asp Leu
```

-continued

```
145                 150                 155                 160

Gly Ala Asn Lys Glu Glu Leu Ile Phe Lys Leu Asp Thr His Asn Leu
                165                 170                 175

Glu Ser Gly Arg Leu Lys Cys Pro Phe Asp Pro Gln Gln Pro Phe Ala
            180                 185                 190

Ser Val Met Thr Asp Glu His Leu Tyr Ser Gly Thr Ala Ser Asp Phe
        195                 200                 205

Leu Gly Lys Asp Thr Ala Phe Thr Arg Ser Leu Gly Leu Met Gln Asp
    210                 215                 220

His His Ser Ile Arg Thr Asp Ile Ser Glu His His Trp Leu Asn Gly
225                 230                 235                 240

Ala Lys Phe Ile Gly Thr Phe Pro Ile Pro Asp Thr Tyr Asn Pro Asp
                245                 250                 255

Asp Asp Lys Ile Tyr Phe Phe Phe Arg Glu Ser Ser Gln Glu Gly Ser
            260                 265                 270

Thr Ser Asp Arg Ser Ile Leu Ser Arg Val Gly Arg Val Cys Lys Asn
        275                 280                 285

Asp Val Gly Gly Gln Arg Ser Leu Ile Asn Lys Trp Thr Thr Phe Leu
    290                 295                 300

Lys Ala Arg Leu Ile Cys Ser Ile Pro Gly Ser Asp Gly Ala Asp Thr
305                 310                 315                 320

His Phe Asp Glu Leu Gln Asp Ile Tyr Leu Leu Pro Thr Arg Asp Glu
                325                 330                 335

Arg Asn Pro Val Val Tyr Gly Val Phe Thr Thr Thr Ser Ser Ile Phe
            340                 345                 350

Lys Gly Ser Ala Val Cys Val Tyr Ser Met Ala Asp Ile Arg Ala Val
        355                 360                 365

Phe Asn Gly Pro Tyr Ala His Lys Glu Ser Ala Asp His Arg Trp Val
    370                 375                 380

Gln Tyr Asp Gly Arg Ile Pro Tyr Pro Arg Pro Gly Thr Cys Pro Ser
385                 390                 395                 400

Lys Thr Tyr Asp Pro Leu Ile Lys Ser Thr Arg Asp Phe Pro Asp Asp
                405                 410                 415

Val Ile Ser Phe Ile Arg Arg His Pro Val Met Tyr Lys Ser Val Tyr
            420                 425                 430

Pro Val Ala Gly Ala Pro Thr Phe Lys Arg Ile Asn Val Asp Tyr Arg
        435                 440                 445

Leu Thr Gln Ile Val Val Asp His Val Val Ala Glu Asp Gly Gln Tyr
    450                 455                 460

Asp Val Met Phe Leu Gly Thr Asp Ile Gly Thr Val Leu Lys Val Val
465                 470                 475                 480

Ser Ile Ser Lys Glu Lys Trp Asn Met Glu Glu Val Val Leu Glu Glu
                485                 490                 495

Leu Gln Val Phe Lys His Pro Thr Ala Ile Leu Asn Met Glu Leu Ser
            500                 505                 510

Leu Lys Gln Gln Gln Leu Tyr Val Gly Ser Trp Asp Gly Leu Val Gln
        515                 520                 525

Leu Ser Leu His Arg Cys Asp Thr Tyr Gly Lys Ala Cys Ala Asp Cys
    530                 535                 540

Cys Leu Ala Arg Asp Pro Tyr Cys Ala Trp Asp Gly Asn Ala Cys Ser
545                 550                 555                 560

Arg Tyr Ala Pro Thr Ser Lys Arg Arg Ala Arg Arg Gln Asp Val Lys
                565                 570                 575
```

```
Tyr Gly Asp Pro Ile Thr Gln Cys Trp Asp Ile Glu Asp Ser Ile Ser
            580                 585                 590

His Glu Thr Ala Asp Glu Lys Val Ile Phe Gly Ile Glu Phe Asn Ser
        595                 600                 605

Thr Phe Leu Glu Cys Ile Pro Lys Ser Gln Gln Ala Ser Val Glu Trp
    610                 615                 620

Tyr Ile Gln Arg Ser Gly Asp Glu His Arg Glu Glu Leu Lys Pro Asp
625                 630                 635                 640

Glu Arg Ile Ile Lys Thr Asp Tyr Gly Leu Leu Ile Arg Ser Leu Gln
                645                 650                 655

Lys Lys Asp Ser Gly Met Tyr Tyr Cys Lys Ala Gln Glu His Thr Phe
            660                 665                 670

Ile His Thr Ile Val Lys Leu Thr Leu Asn Val Ile Glu Asn Glu Gln
        675                 680                 685

Met Glu Asn Thr Gln Arg Ala Glu Tyr Gln Glu Gly Gln Val Lys Asp
    690                 695                 700

Leu Leu Ala Glu Ser Arg Leu Arg Tyr Lys Asp Tyr Ile Gln Ile Leu
705                 710                 715                 720

Ser Ser Pro Asn Phe Ser Leu Asp Gln Tyr Cys Glu Gln Met Trp Tyr
                725                 730                 735

Lys Glu Lys Arg Arg Gln Arg Asn Lys Gly Ser Pro Lys Trp Lys His
            740                 745                 750

Met Gln Glu Met Lys Lys Lys Arg Asn Arg Arg His His Arg Asp Leu
        755                 760                 765

Asp Glu Leu Gln Arg Ser Val Ala Thr
    770                 775


<210> SEQ ID NO 73
<211> LENGTH: 7
<212> TYPE: PRT
<213> ORGANISM: Artificial Sequence
<220> FEATURE:
<223> OTHER INFORMATION: Amino acid comprised in mutated Semaphorin 3 or
      functional fragment thereof
<220> FEATURE:
<221> NAME/KEY: misc_feature
<222> LOCATION: 2
<223> OTHER INFORMATION: X is K or N
<220> FEATURE:
<221> NAME/KEY: misc_feature
<222> LOCATION: 3
<223> OTHER INFORMATION: X is W, M or L
<220> FEATURE:
<221> NAME/KEY: misc_feature
<222> LOCATION: 4
<223> OTHER INFORMATION: wherein alanine is mutated to a hydrophilic
      amino acid

<400> SEQUENCE: 73

Cys Xaa Xaa Xaa Gly Lys Asp
1               5


<210> SEQ ID NO 74
<211> LENGTH: 774
<212> TYPE: PRT
<213> ORGANISM: Homo sapiens
<220> FEATURE:
<223> OTHER INFORMATION: SEMA3B deltaIg-b-Fc

<400> SEQUENCE: 74

Met Gly Arg Ala Gly Ala Ala Ala Val Ile Pro Gly Leu Ala Leu Leu
1               5                   10                  15
```

-continued

```
Trp Ala Val Gly Leu Gly Ser Ala Ala Pro Ser Pro Pro Arg Leu Arg
            20                  25                  30

Leu Ser Phe Gln Glu Leu Gln Ala Trp His Gly Leu Gln Thr Phe Ser
        35                  40                  45

Leu Glu Arg Thr Cys Cys Tyr Gln Ala Leu Leu Val Asp Glu Glu Arg
    50                  55                  60

Gly Arg Leu Phe Val Gly Ala Glu Asn His Val Ala Ser Leu Asn Leu
65                  70                  75                  80

Asp Asn Ile Ser Lys Arg Ala Lys Lys Leu Ala Trp Pro Ala Pro Val
                85                  90                  95

Glu Trp Arg Glu Glu Cys Asn Trp Ala Gly Lys Asp Ile Gly Thr Glu
            100                 105                 110

Cys Met Asn Phe Val Lys Leu Leu His Ala Tyr Asn Arg Thr His Leu
        115                 120                 125

Leu Ala Cys Gly Thr Gly Ala Phe His Pro Thr Cys Ala Phe Val Glu
    130                 135                 140

Val Gly His Arg Ala Glu Glu Pro Val Leu Arg Leu Asp Pro Gly Arg
145                 150                 155                 160

Ile Glu Asp Gly Lys Gly Lys Ser Pro Tyr Asp Pro Arg His Arg Ala
                165                 170                 175

Ala Ser Val Leu Val Gly Glu Glu Leu Tyr Ser Gly Val Ala Ala Asp
            180                 185                 190

Leu Met Gly Arg Asp Phe Thr Ile Phe Arg Ser Leu Gly Gln Arg Pro
        195                 200                 205

Ser Leu Arg Thr Glu Pro His Asp Ser Arg Trp Leu Asn Glu Pro Lys
    210                 215                 220

Phe Val Lys Val Phe Trp Ile Pro Glu Ser Glu Asn Pro Asp Asp Asp
225                 230                 235                 240

Lys Ile Tyr Phe Phe Phe Arg Glu Thr Ala Val Glu Ala Ala Pro Ala
                245                 250                 255

Leu Gly Arg Leu Ser Val Ser Arg Val Gly Gln Ile Cys Arg Asn Asp
            260                 265                 270

Val Gly Gly Gln Arg Ser Leu Val Asn Lys Trp Thr Thr Phe Leu Lys
        275                 280                 285

Ala Arg Leu Val Cys Ser Val Pro Gly Val Glu Gly Asp Thr His Phe
    290                 295                 300

Asp Gln Leu Gln Asp Val Phe Leu Leu Ser Ser Arg Asp His Arg Thr
305                 310                 315                 320

Pro Leu Leu Tyr Ala Val Phe Ser Thr Ser Ser Ser Ile Phe Gln Gly
                325                 330                 335

Ser Ala Val Cys Val Tyr Ser Met Asn Asp Val Arg Arg Ala Phe Leu
            340                 345                 350

Gly Pro Phe Ala His Lys Glu Gly Pro Met His Gln Trp Val Ser Tyr
        355                 360                 365

Gln Gly Arg Val Pro Tyr Pro Arg Pro Gly Met Cys Pro Ser Lys Thr
    370                 375                 380

Phe Gly Thr Phe Ser Ser Thr Lys Asp Phe Pro Asp Asp Val Ile Gln
385                 390                 395                 400

Phe Ala Arg Asn His Pro Leu Met Tyr Asn Ser Val Leu Pro Thr Gly
                405                 410                 415

Gly Arg Pro Leu Phe Leu Gln Val Gly Ala Asn Tyr Thr Phe Thr Gln
            420                 425                 430
```

```
Ile Ala Ala Asp Arg Val Ala Ala Ala Asp Gly His Tyr Asp Val Leu
        435                 440                 445

Phe Ile Gly Thr Asp Val Gly Thr Val Leu Lys Val Ile Ser Val Pro
    450                 455                 460

Lys Gly Ser Arg Pro Ser Ala Glu Gly Leu Leu Leu Glu Glu Leu His
465                 470                 475                 480

Val Phe Glu Asp Ser Ala Ala Val Thr Ser Met Gln Ile Ser Ser Lys
                485                 490                 495

Arg His Gln Leu Tyr Val Ala Ser Arg Ser Ala Val Ala Gln Ile Ala
            500                 505                 510

Leu His Arg Cys Ala Ala His Gly Arg Val Cys Thr Glu Cys Cys Leu
        515                 520                 525

Ala Arg Asp Pro Tyr Cys Ala Trp Asp Gly Val Ala Cys Thr Arg Phe
    530                 535                 540

Gln Pro Ser Asp Lys Thr His Thr Cys Pro Pro Cys Pro Ala Pro Glu
545                 550                 555                 560

Leu Leu Gly Gly Pro Ser Val Phe Leu Phe Pro Pro Lys Pro Lys Asp
                565                 570                 575

Thr Leu Met Ile Ser Arg Thr Pro Glu Val Thr Cys Val Val Val Asp
            580                 585                 590

Val Ser His Glu Asp Pro Glu Val Lys Phe Asn Trp Tyr Val Asp Gly
        595                 600                 605

Val Glu Val His Asn Ala Lys Thr Lys Pro Arg Glu Glu Gln Tyr Asn
    610                 615                 620

Ser Thr Tyr Arg Val Val Ser Val Leu Thr Val Leu His Gln Asp Trp
625                 630                 635                 640

Leu Asn Gly Lys Glu Tyr Lys Cys Lys Val Ser Asn Lys Ala Leu Pro
                645                 650                 655

Ala Pro Ile Glu Lys Thr Ile Ser Lys Ala Lys Gly Gln Pro Arg Glu
            660                 665                 670

Pro Gln Val Tyr Thr Leu Pro Pro Ser Arg Asp Glu Leu Thr Lys Asn
        675                 680                 685

Gln Val Ser Leu Thr Cys Leu Val Lys Gly Phe Tyr Pro Ser Asp Ile
    690                 695                 700

Ala Val Glu Trp Glu Ser Asn Gly Gln Pro Glu Asn Asn Tyr Lys Thr
705                 710                 715                 720

Thr Pro Pro Val Leu Asp Ser Asp Gly Ser Phe Phe Leu Tyr Ser Lys
                725                 730                 735

Leu Thr Val Asp Lys Ser Arg Trp Gln Gln Gly Asn Val Phe Ser Cys
            740                 745                 750

Ser Val Met His Glu Ala Leu His Asn His Tyr Thr Gln Lys Ser Leu
        755                 760                 765

Ser Leu Ser Pro Gly Lys
    770
```

<210> SEQ ID NO 75
<211> LENGTH: 2325
<212> TYPE: DNA
<213> ORGANISM: Homo sapiens
<220> FEATURE:
<223> OTHER INFORMATION: SEMA3B deltaIg-b-Fc

<400> SEQUENCE: 75

```
atgggcagag ctggcgctgc tgctgtgatt cctggactgg ctctgctgtg ggccgtgggc      60

ctgggatctg ctgctccatc tcccccaaga ctgcggctga gcttccagga actgcaggcc     120
```

```
tggcacggac tgcagacctt cagcctggaa cggacatgct gttatcaggc cctgctggtg    180
gacgaggaac ggggcagact gtttgtgggc gccgagaatc atgtggccag cctgaacctg    240
gacaacatca gcaagcgggc caagaagctg gcctggcctg ctcctgtgga atggcgggaa    300
gagtgcaact gggccggcaa ggatatcggc accgagtgca tgaacttcgt gaagctgctg    360
cacgcctaca accggaccca tctgctggcc tgtggaaccg gcgccttcca ccctacctgc    420
gcctttgtgg aagtgggcca cagagccgag gaacccgtgc tgagactgga ccccggcaga    480
atcgaggacg gcaagggcaa gagcccctac gaccctagac atagagccgc cagcgtgctc    540
gtgggagagg aactgtattc tggcgtggcc gccgacctga tgggccggga cttcaccatc    600
ttcagaagcc tgggccagag gcccagcctg agaaccgagc ctcacgactc cagatggctg    660
aacgagccca agttcgtgaa ggtgttctgg attcccgaga gcgagaaccc cgacgacgac    720
aaaatctact tcttcttccg ggaaaccgcc gtggaagccg cccctgctct gggaaggctg    780
tccgtgtcta gagtgggcca gatttgccgg aacgacgtgg gcggacagcg gagcctcgtg    840
aacaagtgga ccaccttcct gaaggccaga ctcgtgtgta gcgtgcccgg cgtggaaggg    900
gacacccact ttgaccagct gcaggacgtg ttcctgctga gcagccggga ccacagaacc    960
cctctgctgt acgccgtgtt cagcaccagc tccagcatct tccagggcag cgccgtgtgc   1020
gtgtacagca tgaacgatgt gcggagagcc ttcctgggcc cctttgccca caaagagggc   1080
cccatgcatc agtgggtgtc ataccagggc agagtgccct accccagacc cggcatgtgt   1140
cccagcaaga ccttcggcac cttcagcagc accaaggact tccccgacga tgtgatccag   1200
ttcgcccgga accacccct gatgtacaac agcgtgctgc ccactggcgg cagaccactg   1260
tttctgcaag tgggcgccaa ctacaccttt acccagatcg ccgccgacag agtggccgct   1320
gccgatggcc attacgacgt gctgttcatc ggcacagacg tgggcaccgt gctgaaagtg   1380
atcagcgtgc ccaagggcag cagacctagc gccgaaggac tgctgctgga agaactgcac   1440
gtgttcgagg actctgccgc cgtgacctcc atgcagatca gcagcaagag acaccagctg   1500
tacgtggcct ccagatccgc cgtggcccag attgccctgc atagatgtgc cgcccacggc   1560
agagtgtgta ccgagtgttg cctggcccgg gacccttact gtgcttggga tggggtggcc   1620
tgcaccagat tccagcccag cgacaagacc cacacctgtc cccttgtcc tgcccctgaa   1680
ctgctgggcg gaccctccgt gtttctgttc cccccaaagc ccaaggacac cctgatgatc   1740
agccggaccc ccgaagtgac ctgcgtggtg gtggatgtgt ctcacgagga ccctgaagtg   1800
aagttcaatt ggtacgtgga cggggtggaa gtgcacaacg ccaagaccaa gcccagagag   1860
gaacagtaca actccaccta ccgggtggtg tccgtgctga ccgtgctgca ccaggactgg   1920
ctgaatggca aagagtacaa gtgcaaggtg tccaacaagg ccctgcctgc ccccatcgag   1980
aaaaccatct ccaaggccaa gggccagccc cgcgaacccc aggtgtacac actgcccccct   2040
agcagggacg agctgaccaa gaaccaggtg tccctgacct gtctcgtgaa gggcttctac   2100
cctccgaca ttgccgtgga atgggagagc aatggccagc ccgagaacaa ctacaagacc   2160
accccccctg tgctggacag cgacggctca ttcttcctgt acagcaagct gacagtggac   2220
aagagccggt ggcagcaggg caacgtgttc tcctgcagcg tgatgcacga ggccctgcac   2280
aaccactaca cccagaagtc cctgagcctg agccccggca aatga                   2325
```

<210> SEQ ID NO 76
<211> LENGTH: 774
<212> TYPE: PRT

<213> ORGANISM: Homo sapiens
<220> FEATURE:
<223> OTHER INFORMATION: SEMA3B (A105K) deltaIg-b-Fc

<400> SEQUENCE: 76

Met Gly Arg Ala Gly Ala Ala Ala Val Ile Pro Gly Leu Ala Leu Leu
1 5 10 15

Trp Ala Val Gly Leu Gly Ser Ala Ala Pro Ser Pro Pro Arg Leu Arg
20 25 30

Leu Ser Phe Gln Glu Leu Gln Ala Trp His Gly Leu Gln Thr Phe Ser
35 40 45

Leu Glu Arg Thr Cys Cys Tyr Gln Ala Leu Leu Val Asp Glu Glu Arg
50 55 60

Gly Arg Leu Phe Val Gly Ala Glu Asn His Val Ala Ser Leu Asn Leu
65 70 75 80

Asp Asn Ile Ser Lys Arg Ala Lys Lys Leu Ala Trp Pro Ala Pro Val
85 90 95

Glu Trp Arg Glu Glu Cys Asn Trp Lys Gly Lys Asp Ile Gly Thr Glu
100 105 110

Cys Met Asn Phe Val Lys Leu Leu His Ala Tyr Asn Arg Thr His Leu
115 120 125

Leu Ala Cys Gly Thr Gly Ala Phe His Pro Thr Cys Ala Phe Val Glu
130 135 140

Val Gly His Arg Ala Glu Glu Pro Val Leu Arg Leu Asp Pro Gly Arg
145 150 155 160

Ile Glu Asp Gly Lys Gly Lys Ser Pro Tyr Asp Pro Arg His Arg Ala
165 170 175

Ala Ser Val Leu Val Gly Glu Glu Leu Tyr Ser Gly Val Ala Ala Asp
180 185 190

Leu Met Gly Arg Asp Phe Thr Ile Phe Arg Ser Leu Gly Gln Arg Pro
195 200 205

Ser Leu Arg Thr Glu Pro His Asp Ser Arg Trp Leu Asn Glu Pro Lys
210 215 220

Phe Val Lys Val Phe Trp Ile Pro Glu Ser Glu Asn Pro Asp Asp Asp
225 230 235 240

Lys Ile Tyr Phe Phe Phe Arg Glu Thr Ala Val Glu Ala Ala Pro Ala
245 250 255

Leu Gly Arg Leu Ser Val Ser Arg Val Gly Gln Ile Cys Arg Asn Asp
260 265 270

Val Gly Gly Gln Arg Ser Leu Val Asn Lys Trp Thr Thr Phe Leu Lys
275 280 285

Ala Arg Leu Val Cys Ser Val Pro Gly Val Glu Gly Asp Thr His Phe
290 295 300

Asp Gln Leu Gln Asp Val Phe Leu Leu Ser Ser Arg Asp His Arg Thr
305 310 315 320

Pro Leu Leu Tyr Ala Val Phe Ser Thr Ser Ser Ser Ile Phe Gln Gly
325 330 335

Ser Ala Val Cys Val Tyr Ser Met Asn Asp Val Arg Arg Ala Phe Leu
340 345 350

Gly Pro Phe Ala His Lys Glu Gly Pro Met His Gln Trp Val Ser Tyr
355 360 365

Gln Gly Arg Val Pro Tyr Pro Arg Pro Gly Met Cys Pro Ser Lys Thr
370 375 380

Phe Gly Thr Phe Ser Ser Thr Lys Asp Phe Pro Asp Asp Val Ile Gln 385 390 395 400

Phe Ala Arg Asn His Pro Leu Met Tyr Asn Ser Val Leu Pro Thr Gly
405 410 415

Gly Arg Pro Leu Phe Leu Gln Val Gly Ala Asn Tyr Thr Phe Thr Gln
420 425 430

Ile Ala Ala Asp Arg Val Ala Ala Ala Asp Gly His Tyr Asp Val Leu
435 440 445

Phe Ile Gly Thr Asp Val Gly Thr Val Leu Lys Val Ile Ser Val Pro
450 455 460

Lys Gly Ser Arg Pro Ser Ala Glu Gly Leu Leu Leu Glu Glu Leu His
465 470 475 480

Val Phe Glu Asp Ser Ala Ala Val Thr Ser Met Gln Ile Ser Ser Lys
485 490 495

Arg His Gln Leu Tyr Val Ala Ser Arg Ser Ala Val Ala Gln Ile Ala
500 505 510

Leu His Arg Cys Ala Ala His Gly Arg Val Cys Thr Glu Cys Cys Leu
515 520 525

Ala Arg Asp Pro Tyr Cys Ala Trp Asp Gly Val Ala Cys Thr Arg Phe
530 535 540

Gln Pro Ser Asp Lys Thr His Thr Cys Pro Pro Cys Pro Ala Pro Glu
545 550 555 560

Leu Leu Gly Gly Pro Ser Val Phe Leu Phe Pro Pro Lys Pro Lys Asp
565 570 575

Thr Leu Met Ile Ser Arg Thr Pro Glu Val Thr Cys Val Val Val Asp
580 585 590

Val Ser His Glu Asp Pro Glu Val Lys Phe Asn Trp Tyr Val Asp Gly
595 600 605

Val Glu Val His Asn Ala Lys Thr Lys Pro Arg Glu Glu Gln Tyr Asn
610 615 620

Ser Thr Tyr Arg Val Val Ser Val Leu Thr Val Leu His Gln Asp Trp
625 630 635 640

Leu Asn Gly Lys Glu Tyr Lys Cys Lys Val Ser Asn Lys Ala Leu Pro
645 650 655

Ala Pro Ile Glu Lys Thr Ile Ser Lys Ala Lys Gly Gln Pro Arg Glu
660 665 670

Pro Gln Val Tyr Thr Leu Pro Pro Ser Arg Asp Glu Leu Thr Lys Asn
675 680 685

Gln Val Ser Leu Thr Cys Leu Val Lys Gly Phe Tyr Pro Ser Asp Ile
690 695 700

Ala Val Glu Trp Glu Ser Asn Gly Gln Pro Glu Asn Asn Tyr Lys Thr
705 710 715 720

Thr Pro Pro Val Leu Asp Ser Asp Gly Ser Phe Phe Leu Tyr Ser Lys
725 730 735

Leu Thr Val Asp Lys Ser Arg Trp Gln Gln Gly Asn Val Phe Ser Cys
740 745 750

Ser Val Met His Glu Ala Leu His Asn His Tyr Thr Gln Lys Ser Leu
755 760 765

Ser Leu Ser Pro Gly Lys
770

<210> SEQ ID NO 77
<211> LENGTH: 2325
<212> TYPE: DNA
<213> ORGANISM: Homo sapiens
<220> FEATURE:
<223> OTHER INFORMATION: SEMA3B (A105K) deltaIg-b-Fc

<400> SEQUENCE: 77

```
atgggcagag ctggcgctgc tgctgtgatt cctggactgg ctctgctgtg ggccgtgggc     60
ctgggatctg ctgctccatc tcccccaaga ctgcggctga gcttccagga actgcaggcc    120
tggcacggac tgcagacctt cagcctggaa cggacatgct gttatcaggc cctgctggtg    180
gacgaggaac ggggcagact gtttgtgggc gccgagaatc atgtggccag cctgaacctg    240
gacaacatca gcaagcgggc caagaagctg gcctggcctg ctcctgtgga atggcgggaa    300
gagtgcaact ggaagggcaa ggacatcggc accgagtgca tgaacttcgt gaagctgctg    360
cacgcctaca accggaccca tctgctggcc tgtggaaccg gcgccttcca ccctacctgc    420
gcctttgtgg aagtgggcca cagagccgag gaacccgtgc tgagactgga ccccggcaga    480
atcgaggacg gcaagggcaa gagcccctac gaccctagac atagagccgc cagcgtgctc    540
gtgggagagg aactgtattc tggcgtggcc gccgacctga tgggccggga cttcaccatc    600
ttcagaagcc tgggccagag gcccagcctg agaaccgagc ctcacgactc cagatggctg    660
aacgagccca agttcgtgaa ggtgttctgg attcccgaga gcgagaaccc cgacgacgac    720
aaaatctact tcttcttccg ggaaaccgcc gtggaagccg cccctgctct gggaaggctg    780
tccgtgtcta gagtgggcca gatttgccgg aacgacgtgg gcggacagcg gagcctcgtg    840
aacaagtgga ccaccttcct gaaggccaga ctcgtgtgta gcgtgcccgg cgtggaaggg    900
gacacccact ttgaccagct gcaggacgtg ttcctgctga gcagccggga ccacagaacc    960
cctctgctgt acgccgtgtt cagcaccagc tccagcatct tccagggcag cgccgtgtgc   1020
gtgtacagca tgaacgatgt gcggagagcc ttcctgggcc cctttgccca caaagagggc   1080
cccatgcatc agtgggtgtc ataccagggc agagtgccct accccagacc cggcatgtgt   1140
cccagcaaga ccttcggcac cttcagcagc accaaggact tccccgacga tgtgatccag   1200
ttcgcccgga accacccccct gatgtacaac agcgtgctgc ccactggcgg cagaccactg   1260
tttctgcaag tgggcgccaa ctacaccttt acccagatcg ccgccgacag agtggccgct   1320
gccgatggcc attacgacgt gctgttcatc ggcacagacg tgggcaccgt gctgaaagtg   1380
atcagcgtgc ccaagggcag cagacctagc gccgaaggac tgctgctgga agaactgcac   1440
gtgttcgagg actctgccgc cgtgacctcc atgcagatca gcagcaagag acaccagctg   1500
tacgtggcct ccagatccgc cgtggcccag attgccctgc atagatgtgc cgcccacggc   1560
agagtgtgta ccgagtgttg cctggcccgg gacccttact gtgcttggga tggggtggcc   1620
tgcaccagat tccagcccag cgacaagacc cacacctgtc cccttgtcc tgcccctgaa   1680
ctgctgggcg gaccctccgt gtttctgttc cccccaaagc ccaaggacac cctgatgatc   1740
agccggaccc ccgaagtgac ctgcgtggtg gtggatgtgt ctcacgagga ccctgaagtg   1800
aagttcaatt ggtacgtgga cggggtggaa gtgcacaacg ccaagaccaa gcccagagag   1860
gaacagtaca actccaccta ccgggtggtg tccgtgctga ccgtgctgca ccaggactgg   1920
ctgaatggca aagagtacaa gtgcaaggtg tccaacaagg ccctgcctgc ccccatcgag   1980
aaaaccatct ccaaggccaa gggccagccc cgcgaacccc aggtgtacac actgcccccct   2040
agcagggacg agctgaccaa gaaccaggtg tccctgacct gtctcgtgaa gggcttctac   2100
cctccgaca ttgccgtgga atgggagagc aatggccagc ccgagaacaa ctacaagacc   2160
acccccccctg tgctggacag cgacggctca ttcttcctgt acagcaagct gacagtggac   2220
```

aagagccggt ggcagcaggg caacgtgttc tcctgcagcg tgatgcacga ggccctgcac 2280
aaccactaca cccagaagtc cctgagcctg agccccggca aatga 2325

<210> SEQ ID NO 78
<211> LENGTH: 772
<212> TYPE: PRT
<213> ORGANISM: Homo sapiens
<220> FEATURE:
<223> OTHER INFORMATION: SEMA3C A104K deltaIg-b-Fc

<400> SEQUENCE: 78

Met Ala Phe Arg Thr Ile Cys Val Leu Val Gly Val Phe Ile Cys Ser
1 5 10 15

Ile Cys Val Lys Gly Ser Ser Gln Pro Gln Ala Arg Val Tyr Leu Thr
20 25 30

Phe Asp Glu Leu Arg Glu Thr Lys Thr Ser Glu Tyr Phe Ser Leu Ser
35 40 45

His His Pro Leu Asp Tyr Arg Ile Leu Leu Met Asp Glu Asp Gln Asp
50 55 60

Arg Ile Tyr Val Gly Ser Lys Asp His Ile Leu Ser Leu Asn Ile Asn
65 70 75 80

Asn Ile Ser Gln Glu Ala Leu Ser Val Phe Trp Pro Ala Ser Thr Ile
85 90 95

Lys Val Glu Glu Cys Lys Met Lys Gly Lys Asp Pro Thr His Gly Cys
100 105 110

Gly Asn Phe Val Arg Val Ile Gln Thr Phe Asn Arg Thr His Leu Tyr
115 120 125

Val Cys Gly Ser Gly Ala Phe Ser Pro Val Cys Thr Tyr Leu Asn Arg
130 135 140

Gly Arg Arg Ser Glu Asp Gln Val Phe Met Ile Asp Ser Lys Cys Glu
145 150 155 160

Ser Gly Lys Gly Arg Cys Ser Phe Asn Pro Asn Val Asn Thr Val Ser
165 170 175

Val Met Ile Asn Glu Glu Leu Phe Ser Gly Met Tyr Ile Asp Phe Met
180 185 190

Gly Thr Asp Ala Ala Ile Phe Arg Ser Leu Thr Lys Arg Asn Ala Val
195 200 205

Arg Thr Asp Gln His Asn Ser Lys Trp Leu Ser Glu Pro Met Phe Val
210 215 220

Asp Ala His Val Ile Pro Asp Gly Thr Asp Pro Asn Asp Ala Lys Val
225 230 235 240

Tyr Phe Phe Phe Lys Glu Lys Leu Thr Asp Asn Asn Arg Ser Thr Lys
245 250 255

Gln Ile His Ser Met Ile Ala Arg Ile Cys Pro Asn Asp Thr Gly Gly
260 265 270

Leu Arg Ser Leu Val Asn Lys Trp Thr Thr Phe Leu Lys Ala Arg Leu
275 280 285

Val Cys Ser Val Thr Asp Glu Asp Gly Pro Glu Thr His Phe Asp Glu
290 295 300

Leu Glu Asp Val Phe Leu Leu Glu Thr Asp Asn Pro Arg Thr Thr Leu
305 310 315 320

Val Tyr Gly Ile Phe Thr Thr Ser Ser Ser Val Phe Lys Gly Ser Ala
325 330 335

Val Cys Val Tyr His Leu Ser Asp Ile Gln Thr Val Phe Asn Gly Pro
340 345 350

```
Phe Ala His Lys Glu Gly Pro Asn His Gln Leu Ile Ser Tyr Gln Gly
        355                 360                 365

Arg Ile Pro Tyr Pro Arg Pro Gly Thr Cys Pro Gly Gly Ala Phe Thr
    370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445

Leu Gly Thr Asp Arg Gly Thr Val Gln Lys Val Val Val Leu Pro Thr
    450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
    530                 535                 540

Thr Asp Lys Thr His Thr Cys Pro Pro Cys Pro Ala Pro Glu Leu Leu
545                 550                 555                 560

Gly Gly Pro Ser Val Phe Leu Phe Pro Pro Lys Pro Lys Asp Thr Leu
                565                 570                 575

Met Ile Ser Arg Thr Pro Glu Val Thr Cys Val Val Val Asp Val Ser
            580                 585                 590

His Glu Asp Pro Glu Val Lys Phe Asn Trp Tyr Val Asp Gly Val Glu
        595                 600                 605

Val His Asn Ala Lys Thr Lys Pro Arg Glu Glu Gln Tyr Asn Ser Thr
    610                 615                 620

Tyr Arg Val Val Ser Val Leu Thr Val Leu His Gln Asp Trp Leu Asn
625                 630                 635                 640

Gly Lys Glu Tyr Lys Cys Lys Val Ser Asn Lys Ala Leu Pro Ala Pro
                645                 650                 655

Ile Glu Lys Thr Ile Ser Lys Ala Lys Gly Gln Pro Arg Glu Pro Gln
            660                 665                 670

Val Tyr Thr Leu Pro Pro Ser Arg Asp Glu Leu Thr Lys Asn Gln Val
        675                 680                 685

Ser Leu Thr Cys Leu Val Lys Gly Phe Tyr Pro Ser Asp Ile Ala Val
    690                 695                 700

Glu Trp Glu Ser Asn Gly Gln Pro Glu Asn Asn Tyr Lys Thr Thr Pro
705                 710                 715                 720

Pro Val Leu Asp Ser Asp Gly Ser Phe Phe Leu Tyr Ser Lys Leu Thr
                725                 730                 735

Val Asp Lys Ser Arg Trp Gln Gln Gly Asn Val Phe Ser Cys Ser Val
            740                 745                 750

Met His Glu Ala Leu His Asn His Tyr Thr Gln Lys Ser Leu Ser Leu
        755                 760                 765
```

Ser Pro Gly Lys
770

<210> SEQ ID NO 79
<211> LENGTH: 792
<212> TYPE: PRT
<213> ORGANISM: Homo sapiens
<220> FEATURE:
<223> OTHER INFORMATION: SEMA3D A120K deltaIg-b-Fc

<400> SEQUENCE: 79

Met Asn Ala Asn Lys Asp Glu Arg Leu Lys Ala Arg Ser Gln Asp Phe
1 5 10 15

His Leu Phe Pro Ala Leu Met Met Leu Ser Met Thr Met Leu Phe Leu
20 25 30

Pro Val Thr Gly Thr Leu Lys Gln Asn Ile Pro Arg Leu Lys Leu Thr
35 40 45

Tyr Lys Asp Leu Leu Leu Ser Asn Ser Cys Ile Pro Phe Leu Gly Ser
50 55 60

Ser Glu Gly Leu Asp Phe Gln Thr Leu Leu Leu Asp Glu Glu Arg Gly
65 70 75 80

Arg Leu Leu Leu Gly Ala Lys Asp His Ile Phe Leu Leu Ser Leu Val
85 90 95

Asp Leu Asn Lys Asn Phe Lys Lys Ile Tyr Trp Pro Ala Ala Lys Glu
100 105 110

Arg Val Glu Leu Cys Lys Leu Lys Gly Lys Asp Ala Asn Thr Glu Cys
115 120 125

Ala Asn Phe Ile Arg Val Leu Gln Pro Tyr Asn Lys Thr His Ile Tyr
130 135 140

Val Cys Gly Thr Gly Ala Phe His Pro Ile Cys Gly Tyr Ile Asp Leu
145 150 155 160

Gly Val Tyr Lys Glu Asp Ile Ile Phe Lys Leu Asp Thr His Asn Leu
165 170 175

Glu Ser Gly Arg Leu Lys Cys Pro Phe Asp Pro Gln Gln Pro Phe Ala
180 185 190

Ser Val Met Thr Asp Glu Tyr Leu Tyr Ser Gly Thr Ala Ser Asp Phe
195 200 205

Leu Gly Lys Asp Thr Ala Phe Thr Arg Ser Leu Gly Pro Thr His Asp
210 215 220

His His Tyr Ile Arg Thr Asp Ile Ser Glu His Tyr Trp Leu Asn Gly
225 230 235 240

Ala Lys Phe Ile Gly Thr Phe Phe Ile Pro Asp Thr Tyr Asn Pro Asp
245 250 255

Asp Asp Lys Ile Tyr Phe Phe Phe Arg Glu Ser Ser Gln Glu Gly Ser
260 265 270

Thr Ser Asp Lys Thr Ile Leu Ser Arg Val Gly Arg Val Cys Lys Asn
275 280 285

Asp Val Gly Gly Gln Arg Ser Leu Ile Asn Lys Trp Thr Thr Phe Leu
290 295 300

Lys Ala Arg Leu Ile Cys Ser Ile Pro Gly Ser Asp Gly Ala Asp Thr
305 310 315 320

Tyr Phe Asp Glu Leu Gln Asp Ile Tyr Leu Leu Pro Thr Arg Asp Glu
325 330 335

Arg Asn Pro Val Val Tyr Gly Val Phe Thr Thr Thr Ser Ser Ile Phe
340 345 350

-continued

```
Lys Gly Ser Ala Val Cys Val Tyr Ser Met Ala Asp Ile Arg Ala Val
        355                 360                 365

Phe Asn Gly Pro Tyr Ala His Lys Glu Ser Ala Asp His Arg Trp Val
    370                 375                 380

Gln Tyr Asp Gly Arg Ile Pro Tyr Pro Arg Pro Gly Thr Cys Pro Ser
385                 390                 395                 400

Lys Thr Tyr Asp Pro Leu Ile Lys Ser Thr Arg Asp Phe Pro Asp Asp
                405                 410                 415

Val Ile Ser Phe Ile Lys Arg His Ser Val Met Tyr Lys Ser Val Tyr
            420                 425                 430

Pro Val Ala Gly Gly Pro Thr Phe Lys Arg Ile Asn Val Asp Tyr Arg
        435                 440                 445

Leu Thr Gln Ile Val Val Asp His Val Ile Ala Glu Asp Gly Gln Tyr
    450                 455                 460

Asp Val Met Phe Leu Gly Thr Asp Ile Gly Thr Val Leu Lys Val Val
465                 470                 475                 480

Ser Ile Ser Lys Glu Lys Trp Asn Met Glu Glu Val Val Leu Glu Glu
                485                 490                 495

Leu Gln Ile Phe Lys His Ser Ser Ile Ile Leu Asn Met Glu Leu Ser
            500                 505                 510

Leu Lys Gln Gln Gln Leu Tyr Ile Gly Ser Arg Asp Gly Leu Val Gln
        515                 520                 525

Leu Ser Leu His Arg Cys Asp Thr Tyr Gly Lys Ala Cys Ala Asp Cys
    530                 535                 540

Cys Leu Ala Arg Asp Pro Tyr Cys Ala Trp Asp Gly Asn Ala Cys Ser
545                 550                 555                 560

Arg Tyr Ala Pro Thr Asp Lys Thr His Thr Cys Pro Pro Cys Pro Ala
                565                 570                 575

Pro Glu Leu Leu Gly Gly Pro Ser Val Phe Leu Phe Pro Pro Lys Pro
            580                 585                 590

Lys Asp Thr Leu Met Ile Ser Arg Thr Pro Glu Val Thr Cys Val Val
        595                 600                 605

Val Asp Val Ser His Glu Asp Pro Glu Val Lys Phe Asn Trp Tyr Val
    610                 615                 620

Asp Gly Val Glu Val His Asn Ala Lys Thr Lys Pro Arg Glu Glu Gln
625                 630                 635                 640

Tyr Asn Ser Thr Tyr Arg Val Val Ser Val Leu Thr Val Leu His Gln
                645                 650                 655

Asp Trp Leu Asn Gly Lys Glu Tyr Lys Cys Lys Val Ser Asn Lys Ala
            660                 665                 670

Leu Pro Ala Pro Ile Glu Lys Thr Ile Ser Lys Ala Lys Gly Gln Pro
        675                 680                 685

Arg Glu Pro Gln Val Tyr Thr Leu Pro Pro Ser Arg Asp Glu Leu Thr
    690                 695                 700

Lys Asn Gln Val Ser Leu Thr Cys Leu Val Lys Gly Phe Tyr Pro Ser
705                 710                 715                 720

Asp Ile Ala Val Glu Trp Glu Ser Asn Gly Gln Pro Glu Asn Asn Tyr
                725                 730                 735

Lys Thr Thr Pro Pro Val Leu Asp Ser Asp Gly Ser Phe Phe Leu Tyr
            740                 745                 750

Ser Lys Leu Thr Val Asp Lys Ser Arg Trp Gln Gln Gly Asn Val Phe
        755                 760                 765

Ser Cys Ser Val Met His Glu Ala Leu His Asn His Tyr Thr Gln Lys
```

```
    770                 775                 780

Ser Leu Ser Leu Ser Pro Gly Lys
785                 790


<210> SEQ ID NO 80
<211> LENGTH: 775
<212> TYPE: PRT
<213> ORGANISM: Homo sapiens
<220> FEATURE:
<223> OTHER INFORMATION: SEMA3E

<400> SEQUENCE: 80

Met Ala Ser Ala Gly His Ile Ile Thr Leu Leu Leu Trp Gly Tyr Leu
1               5                   10                  15

Leu Glu Leu Trp Thr Gly Gly His Thr Ala Asp Thr Thr His Pro Arg
            20                  25                  30

Leu Arg Leu Ser His Lys Glu Leu Leu Asn Leu Asn Arg Thr Ser Ile
        35                  40                  45

Phe His Ser Pro Phe Gly Phe Leu Asp Leu His Thr Met Leu Leu Asp
    50                  55                  60

Glu Tyr Gln Glu Arg Leu Phe Val Gly Gly Arg Asp Leu Val Tyr Ser
65                  70                  75                  80

Leu Ser Leu Glu Arg Ile Ser Asp Gly Tyr Lys Glu Ile His Trp Pro
                85                  90                  95

Ser Thr Ala Leu Lys Met Glu Glu Cys Ile Met Lys Gly Lys Asp Ala
            100                 105                 110

Gly Glu Cys Ala Asn Tyr Val Arg Val Leu His His Tyr Asn Arg Thr
        115                 120                 125

His Leu Leu Thr Cys Gly Thr Gly Ala Phe Asp Pro Val Cys Ala Phe
    130                 135                 140

Ile Arg Val Gly Tyr His Leu Glu Asp Pro Leu Phe His Leu Glu Ser
145                 150                 155                 160

Pro Arg Ser Glu Arg Gly Arg Gly Arg Cys Pro Phe Asp Pro Ser Ser
                165                 170                 175

Ser Phe Ile Ser Thr Leu Ile Gly Ser Glu Leu Phe Ala Gly Leu Tyr
            180                 185                 190

Ser Asp Tyr Trp Ser Arg Asp Ala Ala Ile Phe Arg Ser Met Gly Arg
        195                 200                 205

Leu Ala His Ile Arg Thr Glu His Asp Asp Glu Arg Leu Leu Lys Glu
    210                 215                 220

Pro Lys Phe Val Gly Ser Tyr Met Ile Pro Asp Asn Glu Asp Arg Asp
225                 230                 235                 240

Asp Asn Lys Val Tyr Phe Phe Phe Thr Glu Lys Ala Leu Glu Ala Glu
                245                 250                 255

Asn Asn Ala His Ala Ile Tyr Thr Arg Val Gly Arg Leu Cys Val Asn
            260                 265                 270

Asp Val Gly Gly Gln Arg Ile Leu Val Asn Lys Trp Ser Thr Phe Leu
        275                 280                 285

Lys Ala Arg Leu Val Cys Ser Val Pro Gly Met Asn Gly Ile Asp Thr
    290                 295                 300

Tyr Phe Asp Glu Leu Glu Asp Val Phe Leu Leu Pro Thr Arg Asp His
305                 310                 315                 320

Lys Asn Pro Val Ile Phe Gly Leu Phe Asn Thr Thr Ser Asn Ile Phe
                325                 330                 335

Arg Gly His Ala Ile Cys Val Tyr His Met Ser Ser Ile Arg Ala Ala
```

```
            340                 345                 350

Phe Asn Gly Pro Tyr Ala His Lys Glu Gly Pro Glu Tyr His Trp Ser
        355                 360                 365

Val Tyr Glu Gly Lys Val Pro Tyr Pro Arg Pro Gly Ser Cys Ala Ser
    370                 375                 380

Lys Val Asn Gly Gly Arg Tyr Gly Thr Thr Lys Asp Tyr Pro Asp Asp
385                 390                 395                 400

Ala Ile Arg Phe Ala Arg Ser His Pro Leu Met Tyr Gln Ala Ile Lys
                405                 410                 415

Pro Ala His Lys Lys Pro Ile Leu Val Lys Thr Asp Gly Lys Tyr Asn
            420                 425                 430

Leu Lys Gln Ile Ala Val Asp Arg Val Glu Ala Glu Asp Gly Gln Tyr
        435                 440                 445

Asp Val Leu Phe Ile Gly Thr Asp Asn Gly Ile Val Leu Lys Val Ile
    450                 455                 460

Thr Ile Tyr Asn Gln Glu Met Glu Ser Met Glu Glu Val Ile Leu Glu
465                 470                 475                 480

Glu Leu Gln Ile Phe Lys Asp Pro Val Pro Ile Ile Ser Met Glu Ile
                485                 490                 495

Ser Ser Lys Arg Gln Gln Leu Tyr Ile Gly Ser Ala Ser Ala Val Ala
            500                 505                 510

Gln Val Arg Phe His His Cys Asp Met Tyr Gly Ser Ala Cys Ala Asp
        515                 520                 525

Cys Cys Leu Ala Arg Asp Pro Tyr Cys Ala Trp Asp Gly Ile Ser Cys
    530                 535                 540

Ser Arg Tyr Tyr Pro Thr Gly Thr His Ala Lys Arg Arg Phe Arg Arg
545                 550                 555                 560

Gln Asp Val Arg His Gly Asn Ala Ala Gln Gln Cys Phe Gly Gln Gln
                565                 570                 575

Phe Val Gly Asp Ala Leu Asp Lys Thr Glu Glu His Leu Ala Tyr Gly
            580                 585                 590

Ile Glu Asn Asn Ser Thr Leu Leu Glu Cys Thr Pro Arg Ser Leu Gln
        595                 600                 605

Ala Lys Val Ile Trp Phe Val Gln Lys Gly Arg Glu Thr Arg Lys Glu
    610                 615                 620

Glu Val Lys Thr Asp Asp Arg Val Val Lys Met Asp Leu Gly Leu Leu
625                 630                 635                 640

Phe Leu Arg Leu His Lys Ser Asp Ala Gly Thr Tyr Phe Cys Gln Thr
                645                 650                 655

Val Glu His Ser Phe Val His Thr Val Arg Lys Ile Thr Leu Glu Val
            660                 665                 670

Val Glu Glu Glu Lys Val Glu Asp Met Phe Asn Lys Asp Asp Glu Glu
        675                 680                 685

Asp Arg His His Arg Met Pro Cys Pro Ala Gln Ser Ser Ile Ser Gln
    690                 695                 700

Gly Ala Lys Pro Trp Tyr Lys Glu Phe Leu Gln Leu Ile Gly Tyr Ser
705                 710                 715                 720

Asn Phe Gln Arg Val Glu Glu Tyr Cys Glu Lys Val Trp Cys Thr Asp
                725                 730                 735

Arg Lys Arg Lys Lys Leu Lys Met Ser Pro Ser Lys Trp Lys Tyr Ala
            740                 745                 750

Asn Pro Gln Glu Lys Lys Leu Arg Ser Lys Pro Glu His Tyr Arg Leu
        755                 760                 765
```

```
Pro Arg His Thr Leu Asp Ser
    770                 775


<210> SEQ ID NO 81
<211> LENGTH: 775
<212> TYPE: PRT
<213> ORGANISM: Mus musculus
<220> FEATURE:
<223> OTHER INFORMATION: Sema3E

<400> SEQUENCE: 81

Met Ala Pro Ala Gly His Ile Leu Thr Leu Leu Leu Trp Gly His Leu
1               5                   10                  15

Leu Glu Leu Trp Thr Pro Gly His Ser Ala Asn Pro Ser Tyr Pro Arg
            20                  25                  30

Leu Arg Leu Ser His Lys Glu Leu Leu Glu Leu Asn Arg Thr Ser Ile
        35                  40                  45

Phe Gln Ser Pro Leu Gly Phe Leu Asp Leu His Thr Met Leu Leu Asp
    50                  55                  60

Glu Tyr Gln Glu Arg Leu Phe Val Gly Gly Arg Asp Leu Val Tyr Ser
65                  70                  75                  80

Leu Asn Leu Glu Arg Val Ser Asp Gly Tyr Arg Glu Ile Tyr Trp Pro
                85                  90                  95

Ser Thr Ala Val Lys Val Glu Glu Cys Ile Met Lys Gly Lys Asp Ala
            100                 105                 110

Asn Glu Cys Ala Asn Tyr Ile Arg Val Leu His His Tyr Asn Arg Thr
        115                 120                 125

His Leu Leu Thr Cys Ala Thr Gly Ala Phe Asp Pro His Cys Ala Phe
    130                 135                 140

Ile Arg Val Gly His His Ser Glu Glu Pro Leu Phe His Leu Glu Ser
145                 150                 155                 160

His Arg Ser Glu Arg Gly Arg Gly Arg Cys Pro Phe Asp Pro Asn Ser
                165                 170                 175

Ser Phe Val Ser Thr Leu Val Gly Asn Glu Leu Phe Ala Gly Leu Tyr
            180                 185                 190

Ser Asp Tyr Trp Gly Arg Asp Ser Ala Ile Phe Arg Ser Met Gly Lys
        195                 200                 205

Leu Gly His Ile Arg Thr Glu His Asp Asp Glu Arg Leu Leu Lys Glu
    210                 215                 220

Pro Lys Phe Val Gly Ser Tyr Met Ile Pro Asp Asn Glu Asp Arg Asp
225                 230                 235                 240

Asp Asn Lys Met Tyr Phe Phe Phe Thr Glu Lys Ala Leu Glu Ala Glu
                245                 250                 255

Asn Asn Ala His Thr Ile Tyr Thr Arg Val Gly Arg Leu Cys Val Asn
            260                 265                 270

Asp Met Gly Gly Gln Arg Ile Leu Val Asn Lys Trp Ser Thr Phe Leu
        275                 280                 285

Lys Ala Arg Leu Val Cys Ser Val Pro Gly Met Asn Gly Ile Asp Thr
    290                 295                 300

Tyr Phe Asp Glu Leu Glu Asp Val Phe Leu Leu Pro Thr Arg Asp Pro
305                 310                 315                 320

Lys Asn Pro Val Ile Phe Gly Leu Phe Asn Thr Thr Ser Asn Ile Phe
                325                 330                 335

Arg Gly His Ala Val Cys Val Tyr His Met Ser Ser Ile Arg Glu Ala
            340                 345                 350
```

```
Phe Asn Gly Pro Tyr Ala His Lys Glu Gly Pro Glu Tyr His Trp Ser
        355                 360                 365

Leu Tyr Glu Gly Lys Val Pro Tyr Pro Arg Pro Gly Ser Cys Ala Ser
    370                 375                 380

Lys Val Asn Gly Gly Lys Tyr Gly Thr Thr Lys Asp Tyr Pro Asp Asp
385                 390                 395                 400

Ala Ile Arg Phe Ala Arg Met His Pro Leu Met Tyr Gln Pro Ile Lys
                405                 410                 415

Pro Val His Lys Lys Pro Ile Leu Val Lys Thr Asp Gly Lys Tyr Asn
            420                 425                 430

Leu Arg Gln Leu Ala Val Asp Arg Val Glu Ala Glu Asp Gly Gln Tyr
        435                 440                 445

Asp Val Leu Phe Ile Gly Thr Asp Thr Gly Ile Val Leu Lys Val Ile
    450                 455                 460

Thr Ile Tyr Asn Gln Glu Thr Glu Trp Met Glu Glu Val Ile Leu Glu
465                 470                 475                 480

Glu Leu Gln Ile Phe Lys Asp Pro Ala Pro Ile Ile Ser Met Glu Ile
                485                 490                 495

Ser Ser Lys Arg Gln Gln Leu Tyr Ile Gly Ser Ala Ser Ala Val Ala
            500                 505                 510

Gln Val Arg Phe His His Cys Asp Met Tyr Gly Ser Ala Cys Ala Asp
        515                 520                 525

Cys Cys Leu Ala Arg Asp Pro Tyr Cys Ala Trp Asp Gly Ile Ser Cys
    530                 535                 540

Ser Arg Tyr Tyr Pro Thr Gly Ala His Ala Lys Arg Arg Phe Arg Arg
545                 550                 555                 560

Gln Asp Val Arg His Gly Asn Ala Ala Gln Gln Cys Phe Gly Gln Gln
                565                 570                 575

Phe Val Gly Asp Ala Leu Asp Arg Thr Glu Glu Arg Leu Ala Tyr Gly
            580                 585                 590

Ile Glu Ser Asn Ser Thr Leu Leu Glu Cys Thr Pro Arg Ser Leu Gln
        595                 600                 605

Ala Lys Val Ile Trp Phe Val Gln Lys Gly Arg Asp Val Arg Lys Glu
    610                 615                 620

Glu Val Lys Thr Asp Asp Arg Val Val Lys Met Asp Leu Gly Leu Leu
625                 630                 635                 640

Phe Leu Arg Val Arg Lys Ser Asp Ala Gly Thr Tyr Phe Cys Gln Thr
                645                 650                 655

Val Glu His Asn Phe Val His Thr Val Arg Lys Ile Thr Leu Glu Val
            660                 665                 670

Val Glu Glu His Lys Val Glu Gly Met Phe His Lys Asp His Glu Glu
        675                 680                 685

Glu Arg His His Lys Met Pro Cys Pro Pro Leu Ser Gly Met Ser Gln
    690                 695                 700

Gly Thr Lys Pro Trp Tyr Lys Glu Phe Leu Gln Leu Ile Gly Tyr Ser
705                 710                 715                 720

Asn Phe Gln Arg Val Glu Glu Tyr Cys Glu Lys Val Trp Cys Thr Asp
                725                 730                 735

Lys Lys Arg Lys Lys Leu Lys Met Ser Pro Ser Lys Trp Lys Tyr Ala
            740                 745                 750

Asn Pro Gln Glu Lys Arg Leu Arg Ser Lys Ala Glu His Phe Arg Leu
        755                 760                 765
```

```
Pro Arg His Thr Leu Leu Ser
    770                 775


<210> SEQ ID NO 82
<211> LENGTH: 785
<212> TYPE: PRT
<213> ORGANISM: Homo sapiens
<220> FEATURE:
<223> OTHER INFORMATION: SEMA3F

<400> SEQUENCE: 82

Met Leu Val Ala Gly Leu Leu Leu Trp Ala Ser Leu Leu Thr Gly Ala
1               5                   10                  15

Trp Pro Ser Phe Pro Thr Gln Asp His Leu Pro Ala Thr Pro Arg Val
            20                  25                  30

Arg Leu Ser Phe Lys Glu Leu Lys Ala Thr Gly Thr Ala His Phe Phe
        35                  40                  45

Asn Phe Leu Leu Asn Thr Thr Asp Tyr Arg Ile Leu Leu Lys Asp Glu
    50                  55                  60

Asp His Asp Arg Met Tyr Val Gly Ser Lys Asp Tyr Val Leu Ser Leu
65                  70                  75                  80

Asp Leu His Asp Ile Asn Arg Glu Pro Leu Ile Ile His Trp Ala Ala
                85                  90                  95

Ser Pro Gln Arg Ile Glu Glu Cys Val Leu Ser Gly Lys Asp Val Asn
            100                 105                 110

Gly Glu Cys Gly Asn Phe Val Arg Leu Ile Gln Pro Trp Asn Arg Thr
        115                 120                 125

His Leu Tyr Val Cys Gly Thr Gly Ala Tyr Asn Pro Met Cys Thr Tyr
    130                 135                 140

Val Asn Arg Gly Arg Arg Ala Gln Ala Thr Pro Trp Thr Gln Thr Gln
145                 150                 155                 160

Ala Val Arg Gly Arg Gly Ser Arg Ala Thr Asp Gly Ala Leu Arg Pro
                165                 170                 175

Met Pro Thr Ala Pro Arg Gln Asp Tyr Ile Phe Tyr Leu Glu Pro Glu
            180                 185                 190

Arg Leu Glu Ser Gly Lys Gly Lys Cys Pro Tyr Asp Pro Lys Leu Asp
        195                 200                 205

Thr Ala Ser Ala Leu Ile Asn Glu Glu Leu Tyr Ala Gly Val Tyr Ile
    210                 215                 220

Asp Phe Met Gly Thr Asp Ala Ala Ile Phe Arg Thr Leu Gly Lys Gln
225                 230                 235                 240

Thr Ala Met Arg Thr Asp Gln Tyr Asn Ser Arg Trp Leu Asn Asp Pro
                245                 250                 255

Ser Phe Ile His Ala Glu Leu Ile Pro Asp Ser Ala Glu Arg Asn Asp
            260                 265                 270

Asp Lys Leu Tyr Phe Phe Phe Arg Glu Arg Ser Ala Glu Ala Pro Gln
        275                 280                 285

Ser Pro Ala Val Tyr Ala Arg Ile Gly Arg Ile Cys Leu Asn Asp Asp
    290                 295                 300

Gly Gly His Cys Cys Leu Val Asn Lys Trp Ser Thr Phe Leu Lys Ala
305                 310                 315                 320

Arg Leu Val Cys Ser Val Pro Gly Glu Asp Gly Ile Glu Thr His Phe
                325                 330                 335

Asp Glu Leu Gln Asp Val Phe Val Gln Gln Thr Gln Asp Val Arg Asn
            340                 345                 350
```

-continued

```
Pro Val Ile Tyr Ala Val Phe Thr Ser Ser Gly Ser Val Phe Arg Gly
        355                 360                 365

Ser Ala Val Cys Val Tyr Ser Met Ala Asp Ile Arg Met Val Phe Asn
    370                 375                 380

Gly Pro Phe Ala His Lys Glu Gly Pro Asn Tyr Gln Trp Met Pro Phe
385                 390                 395                 400

Ser Gly Lys Met Pro Tyr Pro Arg Pro Gly Thr Cys Pro Gly Gly Thr
                405                 410                 415

Phe Thr Pro Ser Met Lys Ser Thr Lys Asp Tyr Pro Asp Glu Val Ile
            420                 425                 430

Asn Phe Met Arg Ser His Pro Leu Met Tyr Gln Ala Val Tyr Pro Leu
        435                 440                 445

Gln Arg Arg Pro Leu Val Val Arg Thr Gly Ala Pro Tyr Arg Leu Thr
    450                 455                 460

Thr Ile Ala Val Asp Gln Val Asp Ala Ala Asp Gly Arg Tyr Glu Val
465                 470                 475                 480

Leu Phe Leu Gly Thr Asp Arg Gly Thr Val Gln Lys Val Ile Val Leu
                485                 490                 495

Pro Lys Asp Asp Gln Glu Leu Glu Glu Leu Met Leu Glu Glu Val Glu
            500                 505                 510

Val Phe Lys Asp Pro Ala Pro Val Lys Thr Met Thr Ile Ser Ser Lys
        515                 520                 525

Arg Gln Gln Leu Tyr Val Ala Ser Ala Val Gly Val Thr His Leu Ser
    530                 535                 540

Leu His Arg Cys Gln Ala Tyr Gly Ala Ala Cys Ala Asp Cys Cys Leu
545                 550                 555                 560

Ala Arg Asp Pro Tyr Cys Ala Trp Asp Gly Gln Ala Cys Ser Arg Tyr
                565                 570                 575

Thr Ala Ser Ser Lys Arg Arg Ser Arg Arg Gln Asp Val Arg His Gly
            580                 585                 590

Asn Pro Ile Arg Gln Cys Arg Gly Phe Asn Ser Asn Ala Asn Lys Asn
        595                 600                 605

Ala Val Glu Ser Val Gln Tyr Gly Val Ala Gly Ser Ala Ala Phe Leu
    610                 615                 620

Glu Cys Gln Pro Arg Ser Pro Gln Ala Thr Val Lys Trp Leu Phe Gln
625                 630                 635                 640

Arg Asp Pro Gly Asp Arg Arg Arg Glu Ile Arg Ala Glu Asp Arg Phe
                645                 650                 655

Leu Arg Thr Glu Gln Gly Leu Leu Leu Arg Ala Leu Gln Leu Ser Asp
            660                 665                 670

Arg Gly Leu Tyr Ser Cys Thr Ala Thr Glu Asn Asn Phe Lys His Val
        675                 680                 685

Val Thr Arg Val Gln Leu His Val Leu Gly Arg Asp Ala Val His Ala
    690                 695                 700

Ala Leu Phe Pro Pro Leu Ser Met Ser Ala Pro Pro Pro Pro Gly Ala
705                 710                 715                 720

Gly Pro Pro Thr Pro Pro Tyr Gln Glu Leu Ala Gln Leu Leu Ala Gln
                725                 730                 735

Pro Glu Val Gly Leu Ile His Gln Tyr Cys Gln Gly Tyr Trp Arg His
            740                 745                 750

Val Pro Pro Ser Pro Arg Glu Ala Pro Gly Ala Pro Arg Ser Pro Glu
        755                 760                 765

Pro Gln Asp Gln Lys Lys Pro Arg Asn Arg Arg His His Pro Pro Asp
```

770 775 780

Thr
785

<210> SEQ ID NO 83
<211> LENGTH: 754
<212> TYPE: PRT
<213> ORGANISM: Mus musculus
<220> FEATURE:
<223> OTHER INFORMATION: Sema3F

<400> SEQUENCE: 83

Met Leu Val Thr Ala Phe Ile Leu Trp Ala Ser Leu Leu Thr Gly Ala
1 5 10 15

Trp Pro Ala Thr Pro Ile Gln Asp Gln Leu Pro Ala Thr Pro Arg Val
20 25 30

Arg Leu Ser Phe Lys Glu Leu Lys Ala Thr Gly Thr Ala His Phe Phe
35 40 45

Asn Phe Leu Leu Asn Thr Thr Asp Tyr Arg Ile Leu Leu Lys Asp Glu
50 55 60

Asp His Asp Arg Met Tyr Val Gly Ser Lys Asp Tyr Val Leu Ser Leu
65 70 75 80

Asp Leu His Asp Ile Asn Arg Glu Pro Leu Ile Ile His Trp Ala Ala
85 90 95

Ser Pro Gln Arg Ile Glu Glu Cys Ile Leu Ser Gly Lys Asp Gly Asn
100 105 110

Gly Glu Cys Gly Asn Phe Val Arg Leu Ile Gln Pro Trp Asn Arg Thr
115 120 125

His Leu Tyr Val Cys Gly Thr Gly Ala Tyr Asn Pro Met Cys Thr Tyr
130 135 140

Val Asn Arg Gly Arg Arg Ala Gln Asp Tyr Ile Phe Tyr Leu Glu Pro
145 150 155 160

Glu Lys Leu Glu Ser Gly Lys Gly Lys Cys Pro Tyr Asp Pro Lys Leu
165 170 175

Asp Thr Ala Ser Ala Leu Ile Asn Glu Glu Leu Tyr Ala Gly Val Tyr
180 185 190

Ile Asp Phe Met Gly Thr Asp Ala Ala Ile Phe Arg Thr Leu Gly Lys
195 200 205

Gln Thr Ala Met Arg Thr Asp Gln Tyr Asn Ser Arg Trp Leu Asn Asp
210 215 220

Pro Ser Phe Ile His Ala Glu Leu Ile Pro Asp Ser Ala Glu Arg Asn
225 230 235 240

Asp Asp Lys Leu Tyr Phe Phe Phe Arg Glu Arg Ser Ala Glu Ala Pro
245 250 255

Gln Asn Pro Ala Val Tyr Ala Arg Ile Gly Arg Ile Cys Leu Asn Asp
260 265 270

Asp Gly Gly His Cys Cys Leu Val Asn Lys Trp Ser Thr Phe Leu Lys
275 280 285

Ala Arg Leu Val Cys Ser Val Pro Gly Glu Asp Gly Ile Glu Thr His
290 295 300

Phe Asp Glu Leu Gln Asp Val Phe Val Gln Gln Thr Gln Asp Val Arg
305 310 315 320

Asn Pro Val Ile Tyr Ala Val Phe Thr Ser Ser Gly Ser Val Phe Arg
325 330 335

Gly Ser Ala Val Cys Val Tyr Ser Met Ala Asp Ile Arg Met Val Phe

-continued

```
            340                 345                 350

Asn Gly Pro Phe Ala His Lys Glu Gly Pro Asn Tyr Gln Trp Met Pro
        355                 360                 365

Phe Ser Gly Lys Met Pro Tyr Pro Arg Pro Gly Thr Cys Pro Gly Gly
    370                 375                 380

Thr Phe Thr Pro Ser Met Lys Ser Thr Lys Asp Tyr Pro Asp Glu Val
385                 390                 395                 400

Ile Asn Phe Met Arg Thr His Pro Leu Met Tyr Gln Ala Val Tyr Pro
                405                 410                 415

Leu Gln Arg Arg Pro Leu Val Val Arg Thr Gly Ala Pro Tyr Arg Leu
            420                 425                 430

Thr Thr Val Ala Val Asp Gln Val Asp Ala Ala Asp Gly Arg Tyr Glu
        435                 440                 445

Val Leu Phe Leu Gly Thr Asp Arg Gly Thr Val Gln Lys Val Ile Val
    450                 455                 460

Leu Pro Lys Asp Asp Gln Glu Val Glu Glu Leu Met Leu Glu Glu Val
465                 470                 475                 480

Glu Val Phe Lys Glu Pro Ala Pro Val Lys Thr Met Thr Ile Ser Ser
                485                 490                 495

Lys Arg Gln Gln Leu Tyr Val Ala Ser Ala Val Gly Val Thr His Leu
            500                 505                 510

Ser Leu His Arg Cys Gln Ala Tyr Gly Ala Ala Cys Ala Asp Cys Cys
        515                 520                 525

Leu Ala Arg Asp Pro Tyr Cys Ala Trp Asp Gly Gln Ala Cys Ser Arg
    530                 535                 540

Tyr Thr Ala Ser Ser Lys Arg Arg Ser Arg Arg Gln Asp Val Arg His
545                 550                 555                 560

Gly Asn Pro Ile Arg Gln Cys Arg Gly Phe Asn Ser Asn Ala Asn Lys
                565                 570                 575

Asn Ala Val Glu Ser Val Gln Tyr Gly Val Ala Gly Ser Ala Ala Phe
            580                 585                 590

Leu Glu Cys Gln Pro Arg Ser Pro Gln Ala Thr Val Lys Trp Leu Phe
        595                 600                 605

Gln Arg Asp Pro Ser Asp Arg Arg Arg Glu Ile Arg Ala Glu Asp Arg
    610                 615                 620

Phe Leu Arg Thr Glu Gln Gly Leu Leu Leu Arg Ala Leu Gln Leu Gly
625                 630                 635                 640

Asp Arg Gly Leu Tyr Ser Cys Thr Ala Thr Glu Asn Asn Phe Lys His
                645                 650                 655

Ile Val Thr Arg Val Gln Leu His Val Leu Gly Arg Asp Ala Val His
            660                 665                 670

Ala Ala Leu Phe Pro Pro Leu Ala Val Ser Val Pro Pro Pro Pro Gly
        675                 680                 685

Thr Gly Pro Pro Thr Pro Pro Tyr Gln Glu Leu Ala Gln Leu Leu Ala
    690                 695                 700

Gln Pro Glu Val Gly Leu Ile His Gln Tyr Cys Gln Gly Tyr Trp Arg
705                 710                 715                 720

His Val Pro Pro Arg Pro Arg Glu Ala Pro Gly Ala Leu Arg Pro Pro
                725                 730                 735

Glu Leu Gln Asp Gln Lys Lys Pro Arg Asn Arg Arg His His Pro Pro
            740                 745                 750

Asp Thr
```

<210> SEQ ID NO 84
<211> LENGTH: 782
<212> TYPE: PRT
<213> ORGANISM: Homo sapiens
<220> FEATURE:
<223> OTHER INFORMATION: SEMA3G

<400> SEQUENCE: 84

```
Met Ala Pro Ser Ala Trp Ala Ile Cys Trp Leu Leu Gly Gly Leu Leu
1               5                   10                  15

Leu His Gly Gly Ser Ser Gly Pro Ser Pro Gly Pro Ser Val Pro Arg
            20                  25                  30

Leu Arg Leu Ser Tyr Arg Asp Leu Leu Ser Ala Asn Arg Ser Ala Ile
        35                  40                  45

Phe Leu Gly Pro Gln Gly Ser Leu Asn Leu Gln Ala Met Tyr Leu Asp
    50                  55                  60

Glu Tyr Arg Asp Arg Leu Phe Leu Gly Gly Leu Asp Ala Leu Tyr Ser
65                  70                  75                  80

Leu Arg Leu Asp Gln Ala Trp Pro Asp Pro Arg Glu Val Leu Trp Pro
                85                  90                  95

Pro Gln Pro Gly Gln Arg Glu Glu Cys Val Arg Lys Gly Arg Asp Pro
            100                 105                 110

Leu Thr Glu Cys Ala Asn Phe Val Arg Val Leu Gln Pro His Asn Arg
        115                 120                 125

Thr His Leu Leu Ala Cys Gly Thr Gly Ala Phe Gln Pro Thr Cys Ala
    130                 135                 140

Leu Ile Thr Val Gly His Arg Gly Glu His Val Leu His Leu Glu Pro
145                 150                 155                 160

Gly Ser Val Glu Ser Gly Arg Gly Arg Cys Pro His Glu Pro Ser Arg
                165                 170                 175

Pro Phe Ala Ser Thr Phe Ile Asp Gly Glu Leu Tyr Thr Gly Leu Thr
            180                 185                 190

Ala Asp Phe Leu Gly Arg Glu Ala Met Ile Phe Arg Ser Gly Gly Pro
        195                 200                 205

Arg Pro Ala Leu Arg Ser Asp Ser Asp Gln Ser Leu Leu His Asp Pro
    210                 215                 220

Arg Phe Val Met Ala Ala Arg Ile Pro Glu Asn Ser Asp Gln Asp Asn
225                 230                 235                 240

Asp Lys Val Tyr Phe Phe Phe Ser Glu Thr Val Pro Ser Pro Asp Gly
                245                 250                 255

Gly Ser Asn His Val Thr Val Ser Arg Val Gly Arg Val Cys Val Asn
            260                 265                 270

Asp Ala Gly Gly Gln Arg Val Leu Val Asn Lys Trp Ser Thr Phe Leu
        275                 280                 285

Lys Ala Arg Leu Val Cys Ser Val Pro Gly Pro Gly Gly Ala Glu Thr
    290                 295                 300

His Phe Asp Gln Leu Glu Asp Val Phe Leu Leu Trp Pro Lys Ala Gly
305                 310                 315                 320

Lys Ser Leu Glu Val Tyr Ala Leu Phe Ser Thr Val Ser Ala Val Phe
                325                 330                 335

Gln Gly Phe Ala Val Cys Val Tyr His Met Ala Asp Ile Trp Glu Val
            340                 345                 350

Phe Asn Gly Pro Phe Ala His Arg Asp Gly Pro Gln His Gln Trp Gly
        355                 360                 365
```

-continued

```
Pro Tyr Gly Gly Lys Val Pro Phe Pro Arg Pro Gly Val Cys Pro Ser
    370                 375                 380

Lys Met Thr Ala Gln Pro Gly Arg Pro Phe Gly Ser Thr Lys Asp Tyr
385                 390                 395                 400

Pro Asp Glu Val Leu Gln Phe Ala Arg Ala His Pro Leu Met Phe Trp
                405                 410                 415

Pro Val Arg Pro Arg His Gly Arg Pro Val Leu Val Lys Thr His Leu
            420                 425                 430

Ala Gln Gln Leu His Gln Ile Val Val Asp Arg Val Glu Ala Glu Asp
        435                 440                 445

Gly Thr Tyr Asp Val Ile Phe Leu Gly Thr Asp Ser Gly Ser Val Leu
    450                 455                 460

Lys Val Ile Ala Leu Gln Ala Gly Gly Ser Ala Glu Pro Glu Glu Val
465                 470                 475                 480

Val Leu Glu Glu Leu Gln Val Phe Lys Val Pro Thr Pro Ile Thr Glu
                485                 490                 495

Met Glu Ile Ser Val Lys Arg Gln Met Leu Tyr Val Gly Ser Arg Leu
            500                 505                 510

Gly Val Ala Gln Leu Arg Leu His Gln Cys Glu Thr Tyr Gly Thr Ala
        515                 520                 525

Cys Ala Glu Cys Cys Leu Ala Arg Asp Pro Tyr Cys Ala Trp Asp Gly
    530                 535                 540

Ala Ser Cys Thr His Tyr Arg Pro Ser Leu Gly Lys Arg Arg Phe Arg
545                 550                 555                 560

Arg Gln Asp Ile Arg His Gly Asn Pro Ala Leu Gln Cys Leu Gly Gln
                565                 570                 575

Ser Gln Glu Glu Glu Ala Val Gly Leu Val Ala Ala Thr Met Val Tyr
            580                 585                 590

Gly Thr Glu His Asn Ser Thr Phe Leu Glu Cys Leu Pro Lys Ser Pro
        595                 600                 605

Gln Ala Ala Val Arg Trp Leu Leu Gln Arg Pro Gly Asp Glu Gly Pro
    610                 615                 620

Asp Gln Val Lys Thr Asp Glu Arg Val Leu His Thr Glu Arg Gly Leu
625                 630                 635                 640

Leu Phe Arg Arg Leu Ser Arg Phe Asp Ala Gly Thr Tyr Thr Cys Thr
                645                 650                 655

Thr Leu Glu His Gly Phe Ser Gln Thr Val Val Arg Leu Ala Leu Val
            660                 665                 670

Val Ile Val Ala Ser Gln Leu Asp Asn Leu Phe Pro Pro Glu Pro Lys
        675                 680                 685

Pro Glu Glu Pro Pro Ala Arg Gly Gly Leu Ala Ser Thr Pro Pro Lys
    690                 695                 700

Ala Trp Tyr Lys Asp Ile Leu Gln Leu Ile Gly Phe Ala Asn Leu Pro
705                 710                 715                 720

Arg Val Asp Glu Tyr Cys Glu Arg Val Trp Cys Arg Gly Thr Thr Glu
                725                 730                 735

Cys Ser Gly Cys Phe Arg Ser Arg Ser Arg Gly Lys Gln Ala Arg Gly
            740                 745                 750

Lys Ser Trp Ala Gly Leu Glu Leu Gly Lys Lys Met Lys Ser Arg Val
        755                 760                 765

His Ala Glu His Asn Arg Thr Pro Arg Glu Val Glu Ala Thr
    770                 775                 780
```

<210> SEQ ID NO 85
<211> LENGTH: 780
<212> TYPE: PRT
<213> ORGANISM: Mus musculus
<220> FEATURE:
<223> OTHER INFORMATION: Sema3G

<400> SEQUENCE: 85

```
Met Asp Pro Ser Ala Trp Ala Ile Cys Cys Leu Leu Gly Ser Leu Leu
1               5                   10                  15

Phe His Val Gly Ile Pro Ser Pro Gly Pro Ser Pro Ser Val Pro Arg
            20                  25                  30

Leu Arg Leu Ser Tyr Arg Asp Leu Leu Ser Thr Asn Arg Ser Ala Ile
        35                  40                  45

Phe Leu Gly Pro Arg Gly Ser Leu Asp Leu Gln Val Met Tyr Leu Asp
    50                  55                  60

Glu Tyr Arg Asp Arg Leu Phe Leu Gly Ser Arg Asp Ala Leu Tyr Ser
65                  70                  75                  80

Leu Arg Leu Asp Gln Ala Trp Pro Asp Pro Arg Glu Val Leu Trp Leu
                85                  90                  95

Pro Gln Pro Gly Gln Lys Val Glu Cys Val Arg Lys Gly Lys Asp Pro
            100                 105                 110

Leu Thr Glu Cys Ala Asn Phe Val Arg Val Leu Gln Pro His Asn Arg
        115                 120                 125

Thr His Leu Leu Ala Cys Gly Thr Gly Ala Phe Gln Pro Ile Cys Thr
    130                 135                 140

Phe Ile Thr Val Gly His Arg Gly Glu His Val Leu Arg Leu Asp Ala
145                 150                 155                 160

Ser Ser Val Glu Asn Gly Arg Gly Arg Cys Pro His Glu Pro Ser Arg
                165                 170                 175

Pro Phe Ala Ser Thr Phe Val Gly Gly Glu Leu Tyr Thr Gly Leu Thr
            180                 185                 190

Ala Asp Phe Leu Gly Arg Glu Ala Met Ile Phe Arg Ser Gly Gly Pro
        195                 200                 205

Arg Pro Ala Leu Arg Ser Asp Ser Asp Gln Ser Leu Leu His Glu Pro
    210                 215                 220

Arg Phe Val Met Ala Ala Arg Ile Pro Asp Asn Ser Asp Arg Asp Asp
225                 230                 235                 240

Asp Lys Val Tyr Phe Phe Phe Ser Glu Thr Val Pro Ser Pro Asp Gly
                245                 250                 255

Gly Pro Gly His Val Thr Ile Ser Arg Val Gly Arg Val Cys Val Asn
            260                 265                 270

Asp Ala Gly Gly Gln Arg Val Leu Val Asn Lys Trp Ser Thr Phe Leu
        275                 280                 285

Lys Ala Arg Leu Val Cys Ser Val Pro Gly Pro Gly Gly Ala Glu Thr
    290                 295                 300

His Phe Asp Gln Leu Glu Asp Val Phe Leu Leu Trp Pro Lys Ala Gly
305                 310                 315                 320

Lys Ser Leu Glu Val Tyr Ala Leu Phe Ser Thr Val Ser Ala Val Phe
                325                 330                 335

Gln Gly Phe Ala Val Cys Val Tyr His Met Val Asp Ile Trp Glu Val
            340                 345                 350

Phe Asn Gly Pro Phe Ala His Arg Asp Gly Pro Gln His Gln Trp Gly
        355                 360                 365

Pro Tyr Gly Gly Lys Val Pro Phe Pro Arg Pro Gly Val Cys Pro Ser
```

-continued

```
    370                 375                 380

Lys Met Thr Ala Gln Pro Gly Arg Pro Phe Gly Ser Thr Lys Asp Tyr
385                 390                 395                 400

Pro Asp Glu Val Leu Gln Phe Val Arg Asp His Pro Leu Met Phe Gln
                405                 410                 415

Pro Val Arg Pro Arg Arg Gly Arg Pro Val Leu Val Lys Thr His Leu
            420                 425                 430

Ala Gln Arg Leu Arg Gln Ile Val Val Asp Arg Val Glu Ala Glu Asp
        435                 440                 445

Gly Thr Tyr Asp Val Ile Phe Leu Gly Thr Asp Ser Gly Ser Val Leu
    450                 455                 460

Lys Val Ile Ala Leu Gln Gly Gly Gly Leu Thr Glu Pro Glu Glu Val
465                 470                 475                 480

Val Leu Glu Glu Leu Gln Val Phe Lys Val Pro Thr Pro Ile Thr Glu
                485                 490                 495

Met Glu Ile Ser Val Lys Arg Gln Thr Leu Tyr Val Gly Ser Pro Leu
            500                 505                 510

Gly Val Ala Arg Leu Gln Leu His Gln Cys Glu Thr Tyr Gly Ser Ala
        515                 520                 525

Cys Ala Glu Cys Cys Leu Ala Arg Asp Pro Tyr Cys Ala Trp Asp Gly
    530                 535                 540

Thr Ala Cys Ala Arg Tyr Arg Pro Ser Ser Gly Lys Arg Arg Phe Arg
545                 550                 555                 560

Arg Gln Asp Ile Arg His Gly Asn Pro Ala Val Gln Cys Leu Gly Gln
                565                 570                 575

Gly Gln Ser Gln Asn Lys Ala Ala Ser Gly Leu Met Thr Arg Val Phe
            580                 585                 590

Gly Thr Glu His Asn Ser Thr Phe Leu Glu Cys Leu Pro Lys Ser Pro
        595                 600                 605

Gln Ala Ala Val Arg Trp Phe Leu Gln Arg Pro Gly Asp Lys Gly Thr
    610                 615                 620

Asp Gln Val Lys Thr Asp Glu Arg Val Val Gln Thr Ala Gln Gly Leu
625                 630                 635                 640

Leu Phe Arg Arg Leu Ser Arg His Asp Ala Gly Asn Tyr Thr Cys Thr
                645                 650                 655

Thr Leu Glu His Gly Phe Ser Gln Thr Val Val Arg Phe Ala Leu Glu
            660                 665                 670

Val Ile Ala Ala Val Gln Leu Asp Ser Leu Phe Leu Arg Glu Ser Arg
        675                 680                 685

Leu Glu Glu Pro Ser Ala Trp Gly Ser Leu Ala Ser Ala Ser Pro Lys
    690                 695                 700

Thr Trp Tyr Lys Asp Ile Leu Gln Leu Thr Gly Phe Ala Asn Leu Pro
705                 710                 715                 720

Arg Val Asp Glu Tyr Cys Glu Arg Val Trp Cys Arg Gly Val Gly Glu
                725                 730                 735

Arg Ser Gly Ser Phe Arg Gly Lys Gly Lys Gln Ala Lys Gly Lys Ser
            740                 745                 750

Trp Ala Gly Leu Glu Leu Gly Lys Lys Met Lys Ser Arg Val Leu Ala
        755                 760                 765

Glu His Asn Arg Thr Pro Arg Glu Val Glu Ala Thr
    770                 775                 780
```